US010631516B2

(12) United States Patent
Spangenberg et al.

(10) Patent No.: US 10,631,516 B2
(45) Date of Patent: Apr. 28, 2020

(54) SELECTION OF SYMBIOTA BY SCREENING MULTIPLE HOST-SYMBIONT ASSOCIATIONS

(71) Applicant: Agriculture Victoria Services Pty Ltd, Bundoora, VIC (AU)

(72) Inventors: German Carlos Spangenberg, Bundoora (AU); John White Forster, Diamond Creek (AU); Noel Cogan, Macleod (AU); Yidong Ran, Bundoora (AU); John Gregory Mason, Preston (AU); Timothy Ivor Sawbridge, Coburg (AU); Kathryn Michaela Guthridge, Hadfield (AU); Simone Jane Rochfort, Reservoir (AU); Ben Cocks, Viewbank (AU)

(73) Assignee: Agriculture Victoria Services PTY LTD, Bundoora, Victoria (AU)

( * ) Notice: Subject to any disclaimer, the term of this patent is extended or adjusted under 35 U.S.C. 154(b) by 673 days.

(21) Appl. No.: 14/404,861

(22) PCT Filed: May 29, 2013

(86) PCT No.: PCT/AU2013/000557
§ 371 (c)(1),
(2) Date: Dec. 1, 2014

(87) PCT Pub. No.: WO2013/177615
PCT Pub. Date: Dec. 5, 2013

(65) Prior Publication Data
US 2015/0156982 A1    Jun. 11, 2015

Related U.S. Application Data

(60) Provisional application No. 61/731,341, filed on Nov. 29, 2012, provisional application No. 61/697,933, filed on Sep. 7, 2012, provisional application No. 61/654,396, filed on Jun. 1, 2012.

(30) Foreign Application Priority Data

Jun. 1, 2012    (AU) ................................ 2012902280
Jun. 1, 2012    (AU) ................................ 2012902282
Jun. 1, 2012    (AU) ................................ 2012902284

(51) Int. Cl.
| | |
|---|---|
| *A01H 17/00* | (2006.01) |
| *C12Q 1/68* | (2018.01) |
| *A01H 5/10* | (2018.01) |
| *C12N 15/10* | (2006.01) |

(52) U.S. Cl.
CPC ............... *A01H 17/00* (2013.01); *A01H 5/10* (2013.01); *C12N 15/1058* (2013.01); *C12Q 1/68* (2013.01)

(58) Field of Classification Search
CPC ..................................................... A01H 17/00
See application file for complete search history.

(56) References Cited

U.S. PATENT DOCUMENTS

| | | | | | |
|---|---|---|---|---|---|
| 2,200,532 | A | * | 5/1940 | Varley | C05F 11/08 435/252.2 |
| 5,382,269 | A | * | 1/1995 | Giroud-Abel | A01C 1/06 47/57.6 |
| 6,072,107 | A | | 6/2000 | Latch et al. | |
| 6,111,170 | A | | 8/2000 | Latch et al. | |

FOREIGN PATENT DOCUMENTS

| | | |
|---|---|---|
| AU | 2012324028 A1 | 6/2013 |
| CN | 85106041 A | 1/1987 |
| CN | 1465227 A | 1/2004 |
| EP | 1 191 103 A1 * | 9/2000 |
| EP | 1191103 A1 | 3/2002 |
| JP | 03155722 A | 7/1991 |
| JP | 07274723 A | 10/1995 |
| WO | 98/50532 A2 | 11/1998 |
| WO | 2004029227 A1 | 4/2004 |
| WO | 2008133533 A1 | 11/2008 |
| WO | 2011/082455 A1 | 7/2011 |

OTHER PUBLICATIONS

Evans et al 2003, Mycological Progress 2(2): 149-160.*
Naffaa et al 1999, Agronomie 19: 133-144.*
Jouany et al 2007, Animal 1(10): 1443-1466.*
Yan et al 2011, J. Zhejiang Univ-Sci B (Biomed & Biotechol) 12(3): 219-225.*
Herrmann et al 2006, Theor. Appl. Genet. 112: 536-545.*
Statement of Grounds and Particulars dated Mar. 16, 2016 filed in opposition against corresponding Australian Patent Application No. 2013203272.
Chinese Search Report dated Dec. 22, 2015 from corresponding Chinese Patent Application No. 201380041138.X.
Chinese Office Action dated Dec. 31, 2015 from corresponding Chinese Patent Application No. 201380041138.X.

(Continued)

*Primary Examiner* — David H Kruse
(74) *Attorney, Agent, or Firm* — Larson & Anderson, LLC

(57) ABSTRACT

The present invention relates to new methods of selecting and breeding organisms, in particular organisms which exhibit symbiotic behaviour with symbionts, and to new organisms and symbiota developed thereby, such as plant or grass and endophyte symbiota. Multiple symbionts are deployed in multiple organisms and selected for improved symbiotic compatibility and performance early in the breeding process. Methods include producing improved organisms from germplasm, by inoculating host organism germplasm libraries with symbionts selected from symbiont libraries and selecting improved host organisms exhibiting desired symbiota characteristics, and selection of organism-symbiont associations with a desired genetic and metabolic profile by metagenomic analysis of nucleic acid libraries from an organism or organism-symbiont association.

14 Claims, 194 Drawing Sheets

(56) References Cited

OTHER PUBLICATIONS

Extended European Search Report dated Dec. 21, 2015 from corresponding European Patent Application No. 13796907.7.
Ambrose, K. V. et al., Counting genes and comprehending processes: How high-throughput sequencing is aiding in piecing together the grass-endophyte symbiosis puzzle, Phytopathology, 2012, p. 1, vol. 102, No. I, Suppl 1, & Annual Meeting of the American-Phytopathological-Society (APS) Northeastern Division, Oct. 12-14, 2011, Abstract.
Chen, J. et al., Construction of a Metagenomic DNA Library of Sponge Symbionts and Screening of Antibacterial Metabolites, Journal of Ocean Univeristy of China, 2006, pp. 119-122, vol. 5, No. 2.
Hernandez-Lucas, I. et al., Phylogenetic Relationships and Host Range of *Rhizobium* spp. That Nodulate *Phaseolus vulgaris* L., Applied and Environmental Microbiology, 1995, pp. 2775-2779, vol. 61, No. 7.
Miller, R. W. et al., Relative Efficacy of Different Alfalfa Cultivar-Rhizobium meliloti Strain Combinations for Symbiotic Nitrogen Fixation, Applied and Environmental Microbiology, 1982, pp. 764-768, vol. 43, No. 4.
Naffaa, W. et al., Creation of stable associations between perennial ryegrass or tall fescue and fungal endophytes, Agronomie, 1999, pp. 133-144, vol. 19, No. 2.
Van Der Veken, L., et al., Susceptibility of banana intercrops for rhizobacteria, arbuscular mycorrhizal fungi and the burrowing nematode *Radopholus similis*, Applied Soil Ecology, 2008, pp. 283-290, vol. 40, No. 2, Elsevier, Amsterdam, NL.
Lu, X. et al., Metagenomics and Its Application in Biological Control of Plant Diseases, Chinese Journal of Biological Control, 2010, pp. 106-112.
Chang, C. et al., Studies on Selection of the Best Symbiotic System of High Yielding and High Protein Content Soybean, High Efficient N Fixation Rhizobium and Mycorrhiza Fungus, Soybean Science, 1992, pp. 226-233, vol. 11, No. 3.
International Preliminary Report on Patentability dated Dec. 2, 2014 from corresponding PCT Application No. PCT/AU2013/000557.
Khan, A. et al, Gene expression profiling of the endophytic fungus *Neotyphodium lolii* in association with its host plant perennial ryegrass, Australian Plant Pathology, 2010, pp. 467-476, vol. 39.
Tartar, A. et al., Parallel metatranscriptome analyses of host and symbiont gene expression in the gut of the termite *Reticulitermes flavipes*, Biotechnology for Biofuels, 2009, pp. 1-19.
Li, M., et al., Effects of sampling location and time, and host animal on assessment of bacterial diversity and fermentation parameters in the bovine rumen, Journal of Applied Microbiology, 2009, pp. 1924-1934, vol. 107.
Spangenberg, G., Transgenesis and genomics in molecular breeding of pasture grasses and legumes for forage quality and other traits, In: Makkar, H.P.S., et al., (eds), Applications of gene-based technologies for improving animal production and health in developing countries, 2005, pp. 357-372.(793 pages), copyright International Atomic Energy Authority (IAEA), Vienna, Austria, published by Springer Netherlands.
Baird, N. A. et al., Rapid SNP Discovery and Genetic Mapping Using Sequenced RAD Markers, PLoS one, 2008, e 3376, vol. 3, Issue 10.
Brulc, J. M. et al., Gene-centric metagenomics of the fiber-adherent bovine rumen microbiome reveals forage specific glycoside hydrolases, PNAS, 2009, pp. 1948-1953, vol. 106, No. 6.
Daetwyler, H.D. et al., Accuracy of Predicting he Genetic Risk of Disease Using a Genome-Wide Approach, PLoS One, 2008, e3395, vol. 3, Issue 10.
Dekkers, J. C. M., Commercial application of marker- and gene-assisted selection in livestock: Strategies and lessons, J. Anim. Sci., 2004, pp. E-Suppl:E313-E328, vol. 82, (13 Suppl), Downloaded from www.journalofanimalscience.org on Jan. 6, 2015.
Dracatos, P. M. et al., Molecular characterisation and genetic mapping of candidate genes for qualitative disease resistance in perennial ryegrass (*Lolium perenne* L.), BMC Plant Biology, 2009, Retrieved from: http://www.biomedcentral.com/bmcplantbiol/content/9/May/2009, pp. 1-22, vol. 9, No. 62.
Dumsday, J. L. et al., SSR-based genetic linkage analysis of resistance to crown rust (*Puccinia coronata* f. sp. lolii) in perennial ryegrass (*Lolium perenne*), Plant Pathology, 2003, pp. 628-637, vol. 52, No. 5.
Elshire, R. J. et al., A Robust, Simple Genotyping-by-Sequencing (GBS) Approach for High Diversity Species, PLoS one, 2011, e19379, vol. 6, Issue 5.
Ganal, M. W. et al., A Large Maize (*Zea mays* L.) SNP Genotyping Array: Development and Germplasm Genotyping, and Genetic Mapping to Compare with the B73 Reference Genome, PLoS one, 2011, e28334, vol. 6, Issue 12.
Gidskehaug, I. et al., Genotype calling and mapping of multisite variants using an Atlantic salmon iSelect SNP array, Bioinfomnatics, 2011, pp. 303-310, vol. 27, No. 3.
Habier, D. et al., Genomic Selection Using Low-Density Marker Panels, Genetics, 2009, pp. 343-353, vol. 182.
Hand, M. L., et al., Evolutionary history of tall fescue morphotypes inferred from molecular phylogenetics of the Lolium-Festuca species complex, BMC Evol. Biol., 2010, pp. 1-17, vol. 10:303, , Retrieved from http://www.biomedcentral.com/1471-2148/10/303.
Hayes, B. J., et al., Accuracy of genomic selection: comparing theory and results, Proc. 14th Conf. Assoc. Advanc. Anim. Br. Genet., 2009, pp. 34-37, No. 18.
Henderson, C. R., Applications of linear models in animal breeding, University of Guelph, 1984, Ontario, Canada.
Huang, X. et al., High-throughput genotyping by whole-genome resequencing, Genome Research, 2009, pp. 1068-1076, vol. 19.
Jannink, J-L et al., Genomic selection in plant breeding: from theory to practice, Briefings Funct. Genom., 2010, pp. 166-177, vol. 9, No. 2.
Kaur, S. et al., Identification, characterisation and interpretation of single nucleotide sequence variation in allopolyploid crop plant species, Plant Biotechnology Journal, 2012, pp. 125-138, vol. 10.
Meuwissen, T.H.E et al., The use of marker haplotypes in animal breeding schemes, Genet Sel Evol, 1996, pp. 161-176, vol. 28.
Meuwissen, T. H. E. et al, Prediction of Total Genetic Value Using Genome-Wide Dense Marker Maps, Genetics, 2001, pp. 1819-1829, vol. 157.
Meuwissen, T. H. E. et al, Mapping multiple QTL using linkage disequilibrium and linkage analysis information and multitrait data, Genet. Sel. Evol., 2004, pp. 261-279, vol. 36.
Meuwissen, T. H. E., Accuracy of breeding values of 'unrelated' individuals predicted by dense SNP genotyping, Genetics Selection Evolution, 2009, vol. 41, No. 35, Retrieved from http://www.gsejournal.org/content/41/1/35, pp. 1-9.
Odegard, J. et al., Incorporating Desireable genetic Charateristics From an Inferior Into a Superior Population Using Genomic Selection, Genetics, 2008, pp. 737-745, vol. 181.
Sanna, S. et al., Common variants in the GDF5-UQCC region are associated with variation in human height, Nat Genet, 2008, pp. 198-203, vol. 40, No. 2.
Skot L. et al., Allelic Variation in the Perennial Ryegrass Flowering Locus T Gene Is Associated with Changes in Flowering Time across a Range of Populations, Plant Physiology, 2011, pp. 1013-1022, vol. 155.
Walter, A. et al., Advanced phenotyping offers opportunities for improved breeding of forage and turf species, Annals of Botany, 2012, pp. 1271-1279, vol. 110.
Yan, J. et al., Genetic Characterization and Linkage Disequilibrium Estimation of a Global Maize Collection Using SNP Markers, PLoS One, 2009, e8451, vol. 4, Issue 12.
Albrecht, T. et al., Genome-based prediction of testcross values in maize, Theor Appl Genet, 2011, pp. 339-350, vol. 123.
Auzanneau, J. et al., Linkage disequilibrium in synthetic varieties of perennial ryegrass, Theor Appl Genet, 2007, pp. 837-847, vol. 115.
Brazauskas, G. et al., Nucleotide diversity and linkage disequilibrium in five Lolium perenne genes with putative role in shoot morphology, Plant Science, 2010, pp. 194-201, vol. 179.

(56) References Cited

OTHER PUBLICATIONS

Cogan, N. O. I. et al., QTL analysis and comparative genomics of herbage quality traits in perennial ryegrass (*Lolium perenne* L.), Theor Appl Genet, 2005, pp. 364-380, vol. 110.
Cogan, N. O. I. et al., Gene-associated single nucleotide polymorphism discovery in perennial ryegrass (*Lolium perenne* L.), Mol Gen Genomics, 2006, pp. 101-112, vol. 276.
Dracatos, P. M., et al., Discovery and genetic mapping of single nucleotide polymorphisms in candidate genes for pathogen defence response in perennial ryegrass (*Lolium perenne* L.), Theor Appl Genet, 2008, pp. 203-219, vol. 117.
Dracatos, P. M., et al., Biology and Genetics of Crown Rust Disease in Ryegrasses, Crop Science, 2010, pp. 1605-1624, vol. 50.
Faville, M. J. et al., Functionally associated molecular genetic marker map construction in perennial ryegrass (*Lolium perenne* L.), Theor Appl Genet, 2004, pp. 12-32, vol. 110.
Fiil, A. et al., Nucleotide diversity and linkage disequilibrium on nine genes with putative effects on flowering time in perennial ryegrass (*Lolium perenne* L.), Plant Science, 2011, pp. 228-237, vol. 180.
Forster, J. W. et al., Functionally Associated Molecular Genetic Markers for Temperate Pasture Plant Improvement, In: R.J. Henry (ed.) Plant Genotyping II: SNP Technology, 2008, pp. 154-187, CABI Press, Wallingford, Oxford, UK.
Furbank, R. T., Plant phenomics: from gene to form and function, Functional Plant Biology, 2009, pp. v-vi, vol. 36.
Goddard, M., Genomic selection: prediction of accuracy and maximisation of long term response, Genetica, 2009, pp. 245-257, vol. 136.
Gupta, P. K., Single-molecule DNA sequencing technologies for future genomics research, Trends Biotechnol., 2008, pp. 602-611, vol. 26.
Guthridge, K. M. et al., AFLP analysis of genetic diversity within and between populations of perennial ryegrass (*Lolium perenne* L.), Euphytica, 2001, pp. 191-201, vol. 122.
Hand, M. L., et al., Identification of homologous, homoeologous and paralogous sequence variants in an outbreeding allopolyploid species based on comparison with progenitor taxa, Mol Genet Genomics, 2008, pp. 293-304, vol. 280.
Hayward, M. D. et al., Genetic analysis of Lolium. I. Identification of linkage groups and the establishment of a genetic map, Plant Breeding, 1998, pp. 451-455, vol. 117.
Heffner, E. L. et al., Genomic Selection for Crop Improvement, Crop Science, 2009, pp. 1-12, vol. 49.
Hess, M. et al., Metagenomic Discovery of Biomass-Degrading Genes and Genomes from Cow Rumen, Science, 2011, pp. 463-467, vol. 331.
Houle, D. et al., Phenomics: the next challenge, Nature Reviews Genet, 2010, pp. 855-866, vol. 11.
Huang, X. et al., Genome-wide association studies of 14 agronomic traits in rice landraces, Nature Genetics, 2010, pp. 961-967, vol. 42, No. 11.
Jones, E. S. et al., Development and characterisation of simple sequence repeat (SSR) markers for perennial ryegrass (*Lolium perenne* L.), Theor Appl Genet, 2001, pp. 405-415, vol. 102.
Jones, E. S. et al., An enhanced molecular marker based genetic map of perennial ryegrass (*Lolium perenne*) reveals comparative relationships with other Poaceae genomes, Genome, 2002, pp. 282-295, vol. 45.
Jones, E. S. et al., An SSR-based genetic linkage map for perennial ryegrass (*Lolium perenne* L.), Theor Appl Genet, 2002, pp. 577-584, vol. 105.
Lawless, K. A. et al., Interpretation of SNP Haplotype Complexity in White Clover (*Trigolium repens* L.), an Outbreeding Allotetraploid Species, In: T. Yamada and G. Spangenberg (eds) Molecular Breeding of Forage and Turf: The Proceedings of the 5th International Symposium on the Molecular Breeding of Forage and Turf, 2009, pp. 211-221, springer, New York, USA.
Lango Allen, H.K. et al., Hundreds of variants clustered in genomic loci and biological pathways affect human height, Nature, 2010, pp. 832-838, vol. 467.

Mackay,K T. F. C., The Genetic Architecture of Quantitative Traits, Annu. Rev. Genet, 2001 pp. 303-339, vol. 35.
Margulies, M, et al., Genome sequencing in microfabricated high-density picolitre reactors, Nature, 2005, pp. 376-380, vol. 437.
Pearson, A. et al., Identification of QTLs for morphological traits influencing waterlogging tolerance in perennial ryegrass (*Lolium perenne* L.), Theor Appl Genet, 2011, pp. 609-622, vol. 122.
Pessino, S. C. et al., The molecular genetics of gametophytic apomixis, Hereditas, 1999, pp. 1-11, vol. 130.
Ponting, R. C., et al, SNP discovery, validation, haplotype structure and linkage disequilibrium in full-length herbage nutritive quality genes of perennial ryegrass (*Lolium perenne* L.), Mol Genet Genomics, 2007, pp. 585-597.
Pryce, J. E. et al., Novel strategies to minimize progeny inbreeding while maximizing genetic gain using genomic information, J. Dairy Sci., 2012, pp. 377-388, vol. 95.
Riedelsheimer, C. et al., Genomic and metabolic prediction of complex heterotic traits in hybrid maize, Nature Genetics, 2012, pp. 217-220, vol. 15.
Xing, Y., et al., Nucleotide diversity and linkage disequilibrium in 11 expressed resistance candidate genes in Lolium perenne, BMC Plant Biology, 2007, 7:43.
Sessitsch, A. et al., Advances in Rhizobium Research, Critical Reviews in Plant Sciences, 2002, pp. 323-378, vol. 21, No. 4.
Shinozuka, H. et al., Fine-scale comparative genetic and physical mapping supports map-based cloning strategies for the self-incompatibility loci of perennial ryegrass (*Lolium perenne* L.), Plant Mol Biol, 2010, pp. 343-355, vol. 72.
Skot, L. et al., Association of Candidate Genes With Flowering Time and Water-Soluble Carbohydrate Content in *Lolium perenne* (L.), Genetics, 2007, pp. 535-547, vol. 177.
Spelman, R. J., et al., Utilisation of genetic variation by marker assisted selection in commercial dairy cattle populations, Livestock Production Science, 1999, pp. 51-60, vol. 59.
Spielman, M. et al., Genetic mechanisms of apomixis, Phil. Trans. R. Soc. Lond. B, 2003, pp. 1095-1103, vol. 358.
Sved, J. A., Linkage Disequilibrium and Homozygosity of Chromosome Segments in Finite Populations, Theoretical Population Biology, 1971, pp. 125-141, vol. 2.
Tian, F. et al., Genome-wide association study of leaf architecture in the maize nested association mapping population, Nature Genetics, 2011, pp. 159-162, vol. 43, No. 2.
Gibbs, R. A. et al., The Bovine Hapmap Consortium, Genome-Wide Survey of SNP Variation Uncovers the Genetic Structure of Cattle Breeds, Science, 2009, pp. 528-532, vol. 324.
Turner, L. B, et al., Testing water-soluble carbohydrate QTL effects in perennial ryegrass (*Lolium perenne* L.) by marker selection, Theor Appl Genet, 2010, pp. 1405-1417, vol. 121.
Vanraden, P. M. et al., Invited review: Reliability of genomic predictions for North American Holstein bulls, J. Dairy Sci., 2009, pp. 16-24, vol. 92.
Vogel, K. P., et al., Breeding Systems for Cross-Pollinated Perennial Grasses, Plant Breed Reviews, 1993, pp. 251-274, vol. 11.
Wang, J. et al., Assignment of Individual Genotypes to Specific Forage Cultivars of Perennial ryegrass Based on SSR Markers, Crop Science, 2009, pp. 49-58, vol. 49.
Wang, L. et al., Mapping 49 quantitative trait loci at high resolution through sequencing-based genotyping of rice recombinant inbred lines, Theor Appl Genet, 2011, pp. 327-340, vol. 122.
Wilkins, P. W. et al., Progress in breeding perennial forage grasses for temperate agriculture, Journal of Agricultural Science, 2003, pp. 129-150, vol. 140.
Van Inghelandt, D. et al., Extent and genome-wide distribution of linkage disequilibrium in commercial maize germplasm, Theor Appl Genet, 2011, pp. 11-20, vol. 123.
Visscher, P. M., Sizing up human height variation, Nature Genetics, 2008, pp. 489-490, vol. 40, No. 5.
Forster, J. W., et al., Molecular Breeding Technologies for Forage and Turf Plants, In: C. Kole and A. Abbott (eds) Principles and Practices of Plant Genomics, Molecular Breeding, 2008, pp. 395-430, vol. 2.

(56) References Cited

OTHER PUBLICATIONS

Cogan, N. O. I., et al., Genomic Tools for Pasture Plant Breeding, Plant and Animal Genome XIX, 2011, Abstract W335, San Diego, CA, USA.

Forster, J. W., et al., Development and implementation of molecular genetic tools for enhancement of herbage quality and other agronomic traits in perennial ryegrass (*Lolium perenne* L.), Molecular Breeding of Forage and Turf, 2010, Abstract, 18-19, Buenos Aires, Argentina.

Cogan, N. O. I., et al., Accelerated SNP discovery in perennial ryegrass (*Lolium perenne* L.) based on pooled amplicon resequencing, Molecular Breeding of Forage and Turf, 2010, pp. 47-48, Abstract P-4, Buenos Aires, Argentina.

Cogan, N. O. I., et al., Association mapping of forage quality traits in perennial ryegrass (Lolium perenne L.), Molecular Breeding of Forage and Turf, 2010, p. 211, Abstract P-148, Buenos Aires, Argentina.

Cogan, N. O. I., et al, Massively-parallel sequencing technology permits direct detection of novel SNP haplotypes in perennial ryegrass (*Lolium perenne* L.), Molecular Breeding of Forage and Turf, 2010, pp. 51-52, Abstract P-6, Buenos Aires, Argentina.

Cogan, N. O. I., et al., Comparative genomics in the grass family Poaceae for structured genome-wide SNP discovery in perennial ryegrass (*Lolium perenne* L.), Molecular Breeding of Forage and Turf, 2010, pp. 49-50, Abstract P-5, Buenos Aires, Argentina.

Beavis, W. D., QTL Analyses: Power, Precision, and Accuracy, In: A. Paterson (ed.) Molecular Dissection of Complex Traits, 1994, pp. 145-162, CRC, Boca Raton, Louisiana, USA.

Bray, R.A. et al., *Medicago sativa* L. (lucerne) cv. Hallmark, Australian Journal of Experimental Agriculture, 1999, pp. 643-644, vol. 39.

Australian Re-examination Report dated Apr. 11, 2018 from related Australian Patent Application No. 2013203272.

Sessitsch, A. et al., Functional Characteristics of an Endophyte Community Colonizing Rice Roots as Revealed by Metagenomic Analysis, Molecular Plant-Microbe Interactions, 2012, pp. 28-36, vol. 25, No. 1.

English translation of Chinese Re-examination Notice dated Jan. 18, 2019 from corresponding Chinese Patent Application No. 2019011500687300.

Horticultural Plant Breeding, edited by Shen Huolin, Central Radio & TV University Press, Published in Apr. 2011, p. 234.

Bouton, J. "The use of Endophytic Fungi for Pasture Improvement in the USA", University of Georgia, 2000, pp. 163-168.

Bouton, J. et al. "Reinfection of Tall Fescue Cultivars with Non-Ergot Alkaloid-Producing Endophytes" Agronomy J., 2002, pp. 567-574, vol. 94, No. 3.

MaxQ Development, Grasslanz downloaded from http://www.grasslanz.com/UnderstandingtheScience/MaxQdevelopment Oct. 19, 2016.

Johnson, RD. et al. "A multidisciplinary approach to dissect the molecular basis of the Neotyphodium lolii/rygrass symbiosis" Breeding for Success:Diversity in Action' C.F. Mercer (ed). Proceedings of the 13th Australasian Plant Breeding Conference, Apr. 2006, pp. 537-547.

AgResearch PowerPoint Presentation presented at the NZBIO conference in 2011.

Philipson, M. "A symptomless endophyte of ryegrass (*Lolium perenne*) that spores on its host—a light microscope" New Zealand Journal of Botany, 1989, pp. 513-519, vol. 27.

Qi, M. et al. "Snapshot of the Eukaryotic Gene Expression in Muskoxen Rumen—A Metatranscriptomic Approach", PLOS One, May 2011, pp. 1-12, vol. 6, Issue 5.

Saiprasad, G.V.S. "Artificial Seeds and their Applications" Resonance, May 2001, pp. 39-47.

Young, C. et al. "A Complex gene cluster for indole-diterpene biosynthesis in the grass endophyte Neotyphodium lolii" Fungal Genetics and Biology, 2006, pp. 679-693, vol. 43.

Zhang, X. "Functional Analysis of a Thiamine Biosynthetic Gene in the Interaction of Epichloe Typhina with Perennial Ryegrass" Massey University, 2004, pp. 1-358 (parts 1 and 2).

Rasmussen, H.N. et al., Symbiotic In Vitro Culture of Immature Embryos and Seeds from Listera Ovata, Lindleyana, 1991, pp. 134-139, vol. 6, No. 3.

Notice of Reasons for Rejection dated Apr. 3, 2017 from corresponding Japanese Patent Application No. 2015-514286.

\* cited by examiner

*Colletotrichum graminicola*

*Bipolaris portulaceae*

Experimental design for semi-quantitative analysis of metabolites

| Gene | Genbank Accession No | N. lolii | | | | | | LpTG-2 | | non-N.lolii | E. festucae |
|------|----|----|----|----|----|----|----|----|----|----|----|
| | | ST | LP19 | AR1 | NEA3 | E9 | G4 | NEA10 | NEA11 | NEA12 | E1 | E2368 |
| Metabolite production in planta | | L | L | --- | --- | L | L | --- | --- | --- | TBD | --- |
| Lolitrems | | | | | | | | | | | | |
| *ltmB* | DQ443465 | | | | | | | | | | | |
| *ltmQ* | DQ443465 | | | | | | | | | | | |
| *ltmP* | DQ443465 | | | | | | | | | | | |
| *ltmJ* | DQ443465 | | | ▨ | ▨ | ▨ | ▨ | ▨ | | | | |
| *ltmE* | DQ443465 | | | | | | | | | | | |
| *ltmF* | DQ443465 | | | | | | | | | | | |
| *ltmC* | DQ443465 | | | | | | | | | | | |
| *ltmG* | AY742903 | | | | | | | | | | | |
| *ltmM* | AY742903 | | | | | | | ▨ | ▨ | ▨ | | |
| *ltmK* | AY742903 | | | | | | | | | | | |
| Metabolite production in planta | | P | P | P | P | P | P | P | --- | P | TBD | ▨ |
| Peramine *perA* | AB205145 | | | | | | | | | | | |
| Metabolite Production in planta | | E | E | --- | E | --- | --- | E | E | --- | TBD | E |

Fig. 187

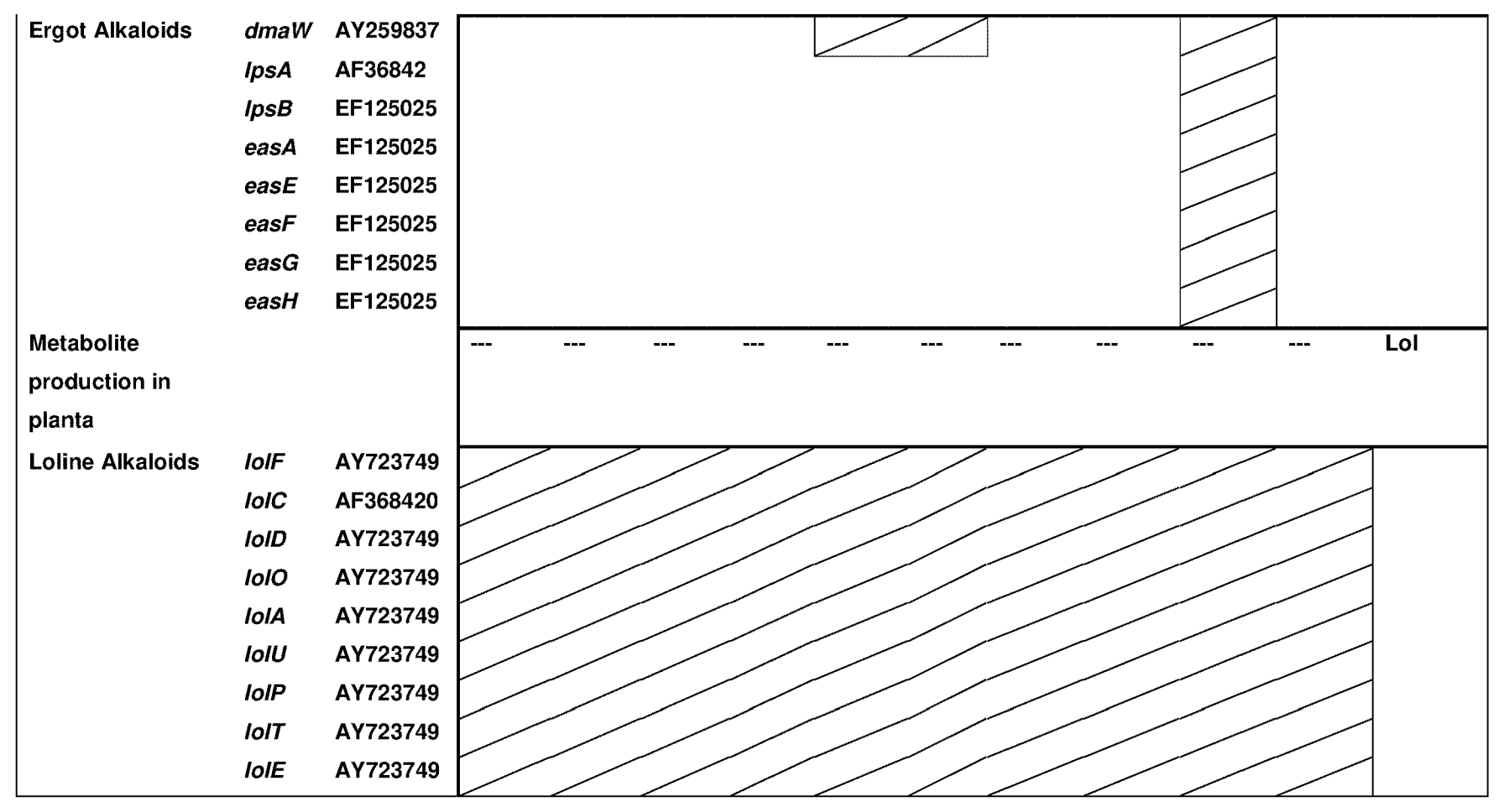

| | | |
|---|---|---|
| Ergot Alkaloids | dmaW | AY259837 |
| | lpsA | AF36842 |
| | lpsB | EF

| | | N. lolii | | | | | | LpTG-2 | non-N.lolii | | E. festucae |
|---|---|---|---|---|---|---|---|---|---|---|---|
| Gene | GenBank Accession No | ST | Lp19 | AR1 | NEA3 | E9 | G4 | NEA10 | NEA11 | NEA12 | E1 | E2368 |
| Metabolite production in Planta | | | | | | | | | | | | |
| Lolitrems | | | | | | | | | | | | |
| ltmB | DQ443465 | L | L | --- | --- | | | | | | TBD | --- |
| ltmQ | DQ443465 | | | | | | | | | | | |
| ltmP | DQ443465 | | | | | | | | | | | |
| ltmJ | DQ443465 | | | | | | | | | | | |
| ltmE | DQ443465 | L | L | | | L | L | | | | | |
| ltmF | DQ443465 | | | | | | | | | | | |
| ltmC | DQ443465 | | | | | | | | | | | |
| ltmG | AY742903 | | | | | | | | | | | |
| ltmM | AY742903 | | | | | | | | | | | |
| ltmK | AY742903 | | | | | | | | | | | |

Fig. 188

|   |   |   | ST | \multicolumn{6}{c|}{N. lolii} | \multicolumn{3}{c|}{LpTG-2 Non-N.lolii} | E. festucae |
|---|---|---|---|---|---|---|---|---|---|---|---|---|---|
|   | Gene | GenBank Accession No | | Lp19 | AR1 | NEA3 | E9 | G4 | NEA10 | NEA11 | NEA12 | E1 | E2368 |
| Metabolite production in planta | | | E | E | --- | E | --- | --- | E | E | --- | TBD | E |
| Ergot Alkaloids | dmaW | AY259837 | | | | | | | | | | | |
| | lpsA | AF368420 | | | | | | | | | | | |
| | lpsB | EF125025 | | | | | | | | | | | |
| | easA | EF125025 | | | | | | | | | | | |
| | easE | EF125025 | | | | | | | | | | | |
| | easF | EF125025 | | | | | | | | | | | |
| | easG | EF125025 | | | | | | | | | | | |
| | easH | EF125025 | | | | | | | | | | | |

Fig. 189

SELECTION OF SYMBIOTA BY SCREENING MULTIPLE HOST-SYMBIONT ASSOCIATIONS

FIELD OF THE INVENTION

The present invention relates to new methods of selecting and breeding organisms, in particular organisms which exhibit symbiotic behaviour with symbionts such as fungal endophytes or epiphytes or bacterial microbiome in plants, and such as rumen microbiome in ruminant livestock, and to new organisms and symbiota developed thereby.

BACKGROUND OF THE INVENTION

The phenotype of many species of livestock, crops and pastures depends on the interaction between the genotype of the individual and the genotype of a symbiont. Important plants, including forage grasses, legumes, trees, shrubs, and vines are commonly found in association with endophytes including fungi, bacteria, viruses and microbes. Similarly, important animals, including cattle, sheep, pigs, goats, etc. have microbiomes present in their gut and rumen.

Both beneficial and detrimental horticultural, agronomic and veterinary properties result from such associations, including improved tolerance to water and nutrient stress and resistance to insect pests.

For example, ryegrass plants can show improved drought tolerance and persistency if a fungal endophyte of the correct genotype colonises the plant. Similarly, in grasses, insect resistance may be provided by specific metabolites produced by the endophyte, in particular loline alkaloids and peramine. Other metabolites produced by the fungal endophyte, for example lolitrems and ergot alkaloids, may be toxic to grazing animals and reduce herbivore feeding.

Considerable variation is known to exist in the metabolite profile of symbionts. For example, fungal endophyte strains that lack either or both of the animal toxins have been introduced into commercial ryegrass varieties.

Bacterial microbiomes also influence plant performance (e.g. in ryegrass, wheat).

In animals, the microorganisms present in the gut are responsible for digestion of an animal's feed. Ruminants host an extremely large and complex array of microorganisms in their rumen, and it is this microbial community which allow them to convert low quality forage into high quality protein and lipids for human consumption in the form of meat and milk. During this process methane, a potent greenhouse gas is produced. Rumen microbes-bovine symbiota may be important, for example, in improving feed conversion efficiency and reducing methane production. In ruminants, successful digestion of poor quality feed may depend on having a particular rumen microbiome profile. If it could be demonstrated that regions of the host genome are associated with differences in rumen microbial profile, then this could be exploited to breed cattle with lower methane emissions and improved feed conversion efficiency.

Molecular genetic markers such as simple sequence repeat (SSR) markers have been developed as diagnostic tests to distinguish between symbiont taxa and detect genetic variation within taxa. For example, the markers may be used to discriminate symbiont strains with different toxin profiles.

However, there remains a need for methods of identifying, isolating and/or characterising organisms which exhibit symbiotic behaviour with symbionts. Difficulties in artificially breeding of these symbiota limit their usefulness. For example, many of the novel endophytes known to be beneficial to pasture-based agriculture exhibit low inoculation frequencies and are less stable in elite germplasm.

Moreover, in traditional breeding techniques, for example in forage grasses such as perennial ryegrass and tall fescue, grass varieties are bred using classic cross-breeding techniques and grass genotypes are selected for their superior characteristics, after monitoring their performance over a period of multiple years. The selected grass genotypes that form the experimental variety are then inoculated with a single endophyte and the resulting grass-endophyte associations are evaluated for any favourable characteristics such as insect resistance. The individual experimental synthetic varieties deploying a single endophyte in them are then evaluated for agronomic performance and resulting animal performance by grazing animals over a period of years. This evaluation process may reveal that the single endophyte being deployed in the different experimental synthetic varieties may not show vegetative and/or intergenerational stability in some of these varieties or the desired alkaloid profile conferred by the single endophyte may vary between different synthetic varieties failing to confer appropriate levels of insect resistance or causing animal toxicoses. It would be a significant development in the art if this time-consuming process could be accelerated or otherwise improved.

It is accordingly an object of the present invention to overcome, or at least alleviate, one or more of the difficulties or deficiencies associated with the prior art.

SUMMARY OF THE INVENTION

Accordingly, in a first aspect of the present invention, there is provided a method for producing an improved organism including
  (i) providing a library of germplasm of an organism; and a library of symbionts;
  (ii) inoculating the germplasm library with one or more symbionts selected from the symbiont library to generate symbiota;
  (iii) breeding, selecting, screening and/or evaluating the inoculated germplasm or symbiota for desired symbiota characteristic(s); and
  (iv) subsequently identifying, culturing or otherwise using the symbiota exhibiting desired characteristic(s) to produce the improved organism.

By 'symbiotum' (or plural symbiota) is meant a supra-organism representing an association of organism with symbiont. For example, symbiota may be inoculated plant germplasm.

By 'library' is meant a resource, such as a collection of symbionts.

Applicants have established that it is possible to deploy multiple symbionts in multiple organisms and to select for improved symbiotic compatibility and performance early in the breeding process. That is symbiont-organism genotype combinations are bred and screened for desired characteristics including improved symbiota compatibility and performance ab initio. This may be contrasted with prior art techniques in which an organism host, e.g. a grass variety, would be bred and selected over a period of time after which symbiont inoculation would occur with a single symbiont late in the varietal development.

As used in this application, the term "organism" refers to a eukaryotic multicellular organism, including without limitation animals and plants. In particular embodiments, the animal may be a mammal or an avian. Of particular significance are mammalian animals of agricultural significance, such as cattle, sheep, pigs, goats and the like that harbour microbiomes in the gut or rumen. In particular embodiments, the organism is a plant, including without limitation monocots and dicots. Specific types of plants include, without limitation perennial grasses, legumes, decorative or fruit bearing trees, vines, shrubs and bushes, herbs, and decorative or edible flowers.

In a preferred embodiment of this aspect of the present invention, the organism may be a plant or animal and the symbiont(s) may be capable of forming symbiotic associations with the plant or animal. Preferably, the organism is a plant establishing symbiotic associations with endophytes.

By 'symbiont' is meant a microorganism that is associated with a multicellular organism.

By 'associated with' is meant that the symbiont lives on, in or in close proximity to the organism. For example, the symbiont may be a microorganism that lives within the body or cells of another organism or on or closely associated with the surface of the organism, for example a biofilm in close association with a plant. In the case of a plant the symbiont may be enodophytic, for example living within the internal tissues of the plant, or it may be epiphytic, for example growing externally on the plant.

The symbiont may be selected from one or more of fungi, viruses, bacteria and other microbes. For example, it may be an endophyte, such as a fungal or bacterial endophyte, an epiphyte, such as a fungal or bacterial epiphyte, a bacterial microbiome, or a mycorrhiza such as an arbuscular mycorrhiza.

Accordingly, in a preferred embodiment of the present invention, there is provided a method as described above wherein the organism is a plant, the method including:
(i) providing a library of plant germplasm; and
   a library of endophytes and/or epiphytes and/or plant-associated microbiomes;
(ii) inoculating the plant germplasm library with one or more endophytes and/or epiphytes and/or plant-associated microbiomes selected from the library to generate symbiota;
(iii) breeding, selecting, screening and/or evaluating the symbiota for desired symbiota characteristic(s); and
(iv) identifying, culturing or otherwise using the symbiota exhibiting desired characteristic(s) to produce the improved plant.

In a preferred embodiment, the method may be used to develop improved symbiota varieties exhibiting desired characteristic(s).

In a further aspect of the present invention there is provided a method of genomic selection of organism-symbiont associations, said method including
(i) providing a library of nucleic acid samples from said organism or said organism-symbiont association;
(ii) analysing said samples using metagenomics to obtain a genetic profile for each sample;
(iii) selecting organisms or organism-symbiont associations with a desired genetic and/or metabolic profile.

In a preferred embodiment, the method may include the preliminary steps of:
(i) providing an organism-symbiont association;
(ii) subjecting said organism-symbiont association to one or more environmental conditions; and
(iii) preparing a library of nucleic acid samples from each of the environmentally treated organism-symbiont associations.

In a preferred embodiment of this aspect of the present invention, the organism may be a plant or animal and the symbiont may be a bacterial microbiome.

In a preferred embodiment, the method may be used to develop improved symbiota varieties exhibiting desired characteristic(s).

The plant may be a grass, preferably a perennial grass, legume, vine, shrub, tree, herb, flower, shrub or bush. The method according to this aspect of the present invention is particularly applicable to grasses and legumes.

The endophyte may be a fungal or bacterial endophyte. The epiphyte may be a fungal or bacterial epiphyte. In a preferred embodiment, the library may be a bacterial microbiome.

In a preferred embodiment, the symbiont may be a fungal or bacterial endophyte, a fungal or bacterial epiphyte, or a bacterial microbiome.

By 'analysing said samples by metagenomics' is meant analysing genetic material recovered from the organism or organism-symbiont association, preferably directly from the organism or organism-symbiont association, so that largely unbiased samples of a significant proportion, preferably substantially all, genes from a significant proportion, preferably substantially all, of the members of the sampled association are analysed.

This analysis may involve detecting the presence or absence of polymorphic markers, such as simple sequence repeats (SSRs) or mating-type gene markers.

Alternatively, or in addition, this analysis may involve sequencing genomic and/or mitochondrial DNA and/or ribosomal RNA and performing sequence comparisons to databases of known nucleic acid sequences, for example 16S rRNA sequences which are indicative of bacterial genes.

The one or more environmental conditions to which said organism-symbiont association may be subjected include, but are not limited to, different nutritional conditions, such as nutrient stresses, eg. low nitrogen or phosphorus; and different light, temperature or water conditions, such as low light; cold stress or water stress, respectively.

In a preferred embodiment of the present invention, the symbiont(s) may include a genetic variation, to enhance stability of the symbiotum, abiotic stress tolerance (e.g. water stress) of the symbiotum, biotic stress tolerance (e.g. disease resistance) of the symbiotum, nutrient use efficiency. (e.g. phosphorus use efficiency, nitrogen use efficiency) of the symbiotum; and for example, for symbiont trait introgression in animals such as ruminant livestock species to enhance feed conversion efficiency of the symbiotum (i.e. ruminant livestock organism with its rumen microbiome) or to mitigate methanogenesis from the symbiotum.

The genetic variation may be introduced utilizing any standard techniques, e.g. via one or more of random mutagenesis, di/poly-ploidisation, targeted mutagenesis; cisgenesis; transgenesis; intragenesis.

The genetic analysis may be conducted as described above. The seedlings may for example be screened for bacterial 16S rRNA sequences.

The symbiota may be of any suitable form, including inoculated embryos, plant seeds, germinating seeds, seedlings, plantlets, plants, etc.

In a preferred form the nucleic acid samples may be extracted from the leaves of seedlings, more preferably from the epicotyl, hypocotyl or similar embryonic shoot of the seedlings. In grasses, the DNA/RNA may be extracted from tillers. In another preferred form the nucleic acid samples may be extracted from root samples. Alternatively, the nucleic acid samples may be extracted from whole germinating seeds or seedlings.

Preferably the nucleic acid samples are RNA samples, which may then be used to construct cDNA libraries.

The method according to this aspect of the present invention may further include subjecting the selected symbiota populations to phenotyping for assessment of symbiota performance and/or maintenance of desired characteristics; and selecting symbiota for generating a synthetic symbiota variety, for example by polycrossing.

For example, the selected symbiota variety may be subjected to an symbiont identification assay, followed by polycrossing to generate a next generation seed. Optionally, the above steps may be repeated to confirm symbiota stability, desired characteristics, symbiont identity and/or symbiont incidence in the next generation, for example the next seed generation.

Accordingly, in a further aspect of the present invention, there is provided improved symbiota including one or more organisms containing one or more symbionts produced utilising the method described above.

Accordingly, in a further aspect of the present invention, there is provided an improved organism exhibiting symbiota with an symbiont and produced utilising the method described above.

The improved organism may be a plant or animal.

Where the organism is a plant, the plant may be a grass, tree, flower, herb, shrub or bush, vine or legume, or a product thereof.

The plant material may be in the form of a seed, seedling, embryo or the like.

The method steps described above may be repeated to develop later generations of symbiota seeds, plants or animals.

In a further aspect, the present invention provides a plant, plant seed or other plant part derived from a seed or plant of the present invention and stably infected with and symbiont.

Preferably, the plant cell, plant, plant seed or other plant part is a grass, more preferably a forage, turf or bioenergy grass, such as those of the genera *Lolium* and *Festuca*, including *L. perenne* and *L. arundinaceum*, and of the genera *Brachiaria* and *Urochloa*, including *B. brizantha*, *B. decumbens*, *B. humidicola* and *U. mosambicensis*.

By 'plant cell' is meant any self-propagating cell bounded by a semi-permeable membrane and containing plastid. Such a cell also required a cell wall if further propagation is desired. Plant cell, as used herein includes, without limitation, seeds suspension cultures, embryos, meristematic regions, callus tissue, leaves, roots, shoots, gametophytes, sporophytes, pollen and microspores.

A large scale endophyte discovery program has been undertaken to establish the library of fungal endophyte strains. A collection of perennial ryegrass and tall fescue accessions has been established.

The endophytes selected to inoculate the plant germplasm may be selected utilising the techniques described in an Australian provisional patent application filed 1 Jun. 2012 entitled "Novel Endophytes", the entire disclosure of which is incorporated herein by reference. The novel endophytes described therein are particularly preferred.

Genetic analysis of endophytes in these accessions has led to the identification of a number of novel endophyte strains. These novel endophyte strains are genetically distinct from known endophyte strains. Metabolic profiling may be undertaken to determine the toxin profile of these strains.

Specific detection of endophytes in planta with SSR markers may be used to confirm the presence and identity of endophyte strains artificially inoculated into, for example, grass plants, varieties and cultivars.

In the screening step (iii) according to the method of this aspect of the present invention, the inoculated germplasm may be screed by genetic analysis and/or metabolic profiling. For example, techniques of genetic analysis described in the Australian provisional patent application entitled "Novel Endophytes" may be used.

Alternatively, or in addition, the inoculated germplasm may be subjected to genetic analysis (genetically characterised) to demonstrate genetic distinction from known symbiont-genotype symbiota and to confirm the identity of symbiont strains artificially inoculated into, for example, grass plants, varieties and cultivars.

By 'genetic analysis' is meant analysing the nuclear and/or mitochondrial DNA of the symbiont.

This analysis may involve detecting the presence or absence of polymorphic markers, such as simple sequence repeats (SSRs) or mating-type markers. SSRs, also called microsatellites, are based on a 1-7 nucleotide core element, more typically a 1-4 nucleotide core element, that is tandemly repeated. The SSR array is embedded in complex flanking DNA sequences. Microsatellites are thought to arise due to the property of replication slippage, in which the DNA polymerase enzyme pauses and briefly slips in terms of its template, so that short adjacent sequences are repeated. Some sequence motifs are more slip-prone than others, giving rise to variations in the relative numbers of SSR loci based on different motif types. Once duplicated, the SSR array may further expand (or contract) due to further slippage and/or unequal sister chromatid exchange. The total number of SSR sites is high, such that in principle such loci are capable of providing tags for any linked gene.

SSRs are highly polymorphic due to variation in repeat number and are co-dominantly inherited. Their detection is based on the polymerase chain reaction (PCR), requiring only small amounts of DNA and suitable for automation. They are ubiquitous in eukaryotic genomes, including fungal and plant genomes, and have been found to occur every 21 to 65 kb in plant genomes. Consequently, SSRs are ideal markers for a broad range of applications such as genetic diversity analysis, genotypic identification, genome mapping, trait mapping and marker-assisted selection.

Known SSR markers which may be used to investigate endophyte diversity in perennial ryegrass are described in van Zijll de Jong et al (2003).

Alternatively, or in addition, the genetic analysis may involve sequencing genomic and/or mitochondrial DNA and performing sequence comparisons to assess genetic variation between symbionts.

The inoculated germplasm or organism-symbiont association may be subjected to metabolic analysis to identify the presence of desired metabolic traits.

By 'metabolic analysis' is meant analysing metabolites, in particular toxins, produced by the symbionts. Preferably, this is done by generation of inoculated plants for each of the symbionts and measurement of eg. toxin levels, resistance to pests and/or diseases, or tolerance to water and/or nutrient stress in planta. More preferably, this is done by generation of isogenically inoculated plants for each of the endophytes and measurement of toxin levels in planta.

By a 'desired genetic and metabolic profile' is meant that the symbiont possesses genetic and/or metabolic characteristics that result in a beneficial phenotype in an organism harbouring, or otherwise associated with, the symbiont.

Such beneficial properties include improved tolerance to water and/or nutrient stress, improved resistance to pests and/or diseases, enhanced biotic stress tolerance, enhanced drought tolerance, enhanced water use efficiency, enhanced tolerance to extremes of temperature, reduced toxicity, enhanced nutrient availability and enhanced vigour in, for example, a plant with which the symbiont is associated, relative to a control plant lacking the symbiont or containing a control symbiont such as standard toxic (ST) endophyte.

Such beneficial properties also include reduced toxicity of the associated plant to grazing animals.

For example, tolerance to water and/or nutrient stress may be increased by at least approximately 5%, more preferably at least approximately 10%, more preferably at least approximately 25%, more preferably at least approximately 50%, more preferably at least approximately 100%, relative to a control symbiont such as ST endophyte or to a no symbiont control plant. Preferably, tolerance to water and/or nutrient stress may be increased by between approximately 5% and approximately 50%, more preferably between approximately 10% and approximately 25%, relative to a control symbiont such as ST endophyte or to a no symbiont control plant.

For example, plant resistance to pests and/or diseases may be increased by at least approximately 5%, more preferably at least approximately 10%, more preferably at least approximately 25%, more preferably at least approximately 50%, more preferably at least approximately 100%, relative to a control plant. Preferably, plant resistance to diseases and/or pests may be increased by between approximately 5% and approximately 50%, more preferably between approximately 10% and approximately 25%, relative to a control plant.

For example, water use efficiency and/or plant vigour may be increased by at least approximately 5%, more preferably at least approximately 10%, more preferably at least approximately 25%, more preferably at least approximately 50%, more preferably at least approximately 100%, relative to a control symbiont such as ST endophyte or to a no symbiont control plant. Preferably, tolerance to water and/or nutrient stress may be increased by between approximately 5% and approximately 50%, more preferably between approximately 10% and approximately 25%, relative to a control symbiont such as ST endophyte or to a no symbiont control plant.

For example, toxicity may be reduced by at least approximately 5%, more preferably at least approximately 10%, more preferably at least approximately 25%, more preferably at least approximately 50%, more preferably at least approximately 100%, relative to a control symbiont such as ST endophyte or a no symbiont control plant. Preferably, toxicity may be reduced by between approximately 5% and approximately 100%, more preferably between approximately 50% and approximately 100% relative to a control symbiont such as ST endophyte or a no symbiont control plant.

In a preferred embodiment toxicity may be reduced to a negligible amount or substantially zero toxicity.

In a preferred embodiment, the endophyte may exhibit a desired toxin profile.

Preferably the endophyte is isolated from a fescue species, preferably tall fescue.

Preferably, the endophyte is of the genus *Neotyphodium*, more preferably it is from a species selected from the group consisting of *N uncinatum, N coenophialum* and *N lolii*, most preferably *N coenophialum*. The endophyte may also be from the genus *Epichloe*, including *E typhina, E baconii* and *E festucae*. The endophyte may also be of the non-*Epichloe* out-group. The endophyte may also be from a species selected from the group consisting of FaTG-3 and FaTG-3 like, and FaTG-2 and FaTG-2 like.

The endophyte may also be from the genus *Acremonium*, including *A. implicatum* and endophytes from *Brachiaria*-*Urochloa* grasses as described in Australian patent application No. 2011902393 entitled "Fungi and associated methods", to the present applicant, the entire disclosure of which is incorporated herein by reference.

By a 'desired toxin profile' is meant that the symbiont produces significantly less toxic compounds and/or significantly more beneficial compounds than a control organism.

For example in the case of plants, the endophyte may produce significantly less toxic alkaloids, such as ergovaline, compared with a plant inoculated with a control endophyte such as standard toxic (ST) endophyte; and/or significantly more alkaloids conferring beneficial properties such as improved tolerance to water and/or nutrient stress and improved resistance to pests and/or diseases in the plant with which the endophyte is associated, such as peramine, N-formylloline, N-acetylloline and norloline, again when compared with a plant inoculated with a control endophyte such as ST or with a no endophyte control plant.

In a particularly preferred embodiment, the endophyte maybe selected from the group consisting of E1, NEA10, NEA11 and NEA12, which were deposited at The National Measurement Institute, 1/153 Bertie Street, Port Melbourne, Victoria, Australia, 3207, on 5 Jan. 2010 with accession numbers V10/000001, V10/000002, V10/000003 and V10/000004, respectively, and are described in International patent application PCT/AU2011/000020, the entire disclosure of which is incorporated herein by reference. Replacement deposits were made on Apr. 15, 2016 in response to a notification of non-viability, and were assigned the same accession numbers. A replacement deposit for NEA12 was made on Sep. 3, 2019 in response to a notificatoin of non-viability, and was assigned the same accession number.

In a particularly preferred embodiment, the endophyte may be selected from the group consisting of NEA16, NEA17, NEA18, NEA19, NEA20, NEA21 and NEA23, which were deposited at The National Measurement Institute, 1/153 Bertie Street, Port Melbourne, Victoria, Australia, 3207, on 3 Apr. 2012 with accession numbers V12/001413, V12/001414, V12/001415, V12/001416, V12/001417, V12/001418 and V12/001419, respectively, and are described in an Australian patent application filed 1 Jun. 2012 entitled 'Novel endophytes', to the present applicant, the entire disclosure of which is incorporated herein by reference. Replacement deposits were made on Apr. 15, 2016 in response to a notification of non-viability, and were assigned the same accession numbers.

In a particularly preferred embodiment, the endophyte may be selected from the group consisting of *Acremonium* 1.1.A (1.1A), 3.3.A (3.3A), 5.1.B (5.1B), 9.2.A (9.2A) and 12.1.A (12.1A), which were deposited at The National Measurement Institute, 1/153 Bertie Street, Port Melbourne, Victoria, Australia, 3207, on 15 Jun. 2011 with accession numbers V11/011370, V11/011371, V11/011372, V11/011373, and V11/011374, respectively, which are described in Australian patent application No. 2011902393 entitled "Fungi and associated methods", to the present applicant, the entire disclosure of which is incorporated herein by reference. Replacement deposits were made on Apr. 15, 2016 in response to a notification of non-viability, and were assigned the same accession numbers.

Such endophytes may have a desired toxin profile as hereinbefore described.

In a preferred embodiment of the present invention, the symbiont(s) may include a genetic variation, for example, for endophyte trait introgression in plants such as grasses to enhance vegetative stability of the symbiotum, intergenerational stability of the symbiotum, abiotic stress tolerance (e.g. water stress) of the symbiotum, biotic stress tolerance (e.g. disease resistance) of the symbiotum, nutrient use efficiency (e.g. phosphorus use efficiency, nitrogen use efficiency) of the symbiotum; and for example, for symbiont trait introgression in animals such as ruminant livestock species to enhance feed conversion efficiency of the symbiotum (i.e. ruminant livestock organism with its rumen microbiome) or to mitigate methanogenesis from the symbiotum.

The genetic variation may be introduced utilizing any standard techniques, e.g. via one or more of random mutagenesis, di/poly-ploidisation, targeted mutagenesis; cisgenesis; transgenesis; intragenesis.

In a preferred embodiment, the endophyte(s) may be endophyte variants as described in an Australian patent application filed 1 Jun. 2012 entitled "Designer Endophytes", the entire disclosure of which is incorporated herein by reference.

In a particularly preferred embodiment, the endophyte may be selected from the group consisting of an endophyte variant selected from the group consisting of NEA12dh5, NEA12dh6, NEA12dh13, NEA12dh14, and NEA12dh17, which were deposited at The National Measurement Institute on 3 Apr. 2012 with accession numbers V12/001408, V12/001409, V121001410, V12/001411 and V12/001412, respectively.

Such endophytes may have a desired toxin profile as hereinbefore described.

Preferably, the organism is inoculated with the symbiont by a method selected from the group consisting of infection, breeding, crossing, hybridization and combinations thereof.

In one embodiment, the plant may be inoculated by isogenic inoculation. This has the advantage that phenotypic effects of endophytes may be assessed in the absence of host-specific genetic effects. More particularly, multiple inoculations of endophytes may be made in plant germplasm, and plantlets regenerated in culture before transfer to soil or other growth medium.

In another embodiment, a library of plant germplasm may be inoculated with multiple endophytes. This has the advantage of enabling favourable host-endophyte associations to be identified.

The identification of an endophyte of the opposite mating-type that is highly compatible and stable in planta provides a means for molecular breeding of endophytes for perennial ryegrass. Preferably the plant may be infected by hyper-inoculation.

Hyphal fusion between endophyte strains of the opposite mating-type provides a means for delivery of favourable traits into the host plant, preferably via hyper-inoculation. Such strains are preferably selected from the group including an endophyte strain that exhibits the favourable characteristics of high inoculation frequency and high compatibility with a wide range of germplasm, preferably elite perennial ryegrass and/or tall fescue host germplasm and an endophyte that exhibits a low inoculation frequency and low compatibility, but has a highly favourable alkaloid toxin profile.

The endophyte-infected plants may be cultured by known techniques. The person skilled in the art can readily determine appropriate culture conditions depending on the plant to be cultured.

The screening step (iii) may include analysing plant metabolites. The metabolites may be analysed by known techniques such as chromatographic techniques or mass spectrometry, for example LCMS or HPLC. In a particularly preferred embodiment, endophyte-infected plants may be analysed by reverse phase liquid chromatography mass spectrometry (LCMS). This reverse phase method may allow analysis of specific metabolites (including lolines, peramine, ergovaline, lolitrem, and janthitrems, such as janthitrem I, janthitrem G and janthitem F) in one LCMS chromatographic run from a single endophyte-infected plant extract.

In a particularly preferred embodiment, the endophytes may be selected from the group consisting of consisting of NEA2, NEA3, NEA6, NEA10, NEA11, NEA12, E1, NEA17, NEA21, NEA23, NEA18, NEA19, NEA16, NEA20, NEA12dh5, NEA12dh6, NEA12dh13, NEA12dh14, NEA12dh17, NEA12-DsRed and IRM1-35.

In another particularly preferred embodiment, LCMS including EIC (extracted ion chromatogram) analysis may allow detection of the alkaloid metabolites from small quantities of endophyte-infected plant material. Metabolite identity may be confirmed by comparison of retention time with that of pure toxins or extracts of endophyte-infected plants with a known toxin profile analysed under substantially the same conditions and/or by comparison of mass fragmentation patterns, for example generated.

As stated above, in the method according to this aspect of the present invention, the organism selected may be a plant or animal, preferably a plant. Where the organism is a plant, the plant germplasm may be present as an embryo and the embryo may be treated to form an artificial seed.

Accordingly, in a preferred embodiment there is provided a method for preparing artificial seeds which method includes:
   providing a source of plant seeds;
   subjecting the seed(s) to a surface-sterilisation step;
   isolating seed embryo(s) from the surface-sterilised seed(s); and
   coating the embryo(s) with a coating to form artificial seed(s).

The artificial seeds may be prepared utilising the techniques described in Australian provisional patent applications filed 1 Jun. 2012 and 7 Sep. 2012 entitled "Method for large scale generation of symbiota", the entire disclosures of which are incorporated herein by reference.

The seeds may be from any suitable plant. The plant may be a grass, preferably a perennial grass, legume, vine, shrub, tree, herb, flower, shrub or bush. The method according to this aspect of the present invention is particularly applicable to grasses and legumes.

The seeds may be surface-sterilised by any suitable technique. Preferably the seeds are sterilised by treating them with an acid such as hydrochloric acid and bleach, such as sodium hypochlorite. Preferably the acid and bleach treatments are performed sequentially. The acid treatment may be for a period of from 1 hour to 24 hours, preferably overnight. The bleach treatment may be for a period of 5 minutes to 1 hour, preferably approximately 20 minutes. The bleach treatment may be performed twice on successive days, with the seeds being washed after each treatment, for example using sterile distilled water, and stored at approximately 4 to 30° C., preferably approximately 24° C.

Embryos may be isolated from the treated seeds by techniques known to those skilled in the art.

In a preferred embodiment, the embryos may be treated to create one or more points of entry for the symbiont, eg. endophyte. For example, the embryo may be punctured or its surface otherwise damaged, for example by scratching or etching, to facilitate entry of the symbiont. In a particularly preferred embodiment, a hypodermic needle or similar may be used to create singly or multiple puncture holes in the surface of the embryo.

The coating may be of any suitable type to encapsulate the embryo, including alginate, agar, polyco 2133, carboxy methyl cellulose, carrageenan, gelrite, guargum, sodium pectate, tragacanth gum and the like. In a preferred embodiment the coating is alginate, more particularly calcium alginate.

In a preferred embodiment, the embryos may be mixed with the coating and drops of coating containing individual embryos placed in a polymerising solution such as calcium chloride solution, preferably while stirring, to form artificial seeds. Artificial seeds may be collected following approximately 1-60 minutes stirring, preferably after approximately 15 minutes stirring.

In a preferred embodiment the embryos may be inoculated with a symbiont such as a fungal endophyte prior to coating. In a preferred form, the embryos may be directly inoculated with endophyte mycelium.

Alternatively, in a particularly preferred embodiment, isolated embryos may be coated with a symbiont-containing coating layer, such as a fungal endophyte-containing coating layer.

In this embodiment, the inoculation step may include:
providing a source of seed embryos;
inoculating the embryos with one or more symbionts such as fungal endophytes; and
coating the inoculated embryo(s) with a coating to form artificial seed(s).
Alternatively, the inoculation step may include:
providing a source of seed embryos; and
coating the embryos with a coating containing symbionts such as fungal endophytes to form artificial seed(s).

In a preferred embodiment the seeds may be double coated. Preferably the second coating layer is alginate, more preferably calcium alginate, even more preferably coloured calcium alginate. In a preferred embodiment, the artificial seeds with the first coating layer may be air dried prior to coating with the second layer.

In a preferred embodiment, the method may further include coating the artificial seeds with a second coating layer, said second coating layer preferably containing added nutrients suitable for sustaining the embryo and/or symbiont.

Alternatively, the second coating layer may not contain added nutrients, this nutrient deprived layer being designed to eg. reduce endophyte out-growth during germination and restrict endophyte growth in close proximity to the embryo.

In a preferred embodiment the method may further include
growing the artificial seeds to form plantlets or seedlings; and
screening the plantlets or seedlings for symbiont presence such as fungal endophyte presence.

The step of growing the artificial seeds may be undertaken using any suitable growth medium. A germination medium such as MS (Murashige and Skoog), modified MS or MS+BAP (6-benzylamino purine) is particularly preferred.

The genetic analysis may be conducted as described above. The seedlings may for example be screened for symbiont-specific, eg. endophyte-specific simple sequence repeats (SSRs).

Alternatively, or in addition, the seedlings may be screened for the presence of favourable symbiota via molecular phenotyping. The molecular phenotyping may be performed utilising the methods described in an Australian provisional patent application filed 1 Jun. 2012 entitled "Molecular phenotyping method", the entire disclosure of which is incorporated herein by reference.

In this method seedlings may be screened for the presence of favourable symbiota via molecular phenotyping. The seedlings may, for example, be assessed for improved alkaloid production and/or improved water soluble carbohydrate:protein ratio. Such techniques may utilise an enzymatic assay, colorimetric assay, SSR markers and/or metabolomics analysis. Such analyses may be semi- or substantially fully automated.

Thus the method may include screening symbiota for the presence of desirable characteristics, said method including molecular phenotyping a population of symbiota.

In a preferred embodiment, the method may include assessing the population of symbiota for alkaloid production and/or water soluble carbohydrate (WSC):protein ratio. Preferably this assessment is done using one or more methods selected from the group consisting of enzymatic assays, colorimetric assays, SSR markers and metabolomic analysis.

In a preferred embodiment, assessment of alkaloid production includes measurement of alkaloid profile and/or content in the population. Preferred alkaloids include peramine, lolitrem B and ergovaline. In a preferred embodiment, alkaloids may be inferred by SSR markers and detected by metabolomic analysis, more preferably a combination of SSR marker and metabolomic analysis are used.

In another preferred embodiment, WSC:protein ratio may be assessed. WSC may be quantified using an enzymatic assay. In a preferred embodiment, individual concentrations for sucrose, glucose, fructose and fructans may be determined. Protein may be quantified using a colorimetric assay.

In a particularly preferred embodiment, protein may be quantified by a method including:
extracting proteins from the symbiota using an alkali, such as NaOH, preferably a weak NaOH solution;
quantification of proteins using a colorimetric assay, such as a Bradford assay.
Detection may be carried out, for example, using a plate reader.

The symbiota may be of any suitable form, including inoculated embryos, plant seeds, germinating seeds, seedlings, plantlets, plants, etc.

Preferably the seeds are derived from endophyte-infected plants i.e. plant/endophyte symbiota.

In the method according to this aspect of the present invention, the screening step (iii) may include screening artificial seeds by accelerated ageing, which is described in an Australian patent application filed 1 Jun. 2012 entitled 'Method for selection of stable symbiota', the entire disclosure of which is incorporated herein by reference.

Accordingly, the present invention provides a method of assessing the compatibility and/or stability of a plant/endophyte symbiota, said method including:
providing a source of seeds including symbiont such as fungal endophyte inoculated plant embryos;
screening the seeds and/or their offspring for compatibility and/or stability of the plant/symbiont association (i.e. symbiota) such as plant-fungal endophyte symbiota by applying accelerated ageing thereto.

In the accelerated ageing procedure, the seeds, or their offspring, may be subjected to deteriorative conditions, preferably by means of high temperature and/or increased moisture content. In a particularly preferred embodiment the seeds may be exposed to an environment of high relative humidity. For example, the seeds may be exposed to temperatures of approximately −20 to 50° C., preferably 10 to 45° C., more preferably 15 to 40° C., even more preferably 25 to 40° C. and/or to humidity levels of approximately 60% to 100%, preferably 80% to 100% for periods of e.g. approximately 1 to 30 days, preferably 2 to 10 days, more preferably 4 to 7 days.

Accelerated ageing reduces endophyte viability i.e. it allows counter-selection of unstable associations and permits the ranking of symbiota based on their stability.

Preferably the method includes the further step of subjecting the selected symbiota populations to a rapid symbiont, such as fungal. endophyte viability assay.

Accordingly, the method of the present invention may further include assessing the compatibility and/or stability of a plant/symbiont association (i.e. symbiotum) such as plant-fungal endophyte symbiota including
    providing a source of seeds including symbiont, eg. fungal endophyte inoculated plant embryos;
    screening the seeds and/or their offspring for compatibility and/or stability of the plant/symbiont association (i.e. symbiotum) such as plant-fungal endophyte symbiota by applying accelerated ageing thereto; and
    subjecting the selected symbiota populations to a rapid symbiont such as fungal endophyte viability assay.

The viability assay step according to this aspect of the present invention may include:
    culturing the seeds to generate plantlets, seedlings or germinating seeds;
    extracting DNA and/or RNA from the plantlets, seedlings or germinating seeds; and
    subjecting the extracted DNA and/or RNA to an assay for in plants expressed symbiont-specific gene(s) such as fungal endophyte-specific gene(s).

Preferably the seeds are derived from symbiont-inoculated plants such as fungal endophyte-inoculated plants.

Preferably the seeds are artificial seeds, as hereinbefore described.

The rapid endophyte viability assay is described in an Australian patent application filed 1 Jun. 2012 entitled 'Method for rapid endophyte viability assessment', the entire disclosure of which is incorporated herein by reference.

The method for rapid endophyte viability assessment includes: culturing the seeds to generate plantlets, seedlings or germinating seeds; extracting DNA and/or RNA from the plantlets, seedlings or germinating seeds; and subjecting the extracted DNA and/or RNA to an assay for in planta expressed endophyte-specific gene(s).

Preferably the seeds are cultured for a relatively short period of time such as 1 to 10 days, so that a rapid assessment of endophyte viability may be obtained. Endophyte specific genes are expressed in this time frame, enabling early in planta endophyte viability assessment.

Preferably the seeds are cultured for a relatively short period of time, so that a rapid assessment of symbiont viability such as fungal endophyte viability may be obtained.

Preferably the seeds are cultured for approximately 1 to 10 days, more preferably 3 to 10 days, more preferably 3 to 7 days, more preferably 3 to 5 days.

Applicants have found that endophyte specific genes are expressed in this time frame, enabling early in planta endophyte viability assessment.

In a preferred form the DNA/RNA may be extracted from the leaves of seedlings, more preferably from the epicotyl, hypocotyl or similar embryonic shoot of the seedlings. In grasses, the DNA/RNA may be extracted from tillers. In another preferred form the DNA/RNA may be extracted from whole germinating seeds.

Preferably the RNA and DNA may be co-extracted, preferably in a single step. Preferably, the DNA/RNA may be extracted from 1 to 10 day-old, preferably 3 to 10 day old, more preferably 3 to 7 day old, more preferably 3 to 5 day-old epicotyls, hypocotyls or similar embryonic shoots of seedlings, in order to accelerate the process.

The assay may be an assay used to amplify and simultaneously quantify a targeted DNA/RNA molecule in the extracted DNA/RNA. Preferably the assay is a quantitative real-time polymerase chain reaction (Q-PCR/qRT-PCR) assay, or kinetic polymerase chain reaction (KPCR) assay. In a particularly preferred form, the assay may be a TaqMan or similar assay.

The endophyte specific genes may be of any suitable type. Preferably it is only, mainly or highly expressed in planta. Genes encoding the proteins 7490, 8263, 0005 and 2232 are particularly preferred.

Primers are designed for amplification of the targeted gene(s) by methods known to those skilled in the art.

The seeds may be from any suitable plant. The plant may be a grass, preferably a perennial grass, legume, vine, shrub, tree, herb, flower, shrub or bush. The method according to this aspect of the present invention is particularly applicable to grasses and legumes.

Preferably the seeds are derived from symbiont eg. endophyte-infected plants eg. plant/endophyte symbiota.

Preferably the seeds are artificial seeds.

The method according to this aspect of the present invention may further include subjecting the selected symbiota populations to phenotyping for assessment of symbiota performance and/or maintenance of desired characteristics; and selecting symbiota for generating a synthetic symbiota variety, for example by polycrossing.

For example, the selected symbiota variety may be subjected to an symbiont identification assay, followed by polycrossing to generate a next generation seed. Optionally, the above steps may be repeated to confirm symbiota stability, desired characteristics, symbiont, eg. Fungal endophyte identity and/or symbiont, eg. Fungal endophyte incidence in the next generation, for example the next seed generation.

Accordingly, in a further aspect of the present invention, there is provided improved symbiota including one or more organisms containing one or more symbionts produced utilising the method described above.

Accordingly, in a further aspect of the present invention, there is provided an improved organism exhibiting symbiota with an symbiont and produced utilising the method described above.

The improved organism may be a plant or animal.

Where the organism is a plant, the plant may be a grass, tree, flower, herb, shrub or bush, vine or legume, or a product thereof.

The plant material may be in the form of a seed, seedling, embryo or the like.

The method steps described above may be repeated to develop later generations of symbiota seeds, plants or animals.

In a further aspect, the present invention provides a plant, plant seed or other plant part derived from a seed or plant of the present invention and stably infected with a symbiont, eg. an endophyte.

Preferably, the plant cell, plant, plant seed or other plant part is a grass, more preferably a forage, turf or bioenergy grass, such as those of the genera *Lolium* and *Festuca*, including *L. perenne* and *L. arundinaceum*, and of the genera *Brachiaria* and *Urochloa*, including *B. brizantha*, *B. decumbens*, *B. humidicola* and *U. mosambicensis*.

By 'plant cell' is meant any self-propagating cell bounded by a semi-permeable membrane and containing plastid. Such a cell also required a cell wall if further propagation is desired. Plant cell, as used herein includes, without limitation, seeds suspension cultures, embryos, meristematic regions, callus tissue, leaves, roots, shoots, gametophytes, sporophytes, pollen and microspores.

In an alternative embodiment of the present invention the organism may be an animal, preferably selected from cattle, sheep, goats, deer or the like.

Accordingly, in a preferred embodiment of the present invention, there is provided a method as described above wherein the organism is an animal, the method including:
  (i) providing a library of animal germplasm; and
    a library of symbionts;
  (ii) inoculating the animal germplasm library with one or more symbionts selected from the symbiont library to generate symbiota;
  (iii) breeding, selecting, screening and/or evaluating the symbiota for desired symbiota characteristic(s); and
  (iv) identifying, culturing or otherwise using the symbiota exhibiting desired characteristic(s) to produce the improved animal.

In a further aspect of the present invention, there is provided a method of mapping regions of a host organism's genome that affect rumen microbial profile in the organism, said method including
  (i) providing a library of polymorphisms of the host genome;
  (ii) identifying the effect on rumen microbiome profile of the polymorphisms by carrying out an association study; and
  (iii) identifying one or more regions of the host genome that affect rumen microbial profile in the organism.

In a preferred embodiment, the organism may be a cow.

In a further aspect, the present invention includes identifying and/or cloning nucleic acids including genes encoding polypeptides or transcription factors from the genomes of the symbionts.

Methods for identifying and/or cloning nucleic acids encoding such genes are known to those skilled in the art and include creating nucleic acid libraries, such as cDNA or genomic libraries, and screening such libraries, for example using probes for genes of the desired type; or mutating the genome of the symbiont of the present invention, for example using chemical or transposon mutagenesis, identifying changes in the production of polypeptides or transcription factors of interest, and thus identifying genes encoding such polypeptides or transcription factors.

Thus, in a further aspect of the present invention, there is provided a substantially purified or isolated nucleic acid encoding a polypeptide or transcription factor from the genome of an symbiont of the present invention.

By 'nucleic acid' is meant a chain of nucleotides capable of carrying genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a 'nucleic acid encoding a polypeptide or transcription factor' is meant a nucleic acid encoding an enzyme or transcription factor normally present in an symbiont of the present invention.

The present invention encompasses functionally active fragments and variants of the nucleic acids of the present invention. By 'functionally active' in relation to the nucleic acid is meant that the fragment or variant (such as an analogue, derivative or mutant) is capable of manipulating the function of the encoded polypeptide, for example by being translated into an enzyme or transcription factor that is able to catalyse or regulate a step involved in the relevant pathway, or otherwise regulate the pathway in the symbiont. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

Preferably the fragment has a size of at least 20 nucleotides, more preferably at least 50 nucleotides, more preferably at least 100 nucleotides.

Preferably, said fragments are able to produce the same activity as the original gene when expressed. Preferably, said fragments that maintain conserved regions within consensus sequences.

Preferably said variants are variants of the specified sequences that provide either conserved substitution, or limited modifications in consensus sequences to a level, for example, of no more than approximately 5%, more preferably no more than 1%.

For example, fragments and variants of a sequence encoding X may include a wild type sequence from species Z that encodes X, a fragment of a wild type sequence wherein the fragment encodes X, and that retains conserved regions within consensus sequences from species Z, and variants of the wild type sequence or fragments which encode X activity and have only conservative substitutions, a variant X' that encodes X activity and in which sequence differs only by substitutions found in one or more contributing sequences used in formulating the consensus sequence, or a variant X" that encodes X activity in which the variant has not more than approximately 95% amino acid variation, more preferably not more than approximately 99% amino acid variation from the wild type sequence or fragment.

By 'conservative nucleic acid changes' or 'conserved substitution' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met, Phe, Trp
Uncharged polar: Gly, Ser, Thr, Cys, Tyr, Asn, Gln
Acidic: Asp, Glu
Basic: Lys, Arg, His
Other conservative amino acid substitutions may also be made as follows:
Aromatic: Phe, Tyr, His
Proton Donor: Asn, Gln, Lys, Arg, His, Trp
Proton Acceptor: Glu, Asp, Thr, Ser, Tyr, Asn, Gln In a further aspect of the present invention, there is provided a genetic construct including a nucleic acid according to the present invention.

By 'genetic construct' is meant a recombinant, nucleic acid molecule.

In a preferred embodiment, the genetic construct according to the present invention may be a vector.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the target cell.

In a preferred embodiment of this aspect of the invention, the genetic construct may further include a promoter and a terminator; said promoter, gene and terminator being operatively linked.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'→5' direction along the nucleic acid.

The promoter and terminator may be of any suitable type and may be endogenous to the target cell or may be exogenous, provided that they are functional in the target cell.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV)35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns, antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes [such as beta-glucuronidase (GUS) gene (gusA) and the green fluorescent protein (GFP) gene (gfp)]. The genetic construct may also contain a ribosome binding site for translation initiation. The genetic construct may also include appropriate sequences for amplifying expression.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated.

By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (eg. a cDNA or a genomic or cDNA fragment produced by PCR or restriction endonuclease digestion) independent of other sequences. It also includes a genetic construct which is part of a hybrid gene encoding additional polypeptide sequence.

Preferably, the substantially purified genetic construct is at least approximately 90% pure, more preferably at least approximately 95% pure, even more preferably at least approximately 98% pure.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

The genetic constructs of the present invention may be introduced into organisms, for example plants, animals, microorganisms or fungi by any suitable technique. Techniques for incorporating the genetic constructs of the present invention into plant cells or fungal cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant or fungus to be transformed, and may be readily determined by an appropriately skilled person. For transformation of protoplasts, PEG-mediated transformation is particularly preferred. For transformation of fungi PEG-mediated transformation and electroporation of protoplasts and *Agrobacterium*-mediated transformation of hyphal explants are particularly preferred.

Cells incorporating the genetic constructs of the present invention may be selected, as described below, and then cultured in an appropriate medium to regenerate transformed plants or fungi, using techniques well known in the art. The culture conditions, such as temperature, pH and the like, will be apparent to the person skilled in the art. The resulting plants or fungi may be reproduced, either sexually or asexually, using methods well known in the art, to produce successive generations of transformed plants or fungi.

As used herein, except where the context requires otherwise, the term "comprise" and variations of the term, such as "comprising", "comprises" and "comprised", are not intended to exclude further additives, components, integers or steps.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

DETAILED DESCRIPTION OF THE EMBODIMENTS

Figure 23A:
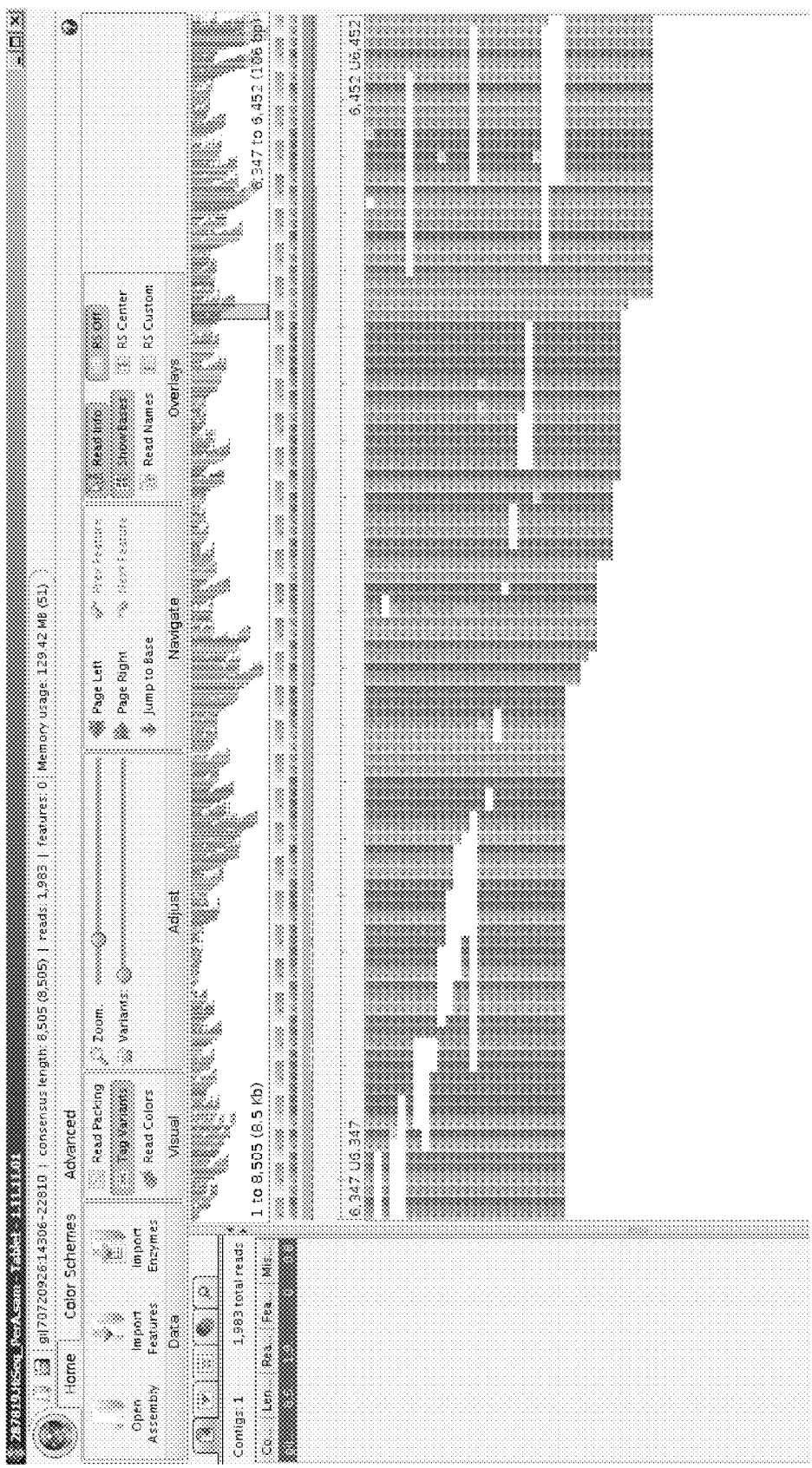
Figure 23B:
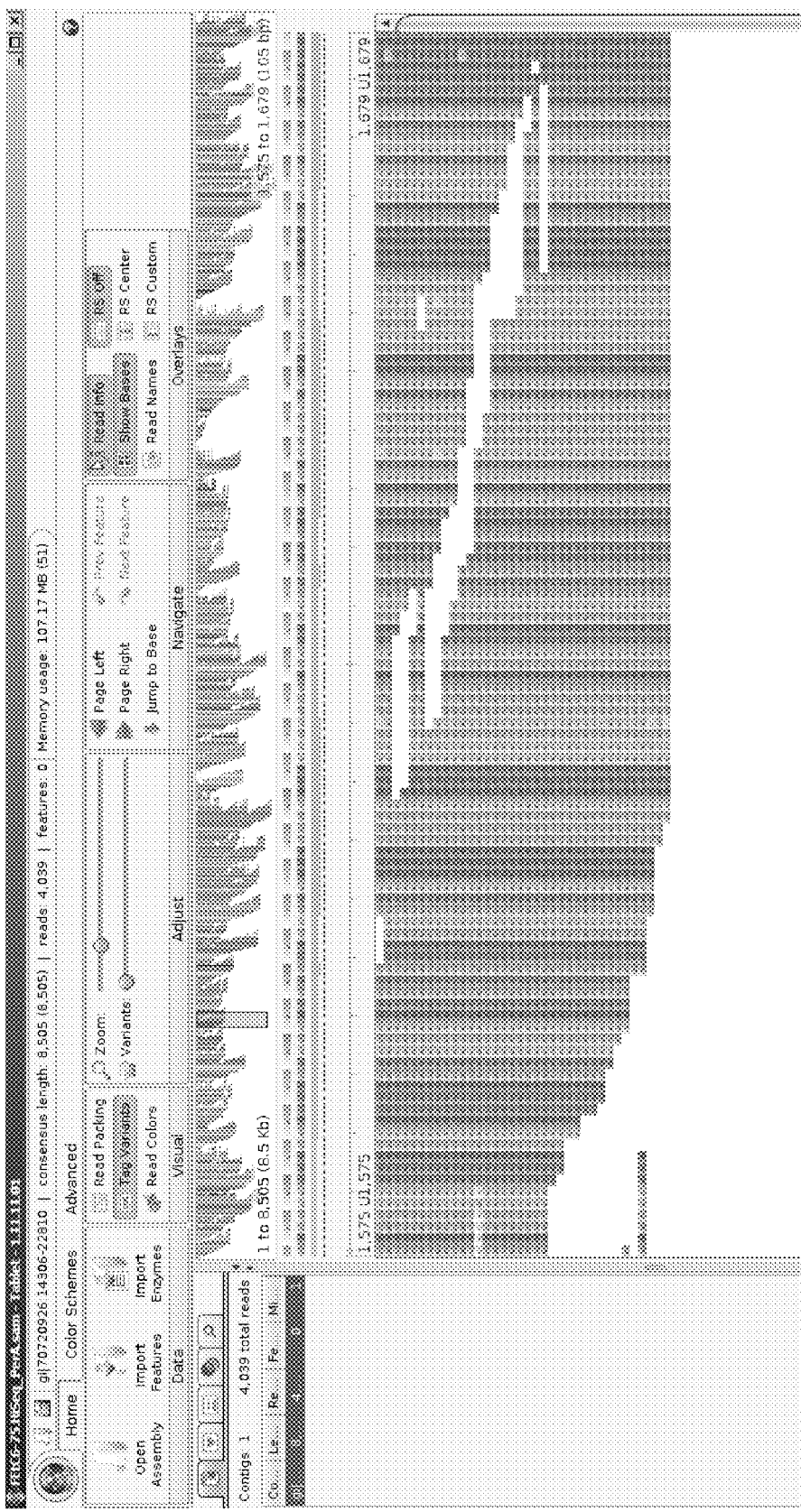
Figure 23C:
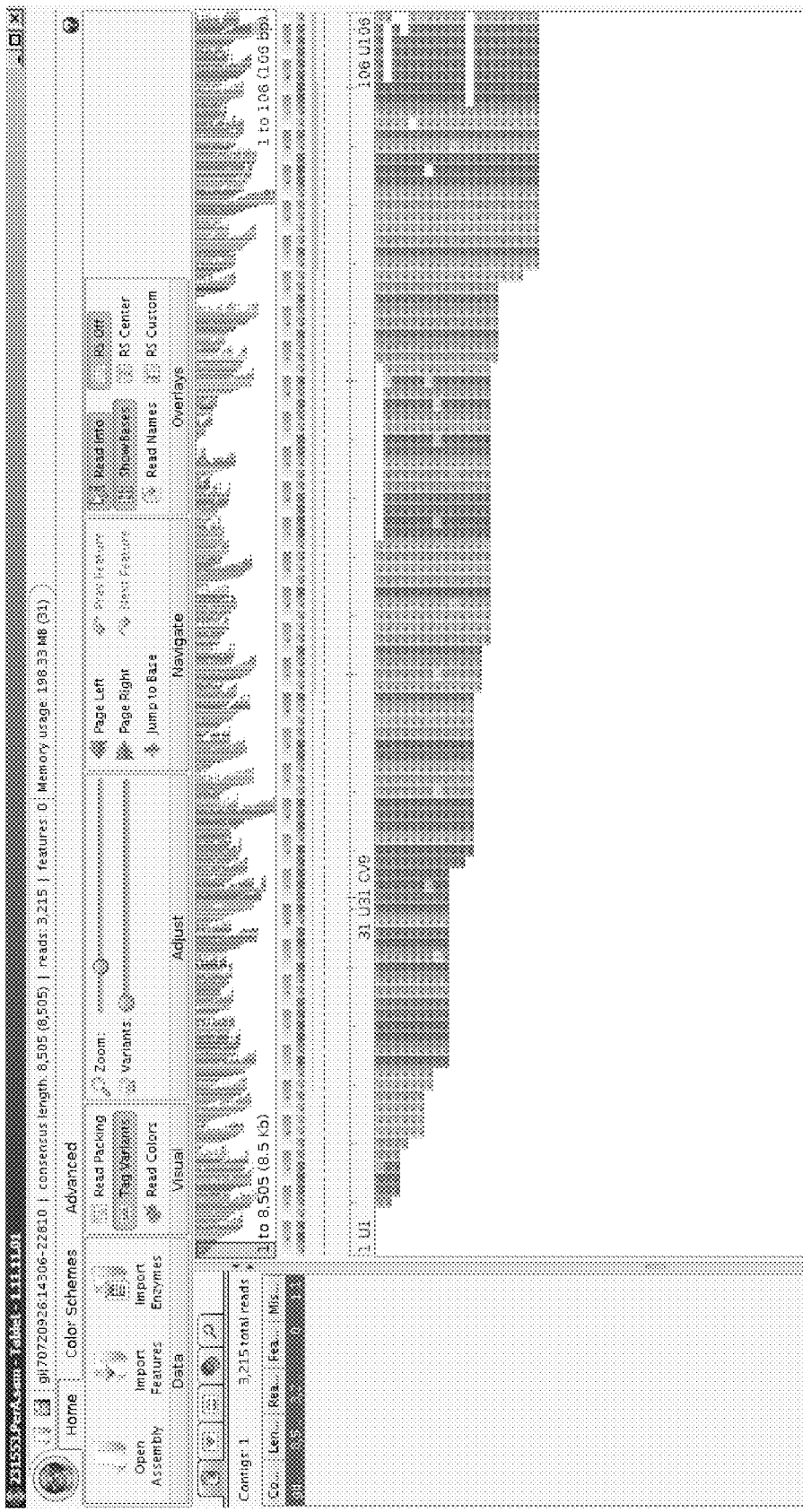

FIGS. 23 A-C show presence of perA gene within non-*Epichloe* out-group endophytes (FIG. 23A NEA17; FIG. 23B NEA18; FIG. 23C NEA19).

Figure 24:
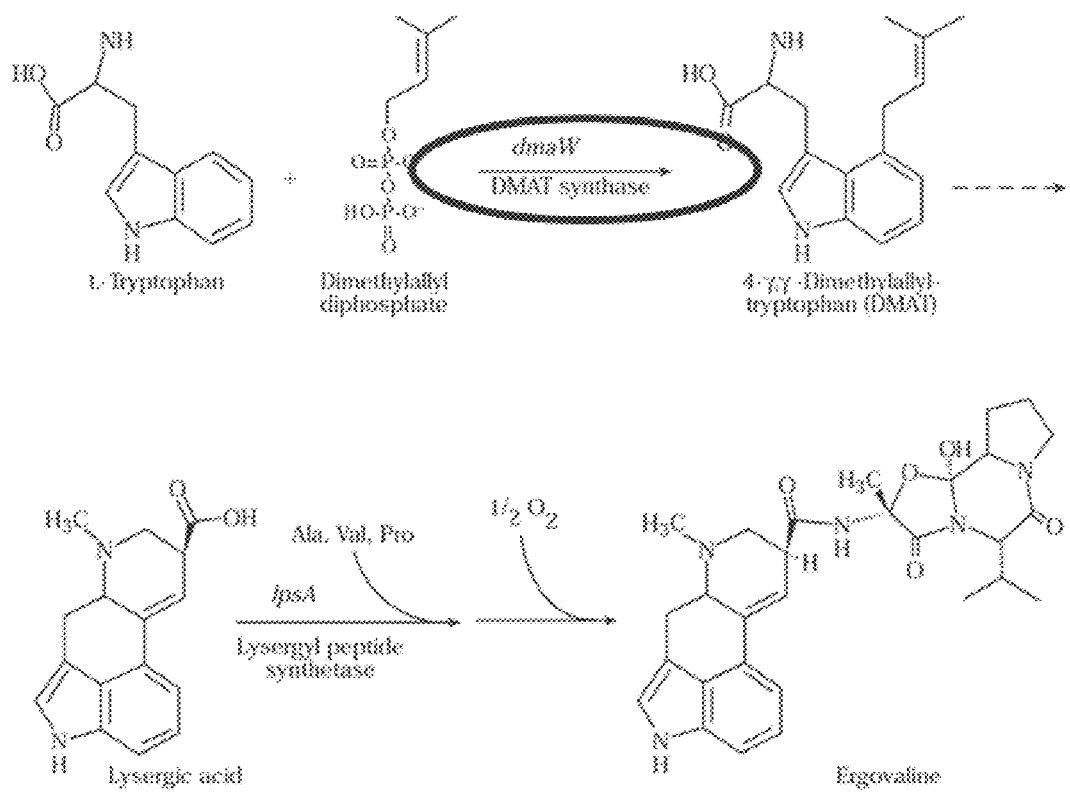

FIG. 24 shows ergovaline biosynthetic pathway.

Figure 25:

FIG. 25 shows genes in the eas gene cluster.

Figure 26A:
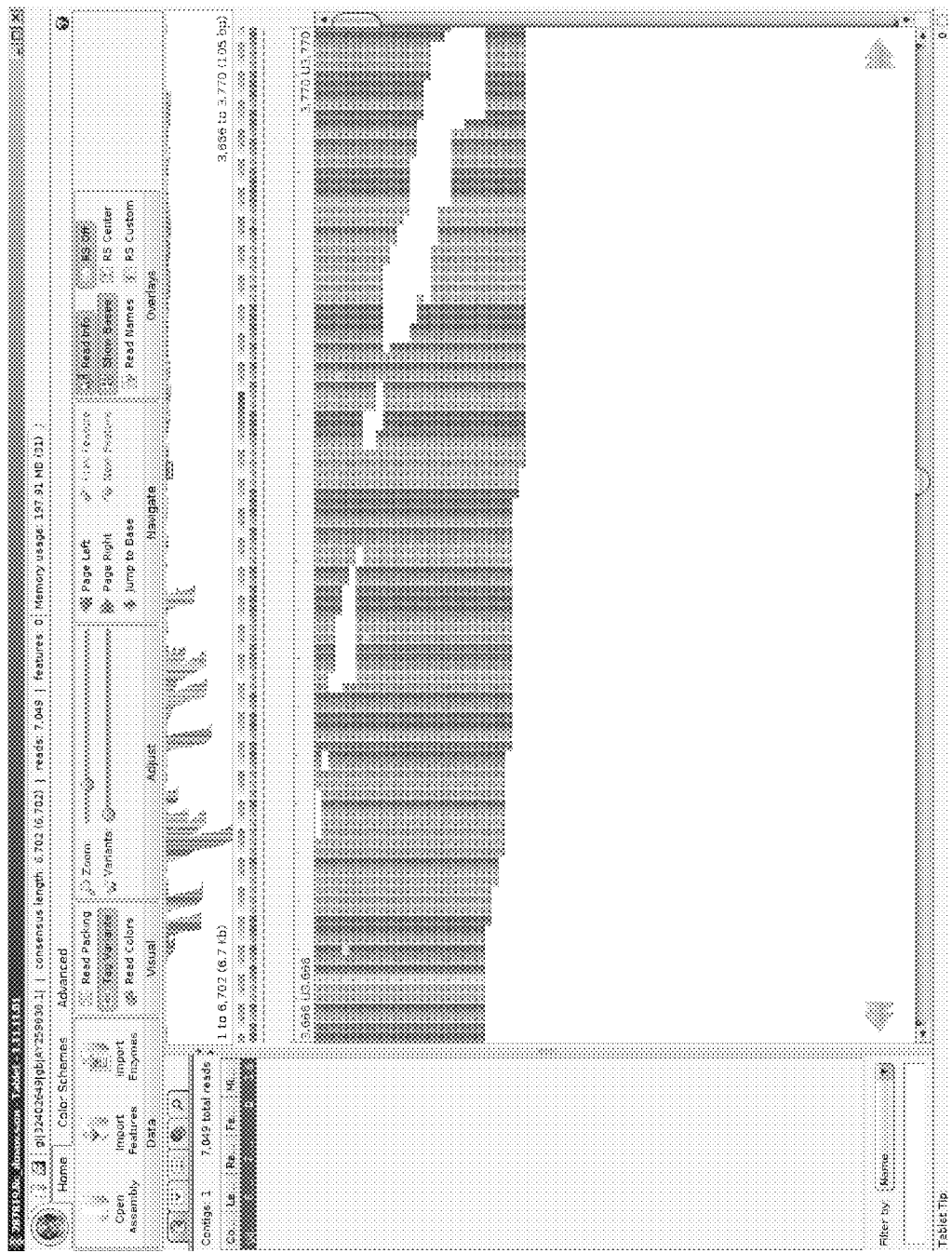
Figure 26B:
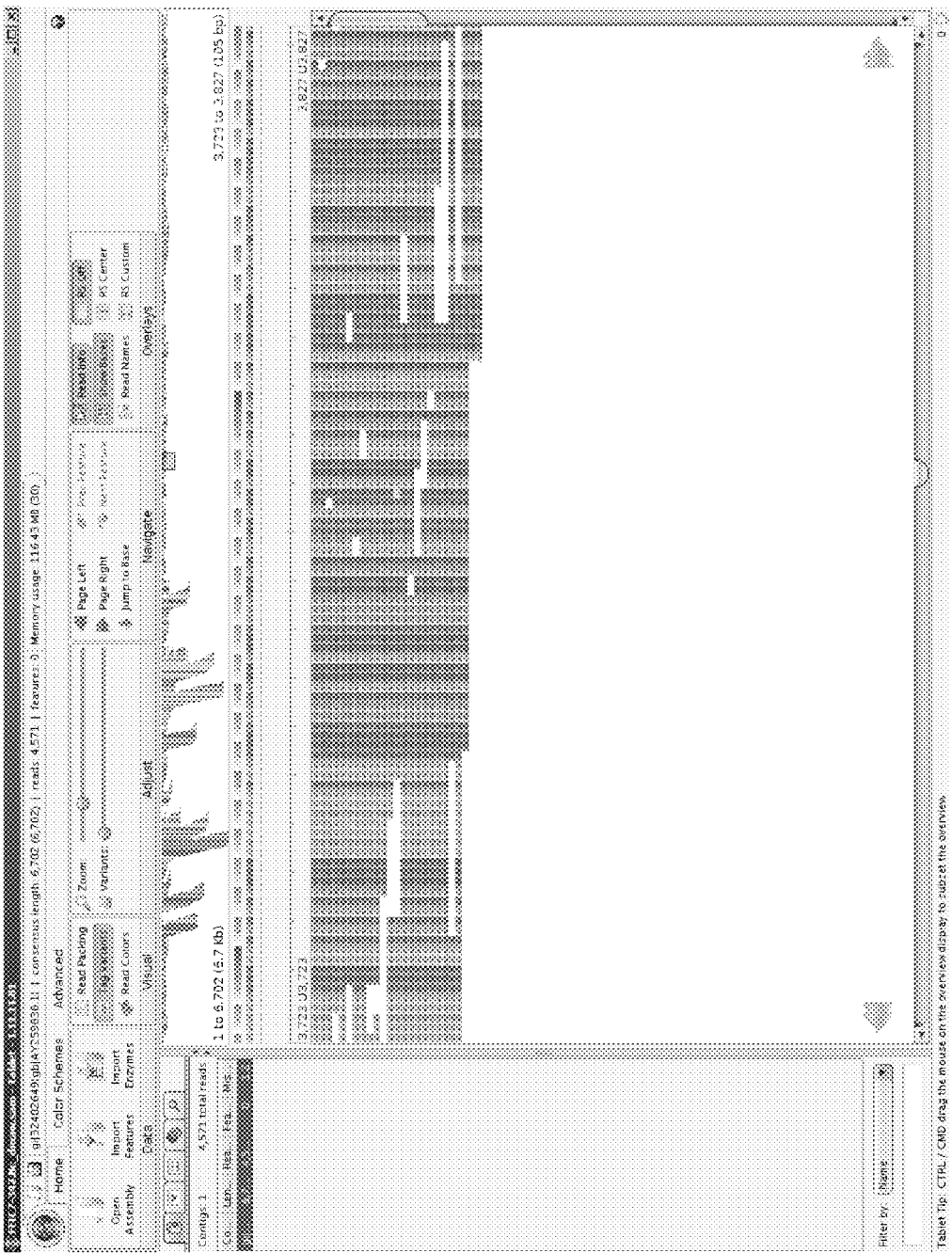
Figure 26C:
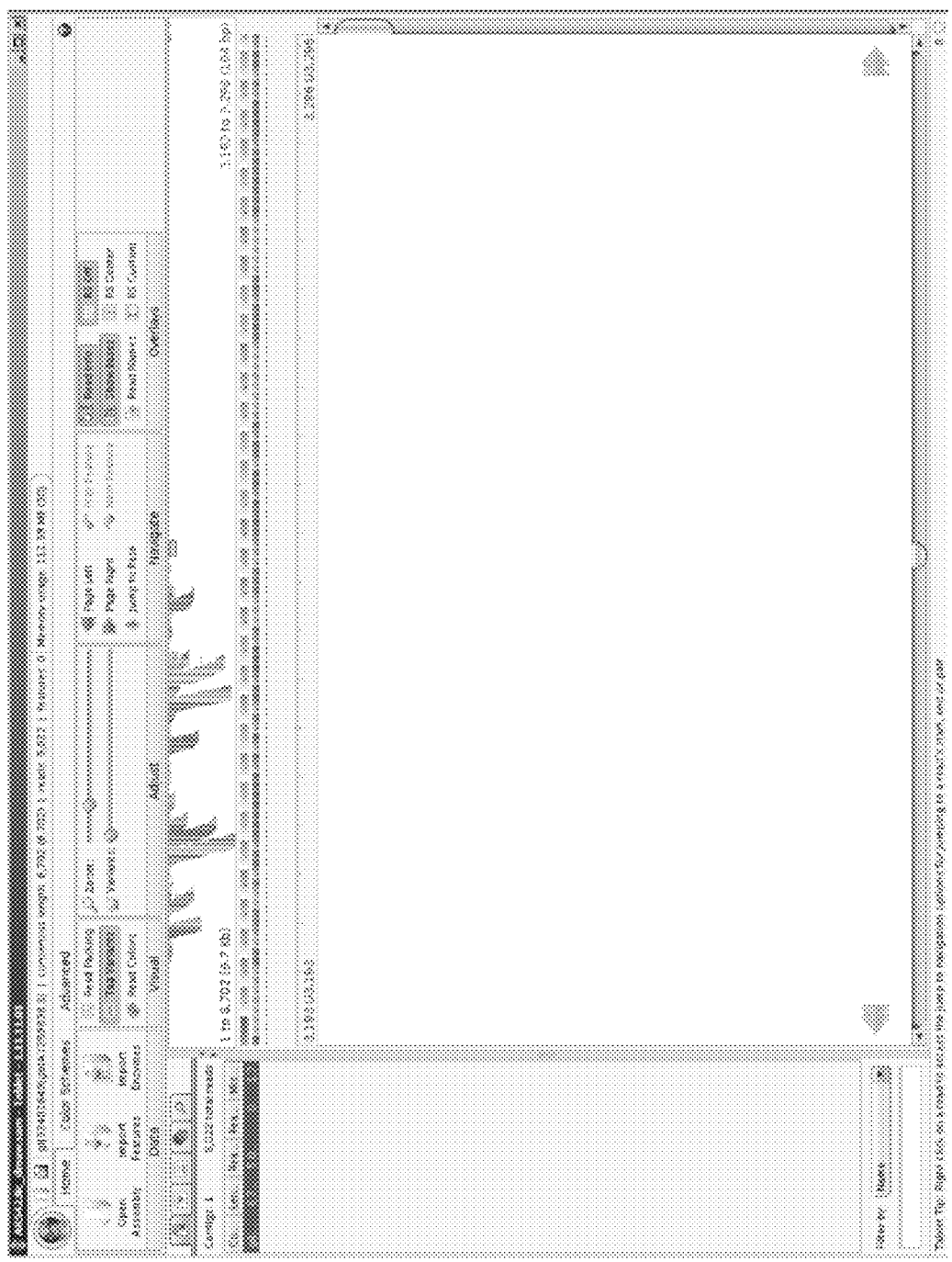
Figure 26D:
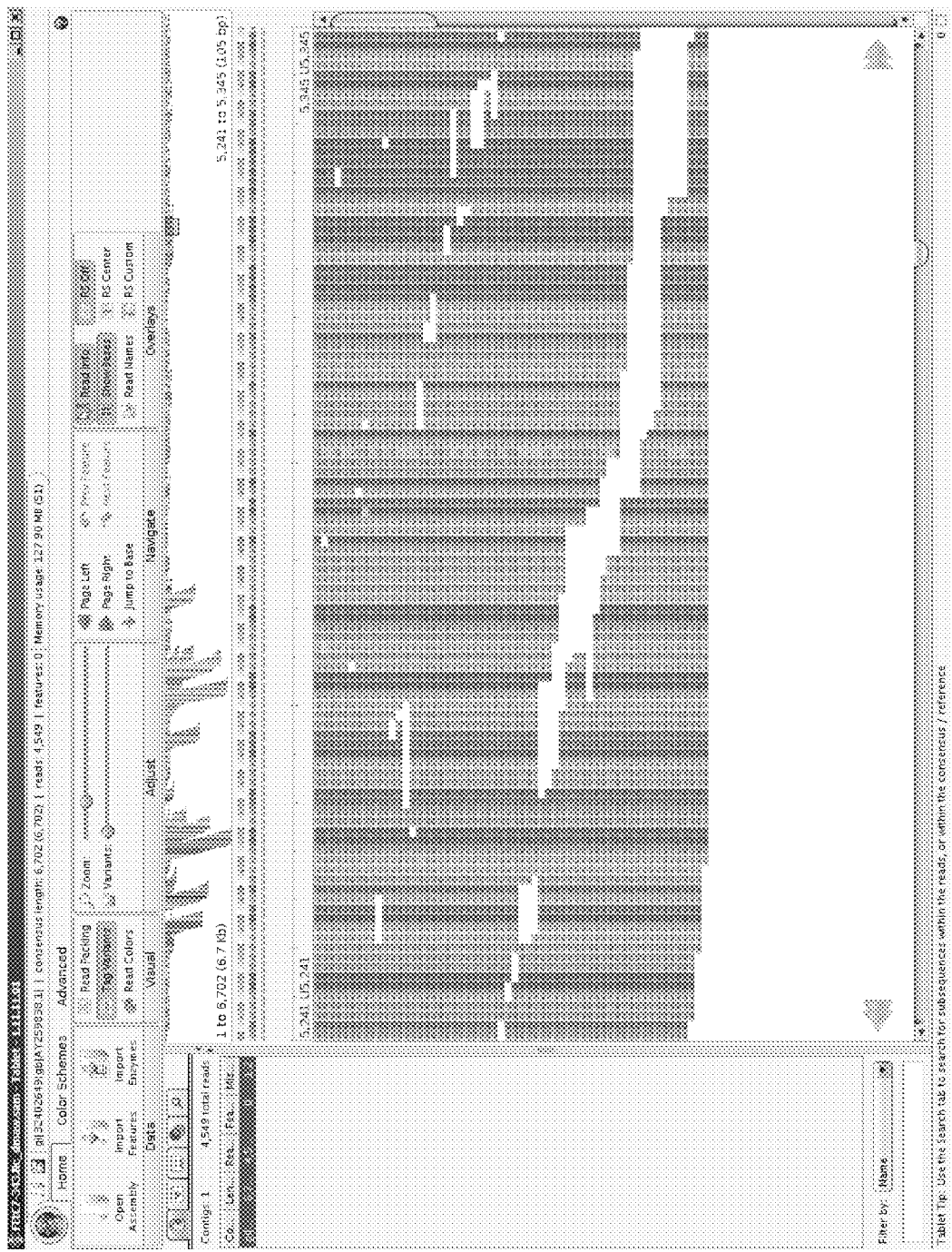
Figure 27A:
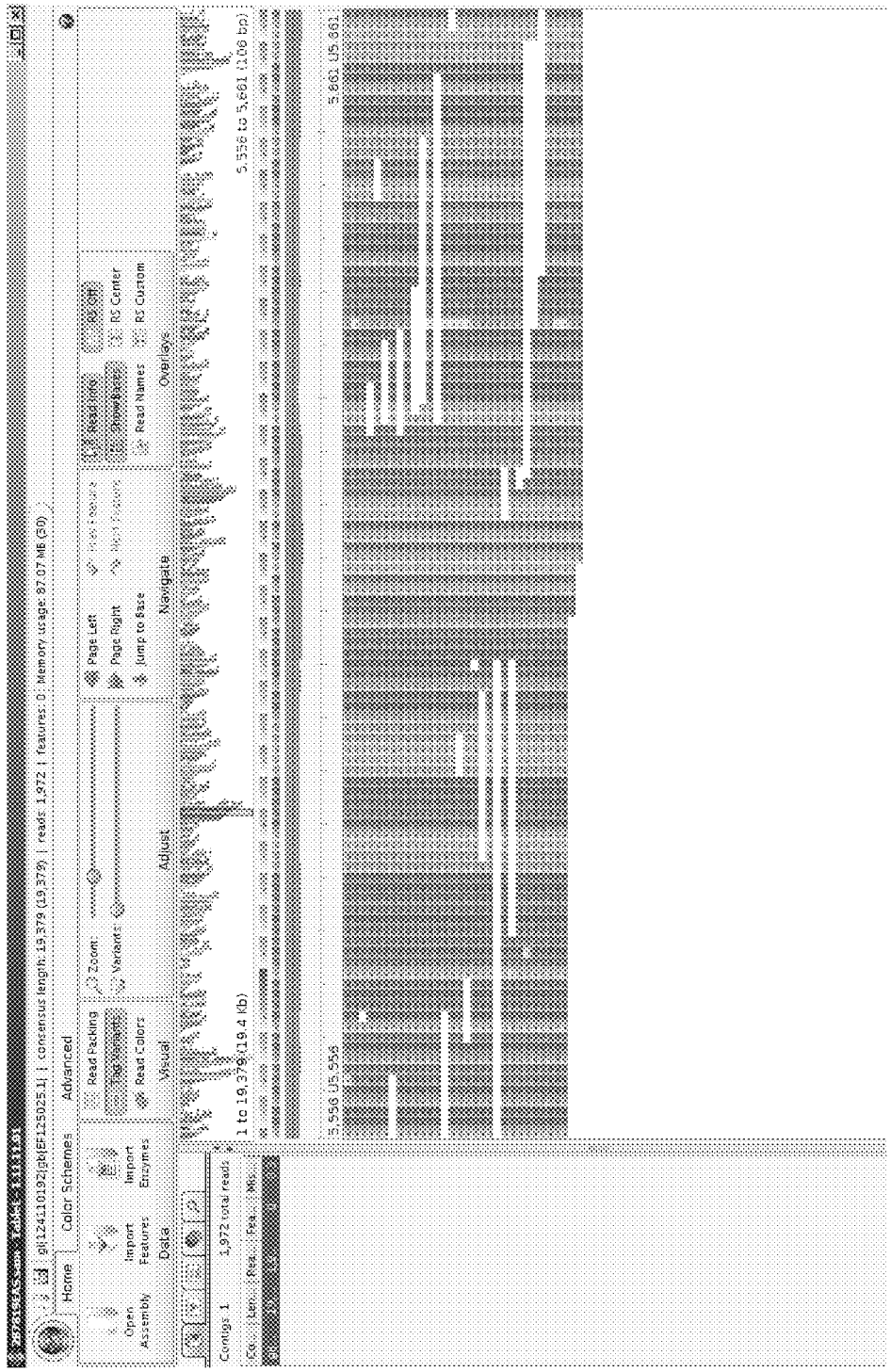
Figure 27B:
Figure 27C:
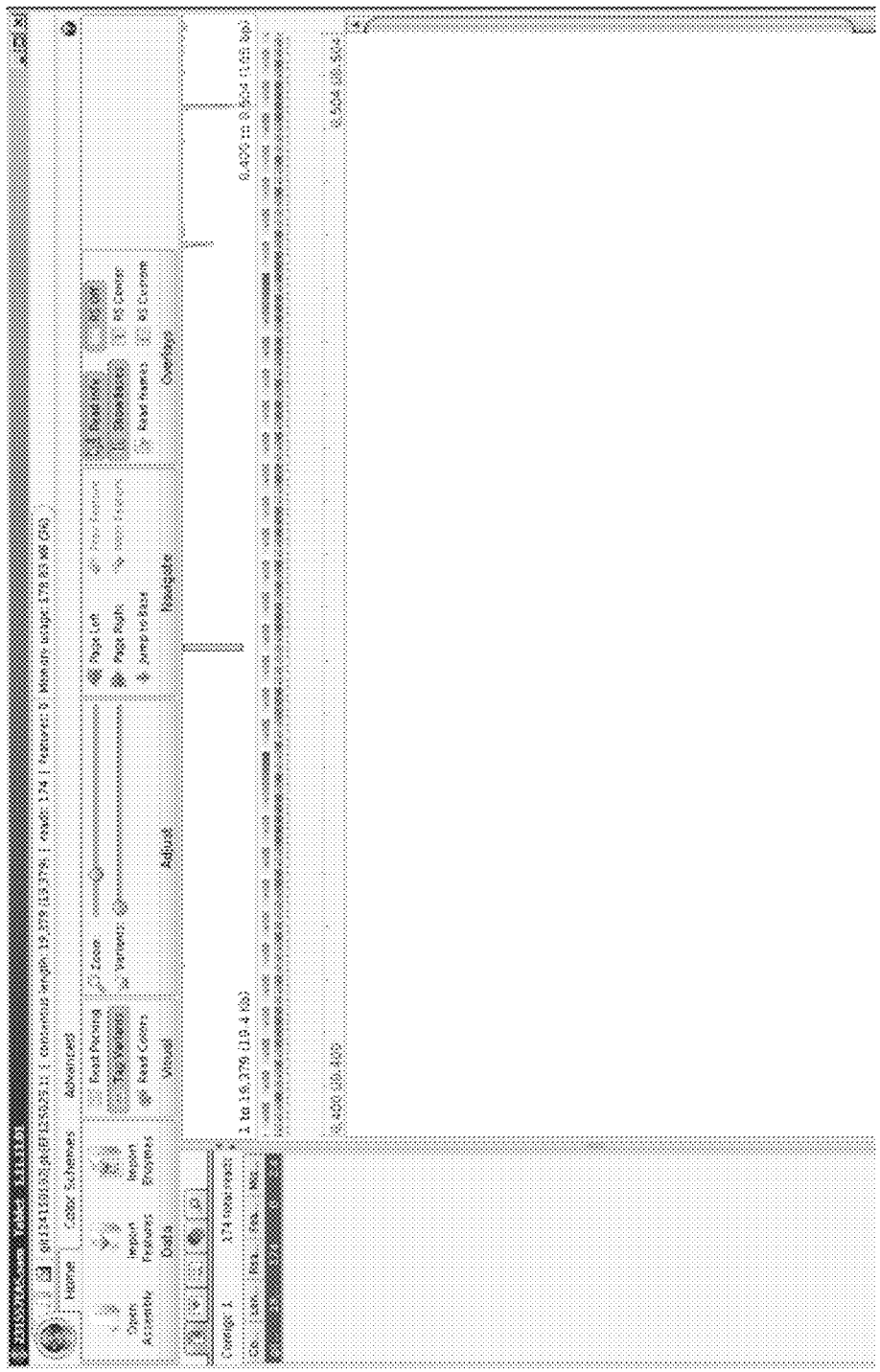
Figure 27D:
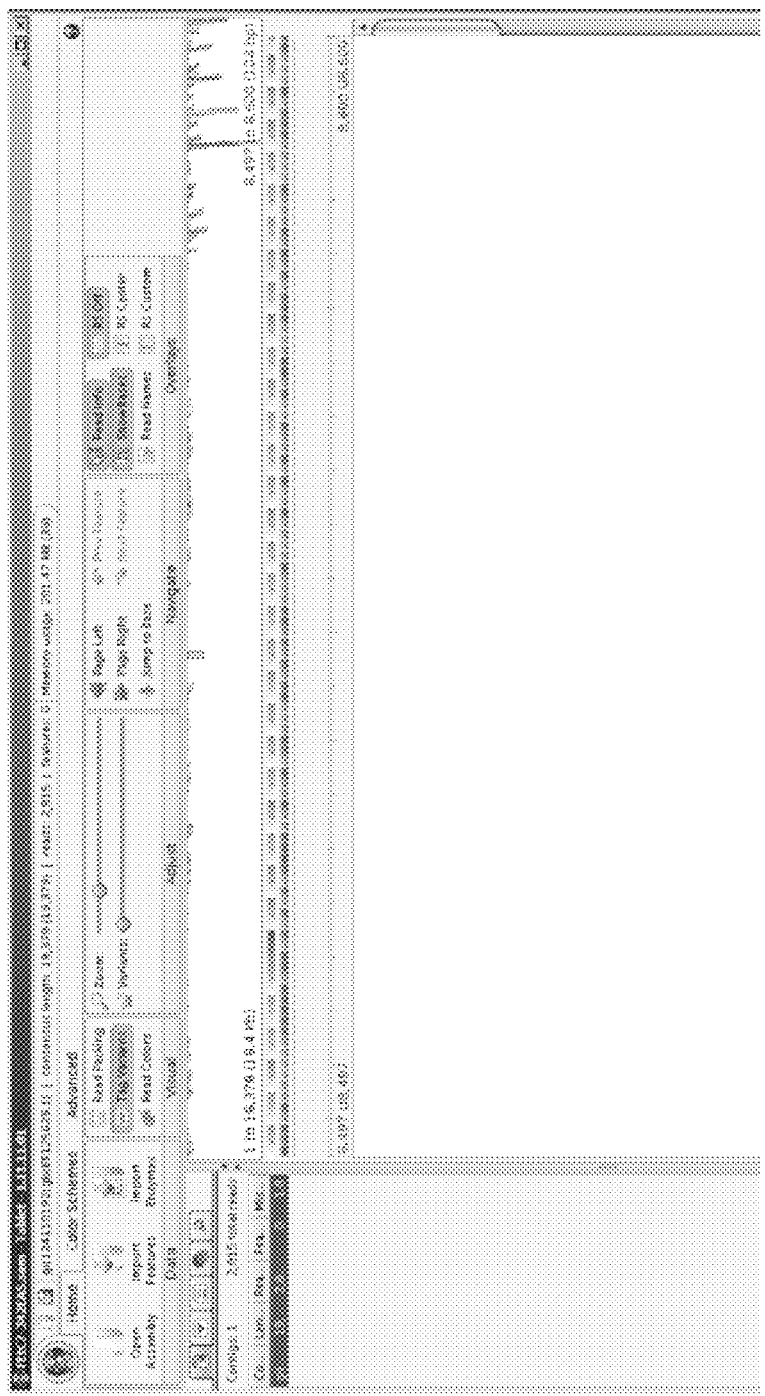

FIGS. 26 A-D show presence of dmaW gene for ergovaline biosynthesis in endophyte strains (FIG. 26A NEA17; FIG. 26B NEA16; FIG. 26C AR542; FIG. 26D NEA20).

FIGS. 27 A-D show presence of eas gene cluster for ergovaline biosynthesis. FIG. 27A FaTG-2 NEA17 (287819); FIG. 27B non-*Epichloe* out-group NEA18 (FEtc6-75); FIG. 27C FATG-3 NEA21 (231557); FIG. 27D *N. coenophialum* NEA16 (FEtc7-342).

Figure 28:
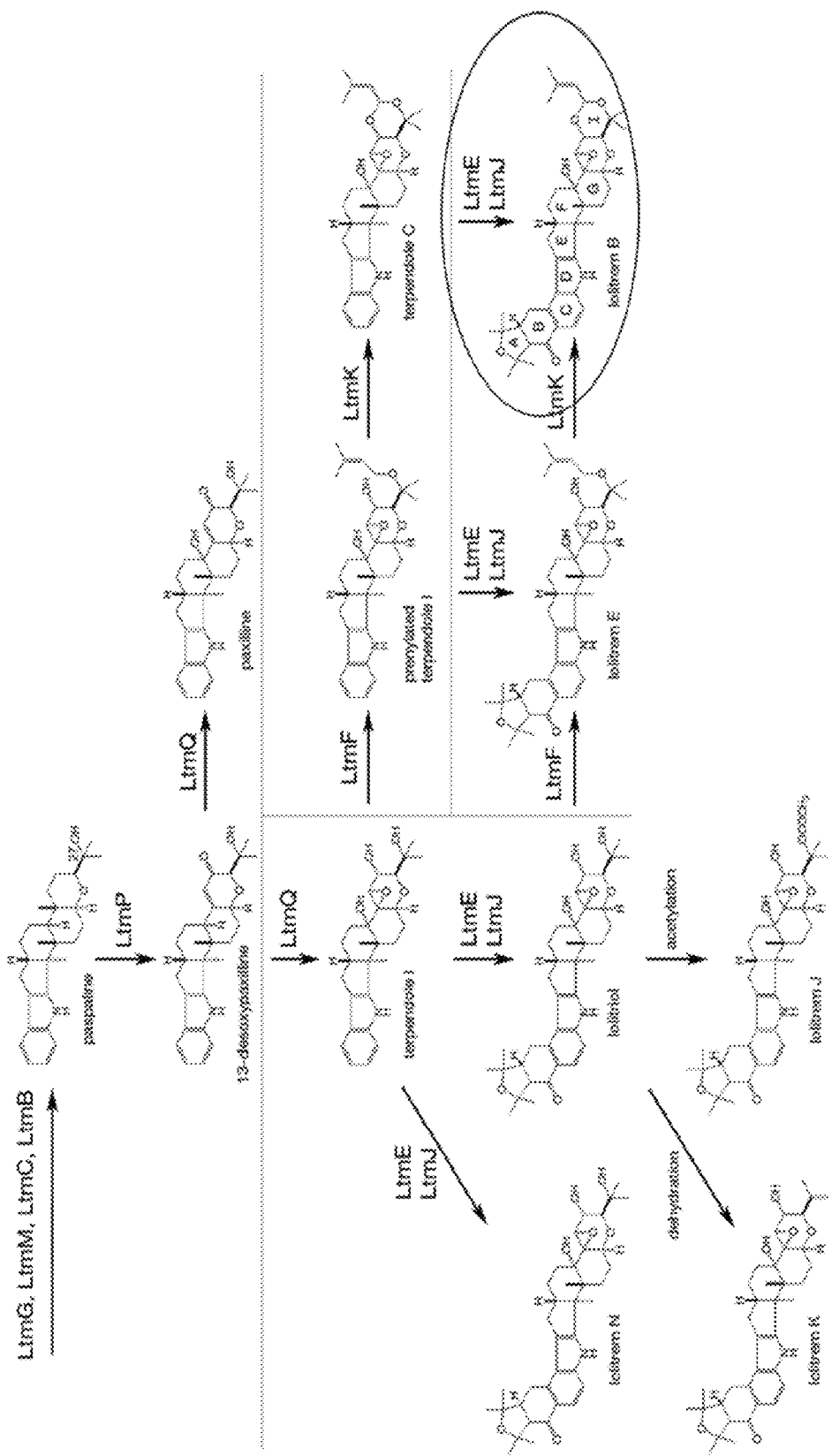

FIG. 28 shows the Lolitrem B biosynthetic pathway.

Figure 29:
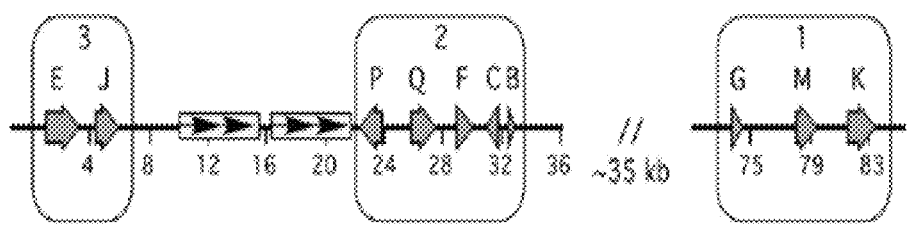
Figure 30A:
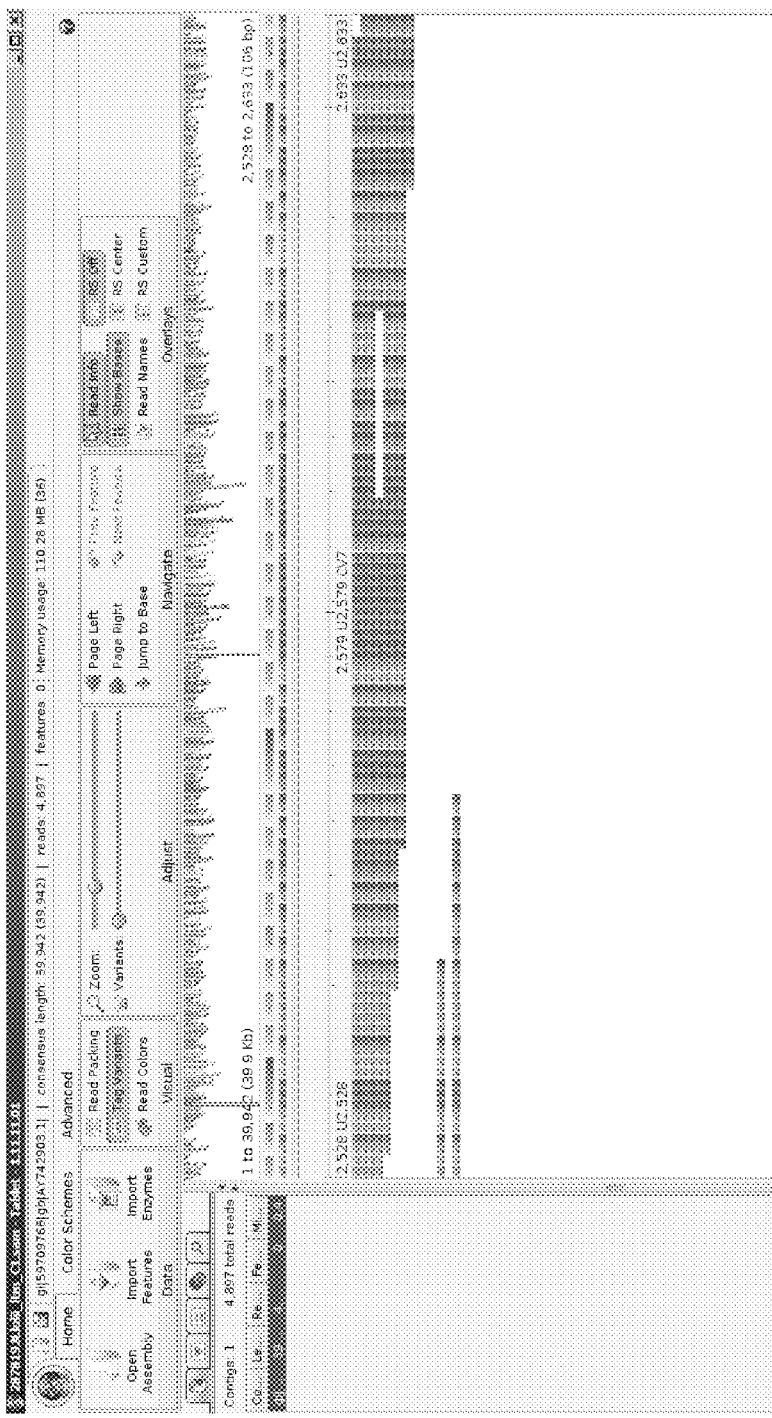
Figure 30B:
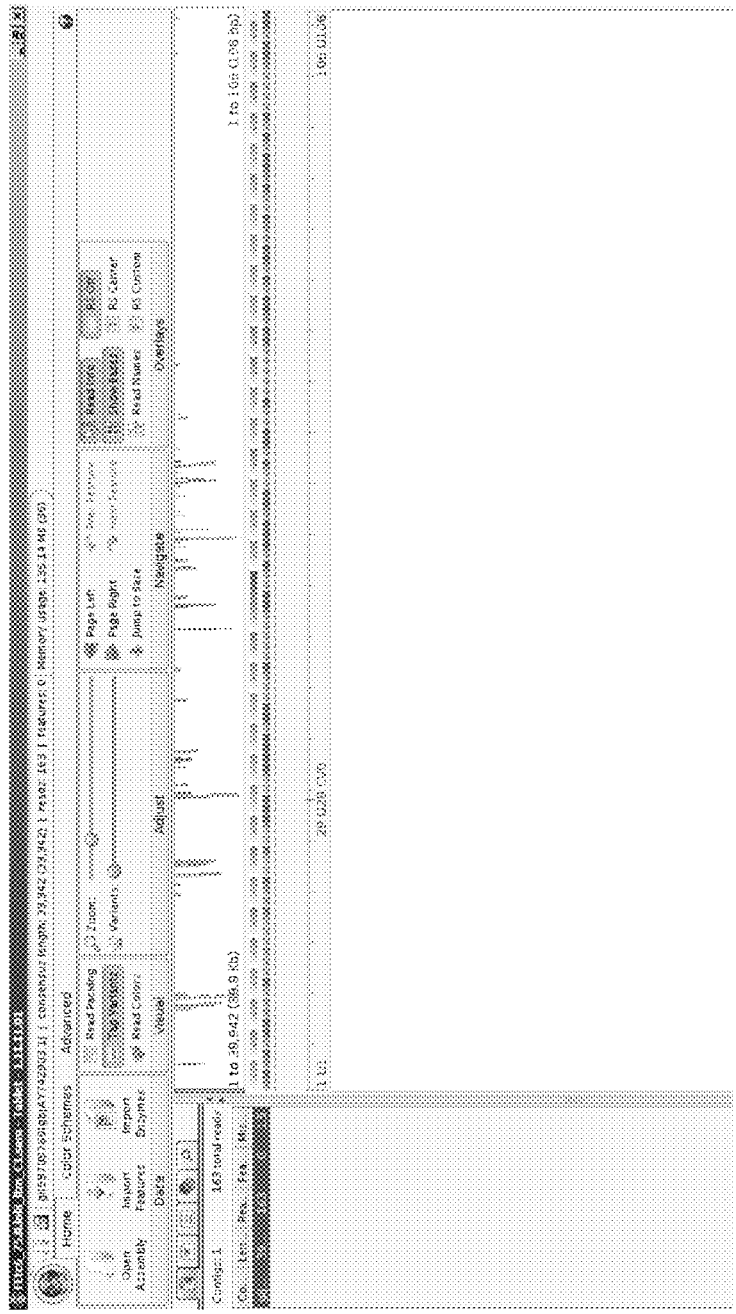
Figure 30C:
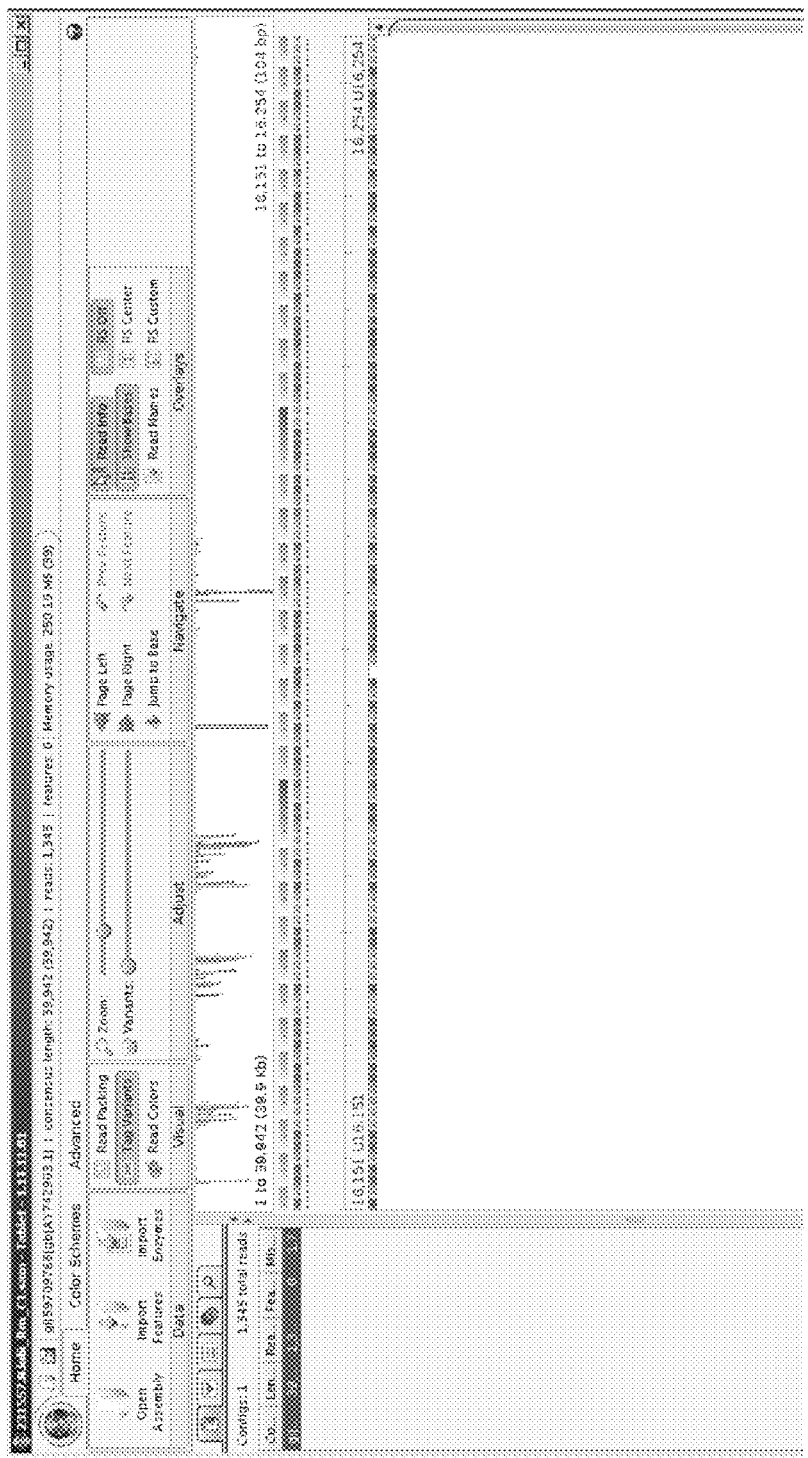
Figure 30D:
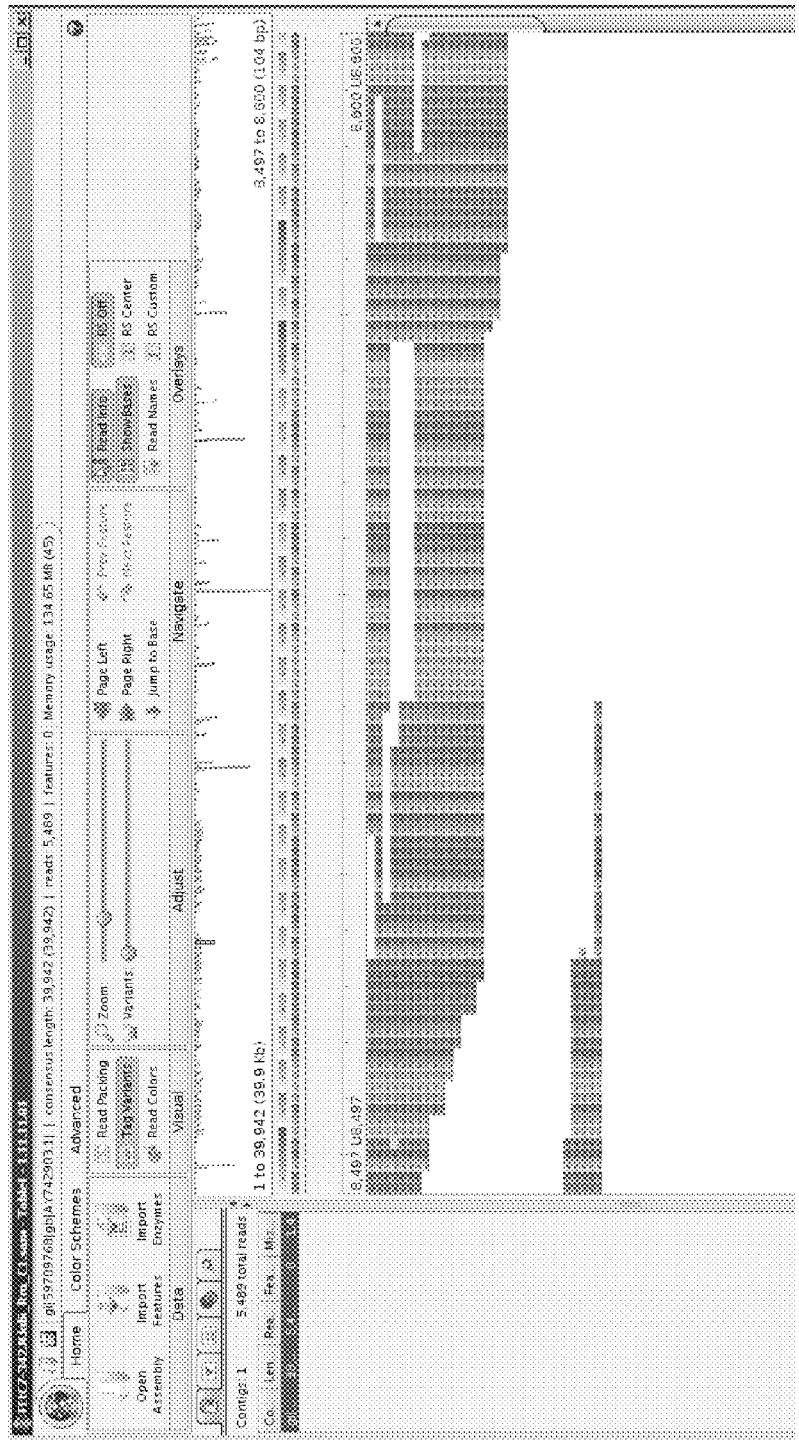
Figure 31A:
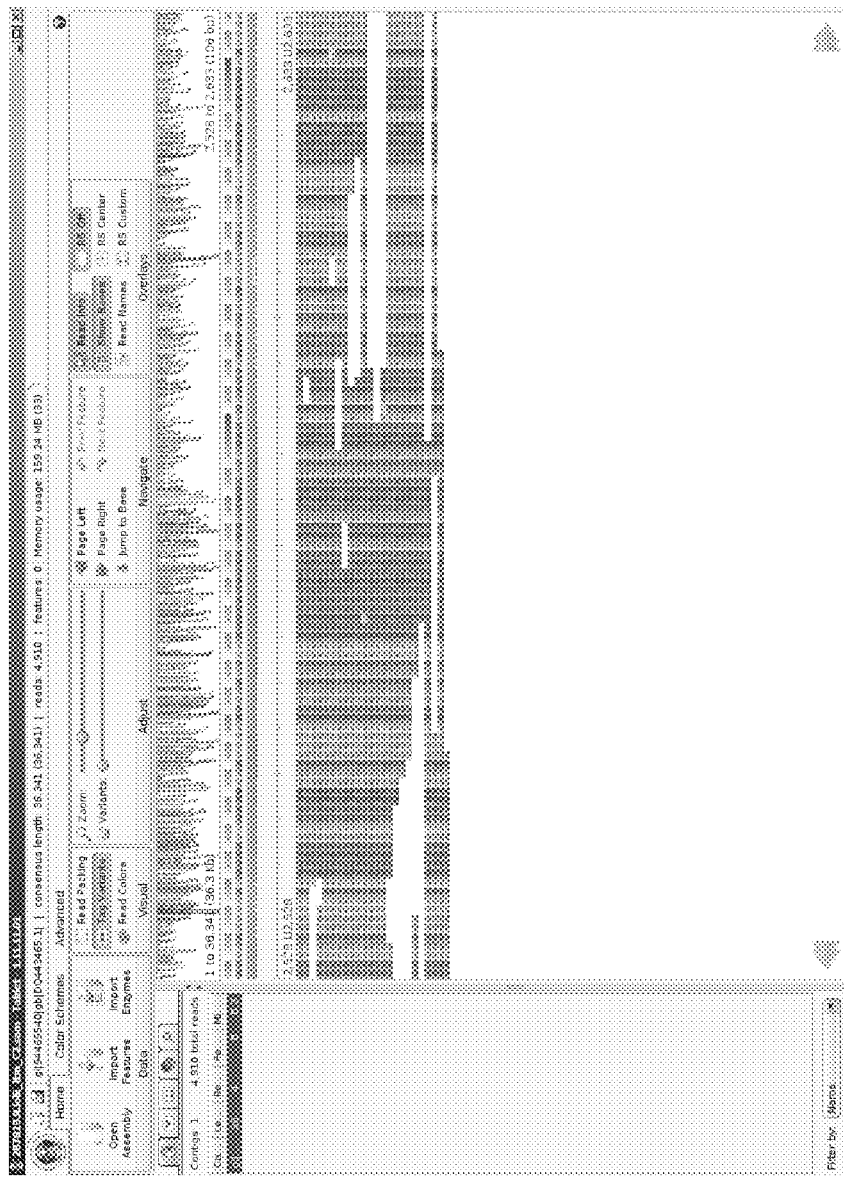
Figure 31B:
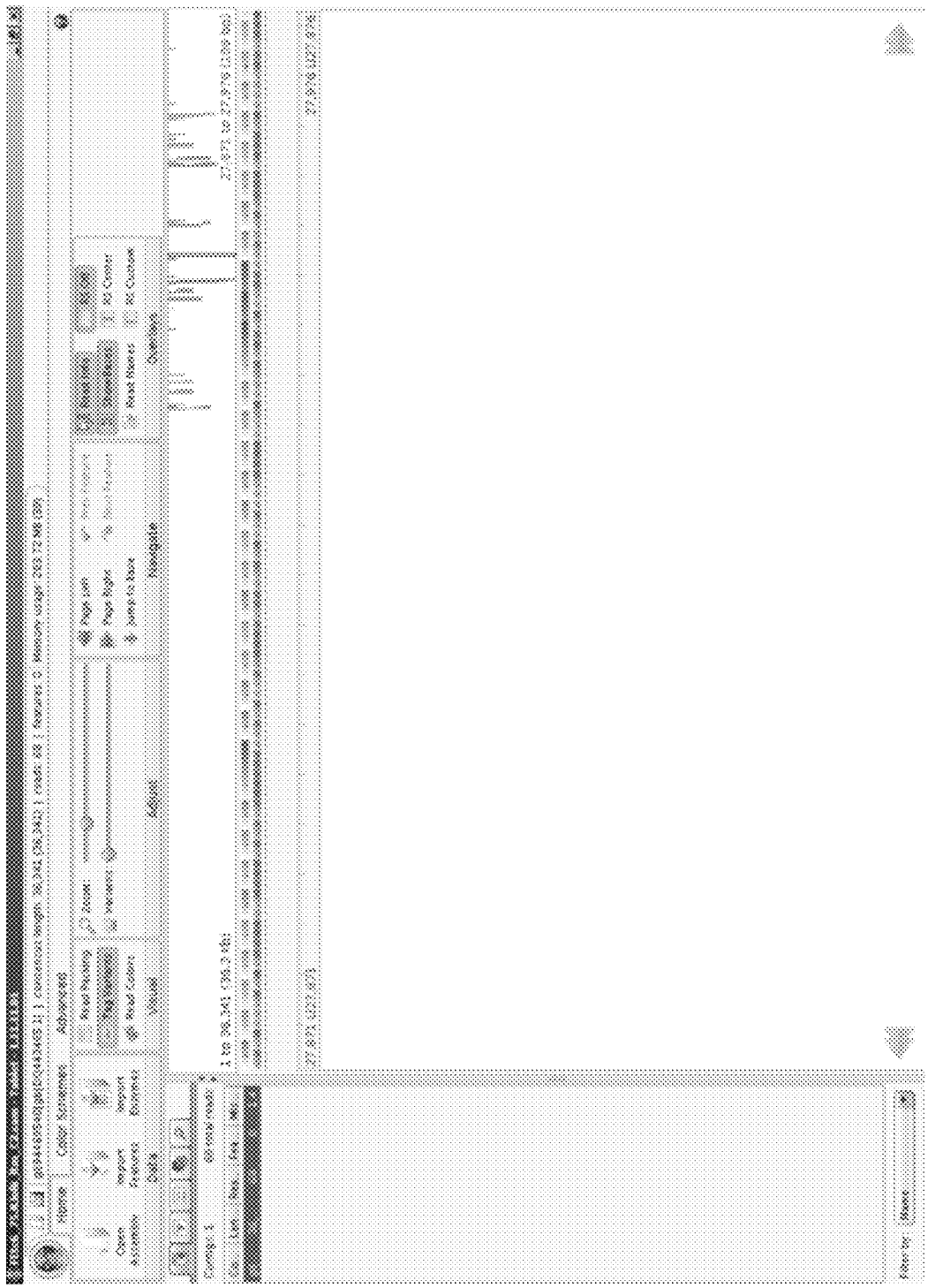
Figure 31C:
Figure 31D:
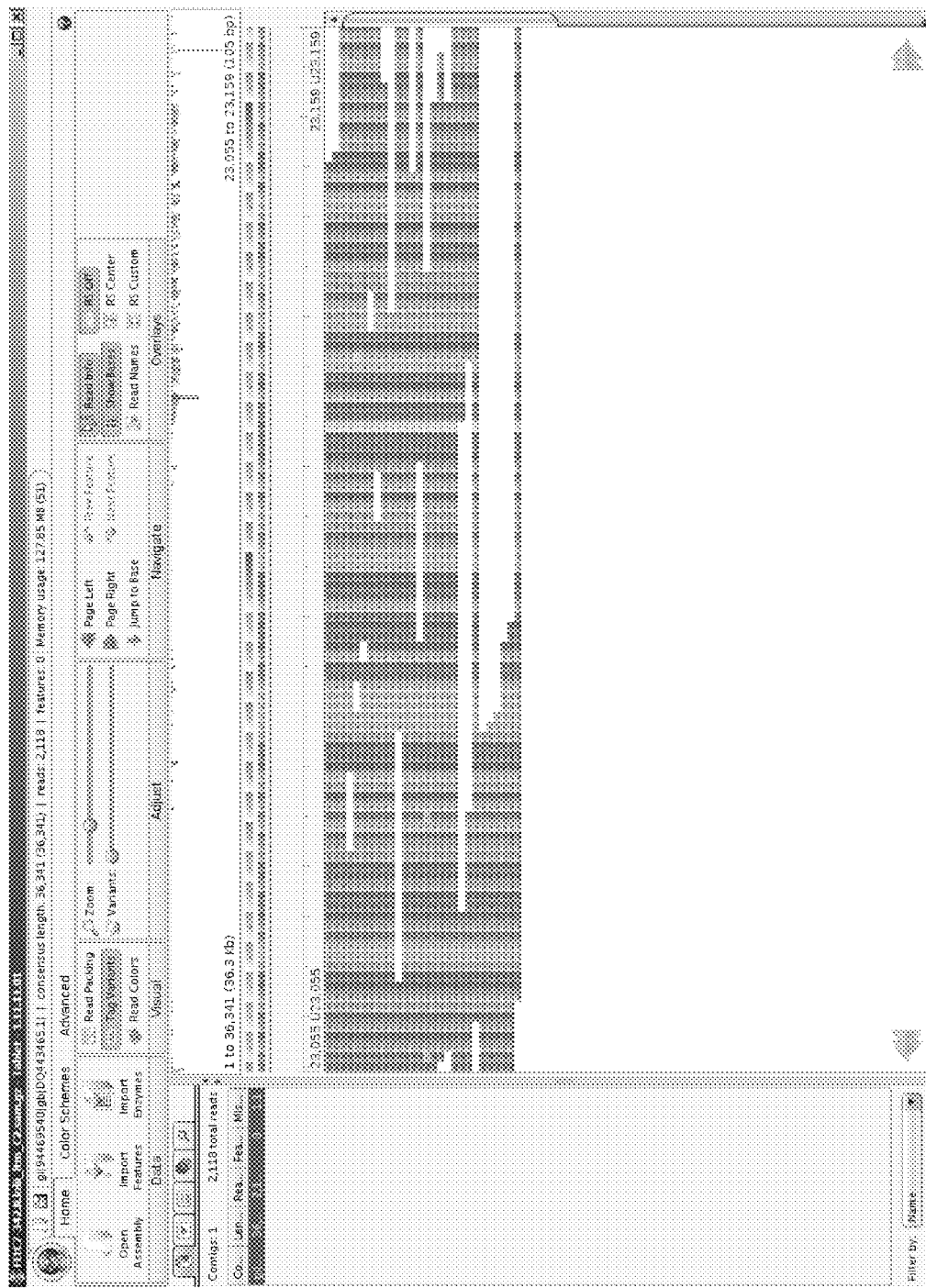
Figure 32A:
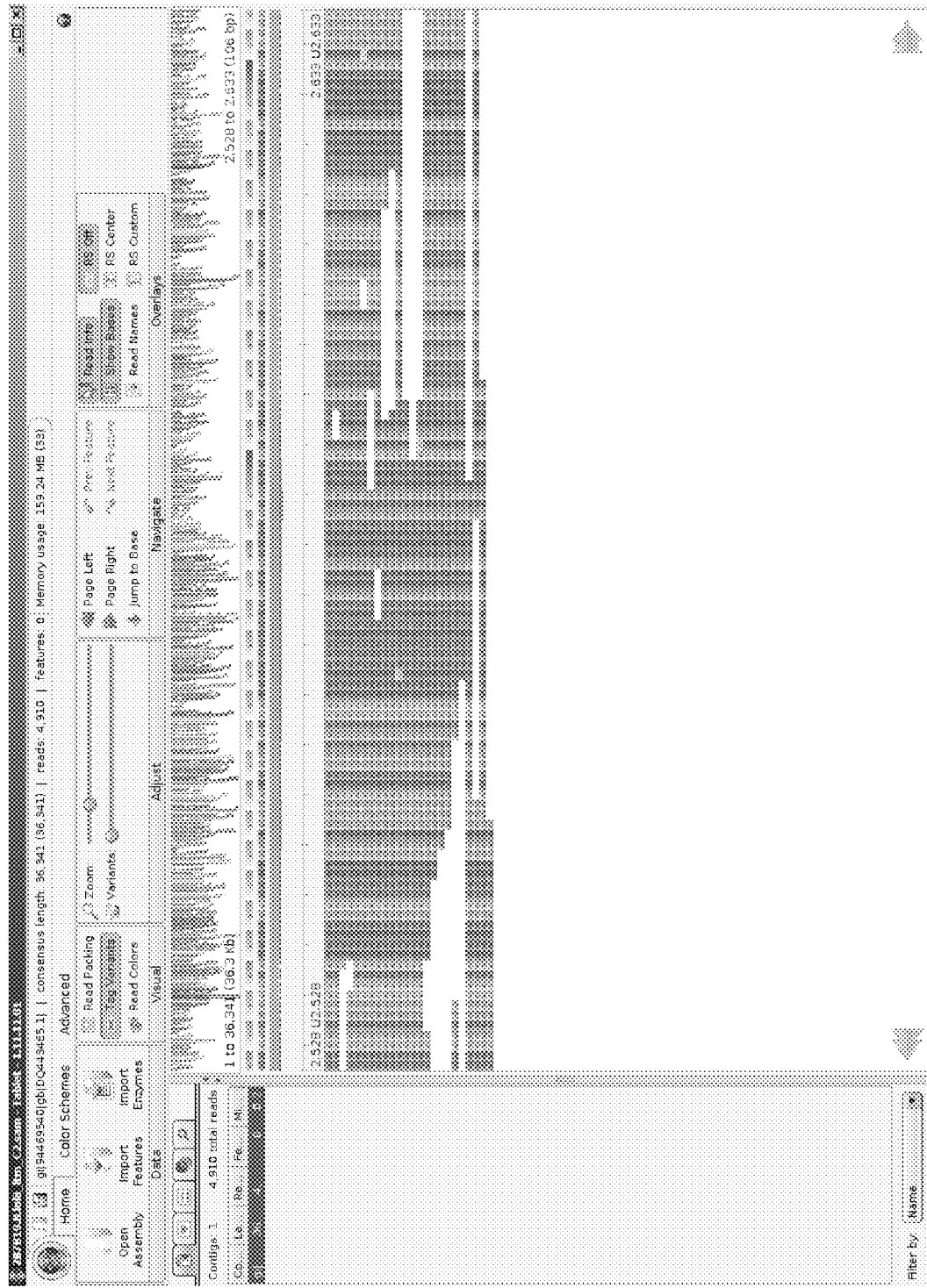
Figure 32B:
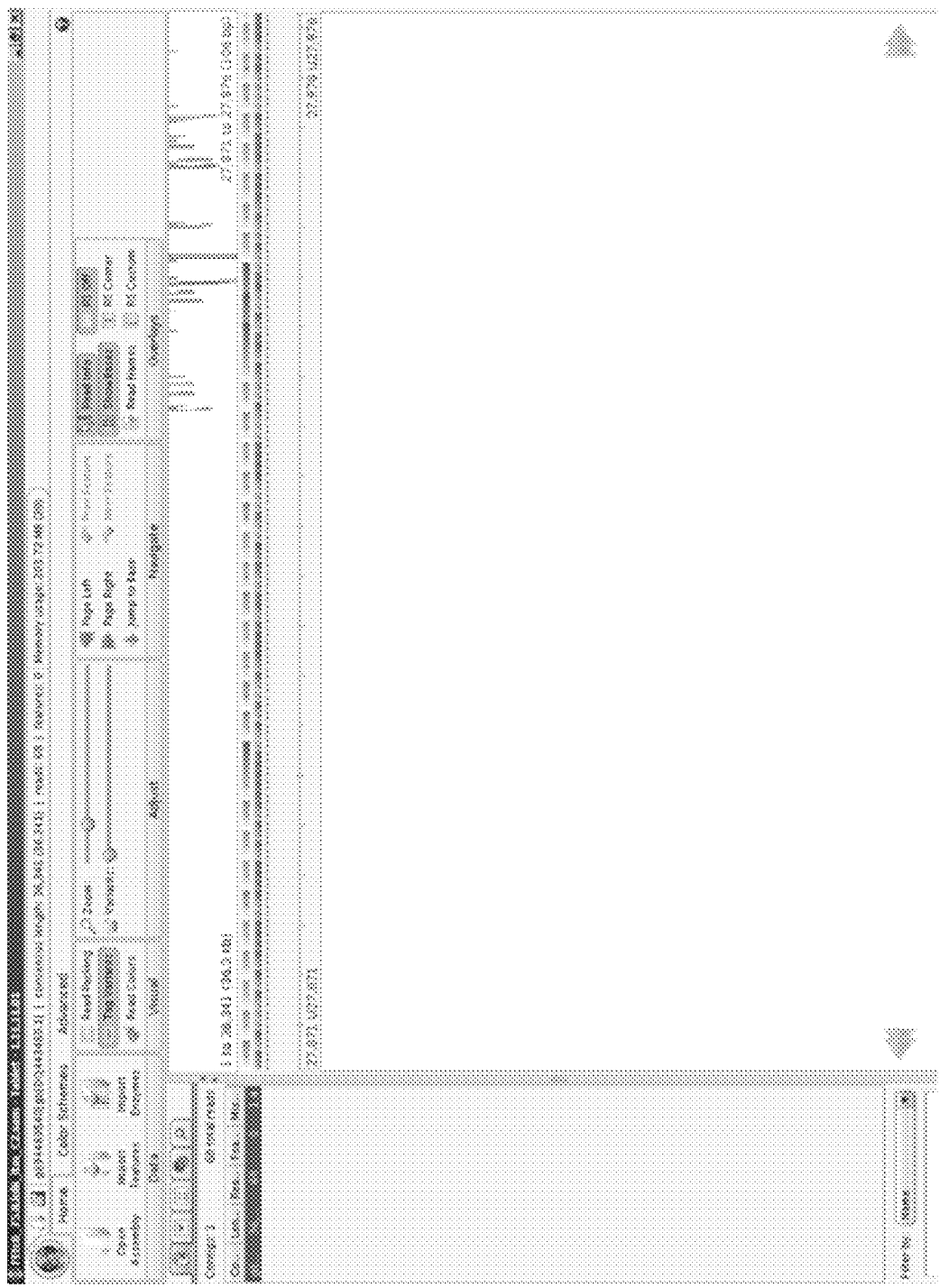
Figure 32C:
Figure 32D:

FIG. 29 shows genes in the Lolitrem B biosynthetic gene cluster.

FIGS. 30 A-D show presence of Lolitrem B biosynthetic gene cluster 1 (ItmG, ItmM and ItmK) in endophyte strains. FIG. 30A FaTG-2 NEA17 (287819); FIG. 30B non-*Epichloe* out-group NEA18 (FEtc6-75); FIG. 30C FATG-3 NEA21 (231557); FIG. 30D *N. coenophialum* NEA16 (FEtc7-342).

FIGS. 31 A-D show presence of Lolitrem B biosynthetic gene cluster 2 (ItmB, ItmQ, ItmP, ItmF and ItmC) in endophyte strains. FIG. 31A FaTG-2 NEA17 (287819); FIG. 31B non-*Epichloe* out-group NEA18 (FEtc6-75); FIG. 31C FATG-3 NEA21 (231557); FIG. 31D *N. coenophialum* NEA16 (FEtc7-342).

FIGS. 32 A-D show presence of Lolitrem B biosynthetic gene cluster 3 (ItmE and KmJ) in endophyte strains. FIG. 32A FaTG-2 NEA17 (287819); FIG. 32B non-*Epichloe* out-group NEA18 (FEtc6-75); FIG. 32C FATG-3 NEA21 (231557); FIG. 32D *N. coenophialum* NEA16 (FEtc7-342).

Figure 33:
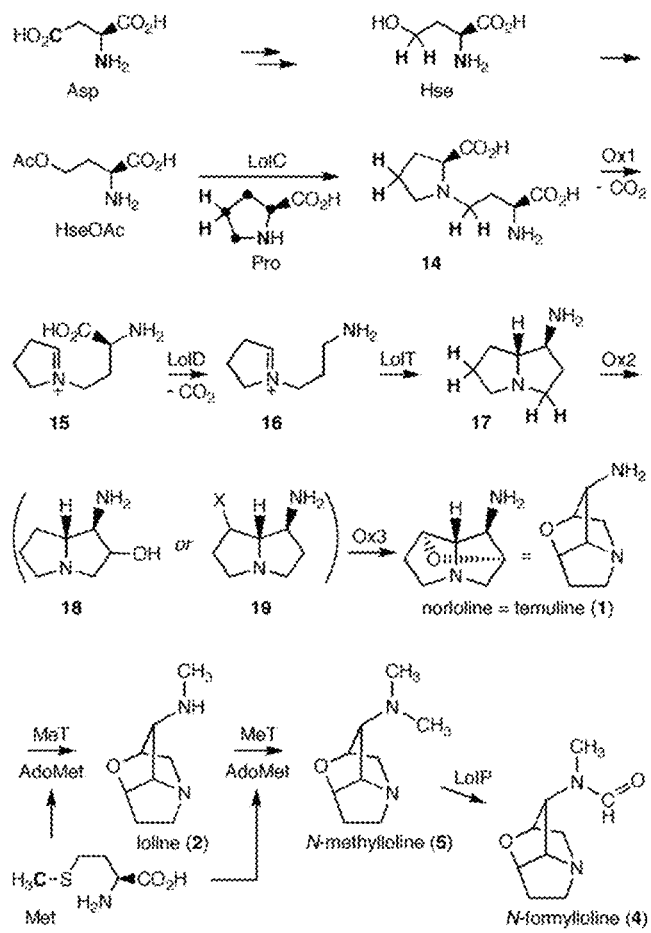

FIG. 33 shows the loline biosynthetic pathway.

Figure 34:
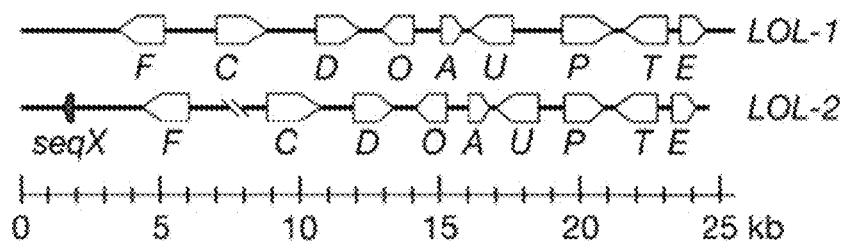
Figure 35A:
Figure 35B:
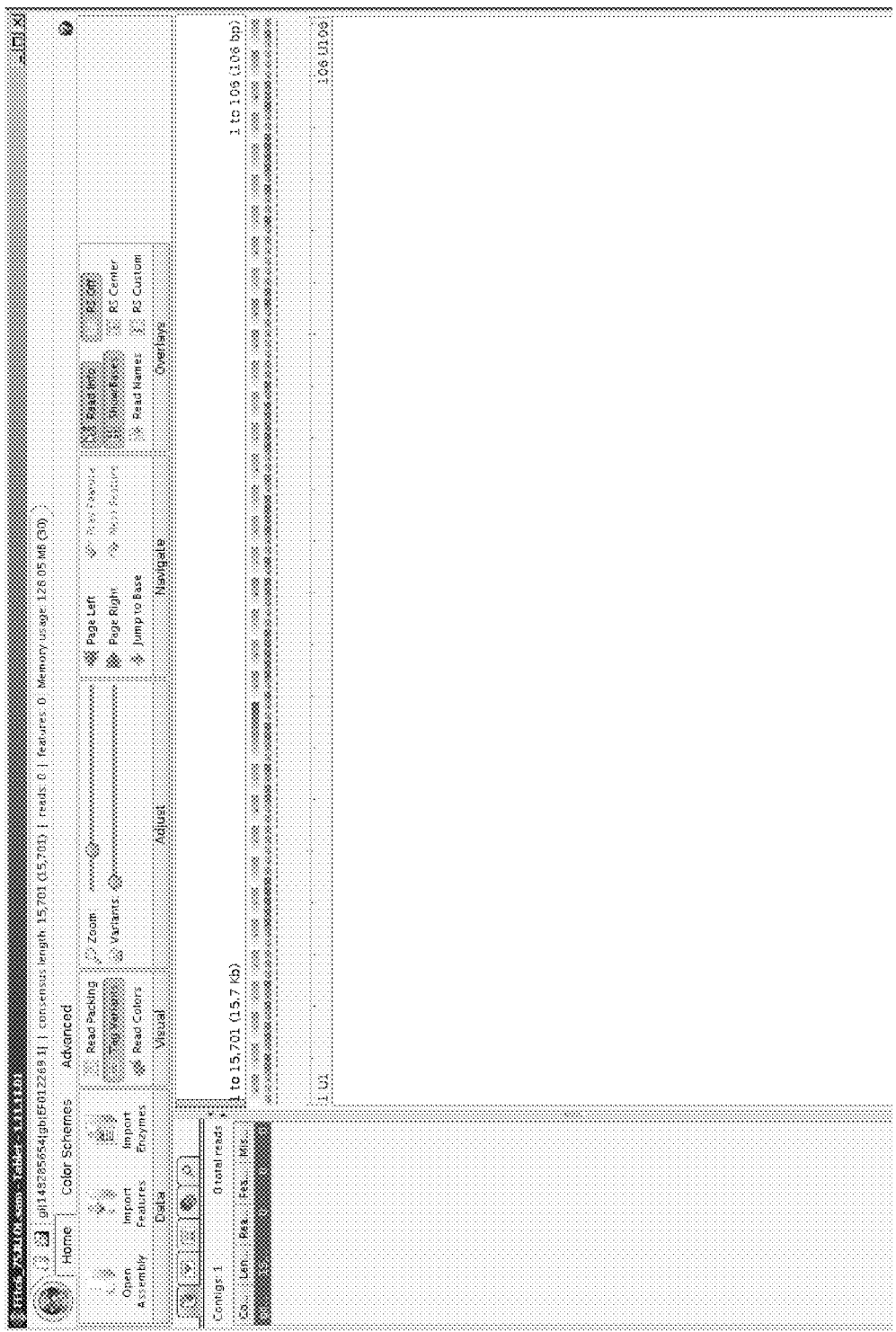
Figure 35C:
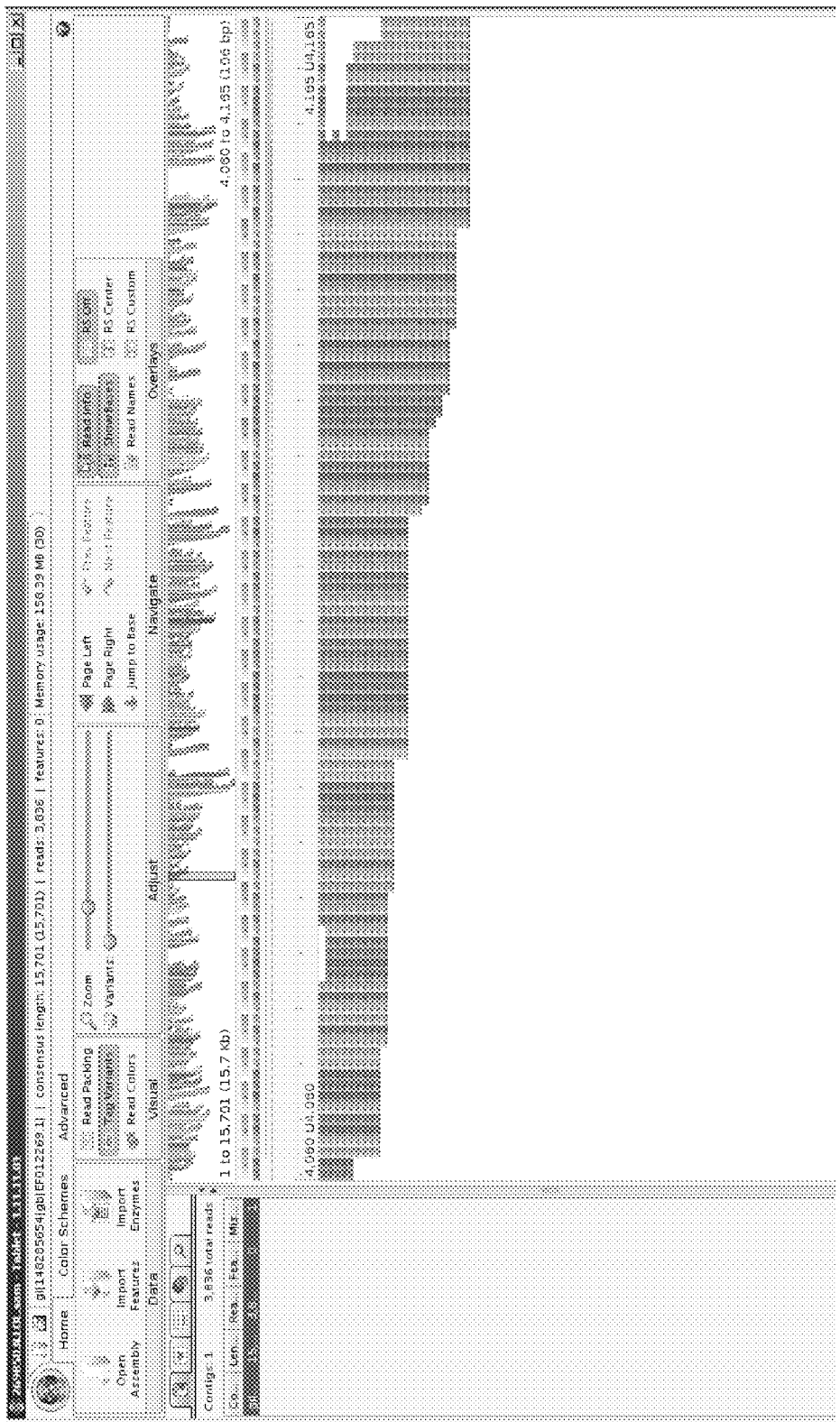
Figure 35D:
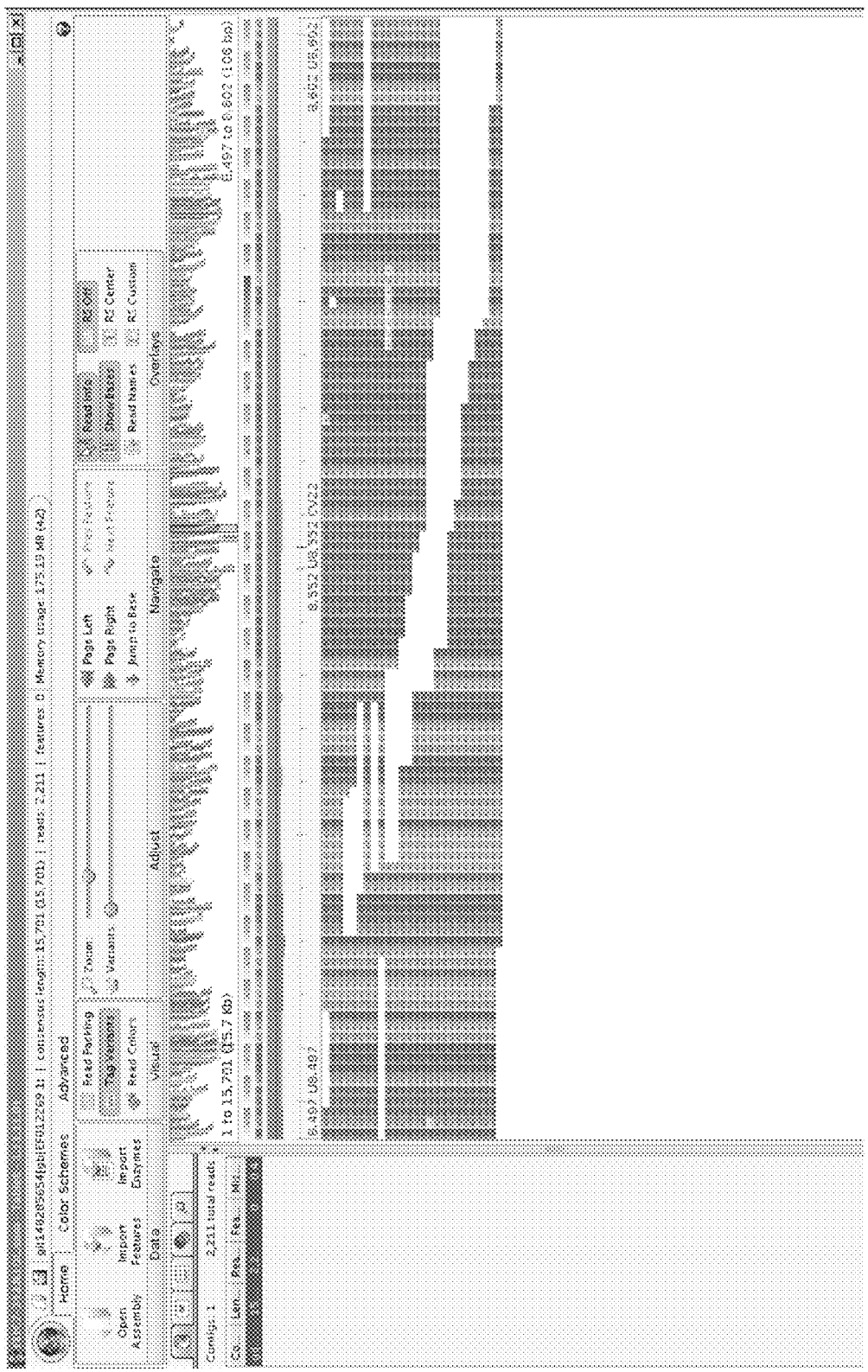
Figure 36A:
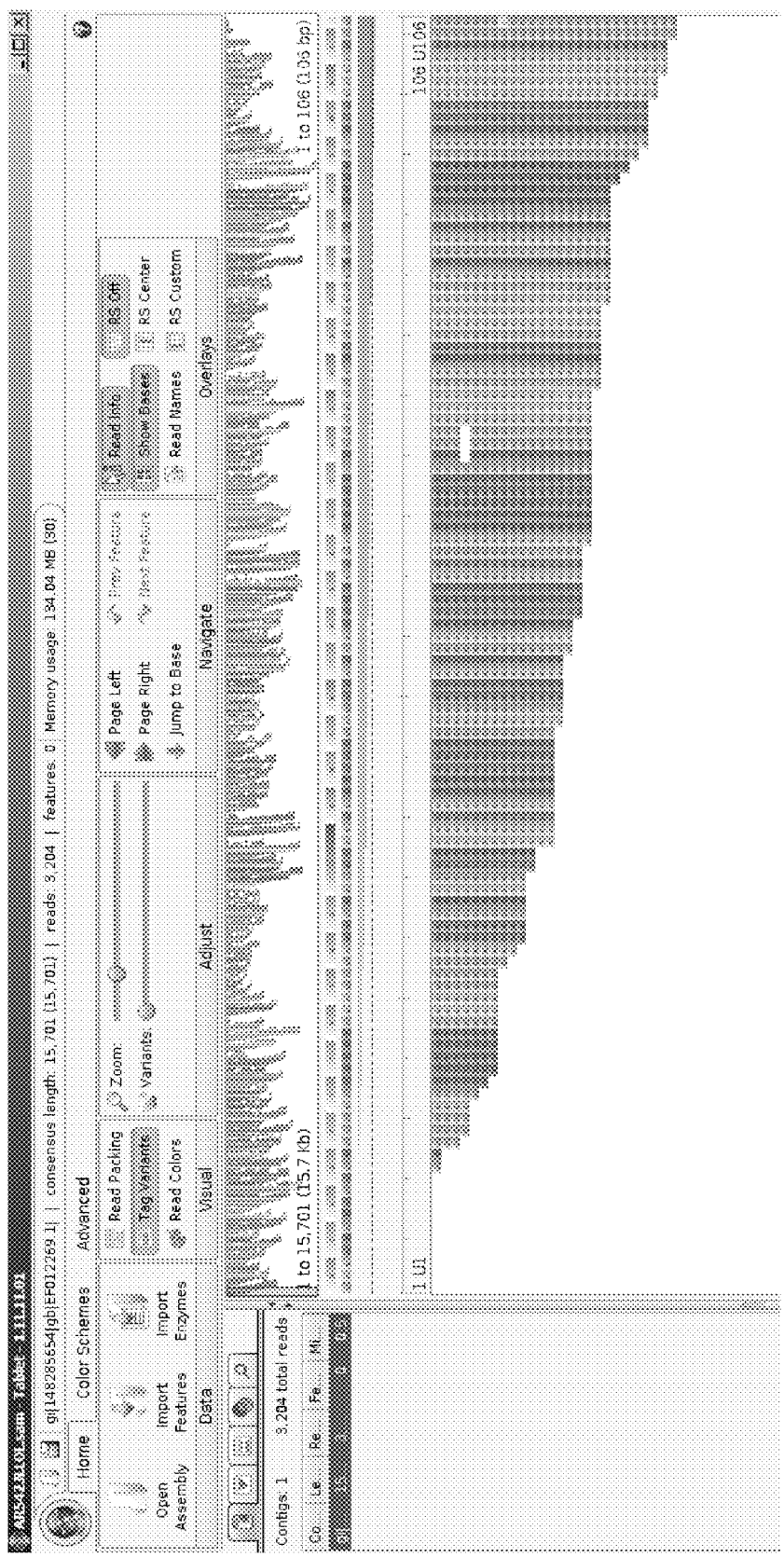
Figure 36B:
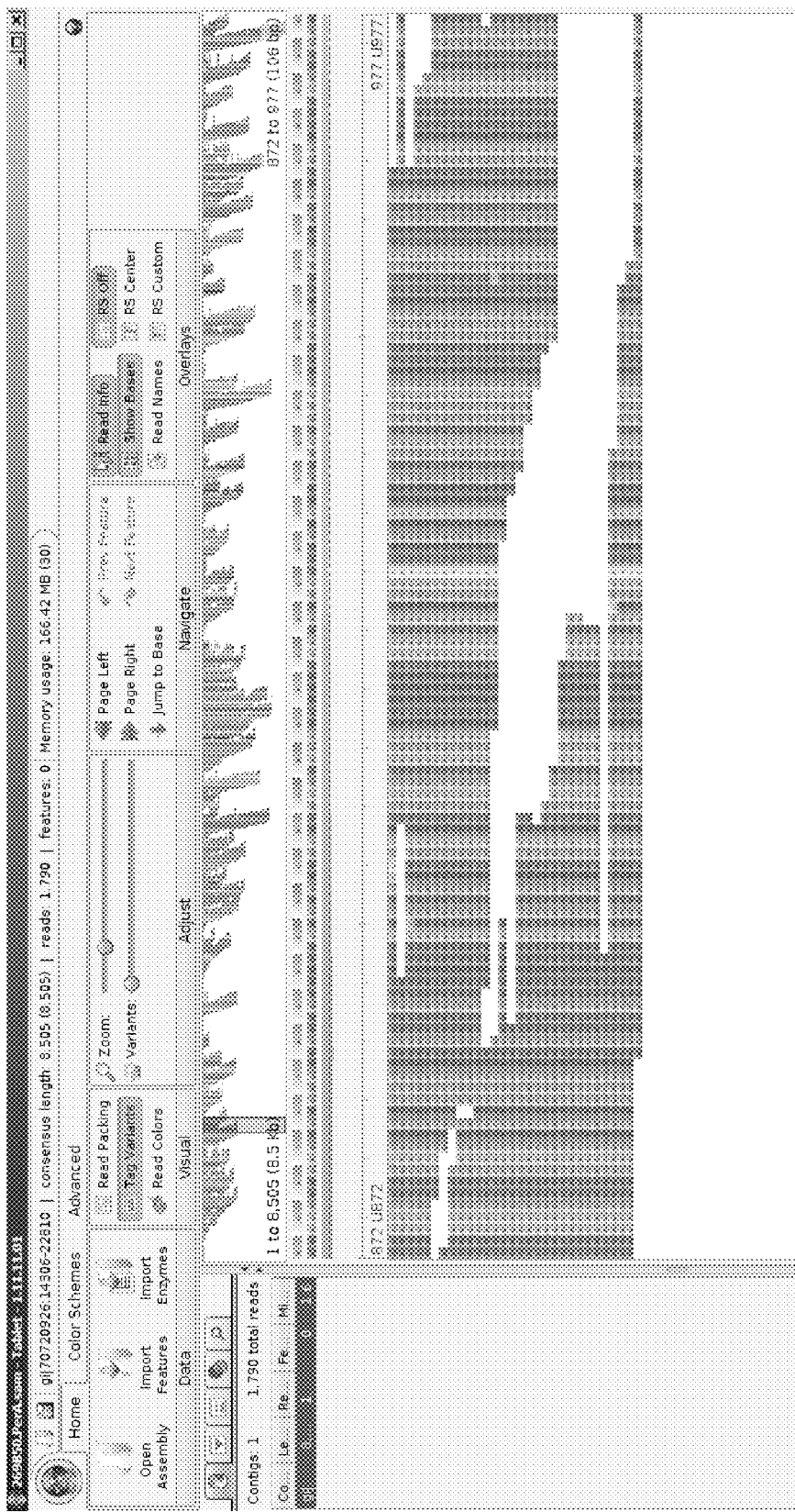
Figure 36C:
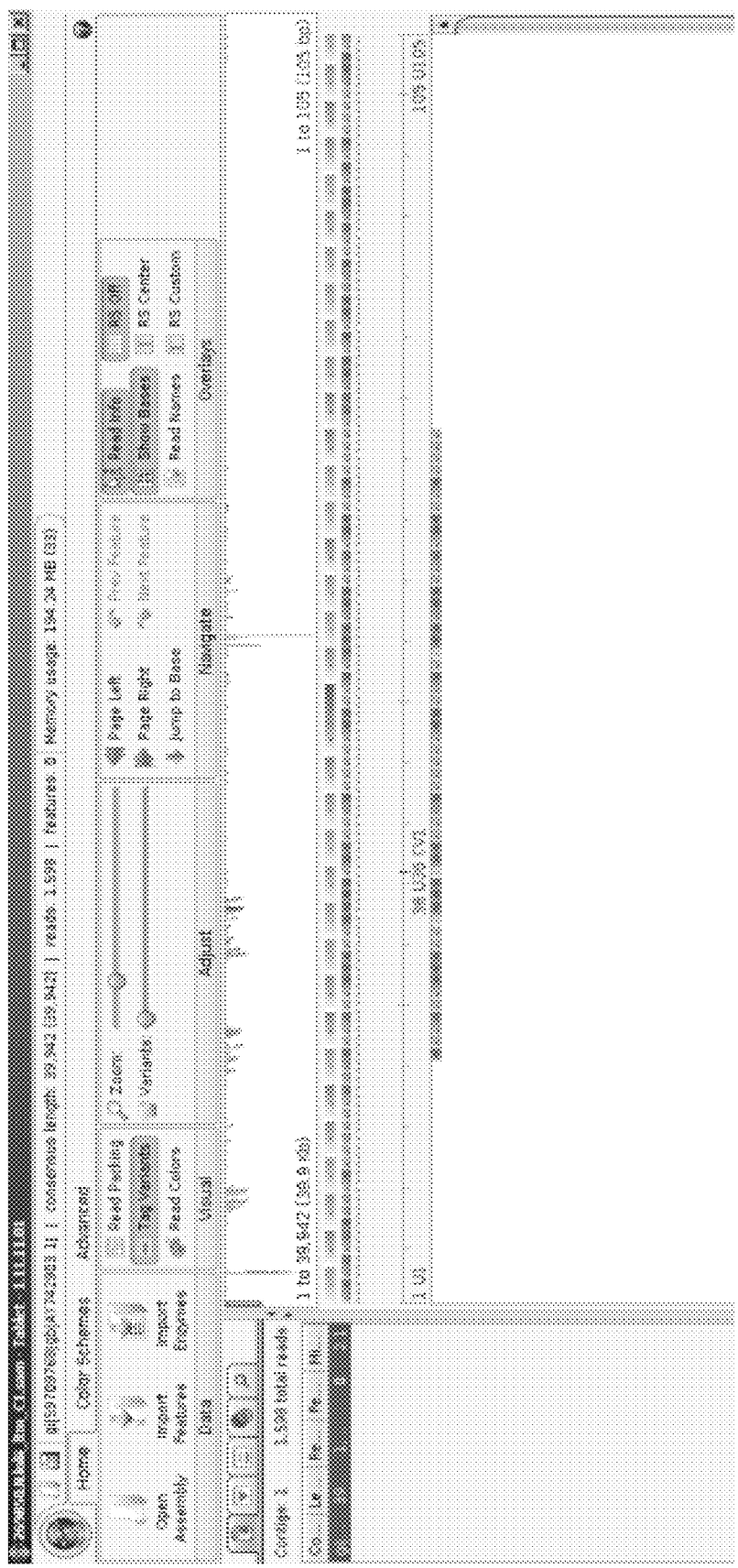
Figure 36D:
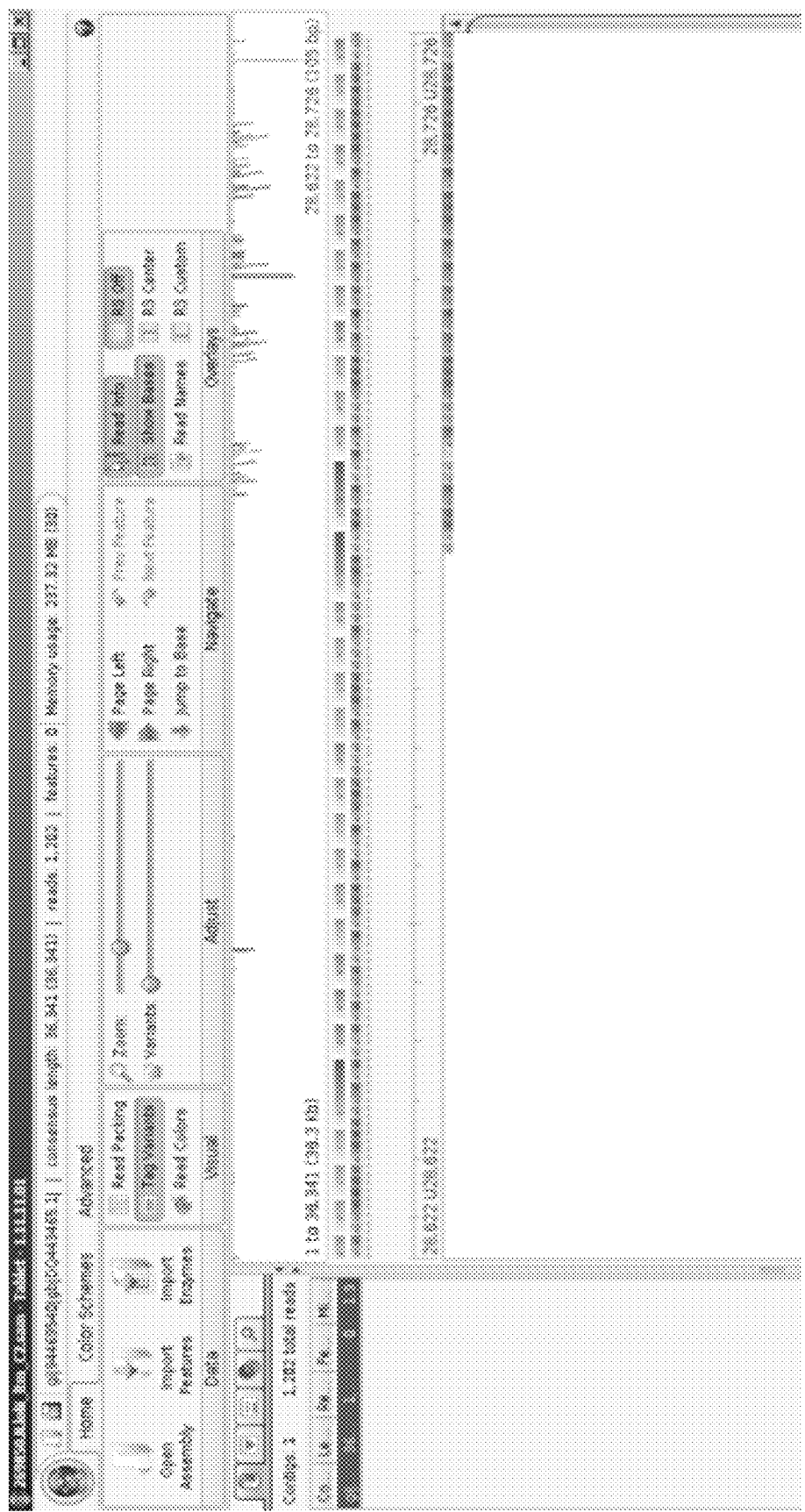
Figure 36E:
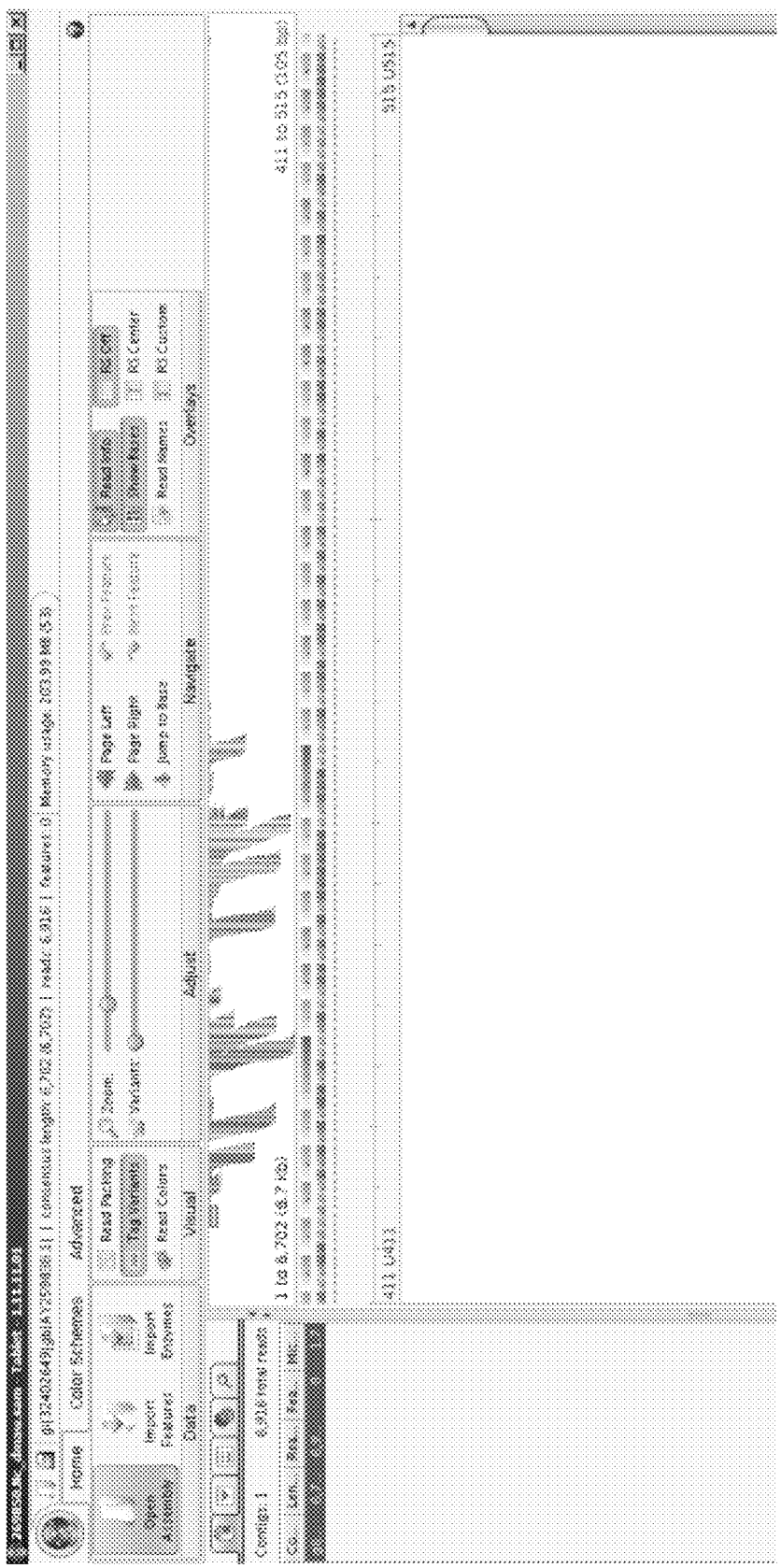
Figure 36F:
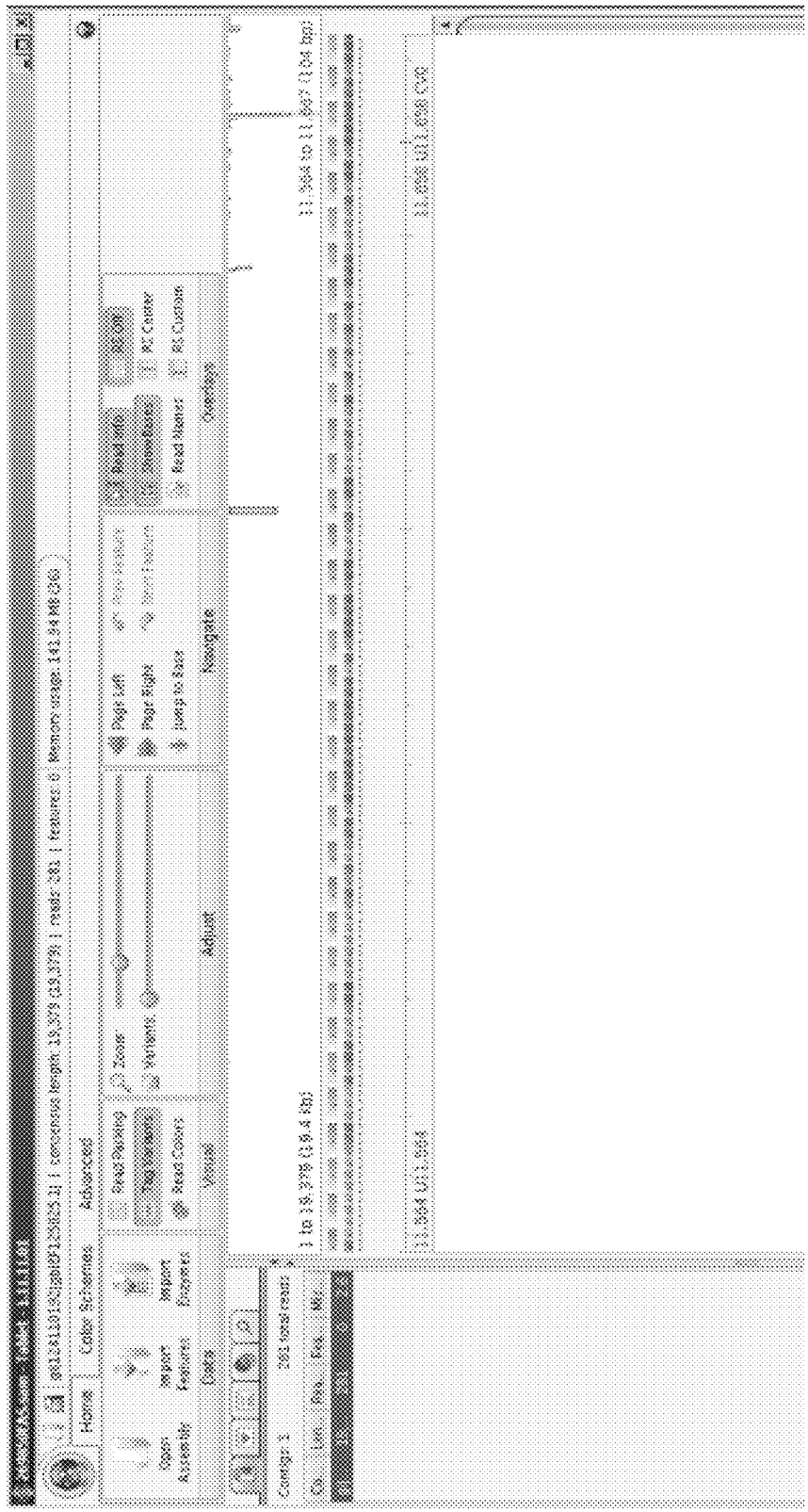

FIG. 34 shows the loline biosynthetic gene cluster.

FIGS. 35 A-D show presence of Loline biosynthetic gene cluster in endophyte strains. FIG. 35A FaTG-2 NEA17 (287819); FIG. 35B non-*Epichloe* out-group NEA18 (FEtc6-75); FIG. 35C FATG-3 NEA21 (231557); FIG. 35D *N. coenophialum* NEA16 (FEtc7-342).

FIGS. 36 A-F show alkaloid biosynthetic gene analysis for endophyte strain NEA23 (269850). FIG. 36A Presence of loline gene cluster; FIG. 36B Presence of peramine gene; FIG. 36C Analysis of Lolitrem gene cluster 01; FIG. 36D Analysis of Lolitrem gene clusters 02 and 03; FIG. 36E Analysis of dmaW gene for ergovaline production; FIG. 36F Analysis of eas gene cluster for ergovaline production.

Figure 37:
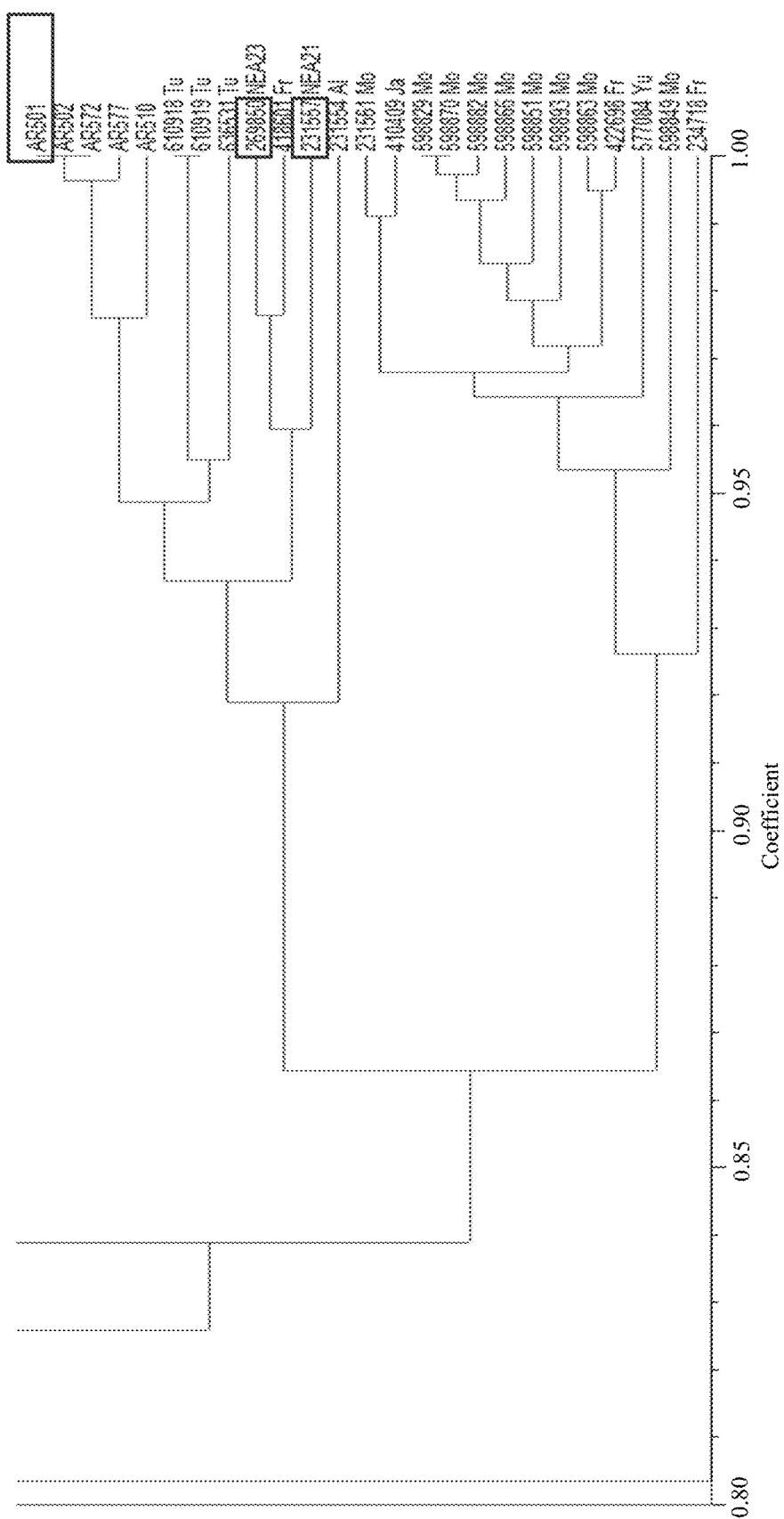

FIG. 37 shows genotypic analysis of NEA23 and NEA21.

Figure 38:
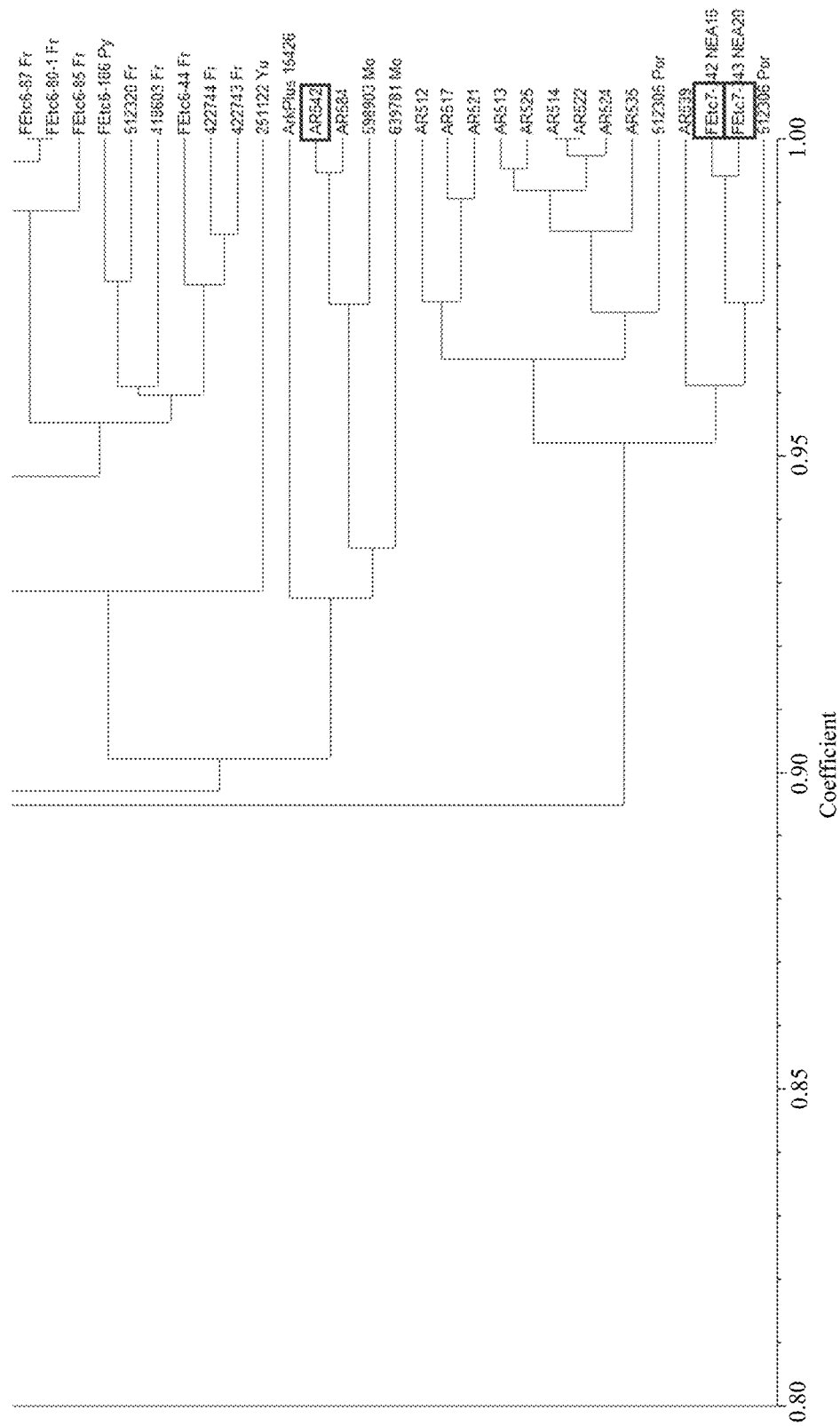

FIG. 38 shows genotypic analysis of NEA16 and NEA20.

Figure 39:
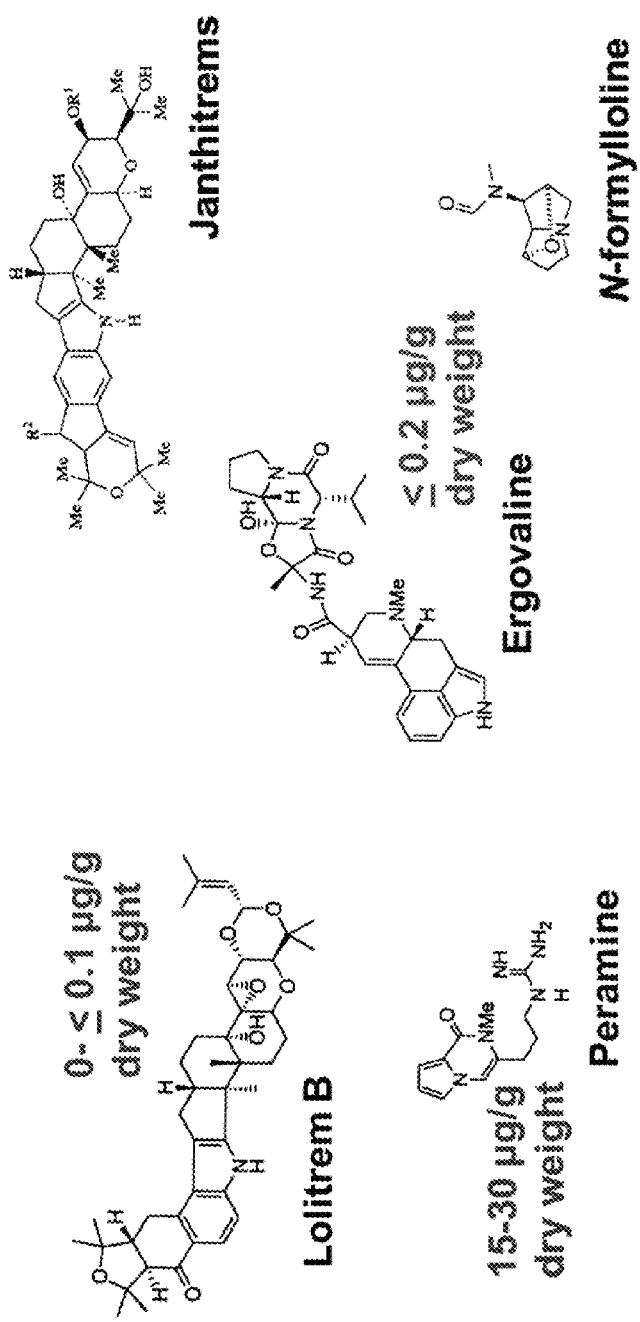

FIG. 39 shows the desired toxin profile of perennial ryegrass endophytes.

Figure 40:
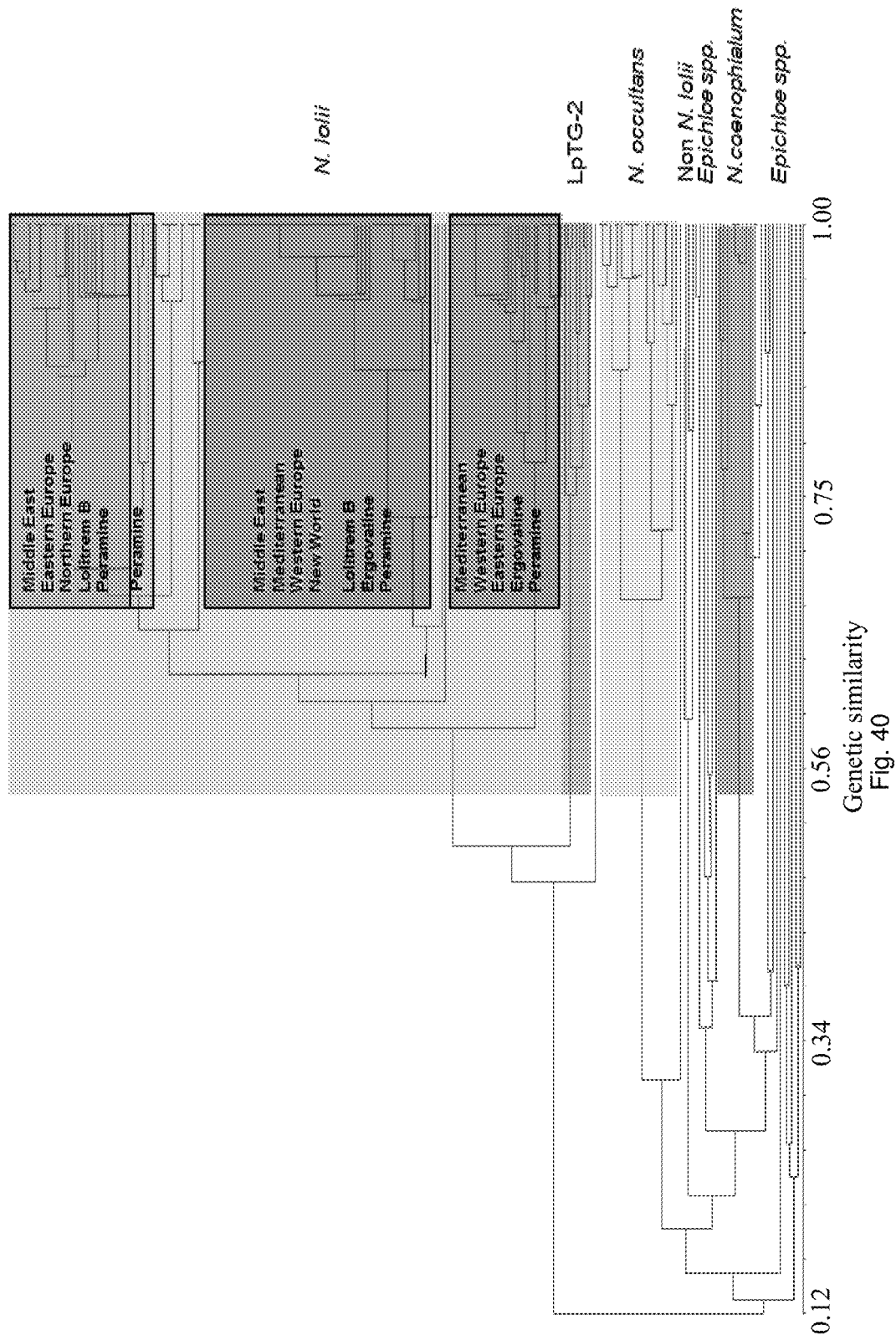

FIG. 40 shows genotypic analysis of endophyte content in accessions from a targeted ryegrass germplasm collection.

Figure 41:
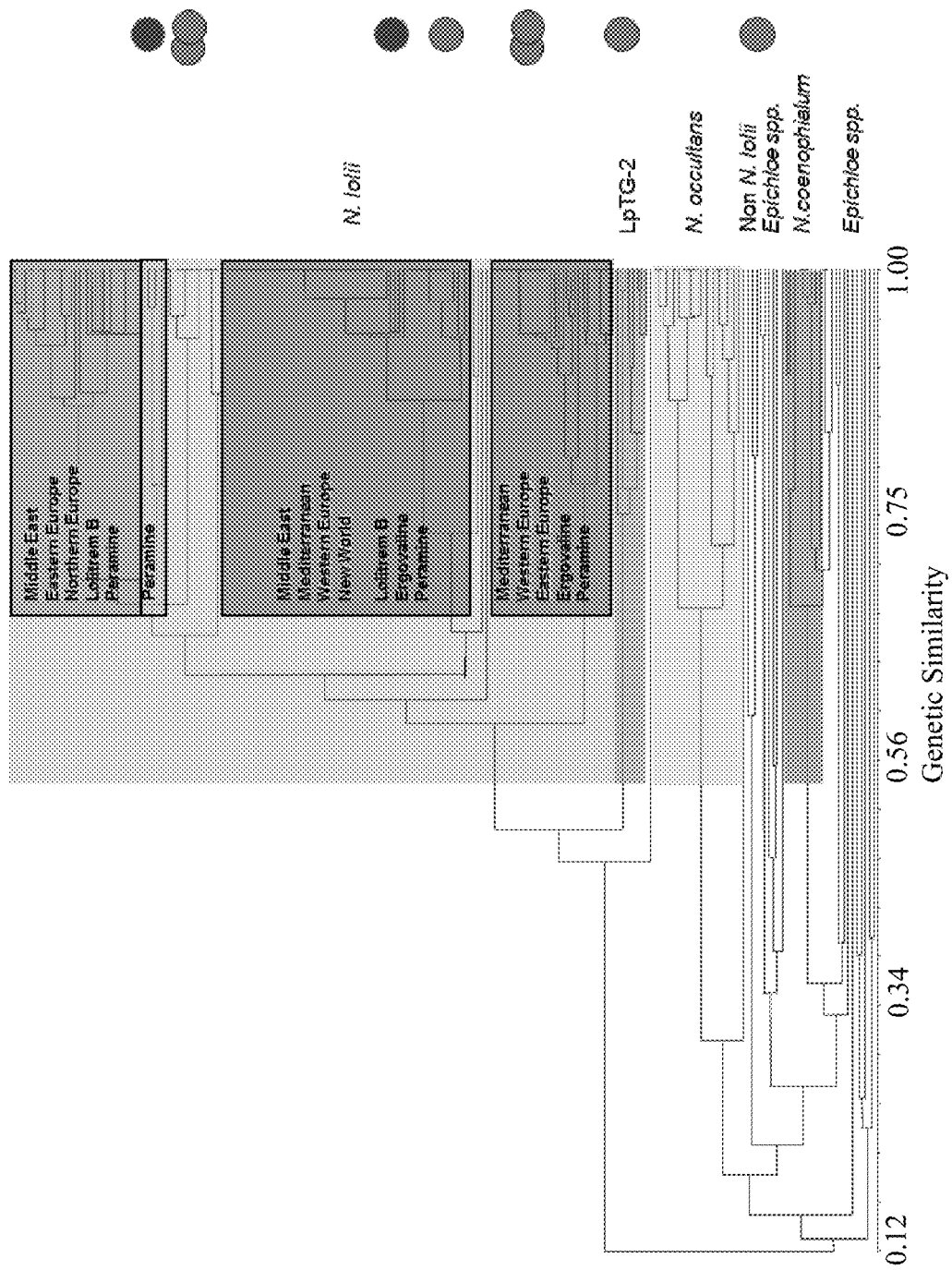

FIG. 41 shows analysis of endophyte content in accessions from a targeted ryegrass germplasm collection. Grey circles—candidates; Black circles—controls.

Figure 42:
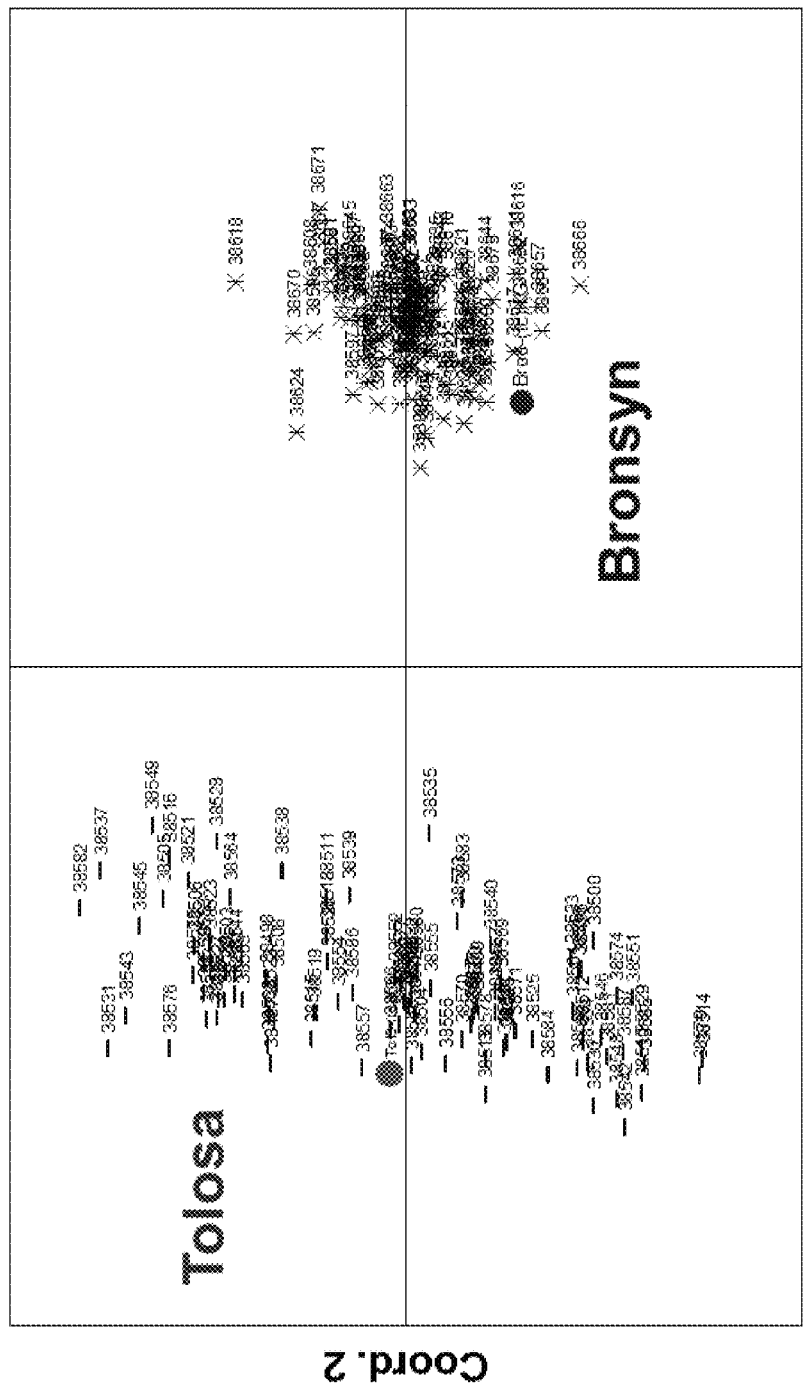

FIG. 42 shows an isogenic host plant genotype cultivar 'likeness' determination

Figure 43:
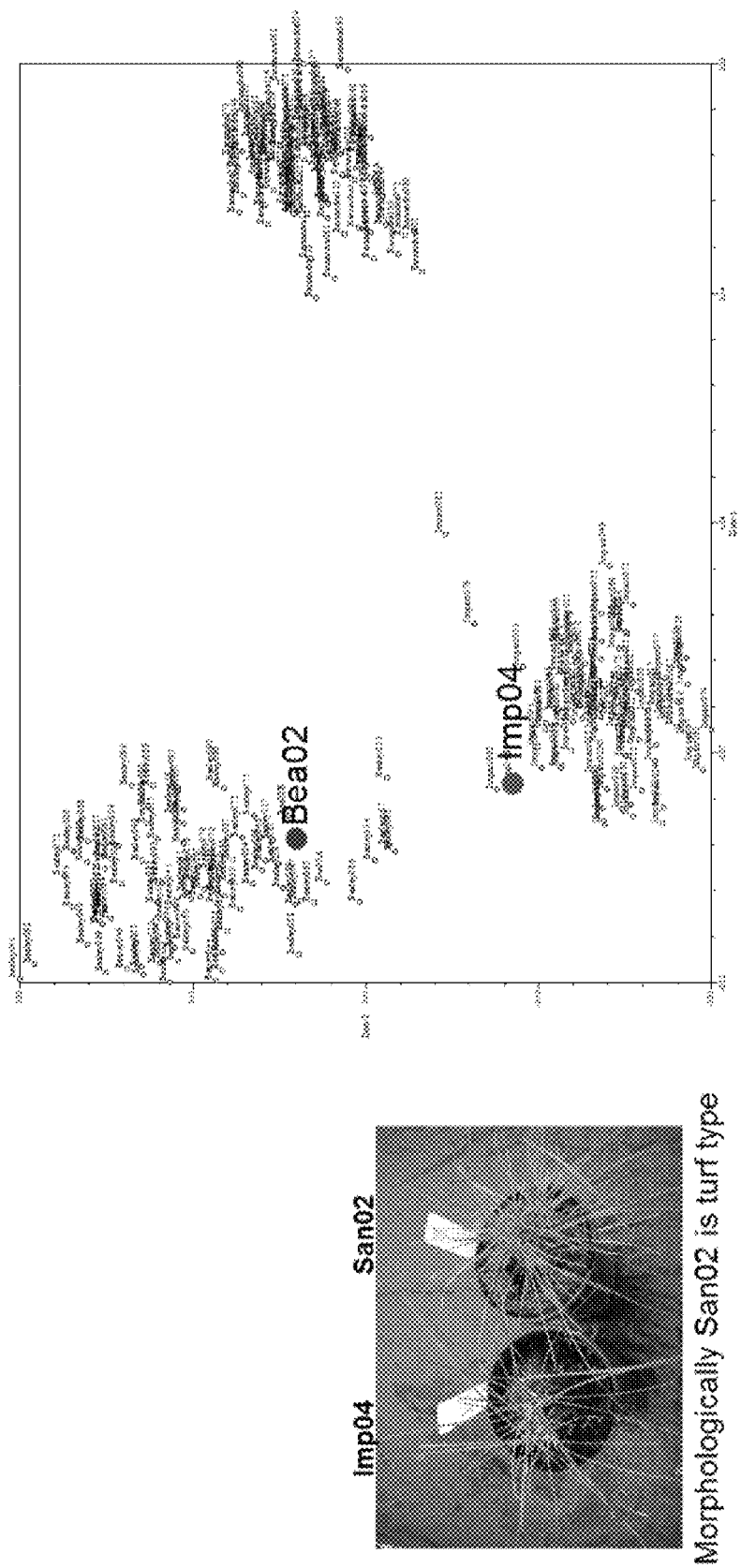

FIG. 43 shows an isogenic host plant genotype cultivar 'likeness' determination.

Figure 44:
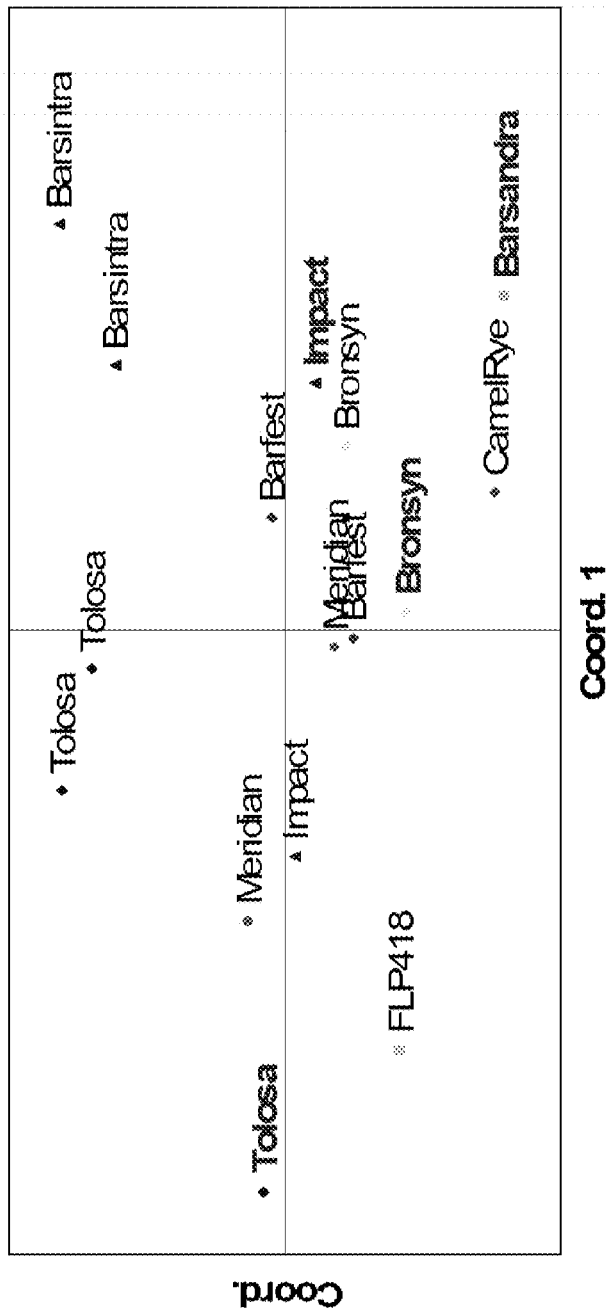

FIG. 44 shows development of a host-panel molecular genetic test for QC of host-endophyte associations.

Figure 45:
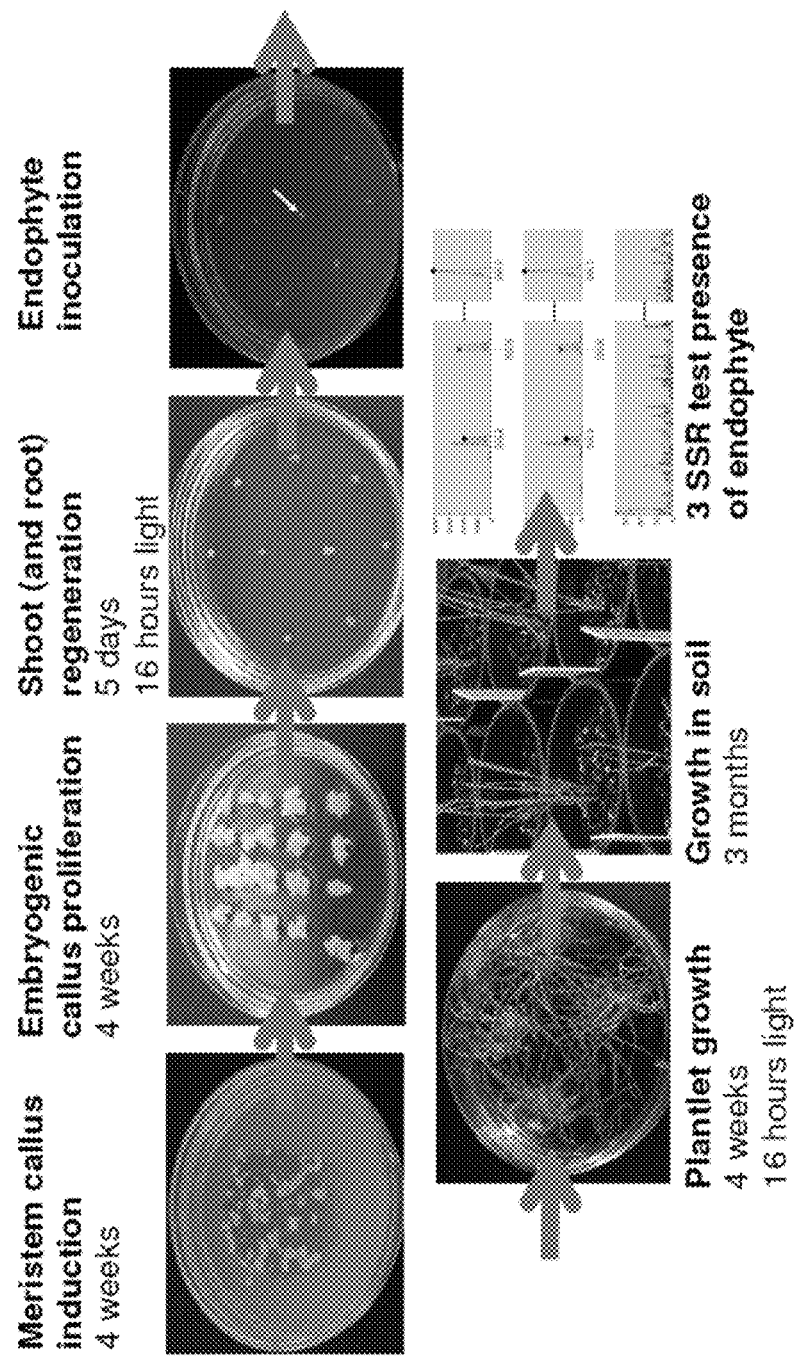

FIG. 45 shows inoculation of candidate endophytes into meristem cultures of diverse ryegrass host panel.

Figure 46:
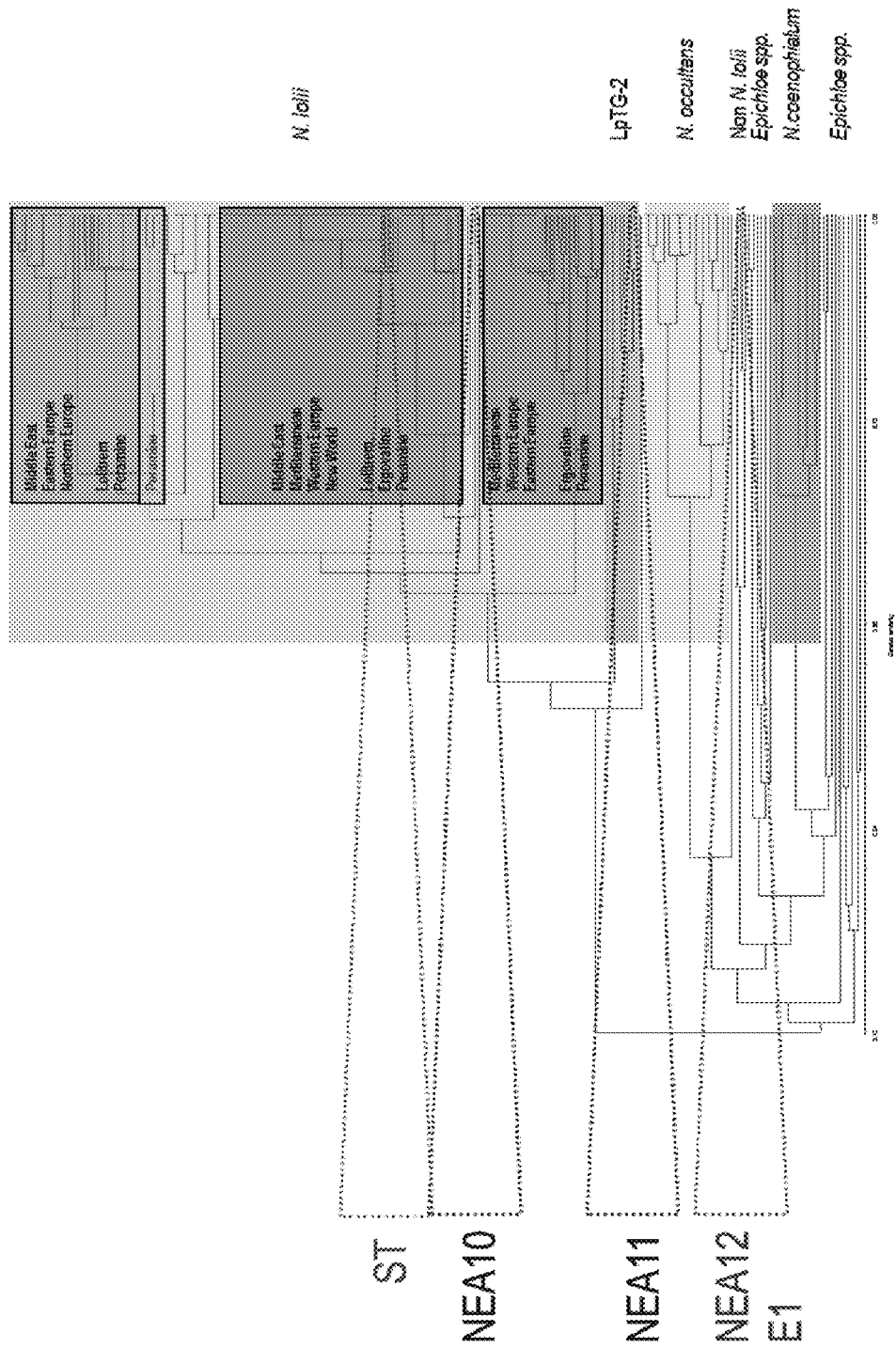

FIG. 46 shows selected endophytes.

Figure 47:
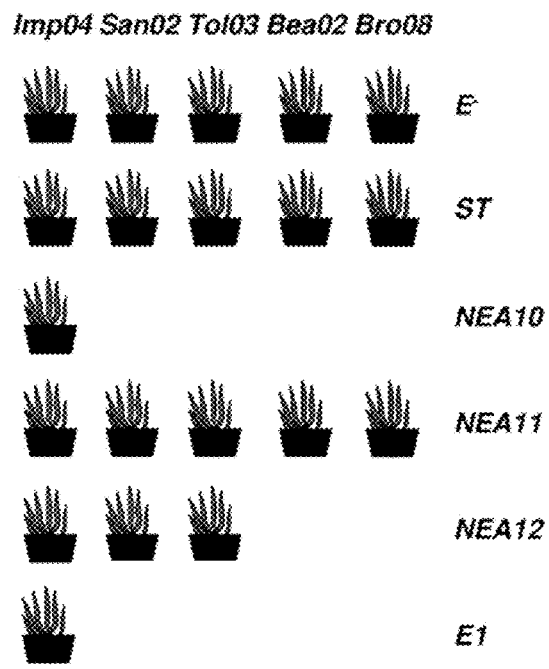

FIG. 47 shows a detailed characterisation of the known knowns and their precursors.

Figure 48:
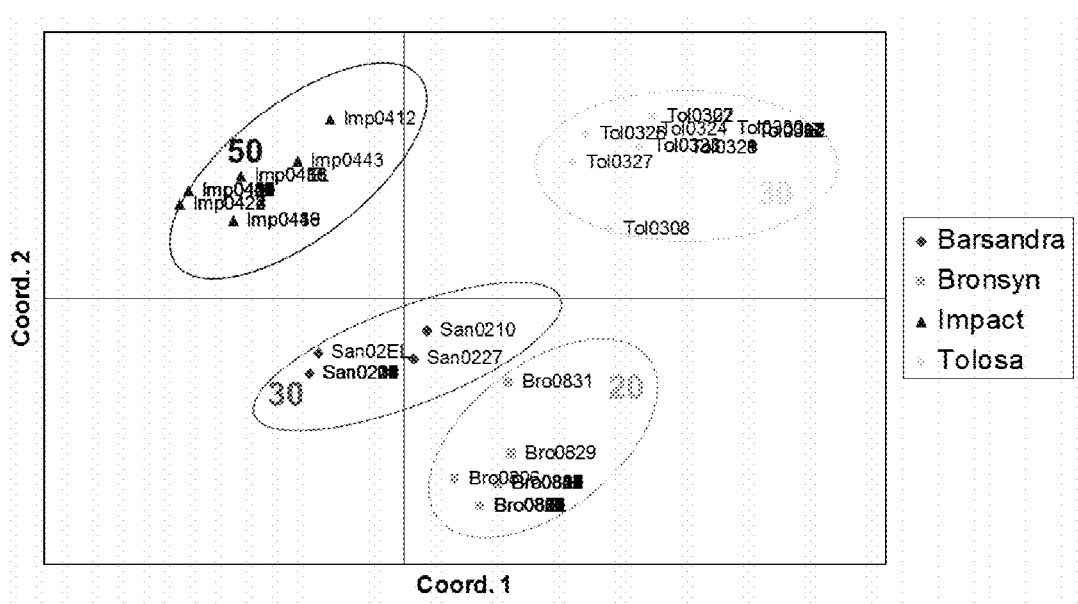

FIG. 48 shows a host-panel identification test.

Figure 49:
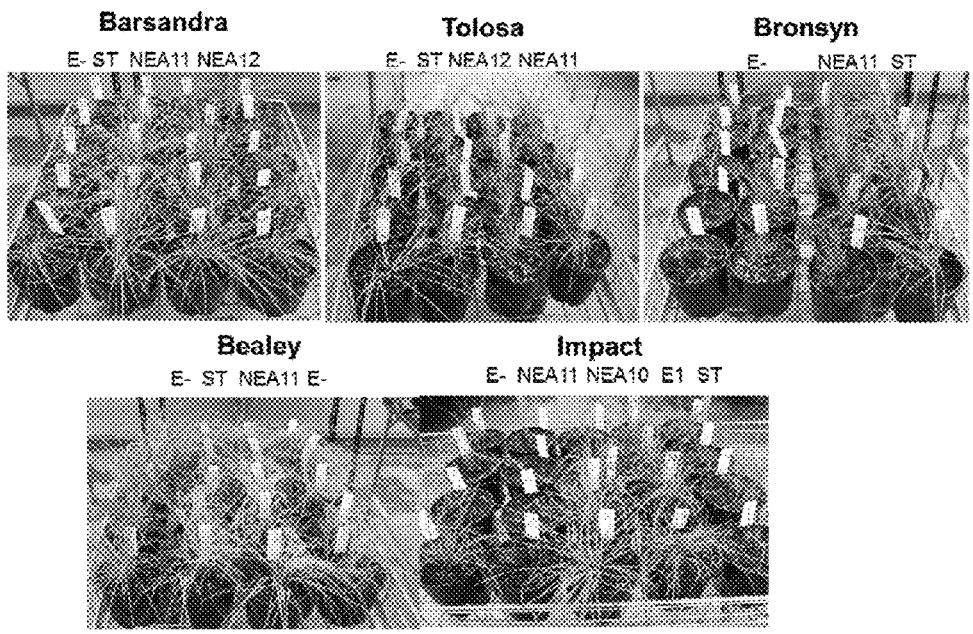
Figure 50:

FIGS. 49 and 50 show in-depth metabolic profiling of novel isogenic host-endophyte associations.

Figure 51:
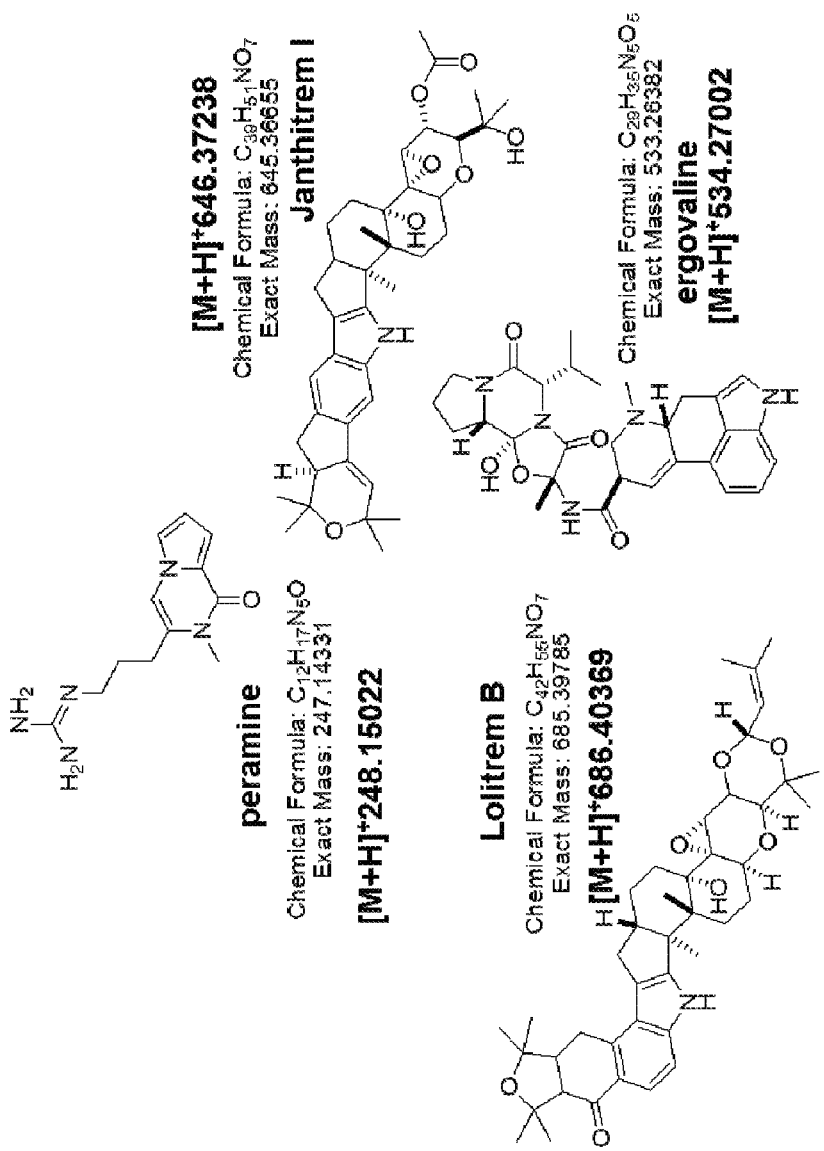

FIG. 51 shows LEPJ: the known knowns.

Figure 52:
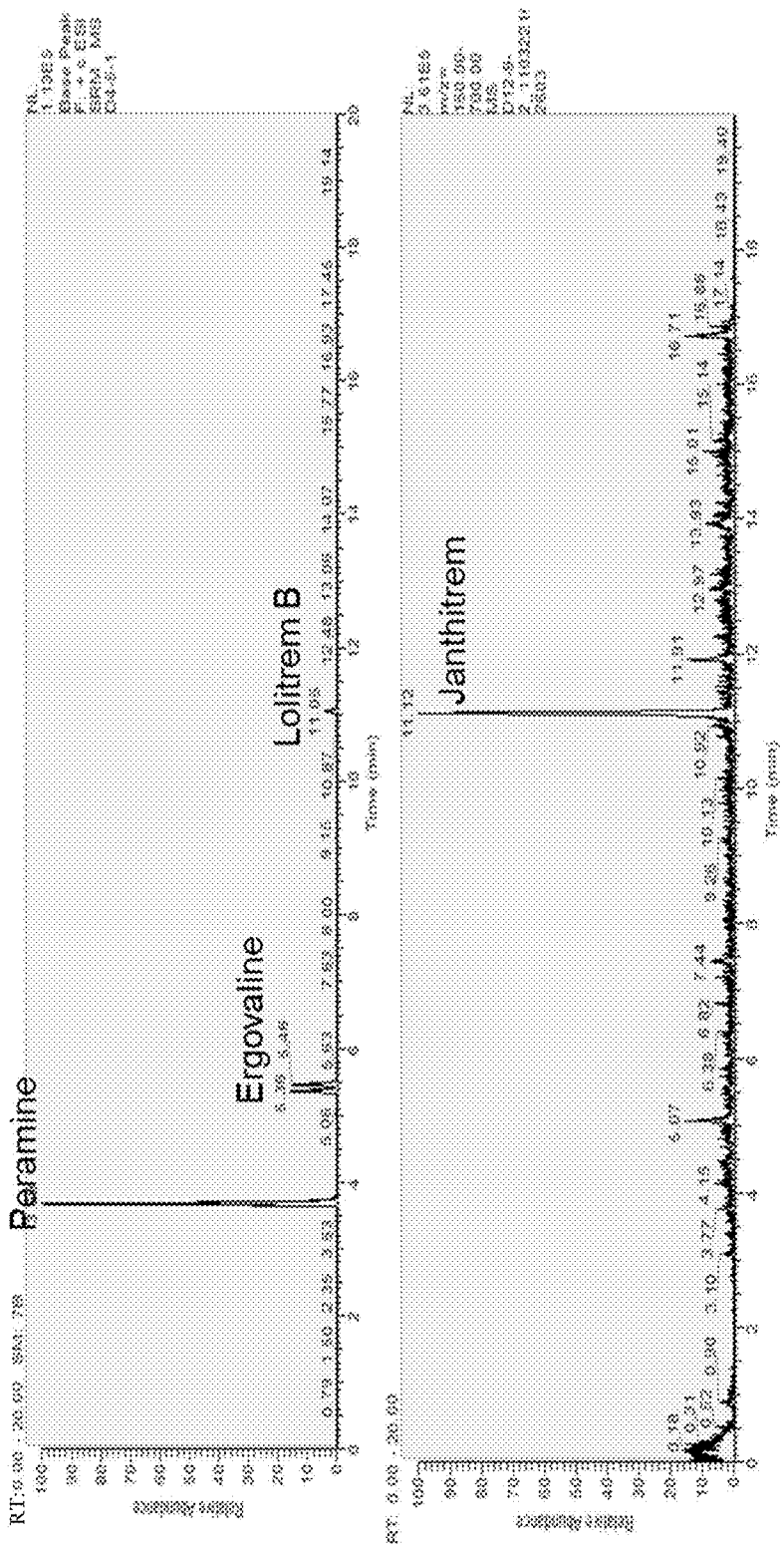

FIG. 52 shows accurate mass of LEPJ.

Figure 53:
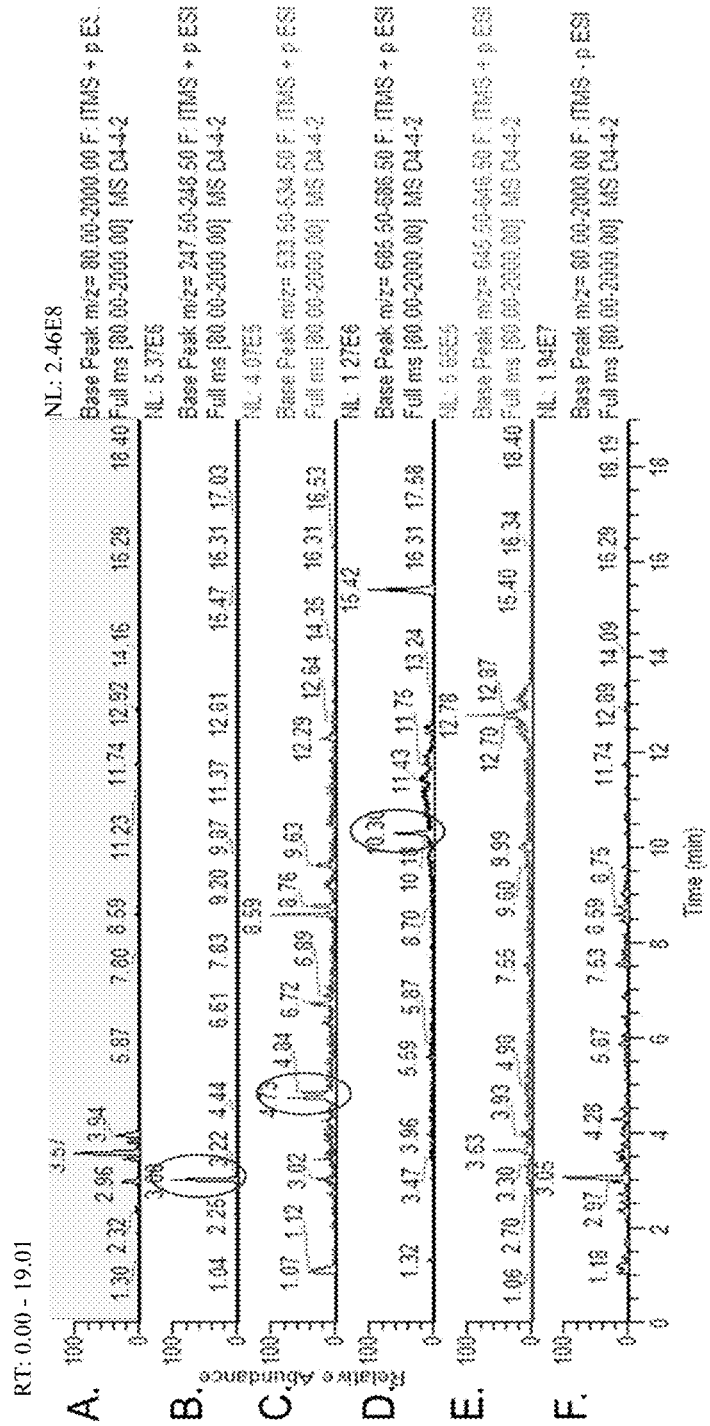

FIG. 53 shows identification of LEPJ. LCMS analysis of one replication of associations of Bro08_ST_1 displaying extracted ion chromatogram. (A) positive ion extraction (B) peramine; (C) ergovaline; (D) lolitrem B (E) Janthitrem (F) Negative ion extraction.

Figure 54:
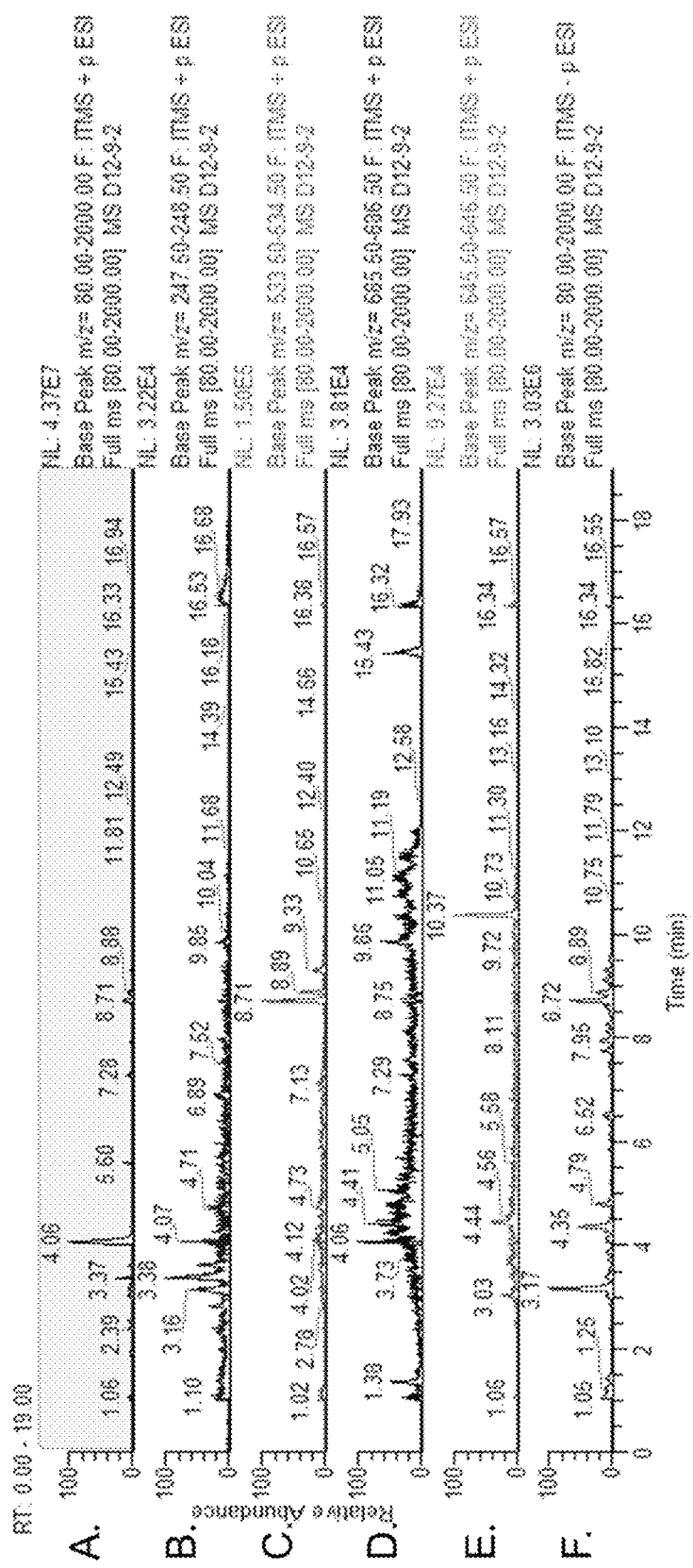

FIG. 54 shows identification of LEPJ. LCMS analysis of one replication of associations of Tolosa_NEA12 displaying extracted ion chromatogram. (A) positive ion extraction (B) peramine; (C) ergovaline; (D) lolitrem B (E) Janthitrem (F) Negative ion extraction.

Figure 55:
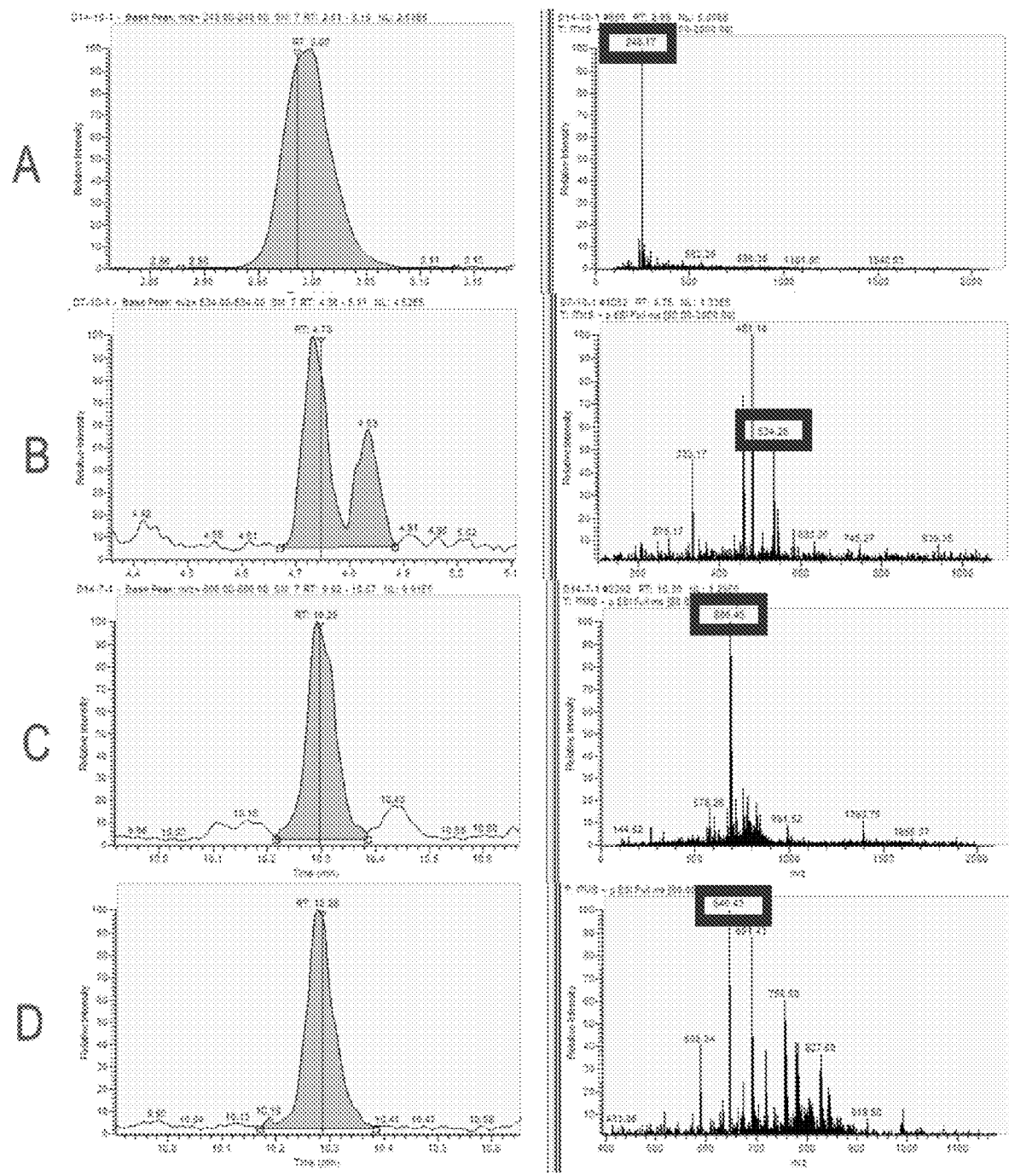

FIG. 55 shows quantification of LEPJ. LCquant analysis of alkaloid content. according to the retention time and spectrum (A) peramine; (B) ergovaline; (C) lolitrem B; (D) Janthitrem.

Figure 56:
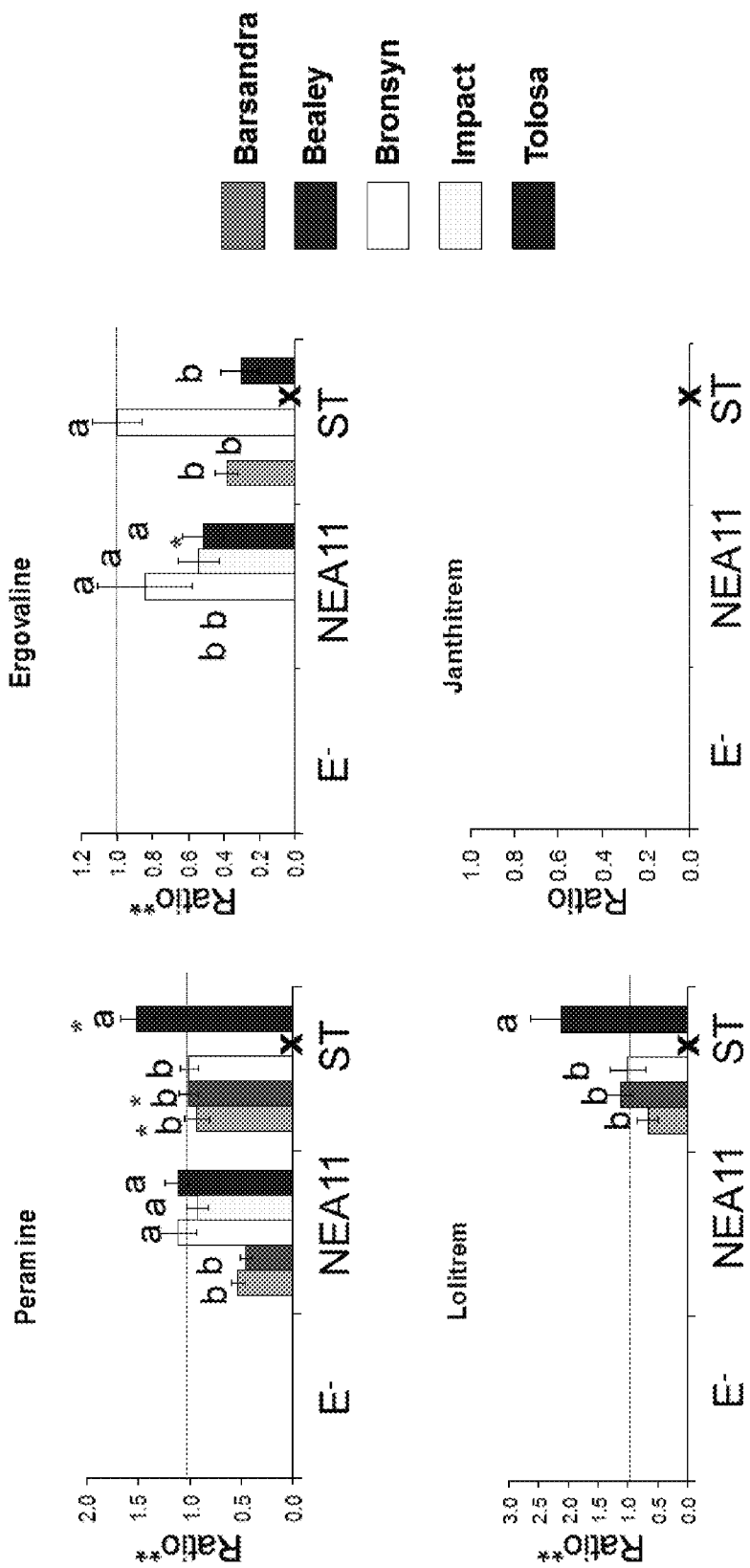

FIG. 56 shows a comparison of semi-quantitative alkaloid (LEPJ) profiles of E$^+$ versus E$^-$ host plants. Y error bars denote standard errors; Letters above each column indicate significant differences between different hosts harbouring same endophyte; *indicate significant differences between the same host harbouring different endophytes; **Ratio values are relative to Bronsyn ST.

Figure 57:
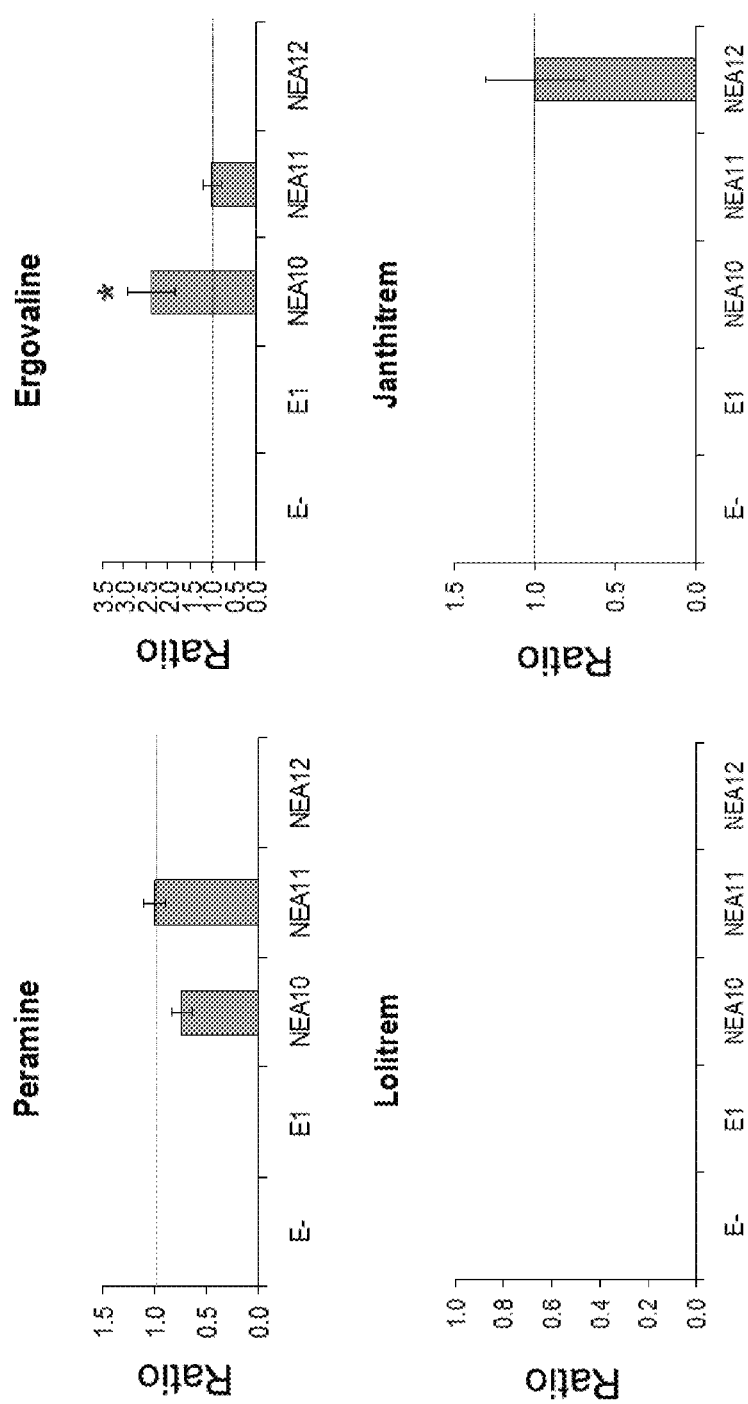

FIG. 57 shows a comparison of semi-quantitative alkaloid profiles for diverse endophytes in an isogenic host (Imp04). The Y error bars denote standard errors; Indicate significant differences between the same host harbouring different endophytes.

Figure 58:
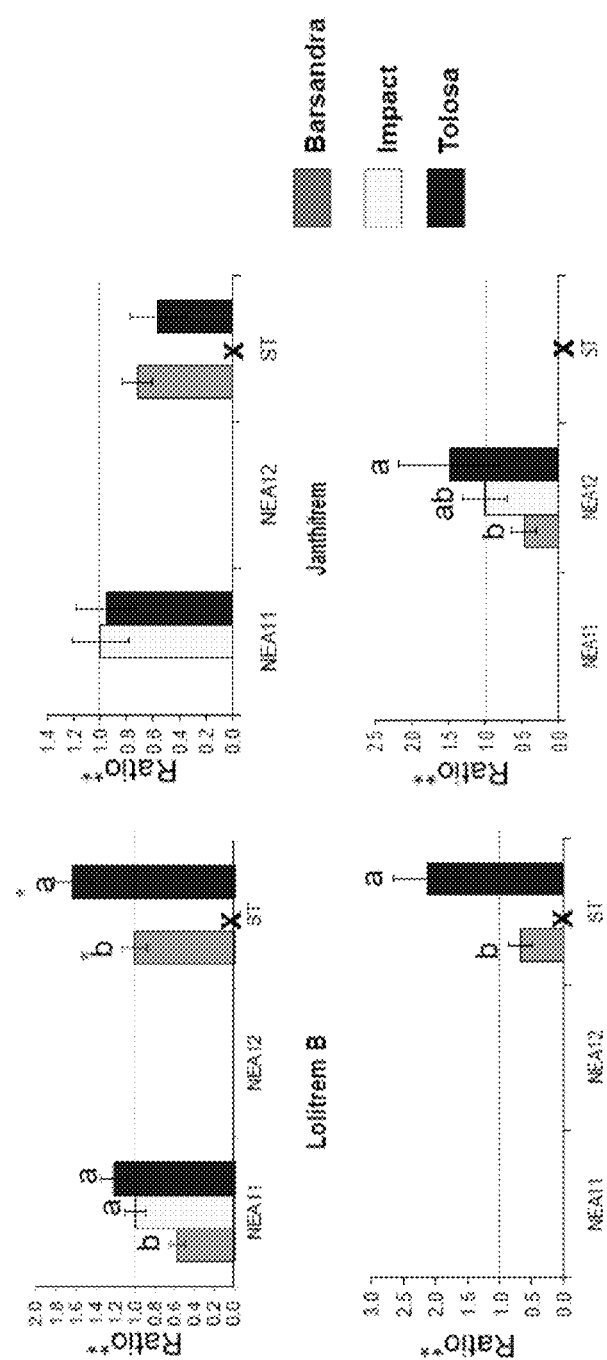

FIG. 58 shows an assessment of stability of alkaloid (LEPJ) profile of selected endophytes across different isogenic hosts. Y error bars denote standard errors; Letters above each column indicate significant differences between different hosts harbouring same endophyte. *indicate significant differences between the same host harbouring different endophytes; **Ratio values are relative to Impact.

Figure 59:
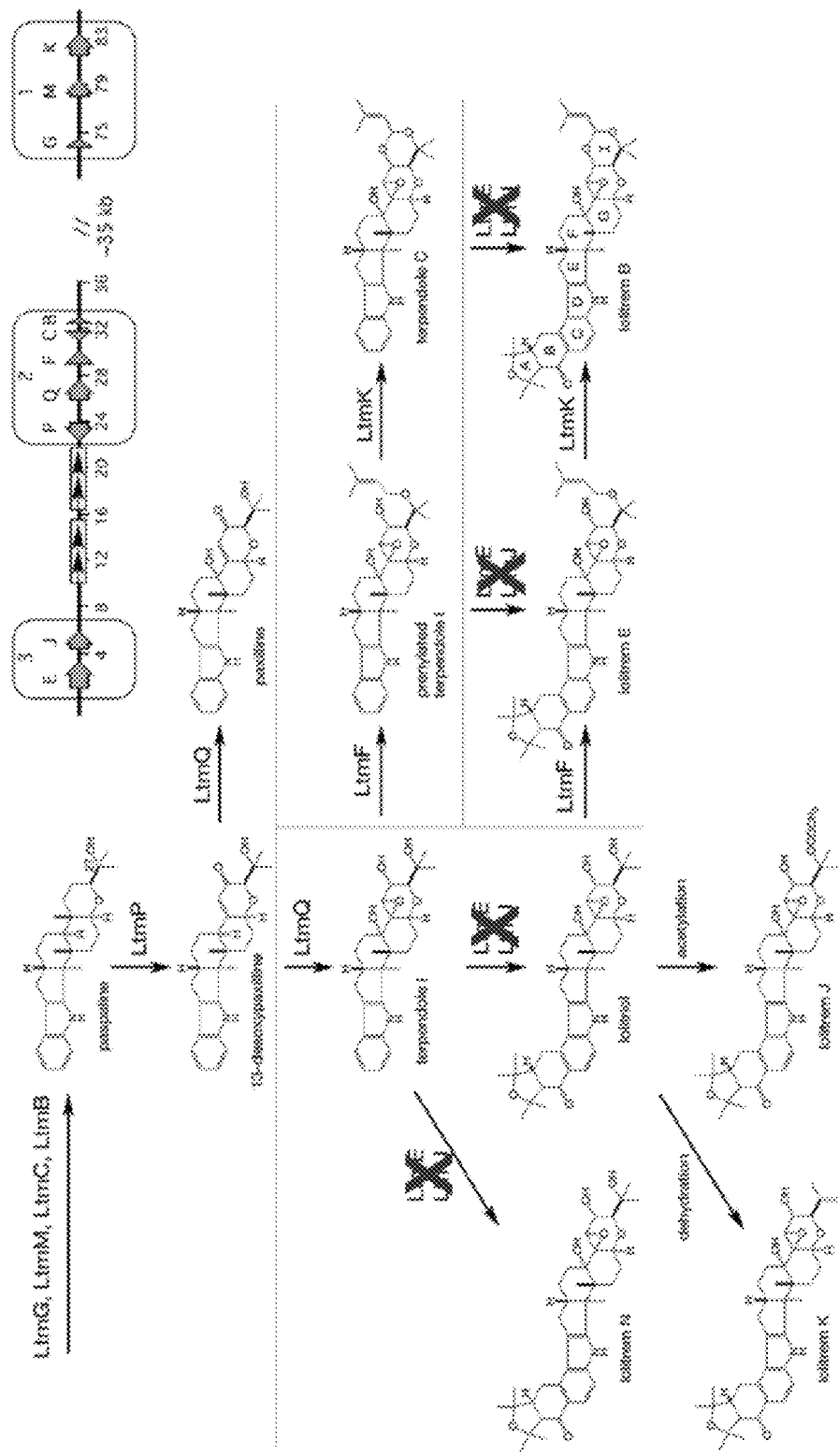

FIG. 59 shows lolitrem B biosynthesis.

Figure 60:
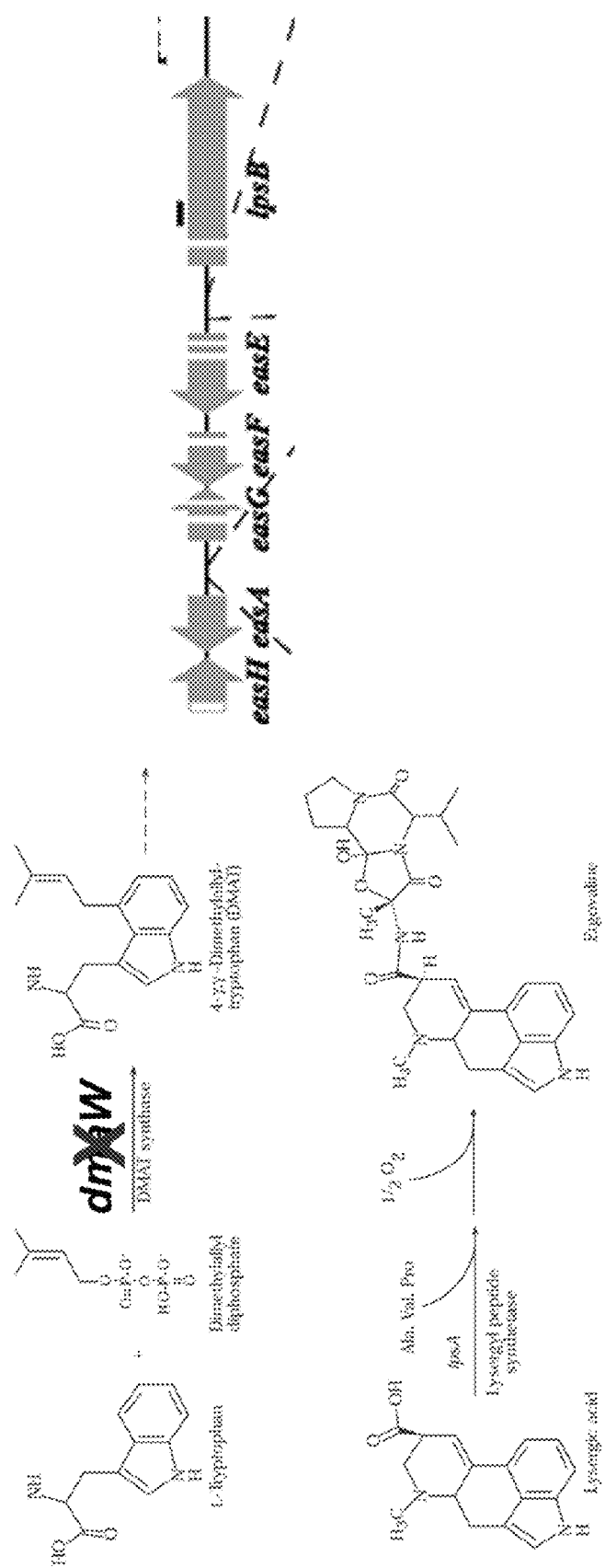

FIG. 60 shows ergovaline biosynthesis.

Figure 61:
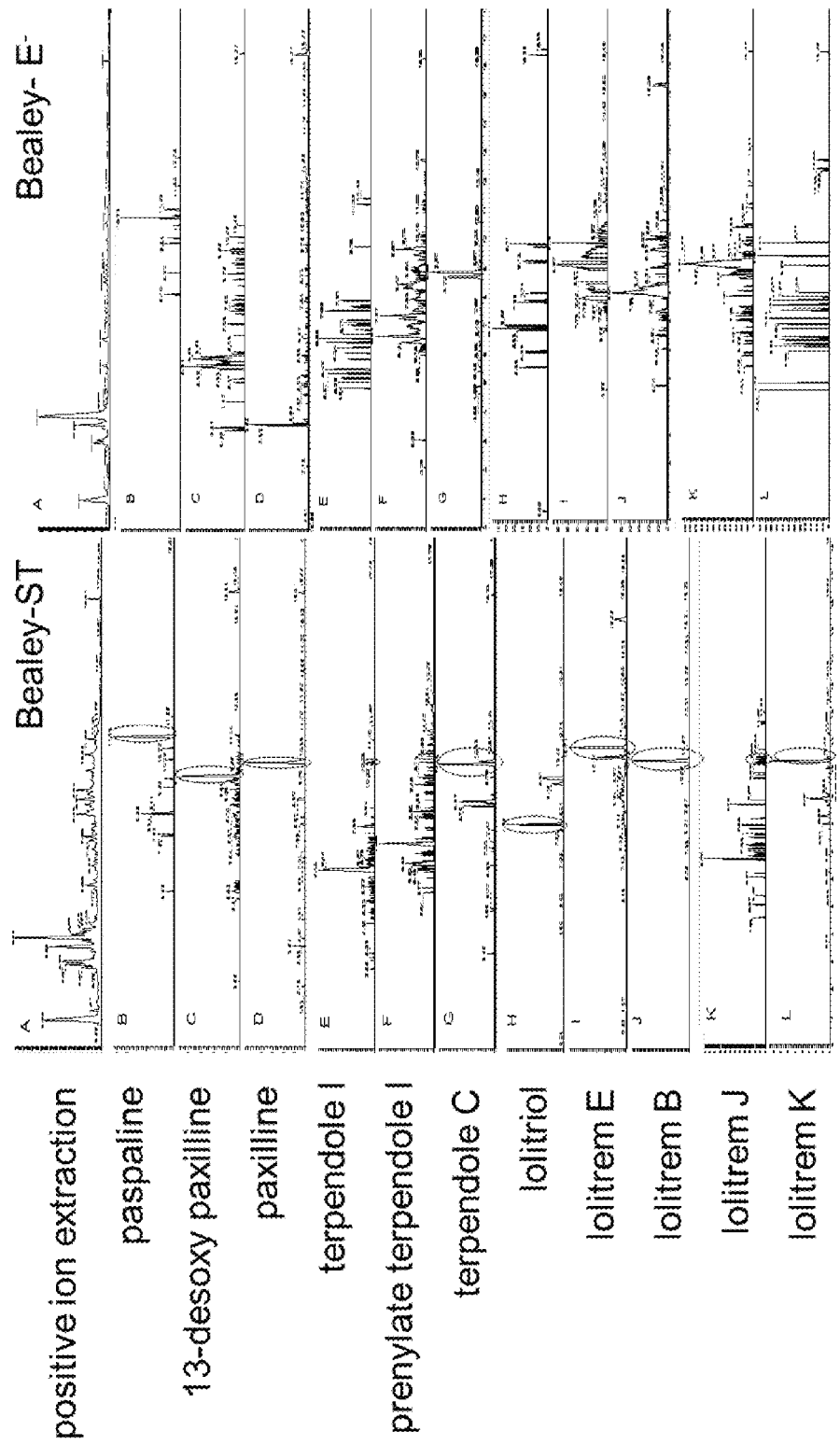

FIG. 61 shows an analysis of the lolitrem B biosynthetic pathway.

Figure 62:
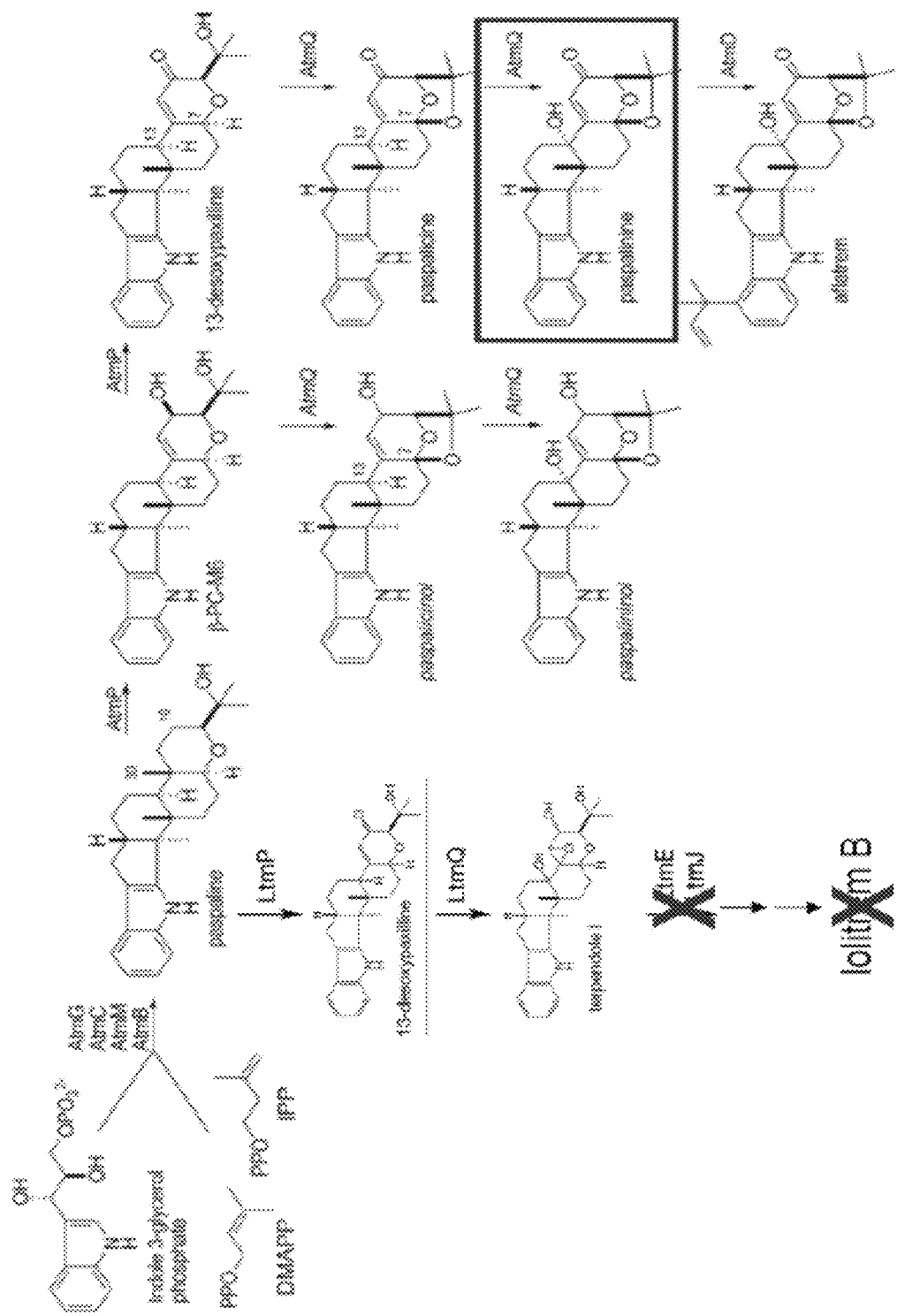

FIG. 62 shows the paspalinine—A tremorgen pathway.

Figure 63:
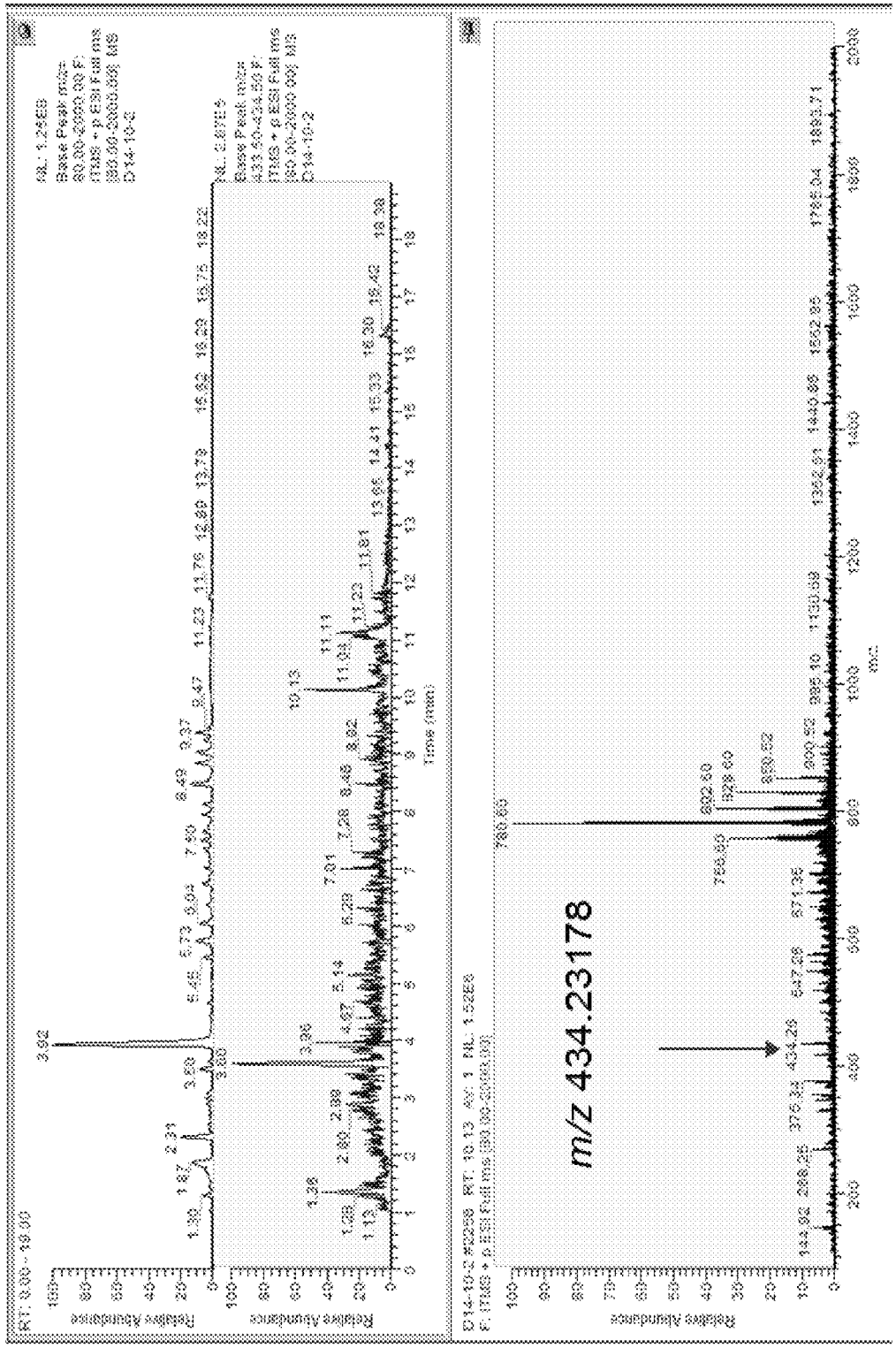

FIG. 63 shows a pathway analysis: paspalinine—A tremorgen.

Figure 64:
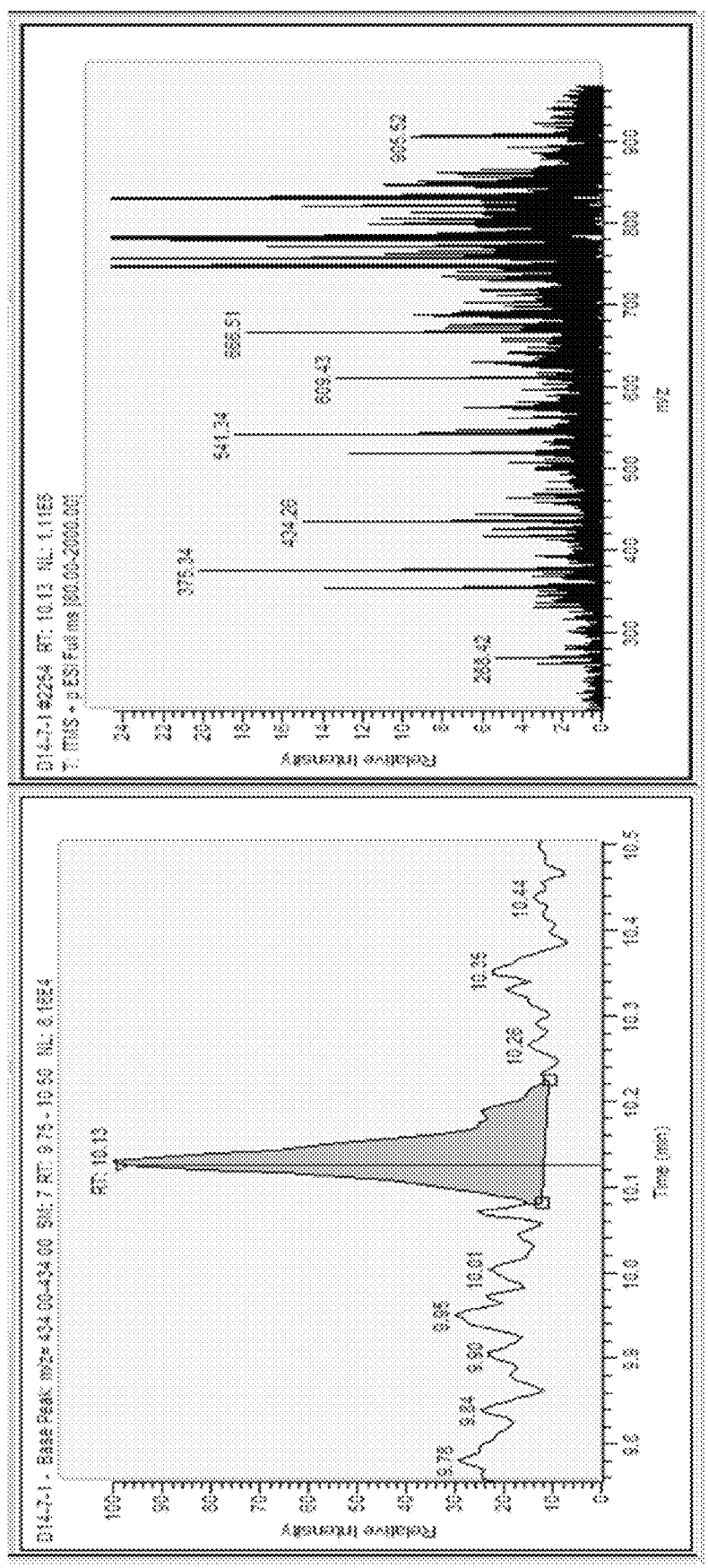

FIG. 64 shows the presence of lolitrem and paspalinine in symbiota.

Figure 65:
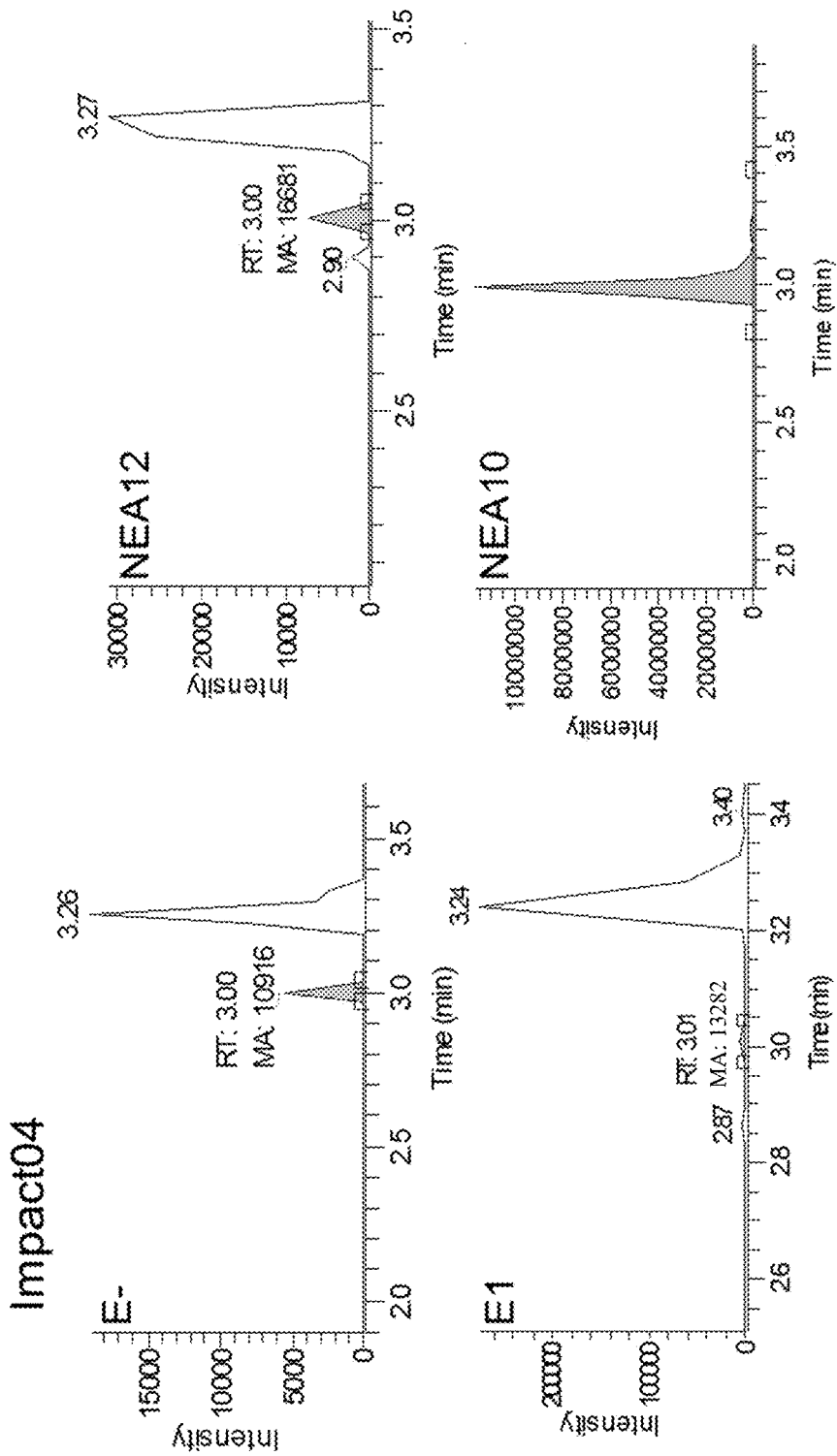

FIG. 65 shows that Peramine is present in planta in trace amounts in absence of a peramine-producing endophyte.

Figure 66:
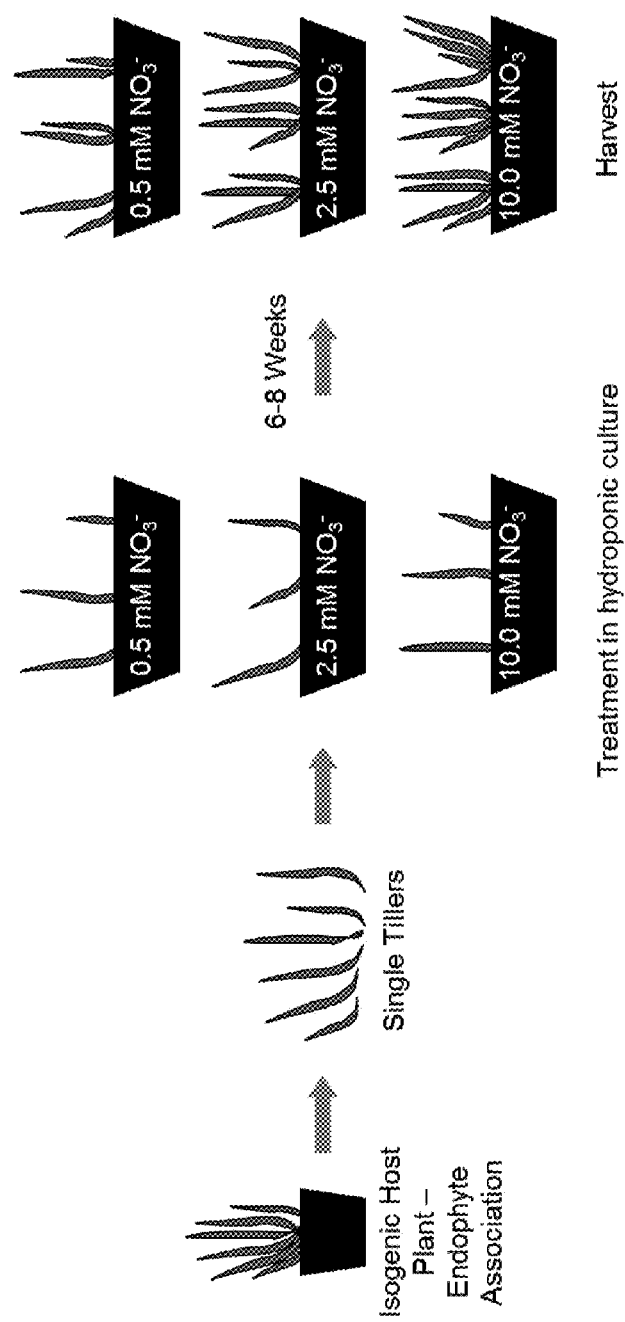
Figure 67A:
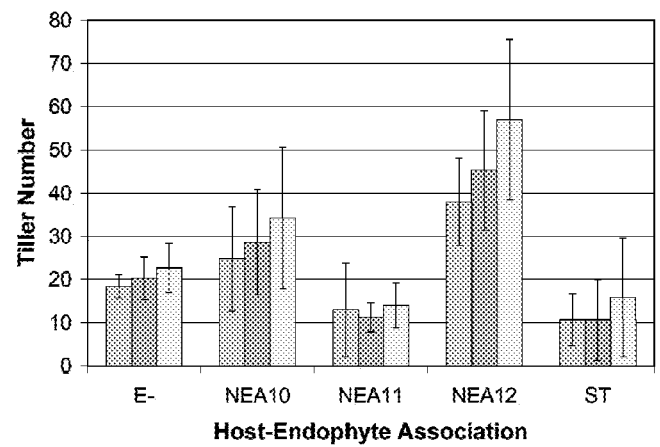
Figure 67B:
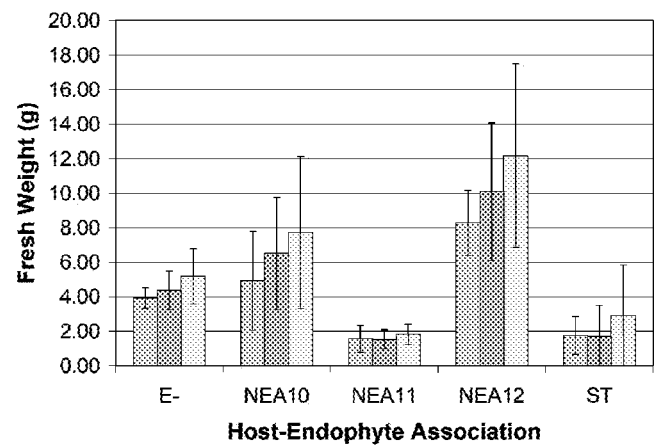
Figure 67C:
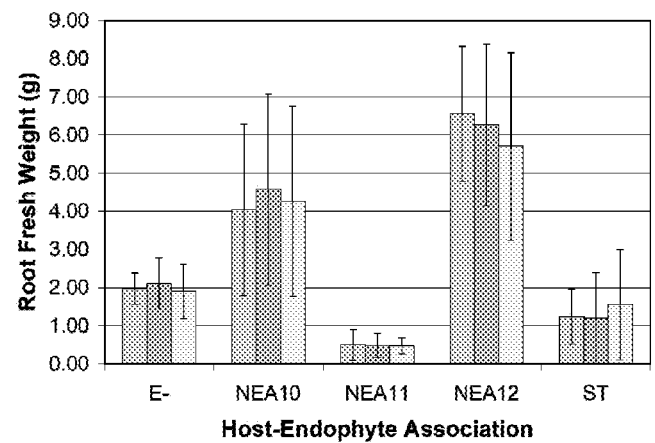
Figure 67D:
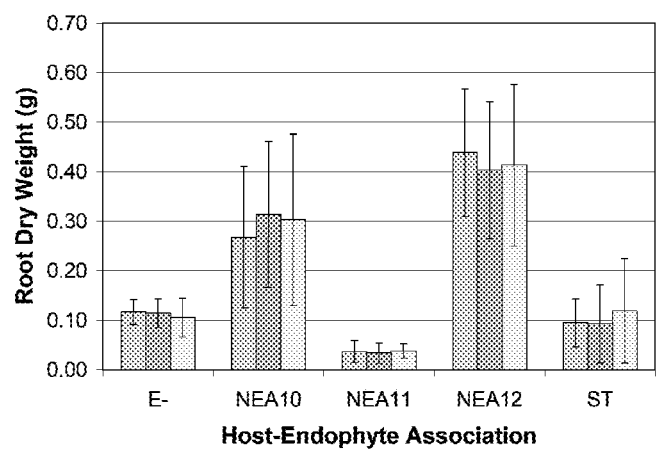

FIG. 66 shows the procedure used to assess changes to host phenotype mediated by the endophyte. 1 isogenic host: Impact (Imp04); 5 host-endophyte associations: NEA10, NEA11, NEA12, ST, E$^-$; 6 clonal replicates.

Figure 68:
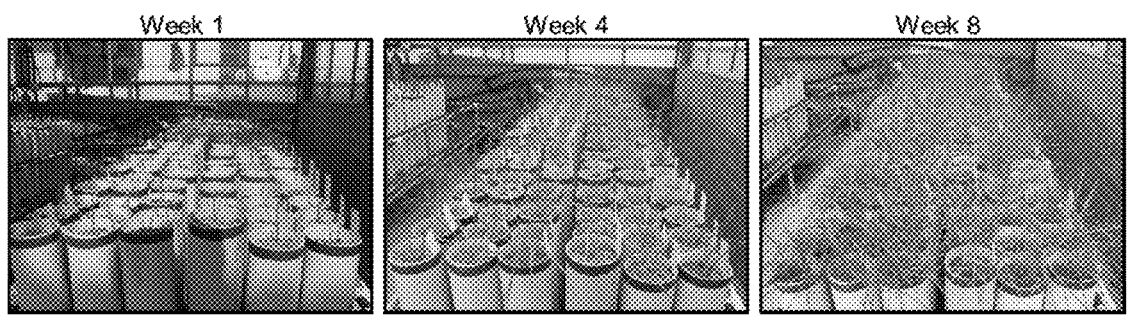

FIG. 67 shows endophyte effect on symbiotum performance. A. Tiller number; B. Shoot fresh weight; C. Root fresh weight; D. Root dry weight Mid grey—0.5 mM $NO_3^-$ Dark grey—2.5 mM $NO_3^-$ Light grey—10.0 mM $NO_3^-$ FIG. 68 shows plants before the T1 harvest.

Figure 69:
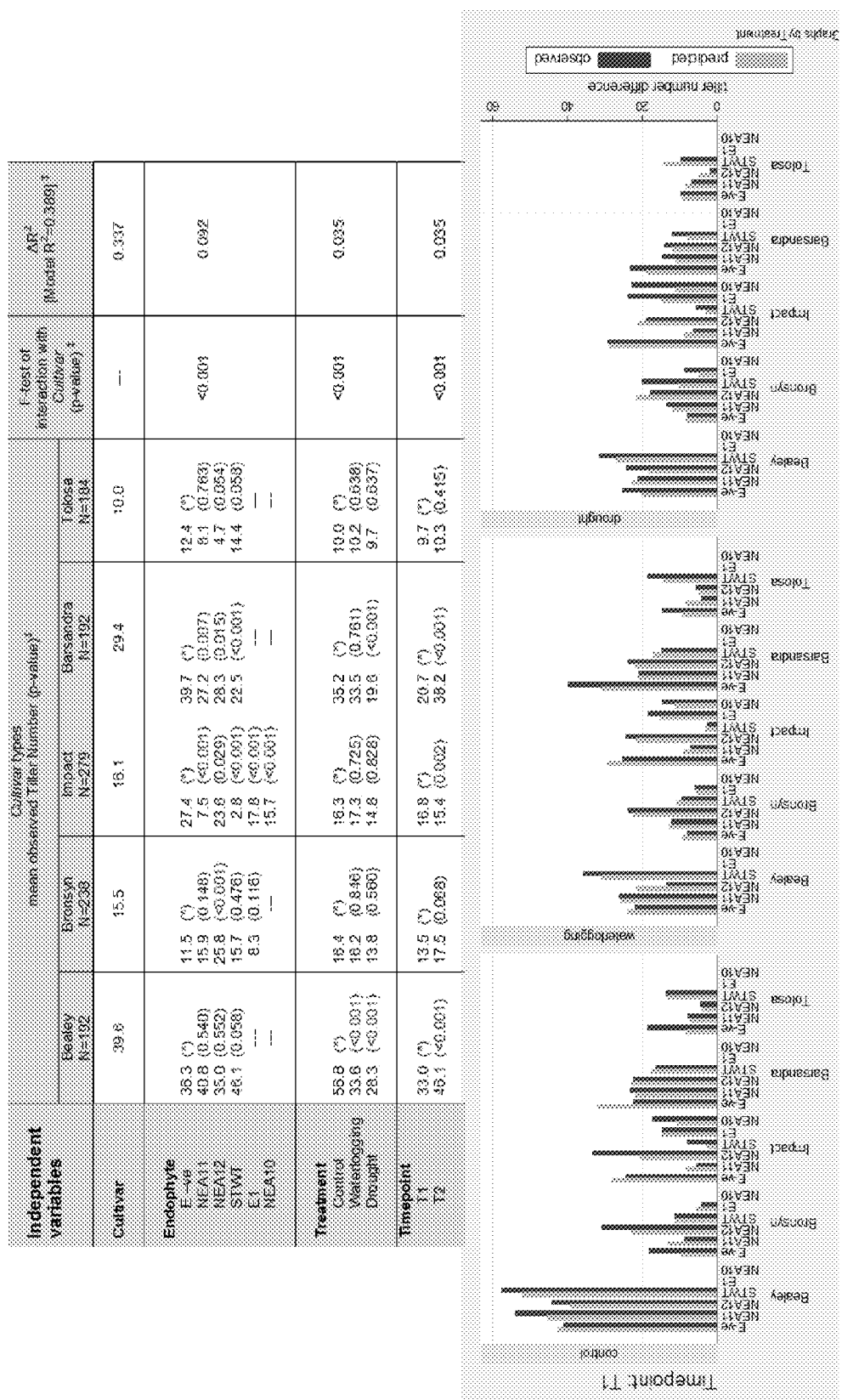

FIG. 69 shows performance as measured by tiller number.

Figure 70:
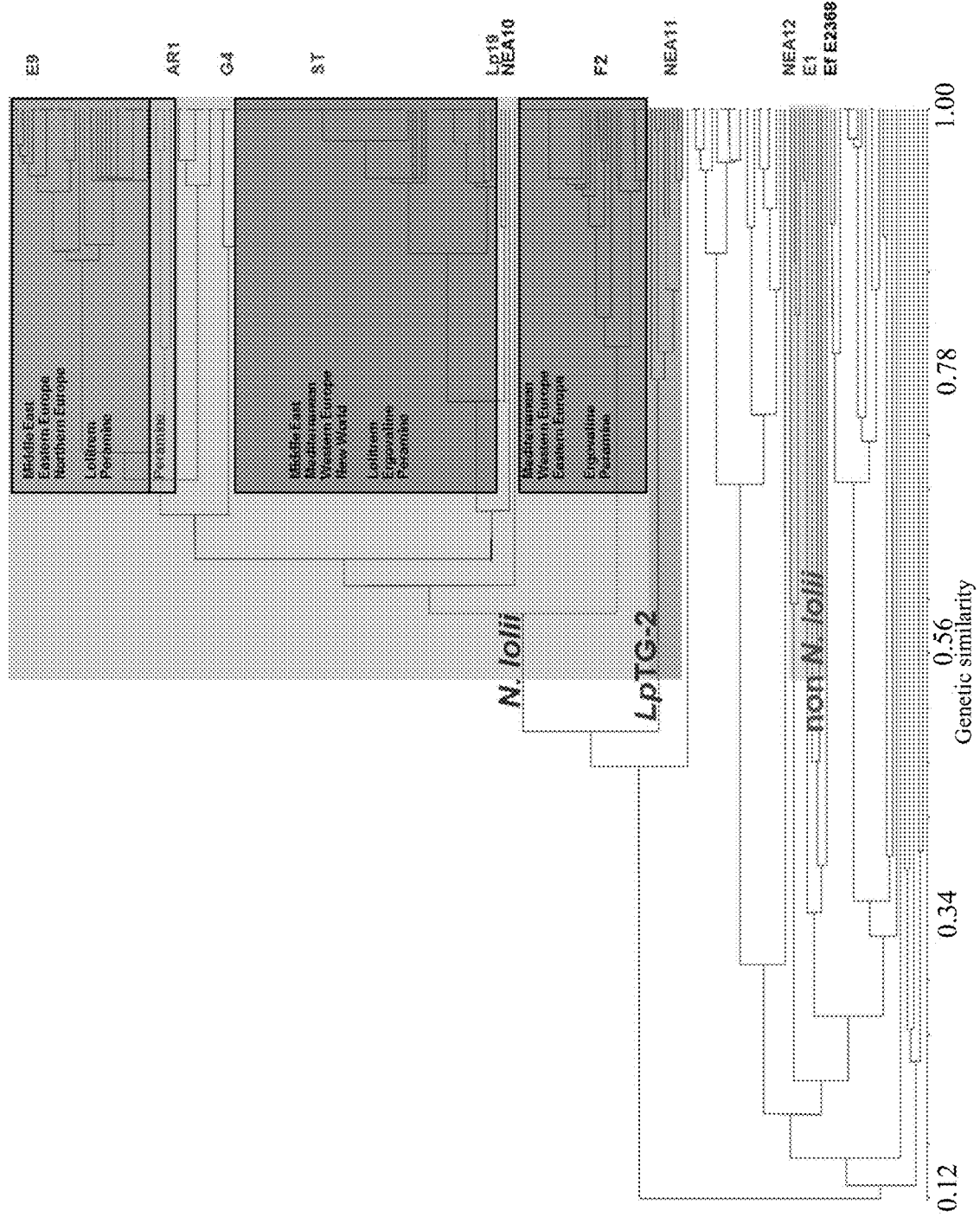

FIG. 70 shows sequence analysis using the 454 sequencing platform.

Figure 71:
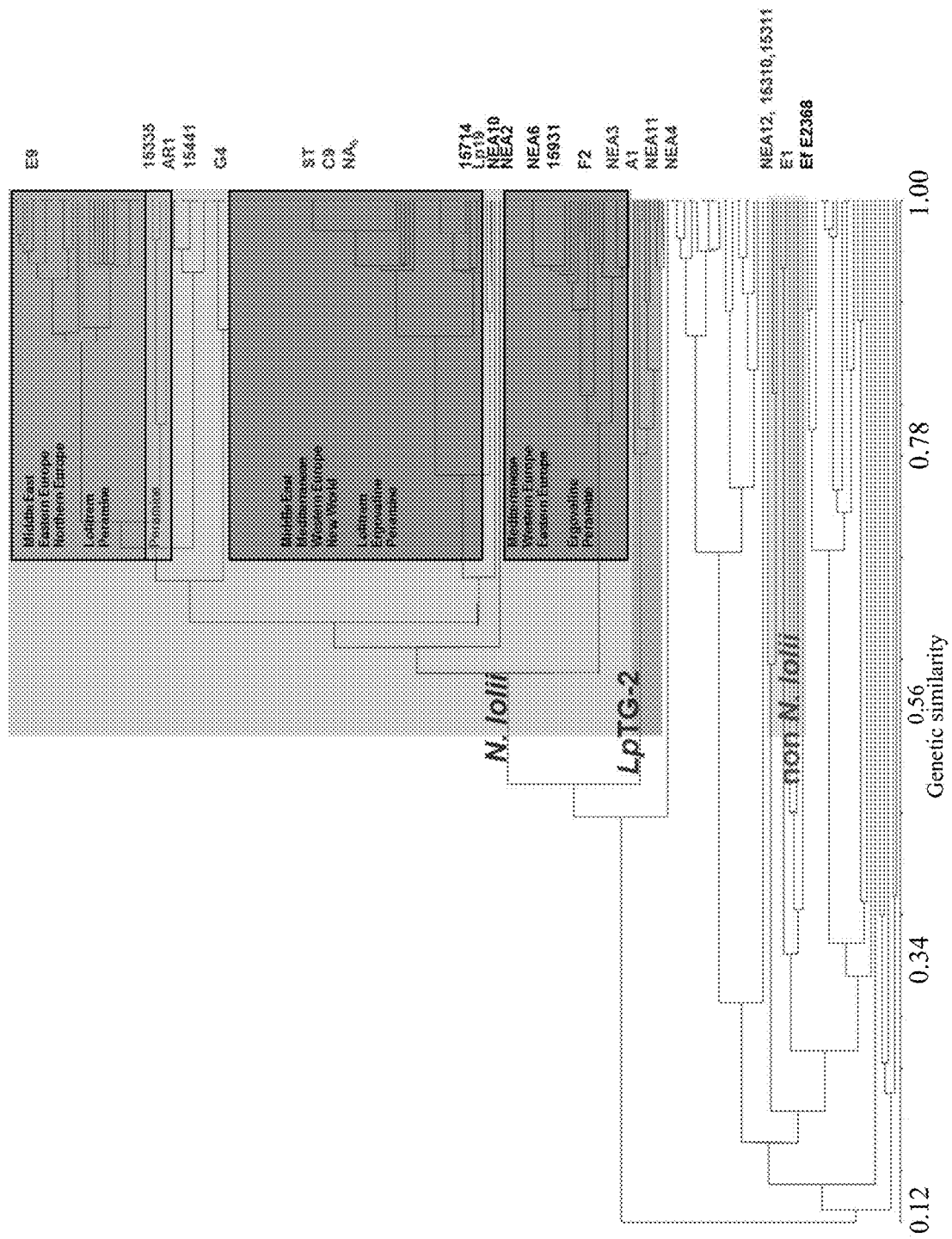

FIG. 71 shows sequence analysis using the Illumina sequencing platform.

Figure 72:
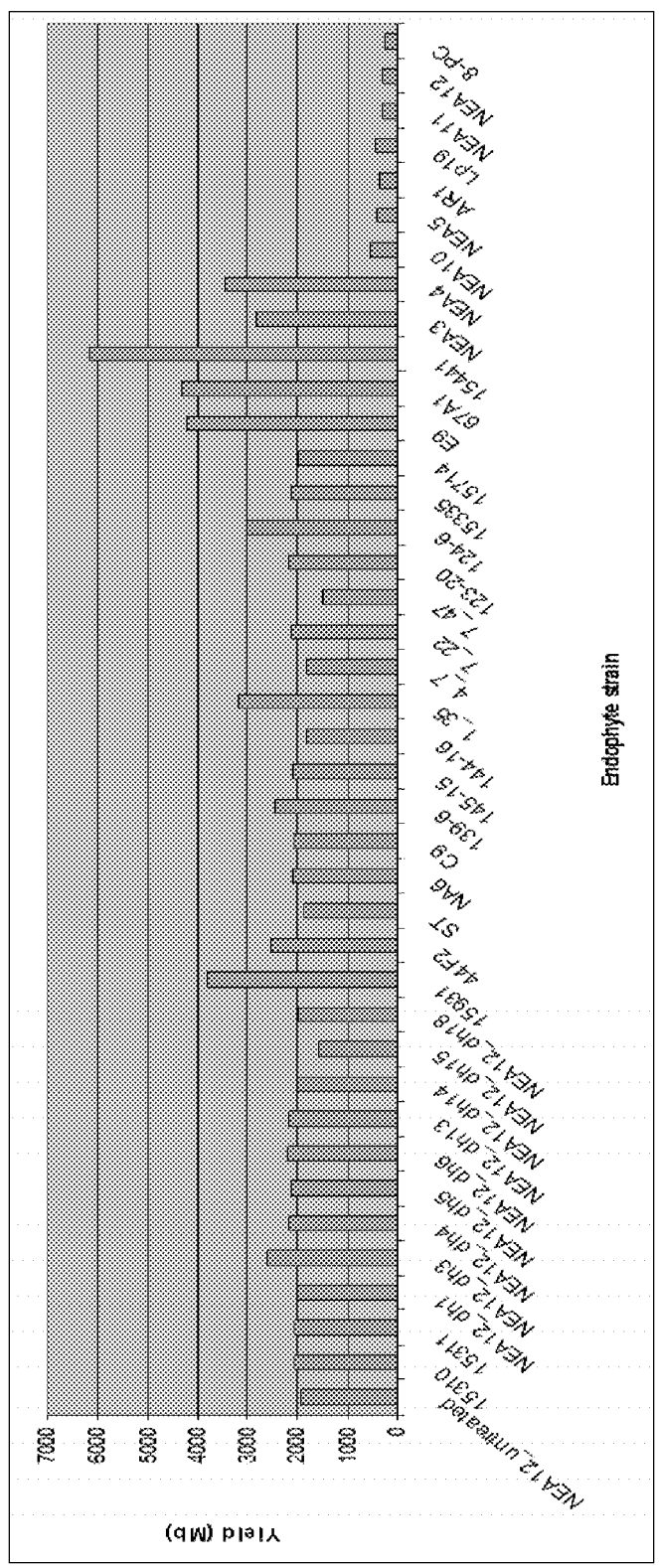

FIG. 72 shows a summary of sequenced perennial ryegrass endophyte genomes. Total Yield=84.8 gigabases (GAII: 7.4 Gb, HiSeq: 77.4 Gb); Average yield on HiSeq=2.2 Gb per strain; Average yield on GAII=373 Mb per strain.

Figure 73:
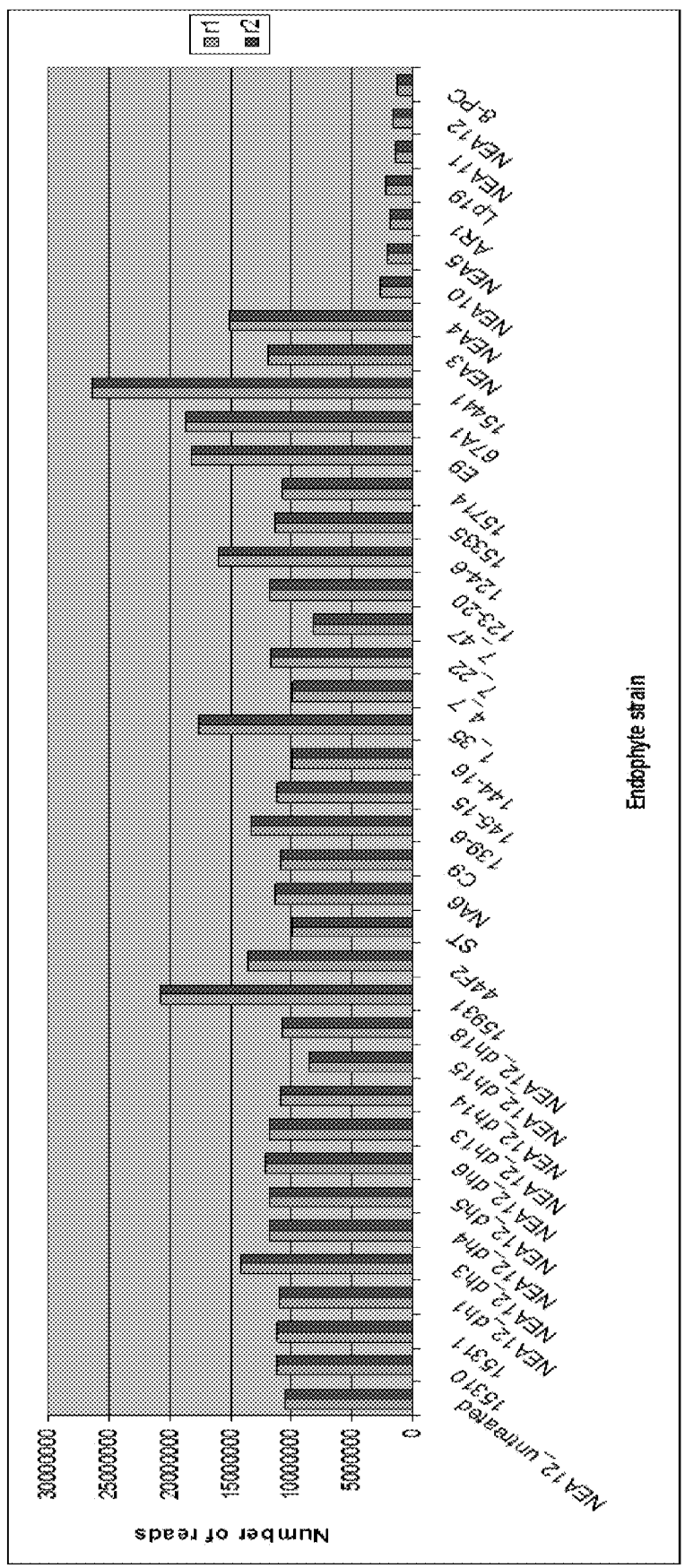

FIG. 73 shows a summary of sequenced perennial ryegrass endophyte genomes. Total number of reads=436,920,622 pairs; Average number of paired reads on HiSeq=12,844,656 per strain; Average number of paired reads on GAII=1,863,852 per strain.

FIGS. 74-78 show Illumina reads v 454 contigs.

Figure 79:
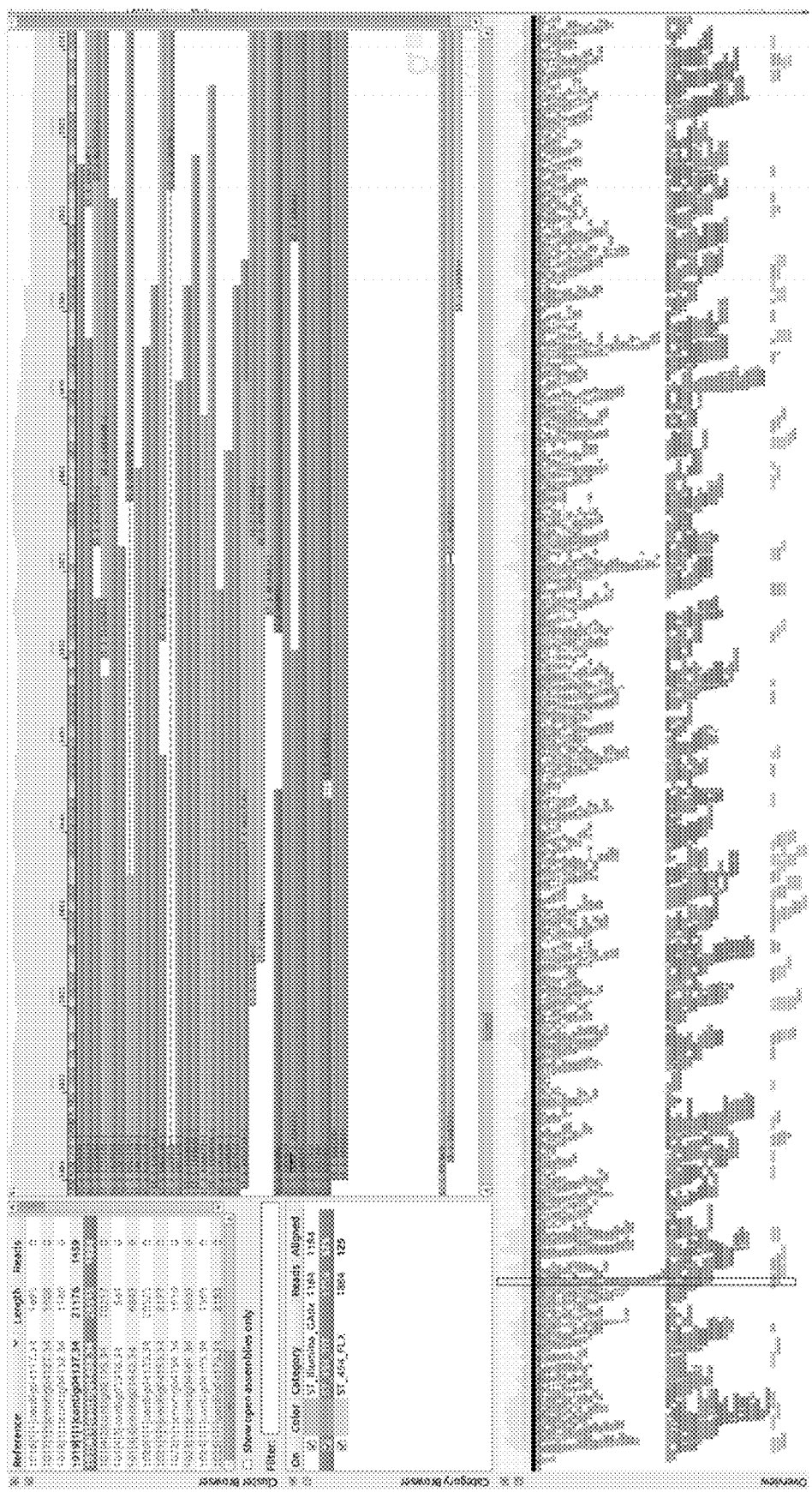

FIG. 79 shows 454 FLX v 454 Titanium v Illumina GAII coverage display.

Figure 80:
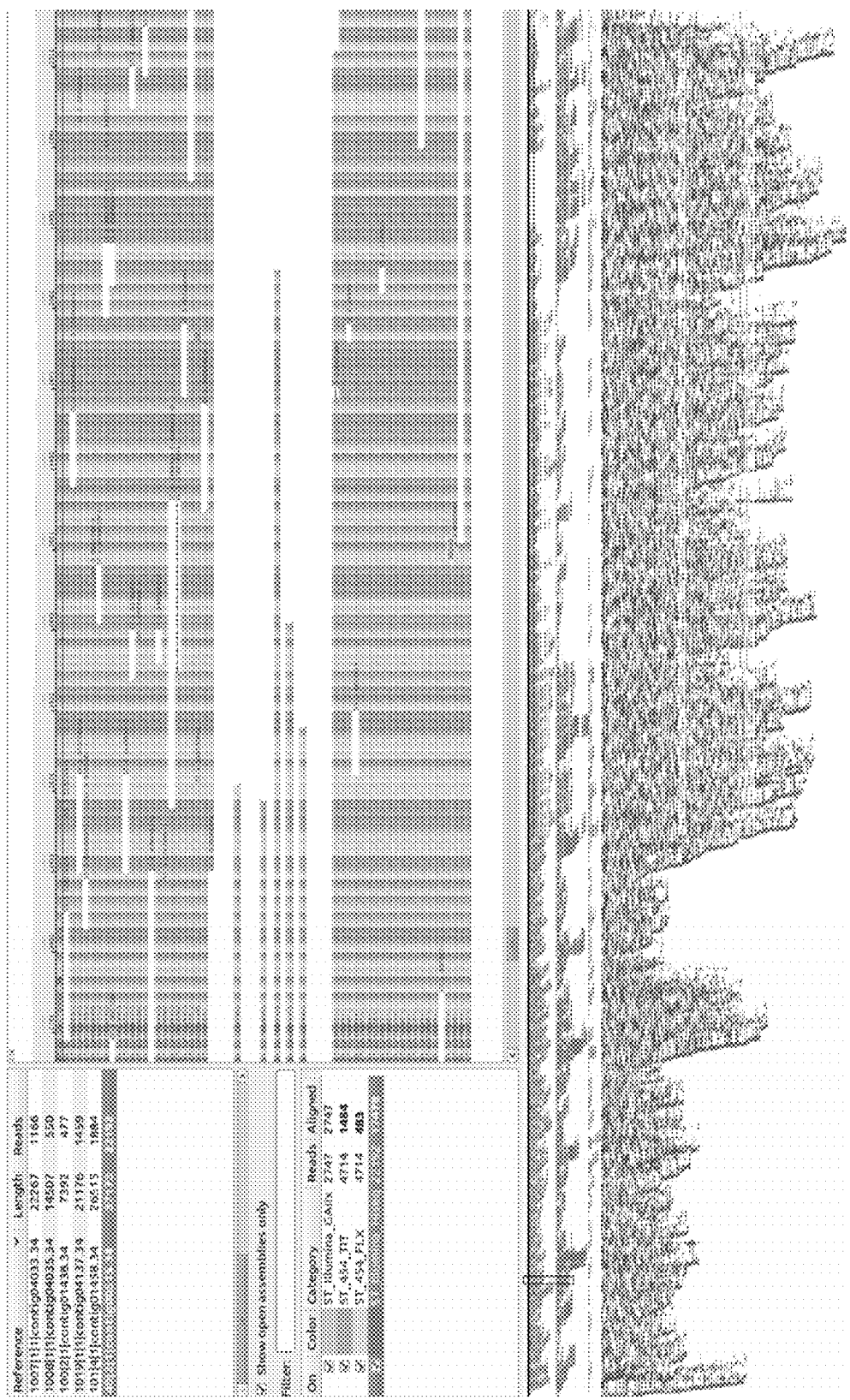

FIG. 80 shows 454 FLX v 454 Titanium v Illumina GAII v Hi Seq coverage display.

Figure 81:

FIG. 81 shows Homo polymer correction: graphical view.

Figure 82:
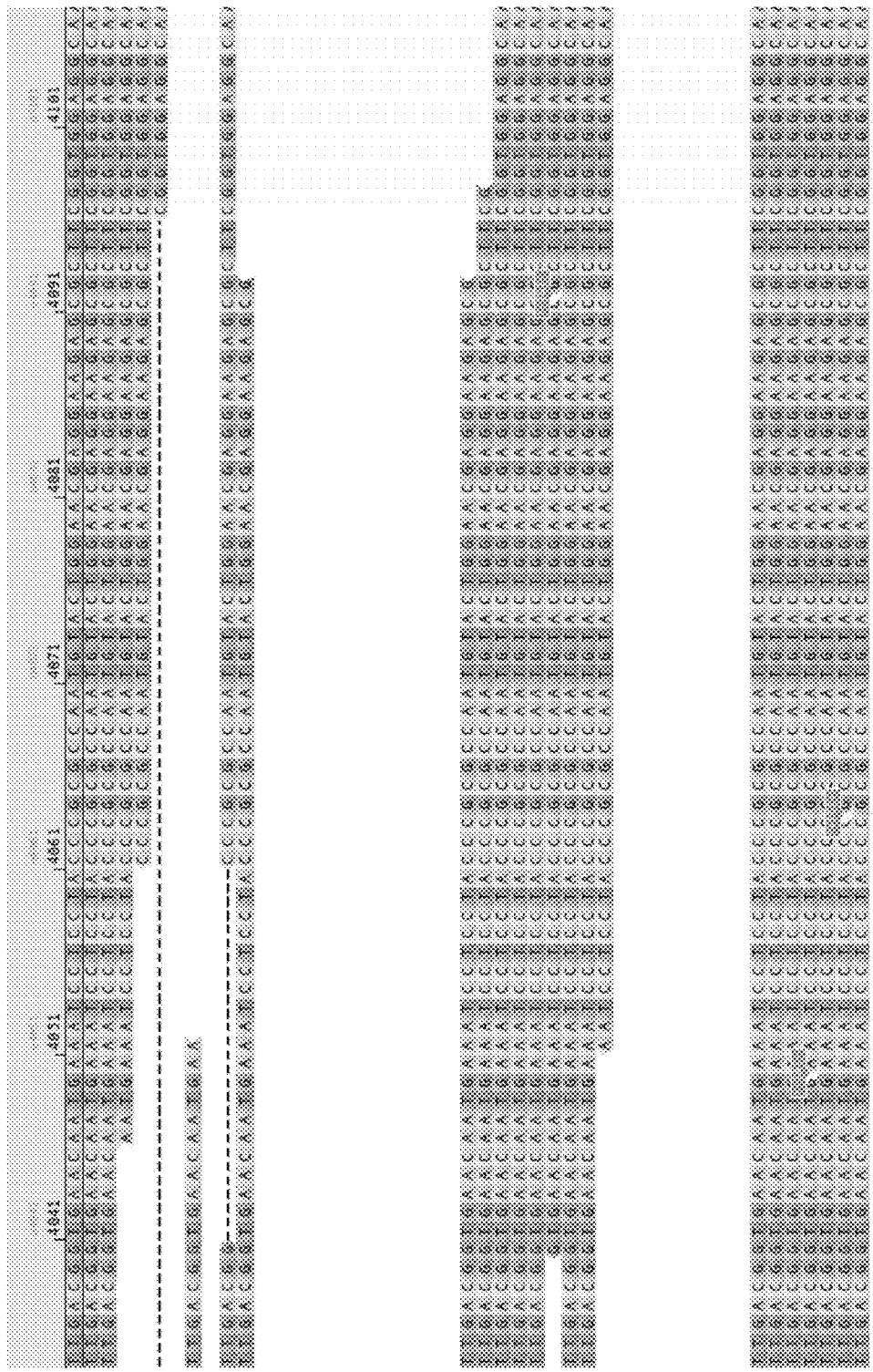

FIG. 82 shows Homo polymer correction: base view.

Figure 83:
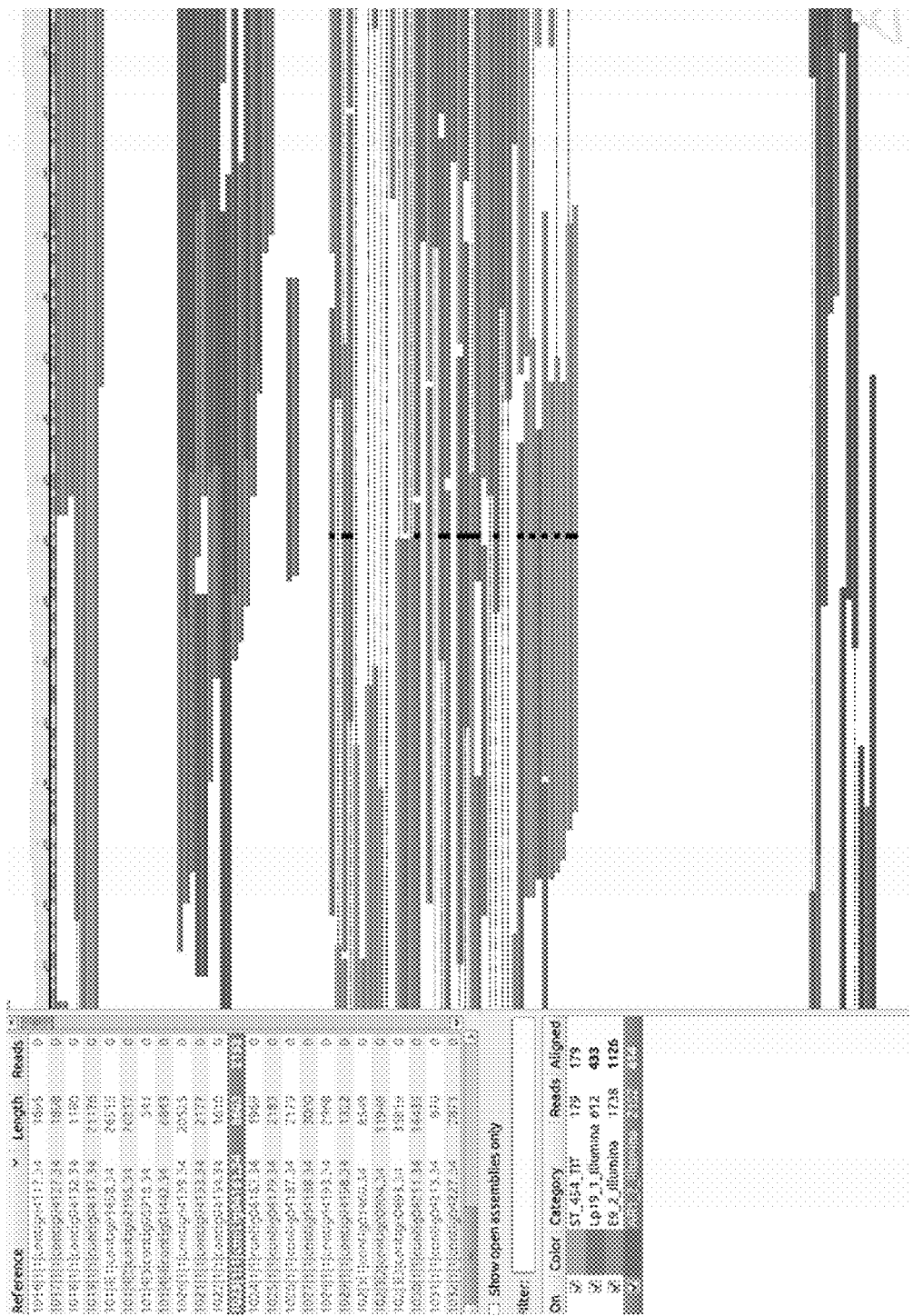

FIG. 83 shows Pan-genome SNP calling: graphical view, read level.

Figure 84:
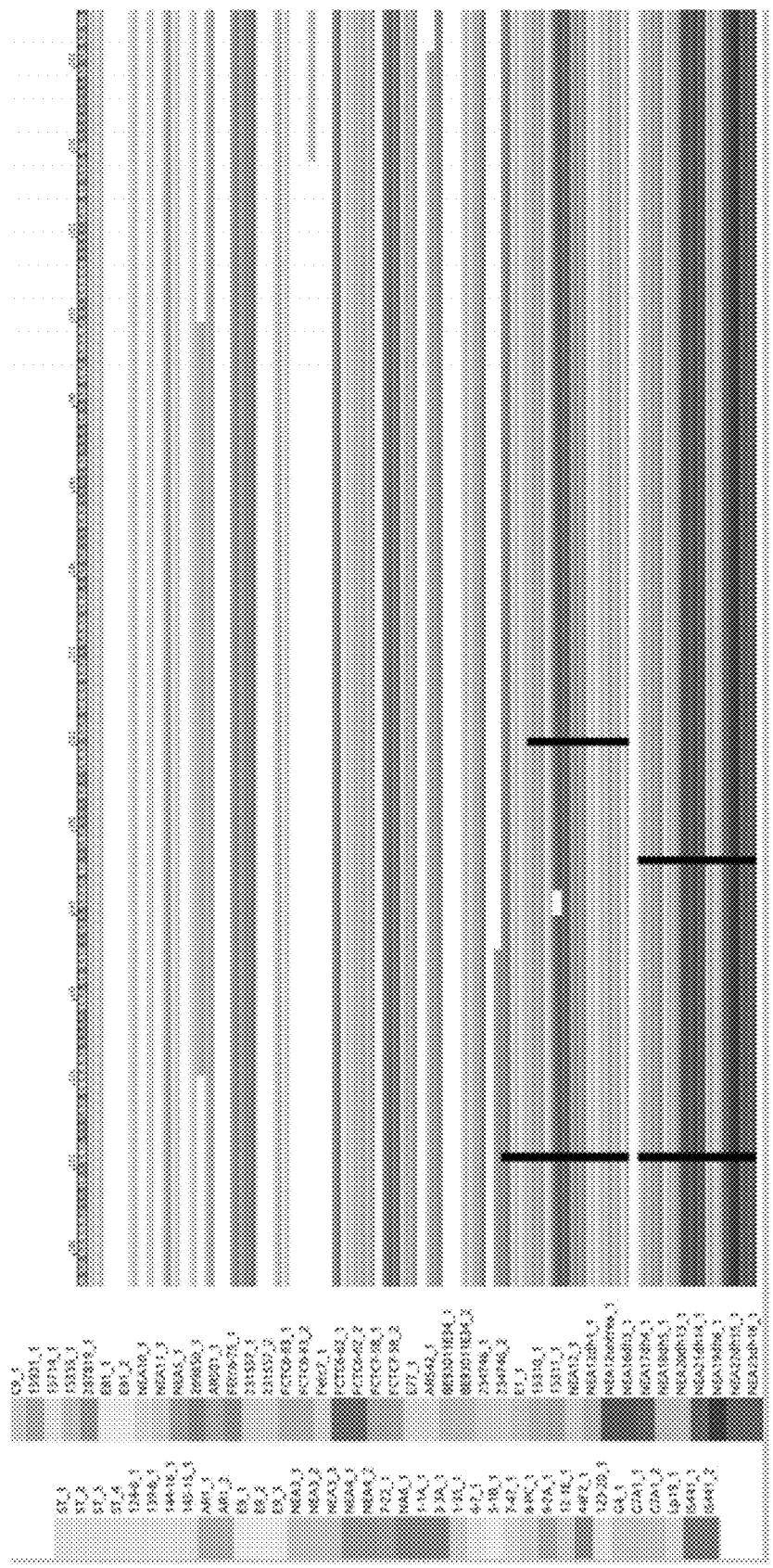

FIG. 84 shows 77 independent sequencing runs, ordered by similarity.

Figure 85:
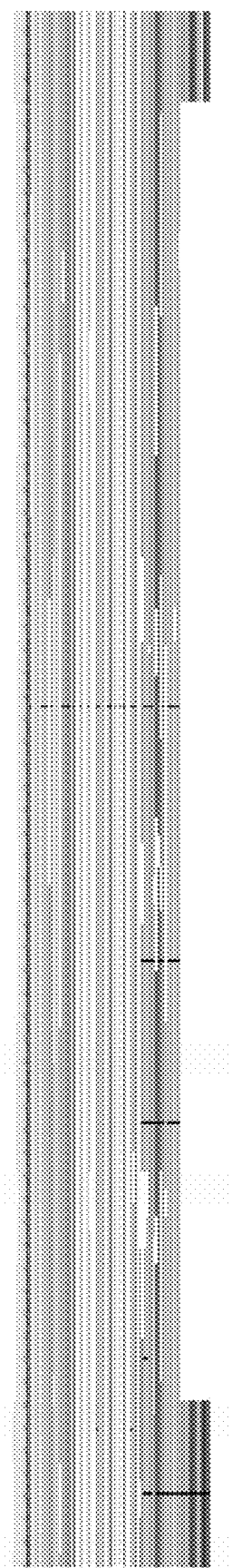

FIG. 85 shows that independent sequencing runs can also display strain specific deletions.

Figure 86:
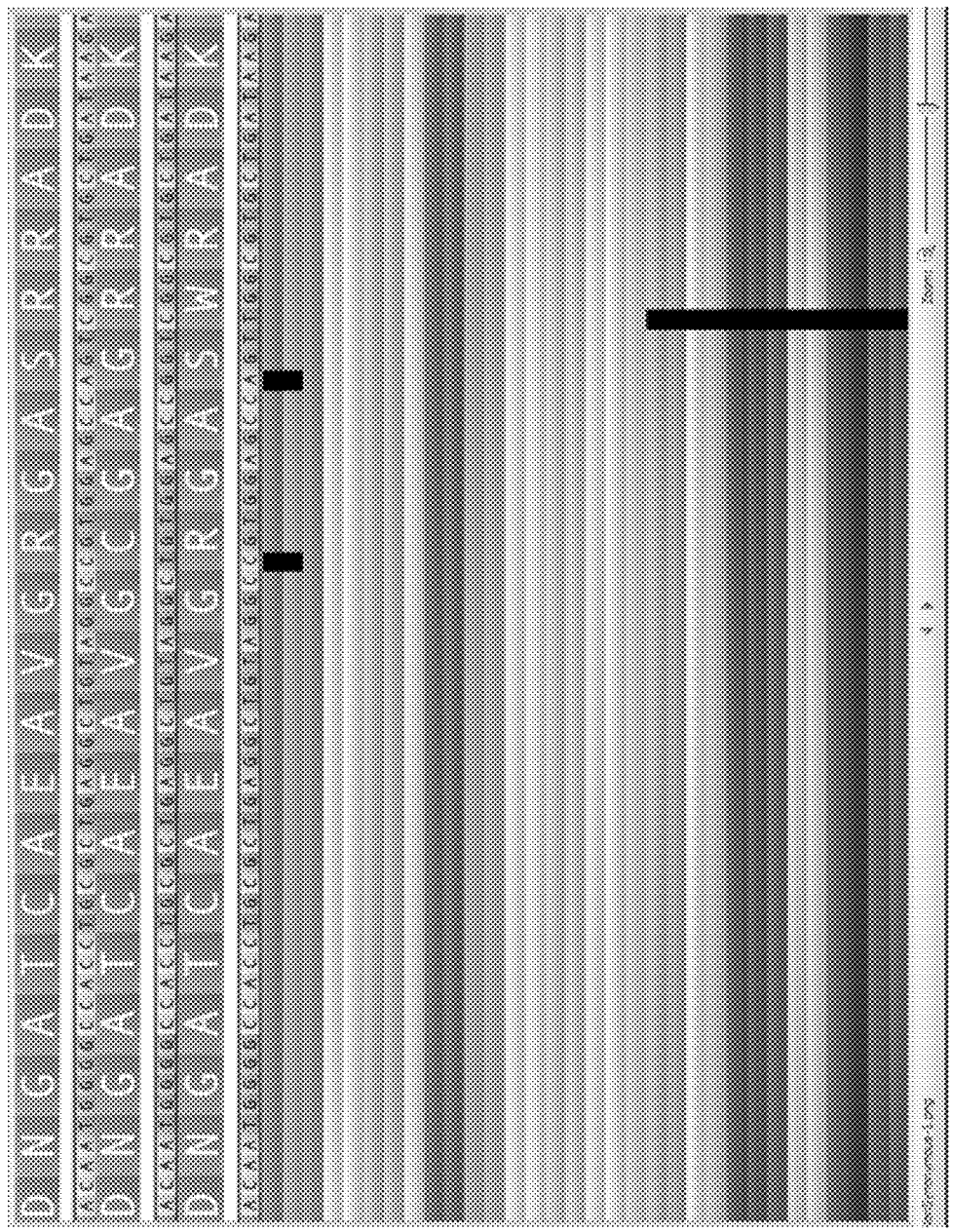

FIG. 86 shows that independent sequencing runs can predict amino acid changes from SNP data.

Figure 87:
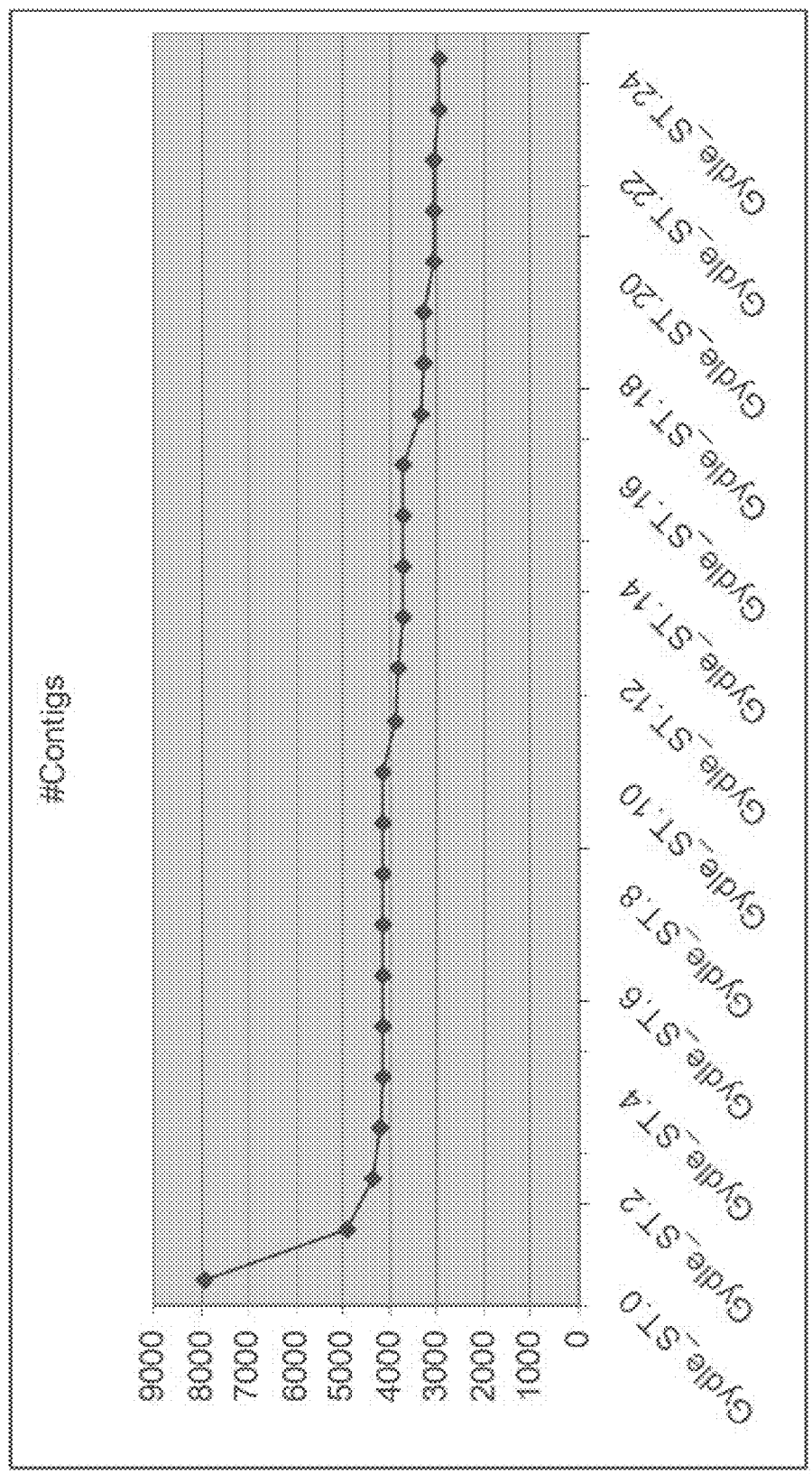

FIG. 87 shows that contig number decreases with rounds of assembly refinement.

Figure 88:
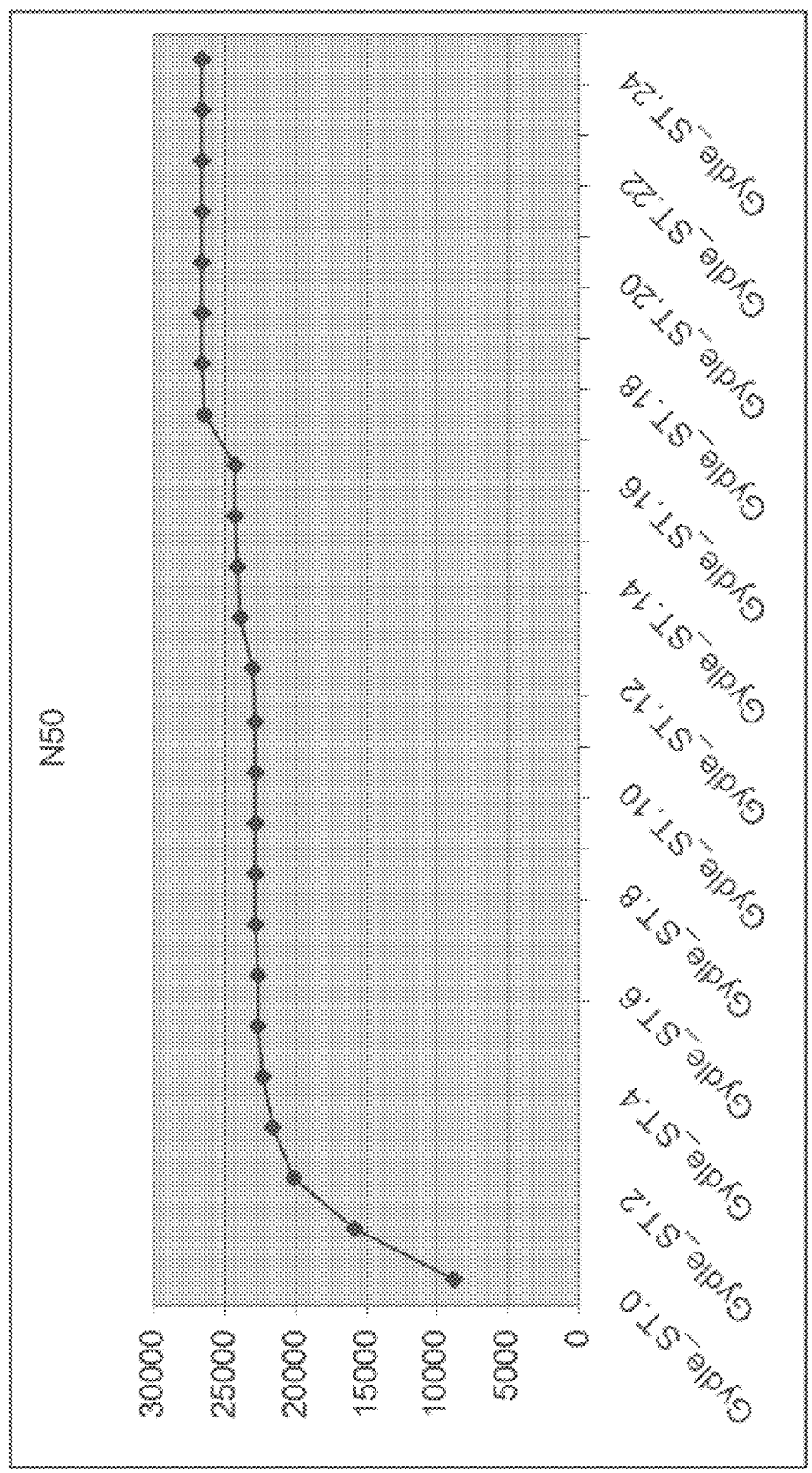

FIG. 88 shows that N50 increases with rounds of assembly refinement.

Figure 89:
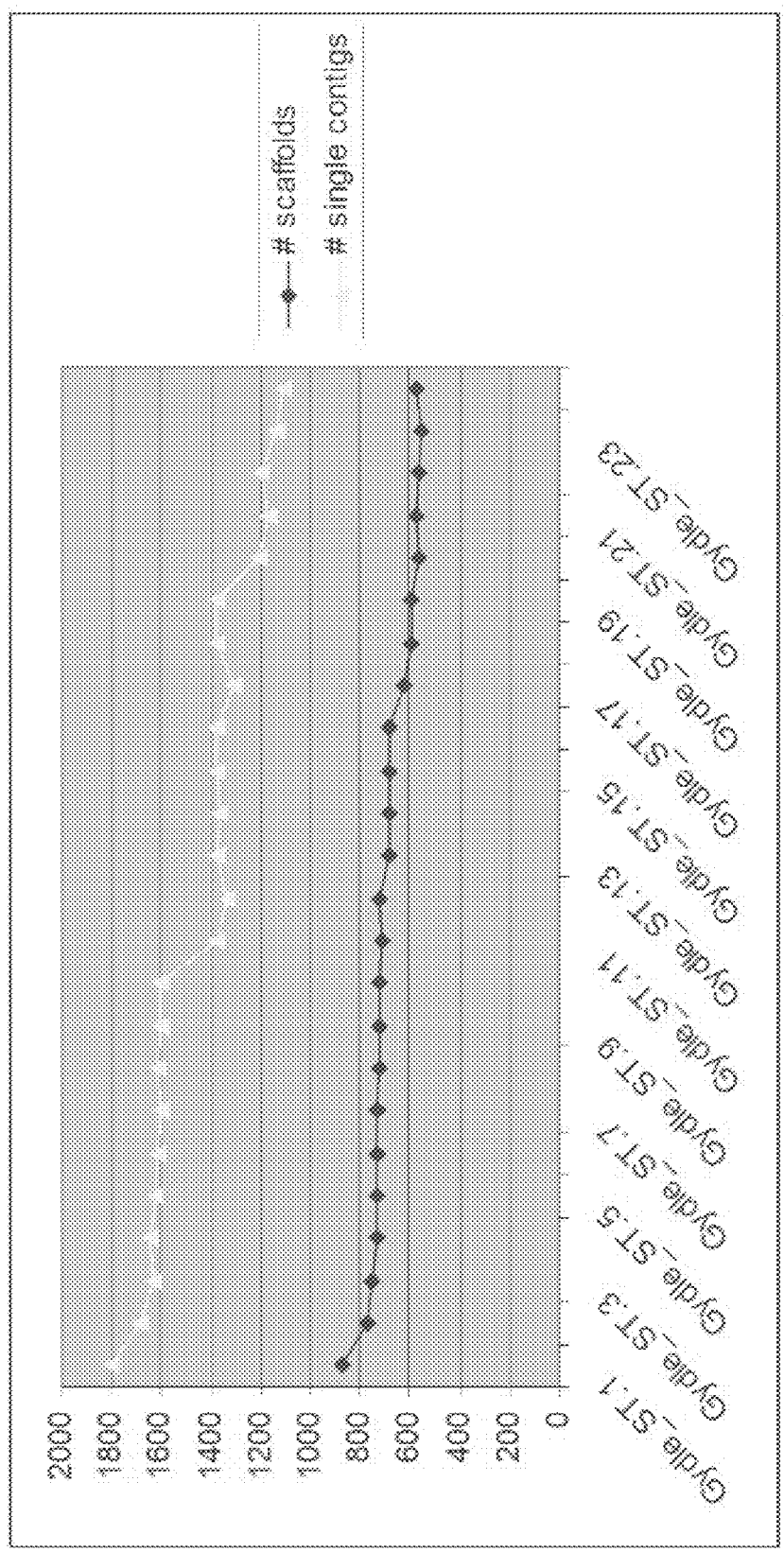

FIG. 89 shows that assembly refinement decreases the number of scaffolds, and single 'unscaffolded' contigs.

Figure 90:
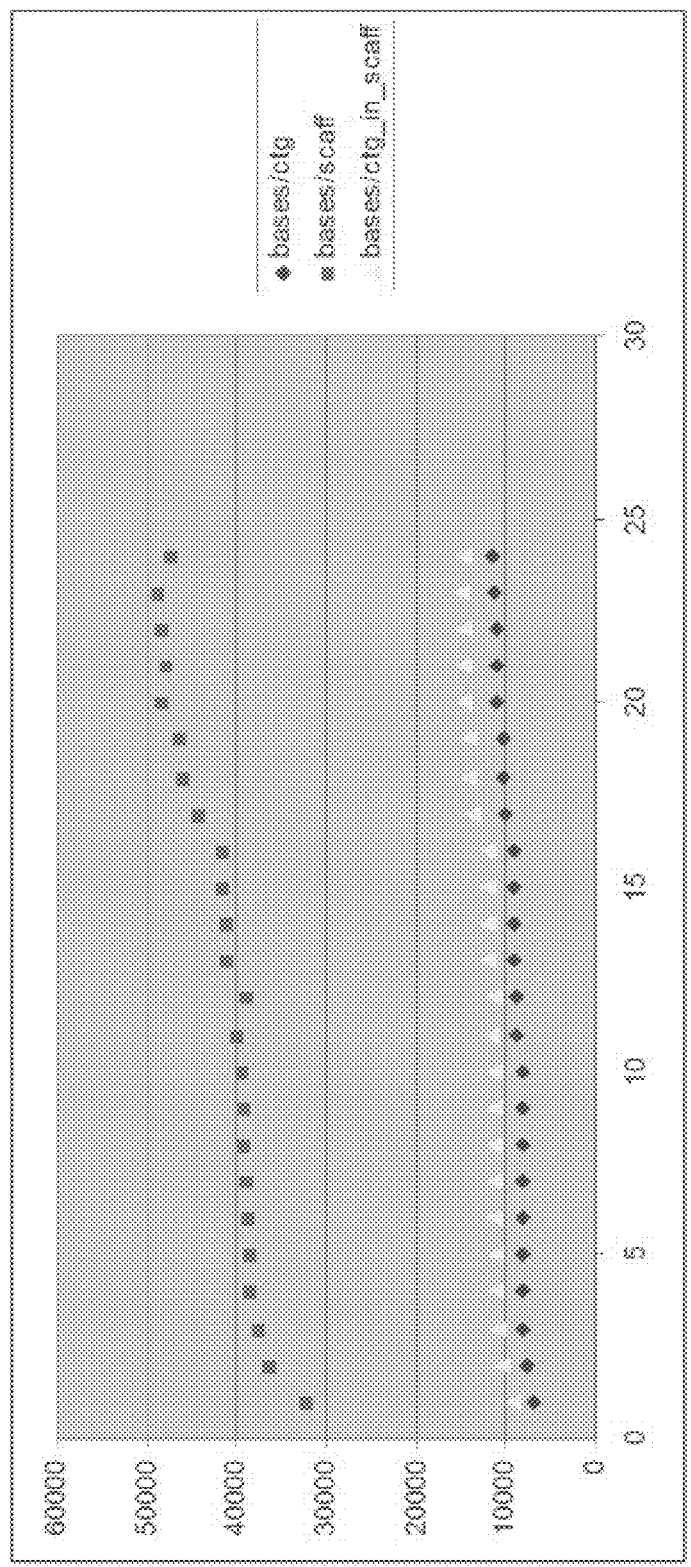

FIG. 90 shows that average number of bases per contig increases with assembly refinement.

Figure 91:
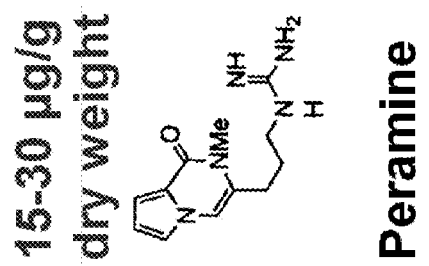
Figure 91:
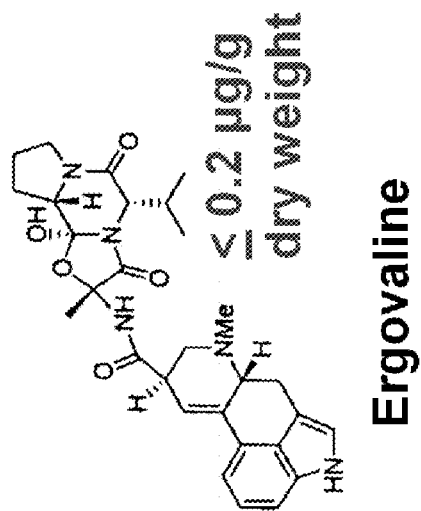
Figure 91:
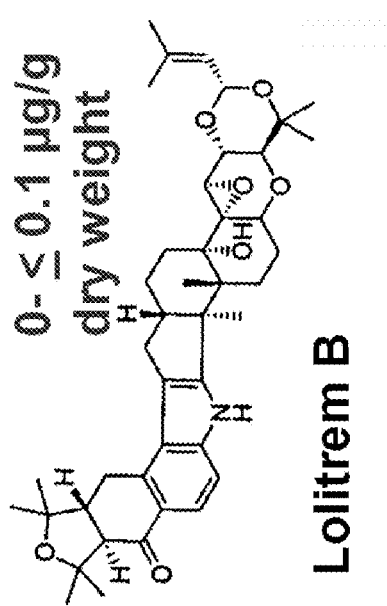

FIG. 91 shows the structures of Lolitrem B, Erogvaline and Peramine, with desirable toxin profiles indicated.

Figure 92:
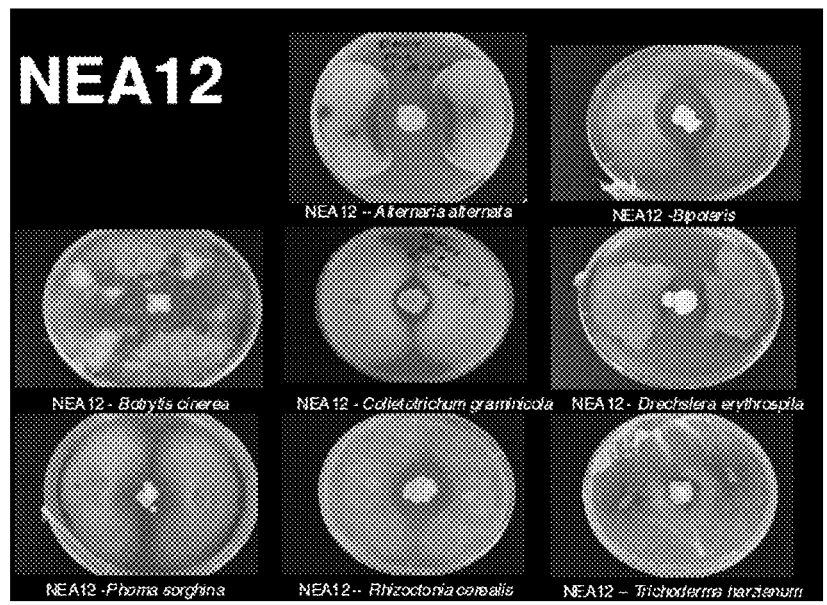

FIG. 92 shows in vitro bioassays to assess antifungal activity of *Neotyphodium* endophytes.

Figure 93:
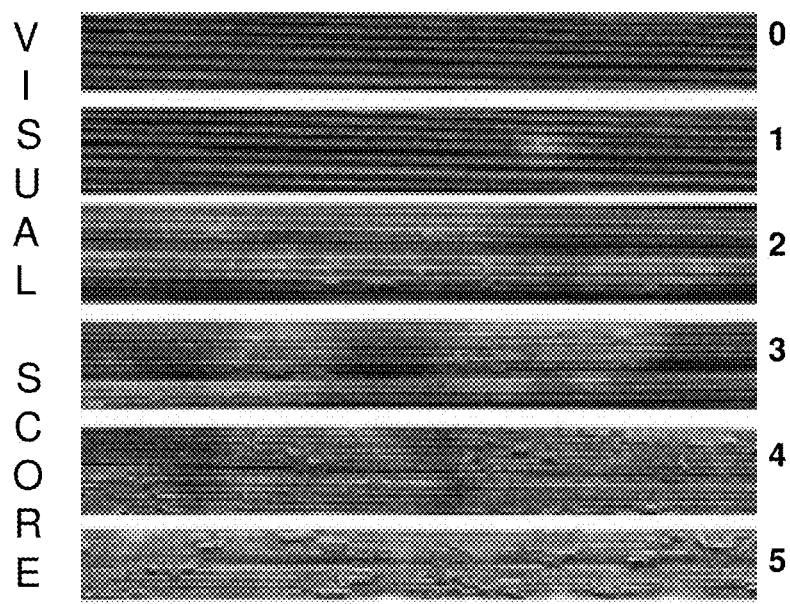

FIG. 93 shows a detached leaf assay to assess resistance to crown rust (*Puccinia coronata* f. sp. *Loiii*) of perennial ryegrass plants with and without *Neotyphodium* endophytes.

Figure 94:

FIG. 94 shows glasshouse and field trial screens for drought tolerance and water use efficiency of perennial ryegrass plants with and without *Neotyphodium* endophytes.

Figure 95:
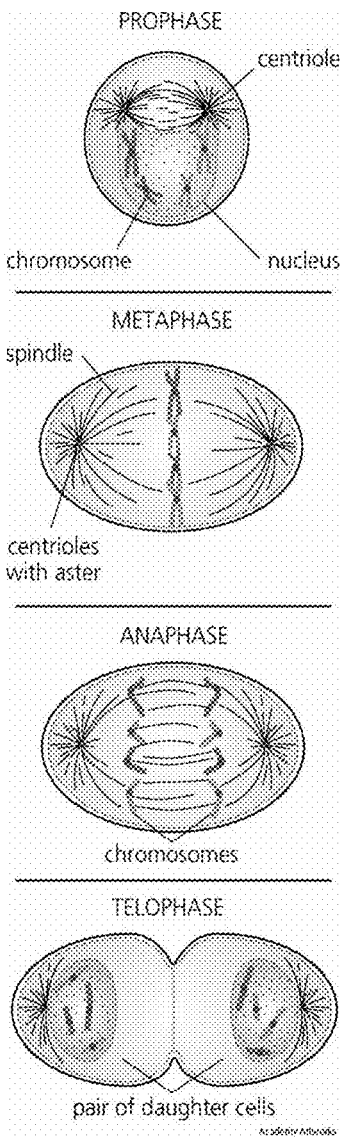

FIG. 95 shows the steps involved in cell division.

Figure 96:
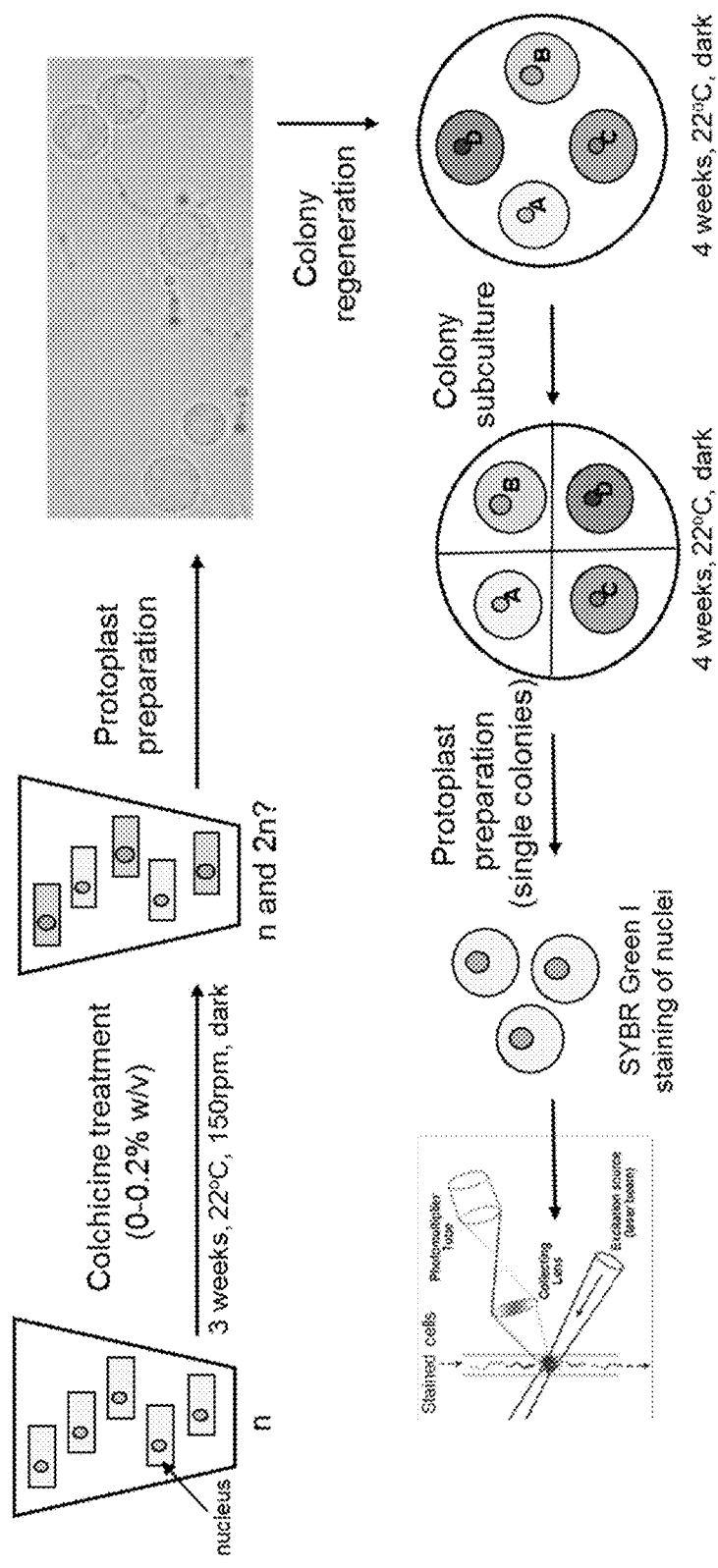

FIG. 96 shows experimental work flow for chromosome doubling of endophyte cells.

Figure 97:
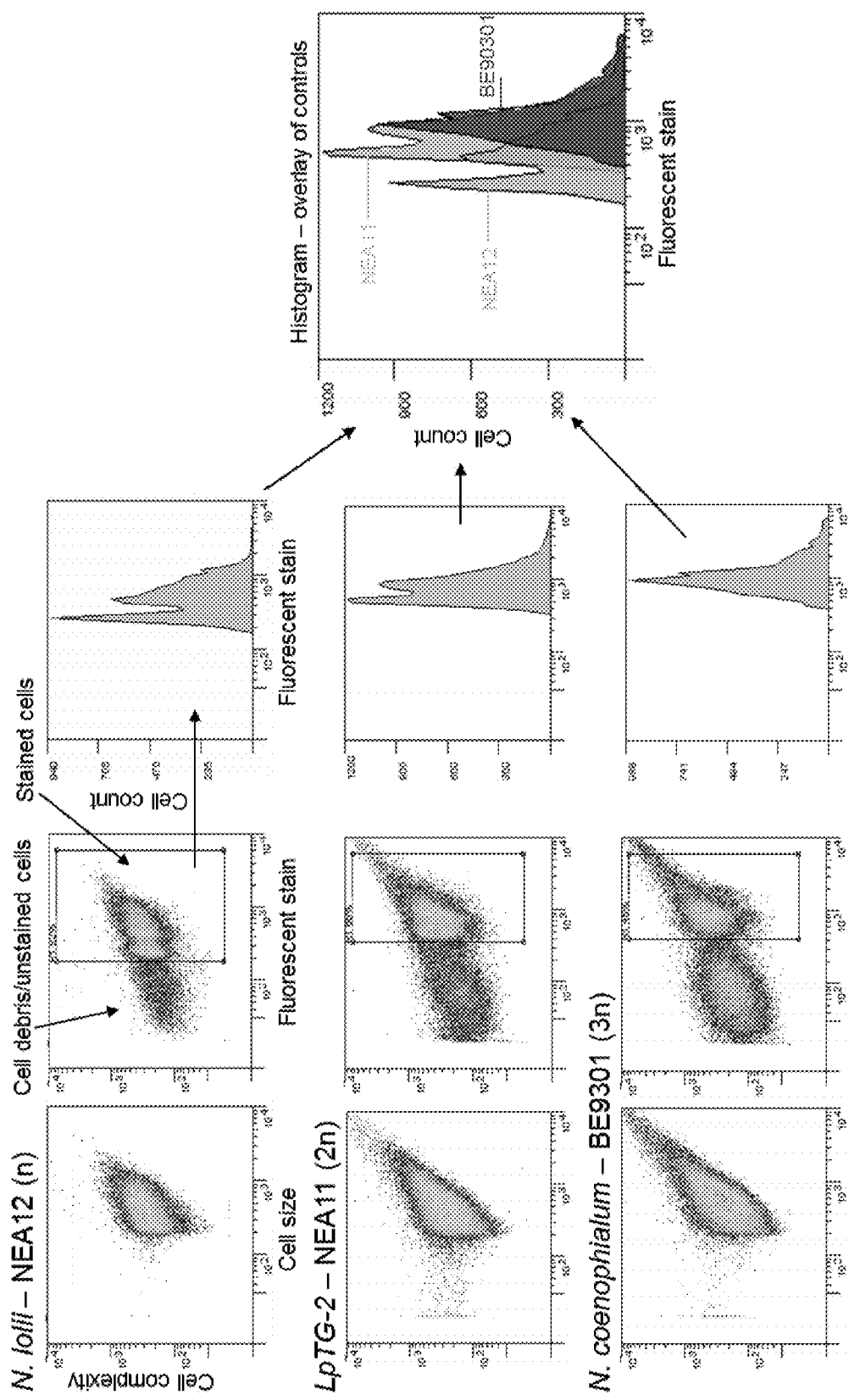

FIG. 97 shows flow cytometry calibrations for DNA content assessment in *Neotyphodium* endophyte strains. Peaks indicate relative nuclear DNA content.

Figure 98:
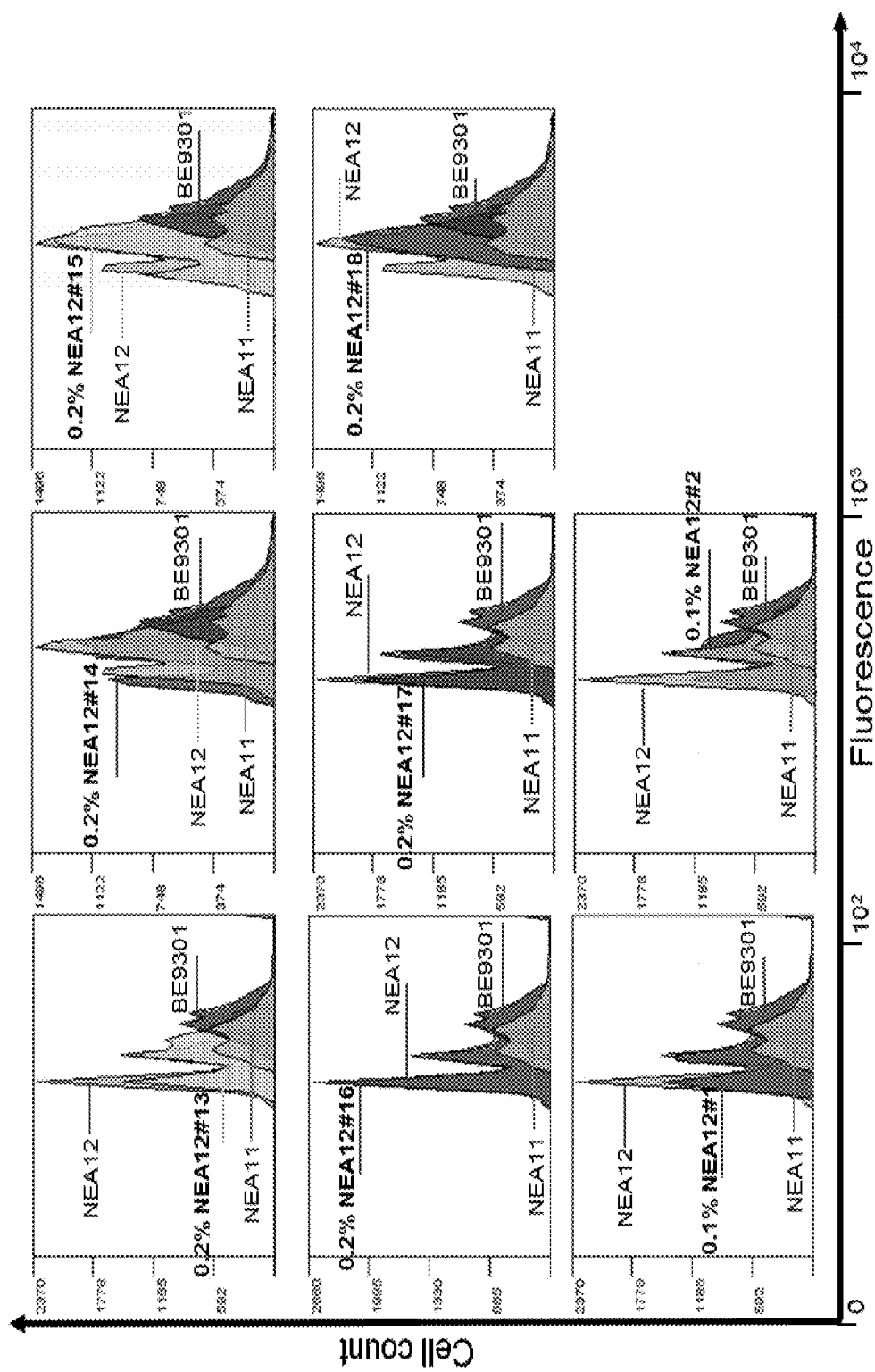

FIG. 98 shows flow cytometryanalysis of NEA12$^{dh}$ *Neotyphodium* endophyte strains.

Figure 99:
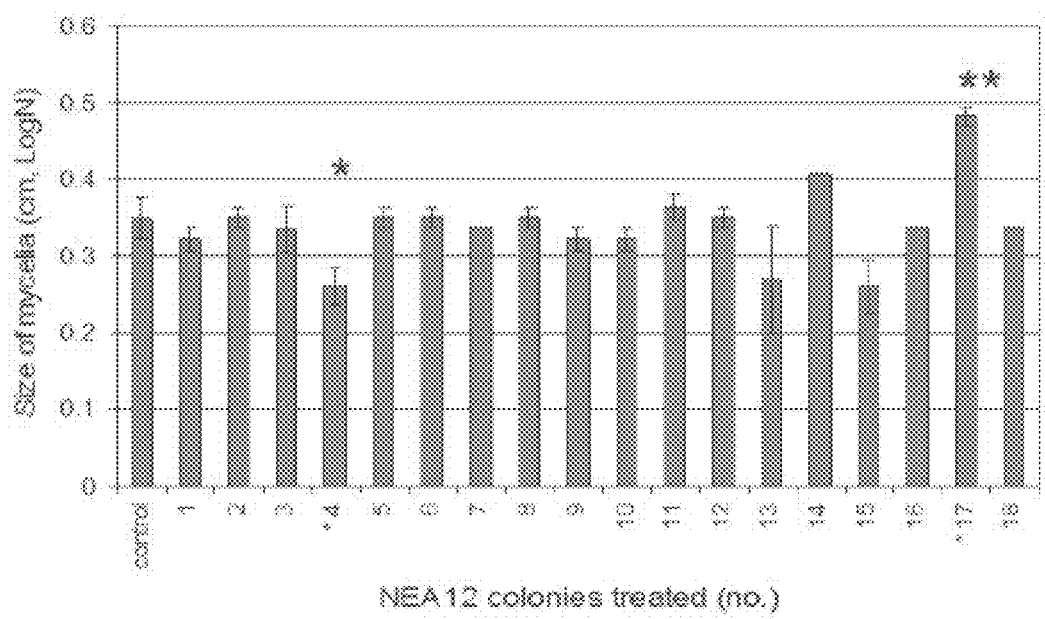

FIG. 99 shows analysis of growth rate in culture after 8 weeks of NEA12$^{dh}$ *Neotyphodium* endophyte strains compared to control endophyte strains.

Figure 100:
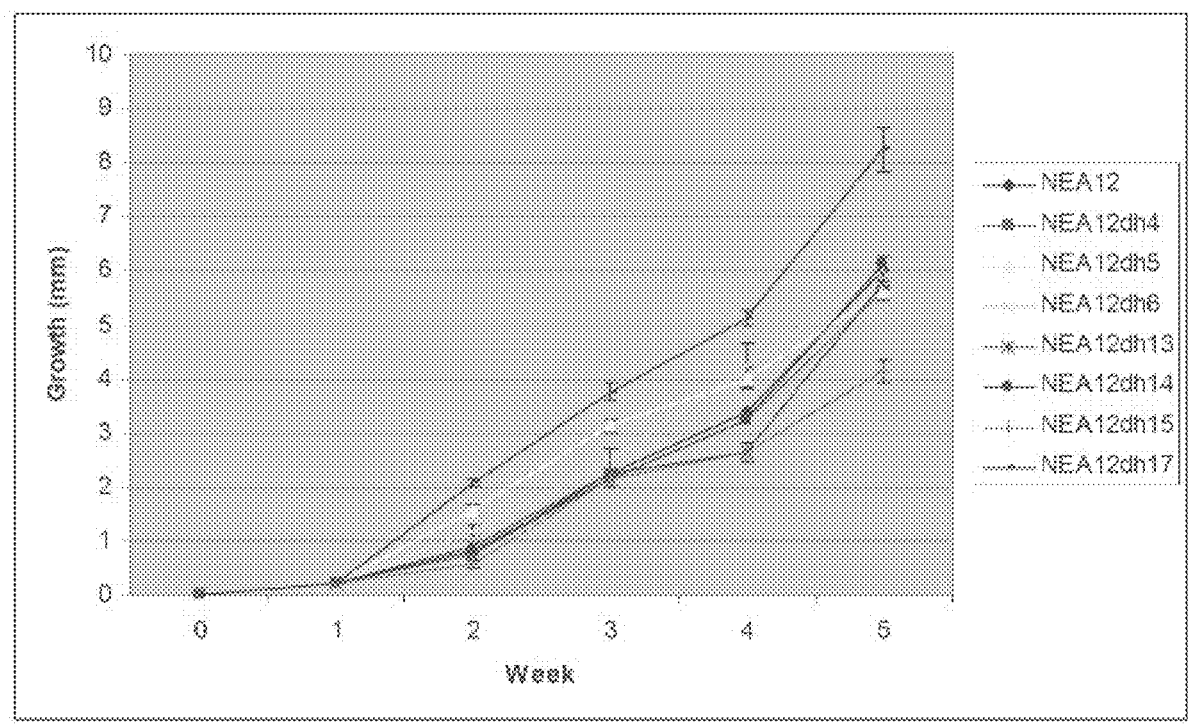

FIG. 100 shows analysis of growth rate in culture over 5 weeks of NEA12$^{dh}$ *Neotyphodium* endophyte strains compared to control endophyte strains.

Figure 101:
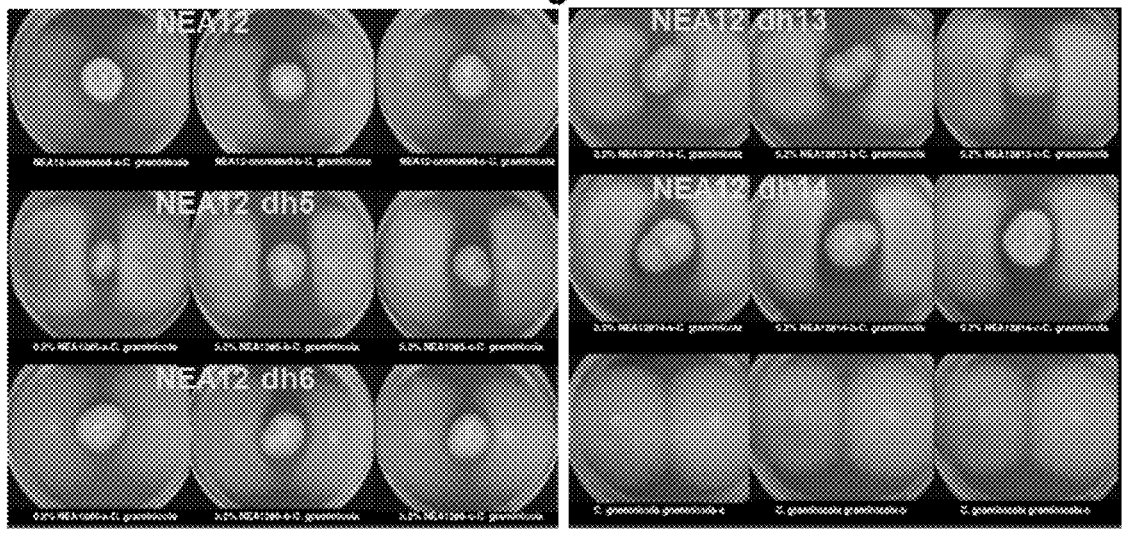
Figure 101:
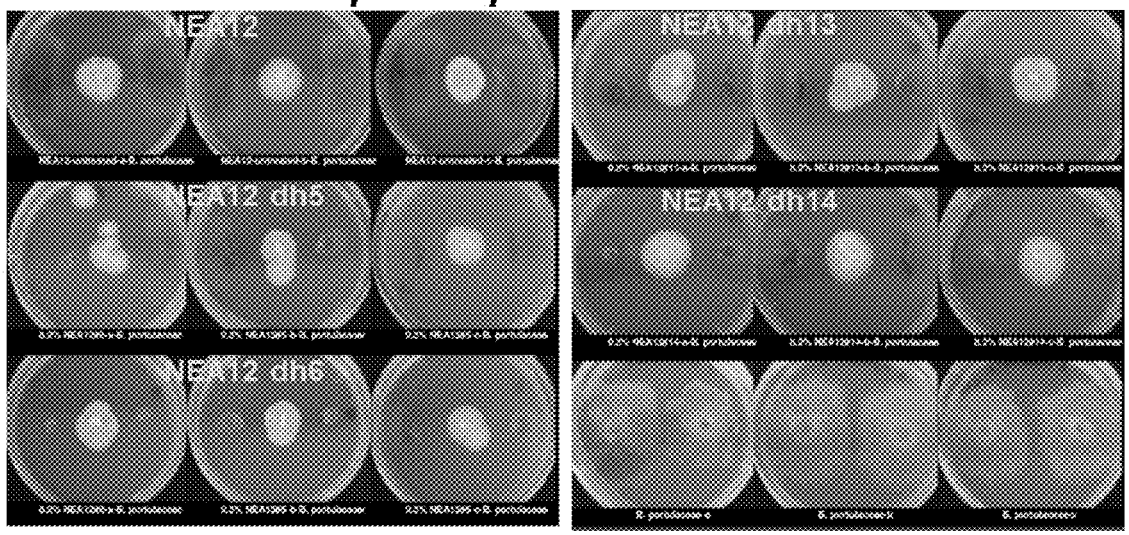

FIG. 101 shows antifungal bioassays of NEA12$^{dh}$ *Neotyphodium* endophyte strains.

Figure 102:
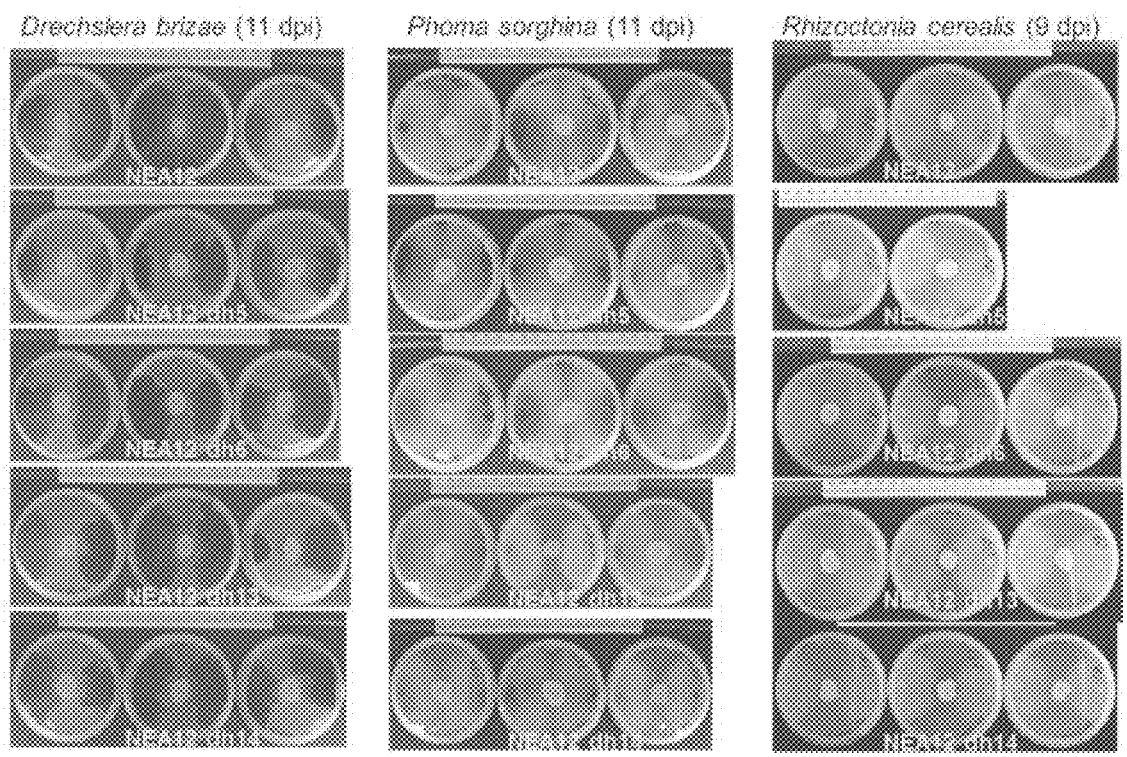

FIG. 102 shows antifungal bioassays of NEA12$^{dh}$ *Neotyphodium* endophyte strains.

Figure 103:
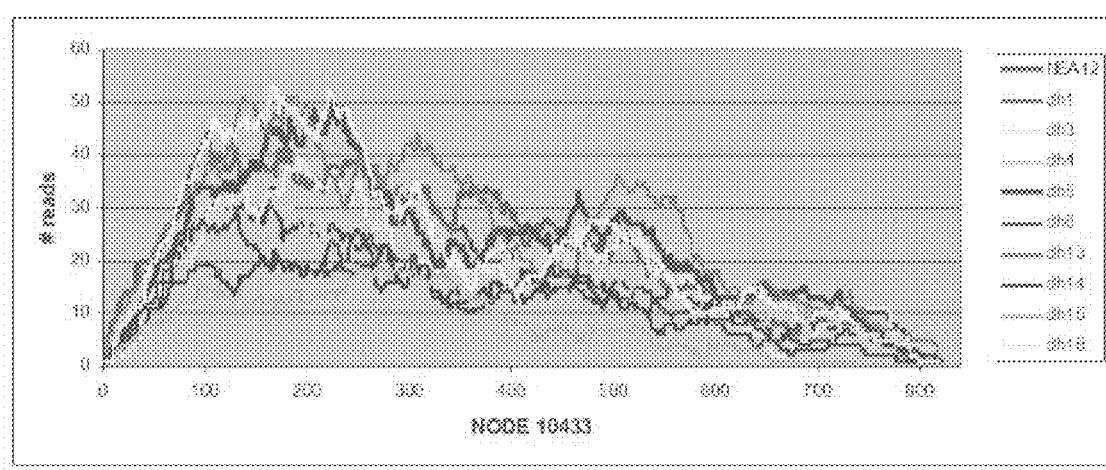

FIG. 103 shows analysis of genome survey sequencing read depth of colchicine-treated *Neotyphodium* endophyte strains.

Figure 104:
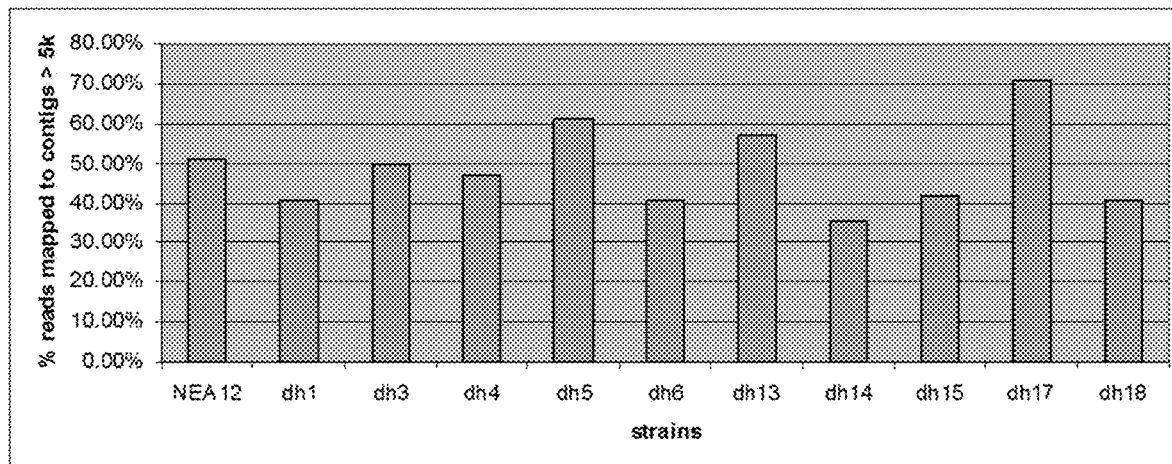

FIG. 104 shows analysis of genome survey sequencing reads mapping to NEA12 genome survey sequence assembly.

Figure 105:
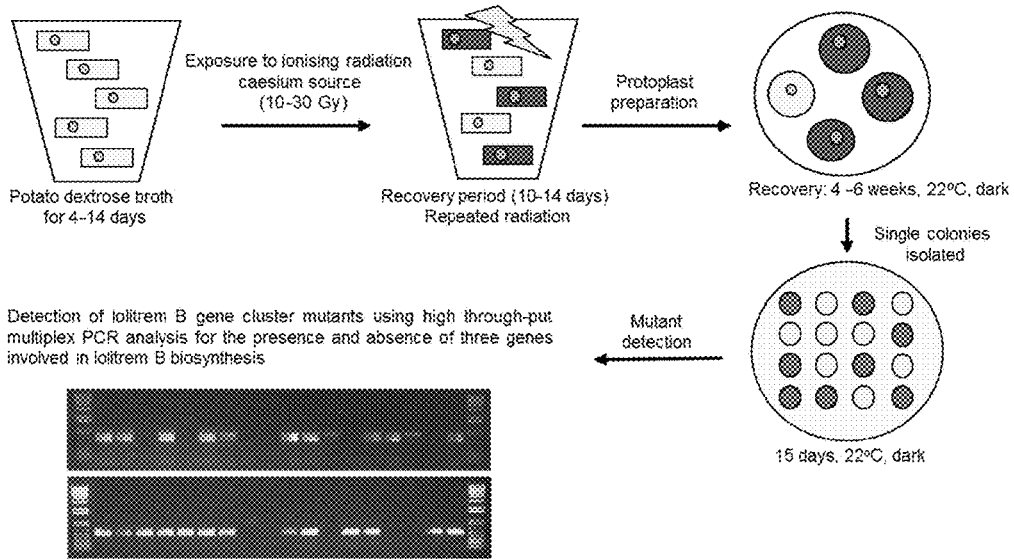

FIG. 105 shows experimental work flow for X-ray mutagenesis.

Figure 106:
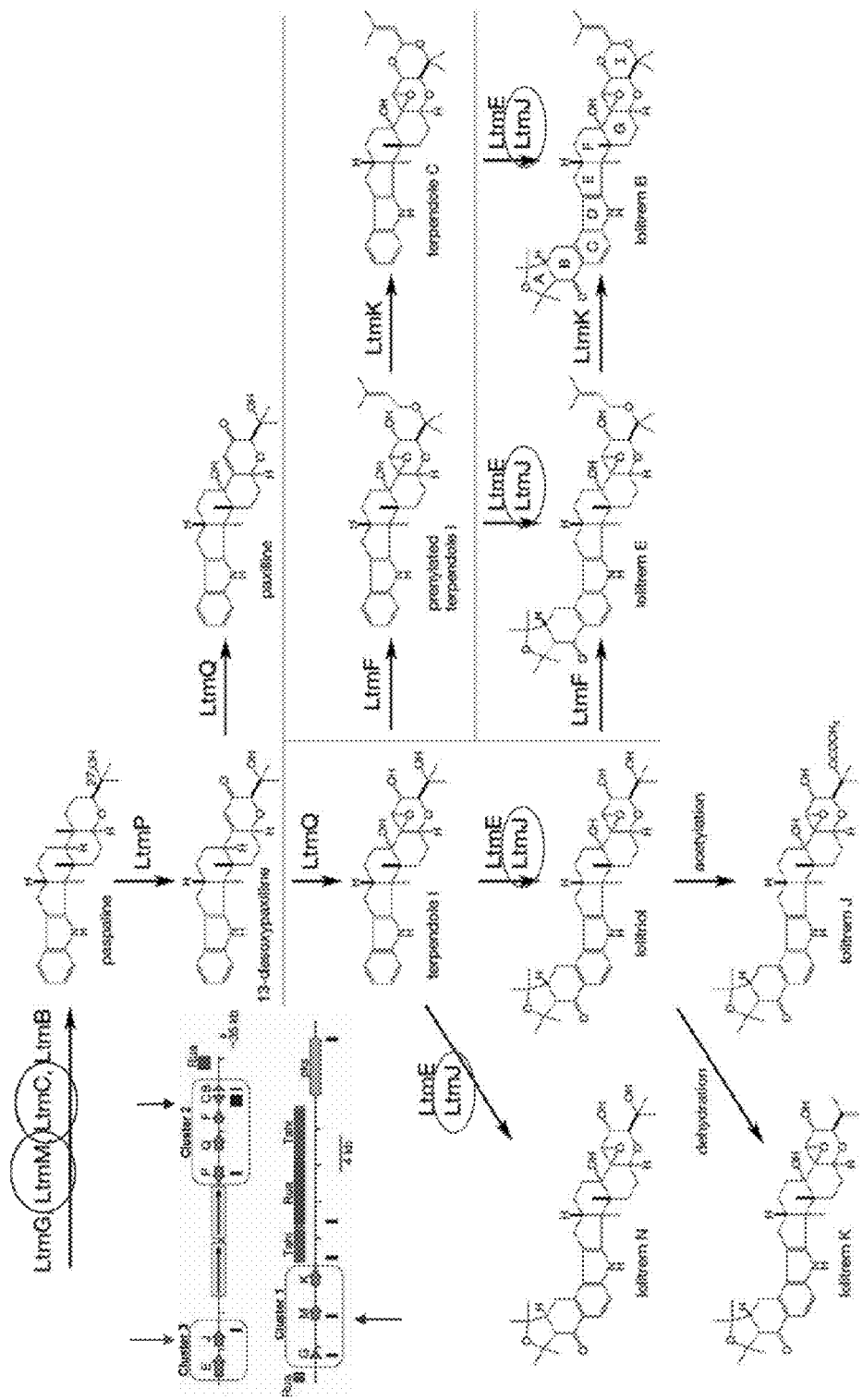

FIG. 106 shows the indole-diterpene biosynthetic pathway of *Neotyphodium* endophytes.

Figure 107:
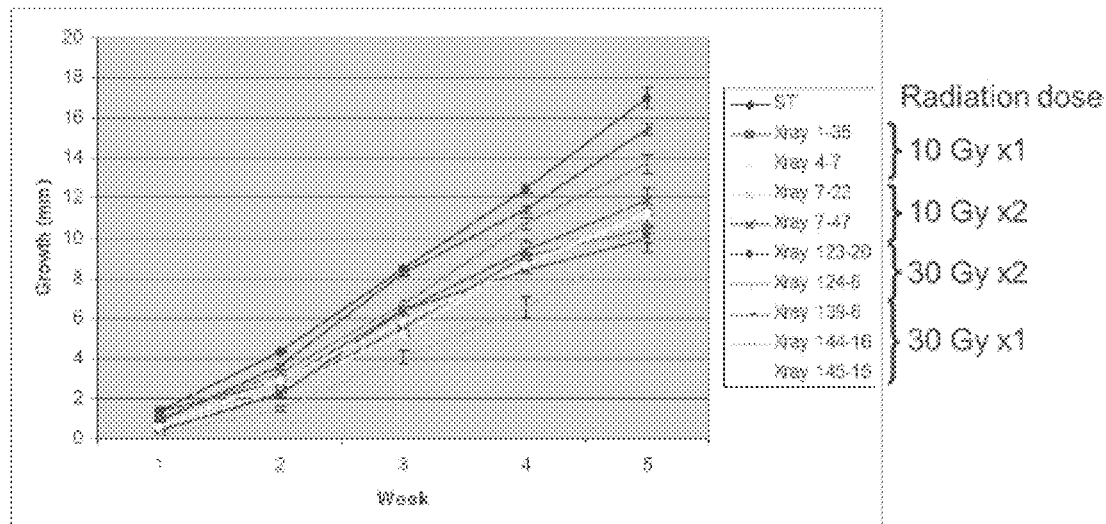

FIG. 107 shows in vitro growth of X-ray irradiated *Neotyphodium* endophyte strains.

Figure 108:
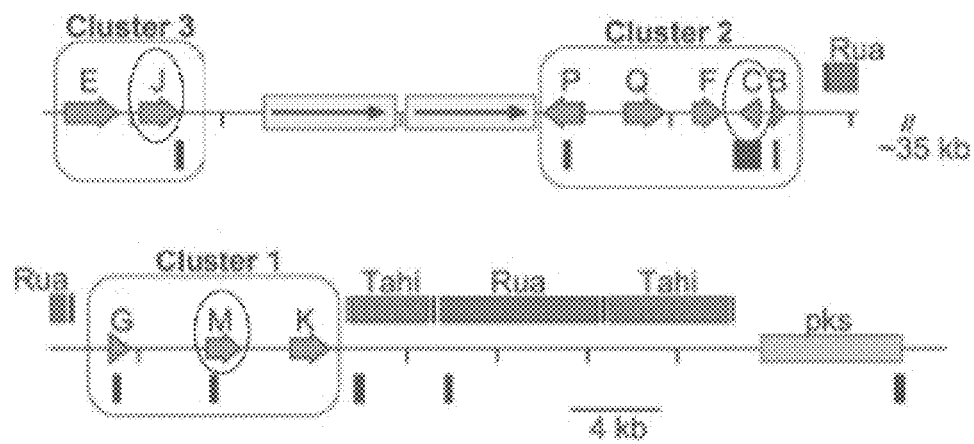

FIG. 108 shows Itm gene clusters of *Neotyphodium* endophytes.

Figure 109:
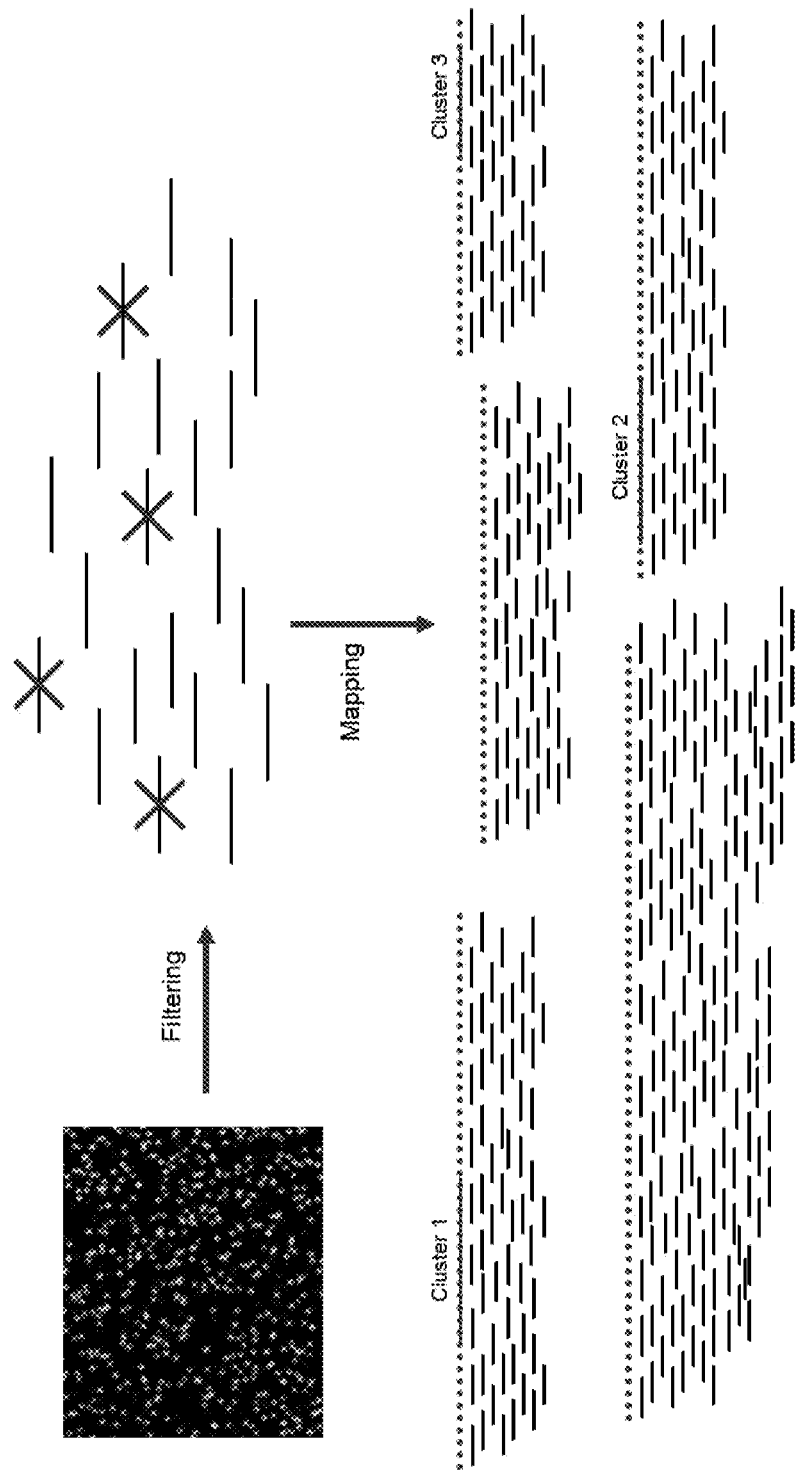

FIG. 109 shows determination of genome sequence variation in X-ray irradiated *Neotyphodium* endophyte strains.

Figures 110, 111:
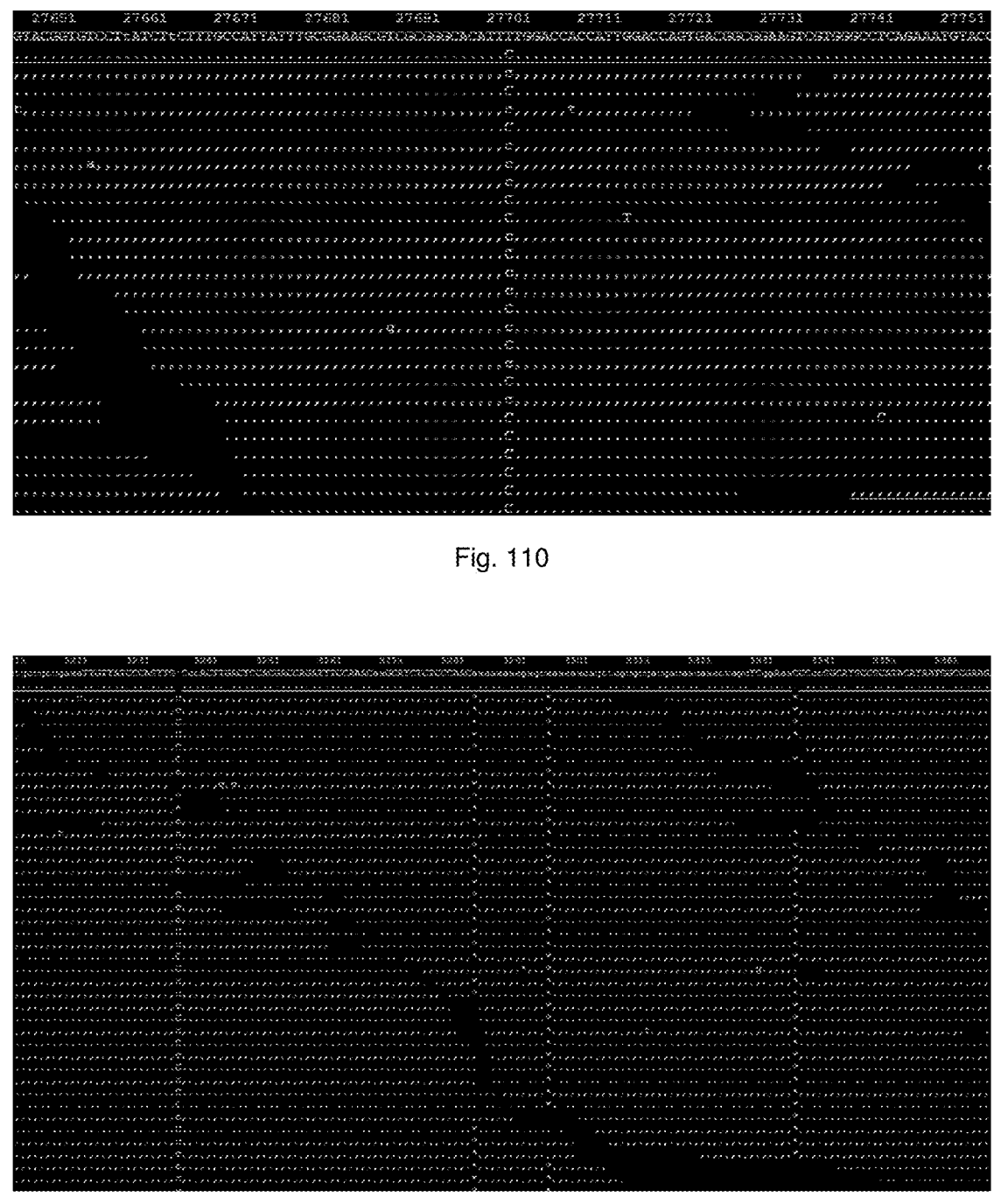

FIG. 110 shows single nucleotide polymorphisms (SNPs) in genome sequences of X-ray irradiated *Neotyphodium* endophyte strains.

FIG. 111 shows small insertions/deletions (INDELs) in genome sequences of X-ray irradiated *Neotyphodium* endophyte strains.

Figure 112:
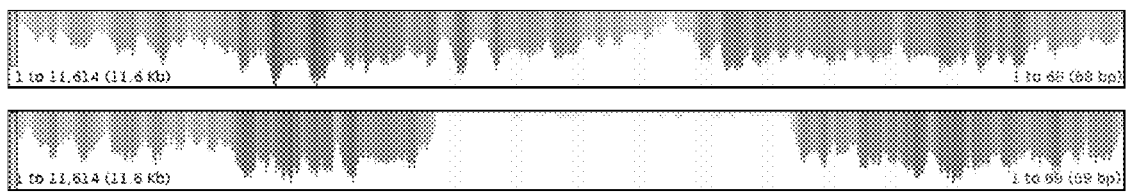
Figure 112:
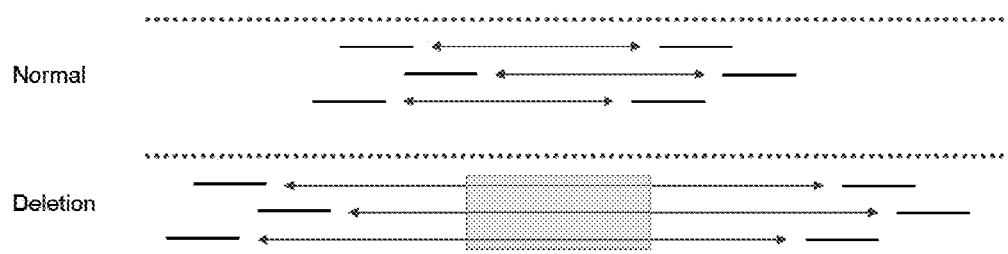

FIG. 112 shows deletions in genome sequences of X-ray irradiated *Neotyphodium* endophyte strains.

Figure 113:
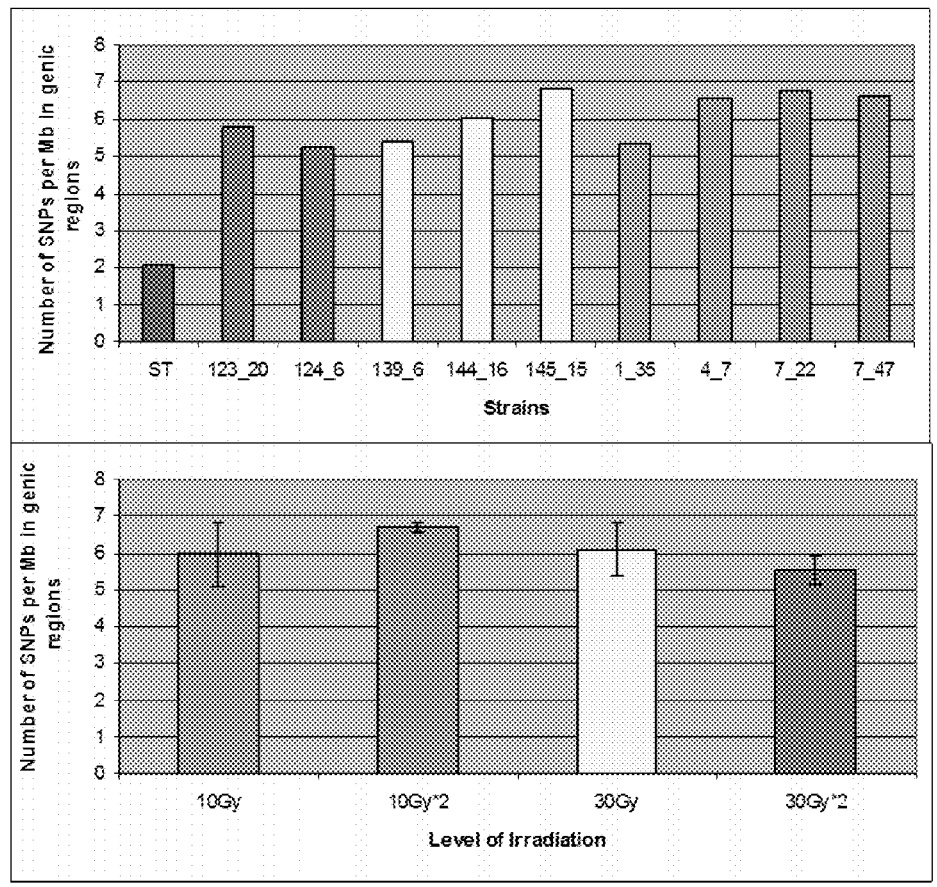

FIG. 113 shows numbers of SNPs in genic regions of genome sequences of X-ray irradiated *Neotyphodium* endophyte strains.

Figure 114:
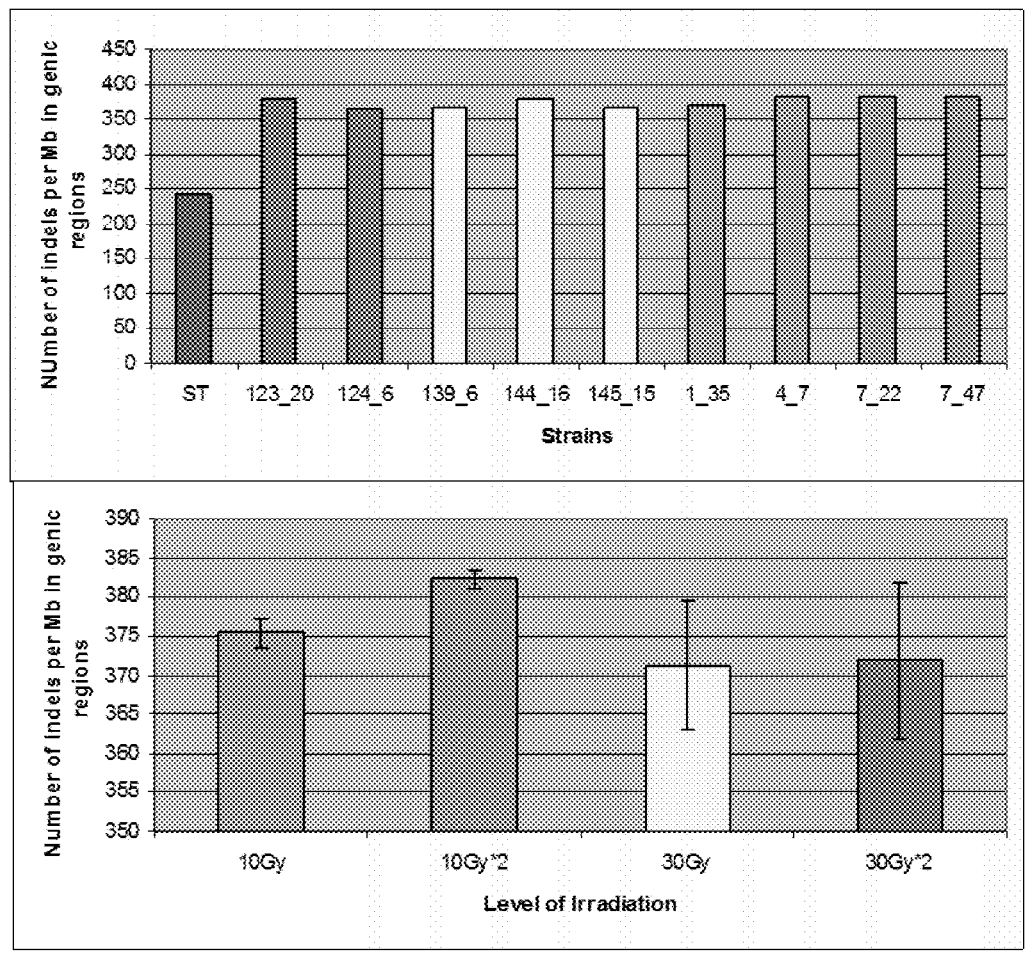

FIG. 114 shows numbers of INDELs in genic regions of genome sequences of X-ray irradiated *Neotyphodium* endophyte strains.

Figure 115:
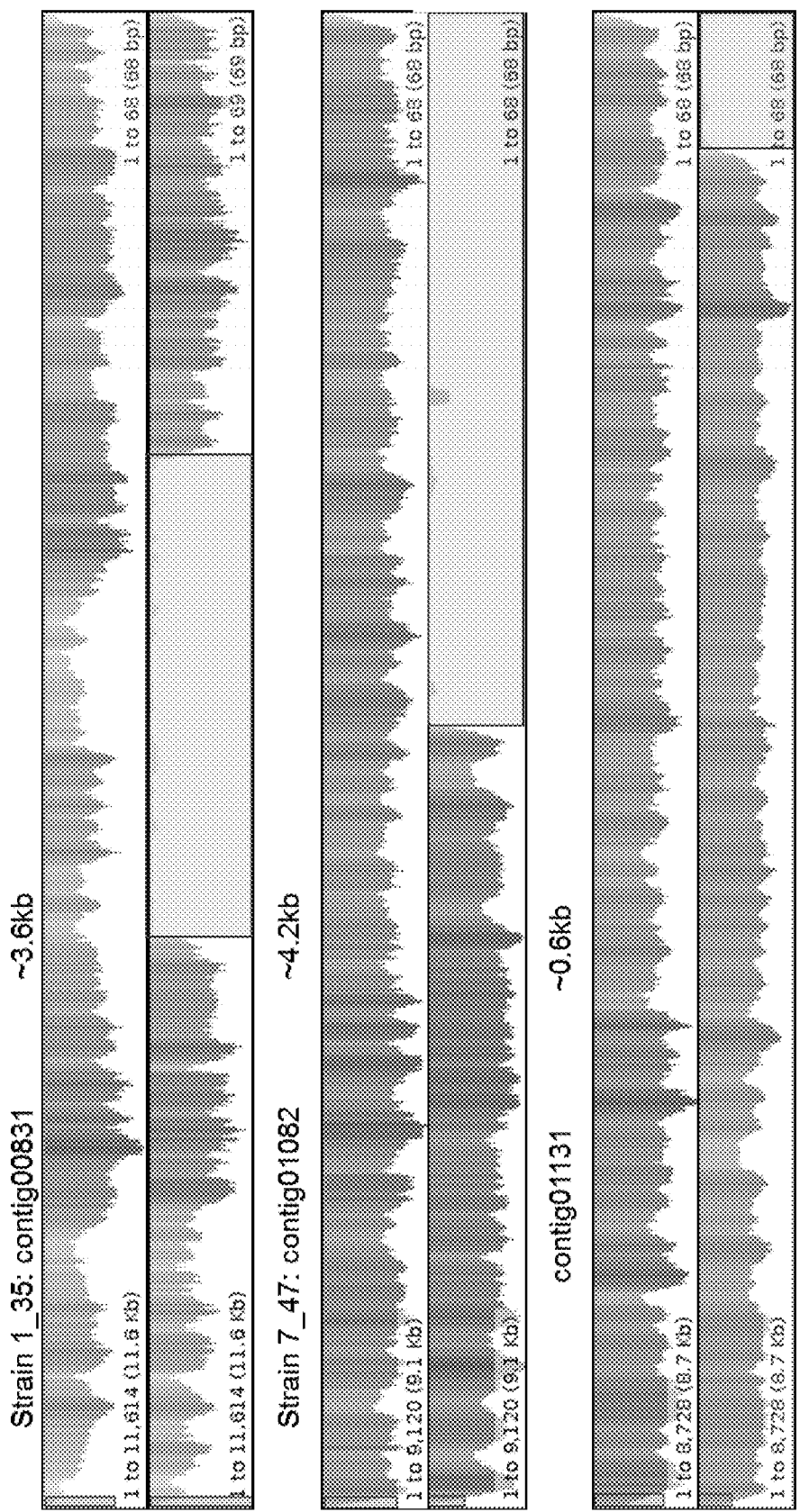

FIG. 115 shows the spectrum of genome sequence changes (deletions) in genome sequences of X-ray irradiated *Neotyphodium* endophyte strains.

Figure 116:
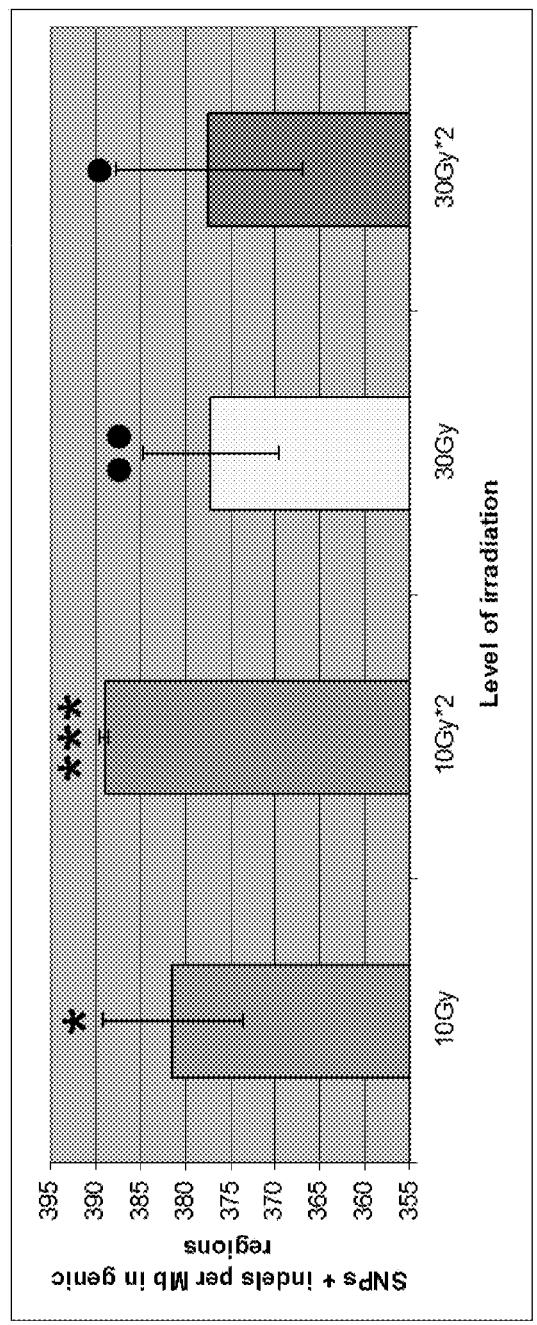

FIG. 116 shows mutagenesis index of X-ray irradiated strains based on number of genome sequence changes observed in genome sequences of X-ray irradiated *Neotyphodium* endophyte strains.

Figure 117:
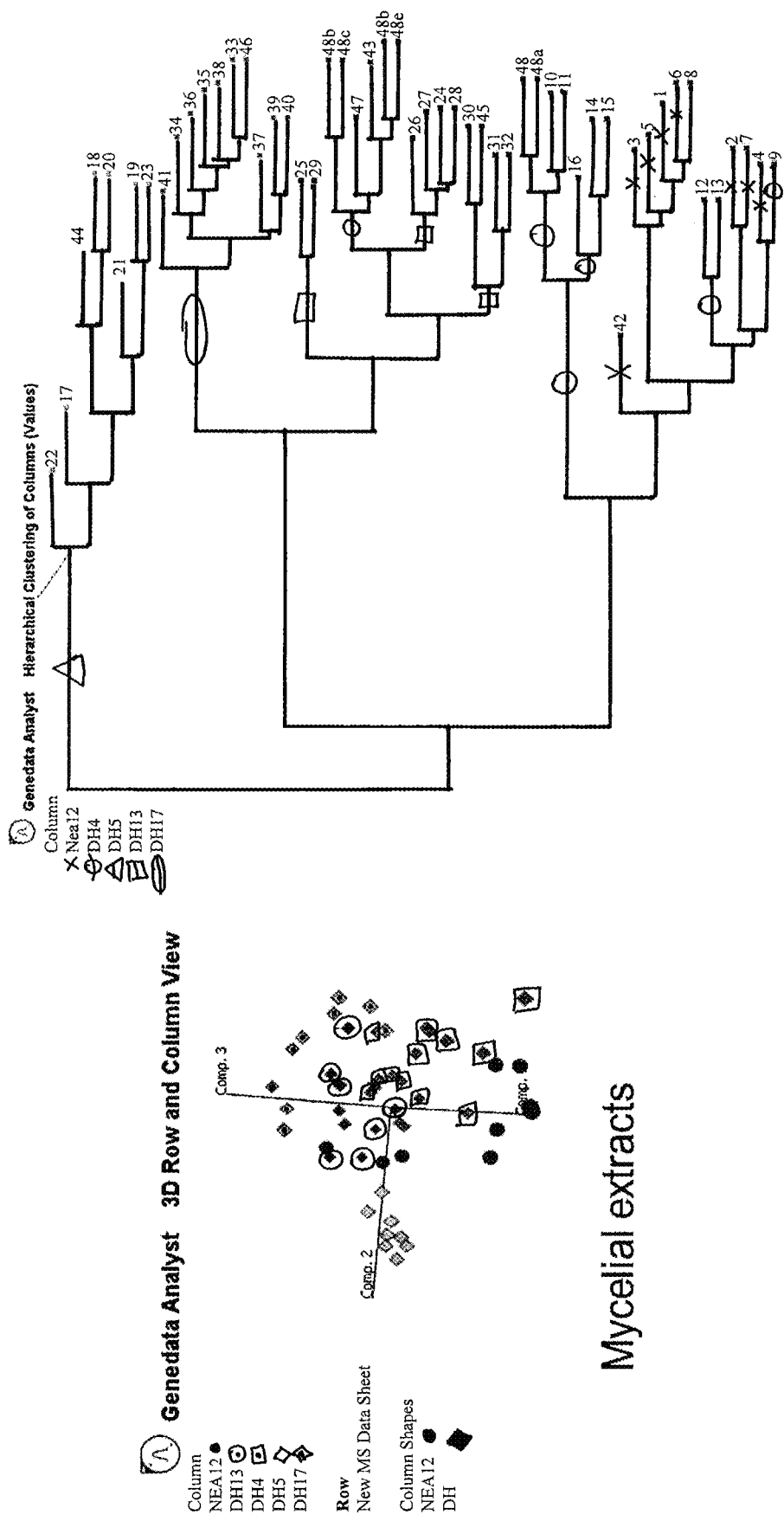

FIG. 117 shows metabolic profiling of NEA12$^{dh}$ *Neotyphodium* endophyte strains.

Figure 118:
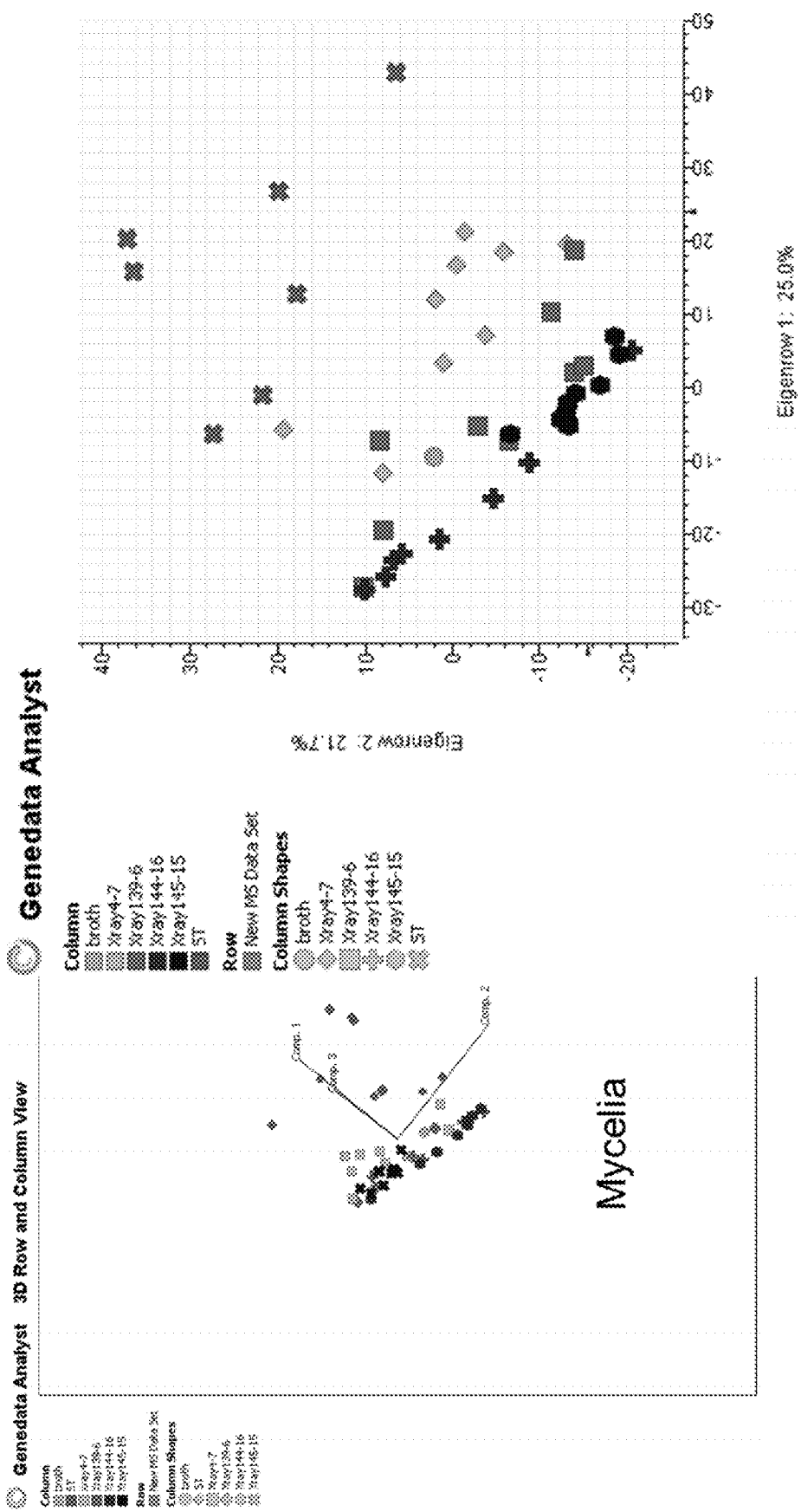

FIG. 118 shows metabolic profiling of X-ray irradiated *Neotyphodium* endophyte strains.

Figure 119:
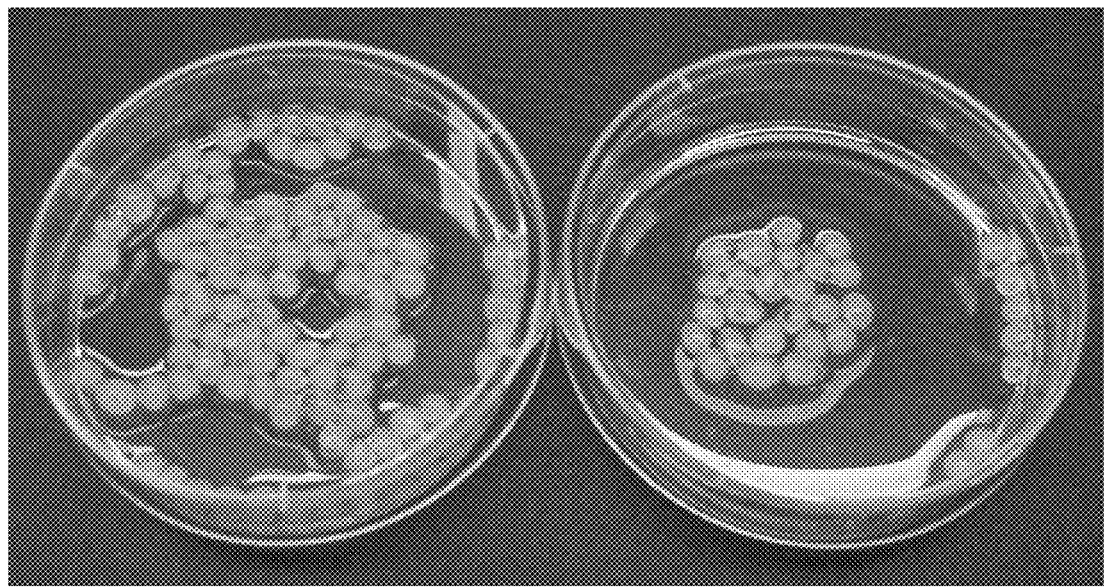

FIG. 119 shows artificial seeds generated through Ca-alginate coating of perennial ryegrass embryos using a coating with Ca-alginate matrix without added nutrients.

Figure 120:
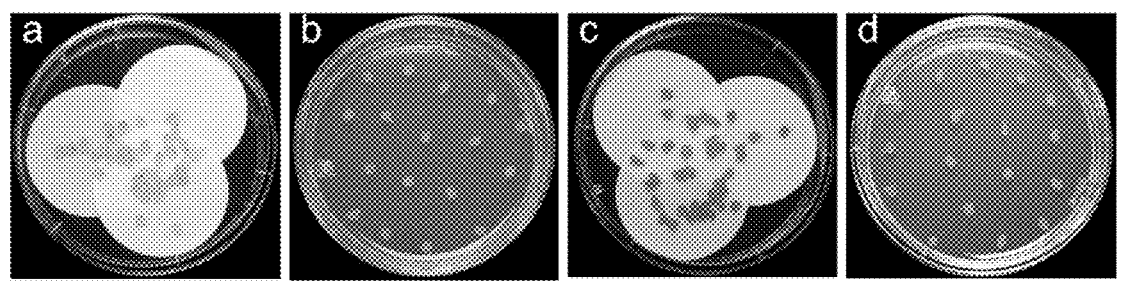

FIG. 120 shows Ca-alginate coating of perennial ryegrass embryos into artificial seeds using coating with coloured Ca-alginate matrix. Artificial seeds of perennial ryegrass coloured with Queen Green (90610); a) air-dried artificial seeds; b) artificial seeds plated on germination medium. Artificial seeds of perennial ryegrass coloured with Queen Pink (92330); c) air-dried artificial seeds; d) artificial seeds plated on germination medium.

Figure 121:
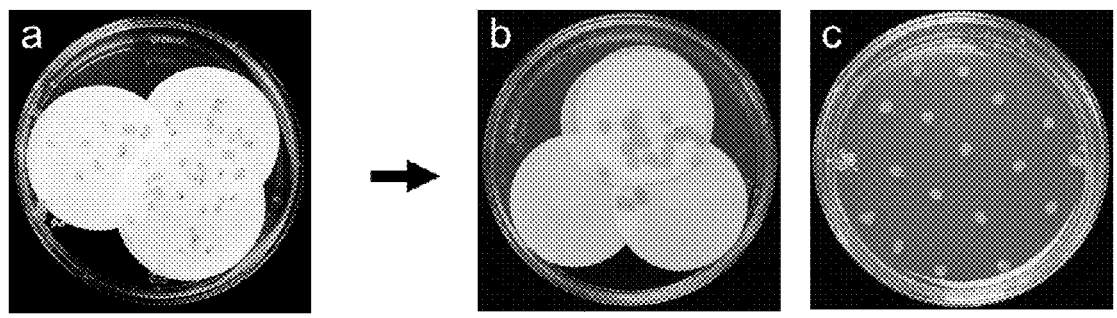

FIG. 121 shows Ca-alginate coating of perennial ryegrass embryos into artificial seeds using coating with multiple Ca-alginate matrix layers. a) Artificial seeds of perennial ryegrass coated with first coating (non-coloured) Ca-alginate layer (layer A) with added nutrients. b) Artificial seeds of perennial ryegrass coated with two (first layer A; non-coloured plus second layer B; Queen Green-coloured) Ca-alginate layers with added nutrients; c) double-coated artificial seeds placed on germination medium.

Figure 122:
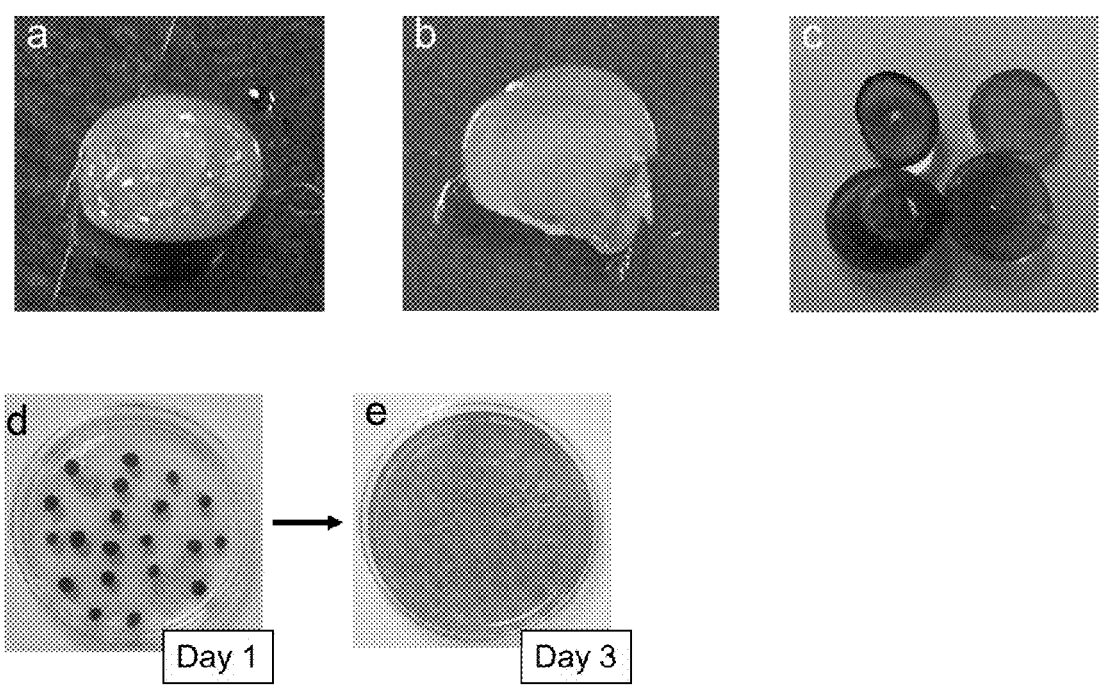

FIG. 122 shows Ca-alginate coating of perennial ryegrass embryos into artificial seeds using coating with multiple Ca-alginate matrix layers. a)-c) Cross-sections of artificial seeds of perennial ryegrass coated with first coating (non-coloured) Ca-alginate layer (layer A) and second coating with Queen-Pink or Queen-Green coloured Ca-alginate layer (layer B). d)-e) Cross-sections of artificial seeds of perennial ryegrass coated with first coating (non-coloured) Ca-alginate layer (layer A) and second coating with Queen-Green coloured Ca-alginate layer (layer B).

Figure 123:
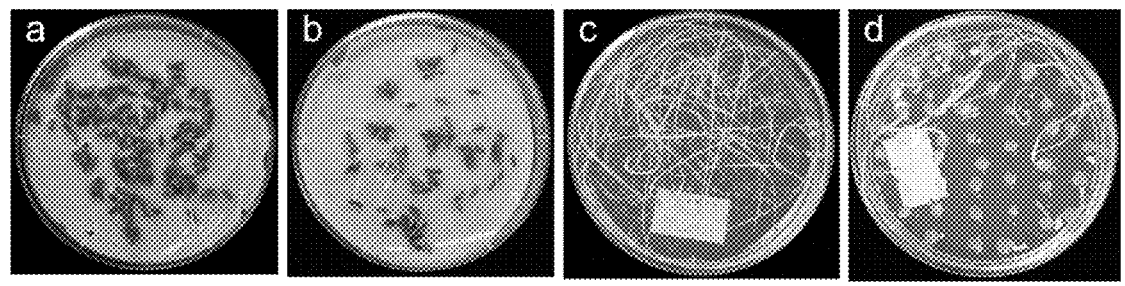

FIG. 123 shows germination of seeds, embryos and artificial seeds of perennial ryegrass cv. Bronsyn E− (endophyte free, 2668 seed batch). a) Original seeds: 1% germination frequency on filter paper; b) Surface-sterilized seeds: 10% germination frequency on filter paper; c) Isolated embryos: 48% germination frequency on germination medium; d) Artificial seeds (with germination medium): 40% germination frequency on MS medium.

Figure 124:
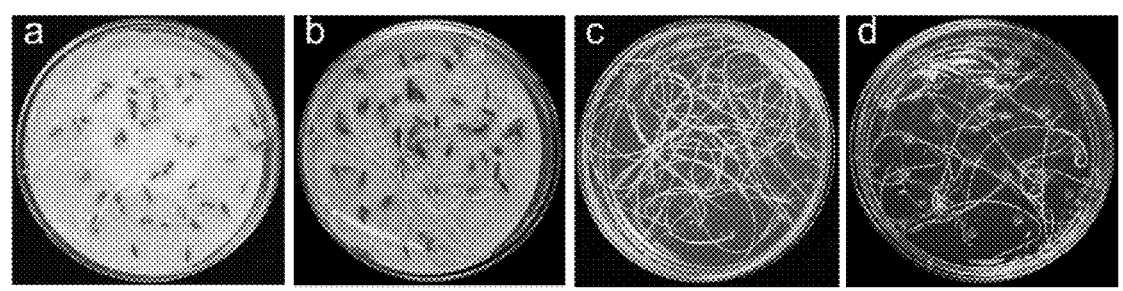

FIG. 124 shows Germination of seeds, embryos and artificial seeds of perennial ryegrass cv. Bronsyn E+(endophyte plus, 2667 seed batch). a) Original seeds: 10% germination frequency on filter paper; b) Surface-sterilized seeds: 30% germination frequency on filter paper; c) Isolated embryos: 90% germination frequency on germination medium; d) Artificial seeds (with germination medium): 81% germination frequency on MS medium.

Figure 125:
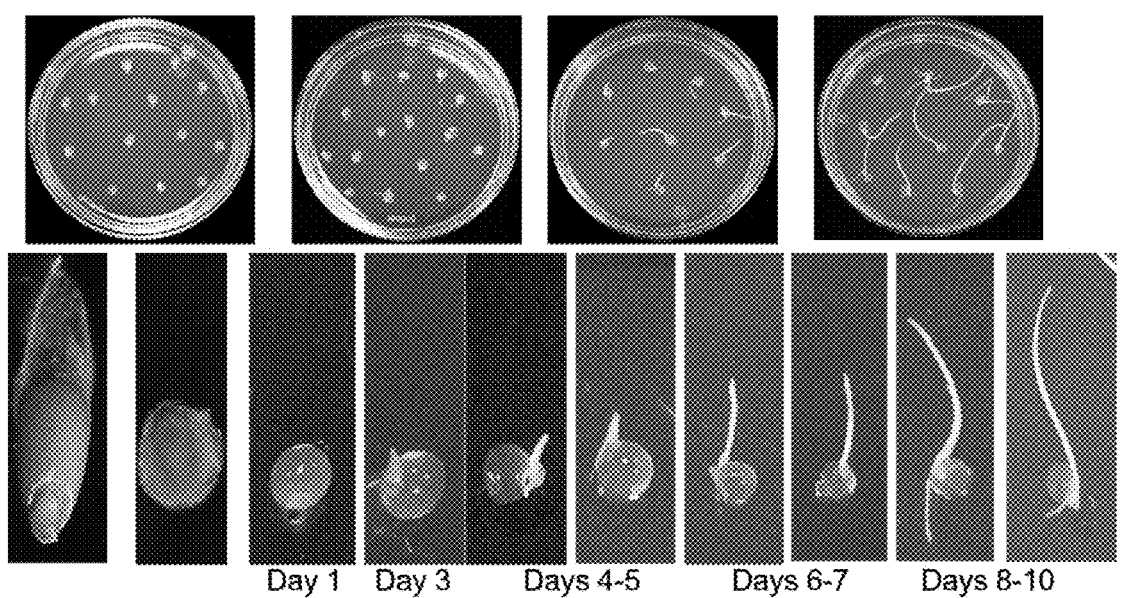

FIG. 125 shows germination of artificial seeds and development of artificial-seed derived seedlings in perennial ryegrass.

Figure 126:
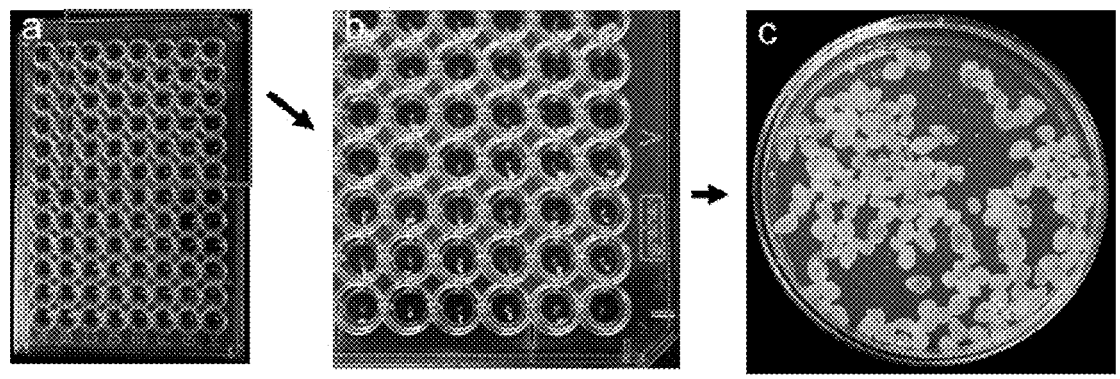

FIG. 126 shows freshly isolated seed-derived embryos of perennial ryegrass individually placed in wells of a) 96-well and b) endophyte mycelium suspension added to individual wells and allowed to partly air-dry under laminar flow prior to c) production of artificial seeds coated with Ca-alginate layer.

Figure 127:
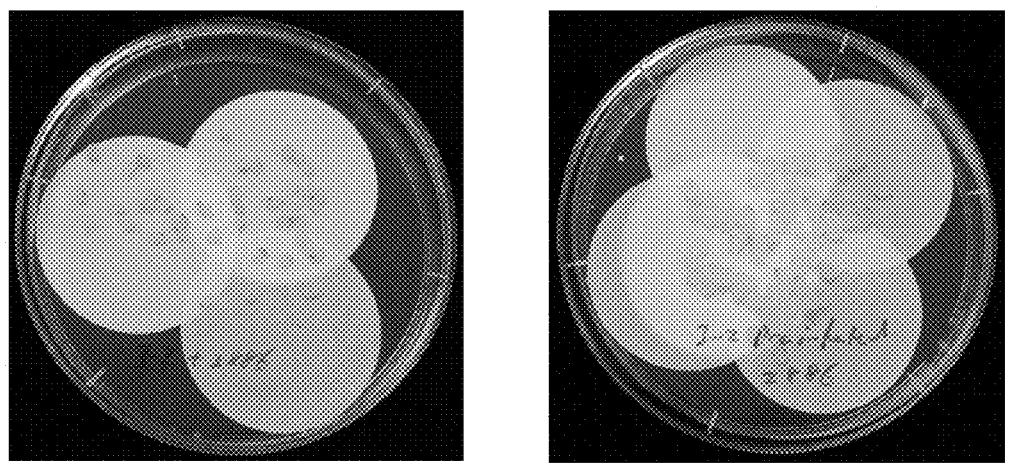

FIG. 127 shows artificial seeds produced by method 1.

Figure 128:
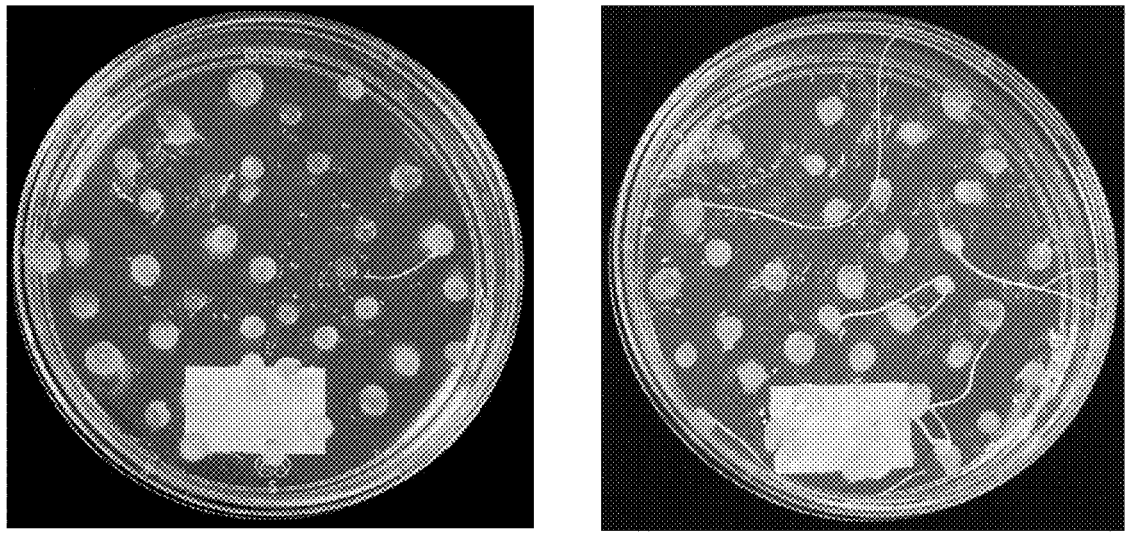

FIG. 128 shows germinating artificial seeds produced by method 1.

Figure 129:
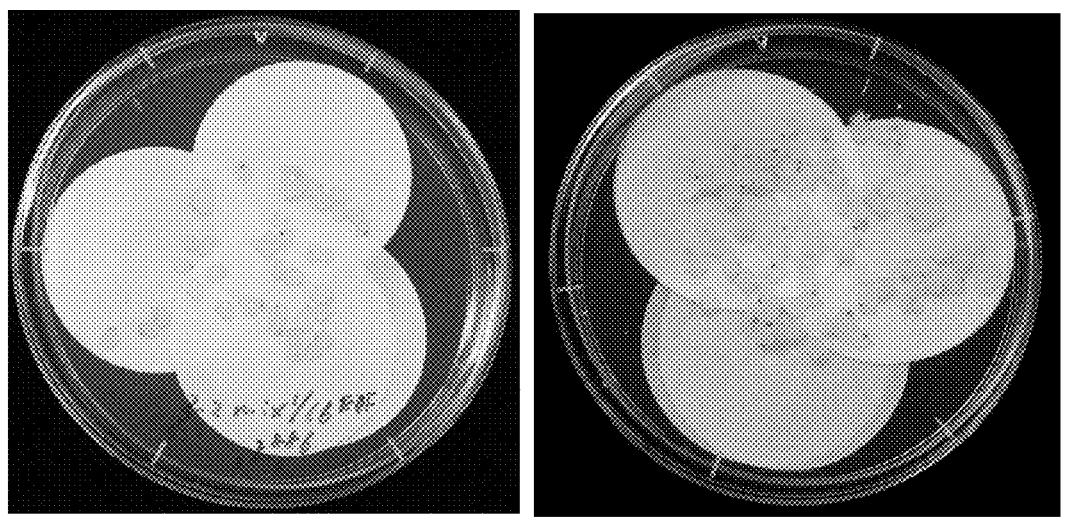

FIG. 129 shows artificial seeds produced by method 2.

Figure 130:
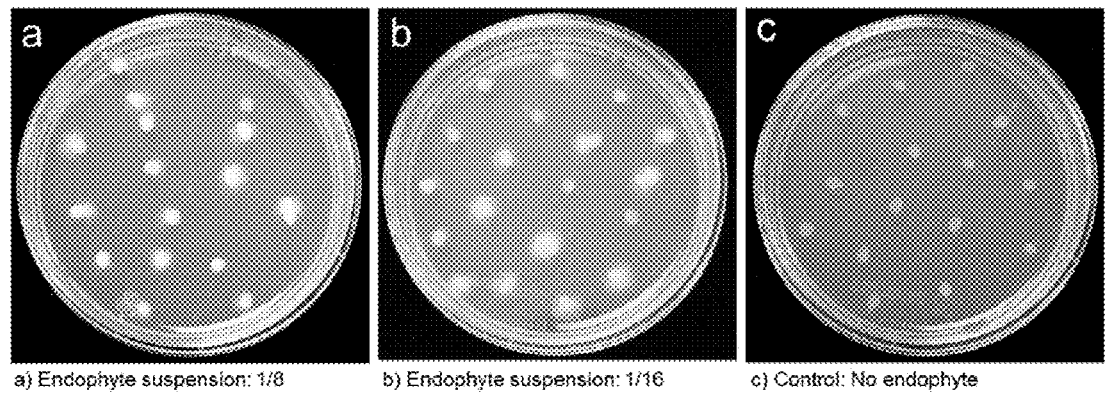

FIG. 130 shows artificial seeds produced by method 2 with endophyte outgrowth.

Figure 131:
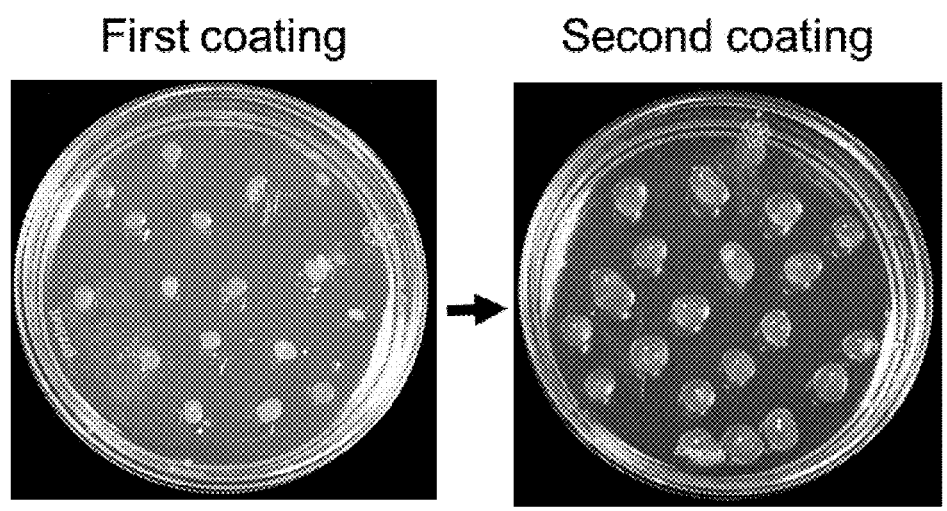

FIG. 131 shows artificial seeds produced by method 3.

Figure 132:
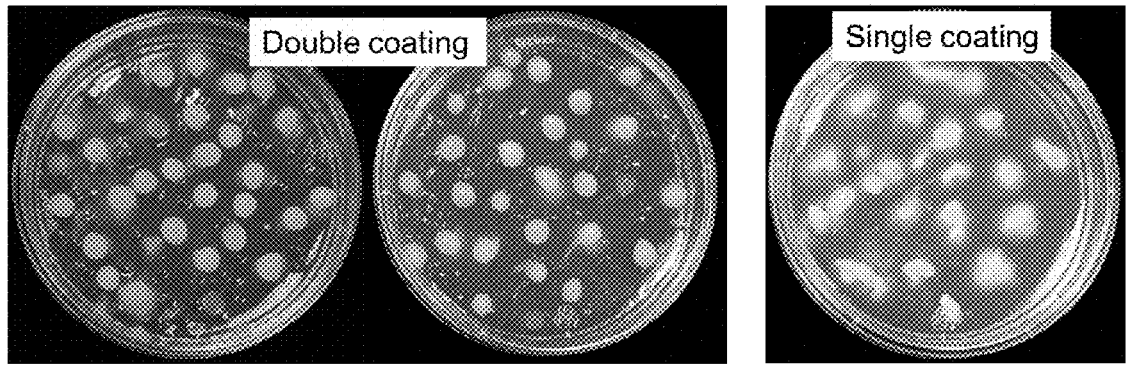

FIG. 132 shows artificial seeds produced by method 3 with endophyte outgrowth.

Figure 133:
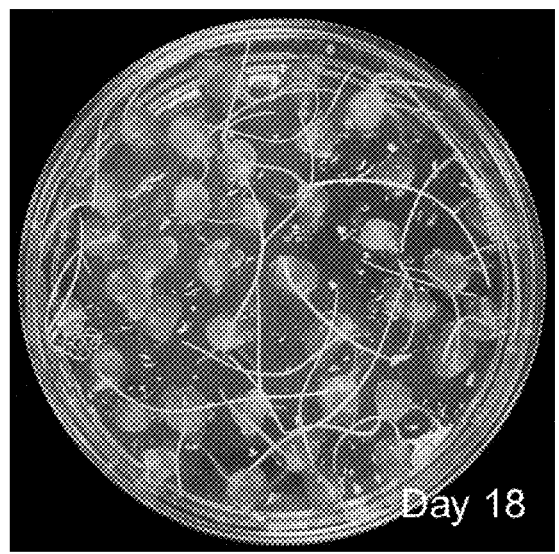

FIG. 133 shows germinating artificial seeds produced by method 3.

Figure 134:
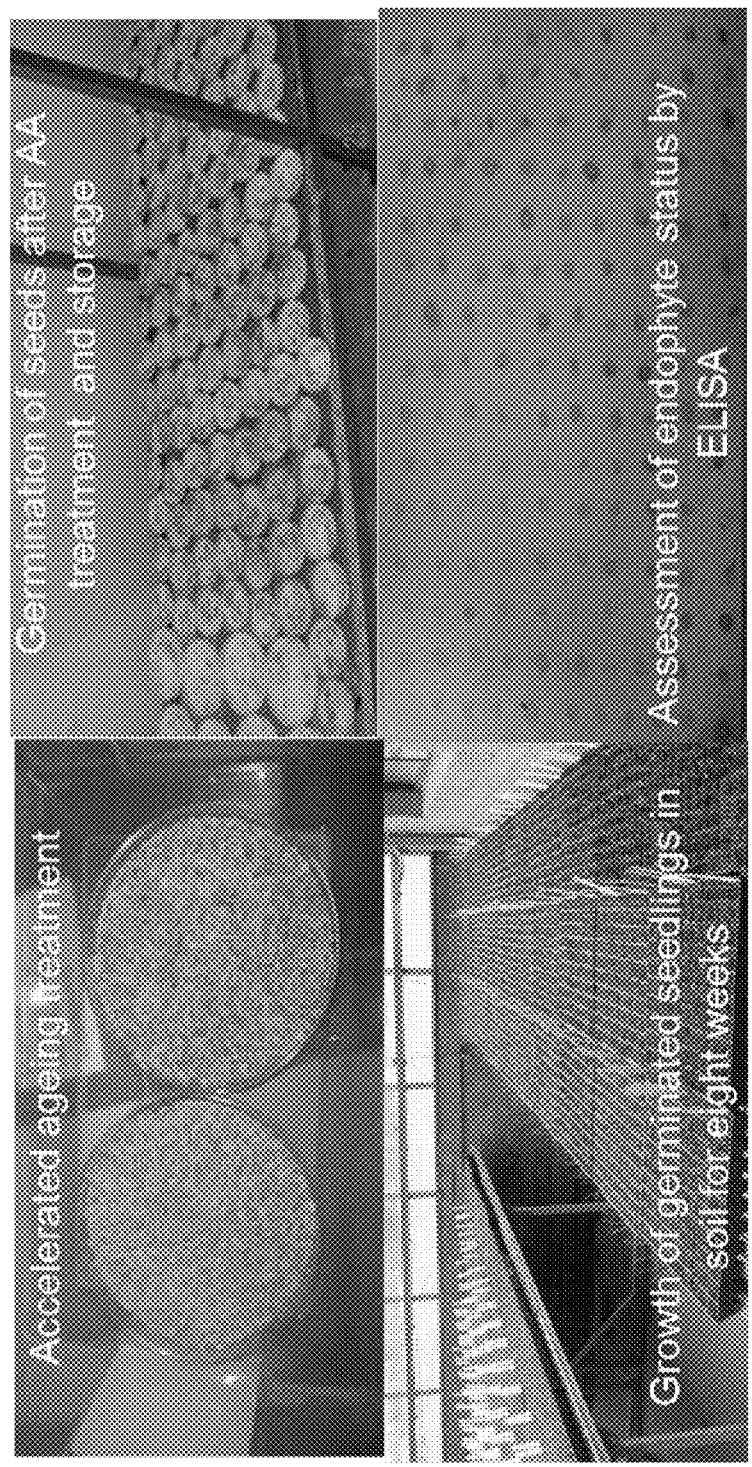

FIG. 134 shows an outline of accelerated ageing.

Figure 135:
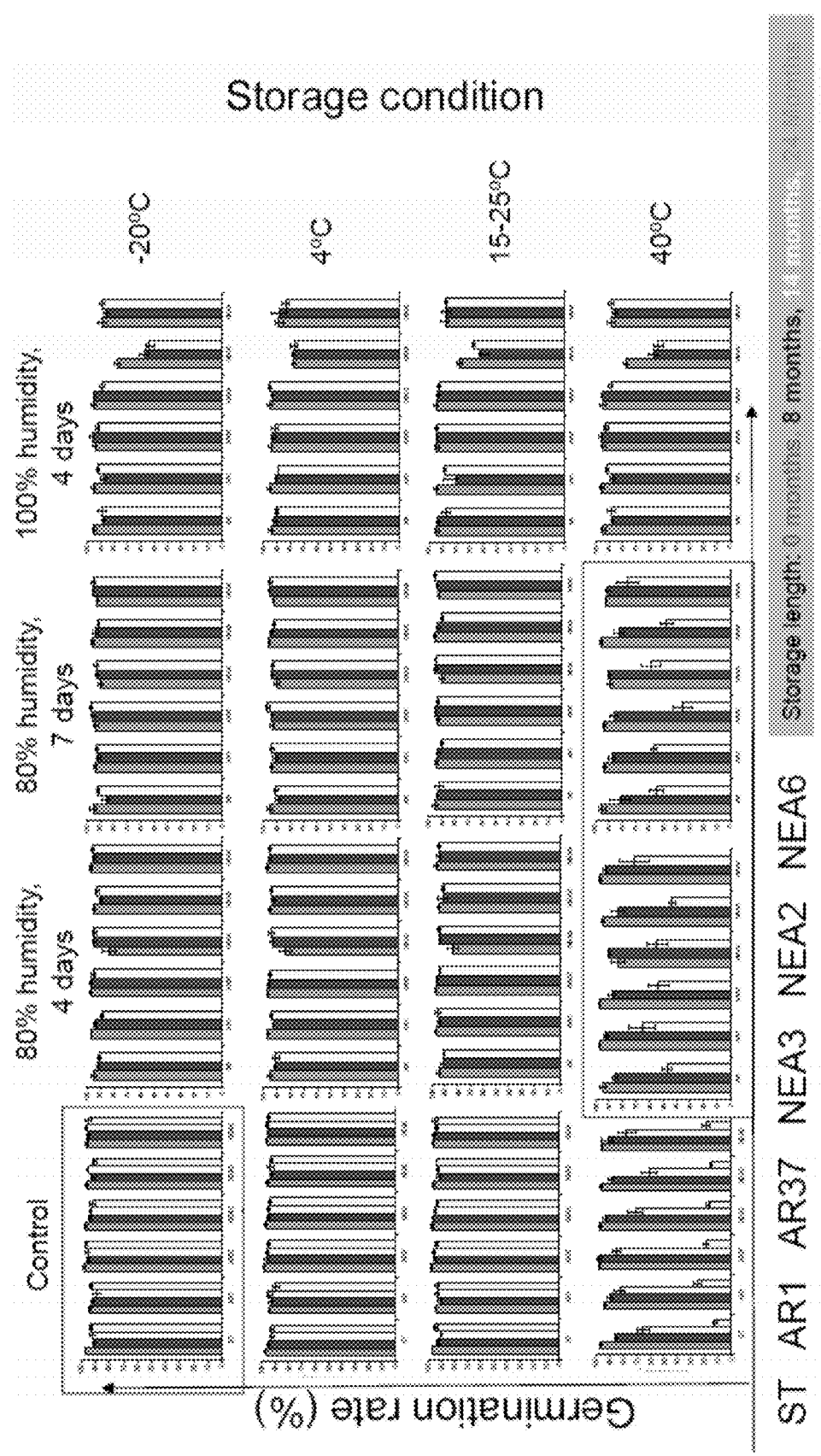

FIG. 135 shows seed germination rate of perennial ryegrass cv. Bronsyn with different endophytes after accelerated ageing treatment of seed followed by seed storage.

Figure 136:
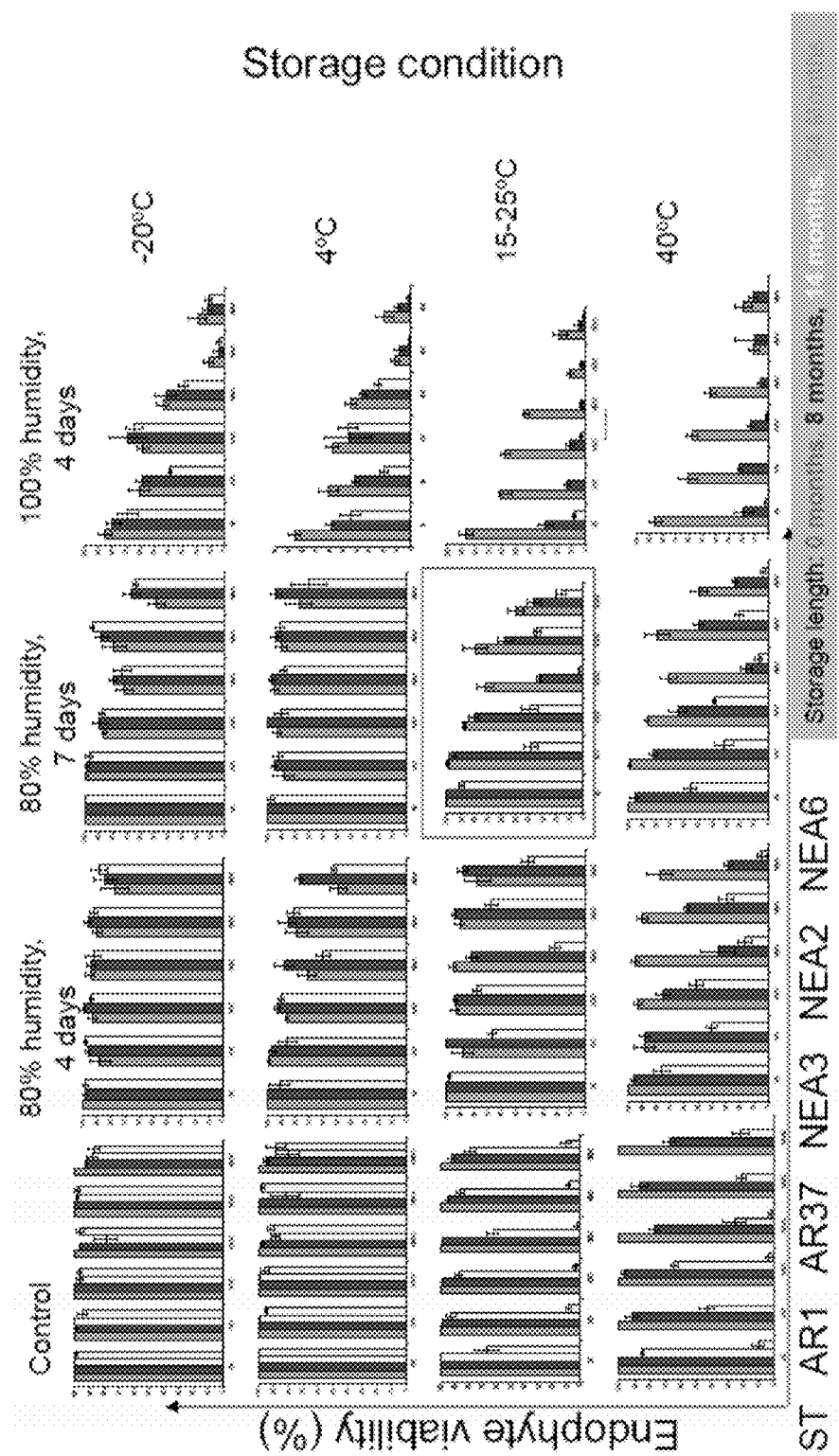

FIG. 136 shows endophyte viability in seed from perennial ryegrass cv. Bronsyn with different endophytes after accelerated ageing treatment of seed followed by seed storage.

Figure 137:
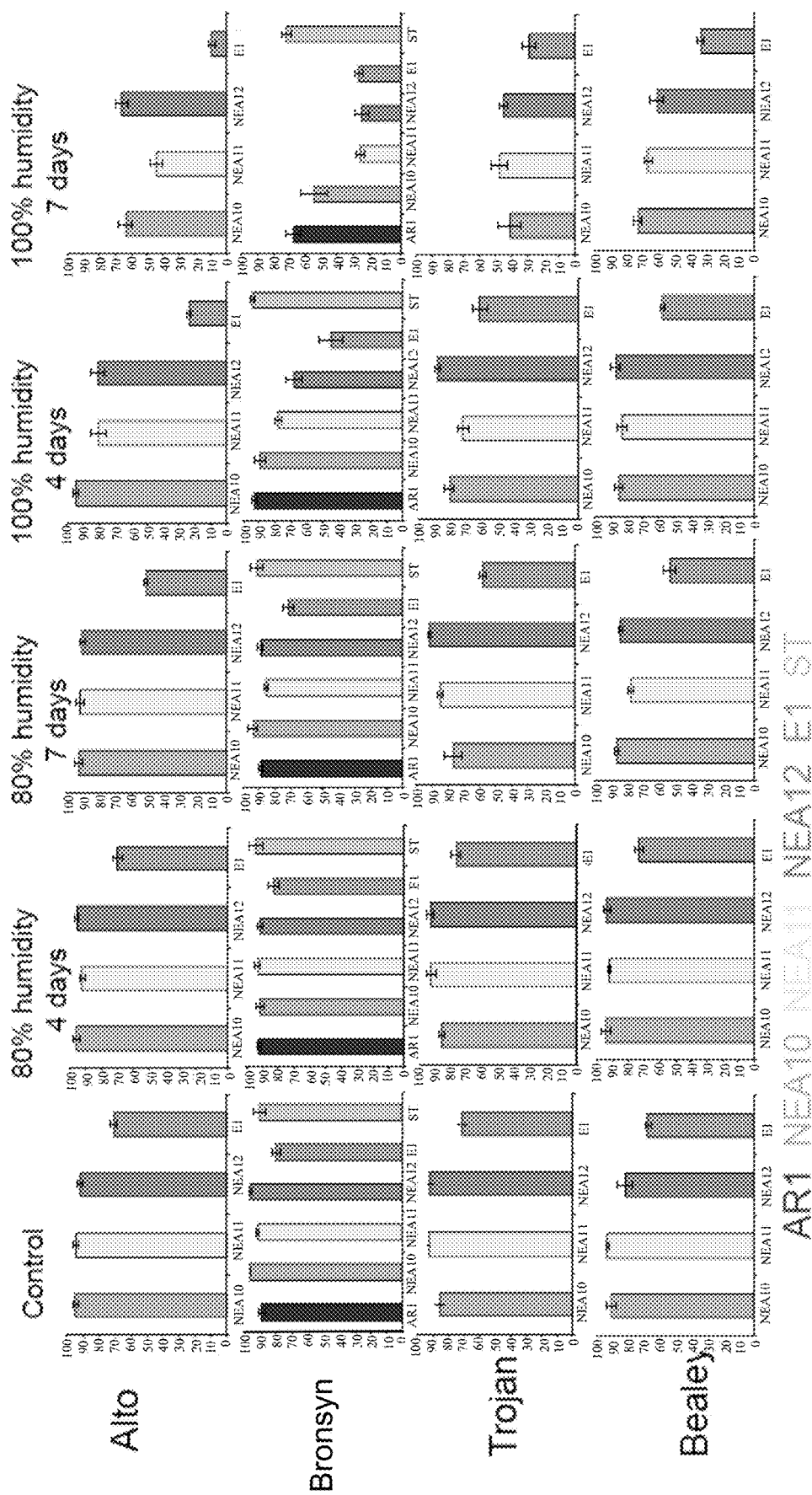

FIG. 137 shows seed germination rates of symbiota representing different endophytes in different host genetic backgrounds after accelerated ageing treatment of seed.

Figure 138:
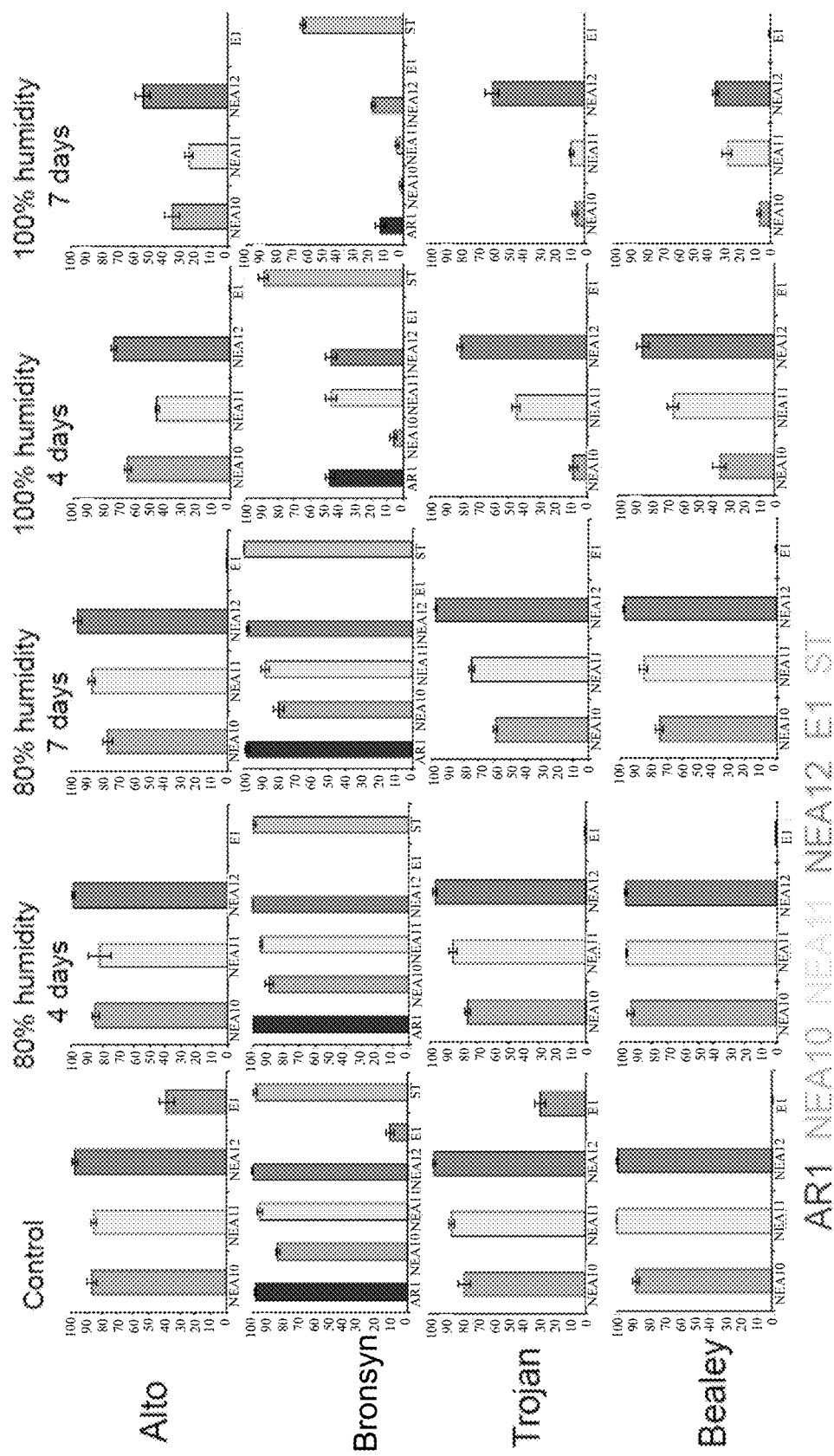

FIG. 138 shows endophyte viability of different endophytes in different host genetic backgrounds after accelerated ageing treatment of seed. In each of the graphs for Alto, Trojan and Bealey, the bars represent the endophytes NEA10, NEA11, NEA12 and E1, in that order from left to right. In each of the graphs for Bronsyn, the bars represent the endophytes AR1, NEA10, NEA11, NEA12, E1 and ST, in that order from left to right.

Figure 139:
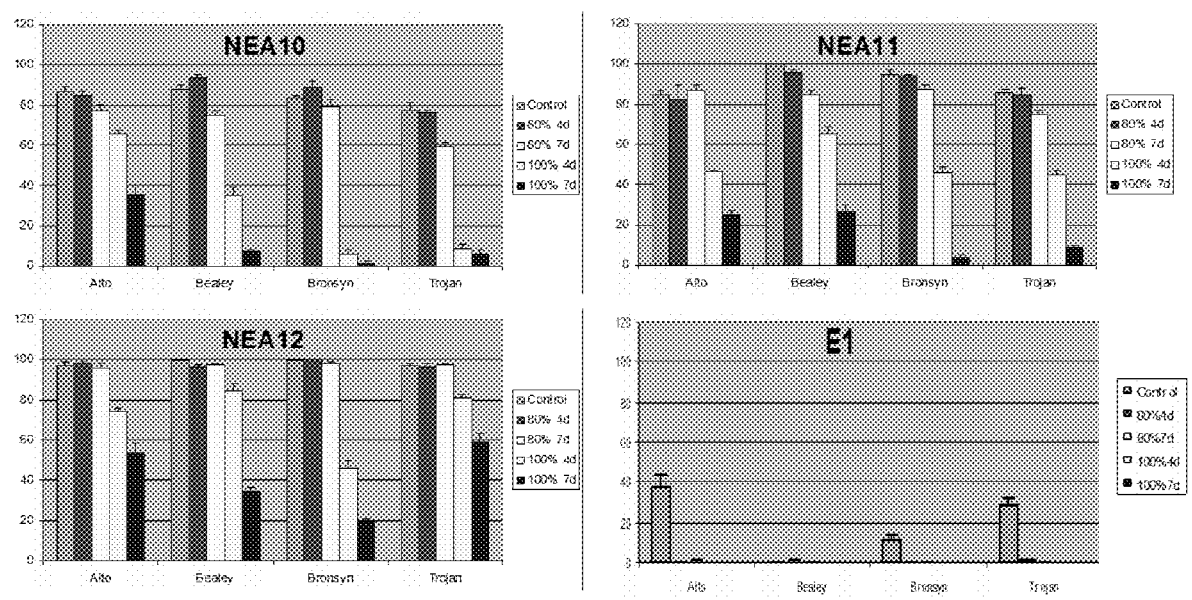

FIG. 139 shows endophyte viability of different endophytes in different host genetic backgrounds after accelerated ageing treatment of seed.

Figure 140:
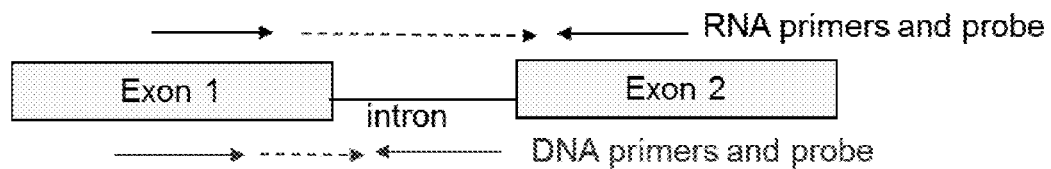

FIG. 140 shows primers designed for TaqMan assay.

Figure 141:
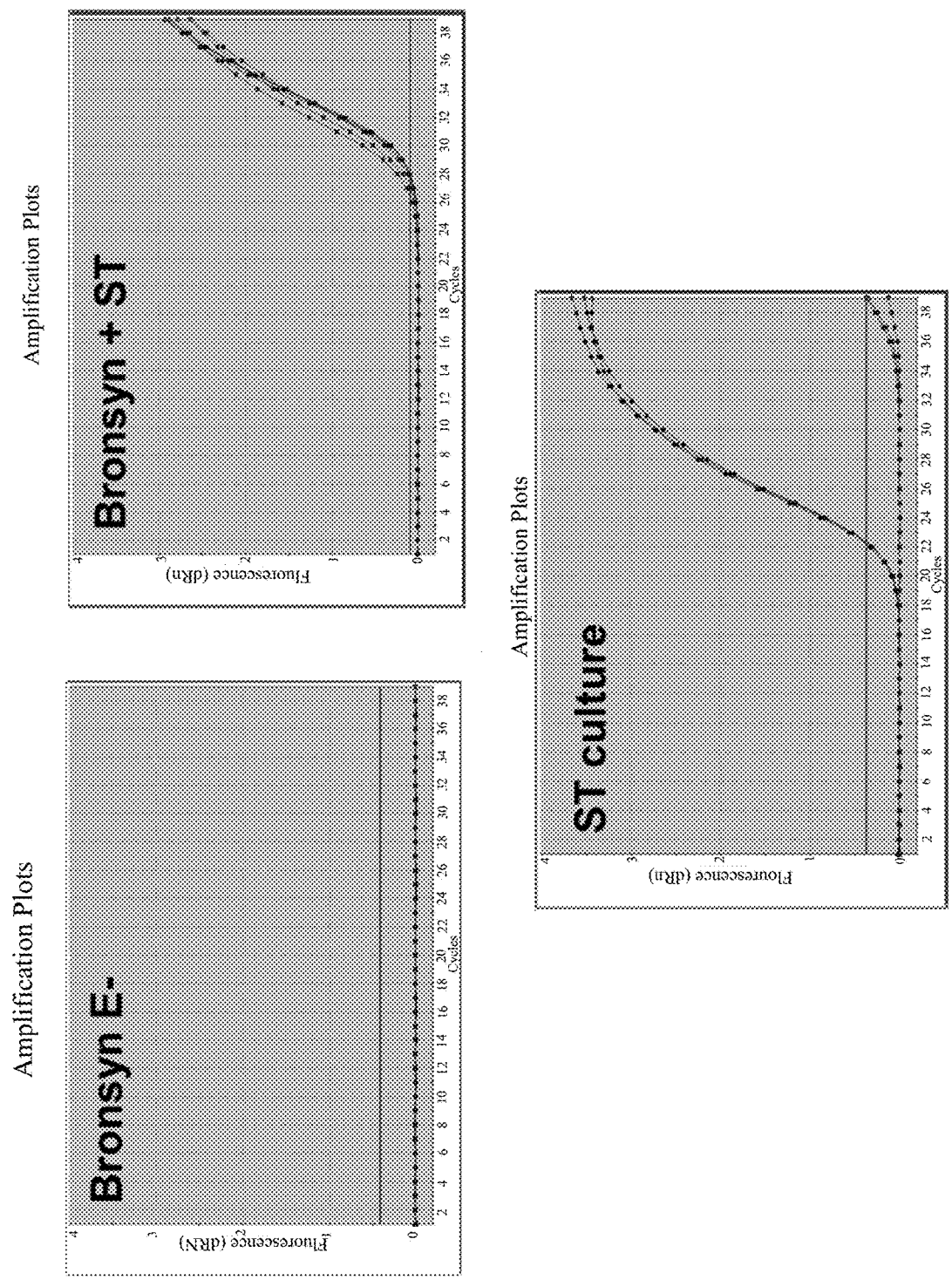

FIG. 141 shows TaqMan Primer Functionality for the Endophyte-Specific Gene LtmJ; RNA and DNA labelled.

Figure 142:
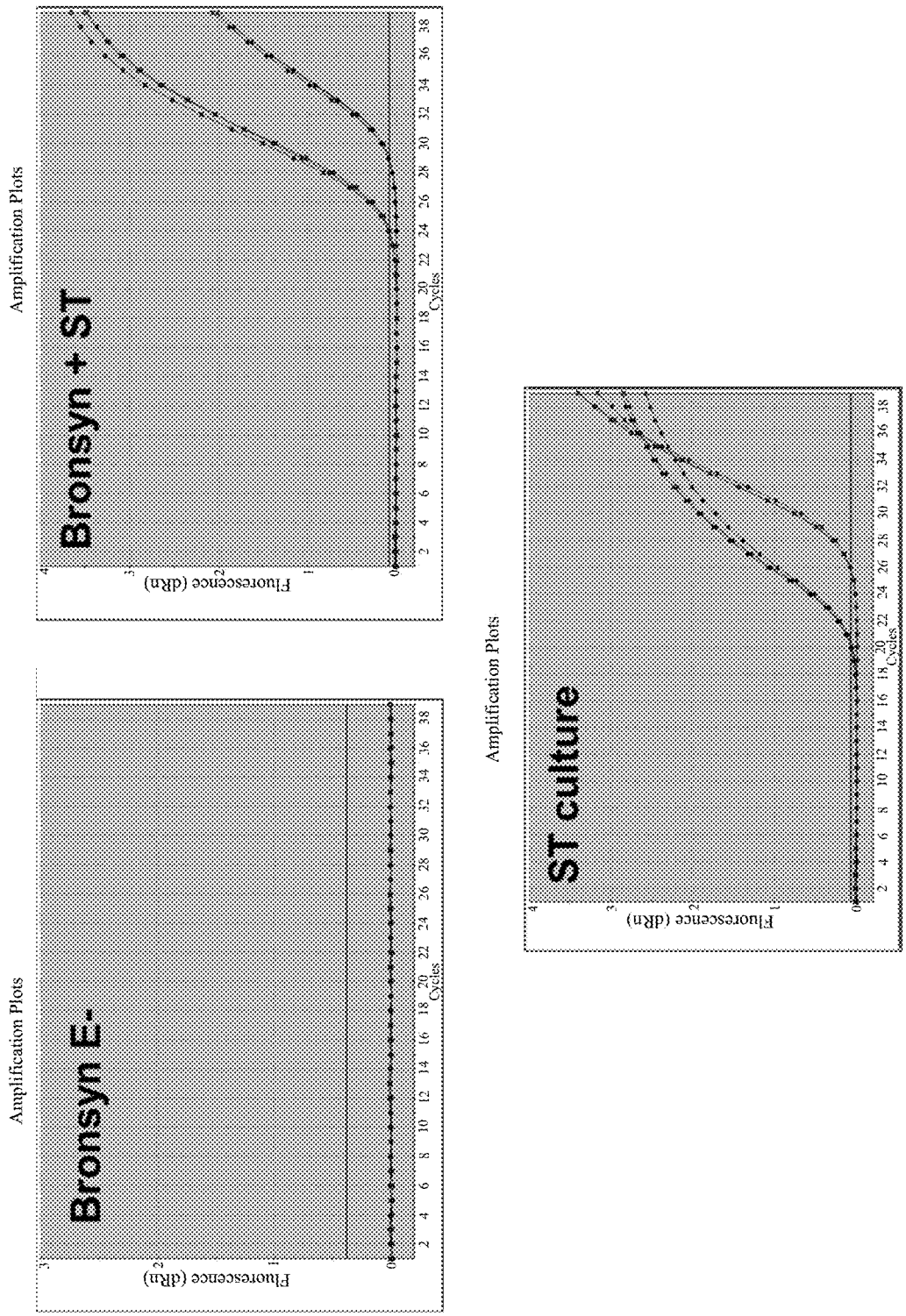

FIG. 142 shows TaqMan Primer Functionality for the Endophyte-Specific Gene 7490; RNA and DNA labelled.

Figure 143:
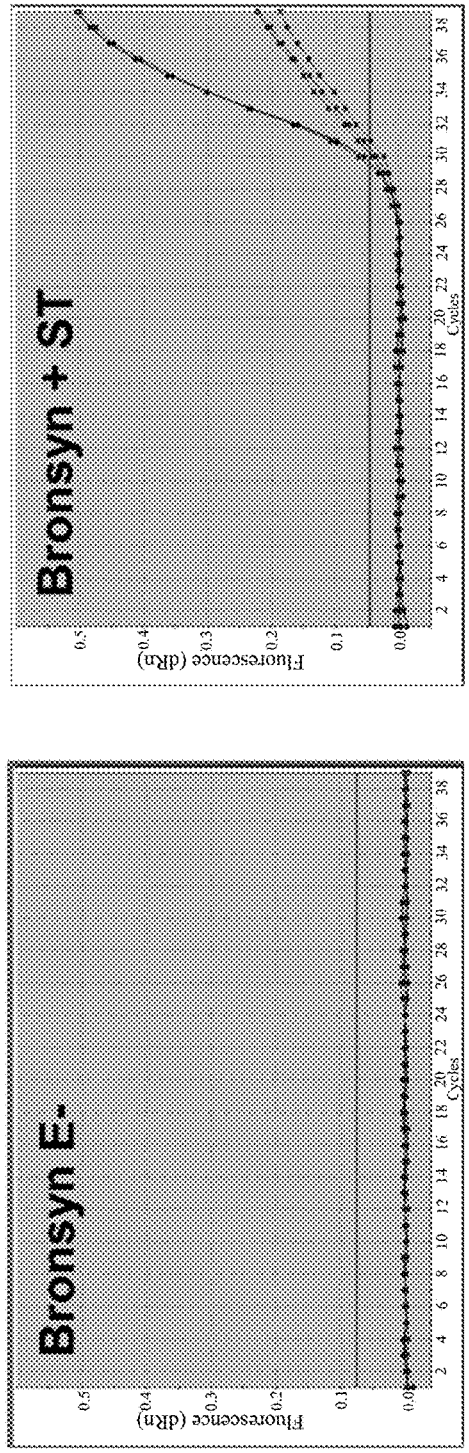
Figure 143:
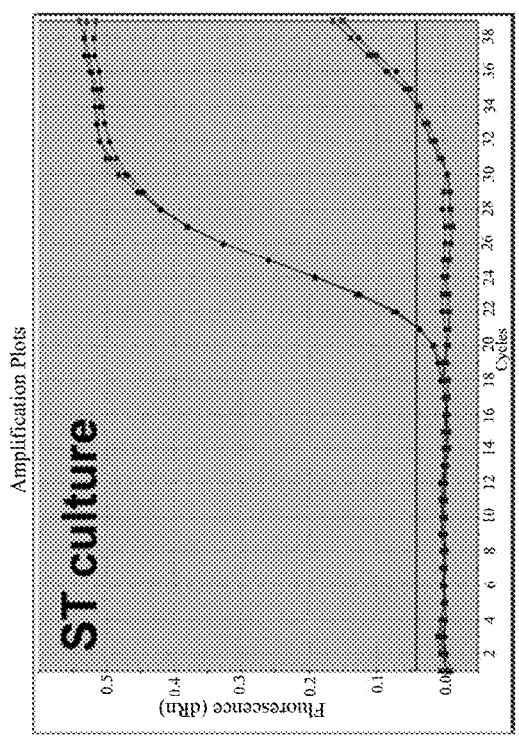

FIG. 143 shows TaqMan Primer Functionality for the Endophyte-Specific Gene 8263; RNA and DNA labelled.

Figure 144:
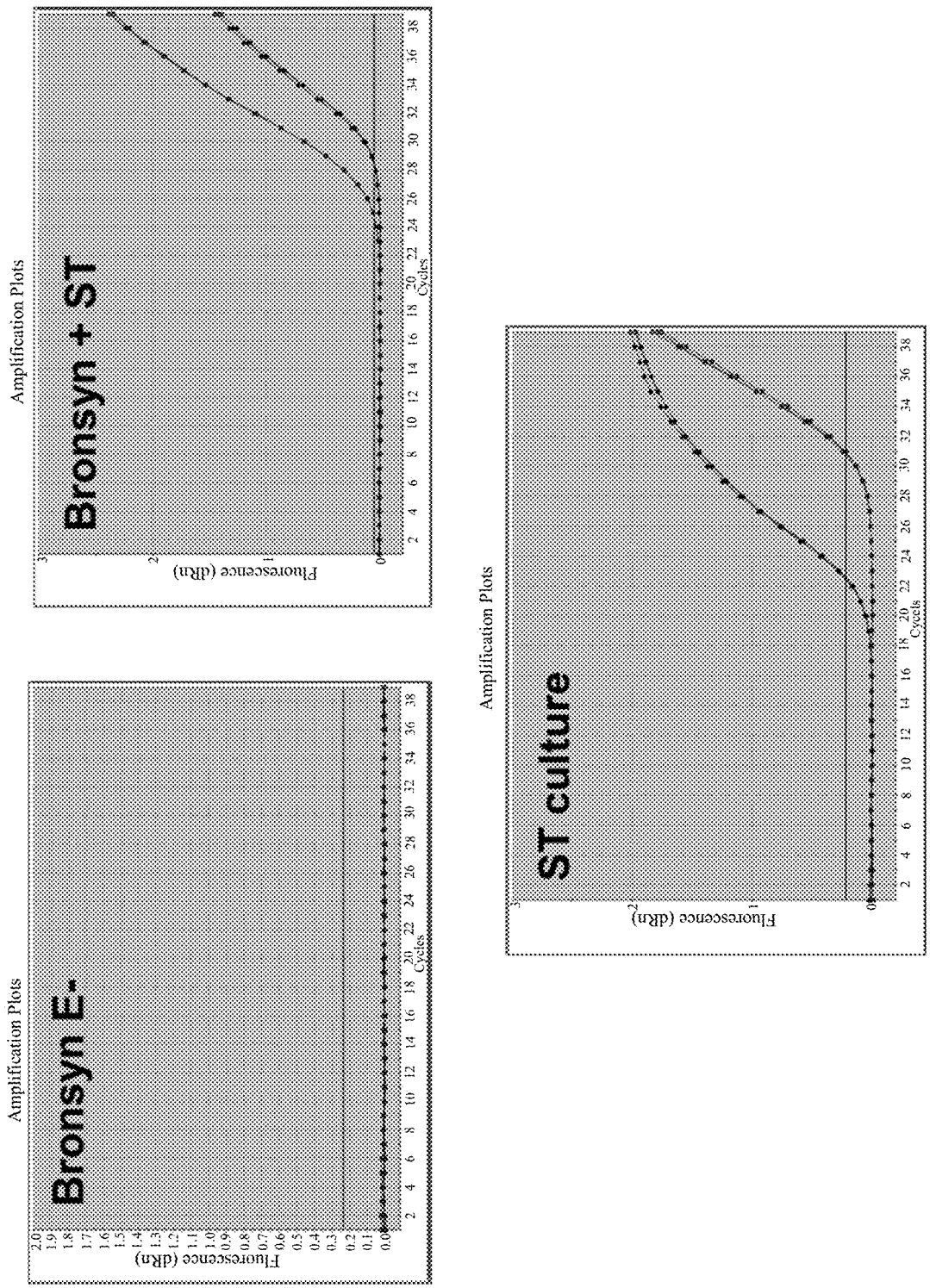

FIG. 144 shows TaqMan Primer Functionality for the Endophyte-Specific Gene 0005; RNA and DNA labelled.

Figure 145:
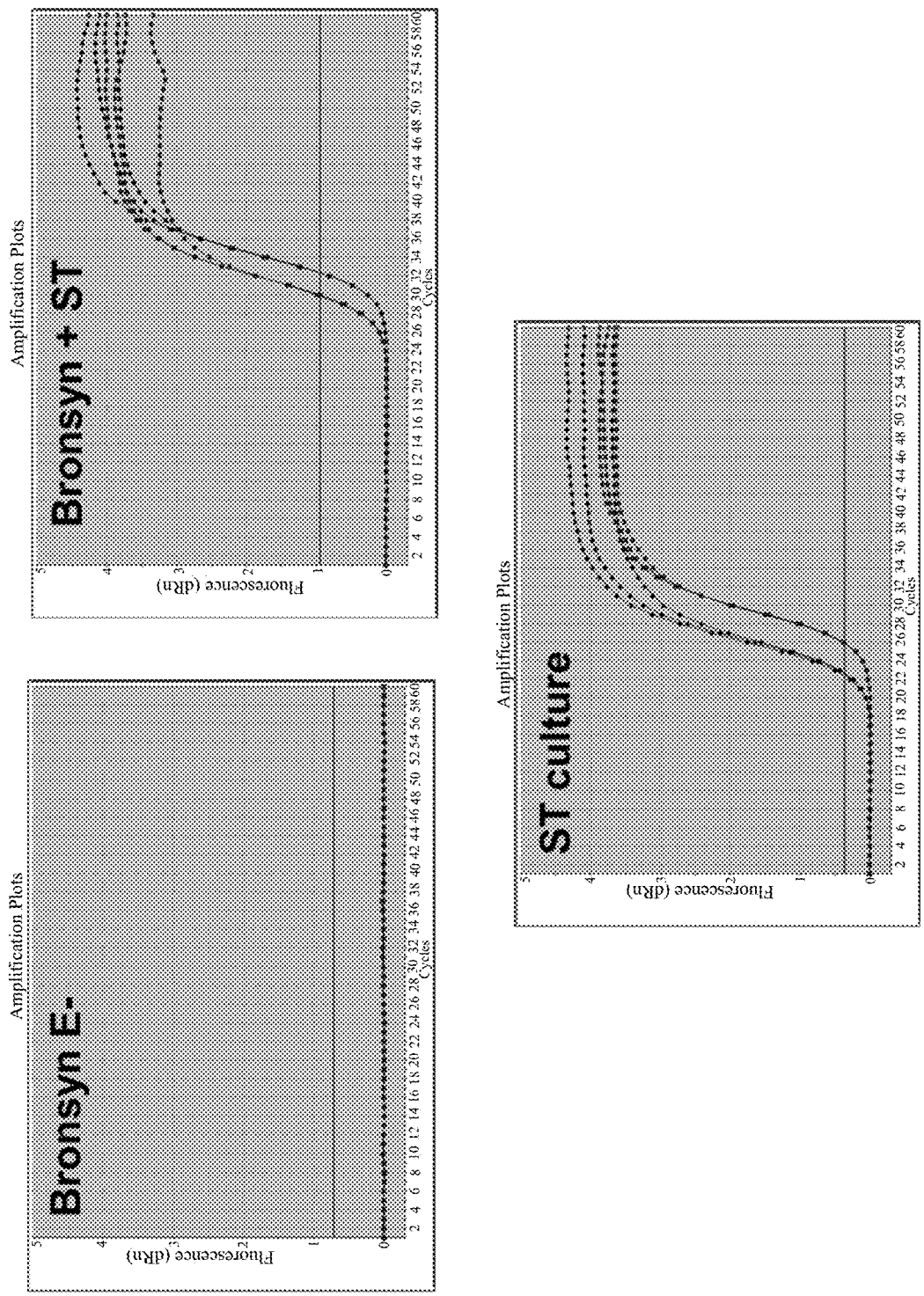

FIG. 145 shows TaqMan Primer Functionality for the Endophyte-Specific Gene 2232; RNA and DNA labelled.

Figure 146:
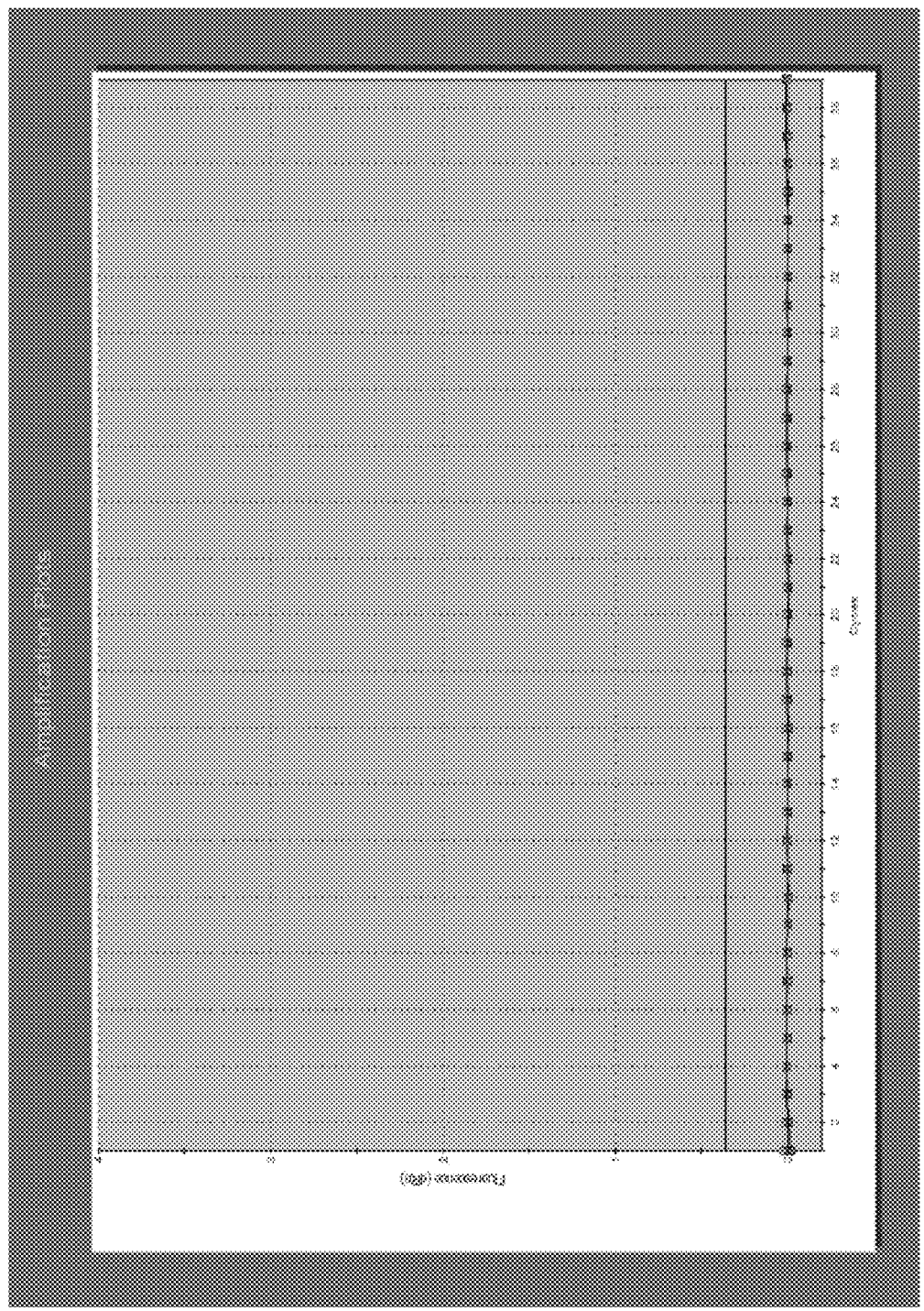

FIG. 146 shows TaqMan assay control—no template.

Figure 147:
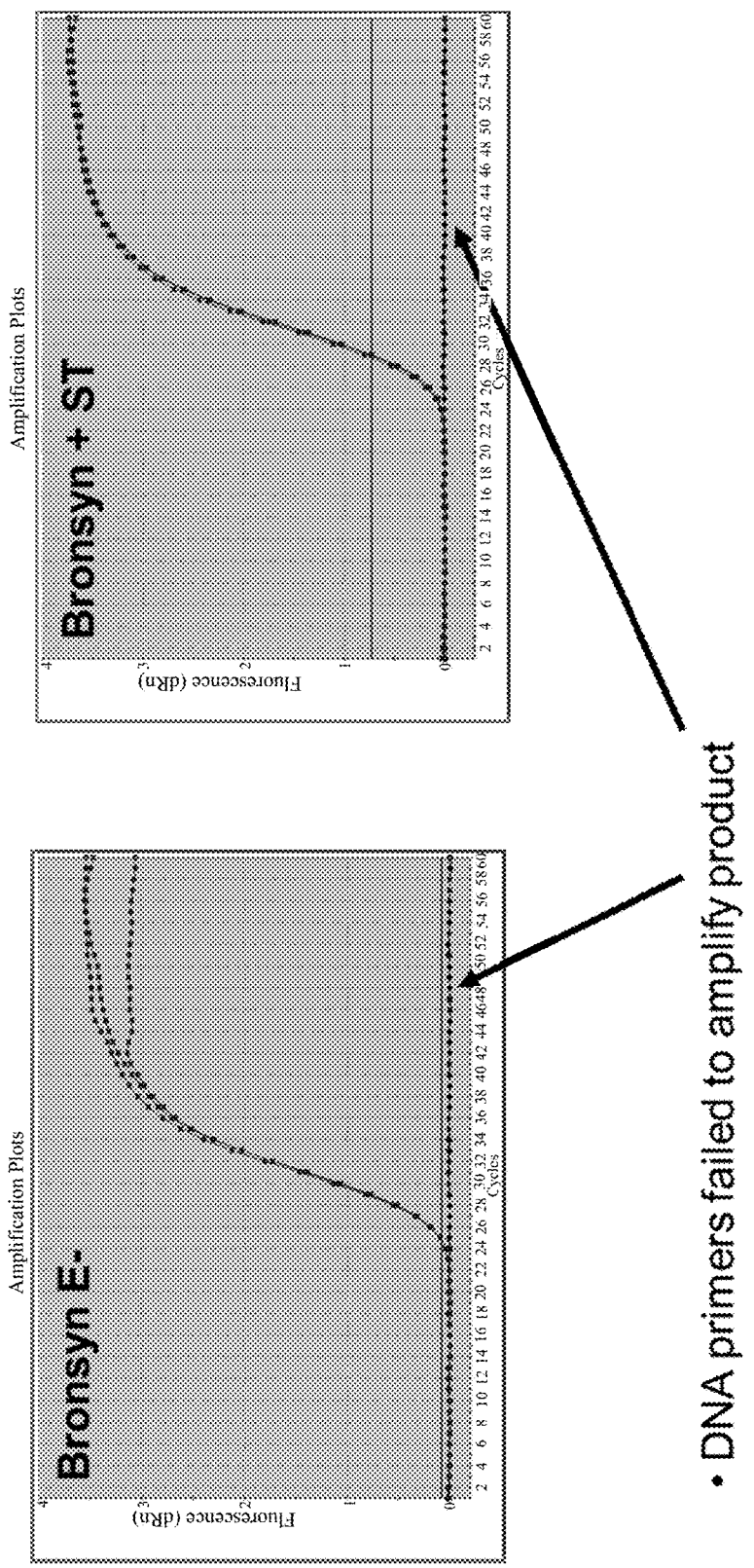

FIG. 147 shows TaqMan assay control—Plant GAPDH. RNA and DNA labelled.

Figure 148:
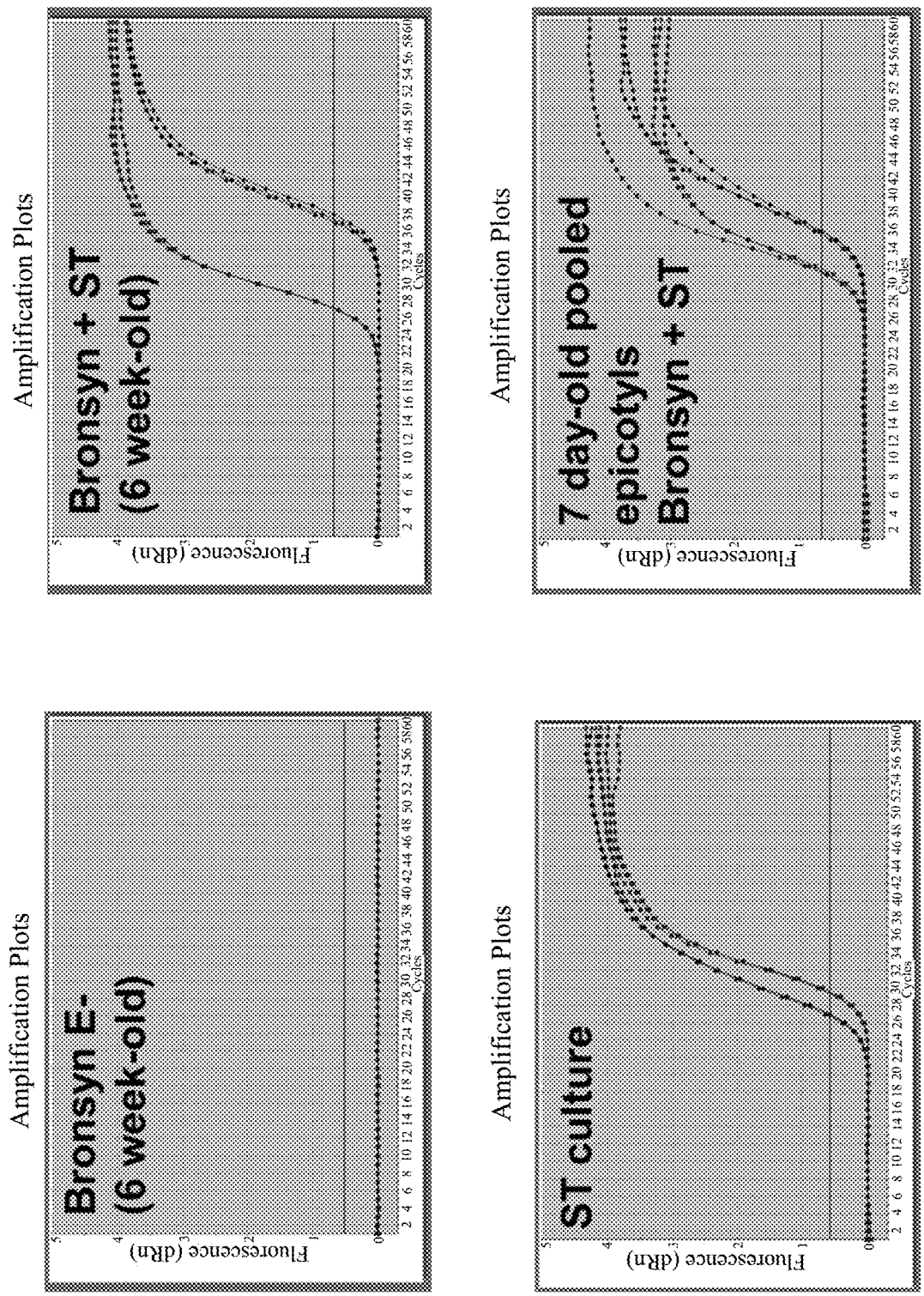

FIG. 148 shows Detection in Co-Extracted DNA/RNA Pooled Samples for the Endophyte-Specific Gene 7490; RNA and DNA labelled.

Figure 149:
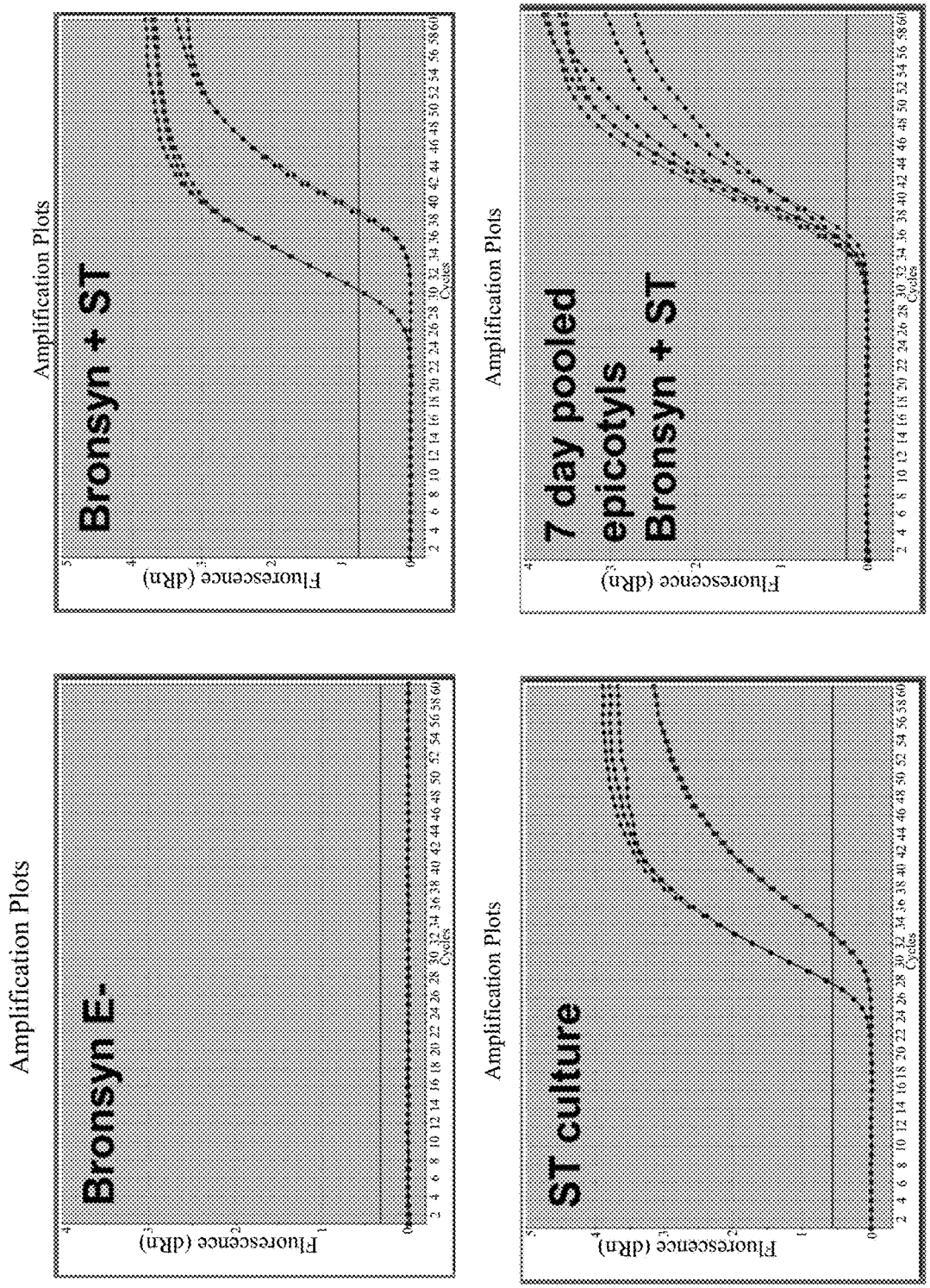

FIG. 149 shows Detection in Co-Extracted DNA/RNA Pooled Samples for the Endophyte-Specific Gene 0005; RNA and DNA labelled.

Figure 150:
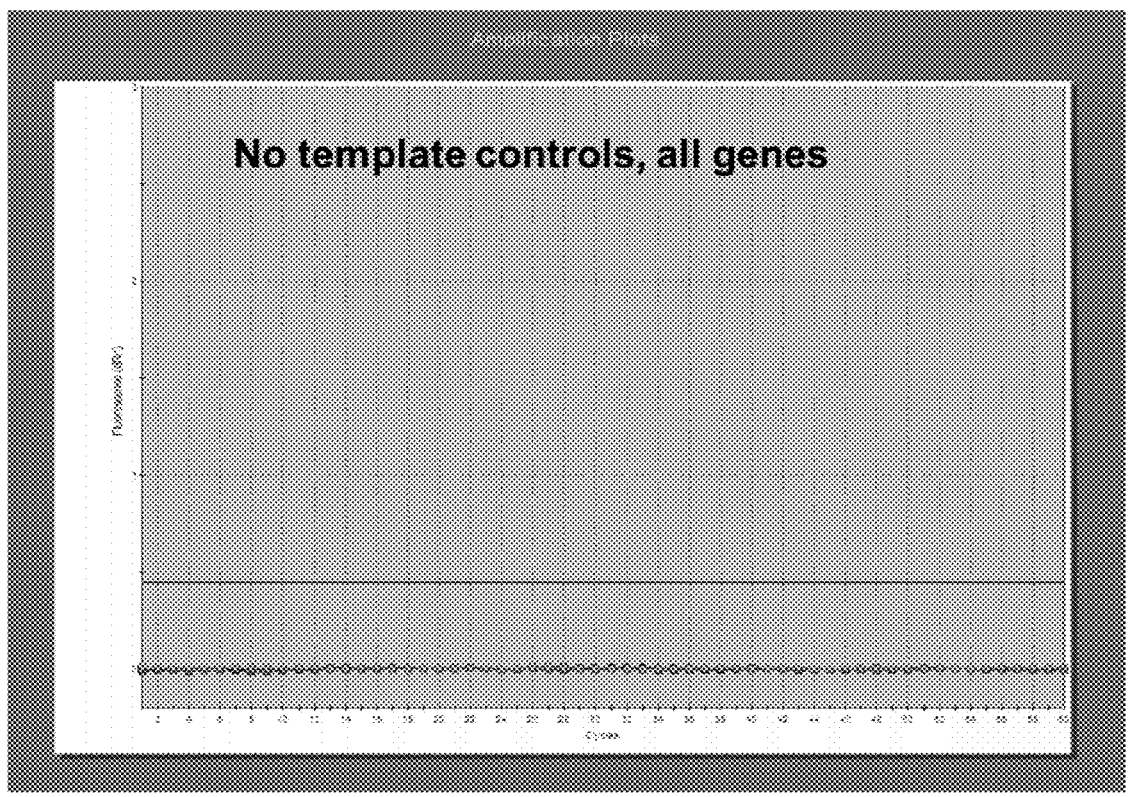

FIG. 150 shows a control (no template) for Detection in Co-Extracted DNA/RNA Pooled Samples; RNA and DNA labelled.

Figure 151:
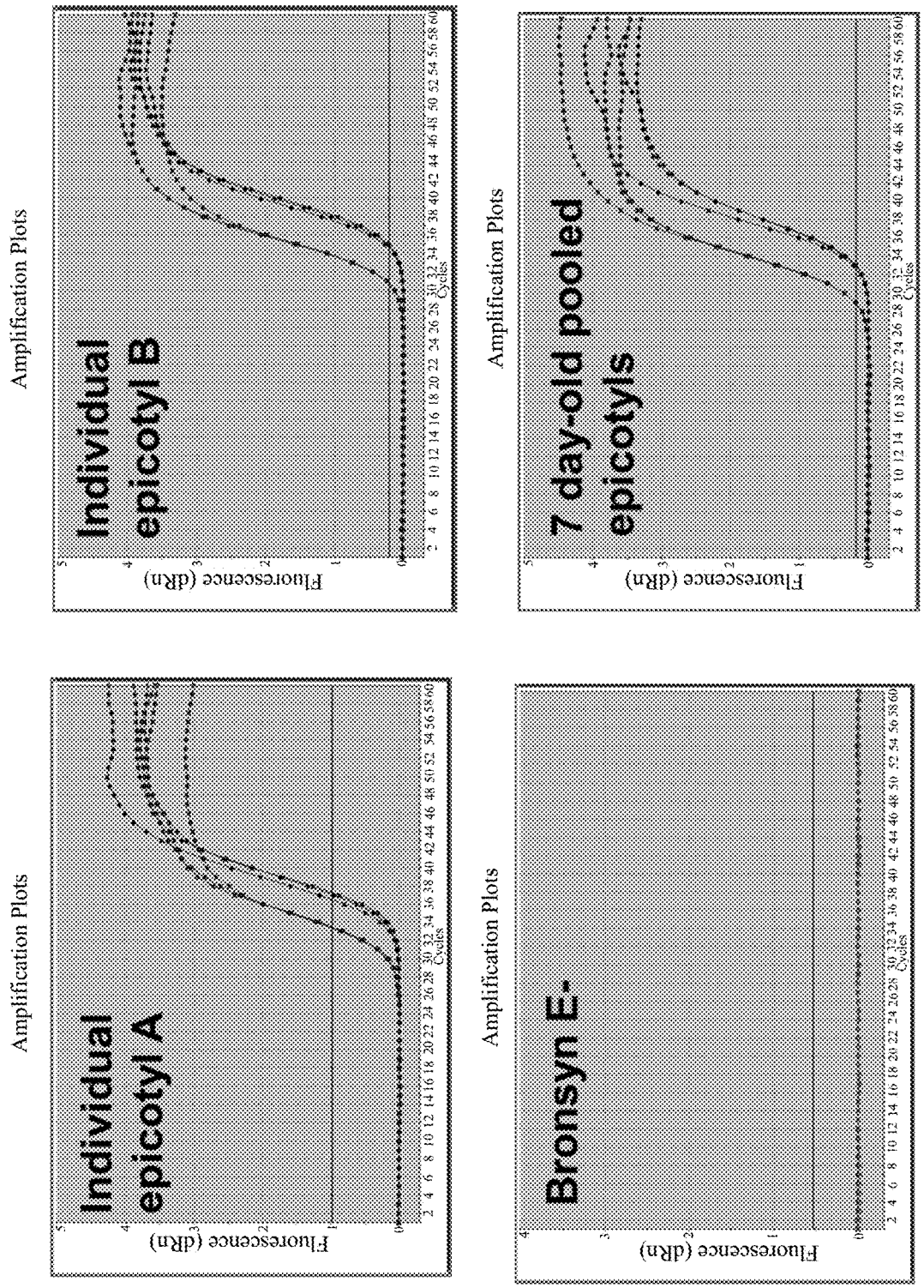

FIG. 151 shows detection in co-extracted DNA/RNA samples from individual 10 day old epicotyls of the endophyte-specific gene 2232; RNA and DNA labelled.

Figure 152:
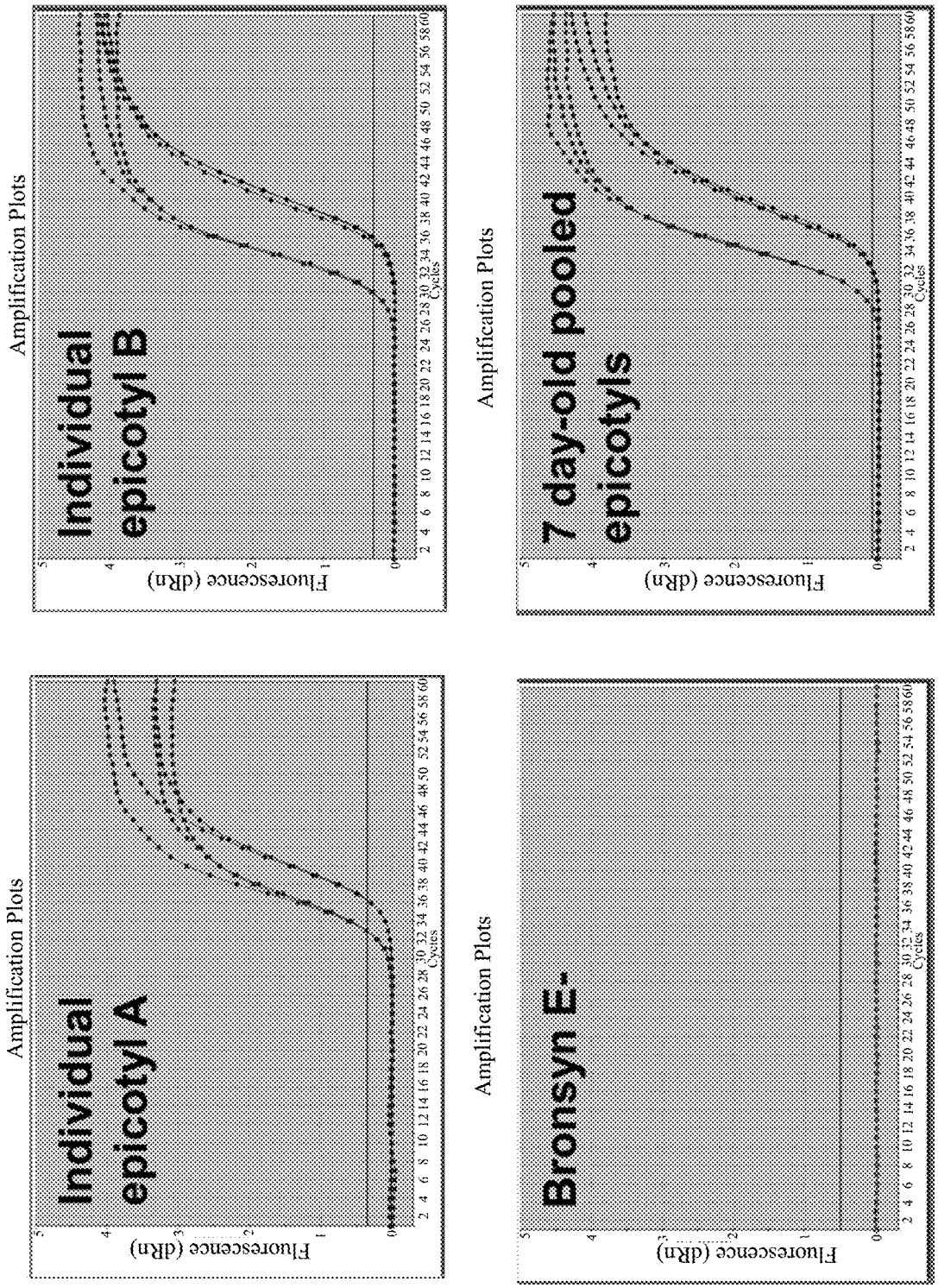

FIG. 152 shows detection in co-extracted DNA/RNA samples from individual 10 day old epicotyls of the endophyte-specific gene 7490; RNA and DNA labelled.

Figure 153:
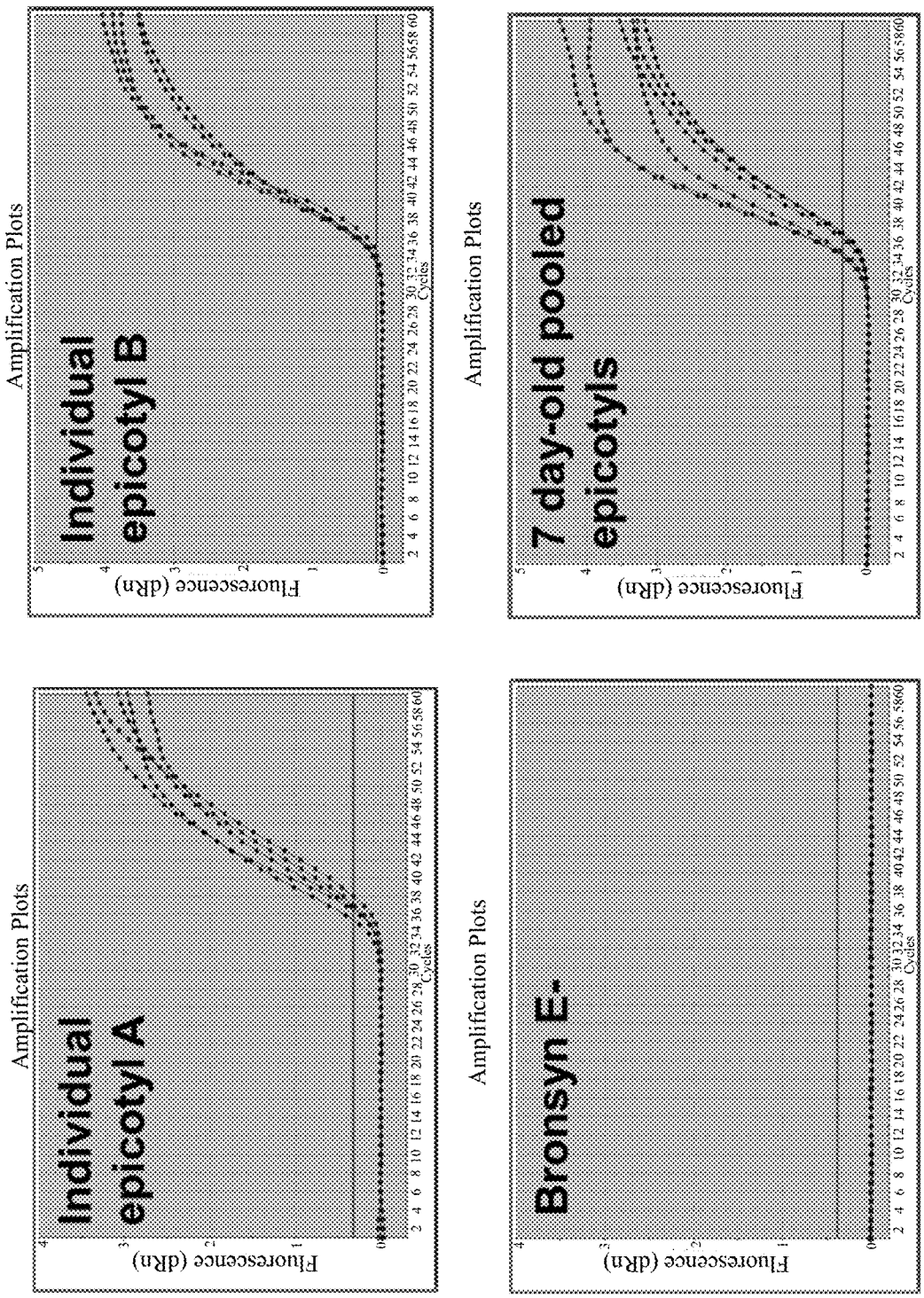

FIG. 153 shows detection in co-extracted DNA/RNA samples from individual 10 day old epicotyls of the endophyte-specific gene 0005; RNA and DNA labelled.

Figure 154:
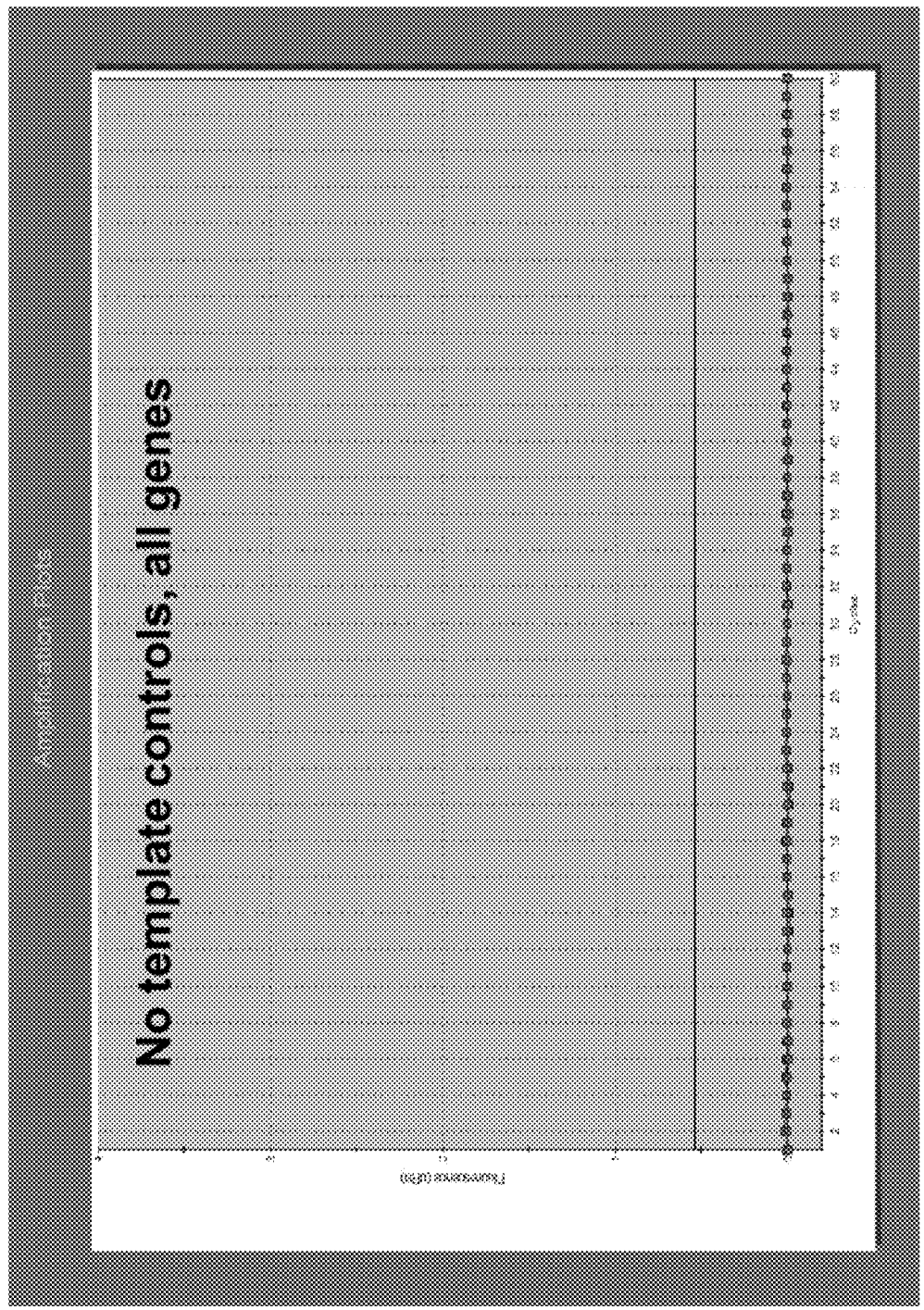

FIG. 154 shows a control (no template) for detection in co-extracted DNA/RNA samples from individual 10 day old epicotyls; RNA and DNA labelled.

Figure 155:
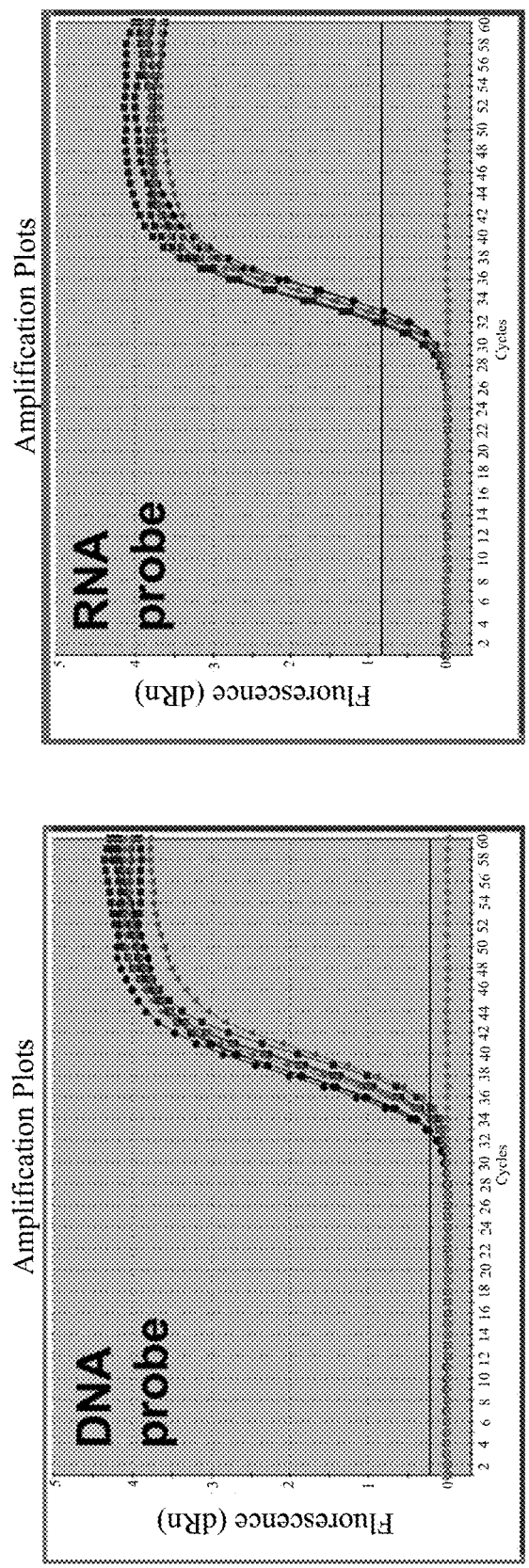

FIG. 155 shows Detection in Co-Extracted DNA/RNA from 3, 5 and 7 Day-Old Pooled Epicotyls of the Endophyte Specific Gene 2232. Circles=Day 7 E+ Pool; Squares=Day 5 E+ Pool; Triangels=Day 3 E+ Pool; Diamonds=Day 7 E− Pool.

Figure 156:
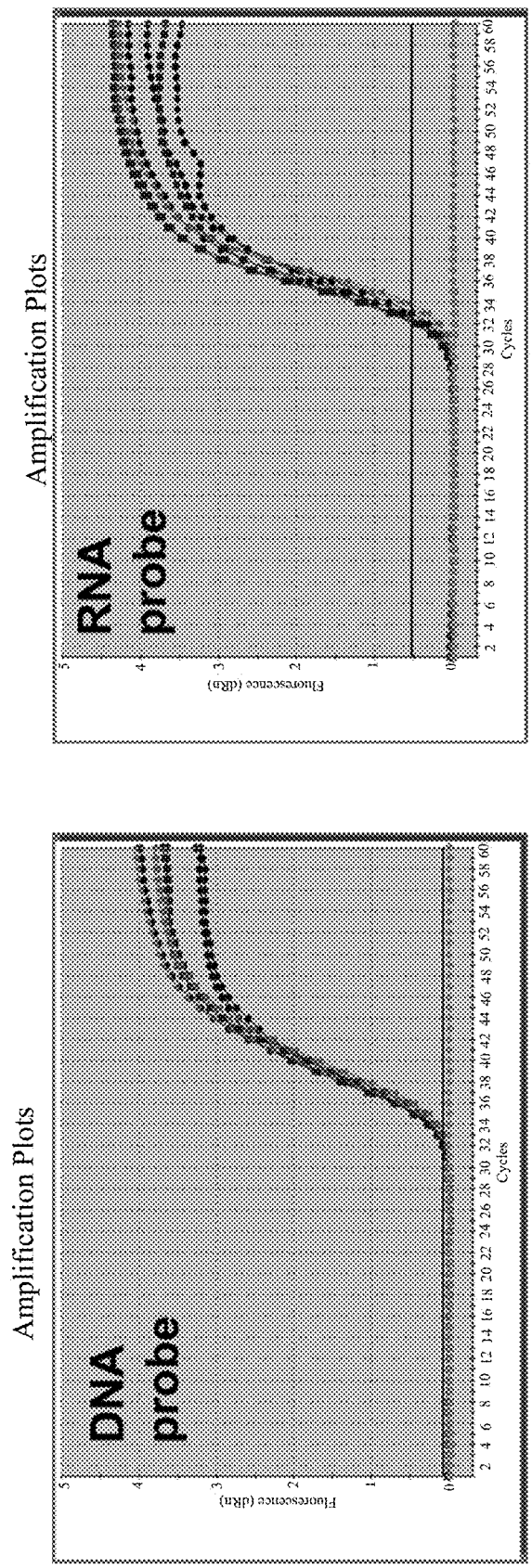

FIG. 156 shows Detection in Co-Extracted DNA/RNA from 3, 5 and 7 Day-Old Pooled Epicotyls of the Endophyte Specific Gene 7490. Circles=Day 7 E+ Pool; Squares=Day 5 E+ Pool; Triangles=Day 3 E+ Pool; Diamonds=Day 7 E− Pool.

Figure 157:
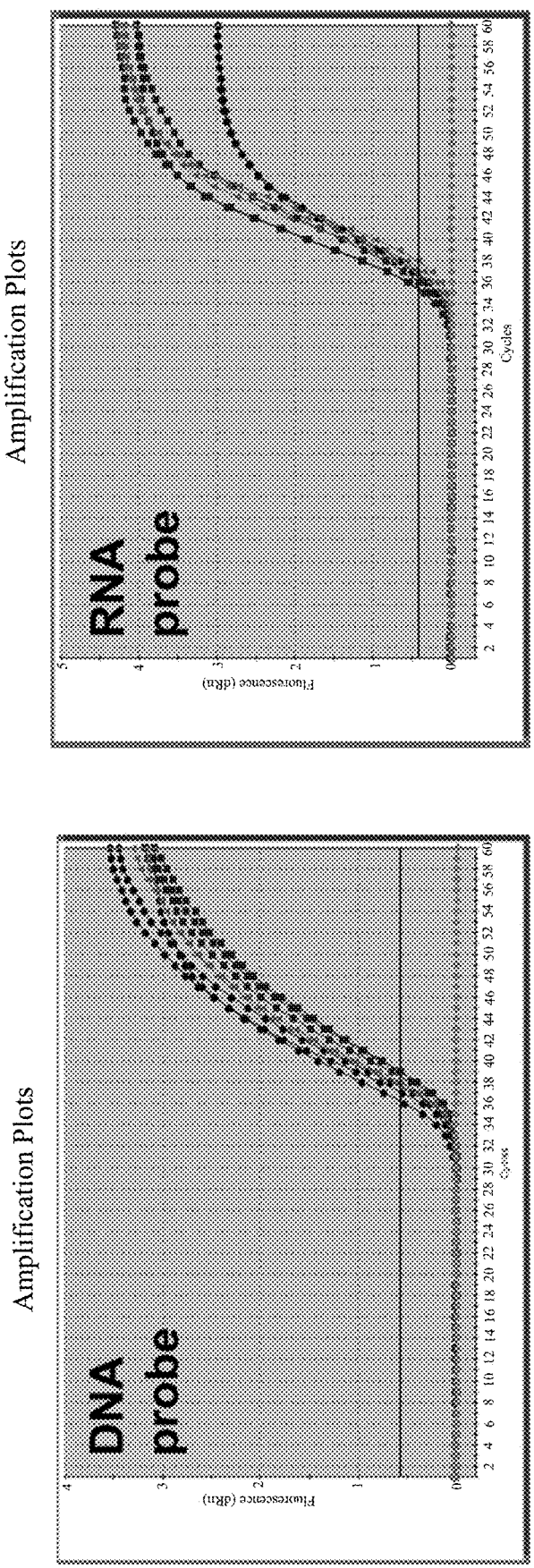

FIG. 157 shows Detection in Co-Extracted DNA/RNA from 3, 5 and 7 Day-Old Pooled Epicotyls of the Endophyte Specific Gene 0005. Circles=Day 7 E+ Pool; Squares=Day 5 E+ Pool; Triangles=Day 3 E+ Pool; Diamonds=Day 7 E− Pool.

Figure 158:
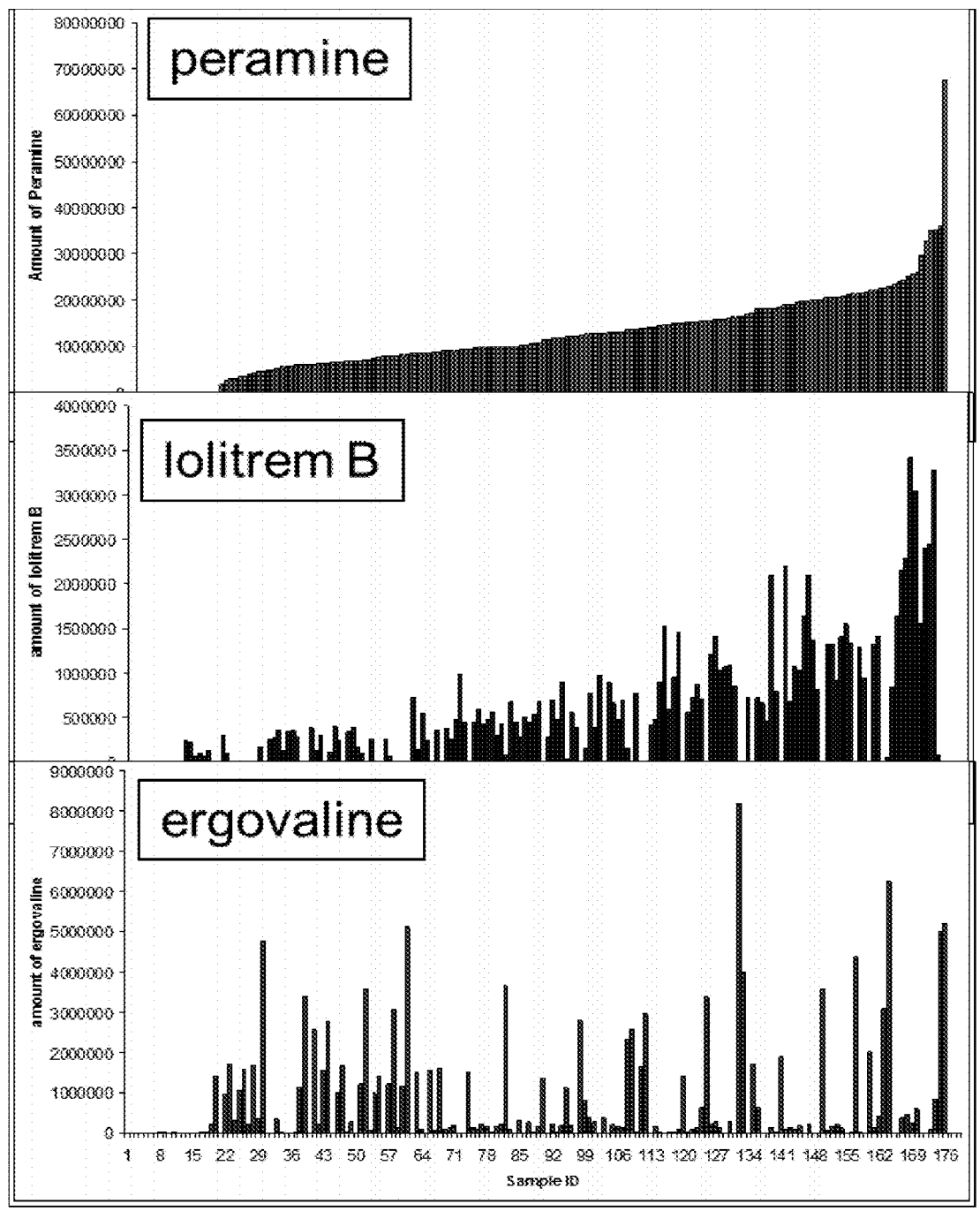

FIG. 158 shows metabolic profiling of population of symbiota to enable ab initio breeding and selection.

Figure 159:
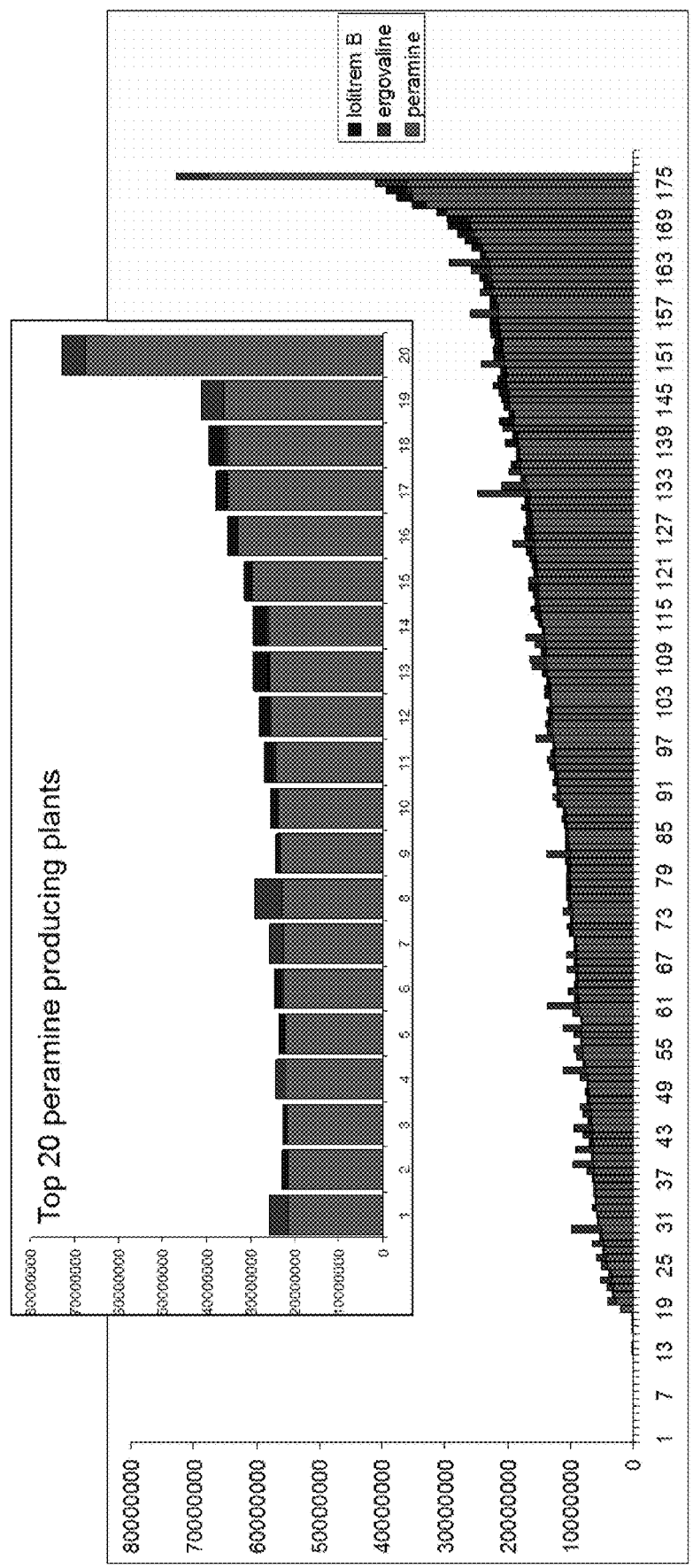

FIG. 159 shows the top 20 peramine producing plants.

Figure 160:
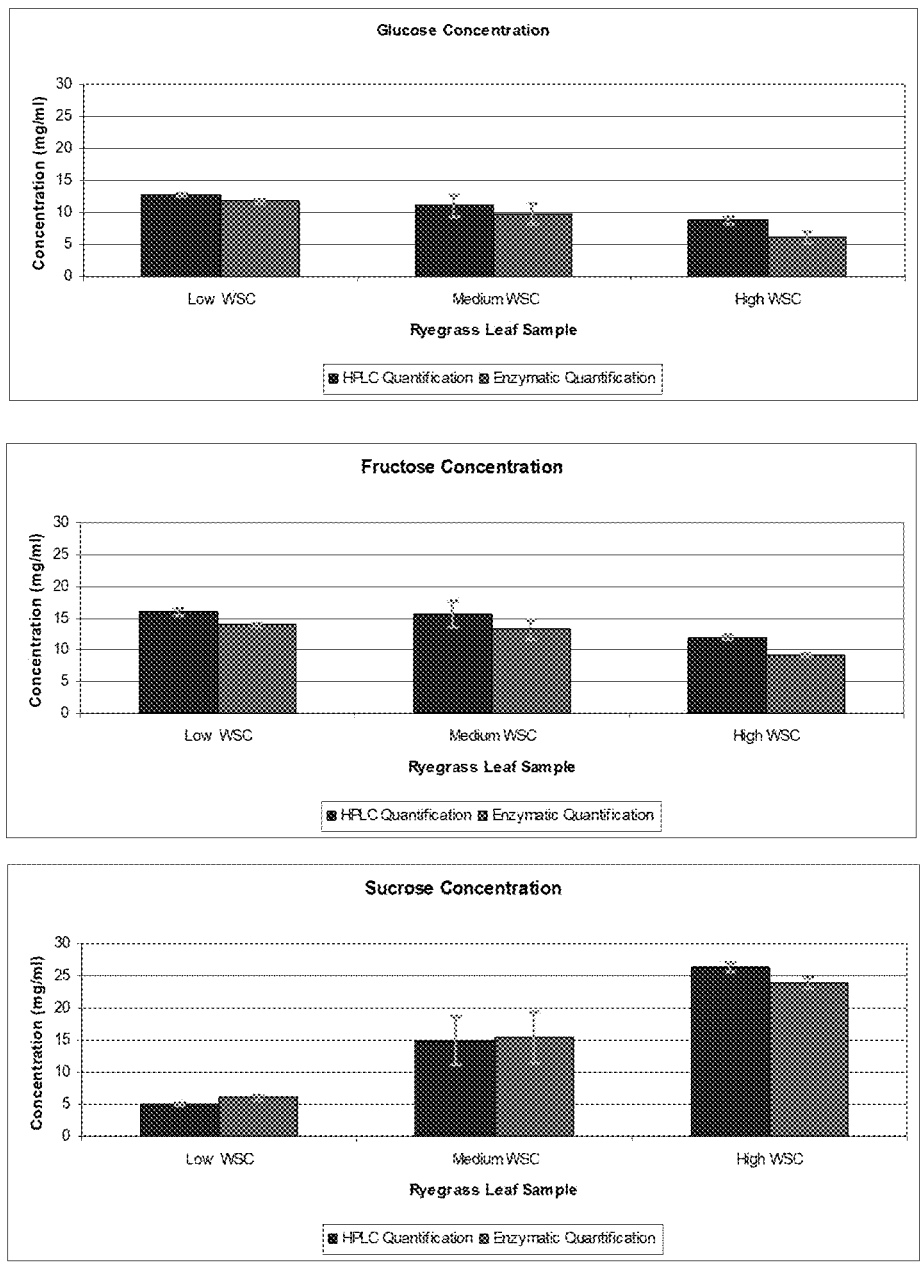

FIG. 160 shows molecular phenotyping of a population of symbiota to enable ab initio breeding and selection.

Figure 161:
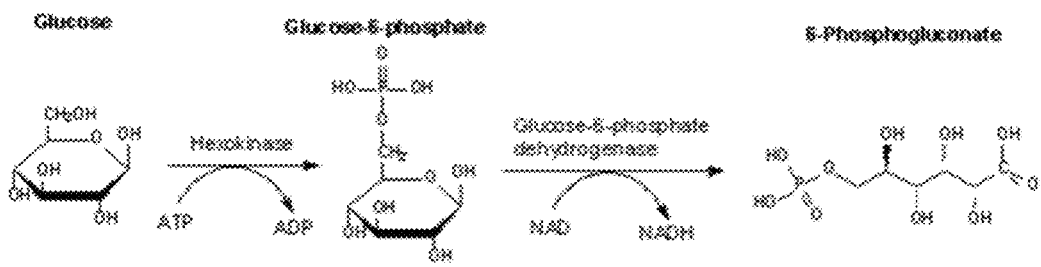

FIG. 161 shows the production of glucose-6-phosphate from glucose.

Figure 162:
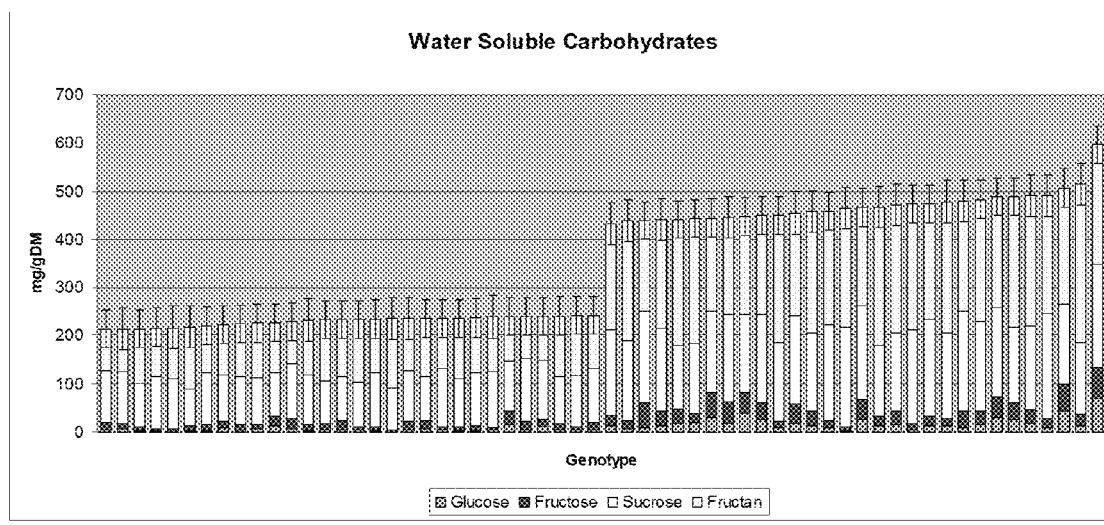

FIG. 162 shows the presence of water soluble carbohydrates in a population of symbiota.

Figure 163:
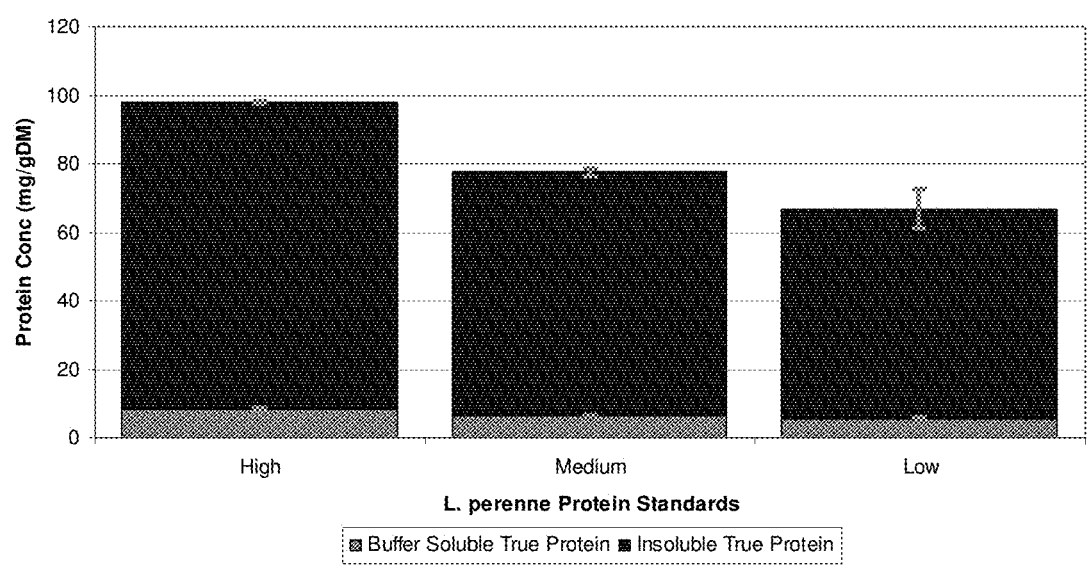

FIG. 163 shows quantification of proteins.

Figure 164:
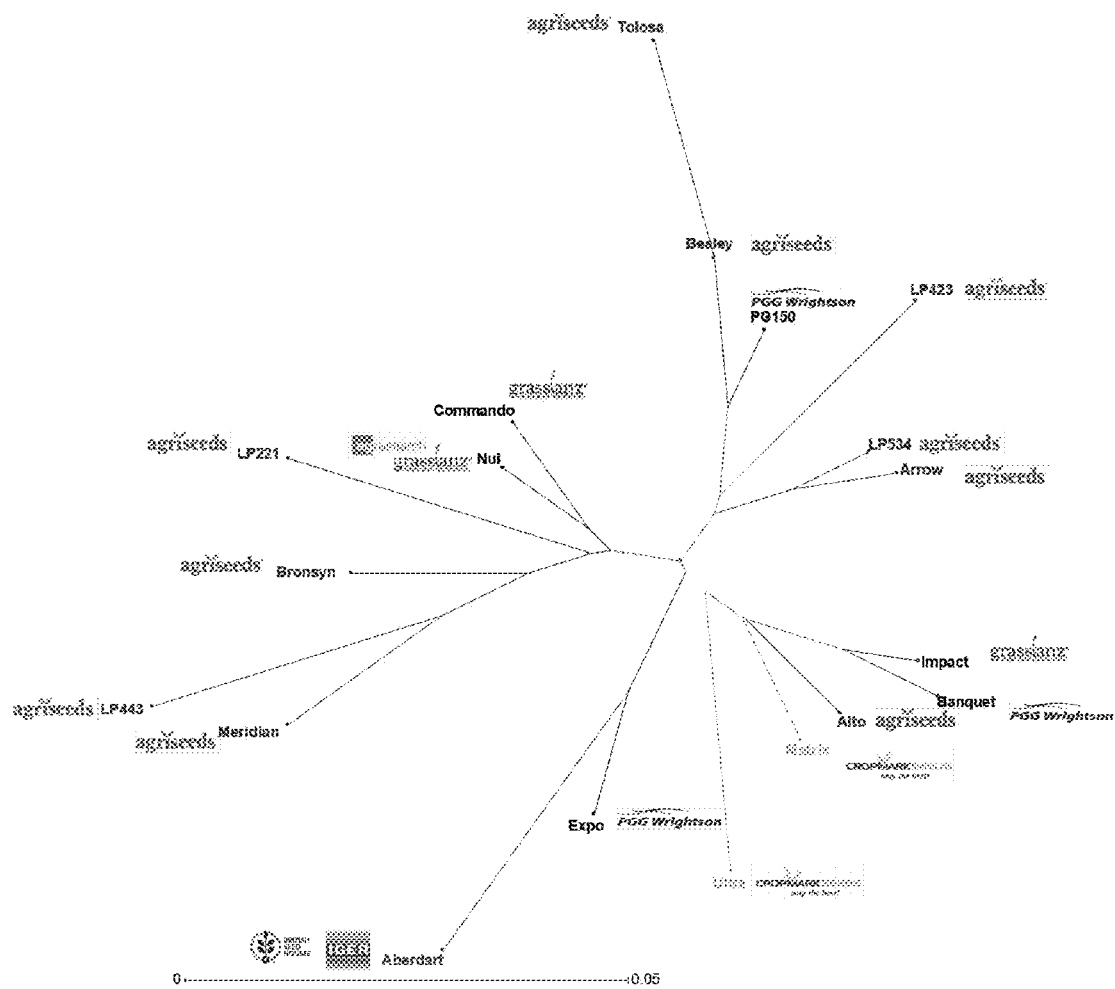

FIG. 164 shows genetic diversity and relatedness between germplasm.

Figure 165:
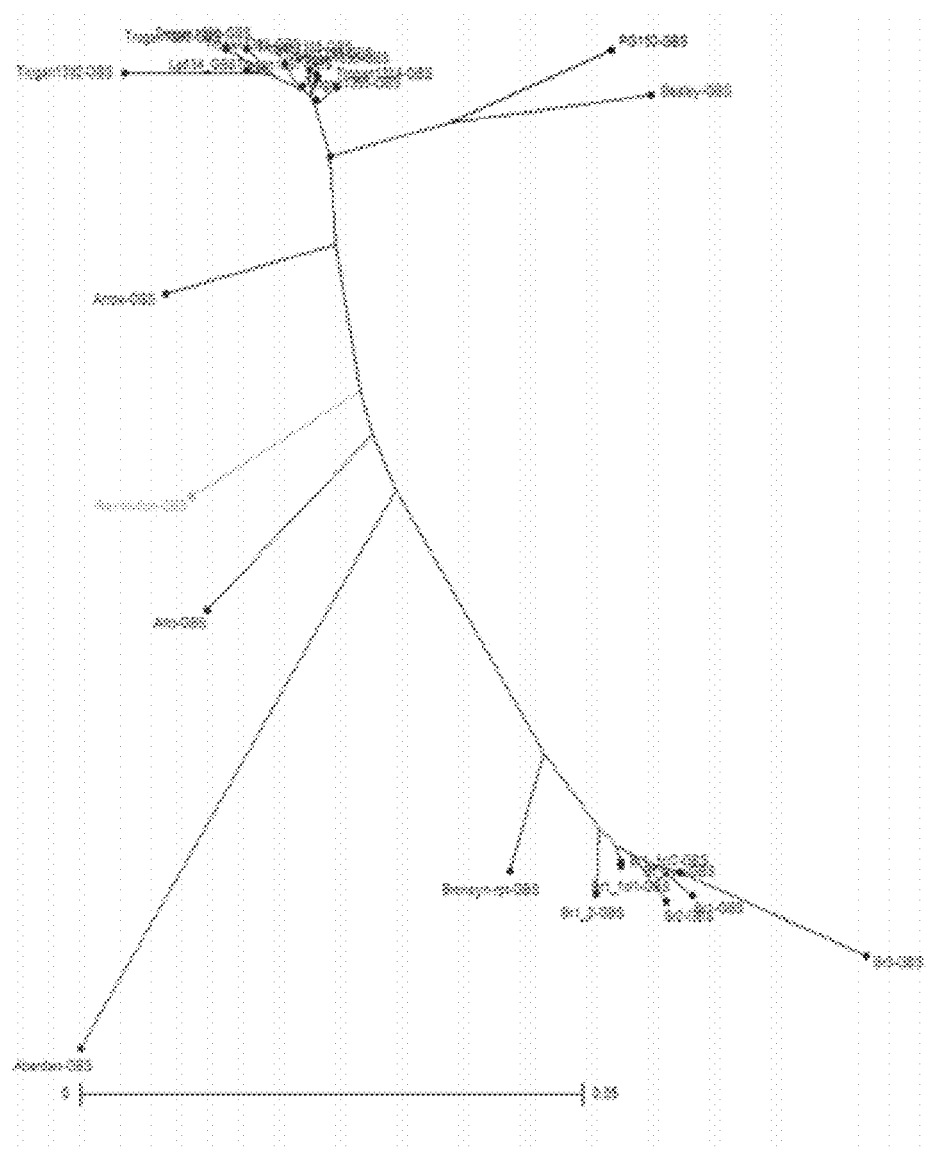

FIG. 165 shows genetic diversity and relatedness between germplasm.

Figure 166:
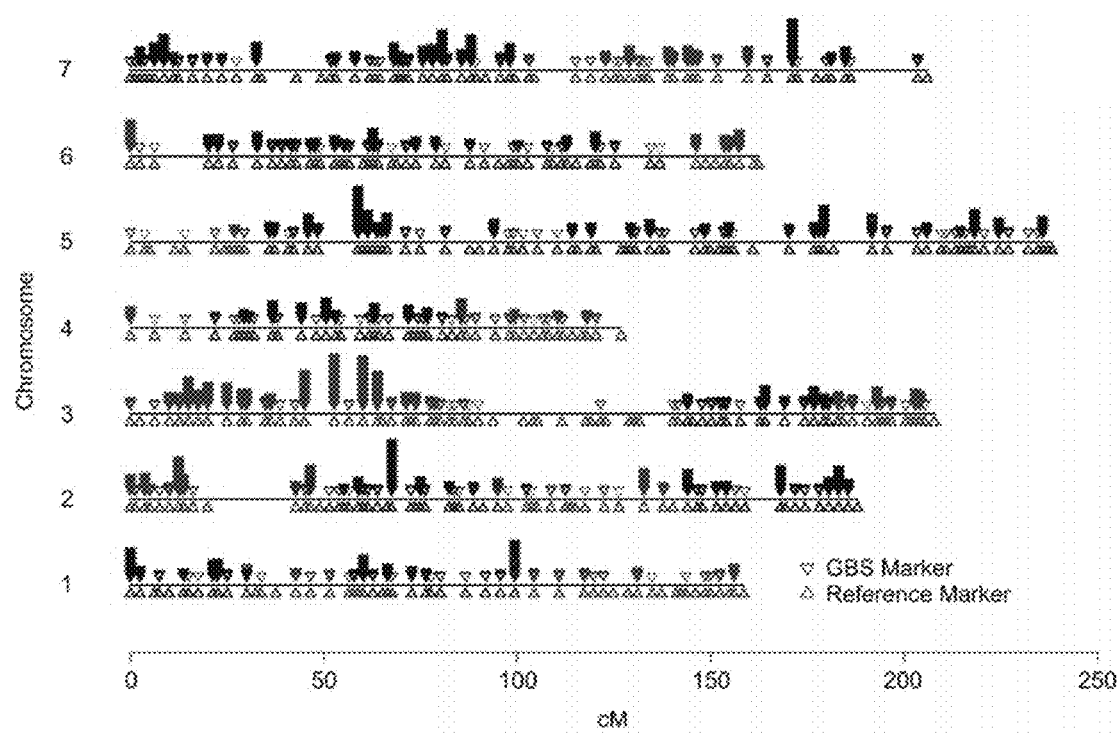

FIG. 166 shows genotyping by sequencing.

Figure 167:
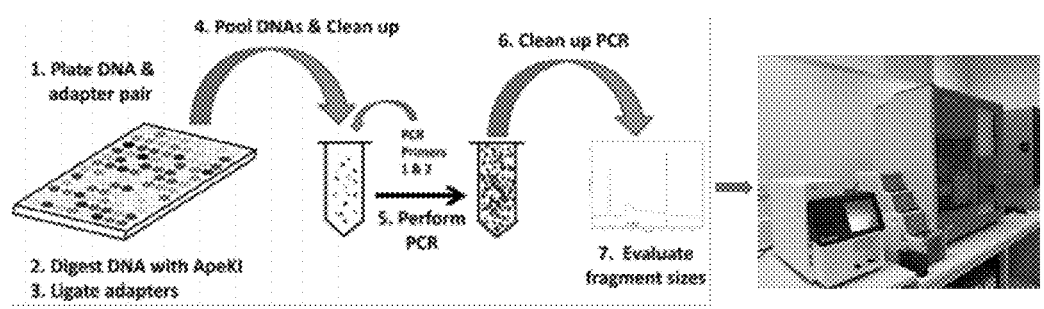

FIG. 167 shows procedure for genotyping by sequencing.

Figure 168:
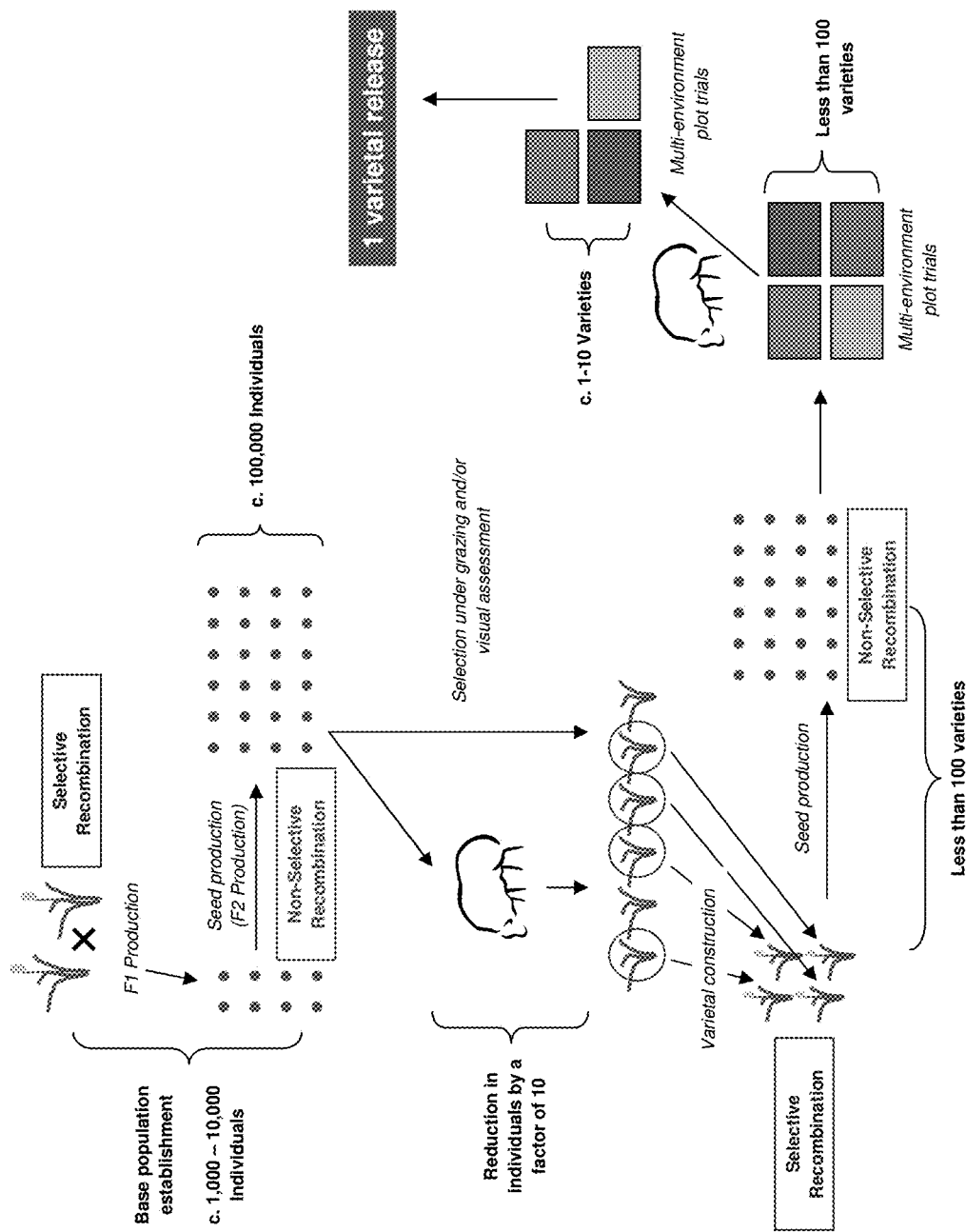

FIG. 168 shows a generic scheme for a current commercial ryegrass breeding program.

Figure 169:
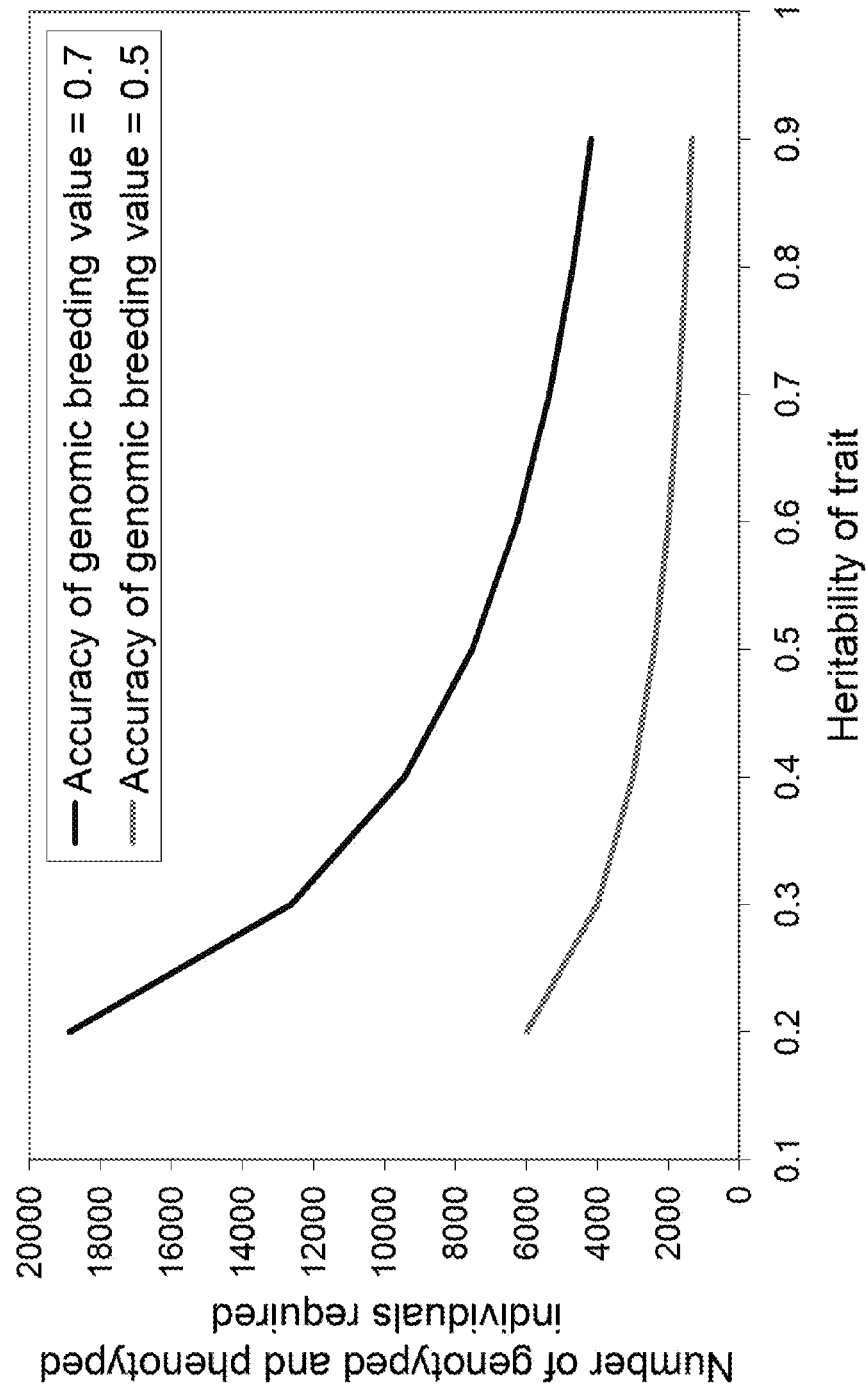

FIG. 169 shows a schematic representation of relationships between requirements for numbers of individuals to be genotyped and phenotyped for genomic selection studies, and values of heritability for specific traits.

Figure 170:
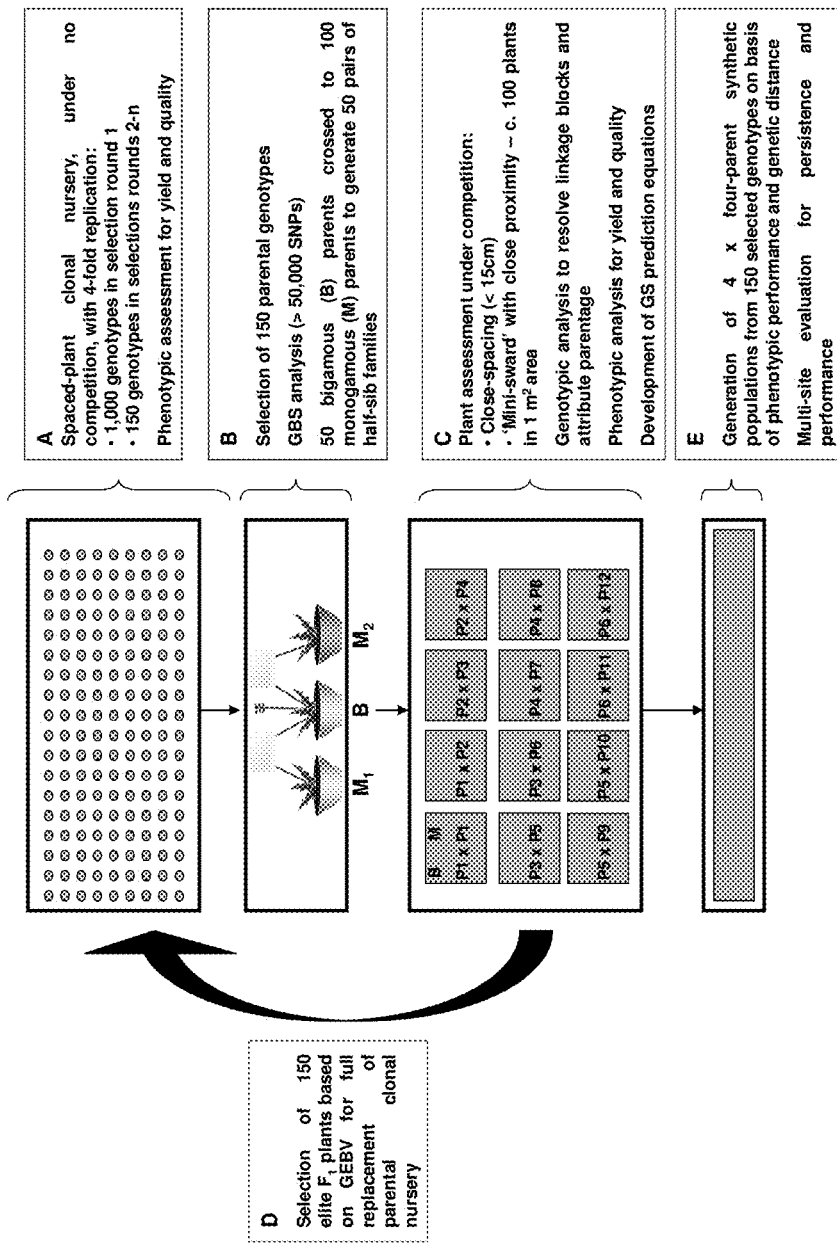

FIG. 170 shows a scheme for genomic selection implementation in a ryegrass breeding program.

Figure 171:
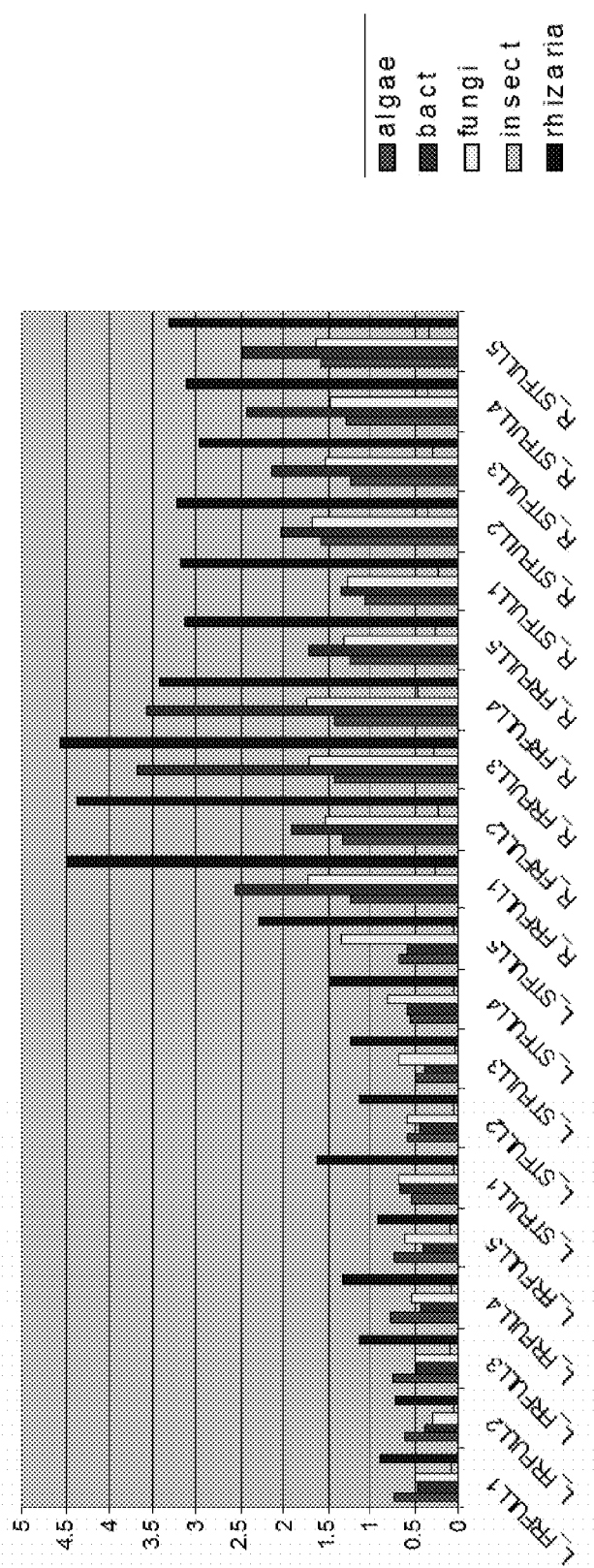

FIG. 171 shows the characterization of the microbiome in perennial ryegrass (*Lolium perenne*). Vertical axis shows % mapped sequences from cDNA libraries of perennial ryegrass-microbiome symbiota grown under full nutrient conditions following mapping to non-plant database sequences in database 1. Horizontal axis shows samples analysed: L=leaf; R=root; FR=free of endophyte; ST=standard toxic endophyte.

Figure 172:
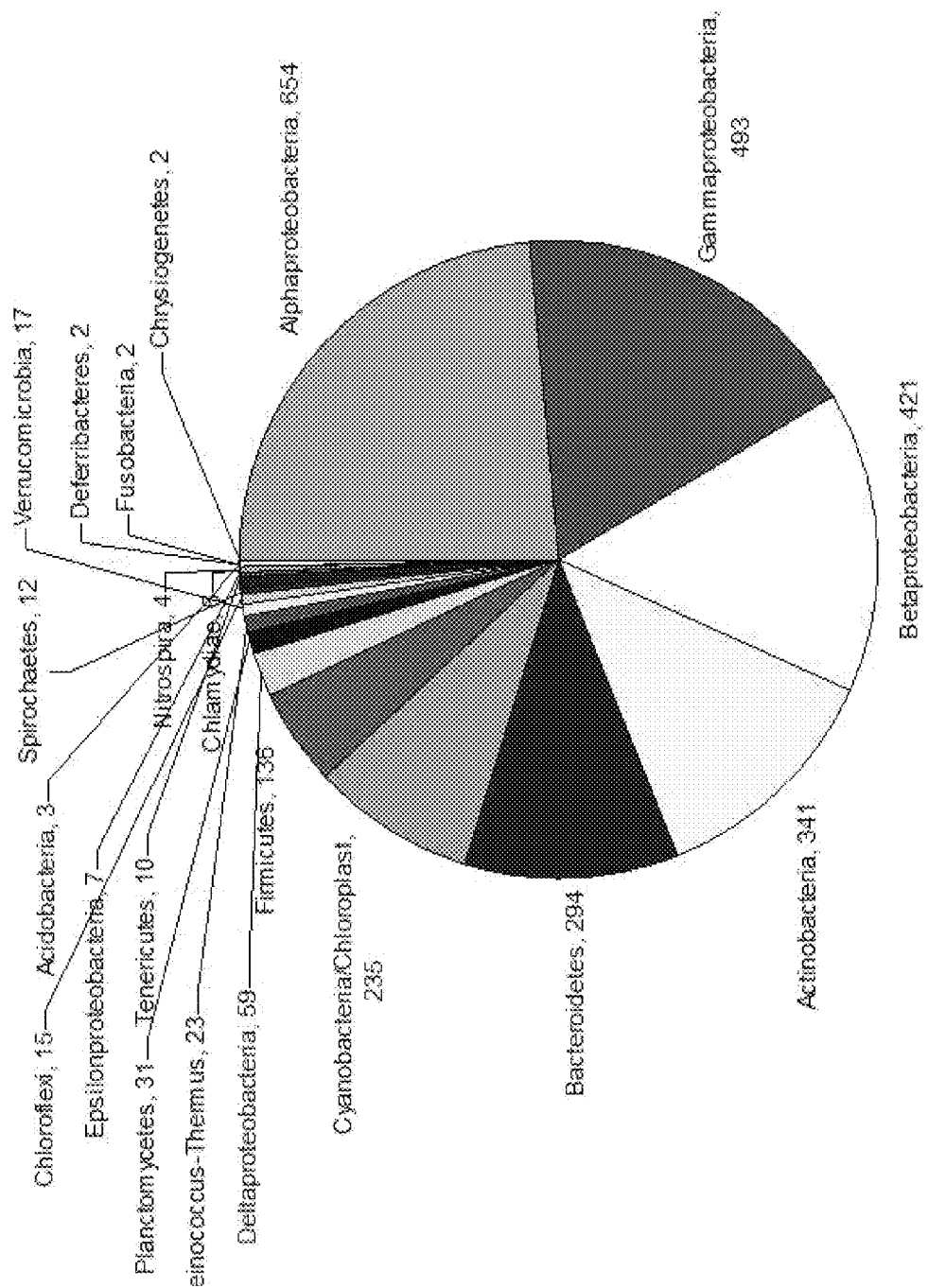

FIG. 172 shows a 16S analysis of microbione in perennial ryegrass (*Lolium perenne*). The figure shows a taxonomic distribution of the microbes represented in the *Lolium perenne* microbiome.

Figure 173:
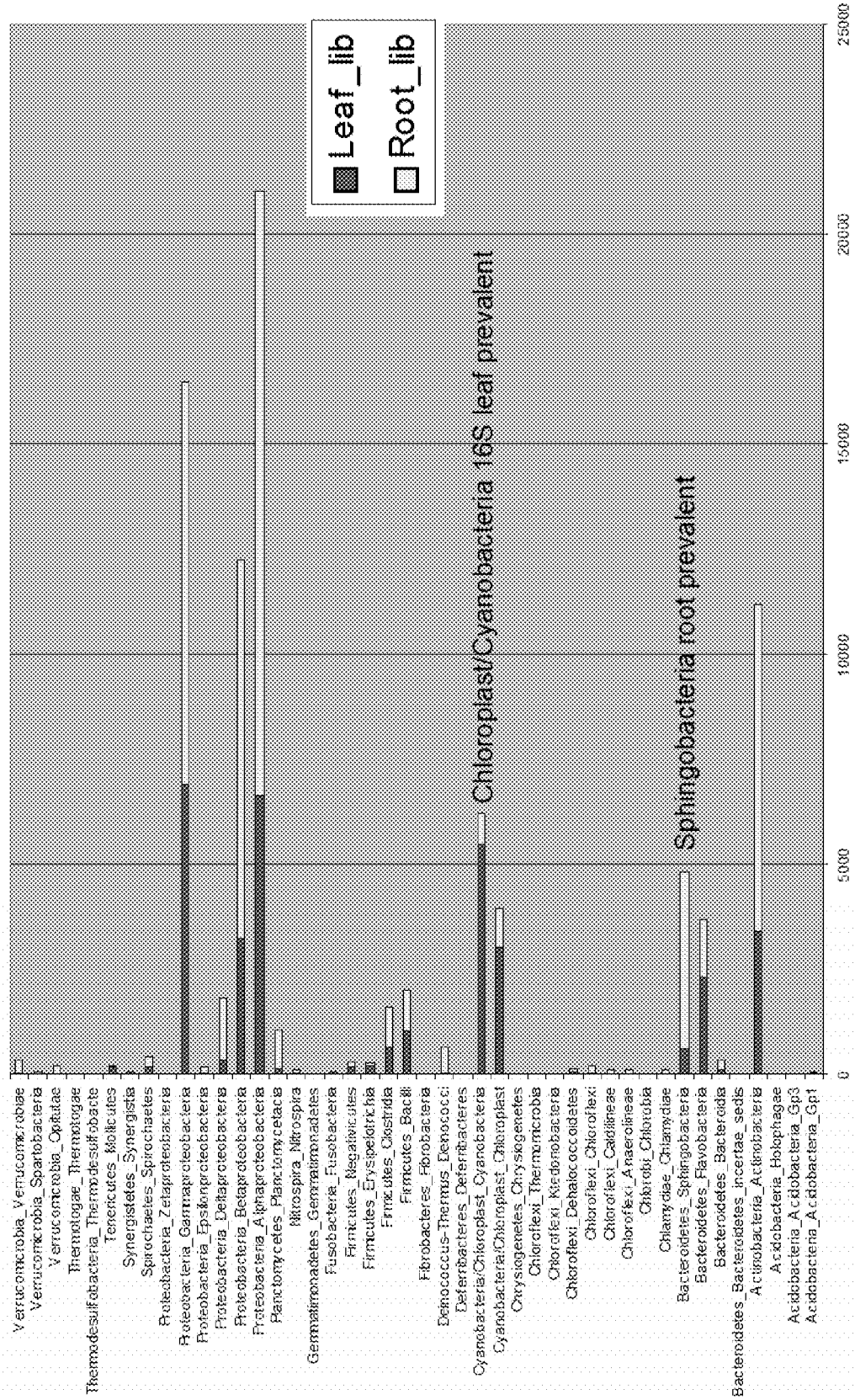

FIG. 173 shows leaf and root microbiomes in perennial ryegrass (*Lolium perenne*). The graph plots the sum by bacterial class of sequence read counts from leaves and roots, respectively.

Figure 174:
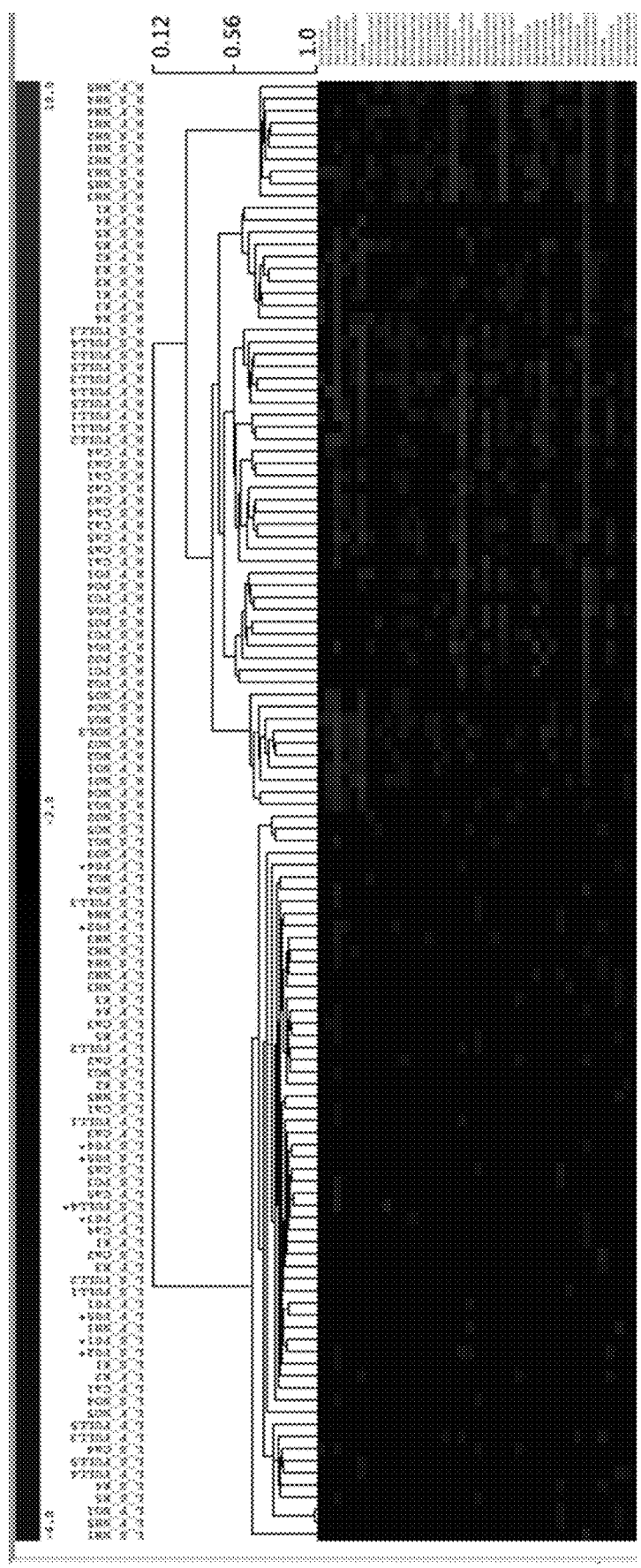

FIG. 174 shows leaf and root microbiomes in perennial ryegrass (*Lolium perenne*). The figure shows a sample tree produced by hierarchical clustering of sample sets.

Figure 175:
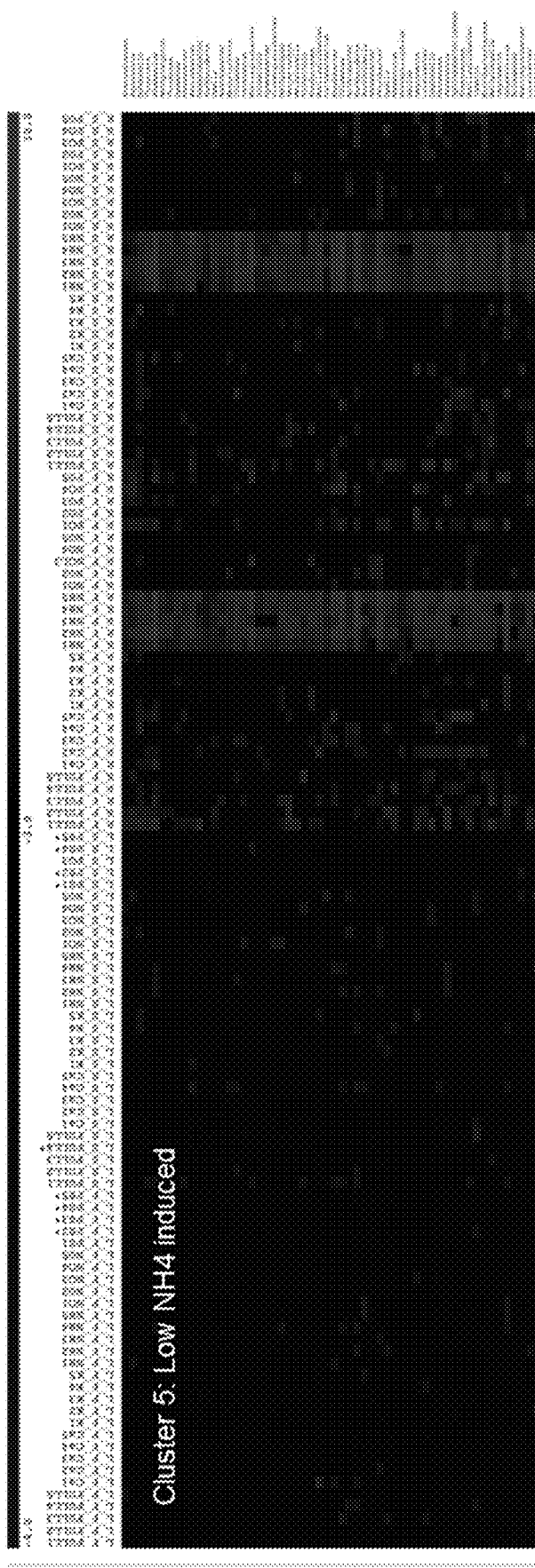
Figure 176:
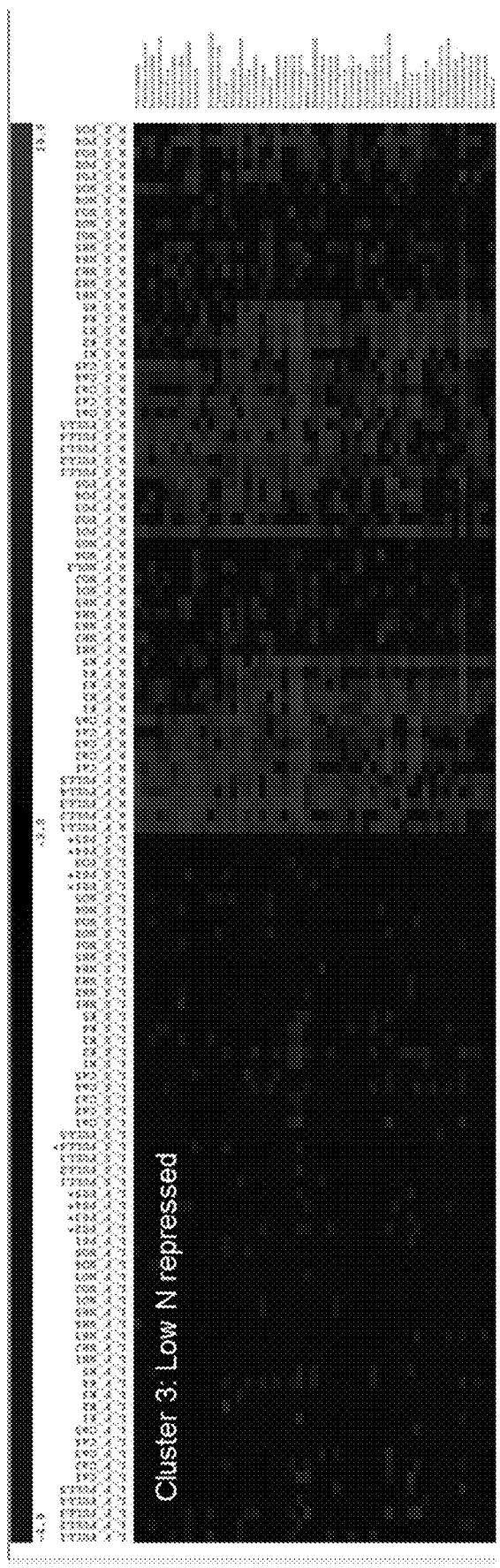

FIGS. 175 and 176 show leaf and root micobiomes in perennial ryegrass (*Lolium perenne*). The figures show two of eleven clusters containing more than 10 genes: FIG. 175: Cluster 5—low $NH_4$ induced; FIG. 176: Cluster 3—low N repressed.

Figure 177:
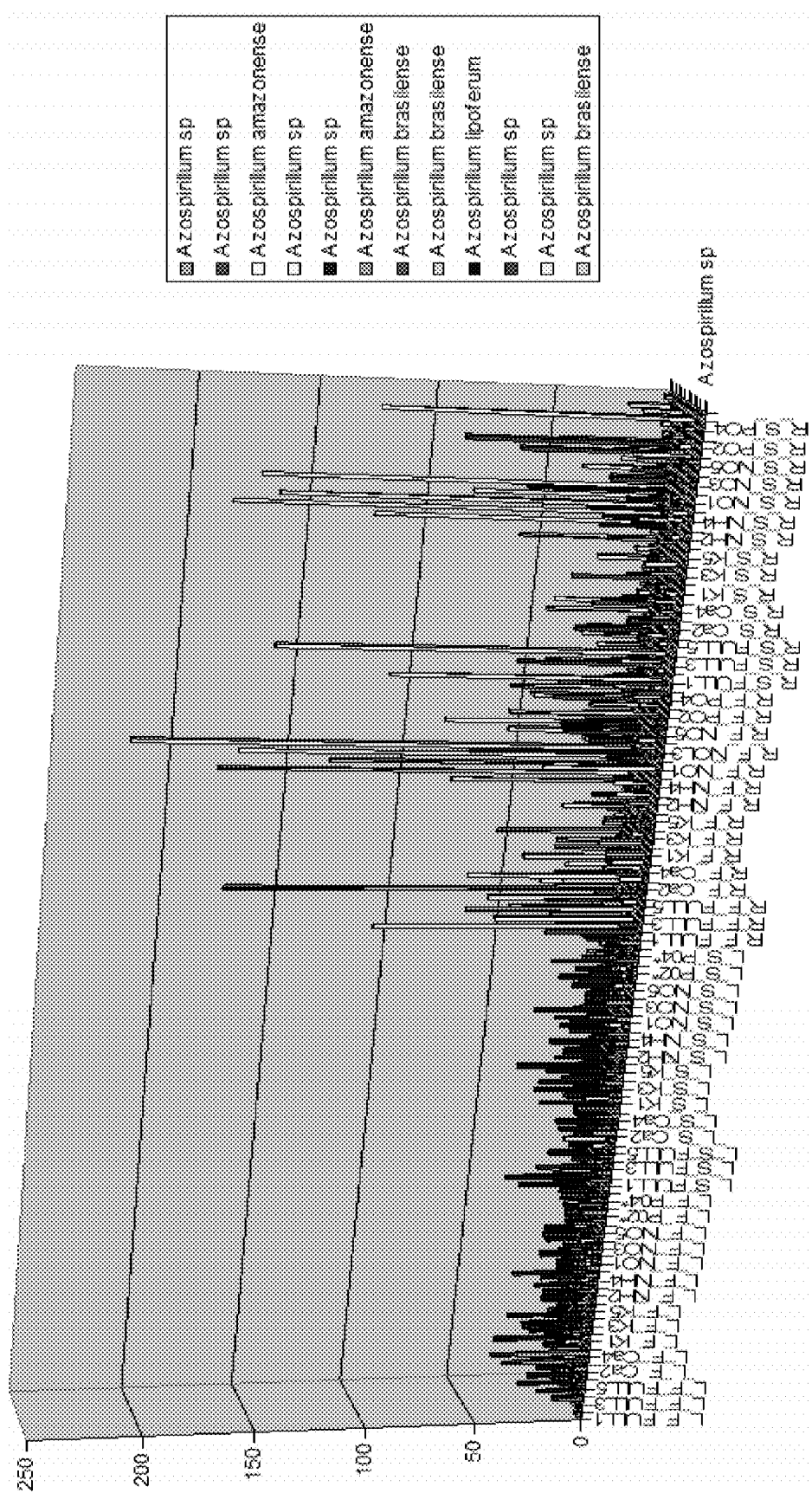

FIG. 177 shows leaf and root microbiomes in perennial ryegrass (*Lolium perenne*). The figures shows reads mapping to sequences annotated as *Azospirillum* species.

Figure 178:
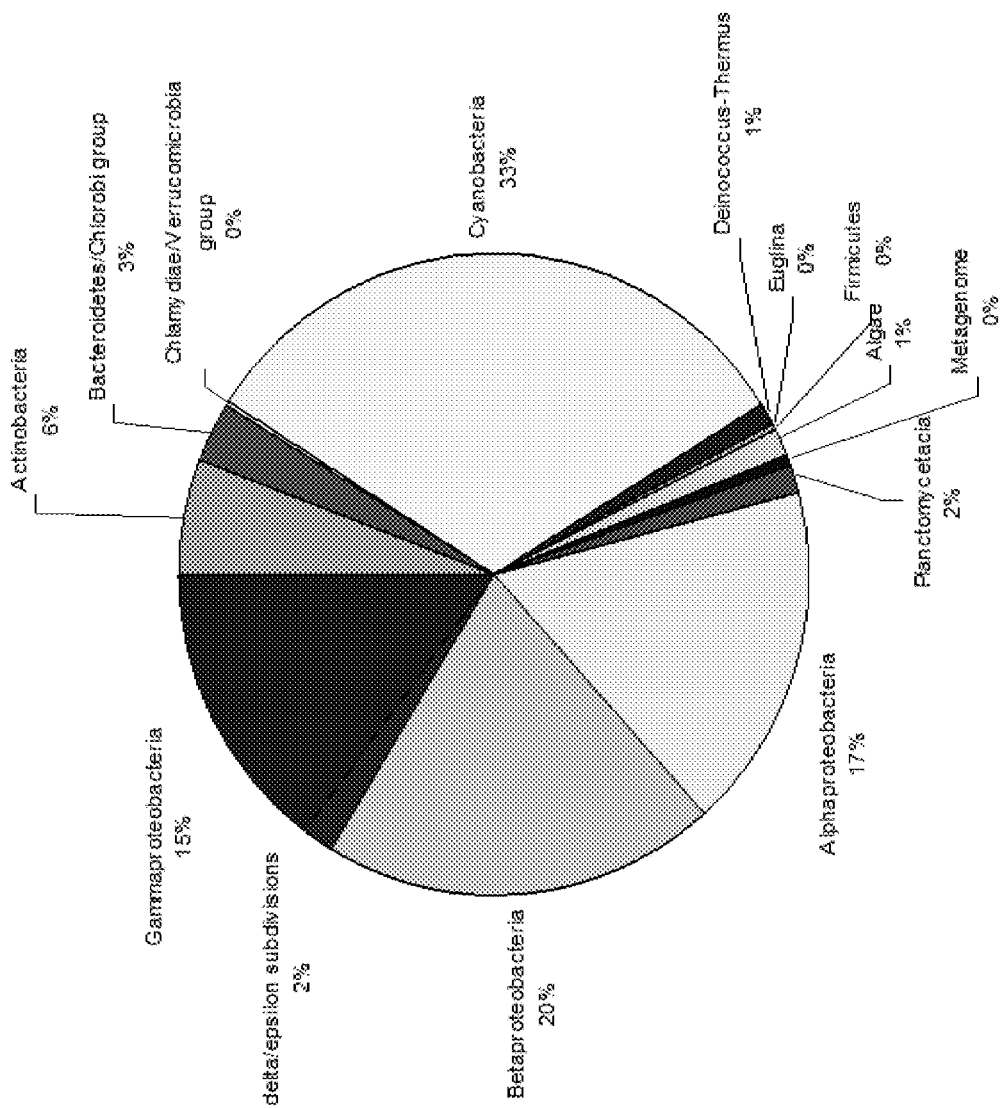

FIG. 178 shows leaf and root micorbiomes in Antarctic hairgrass (*Deschampsia antarctica*). The figure shows a taxonomic distribution of the microbes represented in the *Deschampsia antarctica* leaf and root microbiome.

Figure 179:
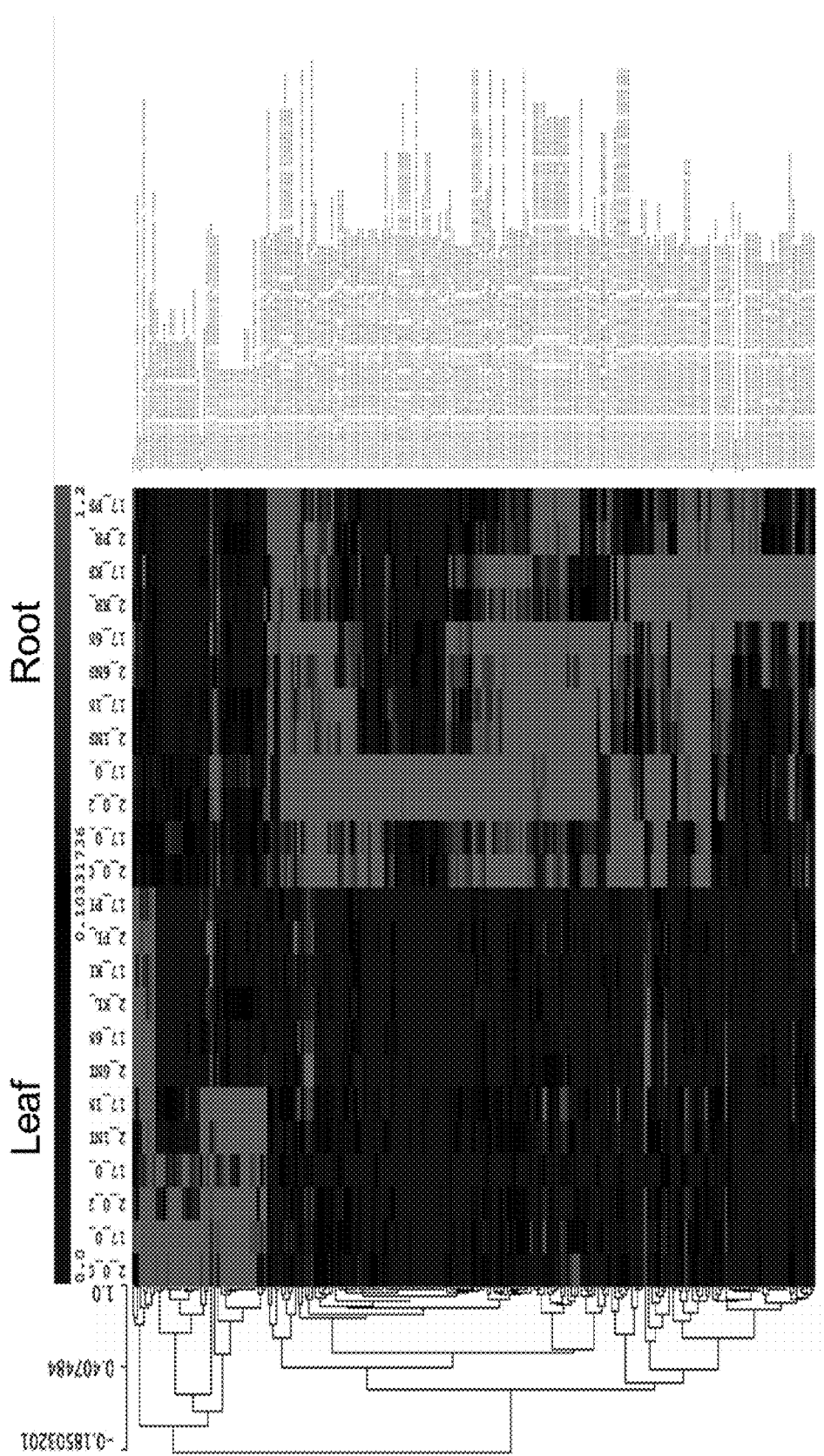

FIG. 179 shows leaf and root microbiomes in Antarctic hairgrass (*Deschampsia antarctica*). The figure shows a heat map displaying differences in bacterial species predominance in shoots and roots.

Figure 180:
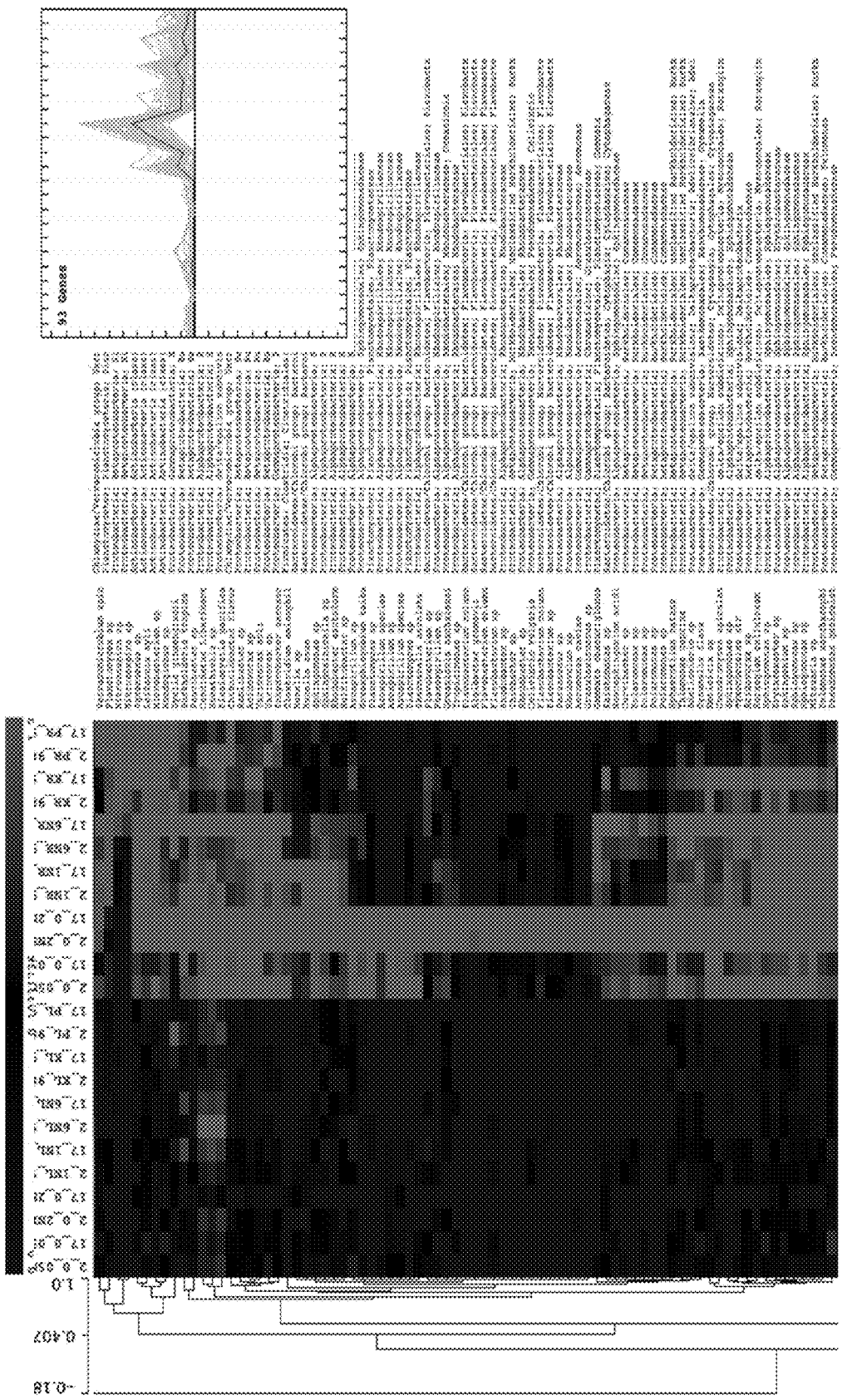

FIG. 180 shows root microbiomes in Antarctic hairgrass (*Deschampsia antarctica*). The figure shows a zoomed region of the heat map displaying differences in bacterial species predominance in response to differing nutritional status in root samples.

Figure 181:
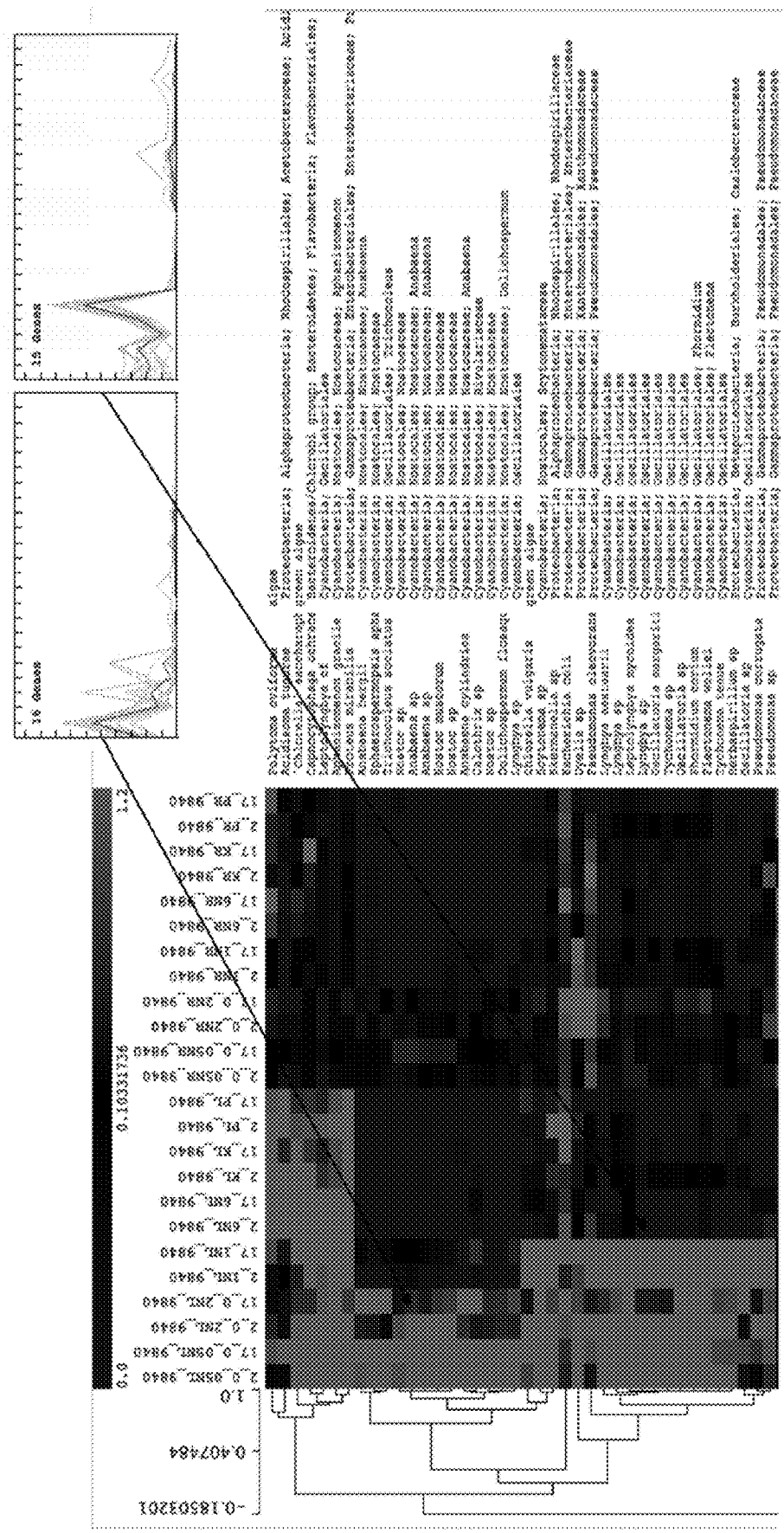

FIG. 181 shows leaf microbiomes in Antarctic hairgrass (*Deschampsia antarctica*). The figure shows a zoomed region of the heat map displaying differences in bacterial species predominance in response to differing nutritional status in leaf samples.

Figure 182:
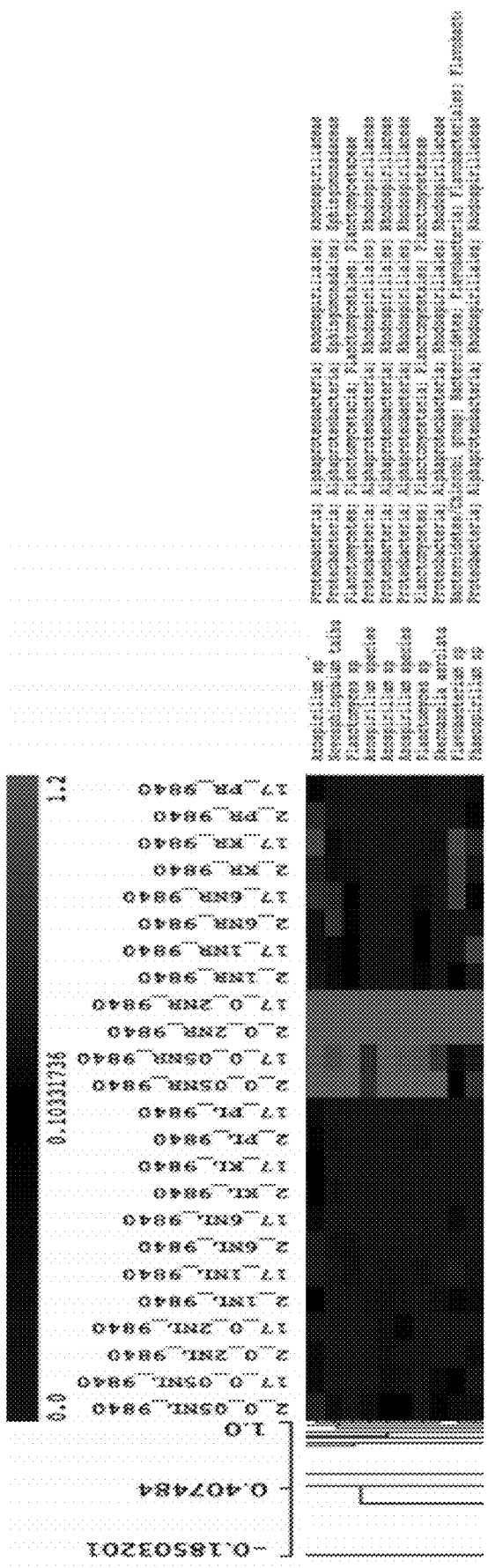

FIG. 182 shows leaf and root microbiomes in Antarctic hairgrass (*Deschampsia antarctica*). The figure shows a zoomed region of the heat map displaying *Azospirillum* species clustered together.

Figure 183:

FIG. 183 shows endophyte suspensions at different dilution rates.

Figure 184:
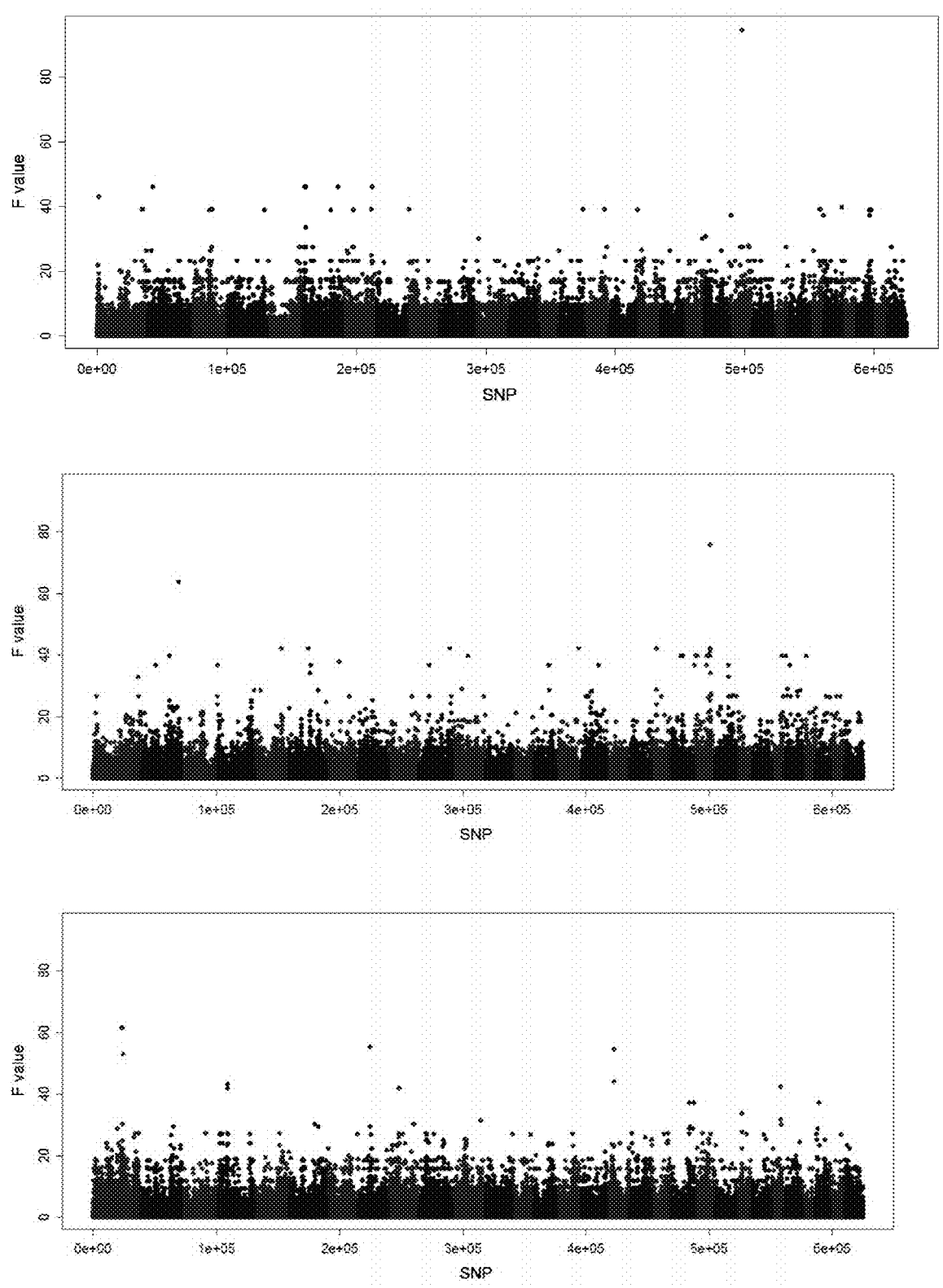
Figure 184:
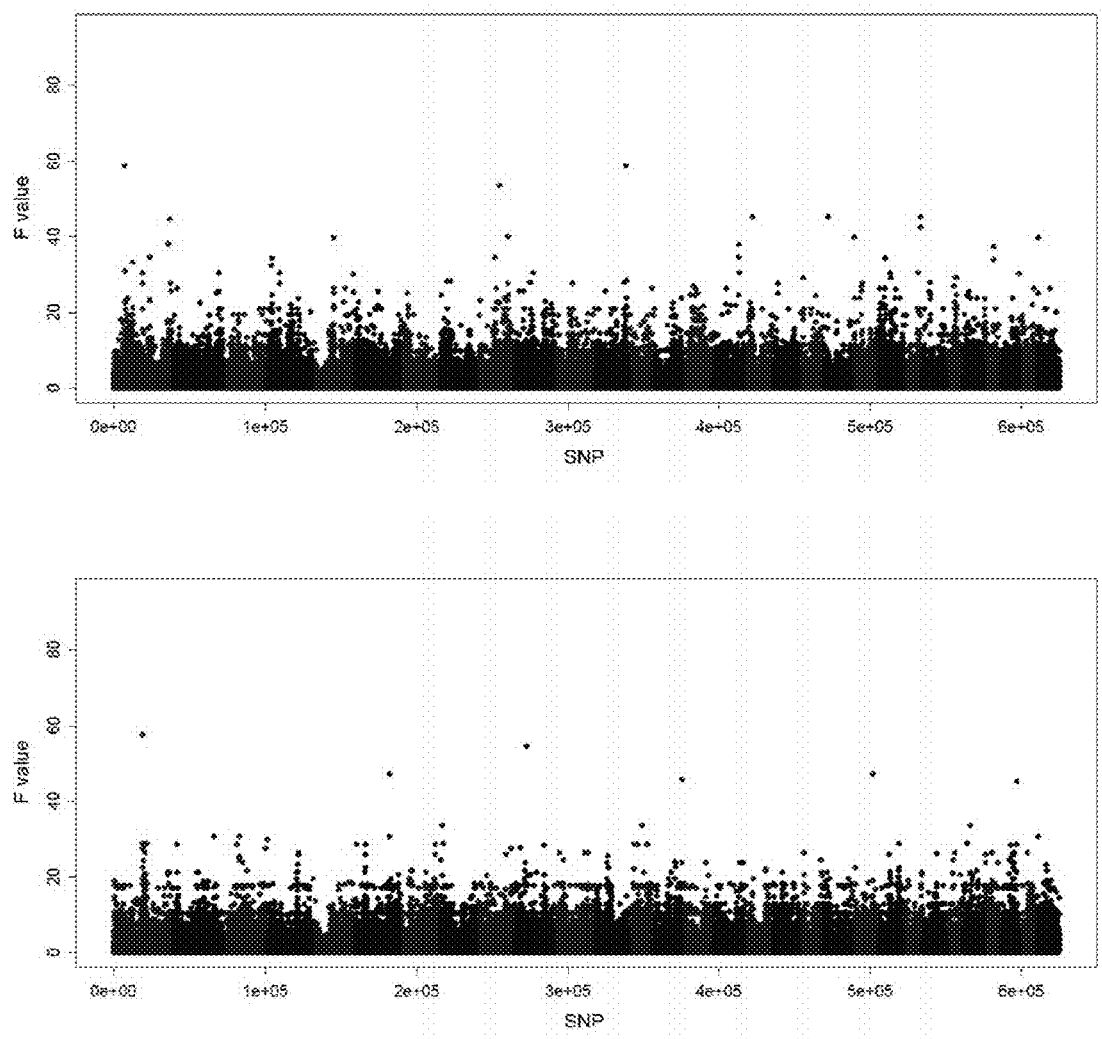

FIG. 184 shows a genome wide association study for assessing effect of 624930 polymorphisms in the host (15 dairy cows) on their rumen microbiome profiles. Results for five contigs are shown. Grey indicates odd numbered chromosomes, black even numbered chromosomes.

Figure 185:
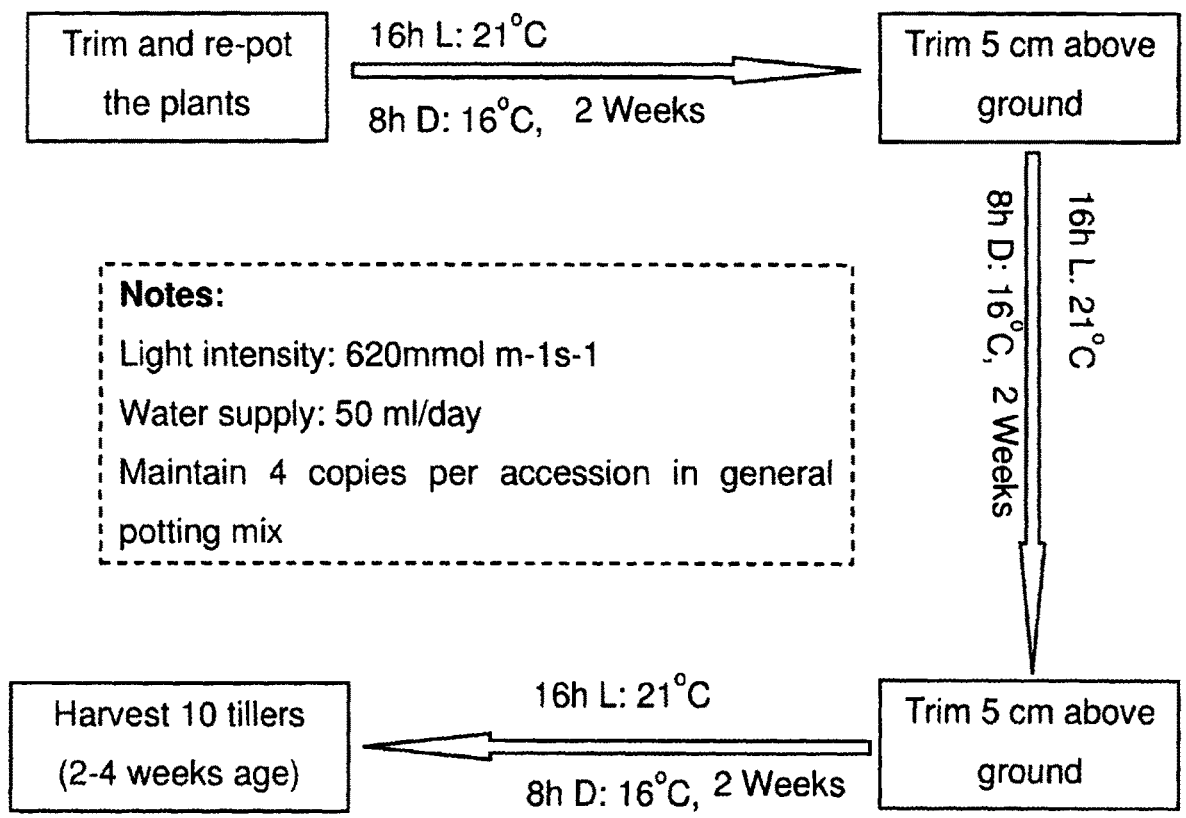

FIG. 185 shows an experimental design for semi-quantitative analysis of metabolites.

Figure 186:
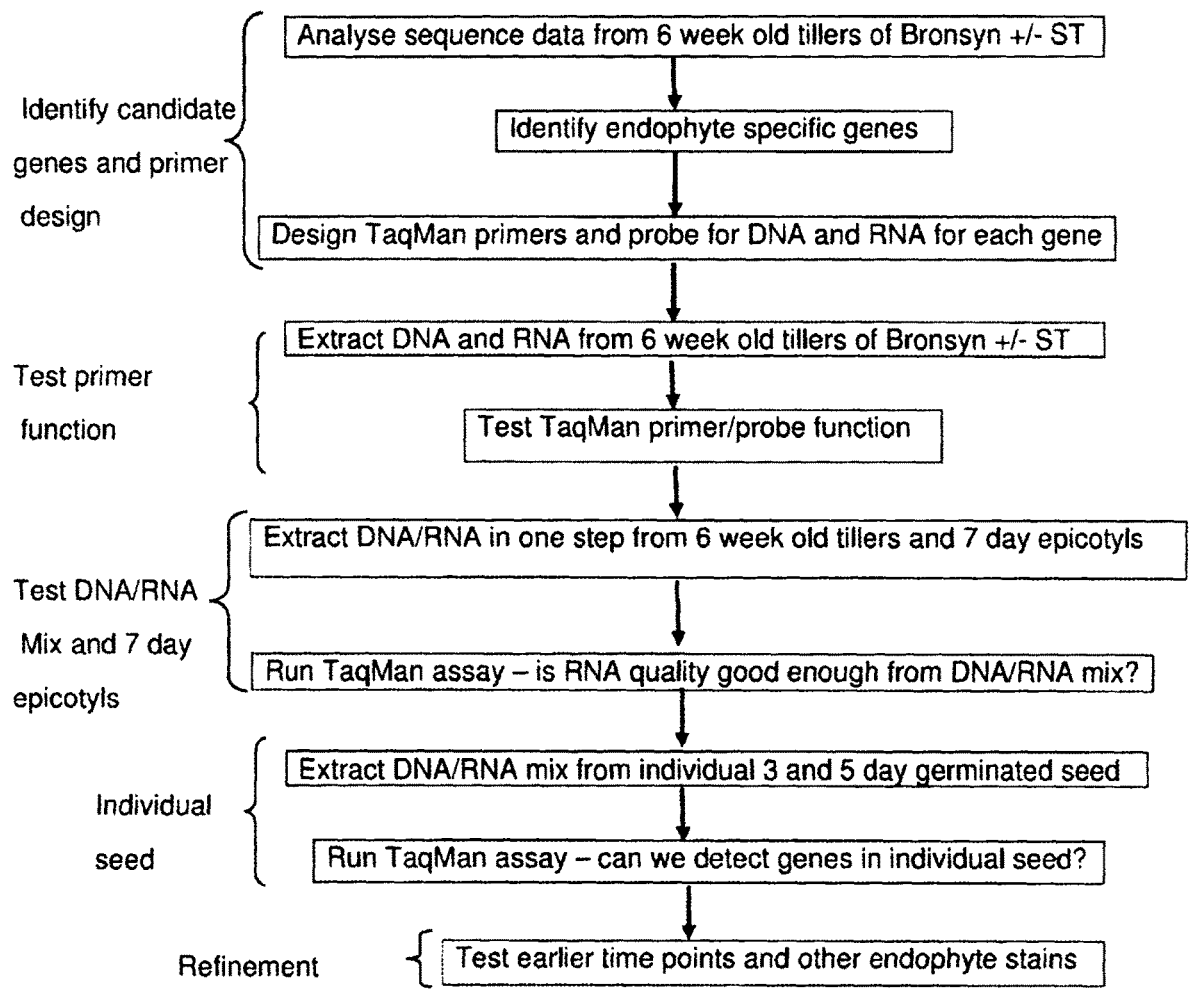

FIG. 186 shows a design for an early endophyte gene expression-based TaqMan Assay.

FIG. 187 shows a semi-quantitative LC-MS used to assess relative amounts of LEPJ across germplasm pools.

FIG. 188 shows production of lolitrems in planta.

FIG. 189 shows production of ergot alkaloids in planta.

Figure 190:
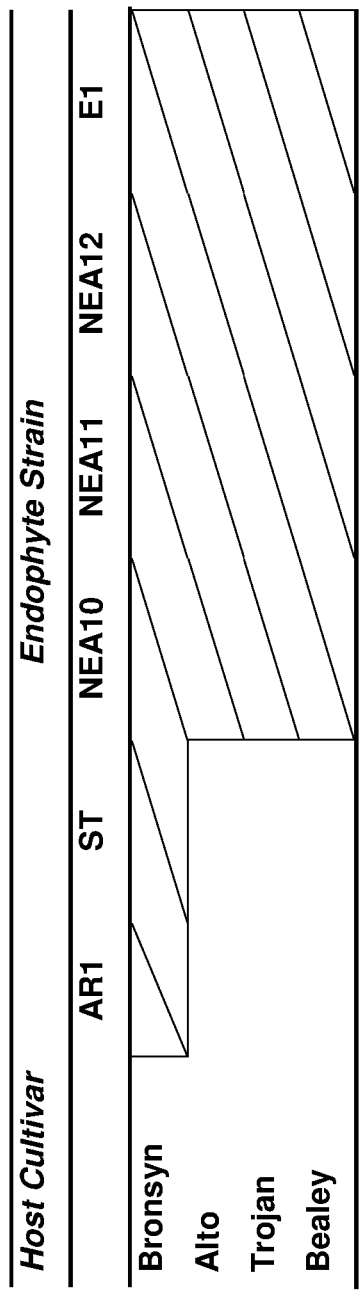

FIG. 190 shows endophyte strains and host cultivars for accelerated aging.

The invention will now be described with reference to the following non-limiting examples.

Example 1—A New Paradigm in Forage Grass Breeding

The Old Paradigm:
Breeding and selection of grass only followed by single endophyte inoculation and symbiota evaluation leading to synthetic grass varieties deploying a single unselected endophyte.

The New Paradigm:
Ab initio breeding and selection of grass-endophyte symbiota followed by symbiota evaluation leading to synthetic symbiota varieties deploying multiple endophytes.

For Application in *Lolium/Festuca* and *Brachiaria/Urochloa*.

Next Generation Ab Initio Molecular Breeding of Grass-Endophyte Symbiota.

| Organism | Endophyte | Symbiota characteristic |
|---|---|---|
| *Lolium perenne* (perennial ryegrass) | *Neotyphodium lolii* | Reduced toxicity to grazing animals |
| *Lolium arundinaceum* (tall fescue) | *Neotyphodium coenophialum* | Enhanced persistence |
| *Brachiaria* species | *Acremonium implicatum* | Biotic stress tolerance |

New Principles and Approaches

Extend Concept of Synthetic Varieties to Both Partners of the Symbiotum i.e. Grass Host and Endophyte Deploy multiple endophyte and grass genotypes in populations selected for optimal symbiota compatibility and performance Capture Ab Initio Plant Genotype X Endophyte Genotype Effects Breed and select ab initio symbiota for optimal symbiota compatibility and performance rather than breed and select grass host only followed by endophyte inoculation and symbiota evaluation Capture and Exploit Broader Endophyte Genotype Effects on Symbiota Performance Exploit significant endophyte genotype effects on symbiota performance well beyond pest resistance (and reduced animal toxicosis)

Capture and Exploit Global Novel Endophyte Genetic Diversity [Step 1]

Deploy multiple novel endophytes ab initio rather than single branded endophytes late in varietal development process thus exploiting wide range of endophyte genotypic diversity [i.e. 'endophyte germplasm collection']

Generate and Exploit De Novo Endophyte Genetic Diversity [Step 2]

Generate de novo genetic variation [i.e. random mutagenesis (e.g. ionizing radiation); di-/poly-ploidisation (e.g. colchicine treatment); targeted mutagenesis (e.g. ExZact-Delete and ExZact-Edit); cisgenesis; transgenesis; intragenesis; integrative genome editing (e.g. ExZact-Add)] in novel endophytes for enhanced endophyte trait introgression in large-scale establishment of grass-endophyte symbiota [i.e. 'breeding designer endophytes']

Capture Broad Genotypic Grass and Endophyte Diversity in Symbiota Populations for Ab Initio Symbiota Breeding [Step 3]

Establish large-scale symbiota populations involving 10s to 100s of endophyte genotypes in 100s to 1000s of grass genotypes for ab initio breeding and selection of symbiota Deploy method for large-scale endophyte inoculation based on artificial seeds generated from isolated grass embryos directly inoculated with different endophytes followed by coating in alginate layers or coated by endophyte-containing alginate layer [i.e. 'symbiota artificial seeds']

For *Brachiaria/Urochloa* grass genotypes inoculate single endophytes and also co-inoculate multiple endophytes in (particularly apomictic) grass host genotypes Undertake Ab Initio Symbiota Breeding and Selection [Steps 4-8]

Select large-scale symbiota populations involving 10s to 100s of endophyte genotypes in 100s to 1000s of grass genotypes for compatibility and stability by applying accelerated ageing to symbiota artificial seeds and/or their offsprings as selection tool [Step 4]

Select symbiota populations from Step 4 for viability by applying rapid endophyte viability assay [Step 5]

Subject symbiota populations from Step 5 to comprehensive, multi-year phenotyping for symbiota performance and alkaloid production [Step 6]

Select Syn0 symbiota from Step 6 for poly-crossing to generate synthetic symbiota experimental varieties [Step 7] followed by determination of endophyte incidence and identity [Step 8]

Next Generation Ab Initio Molecular Breeding of Grass-Endophyte Symbiota—Endophyte Workflow Endophyte Germplasm
  Step 1: Discovery of global diversity in novel endophytes
  Step 2: De novo generation of novel endophyte diversity
Establishing Symbiota
  Step 3: Large scale generation of grass-endophyte symbiota
Selecting Symbiota for Stability, Desired Alkaloid Profile and Performance
  Step 4: Selection tools for symbiota stability
  Step 5: Rapid endophyte viability assay
  Step 6: Multi-year phenotyping (incl molecular) of symbiota
  Step 7: Selection of Syn0 symbiota parents for poly-crossing to generate experimental synthetic varieties for comprehensive evaluation
  Step 8: Endophyte ID assay
Poly-Crossing Syn0 Symbiota Parents
  Step 9: Poly-crossing selected symbiota parents (Syn0) with known endophyte identity and incidence and recovery of Syn1 seed
Confirming Symbiota Stability, Alkaloid Profile and Endophyte Identity and Incidence
  Step 10: Selection tool for symbiota stability
  Step 11: Rapid endophyte viability assay
  Step 12: Molecular phenotyping of symbiota*
  Step 13: Endophyte ID assay*
Evaluating Syn1 Symbiota
  Step 14: Evaluation of symbiota (Syn1) experimental synthetic variety for agronomic performance
    Assessment of alkaloid profile and endophyte identity and incidence on pooled samples at Syn1 generation
Poly-Crossing Syn1 Symbiota Plants
  Step 15: Poly-crossing advance of symbiota (Syn1) with known endophyte identity and incidence and recovery of Syn2 seed
  Step 16: Selection tool for symbiota stability
  Step 17: Rapid endophyte viability assay
  Step 18: Molecular phenotyping of symbiota*
  Step 19: Endophyte ID assay*

Evaluating Syn2 Symbiota
 Step 20: Evaluation of symbiota (Syn2) experimental synthetic variety for agronomic and animal performance
  Assessment of alkaloid profile and endophyte identity and incidence on pooled samples at Syn2 generation Example 2—Tall Fescue Endophyte Discovery The objectives of this work on discovery and characterization of endophytes in tall fescue (*Lolium arundinaceum*) were:
1. Identification and characterisation of novel tall fescue endophytes for evaluation in germplasm.
2. Development and evaluation of optimised associations between novel endophytes and elite germplasm.

The endophyte discovery was based on screening 568 accessions to identify endophyte positive plants followed by genotyping 210 endophytes to identify novel endophytes in tall fescue.

The characterisation in planta of novel endophytes from tall fescue was based on the following steps:
 Meristem cultures for tall fescue cultivars established for isogenic host panel
 Endogenous metabolic profiles determined for 48 samples
 Isolation of 38 endophytes was undertaken
 Inoculation of 15-20 endophytes into isogenic host panel was undertaken
 Isogenic host-endophyte associations were characterised
Genotypic Analysis of Endophyte Content in Accessions from a Targeted Fescue Germplasm Collection Initially, 472 accessions from 30 countries were tested for endophyte incidence; with 2 replicates of 6-10 seeds in each bulk per accession used in the analysis and endophyte incidence assessed with 6 SSRs.

New accessions were included in the analysis from the under-represented geographic origins; with a total of 568 accessions from 40 countries tested for endophyte incidence.

Genotypic analysis of endophyte content in accessions from a targeted fescue germplasm collection is shown in Table 1. 233 endophyte positive accessions (41%) were detected. The geographical origins are represented in the endophyte incidence assessment.

Figure 2:
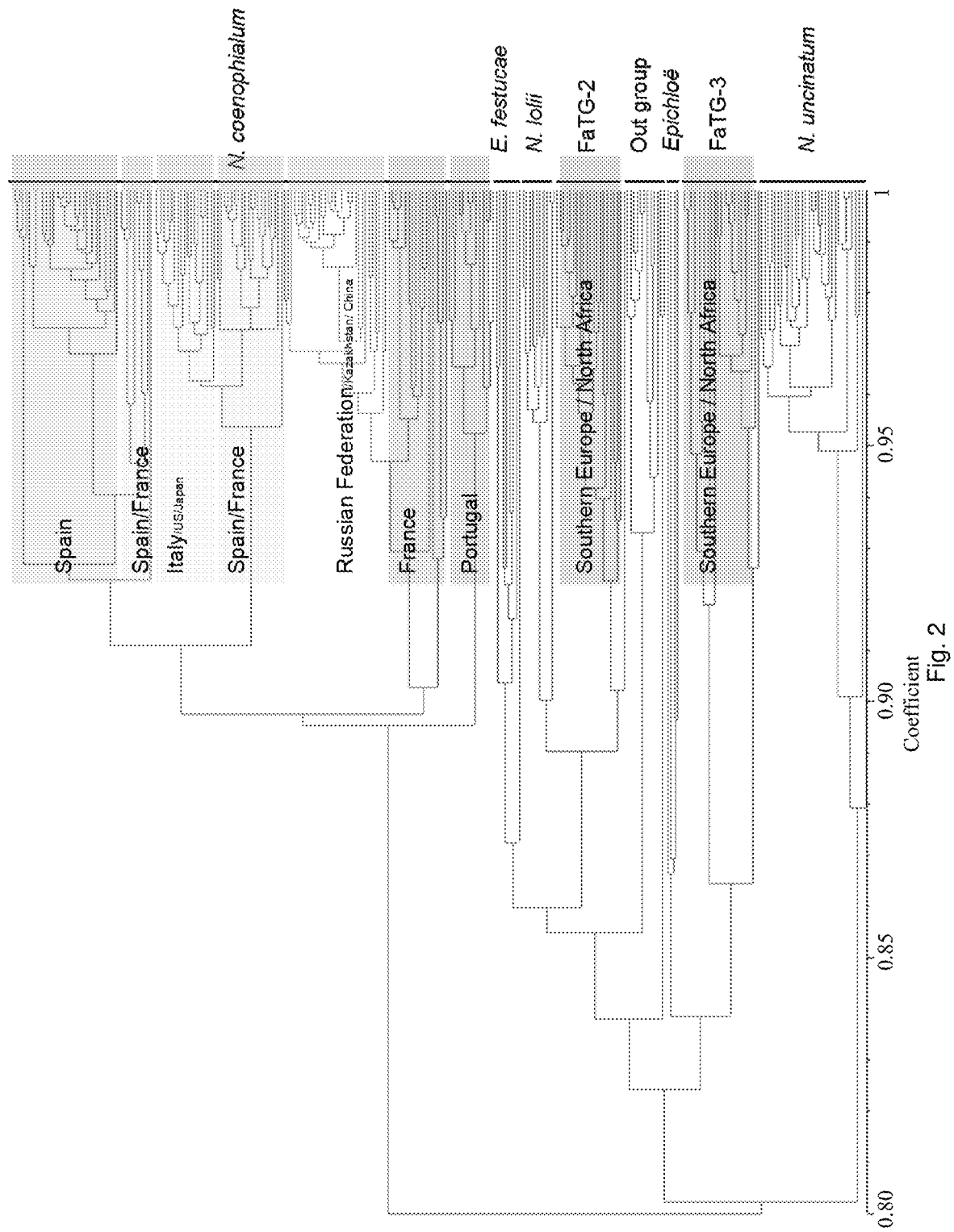
FIG. 2 shows genetic diversity analysis of tall fescue endophytes.

A genetic diversity analysis of tall fescue endophytes is shown in FIG. 2. A selected set of 210 accessions were used to assess genetic diversity of tall fescue endophytes. Genetic diversity was assessed with 38 SSR markers. Six different taxa were detected. The majority were *N. coenophialum*. Twenty were FaTG-2. Six were putative FaTG-3. Thirteen were FaTG-3 like.

Figure 3:
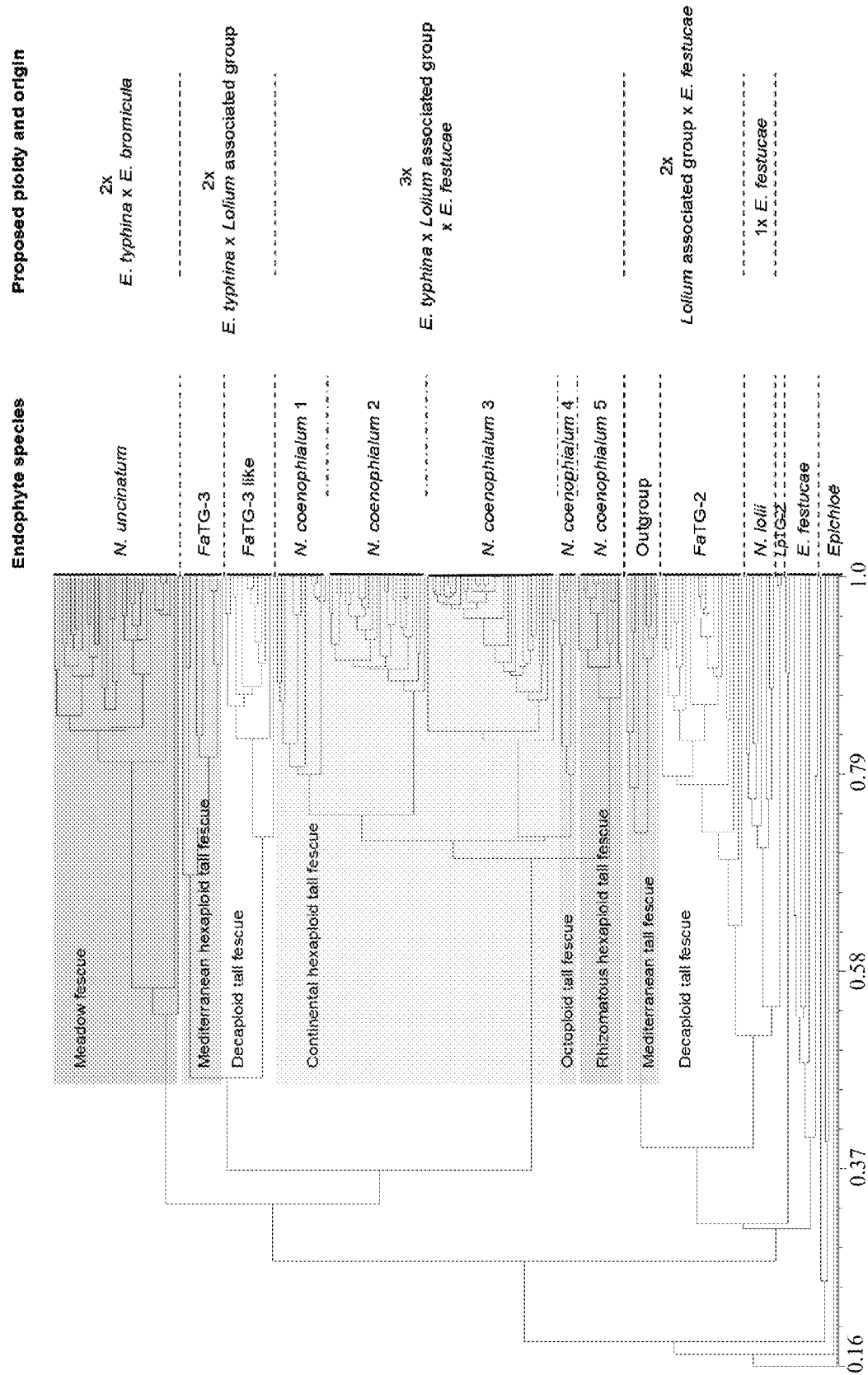
FIG. 3 shows diversity analysis of host and endophyte.

Diversity of host and endophyte is shown in FIG. 3.

Figure 4:
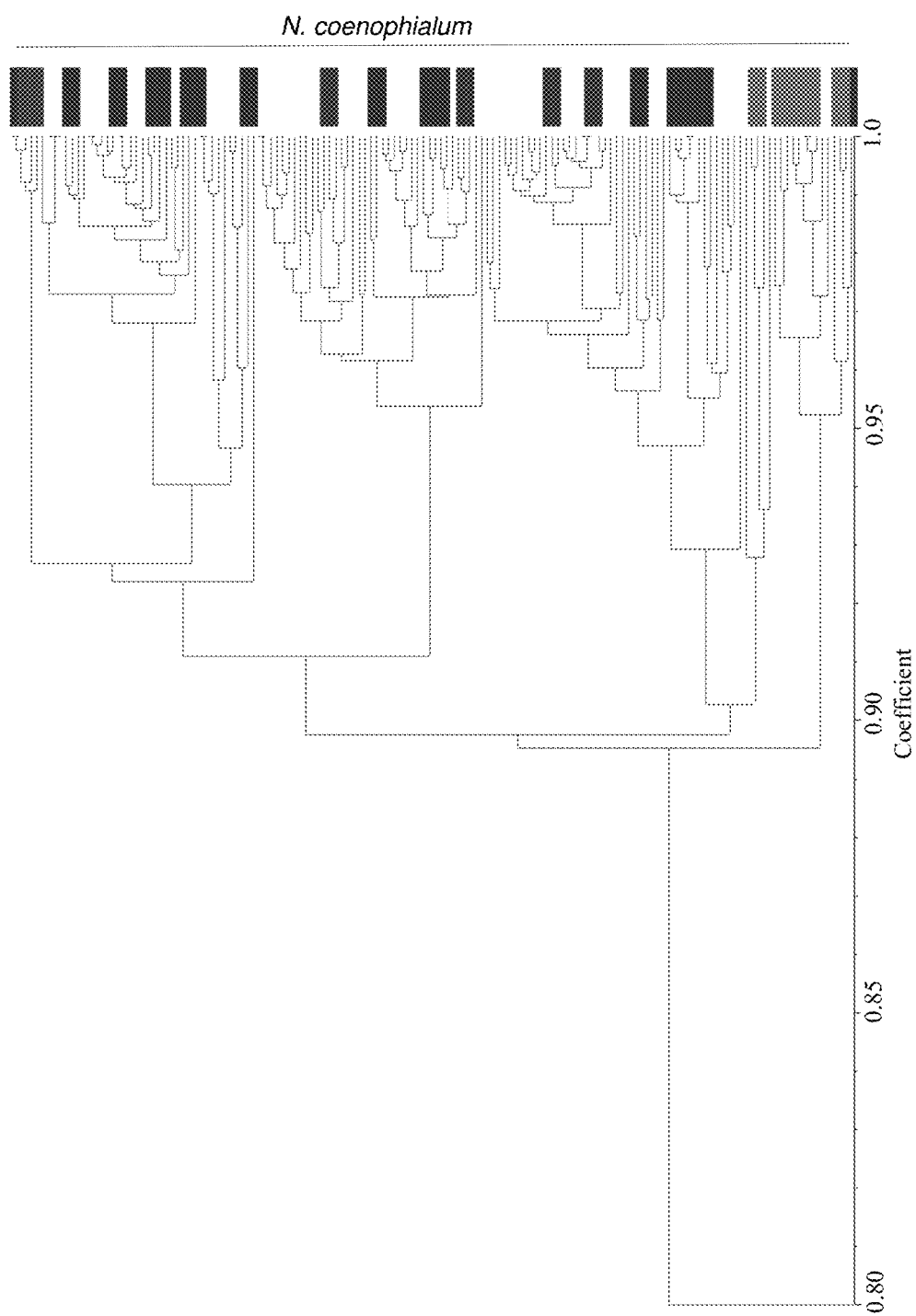
FIG. 4 shows selection of fescue-endophyte combinations for metabolic profiling, endophyte isolation and isogenic inoculation.

Selection of fescue-endophyte combinations for metabolic profiling, endophyte isolation and isogenic inoculation is shown in FIG. 4. 52 accessions were initially selected for metabolic profiling and endophyte isolation. Endophyte presence was consistently detected in 25 accessions (red). An additional 48 accessions from under-represented clusters were established in the glasshouse and screened for endophyte presence. 20 accessions were endophyte positive (blue) and have been selected for further analysis.

Figure 5:
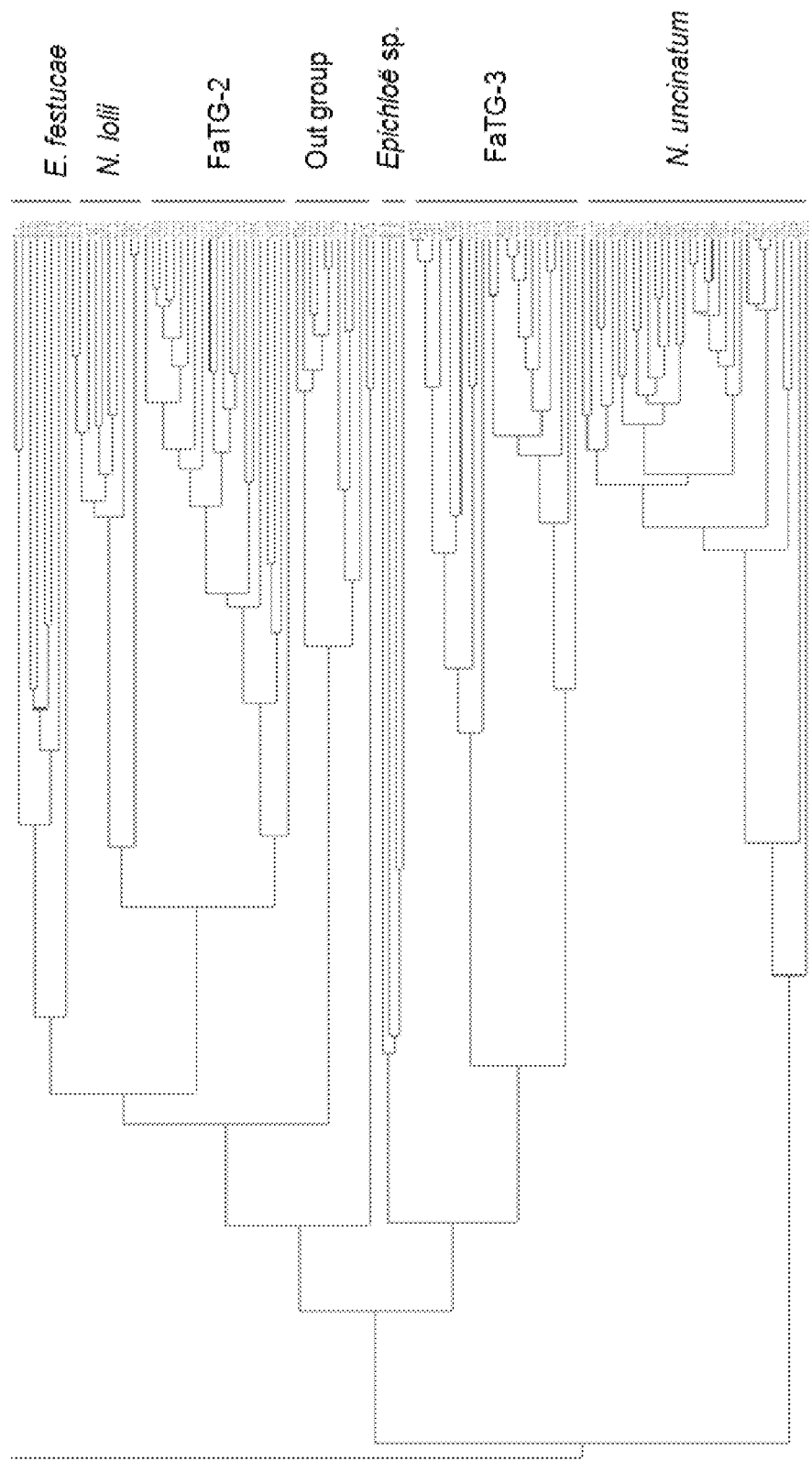
FIG. 5 shows selection of fescue-endophyte combinations for metabolic profiling, endophyte isolation and isogenic inoculation.

Selection of fescue-endophyte combinations for metabolic profiling, endophyte isolation and isogenic inoculation is shown in FIG. 5. Initial selections are shown in red. Additional selections are shown in blue.

Figure 6:
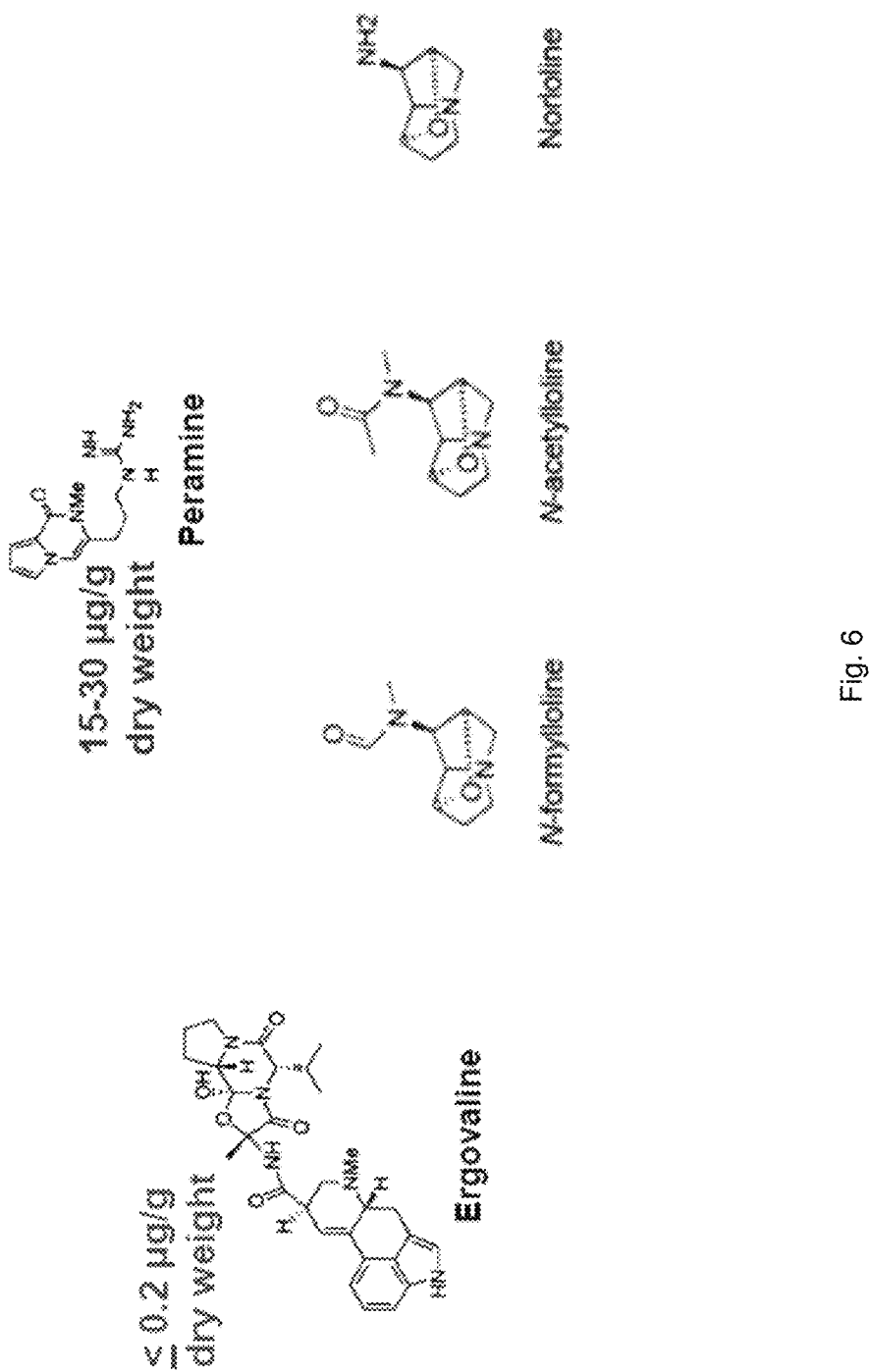
FIG. 6 shows a desired toxin profile of tall fescue endophytes.

The desired toxin profile of tall fescue endophytes is shown in FIG. 6.

Example 3—Metabolic Profiling

The experimental design used for semi-quantitative metabolic profile analysis of tall fescue-endophyte associations for the detection of alkaloid production in the endogenous host background is described below.

An experimental design for semi-quantitative analysis of metabolites is illustrated in FIG. 18S.

Figure 7:
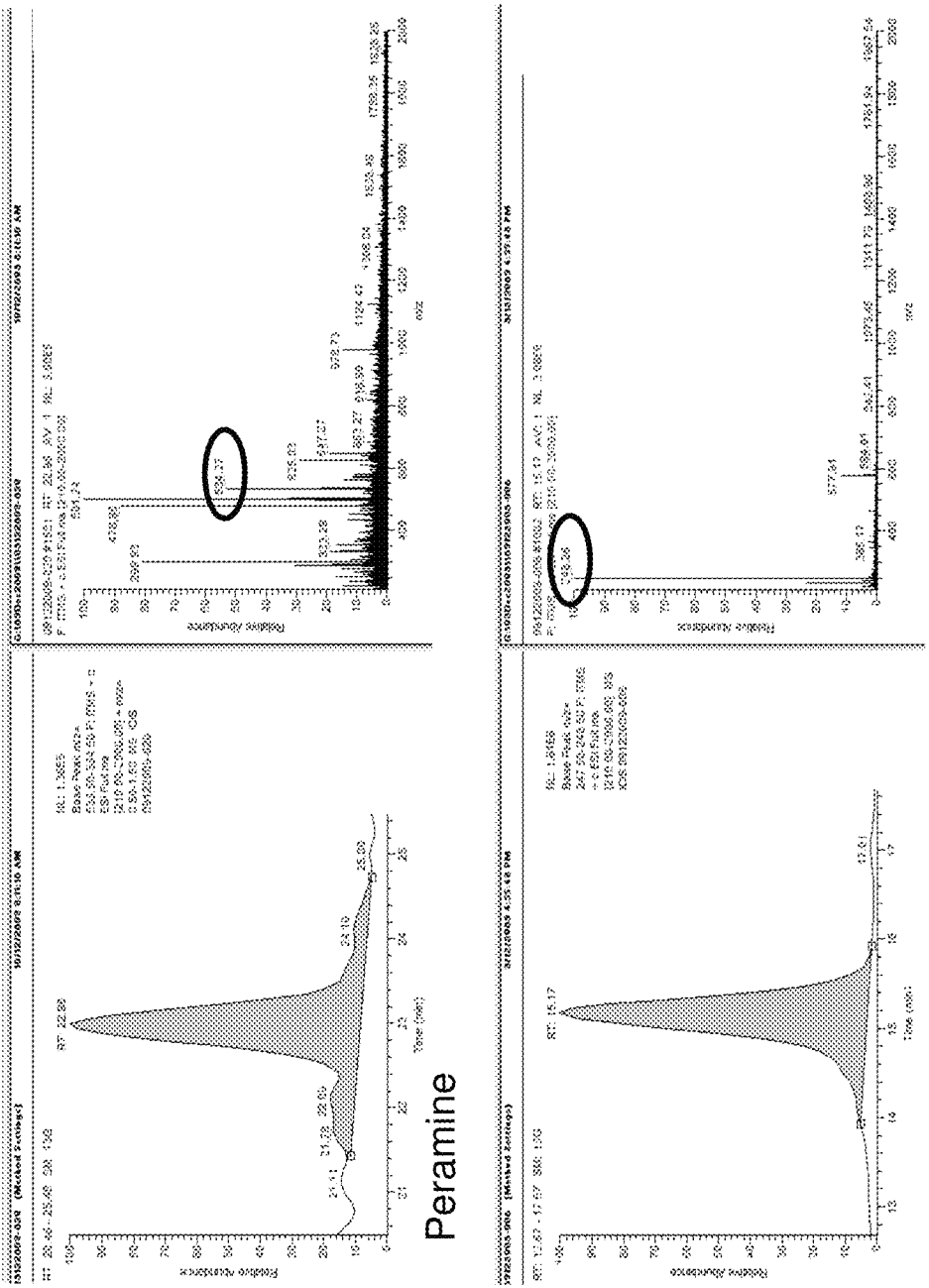
FIG. 7 shows a metabolic profile analysis.

A metabolic profile analysis for detection of ergovaline and peramine is shown in FIG. 7.

Figure 8:
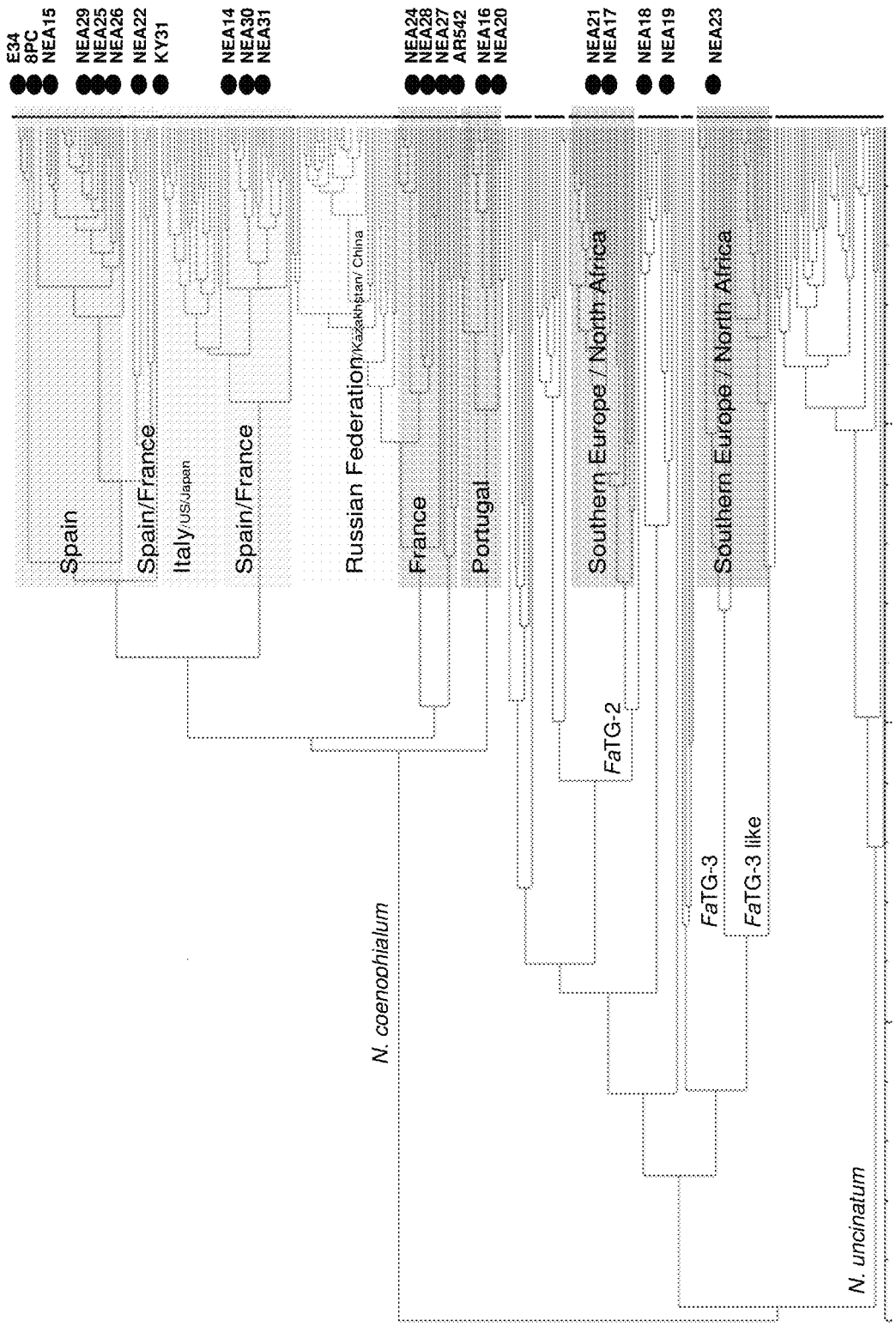
FIG. 8 shows endophytes selected for semi-quantitative analysis of metabolites.
Figure 9:
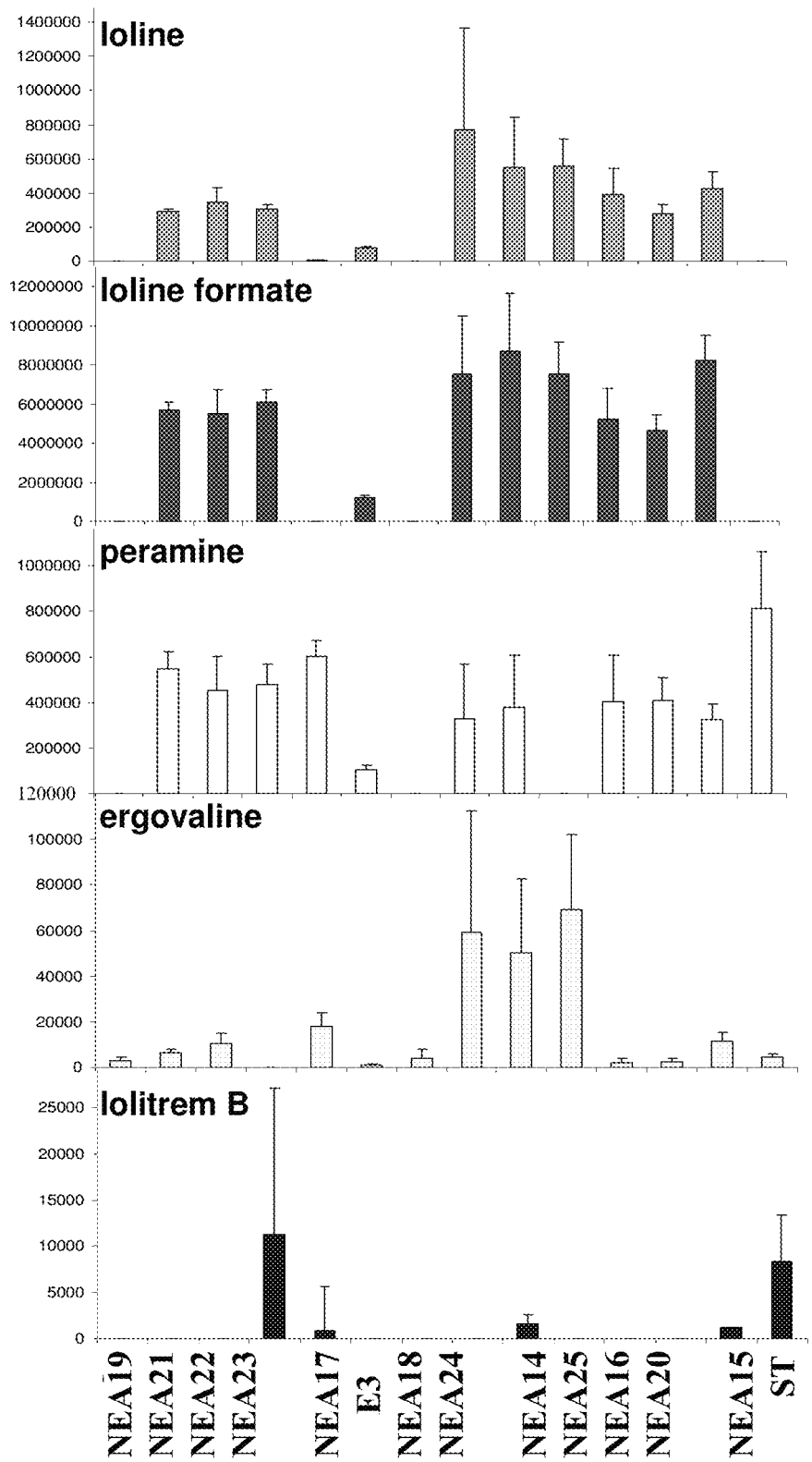
FIGS. 9 and 10 show metabolomics analyses of fescue endophytes.

Endophytes selected for semi-quantitative analysis of metabolites are shown in FIG. 8.
Metabolic, Profile Analysis for the Detection of Alkaloid Production of Different Fescue Endophytes A metabolic analysis of tall fescue-endophyte associations for the detection of alkaloid production including loline, loline formate, peramine, ergovaline and lolitrem B in the endogenous host background is shown in FIG. 9. The alkaloid profile (i.e. lolines, peramine, ergovaline and lolitrem B) of tall fescue-endophyte associations in the endogenous host background for a range of endophyte strains belonging to different endophyte species is shown in Table 2.

TABLE 1

Genotypic analysis of endophyte content in accessions from a targeted fescue germplasm collection

|  | Number of geographic origins | | Percentage positive accessions | |
|---|---|---|---|---|
|  | FEtc collection | GRIN collection | FEtc collection | GRIN collection |
| Incidence assessment 01 | 7 | 23 | 96% | 30% |
| Incidence assessment 02 | — | 10 | — | 45% |

TABLE 2

Alkaloid profile (i.e. lolines, peramine, ergovaline and lolitrem B) of tall fescue-endophyte associations in the endogenous host background for a range of endophyte strains belonging to different endophyte species

| Tall fescue accession details | | | Alkaloid profile | | | |
|---|---|---|---|---|---|---|
| Tall fescue accession | Endophyte strain | Endophyte species | Lolines | Peramine | Ergovaline* | Lolitrem B |
| BE9301 | E34 | *N. coenophialum* | + | + | $+^L$ | — |
| 8PC | NEA13 | *N. coenophialum* | n.d | + | + | n.d |
| FEtc7-180 | NEA14 | *N. coenophialum* | + | + | $+^H$ | — |
| FEtc7-58 | NEA15 | *N. coenophialum* | + | + | $+^M$ | — |

TABLE 2-continued

Alkaloid profile (i.e. lolines, peramine, ergovaline and lolitrem B) of tall fescue-endophyte associations in the endogenous host background for a range of endophyte strains belonging to different endophyte species

| Tall fescue accession details | | | Alkaloid profile | | | |
|---|---|---|---|---|---|---|
| Tall fescue accession | Endophyte strain | Endophyte species | Lolines | Peramine | Ergovaline* | Lolitrem B |
| FEtc7-342 | NEA16 | N. coenophialum | + | + | − | − |
| FEtc7-343 | NEA20 | N. coenophialum | + | + | − | − |
| 234746 | NEA22 | N. coenophialum | + | + | +$^M$ | − |
| FEtc6-83 | NEA24 | N. coenophialum | + | + | +$^H$ | − |
| FEtc7-289 | NEA25 | N. coenophialum | + | − | +$^H$ | − |
| FEtc6-68 | NEA26 | N. coenophialum | + | + | + | − |
| FEtc6-85 | NEA27 | N. coenophialum | n.d | + | + | n.d |
| FEtc6-87 | NEA28 | N. coenophialum | n.d | + | + | n.d |
| FEtc7-127 | NEA29 | N. coenophialum | + | + | + | − |
| FEtc6-128 | NEA30 | N. coenophialum | + | + | + | − |
| FEtc6-129 | NEA31 | N. coenophialum | + | + | + | − |
| 287819 | NEA17 | FaTG-2 | − | + | +$^M$ | − |
| 231557 | NEA21 | FaTG-2 | + | + | − | − |
| 269850 | NEA23 | FaTG-3 | + | + | − | − |
| 231553 | NEA19 | Out group 1 | − | − | − | − |
| FEtc6-75 | NEA18 | Out group 1 | − | − | − | − |
| ST | ST | N. lolii | − | + | + | + |
| AR542* | AR542 | N. coenophialum | + | + | − | − |
| KY31* | KY31 | N. coenophialum | + | + | + | − |
| E77* | E77 | N. coenophialum | + | + | + | − |

(*Published data; n.d = not determined).

Figure 10:
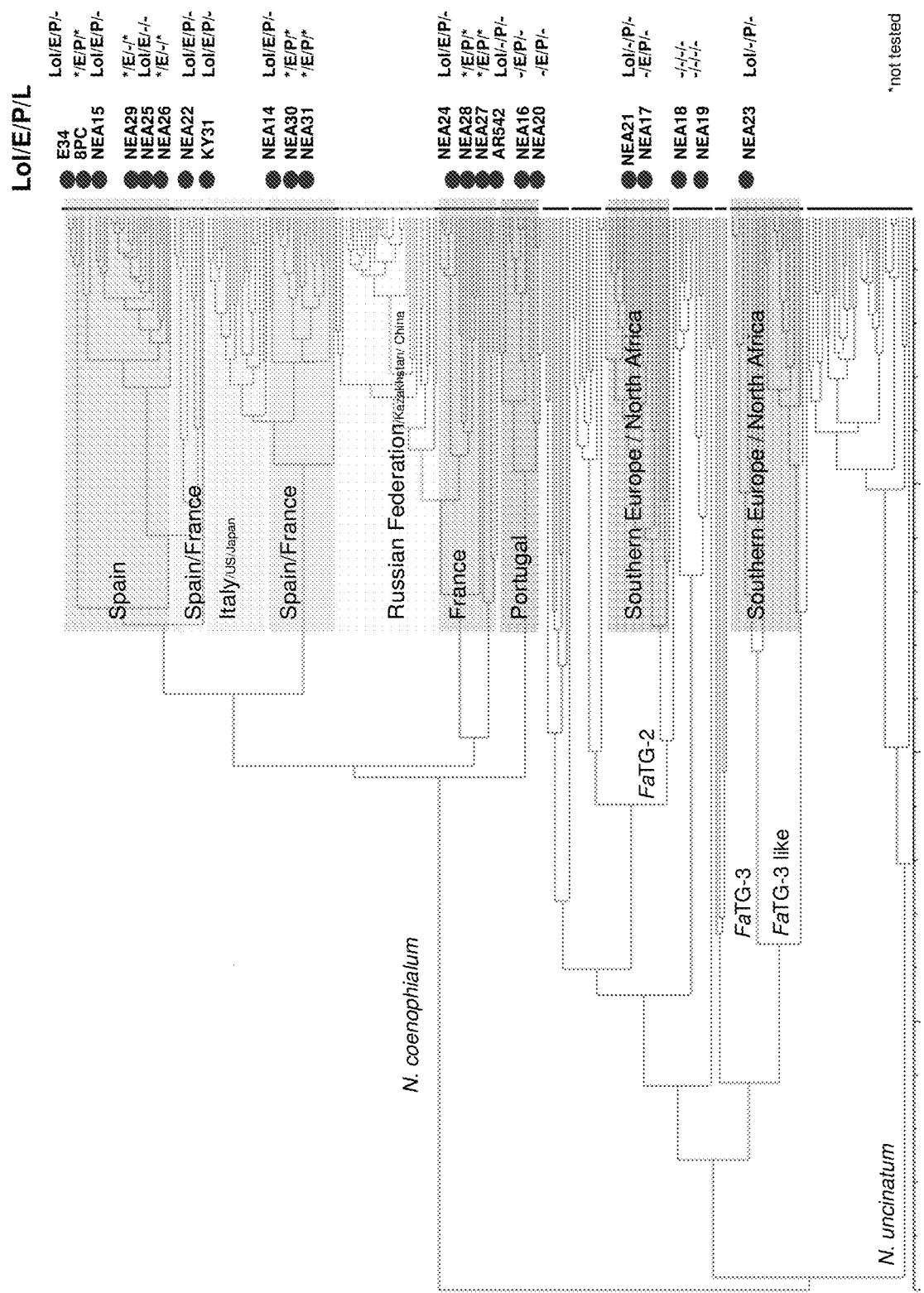

Further metabolic analysis of the fescue endophytes is shown in FIG. 10.

Example 4—Semi-Quantitative Analysis of Metabolic Profile Under Temperature/Water Stress In addition to the metabolic analysis of tall fescue-endophyte associations grown under standard conditions, for the detection of alkaloid production conferred by the endopohytes in the endogenous host background (FIGS. 7-10), a semi-quantitative analysis of metabolic profiles of tall fescue-endophyte associations grown under high temperature and water stress conditions was undertaken. Corresponding tall fescue-endophyte associations were grown under 16 h Light and 30° C.; 18 h Dark and 20° C., and then sampled for alkaloid profile analysis as described below:

Harvest (control)→freeze dry→50 mg pseudostem material→80% methanol extraction→LCMS analysis Recovery and water stress Second harvest (stress)→freeze dry→SSR confirm all of the plant material again.

This was performed in a controlled (growth chamber) environment simulating summer conditions, with light watering as required. Nine copies per accession were planted in general potting mix. A Randomized Complete Block with subsampling was used.

Figure 11:
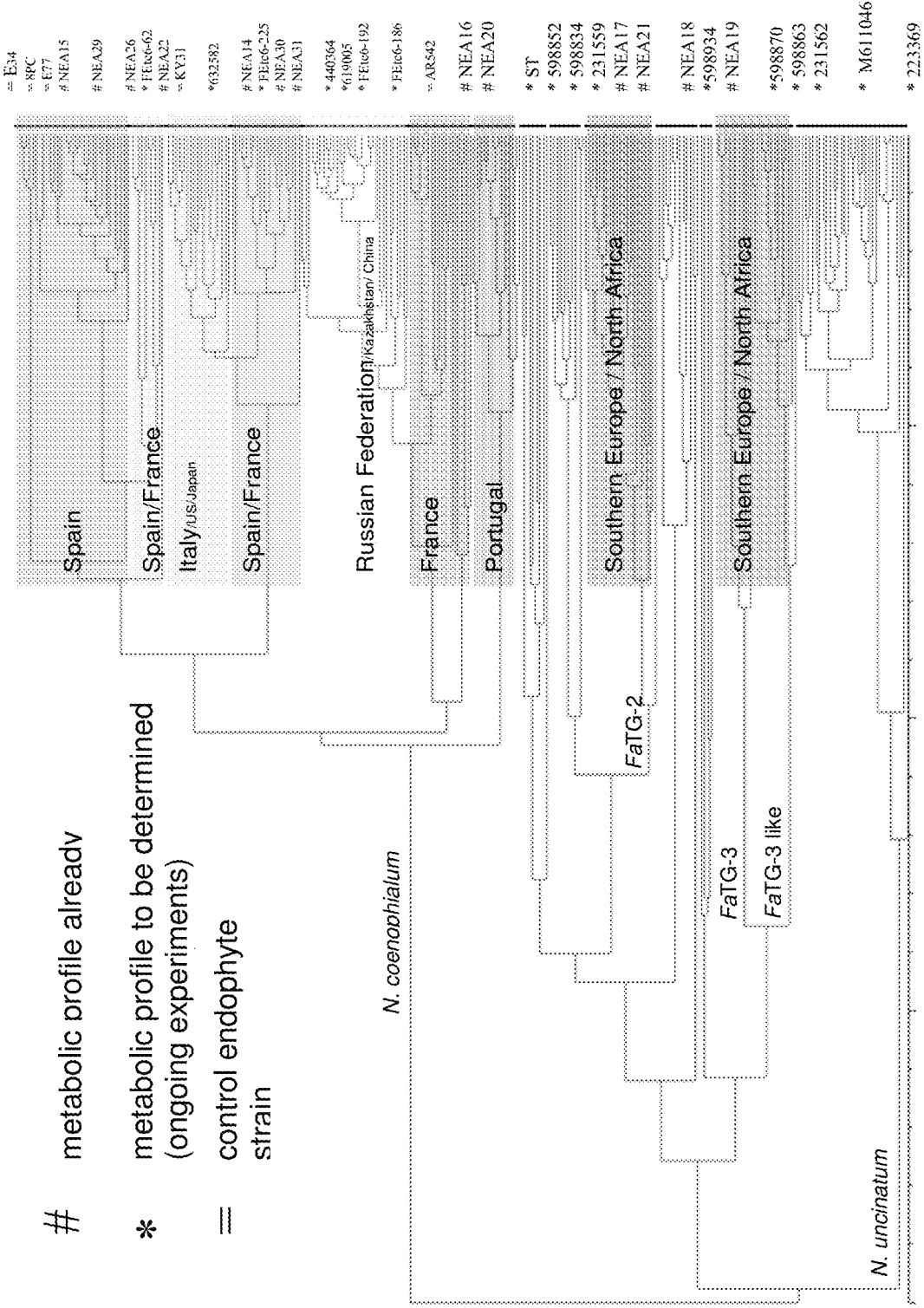
FIG. 11 shows a semi-quantitative analysis of metabolic profile under temperature/water stress.

FIG. 11 shows a semi-quantitative analysis of metabolic profile of tall fescue-endophyte associations grown under high temperature and water stress conditions.

Example 5—In Planta Isogenic Inoculation in Tall Fescue with Novel Endophytes Summary A total of 36 fescue endophytes have been isolated from a range of fescue accessions from different geographic origin as described in Table 3, and found to belong to different taxa as follows: 19 of them being N. coenophialum; 5 of them being FaTG-2; 3 of them being Outgroup; 3 of them being FaTG-3; 3 of them being FaTG-3 like; and 3 of them being N. uncinatum.

TABLE 3

Isolation of fungal cultures from selected fescue-endophyte combinations

| | Fescue Accession | Endophyte Strain | Origin | Cluster | Taxon |
|---|---|---|---|---|---|
| 1 | 8PC | 8PC | | C01.1 | N. coenophialum |
| 2 | BE9301 | E34 | | C01.1 | N. coenophialum |
| 3 | E77 | E77 | | C01.2 | N. coenophialum |
| 4 | FEtc6-62 | | Catalunya (Spain) 4 | C01.2 | N. coenophialum |
| 5 | FEtc6-68 | NEA26 | Catalunya (Spain) 14 | C01.2 | N. coenophialum |
| 6 | FEtc7-127 | NEA29 | Aragon (Spain) 14 | C01.2 | N. coenophialum |
| 7 | FEtc7-289 | NEA25 | Aragon (Spain) 1 | C01.2 | N. coenophialum |
| 8 | FEtc7-58 | NEA15 | Aragon (Spain) 1 | C01.2 | N. coenophialum |
| 9 | 234746 | NEA22 | Spain | C01.2 | N. coenophialum |
| 10 | 632582 | | Italy | C02.1 | N. coenophialum |
| 11 | Kentucky 31 | KY31 | | C02.1 | N. coenophialum |
| 12 | FEtc6-128 | NEA30 | Pyrenees13 | C02.2 | N. coenophialum |
| 13 | FEtc6-129 | NEA31 | Pyrenees17 | C02.2 | N. coenophialum |

TABLE 3-continued

Isolation of fungal cultures from selected fescue-endophyte combinations

| | Fescue Accession | Endophyte Strain | Origin | Cluster | Taxon |
|---|---|---|---|---|---|
| 14 | FEtc7-180 | NEA14 | PaySardegna (Basque (France | C02.2 | N. coenophialum |
| 15 | 440364 | | Kazakhstan | C03 | N. coenophialum |
| 16 | 619005 | | China | C03 | N. coenophialum |
| 17 | FEtc6-83 | NEA24 | Corsica (France) 7 | C04 | N. coenophialum |
| 18 | FEtc6-85 | NEA27 | Corsica (France) 15 | C04 | N. coenophialum |
| 19 | FEtc6-87 | NEA28 | Corsica (France) 17 | C04 | N. coenophialum |
| 20 | AR542 | AR542 | Morocco | C05 | N. coenophialum |
| 21 | FEtc7-342 | NEA16 | Gaurda (Portugal) | C06 | N. coenophialum |
| 22 | FEtc7-343 | NEA20 | Gaurda (Portugal) | C06 | N. coenophialum |
| 23 | 231557 | NEA21 | Morocco | C09 | FaTG-2 |
| 24 | 287819 | NEA17 | Spain | C09 | FaTG-2 |
| 25 | 596834 | | Morocco | C09 | FaTG-2 |
| 26 | 231559 | | Morocco | C09 | FaTG-2 |
| 27 | 598852 | | Morocco | C09 | FaTG-2 |
| 28 | 598934 | | Italy | C10 | Outgroup |
| 29 | 231553 | NEA19 | Algeria | C10 | Outgroup |
| 30 | FEtc6-75 | NEA18 | Sardegna (NW Italy) 5 | C10 | Outgroup |
| 31 | 269850 | NEA23 | Tunisia | C12 | FaTG-3 |
| 32 | 610918 | | Tunisia | C12 | FaTG-3 |
| 33 | 610919 | | Tunisia | C12 | FaTG-3 |
| 34 | 598829 | | Morocco | C13 | FaTG-3 like |
| 35 | 598863 | | Morocco | C13 | FaTG-3 like |
| 36 | 598870 | | Morocco | C13 | FaTG-3 like |
| 37 | M311046 | | Russian Federation | C14 | N. uncinatum |
| 38 | M595026 | | United Kingdom | C14 | N. uncinatum |
| 39 | M611046 | | Russian Federation | C14 | N. uncinatum |

Establishment of Meristem Cultures for Diverse Fescue Host Panel for in Planta Inoculation of Fescue Endophytes Table 4 shows selected tall fescue and perennial ryegrass cultivars used to identify representative plant genotypes included in the diverse host panel for in planta inoculation of fescue endophytes. All the selected plant genotypes have a high regeneration frequency of >80%.

TABLE 4

Selected tall fescue and perennial ryegrass cultivars used to identify representative plant genotypes included in the diverse host panel for in planta inoculation of fescue endophytes

| Cultivar | Genotype code | Species | Characteristics |
|---|---|---|---|
| Bariane | BARI 27 | L. arundinaceum | Soft leaved, later maturing, highly palatable |
| Dovey | DOV 24 | L. arundinaceum | High yielding, fast establishing |
| Quantum | QUAN 17 | L. arundinaceum | Soft leaved with improved rust resistance |
| Jesup | JES 01 | L. arundinaceum | Cool season perennial forage |
| Bronsyn | BRO 08 | L. perenne | Standard perennial ryegrass forage type |

Figure 12:
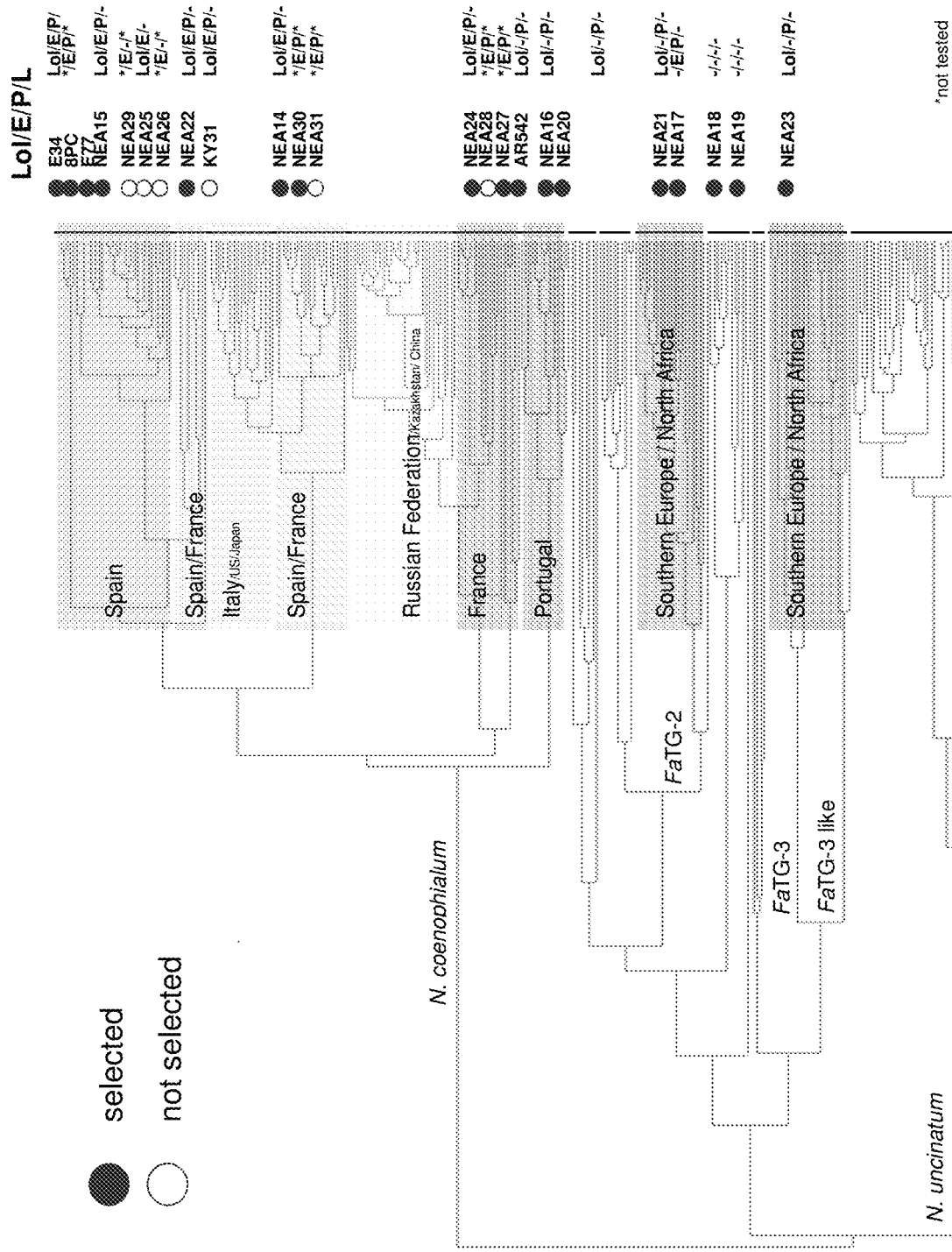
FIG. 12 shows endophytes selected for isogenic inoculation.
Figure 13:
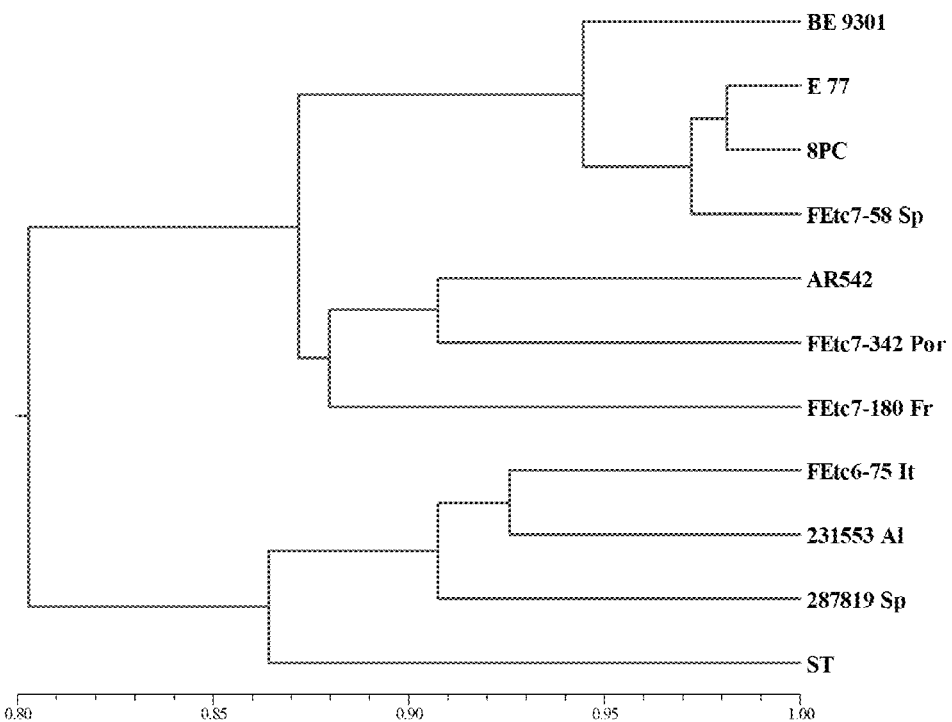
FIG. 13 shows SSR-based genotyping of isolated endophytes cultures prior to isogenic inoculation.

Isolated fungal endophytes from endophyte-containing fescue accessions selected for in planta isogenic inoculation into the diverse host panel are shown in FIG. 12. FIG. 13 shows SSR-based genotyping of isolated endophyte cultures prior to in planta isogenic inoculation to confirm their identity.

Results from the SSR genotyping indicating the allele number and sizes for different SSR markers for the different fescue endophyte strains are shown in Table 5.

TABLE 5

Presence of alleles in endophyte strains

| Endophyte Strain ID | Tall Fescue Accession ID | NCESTA1DH04 (FAM) | | | NLESTA1TA10 (FAM) | | | NCESTA1HA02 (HEX) | | | NCESTA1CC10 (HEX) | | |
|---|---|---|---|---|---|---|---|---|---|---|---|---|---|
| | | Allele 1 | Allele 2 | Allele 3 | Allele 1 | Allele 2 | Allele 3 | Allele 1 | Allele 2 | Allele 3 | Allele 1 | Allele 2 | Allele 3 |
| AR542 | — | 212 | 218 | 227 | 165 | 175 | | 322 | 327 | 330 | 198 | 201 | 211 |
| E34 | BE_9301 | 212 | 218 | 224 | 165 | 175 | | 322 | 329 | 330 | 198 | 201 | 211 |
| E77 | — | 212 | 218 | 224 | 165 | 175 | | 308 | 322 | 330 | 197 | 201 | 211 |
| NEA13 | 8PC | 212 | 218 | 224 | 165 | 175 | | 322 | 330 | | 197 | 200 | 210 |
| NEA14 | FEtc7-180 | 215 | 218 | 229 | 165 | 175 | | 322 | 329 | 330 | 198 | 201 | |
| NEA15 | FEtc7-58 | 212 | 218 | 224 | 165 | 175 | | 322 | 329 | 330 | 197 | 201 | 211 |
| NEA16 | FEtc7-342 | 215 | 227 | | 165 | 175 | | 309 | 322 | 330 | 198 | 201 | 211 |
| NEA17 | 287819 | 215 | 221 | 227 | 171 | 175 | | 322 | | | | 201 | 203 |

TABLE 5-continued

| | | \multicolumn{12}{c}{Presence of alleles in endophyte strains} | | | | | | | | | | | |
|---|---|---|---|---|---|---|---|---|---|---|---|---|
| Endophyte | Tall Fescue | NCESTA1DH04 (FAM) | | | NLESTA1TA10 (FAM) | | | NCESTA1HA02 (HEX) | | | NCESTA1CC10 (HEX) | | |
| Strain ID | Accession ID | Allele 1 | Allele 2 | Allele 3 | Allele 1 | Allele 2 | Allele 3 | Allele 1 | Allele 2 | Allele 3 | Allele 1 | Allele 2 | Allele 3 |
| NEA18 | FEtc6-75 | 218 | 227 | | 171 | 175 | | 304 | 322 | | 201 | | |
| NEA19 | 231553 | 221 | 227 | | 171 | 175 | | 304 | 325 | | 201 | | |

Results from the in planta isogenic inoculation into the diverse host panel of selected isolated fungal endophytes from endophyte-containing fescue accessions are shown in Table 6. Data on number of inoculations tested, number of successful inoculations and % of successful inoculations are provided in Table 6 to illustrate the inoculation ability of tall fescue endophytes in tall fescue and perennial ryegrass hosts.

different tall fescue and perennial host genotypes (i.e. BRO 08, BARI 27, DOV 24) was assessed, showing that:
Several tall fescue endophytes (e.g. NEA17, NEA18, NEA19) were stable in perennial ryegrass (BRO08).
BARI27 formed stable associations with all endophytes except for NEA15.
NEA15 failed to form stable associations with any of host genotypes tested.

TABLE 6

Inoculation Ability of Tall Fescue Endophytes in Tall Fescue and Perennial Ryegrass Hosts

| | E77 | E34 | NEA13 | NEA15 | NEA14 | AR542 | NEA16 | NEA17 | NEA18 | NEA19 | |
|---|---|---|---|---|---|---|---|---|---|---|---|
| | E77 | BE9301 | 8PC | Fetc7-58 | FEtc7-180 | AR542 | FEtc7-342 | 287819 | FEtc6-75 | 231553 | Total |
| \multicolumn{12}{c}{A. Number of Inoculations tested} | | | | | | | | | | | |
| BARI 27 | 23 | 25 | 30 | 34 | 38 | 38 | 24 | 32 | 40 | 27 | 311 |
| BRO 08 | 39 | 31 | 24 | 27 | 35 | 36 | 30 | 33 | 48 | 22 | 325 |
| DOV 24 | 10 | 14 | NI | NI | NI | 17 | 8 | 18 | 14 | 16 | 97 |
| JESS 01 | 23 | 23 | 39 | 27 | 20 | 36 | 33 | 17 | 28 | 14 | 260 |
| QUAN 17 | 8 | 31 | 20 | 15 | 17 | 21 | 18 | 16 | 15 | 8 | 169 |
| Total | 103 | 124 | 113 | 103 | 110 | 148 | 113 | 116 | 145 | 87 | 1162 |
| \multicolumn{12}{c}{B. Number of successful inoculations} | | | | | | | | | | | |
| BARI 27 | 3 | 3 | 4 | 0 | 1 | 11 | 3 | 17 | 18 | 2 | 62 |
| BRO 08 | 0 | 0 | 2 | 0 | 2 | 0 | 0 | 4 | 2 | 5 | 15 |
| DOV 24 | 3 | 0 | NI | NI | NI | 1 | 0 | 1 | 4 | 0 | 9 |
| JESS 01 | 7 | 0 | 5 | 0 | 7 | 10 | 3 | 2 | 1 | 2 | 37 |
| QUAN 17 | 3 | 0 | 1 | 0 | 0 | 0 | 0 | 6 | 5 | 3 | 18 |
| Total | 16 | 3 | 12 | 0 | 10 | 22 | 6 | 30 | 30 | 12 | 141 |
| \multicolumn{12}{c}{C. Percent of successful inoculations} | | | | | | | | | | | |
| BARI 27 | 13.0 | 12.0 | 13.3 | 0.0 | 2.6 | 28.9 | 12.5 | 53.1 | 45.0 | 7.4 | 18.8 |
| BRO 08 | 0.0 | 0.0 | 8.3 | 0.0 | 5.7 | 0.0 | 0.0 | 12.1 | 4.2 | 22.7 | 5.3 |
| DOV 24 | 30.0 | 0.0 | NI | NI | NI | 5.9 | 0.0 | 5.6 | 28.6 | 0.0 | 10.0 |
| JESS 01 | 30.4 | 0.0 | 12.8 | 0.0 | 35.0 | 27.8 | 9.1 | 11.8 | 3.6 | 14.3 | 14.5 |
| QUAN 17 | 37.5 | 0.0 | 5.0 | 0.0 | 0.0 | 0.0 | 0.0 | 37.5 | 33.3 | 37.5 | 15.1 |
| Total | 22.2 | 2.4 | 9.9 | 0.0 | 10.8 | 12.5 | 4.3 | 24.0 | 22.9 | 16.4 | 12.7 |
| Cluster | 1 | 1 | 1 | 1 | 2 | 3 | 3 | 7 | 8 | 8 | |
| Species | \multicolumn{5}{c}{N. coenophialum} | | | | FeTG-2 | Outgroup 1 | | |

NI Not inoculated

Example 6—Endophyte Vegetative Stability in Tall Fescue and Perennial Ryegrass Host Genotypes Following in planta isogenic inoculation with a range of selected isolated endophytes from fescue accessions, the endophyte vegetative stability of these endophytes in the DOV24 formed few stable associations.
The stability of these associations of novel tall fescue endophytes inoculated in different tall fescue and perennial ryegrass genotypes from the diverse host panel was assessed 12 months post-inoculation. Corresponding results are shown in Table 7.

TABLE 7

Stability of associations of novel tall fescue endophytes (e.g. NEA13,
NEA14, NEA15, NEA16, NEA17, etc.) inoculated in different tall fescue and
perennial ryegrass genotypes (BARI 27, BRO 08, DOV 24, JESS 01 and QUAN 17)
from the diverse host panel assessed 12 months post-inoculation.

| Plant Genotype | E77 E77 | E34 BE9301 | NEA13 8PC | NEA15 Fetc7-58 | NEA14 FEtc7-180 | AR542 AR542 | NEA16 FEtc7-342 | NEA17 287819 | NEA18 FEtc6-75 | NEA19 231553 |
|---|---|---|---|---|---|---|---|---|---|---|
| BARI 27 | 1/2 | 2/2 | 1/4 | NA | 1/1 | 7/7 | 1/1 | 1/2 | 8/10 | 1/1 |
| BRO 08 | NA | NA | 0/1 | NA | 0/2 | NA | NA | 5/5 | 2/2 | 3/5 |
| DOV 24 | 1/2 | NA | NI | NI | NI | 0/1 | NA | 2/2 | 2/4 | NA |
| JESS 01 | 5/5 | NA | 4/6 | NA | 5/6 | 5/10 | 2/3 | 0/1 | 0/1 | 3/3 |
| QUAN 17 | 2/3 | NA | 0/1 | NA | NA | NA | NA | 3/6 | 3/5 | 1/2 |

Figure 14:
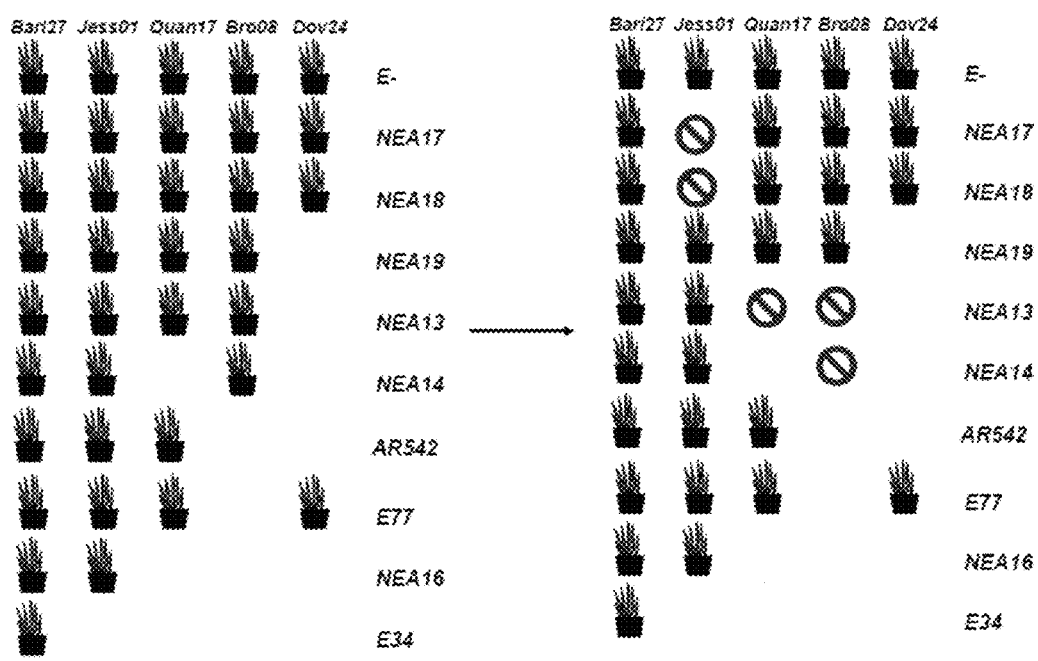
FIG. 14 shows endophyte vegetative stability in tall fescue and perennial ryegrass host genotypes (stability at 12 months post inoculation).

NA—not applicable,
NI—not inoculated, number of stable association/number of associations FIG. 14 shows stability at 12 months post inoculation of selected endophytes in tall fescue and perennial ryegrass host genotypes from the diverse host panel.

Figure 15:
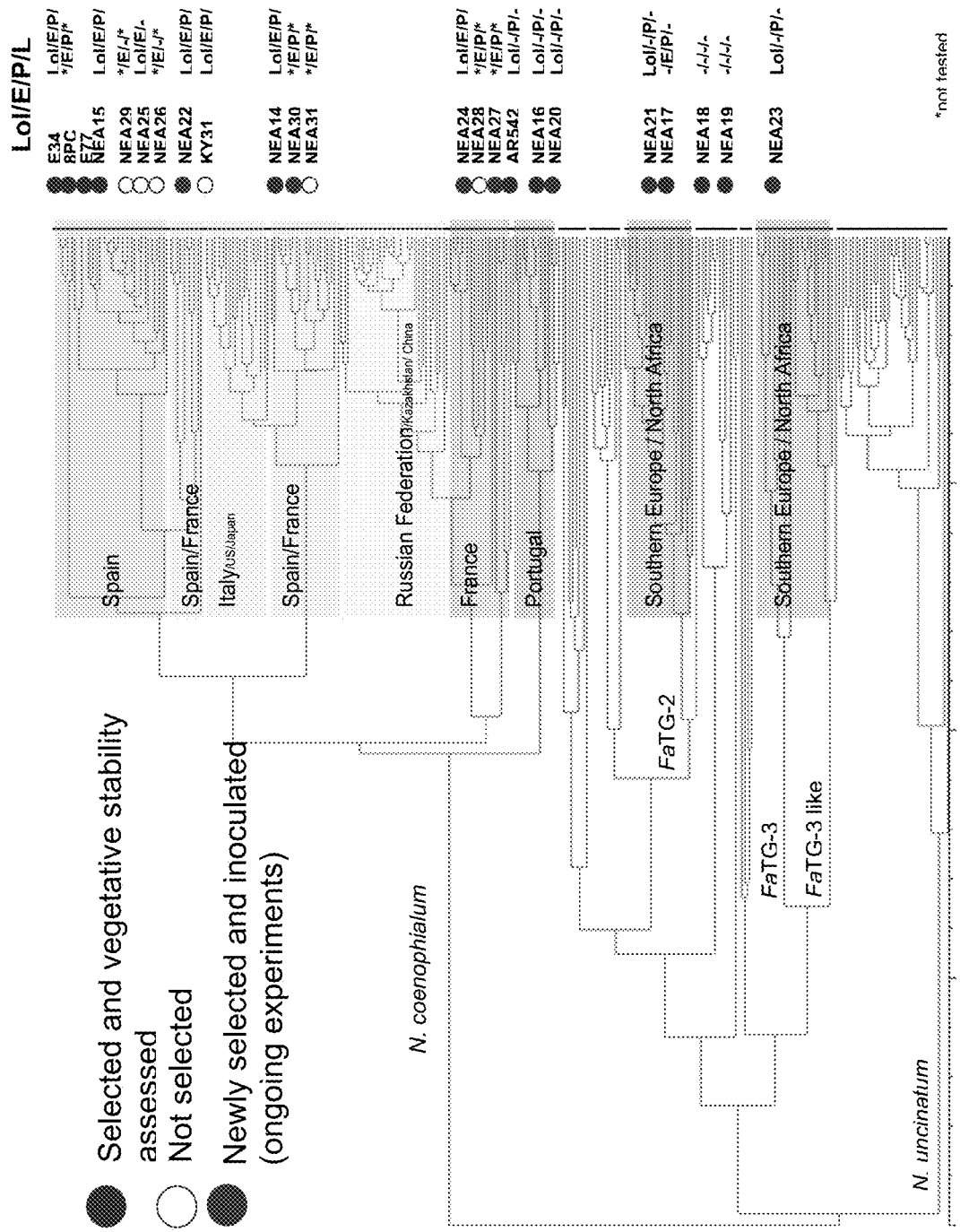
FIG. 15 shows endophytes selected for isogenic inoculation.

The range of novel fescue endophytes selected for in planta isogenic inoculation is shown in FIG. 15.

1. Table 8 shows additional novel tall fescue endophytes (e.g. NEA20, NEA21, NEA22, etc.) selected for in planta isogenic inoculations in tall fescue genotypes (i.e. BARI 27, JESS 01 and QUAN 17) from the diverse host panel, based on the following selection criteria: Produces little or no ergovaline
2. Produces no lolitrem B
3. Produces lolines and/or peramine

TABLE 8

Additional novel tall fescue endophytes (e.g. NEA20, NEA21, NEA22, etc.)
selected for in planta isogenic inoculations in tall fescue genotypes
(i.e. BARI 27, JESS 01 and QUAN 17) from the diverse host panel.

|  | NEA20 FEtc7-343 Nco LoI/−/P/− | NEA21 231557 FaTG-3 LoI/−/P/− | NEA22 234746 Nco LoI/E/P/− | NEA23 269850 FaTG-3 LoI/−/P/− | NEA24 FEtc6-83 Nco LoI/E/P/− | NEA27 FEtc6-85 Nco ?/E/P/? | NEA30 FEtc6-128 Nco ?/E/P/? |
|---|---|---|---|---|---|---|---|
| BARI27 | 28 | 30 | 30 | TBI | 30 | 25 | 30 |
| JESS01 | 23 | 20 | 20 | TBI | 20 | 20 | 30 |
| QUAN17 | 30 | 30 | 40 | TBI | 30 | 35 | 25 |

Nco = *N. coenophialum*;
? = alkaloid profile not tested;
TBI = To Be Inoculated.

Figure 16:
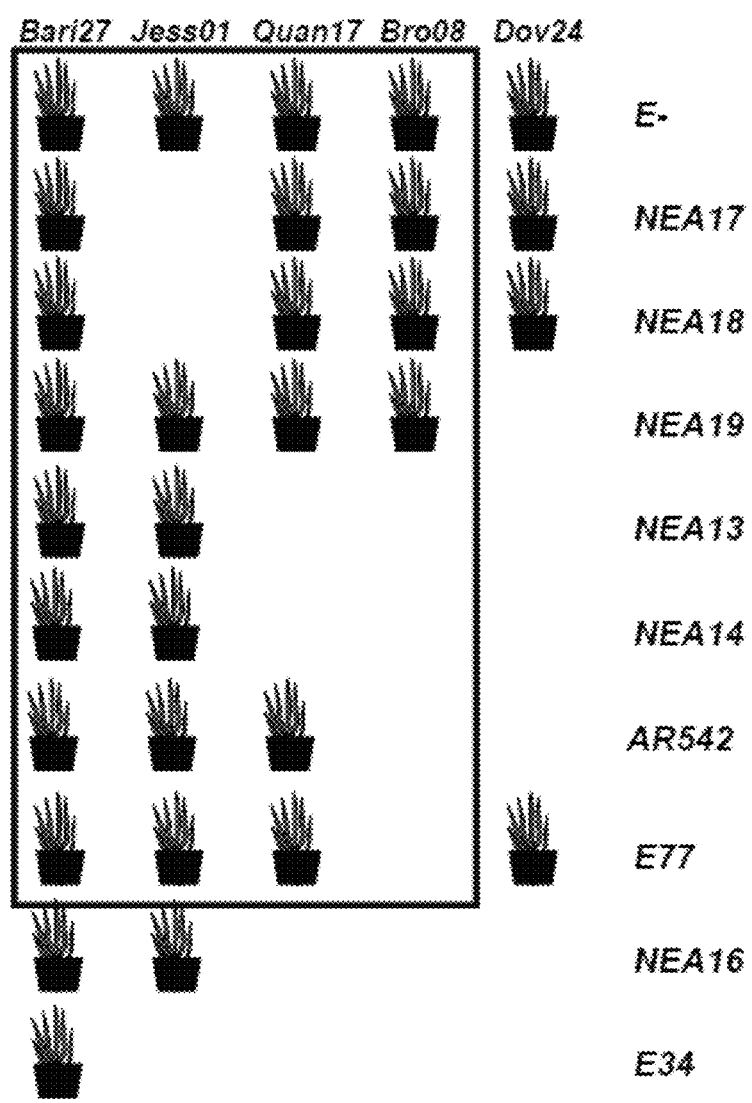
FIGS. 16-19 show metabolic profiling of isogenic tall fescue-endophyte associations.
Figure 18:
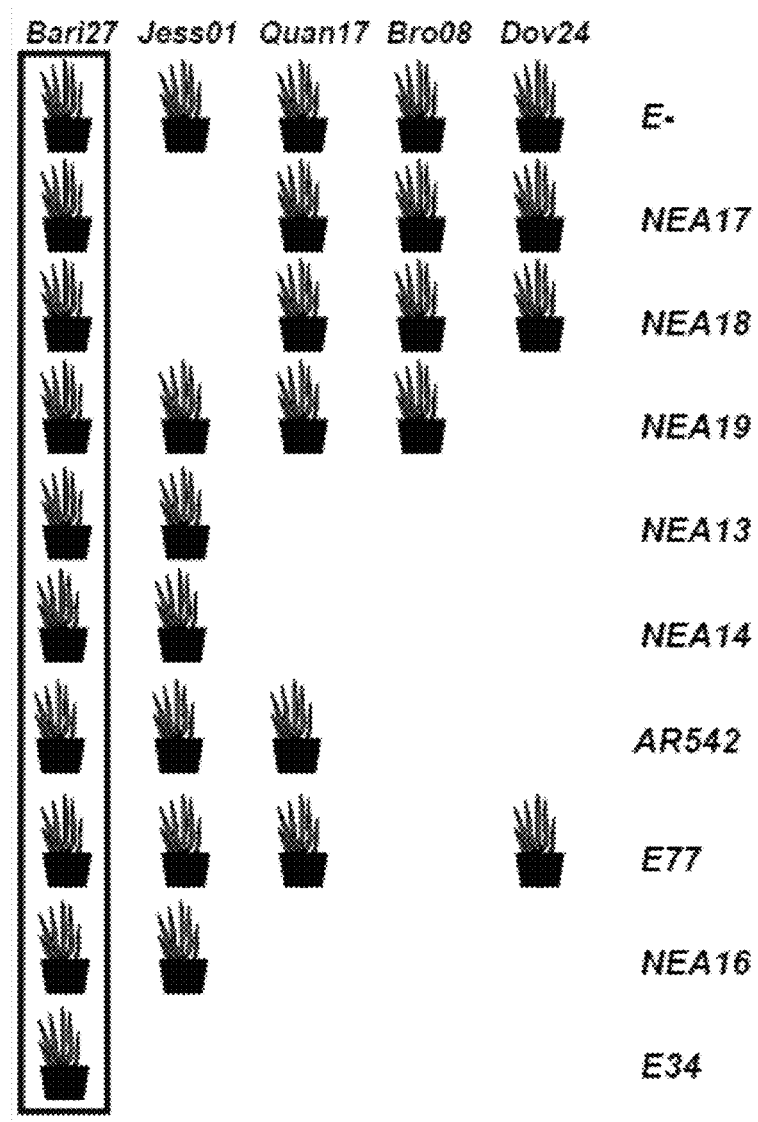
Figure 19:
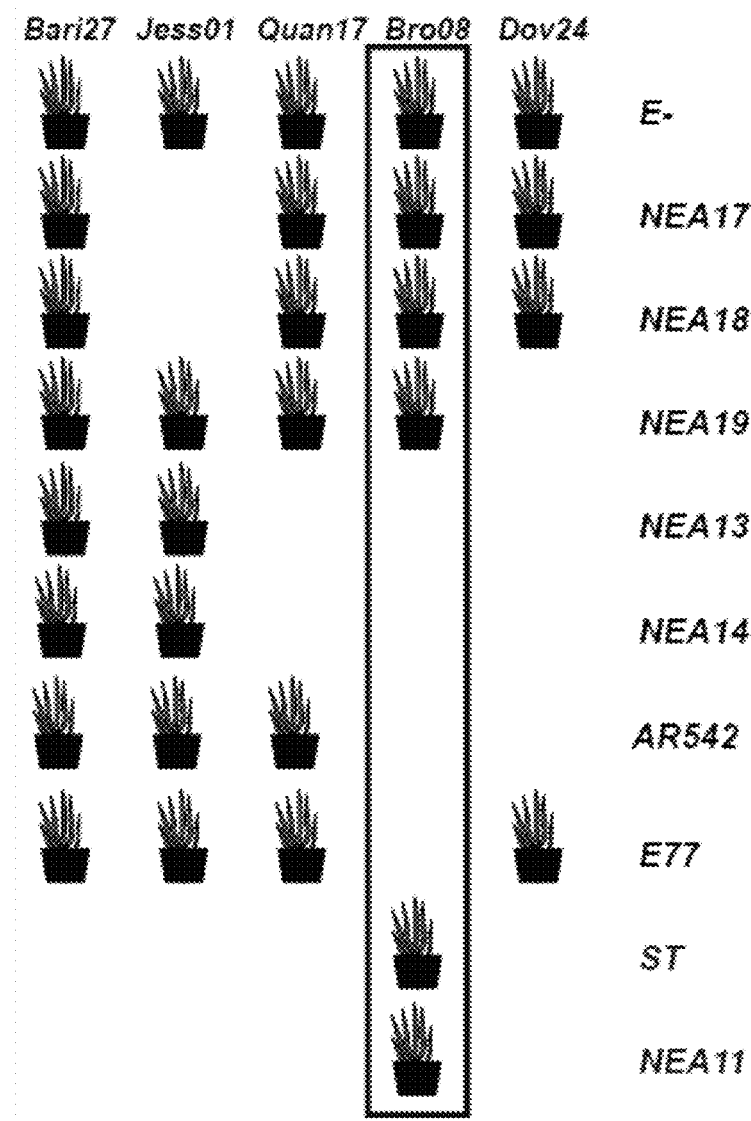

Example 6—Metabolic Profiling of Endophyte-Tall Fescue Associations Established Following in Planta Isogenic Inoculations of Novel Tall Fescue Endophytes in Tall Fescue Genotypes from the Diverse Host Panel Metabolic profiling of endophyte-tall fescue associations established following in planta isogenic inoculations of novel tall fescue endophytes in tall fescue genotypes from the diverse host panel is shown in FIGS. 16, 18 and 19. These figures:
Compare semi-quantitative alkaloid profiles of selected endophytes across different isogenic hosts
Compare semi-quantitative alkaloid profiles for diverse endophytes in an isogenic host
Compare semi-quantitative alkaloid profiles of tall fescue and perennial ryegrass endophytes in the perennial ryegrass genotype Bro08

Figure 17:
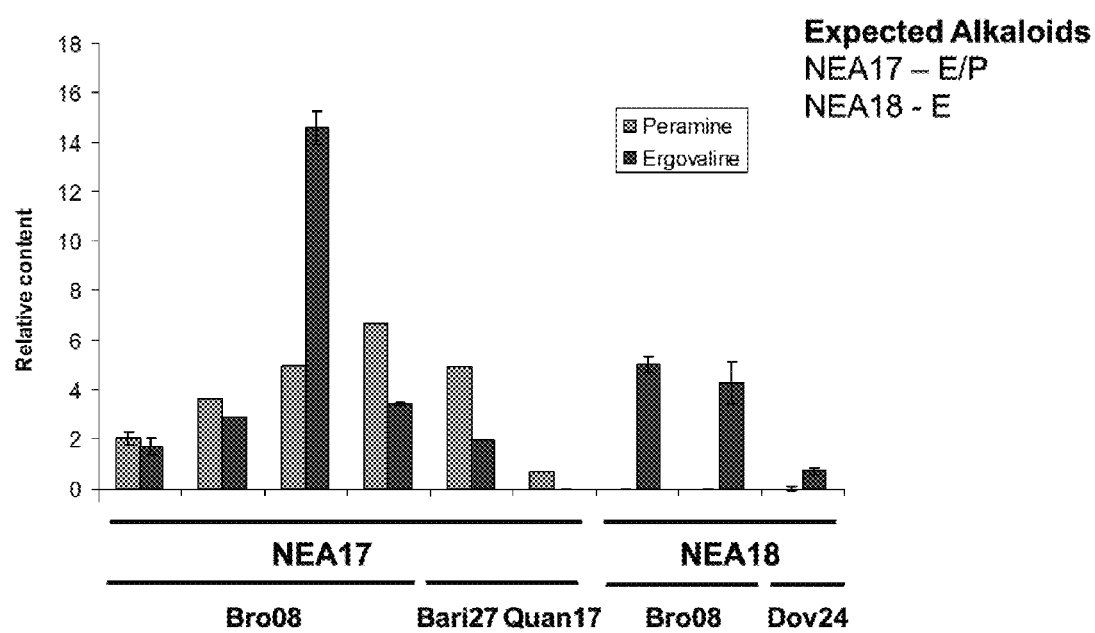

FIG. 17 shows the presence of peramine and ergovaline in endophyte-tall fescue associations established following in planta isogenic inoculations of novel tall fescue endophytes in tall fescue genotypes from the diverse host panel.

Table 9 shows metabolic profiling of endophyte-tall fescue associations established following in planta isogenic inoculations of novel tall fescue endophytes in tall fescue genotypes from the diverse host panel. Confirmed endophyte positive (E+) plants were split to 5 replicates and regularly trimmed to promote filtering. Four months later E+ plants were re-potted in 12 replicates. One month later E+ plants were re-potted if less than 9 positive copies were available at the time. Endophyte status was tested using SSR markers after each re-potting.

TABLE 9

Endophyte-tall fescue associations established following in planta isogenic inoculations of novel tall fescue endophytes in tall fescue genotypes from the diverse host panel used for metabolic profiling.

| Host genotypes | NEA19 231553 | NEA17 287819 | 8PC | AR 542 | E34 BE9301 | E77 | NEA18 FEtc6-75 | NEA14 Fetc7-180 | NEA16 Fetc7-342 | NEA15 Fetc7-58 |
|---|---|---|---|---|---|---|---|---|---|---|
| Barlane (Barl27) | 2/5 2/5 | 3/3 11/11 | 3/3 10/11 | 5/5 10/10 | 1/4 8/12 | NA 9/14 | 5/5 12/12 | 3/4 5/12 | 1/4 1/6 | 16/25 |
| Dovey (DOV 24) | NA | 2/5 8/8 | NA | NA | NA | 3/5 6/12 | 3/5 3/12 | NA | NA | NA |
| Jessup (Jess01) | 2/4 4/8 | NA | 3/3 12/12 | 4/4 12/12 | NA | 2/3 8/11 | NA | 2/4 7/19 | 2/3 12/12 | NA |
| Quantum (Quan17) | 2/5 8/7 | 4/5 12/12 | NA | | NA | 4/5 12/12 | 2/4 5/12 | NA | NA | NA |
| Bronsyn (Bro08) | 9/9 10/11 | 5/5 11/12 | 1/9 0/8 | NA | NA | 3/4 7/7 | 0/5 | NA | NA | |

A range of endophyte-tall fescue associations established following in planta isogenic inoculations of novel tall fescue endophytes in tall fescue genotypes from the diverse host panel were selected for metabolic profiling (Table 9). In total, 29 isogenic host-endophyte associations were subject to LCMS analysis, following the experimental design described below.

Experimental Design
Trim and re-pot plants
16 h L, 30° C.; 18 h D, 20° C.
Harvest (control)→freeze dry→50 mg pseudostem material→80% methanol extraction→LCMS analysis
Recovery and water stress
Second harvest (stressed)→freeze dry→50 mg pseudostem material→80% methanol extraction→LCMS analysis.

This was performed in a controlled (growth chamber) environment simulating summer conditions, with light watering as required. Nine copies per accession were planted in general potting mix. A Randomized Complete Block with subsampling was used.

Example 8—Bio-Protective Properties of Fescue Endophytes

Figure 20:
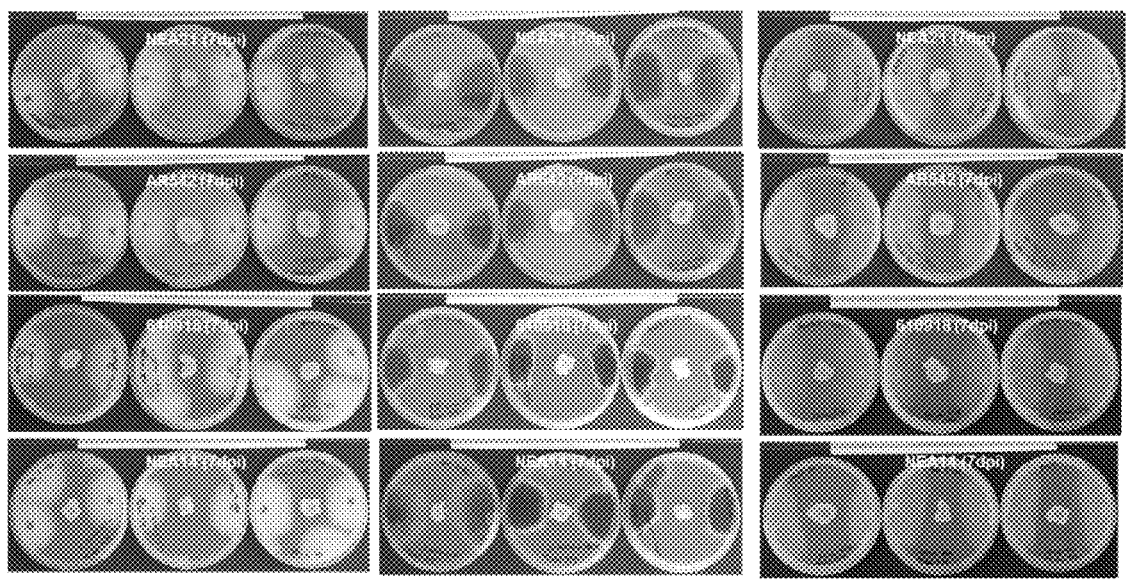
FIG. 20 shows anti-fungal bioassays of fescue endophytes. Column 1 *Colletotrichum graminicola*, Column 2 *Drechslera brizae*, Column 3 *Rhizoctonia cerealis*.

Three fungal pathogens (i.e. *Colletrotrichum graminicola, Drechslera brizae* and *Rhizoctonia cerealis*)—causing a range of fungal diseases and infecting a range of different plant hosts—were included in antifungal bioassays used to analyse the potential anti-fungal activities of isolated fescue endophytes. FIG. 20 shows results from anti-fungal bioassays of isolated fescue endophytes. Results of anti-fungal bioassays are also shown in Table 10. A range of endophytes were found to have high (H) and medium (M) antifungal activity (Table 10).

TABLE 10

Anti-fungal bioassays of isolated novel fescue endophytes

| | Tall Fescue endophytes | | | Antifungal activity against | | |
|---|---|---|---|---|---|---|
| | Strain ID | Accession | Taxon | *Colletotrichum graminicola* | *Drechslera brizae* | *Rhizoctonia cerealis* |
| 1 | 440364 | | *N. coenophialum* | H | H | H |
| 2 | AR542 | AR542 | *N. coenophialum* | M | H | H |
| 3 | E34 | BE9301 | *N. coenophialum* | M | M | H |
| 4 | NEA13 | 8PC | *N. coenophialum* | M | H | H |
| 5 | NEA14 | FEtc7-180 | *N. coenophialum* | M | M | H |
| 6 | NEA15 | FEtc7-58 | *N. coenophialum* | M | H | H |
| 7 | NEA16 | FEtc7-342 | *N. coenophialum* | M | H | H |
| 8 | NEA22 | 234746 | *N. coenophialum* | H | M | M |
| 9 | NEA27 | FEtc6-85 | *N. coenophialum* | L | M | L |
| 10 | NEA30 | FEtc6-128 | *N. coenophialum* | M | H | H |
| 11 | E1 | | Non-*N. lolii* | L | L | M |
| 12 | NEA18 | FEtc6-75 | Outgroup 1 | M | H | H |
| 13 | 598652 | | FaTG-2 | M | H | H |
| 14 | 610918 | | FaTG-3 | M | H | H |
| 15 | NEA21 | 231557 | FaTG-3 | M | H | M |
| 16 | 598829 | | FaTG-3 like | M | L | M |

Antifungal activity: Low, Medium, High

Example 9—Genome Survey Sequencing of Novel Tall Fescue Endophytes

A range of novel tall fescue endophtyes were subjected to genome survey sequencing (GSS).

Figure 21:
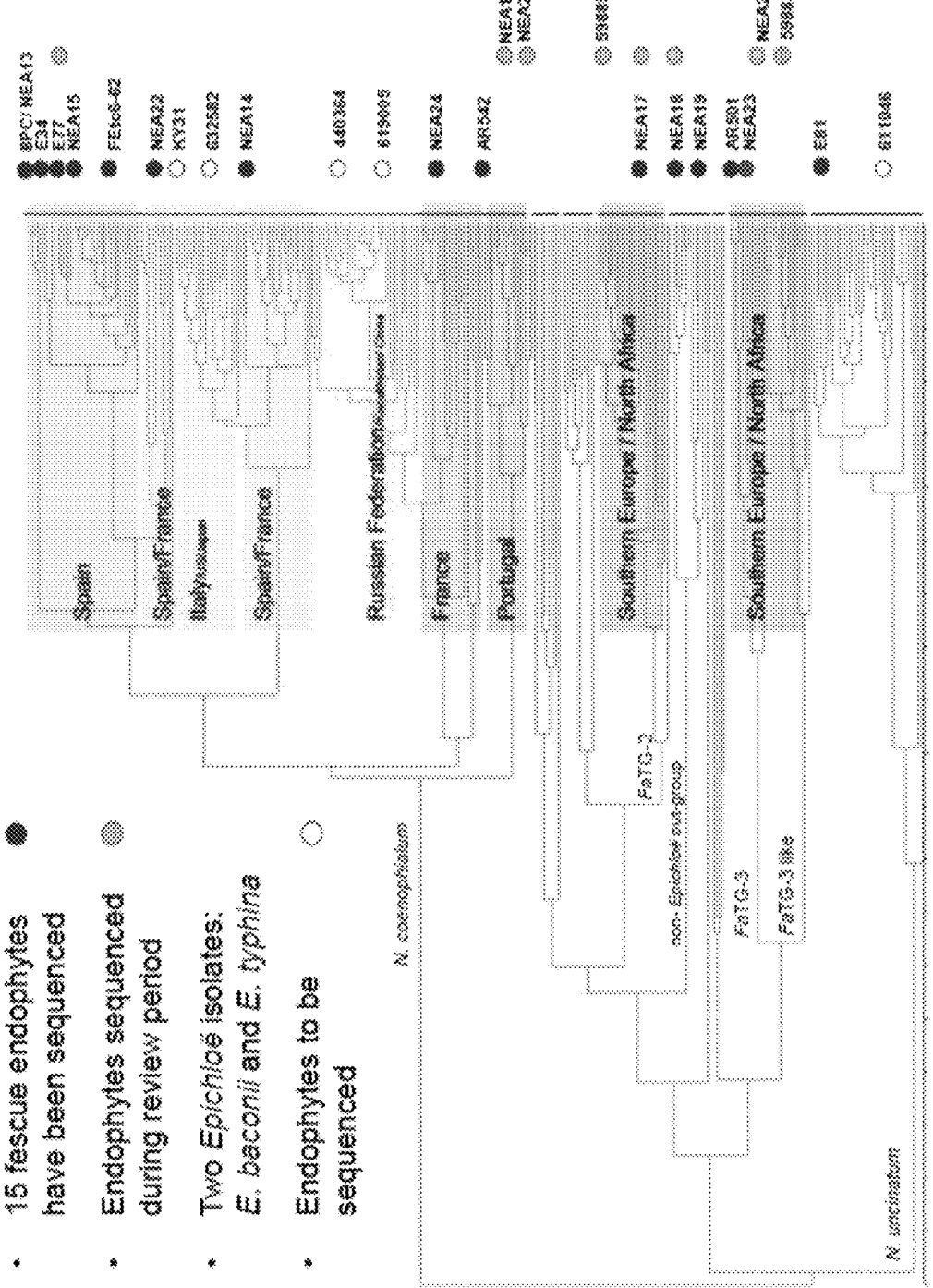
FIG. 21 shows sequencing of selected novel fescue endophytes.

FIG. 21 shows a strategy for GSS of selected novel fescue endophytes. The alkaloid profiles of novel fescue endophytes subjected to GSS analysis are shown in Table 11.

TABLE 11

Alkaloid profiles of sequenced endophytes.

| Tall fescue accession details | | | Alkaloid profile in Endogenous Host | | | |
|---|---|---|---|---|---|---|
| Endophyte strain | Accession No/isolated ID | Endophyte species | Lolines | Peramine | Ergovaline | Lolitrem B |
| E34 | BE9301 | N. coenophialum | (+) | (+) | (+) | (−) |
| NEA13 | 8PC | N. coenophialum | nd | (+) | (+) | nd |
| NEA14 | FEtc7-180 | N. coenophialum | (+) | (+) | (+) | (−) |
| NEA15 | FEtc7-58 | N. coenophialum | (+) | (+) | (+) | (−) |
| NEA16 | FEtc7-342 | N. coenophialum | (+) | (+) | (−) | (−) |
| NEA20 | FEtc7-343 | N. coenophialum | (+) | (+) | (−) | (−) |
| NEA22 | 234746 | N. coenophialum | (+) | (+) | (+) | (−) |
| NEA24 | FEtc6-83 | N. coenophialum | (+) | (+) | (+) | (−) |
| NEA17 | 287819 | FaTG-2 | (−) | (+) | (+) | (−) |
| NEA21 | 231557 | FaTG-3 | (+) | (+) | (−) | (−) |
| NEA23 | 269850 | FaTG-3 | (+) | (+) | (−) | (−) |
| NEA19 | 231553 | non-Epichloë out-group | (−) | (−) | (−) | (−) |
| NEA18 | FEtc6-75 | non-Epichloë out-group | (−) | (−) | (−) | (−) |
| AR542* | AR542* | N. coenophialum | (+) | (+) | (−) | (−) |
| E77* | E77* | N. coenophialum | (+) | (+) | (−) | (−) |
| 598852 | 598852 | FaTG-2 | nd | nd | nd | nd |
| AR501* | AR501* | FaTG-3 | (+) | (+) | (−) | (−) |
| 598829 | 598829 | FaTG-3 like | nd | nd | nd | nd |
| E81 | E81 | N. uncinatum | nd | nd | nd | nd |
| 9340 | 9340 | E. typhina | nd | nd | nd | nd |
| 9707 | 9707 | E. baconii | nd | nd | nd | nd |

Figure 22:
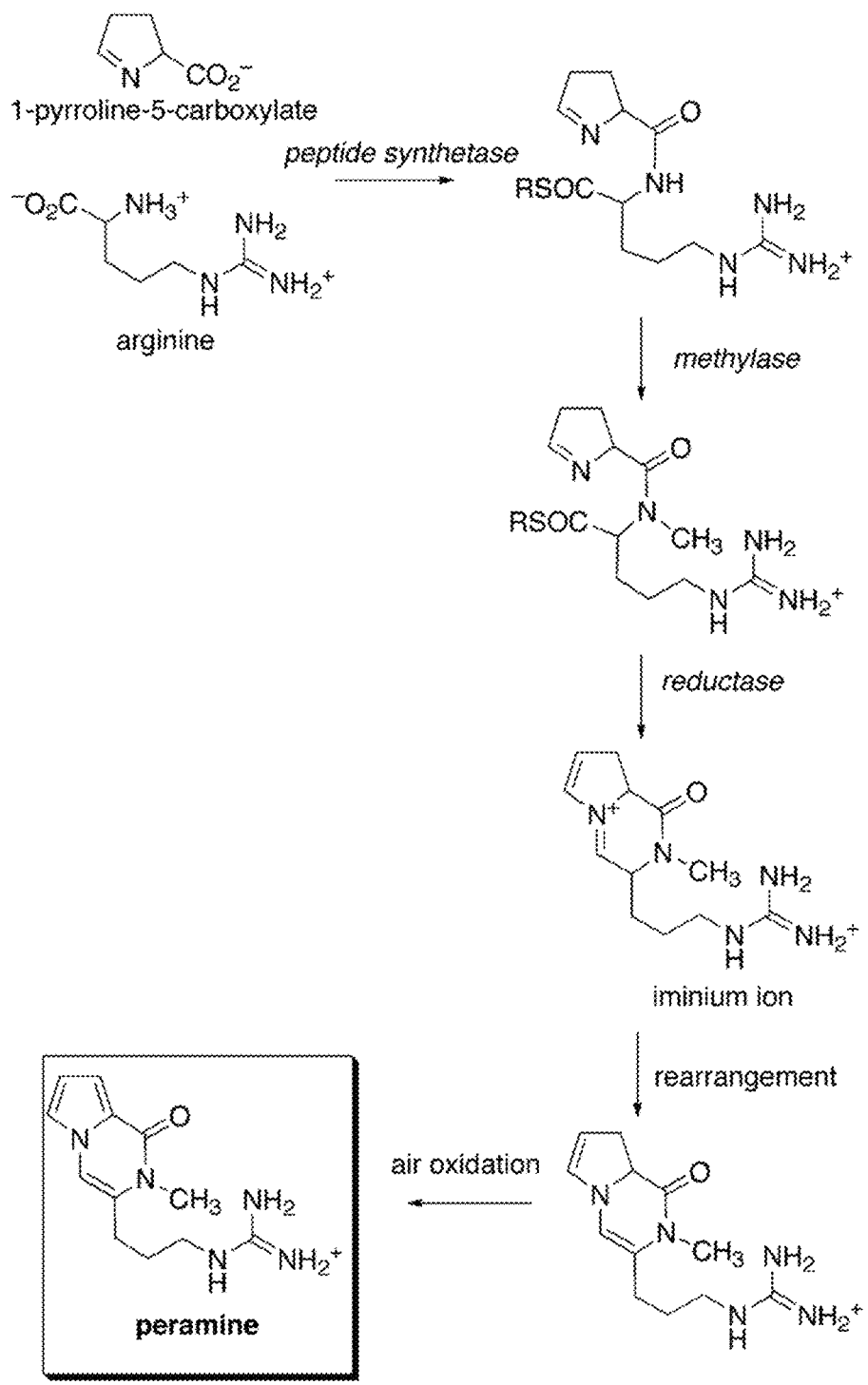
FIG. 22 shows peramine biosynthetic pathway.

(+): alkaloid present,
(−): Alkaloid absent,
nd: alkaloid profile not determined
*Profiles are taken from published data FIG. 22 shows the peramine biosynthetic pathway. PerA encodes a single multifunctional enzyme that catalyses all the biosynthetic steps. GenBank accession Number: AB205145. The presence of the perA gene in non-*Epichloe* out-group endophytes is shown in FIG. 23.

FIG. 24 shows the ergovaline biosynthetic pathway. Genes in the eas gene cluster which are involved in ergovaline biosynthesis are shown in FIG. 25 and Table 12. The dmaW gene encodes DMAT synthase enzyme, which catalyzes the first committed step in ergovaline biosynthesis. Presence of the dmaW gene in novel fescue endophytes is shown in FIG. 26 and presence of the eas gene cluster in novel fescue endophytes is shown in FIG. 27.

TABLE 12

Genes in the eas cluster

| Gene Cluster | Gene | GenBank Accession No |
|---|---|---|
| eas gene cluster | dmaW | AY259838 |
|  | easA | EF125025 |
|  | easE | EF125025 |
|  | easF | EF125025 |
|  | easG | EF125025 |
|  | easH | EF125025 |

TABLE 12-continued

Genes in the eas cluster

| Gene Cluster | Gene | GenBank Accession No |
|---|---|---|
|  | lpsA | AF368420 |
|  | lpsB | EF125025 |

FIG. 28 shows the Lolitrem B biosynthetic pathway. Genes in the gene cluster which are involved in Lolitrem B biosynthesis are shown in FIG. 29 and Table 13. Presence of gene cluster 1 (ItmG, ItmM and ItmK) in endophytes is shown in FIG. 30, presence of gene cluster 2 (ItmB, ItmQ, ItmP, ItmF and ItmC) is shown in FIG. 31 and presence of gene cluster 3 (ItmE and ItmJ) is shown in FIG. 32.

TABLE 13

Genes in the gene cluster involved in Lolitrem B biosynthesis

| Gene Cluster | Gene | GenBank Accession No |
|---|---|---|
| gene cluster 01 | ItmG | AY742903 |
|  | ItmM | AY742903 |
|  | ltmK | AY742903 |
| gene cluster 02 | ltmB | DQ443465 |
|  | ltmQ | DQ443465 |
|  | ItmP | DQ443465 |
|  | ItmF | DQ443465 |
|  | ItmC | DQ443465 |
| gene cluster 03 | ItmJ | DQ443465 |
|  | ItmE | DQ443465 |

FIG. 33 shows the Loline biosynthetic pathway. Genes in the gene cluster which are involved in Loline biosynthesis are shown in FIG. 34 and Table 14. Presence of Loline biosynthetic gene cluster in novel fescue endophytes is shown in FIG. 35.

TABLE 14

Genes in the Loline biosynthetic gene cluster

| Gene Cluster | Gene | GenBank Accession No |
|---|---|---|
| LOL gene cluster | lolF | EF012269 |
|  | lolC | EF012269 |
|  | lolD | EF012269 |
|  | lolO | EF012269 |
|  | lolA | EF012269 |
|  | lolU | EF012269 |

TABLE 14-continued

Genes in the Loline biosynthetic gene cluster

| Gene Cluster | Gene | GenBank Accession No |
|---|---|---|
|  | lolP | EF012269 |
|  | lolT | EF012269 |
|  | lolE | EF012269 |

FIG. 36 and shows an alkaloid biosynthetic gene analysis for endophyte strain NEA23. Tables 15 and 16 show alkaloid biosynthetic gene analyses for various endophyte strains. Table 15 shows results from the assessment of alkaloid biosynthetic gene presence/absence for different endophytes by mapping genome survey sequence reads corresponding to the different alkaloid biosynthetic genes/gene clusters.

TABLE 15

Assessment of alkaloid biosynthetic gene presence/absence for different endophytes by mapping genome survey sequence reads corresponding to the different alkaloid biosynthetic genes/gene clusters.

| | | | | | *N. coenophialum* | | | | | |
|---|---|---|---|---|---|---|---|---|---|---|
| | Gene | GenBank Accession No | BE9301 | 8PC | NEA14 (FEtc7-180) | NEA15 (FEtc7-58) | NEA16 (FEtc7-342) | NEA20 (FEtc7-343) | AR542 | NEA22 (234746) |
| Metabolite production in planta | | | Lol | nd | Lol | Lol | Lol | Lol | Lol | Lol |
| Loline alkaloids | gene cluster | EF012269 | G+ | G+ | G+ | G+ | G+ | G+ | G+ | G+ |
| Metabolite production in planta | | | P | P | P | P | P | P | P | P |
| Peramine | PerA | AB205145 | G+ | G+ | G+ | G+ | G+ | G+ | G+ | G+ |
| Metabolite production in planta | | | E | E | E | E | — | — | — | E |
| Ergot Alkaloids | dmaW | AY259838 | G+ | G+ | G+ | G+ | G+ | G+ | G− | G+ |
|  | eas gene cluster | EF125025 | G+ | G+ | G+ | G+ | G− | G− | G− | G+ |
| Metabolite production in planta | | | — | nd | — | — | — | — | — | — |
| Lolitrems | gene cluster 01 | AY742903 | PG+ | PG+ | PG+ | PG+ | PG+ | PG+ | PG+ | PG+ |
|  | gene cluster 02 | DQ443465 | PG+ | PG+ | PG+ | PG+ | PG+ | PG+ | PG+ | PG+ |
|  | gene cluster 03 | DQ443465 | PG+ | PG+ | PG+ | PG+ | PG+ | PG+ | PG+ | PG+ |

| | | | FaTG-2 | FaTG-3 | | | non-Epichloë out-group | |
|---|---|---|---|---|---|---|---|---|
| | Gene | GenBank Accession No | NEA17 (287819) | NEA21 (231557) | NEA23 (269850) | AR501 | NEA19 (231553) | NEA18 (FEtc6-75) |
| Metabolite production in planta | | | — | Lol | Lol | Lol | — | — |
| Loline alkaloids | gene cluster | EF012269 | G− | G+ | G+ | G+ | G− | G− |
| Metabolite production in planta | | | P | P | P | P | — | — |
| Peramine | PerA | AB205145 | G+ | G+ | G+ | G+ | G+ | G+ |
| Metabolite production in planta | | | E | — | — | — | — | — |
| Ergot Alkaloids | dmaW | AY259838 | G+ | G− | G− | G− | G+ | G− |
|  | eas gene cluster | EF125025 | G+ | G− | G− | G− | G− | G− |

TABLE 15-continued

Assessment of alkaloid biosynthetic gene presence/absence for different endophytes by mapping genome survey sequence reads corresponding to the different alkaloid biosynthetic genes/gene clusters.

| | Metabolite production in planta | | — | — | — | — | — | — |
|---|---|---|---|---|---|---|---|---|
| Lolitrems | gene cluster 01 | AY742903 | G+ | G− | G− | G− | G− | G− |
| | gene cluster 02 | DQ443465 | G+ | G− | G− | G− | G− | G− |
| | gene cluster 03 | DQ443465 | G+ | G− | G− | G− | G− | G− |

G+ = Gene/gene cluster present
G− = Gene/gene cluster absent
PG+ = Gene/gene cluster partially present
(−) = No alkaloid detected
(nd) = not determined
P = Peramine
Lol = Loline
E = Ergovaline Table 16 shows results from the assessment of alkaloid biosynthetic gene presence/absence for different endophytes by mapping genome survey sequence reads corresponding to the different alkaloid biosynthetic genes/gene clusters as well as corresponding alkaloid profile observed for corresponding tall fescue-endophyte associations.

TABLE 16

Alkaloid biosynthetic gene analysis.

| Tall fescue accession details | | | Alkaloid profile and Gene presence | | | |
|---|---|---|---|---|---|---|
| Endophyte strain | Accession No/isolated ID | Endophyte species | Lolines | Peramine | Ergovaline* | Lolitrem B |
| E34 | BE9301 | N. coenophialum | (+) G+ | (+) G+ | (+) G+ | (−) PG+ |
| 8PC | 8PC | N. coenophialum | (nd) G+ | (+) G+ | (+) G+ | (nd) PG+ |
| NEA14 | FEtc7-180 | N. coenophialum | (+) G+ | (+) G+ | (+) G+ | (−) PG+ |
| NEA15 | FEtc7-58 | N. coenophialum | (+) G+ | (+) G+ | (+) G+ | (−) PG+ |
| NEA16 | FEtc7-342 | N. coenophialum | (+) G+ | (+) G+ | (−) G− | (−) PG+ |
| NEA20 | FEtc7-343 | N. coenophialum | (+) G+ | (+) G+ | (−) G− | (−) PG+ |
| NEA22 | 234746 | N. coenophialum | (+) G+ | (+) G+ | (+) G+ | (−) PG+ |
| NEA24 | FEtc6-83 | N. coenophialum | (+) | (+) | (+) | (−) |
| NEA17 | 287819 | FaTG-2 | (−) G− | (+) G+ | (+) G+ | (−) G+ |
| NEA21 | 231557 | FaTG-3 | (+) G+ | (+) G+ | (−) G− | (−) G− |
| NEA23 | 269850 | FaTG-3 | (+) G+ | (+) G+ | (−) G− | (−) G− |
| NEA19 | 231553 | non-Epichloë out-group | (−) G− | (−) G+ | (−) G− | (−) G− |
| NEA18 | FEtc6-75 | non-Epichloë out-group | (−) G− | (−) G− | (−) G− | (−) G− |
| AR542* | AR542* | N. coenophialum | (+) G+ | (+) G+ | (−) G− | (−) PG+ |
| E77* | E77* | N. coenophialum | (+) | (+) | (+) | (−) |
| 598852 | 598852 | FaTG-2 | (nd) | (nd) | (nd) | (nd) |
| AR501* | AR501* | FaTG-3 | (+) G+ | (+) G+ | (−) G− | (−) G− |
| 598829 | 598829 | FaTG-3 like | (nd) | (nd) | (nd) | (nd) |
| E81 | E81 | N. uncinatum | (nd) | (nd) | (nd) | (nd) |
| 9340 | 9340 | E. typhina | (nd) | (nd) | (nd) | (nd) |
| 9707 | 9707 | E. baconii | (nd) G− | (nd) PG+ | (nd) G− | (nd) G− |

(+): alkaloid present,
(−): Alkaloid absent,
(nd): alkaloid profile not determined,
*Profiles are taken from published data,
G+ = gene/gene cluster present,
G− = gene/gene cluster absent,
PG+ = gene/gene cluster partially present Table 17 shows novel fescue endophytes (NEA16, NEA18, NEA19, NEA20, NEA21 and NEA23) with favourable toxin profiles.

TABLE 17

Novel fescue endophytes (NEA16, NEA18, NEA19, NEA20, NEA21 and NEA23) with favourable toxin profiles and antifungal activities observed in bioassays.

| Tall fescue accession | Taxon | Alkaloid profile (Lol/P/E/L) | Antifungal |
|---|---|---|---|
| NEA21 (231557) | FaTG-3 | +/+/−/− | High |
| NEA23 (269850) | FaTG-3 | +/+/−/− | To be tested |
| AR501* | FaTG-3 | +/+/−/− | — |
| NEA18 (FEtc6-75) | Non-*Epichloë* Outgroup | −/−/−/− | High |
| NEA19 (231553) | Non-*Epichloë* Outgroup | −/−/−/− | To be tested |
| NEA16 (FEtc7-342) | *N. coenophialum* | +/+/−/− | High |
| NEA20 (FEtc7-343) | *N. coenophialum* | +/+/−/− | To be tested |
| AR542* | *N. coenophialum* | +/+/−/− | High |

*Control commercial endophyte

A genotypic analysis of the novel fescue endophytes NEA23 and NEA21 is shown in FIG. 37.

Example 10—Perennial Ryegrass Endophyte Discovery and Characterisation

The objectives were:
1. Identification and characterisation of novel perennial ryegrass endophytes for evaluation in germplasm.
2. Development and evaluation of optimised associations between novel endophytes and elite germplasm.
Experimental Strategies
 1. Identification and characterisation of novel perennial ryegrass endophytes for evaluation in proprietary germplasm
  Activity: Establishment of a proprietary 'library' of novel endophyte strains
   Targeted germplasm collection
   Genotypic analysis of germplasm samples
   Metabolomic analysis of germplasm samples
   Fungal culture isolation and inoculation
   Metabolomic analysis of inoculated plants
   Assessment of endophyte stability
 2. Development and Evaluation of Optimised Associations Between Novel Endophytes and Elite Germplasm
  Activity: Delivery of novel endophytes into the germplasm improvement process
   Large-scale inoculation of selected endophytes
   Genetic analysis of selected host-endophyte associations
   Phenotypic analysis of selected host-endophyte associations
The desired toxin profile of perennial ryegrass endophytes is shown in FIG. 6.
The outcome requirements for endophyte stability are as follows:
Intergenerational Stability
 Maximal<5% loss per generation
 Ideally 2-3% loss per generation
Seed Storage Stability
 3 years in seed
Establishment of ryegrass germplasm collection for endophyte discovery—identification and establishment of 244 accessions.
FIG. 40 shows genotypic analysis of endophyte content in accessions from a targeted ryegrass germplasm collection.

FIG. 41 shows analysis of endophyte content in accessions from a targeted ryegrass germplasm collection. Genetically unique; toxin production within required limits based on genotypic prediction.
Isolation of Fungal Cultures from Selected Ryegrass-Endophyte Associations
 In vitro cultures of candidate endophytes established and genotypes confirmed
 Long-term cryopreservation of endophyte cultures established

TABLE 18

Isolation of fungal cultures from selected ryegrass-endophyte associations

| Species | No. Isolates | Examples |
|---|---|---|
| *N. lolii* | 57 | ST, NEA3, NEA2, 38 novel |
| *N. coenophialum* | 37 | KY31, AR542 and 11 other AR strains, E34 and 5 other RBG strains, 19 novel |
| LpTG-2 | 6 | AR6, NEA4, NEA11 |
| Non-*N. lolii* | 6 | NEA12, E1 |
| FaTG-2 | 6 | 8907 and 5 novel |
| FaTG-3 | 8 | AR501 and 4 other AR strains, 3 novel |
| Other fescue endophytes | 6 | 3 novel FaTG3-like, 3 Outgroup |
| *N. uncinatum* | 4 | E81 and 3 novel |
| Total | 130 | |

Example 11—Isogenic Inoculation of Perennial Ryegrass Endophytes

TABLE 19

Establishment of meristem cultures for a diverse perennial ryegrass host panel

| Cultivar | Species | Characteristics |
|---|---|---|
| Barsandra | *L. perenne* | Turf type |
| Barsintra | *L. perenne* | Tetraploid forage type |
| Bealey | *L. perenne* | Tetraploid forage type |
| Bronsyn | *L. perenne* | Standard forage type |
| Impact | *L. perenne* | Late flowering, dense tillering forage type |
| Meridian | *L. perenne* | Early flowering forage type |
| Tolosa | *L. perenne* | Distinct forage type |
| Barfest | *Festulolium* | |

FIG. 42 shows an isogenic host plant genotype cultivar 'likeness' determination
 Bronsyn and Tolosa (96 individuals) were assessed for genetic diversity using 58 perennial ryegrass SSR markers
 Bronsyn and Tolosa cultivars easily discriminated
FIG. 43 shows an isogenic host plant genotype cultivar likeness' determination. 96 Impact, Bealey and Barsandra genotypes were assessed for genetic diversity using 56 perennial ryegrass derived SSR markers.
FIG. 44 shows development of a host-panel molecular genetic test for QC of host-endophyte associations.
 A panel of 5 perennial ryegrass SSR markers has been identified to distinguish the different host-panel genotypes
 Full QC capabilities for isogenic host plant as well as endophyte
FIG. 45 shows inoculation of candidate endophytes into meristem cultures of diverse ryegrass host panel.

Regeneration of Mature Isogenic Ryegrass—Endophyte Associations
- Quantitative score used to assess endophyte inoculation frequency
  - 3 diagnostic SSR markers are used to determine endophyte presence and identity and samples are scored on a scale of 0-3
  - Quantitative score is also used for seed purity testing and endophyte presence and identity testing

TABLE 20

Quantitative score used to assess endophyte inoculation frequency

| Quantitative score | Alleles present and of correct size for given SSR loci* |
|---|---|
| 3 | Endophyte present |
| 2 | Endophyte present |
| 1 | Endophyte absent |
| 0 | Endophyte absent |

*Average inoculation frequency of 15% across all endophyte-host combinations

Inoculation Success Rates

TABLE 21

Percent of successful inoculations

|  | 15285 | NEA12 | 15441 | 15931 | AR1 | NEA11 | F2 | NEA10 | STWT | Average |
|---|---|---|---|---|---|---|---|---|---|---|
| Bea02 | 6.7 | 15.0 | 16.7 | 4.8 | 0.0 | 66.7 | 0.0 | 0.0 | 32.0 | 15.8 |
| Bro08 | 8.3 | 5.0 | 21.1 | 0.0 | 5.0 | 93.3 | 0.0 | 0.0 | 52.0 | 20.5 |
| Fest02 | 4.8 | 0.0 | 33.3 | 0.0 | 0.0 | 31.8 | 0.0 | 0.0 | 17.4 | 9.7 |
| Imp04 | 0.0 | 19.0 | 3.8 | 0.0 | 0.0 | 81.6 | 0.0 | 9.7 | 45.7 | 17.8 |
| Mer05 | NA | 4.5 | 16.0 | 0.0 | 4.0 | 62.5 | 0.0 | 8.7 | 8.0 | 11.5 |
| San02 | 0.0 | 25.0 | 40.0 | 8.7 | 0.0 | 43.6 | 0.0 | 0.0 | 34.4 | 16.9 |
| Sin04 | 0.0 | 4.3 | 44.4 | 0.0 | 0.0 | 45.5 | 0.0 | 0.0 | 55.6 | 16.6 |
| Tol03 | 9.1 | 11.1 | 5.9 | 0.0 | 0.0 | 42.9 | 3.8 | 0.0 | 27.3 | 11.1 |
| Average | 3.6 | 10.5 | 22.7 | 1.7 | 1.1 | 58.5 | 0.5 | 2.3 | 34.0 | 15.3 |

TABLE 22

Number of successful inoculations

|  | 15285 | NEA12 | 15441 | 15931 | AR1 | NEA11 | F2 | NEA10 | STWT | Total |
|---|---|---|---|---|---|---|---|---|---|---|
| Bea02 | 1 | 3 | 4 | 1 | 0 | 12 | 0 | 0 | 8 | 29 |
| Bro08 | 2 | 1 | 4 | 0 | 1 | 14 | 0 | 0 | 13 | 35 |
| Fest02 | 1 | 0 | 8 | 0 | 0 | 7 | 0 | 0 | 4 | 20 |
| Imp04 | 0 | 4 | 1 | 0 | 0 | 40 | 0 | 3 | 16 | 64 |
| Mer05 | NA | 1 | 4 | 0 | 1 | 5 | 0 | 2 | 2 | 15 |
| San02 | 0 | 6 | 10 | 2 | 0 | 17 | 0 | 0 | 11 | 46 |
| Sin04 | 0 | 1 | 4 | 0 | 0 | 5 | 0 | 0 | 10 | 20 |
| Tol03 | 1 | 2 | 1 | 0 | 0 | 3 | 1 | 0 | 3 | 11 |
| Total | 5 | 18 | 36 | 3 | 2 | 103 | 1 | 5 | 67 | 240 |

TABLE 23

Total number of inoculations tested

|  | 15285 | NEA12 | 15441 | 15931 | AR1 | NEA11 | F2 | NEA10 | STWT | Total |
|---|---|---|---|---|---|---|---|---|---|---|
| Bea02 | 15 | 20 | 24 | 21 | 12 | 18 | 22 | 24 | 25 | 181 |
| Bro08 | 24 | 20 | 19 | 20 | 20 | 15 | 25 | 19 | 25 | 187 |
| Fest02 | 21 | 19 | 24 | 18 | 19 | 22 | 20 | 9 | 23 | 175 |
| Imp04 | 25 | 21 | 26 | 25 | 25 | 49 | 44 | 31 | 35 | 281 |
| Mer05 | 0 | 22 | 25 | 24 | 25 | 8 | 23 | 23 | 25 | 175 |
| San02 | 24 | 24 | 25 | 23 | 24 | 39 | 49 | 47 | 32 | 287 |

TABLE 23-continued

Total number of inoculations tested

|  | 15285 | NEA12 | 15441 | 15931 | AR1 | NEA11 | F2 | NEA10 | STWT | Total |
|---|---|---|---|---|---|---|---|---|---|---|
| Sin04 | 7 | 23 | 9 | 18 | 13 | 11 | 24 | 19 | 18 | 142 |
| Tol03 | 11 | 16 | 17 | 15 | 19 | 7 | 26 | 17 | 11 | 141 |
| Total | 127 | 167 | 169 | 164 | 157 | 169 | 233 | 189 | 194 | 1569 |

FIG. 46 shows the endophytes selected.

Endophyte Vegetative Stability in Priority Ryegrass Host Panel Genotypes
- Plants were re-sampled 6-12 months (top line) after, initial inoculation and again after 2 years and 3 years (bottom line) after initial inoculation
- NEA11 endophyte highly stable across all host plants
- NEA12 exhibits varying degrees of stability

TABLE 24

Endophyte vegetative stability in priority ryegrass host panel genotypes

| Plant genotype | ST | NEA10 | NEA11 | NEA12 |
|---|---|---|---|---|
| Impact (Imp04) | 9/10<br>3/3 | 2/3<br>2/2 | 12/12<br>3/3 | 1/4<br>1/1 |
| Barsandra (San02) | 4/6<br>2/3 | NA | 7/7<br>3/3 | 2/4<br>1/2 |
| Tolosa (Tol03) | 1/2<br>1/1 | NA | 3/3<br>2/3 | 2/2<br>2/2 |
| Bealey (Bea02) | 3/3<br>2/3 | NA | 9/9<br>3/3 | 0/2<br>0/1 |
| Bronsyn (Bro08) | 3/6<br>2/2 | NA | 9/9<br>4/4 | 1/1<br>0/1 |

Perennial Ryegrass Isogenic Inoculations
- Endophytes NEA10 and NEA12 are recalcitrant to inoculation, with low frequencies of successful inoculation
- NEA10 is only compatible with Impact and Bronsyn
- NEA12 is only compatible with Impact, Barsandra and Tolosa

TABLE 25

Perennial Ryegrass Isogenic Inoculations

|  | ST | NEA10 | NEA11 | NEA12 | TOTAL |
|---|---|---|---|---|---|
| A. Number of inoculations performed ||||||
| Bea02 | $0^1$ | 40 | $0^1$ | $30^2$ | 70 |
| Bro08 | $0^1$ | 80 | $0^1$ | $75^2$ | 155 |
| Imp04 | $0^1$ | $90^1$ | $0^1$ | $50^1$ | 140 |
| San02 | $0^1$ | 80 | $0^1$ | $50^1$ | 130 |
| Tol03 | $0^1$ | 80 | $0^1$ | $40^1$ | 120 |
| Total | 0 | 370 | 0 | 245 | 615 |
| B. Number of inoculations tested ||||||
| Bea02 | $0^1$ | 31 | $0^1$ | $21^2$ | 52 |
| Bro08 | $0^1$ | 59 | $0^1$ | $50^2$ | 109 |
| Imp04 | $0^1$ | $60^1$ | $0^1$ | $21^1$ | 81 |
| San02 | $0^1$ | 64 | $0^1$ | $31^1$ | 95 |
| Tol03 | $0^1$ | 32 | $0^1$ | $27^1$ | 59 |
| Total | 0 | 246 | 0 | 150 | 396 |
| C. Number of successful inoculations ||||||
| Bea02 | $0^1$ | 0 | $0^1$ | 1 | 1 |
| Bro08 | $0^1$ | 1 | $0^1$ | 0 | 1 |
| Imp04 | $0^1$ | $1^1$ | $0^1$ | $2^1$ | 3 |
| San02 | $0^1$ | 0 | $0^1$ | $1^1$ | 1 |
| Tol03 | $0^1$ | 0 | $0^1$ | $2^1$ | 2 |
| Total | 0 | 2 | 0 | 6 | 8 |
| D. Percent of successful inoculations ||||||
| Bea02 | $0^1$ | 0 | $0^1$ | 1 | 1.0 |
| Bro08 | $0^1$ | 1.7 | $0^1$ | 0 | 1.7 |
| Imp04 | $0^1$ | $1.7^1$ | $0^1$ | $9.5^1$ | 11.2 |
| San02 | $0^1$ | 0 | $0^1$ | $3.2^1$ | 3.2 |
| Tol03 | $0^1$ | 0 | $0^1$ | $7.4^1$ | 7.4 |
| Total | 0 | 3.4 | 0 | 21.2 | 24.5 |
| D. Percent of successful inoculations ||||||
| Bea02 | $0^1$ | 0 | $0^1$ | 1 | 1.0 |
| Bro08 | $0^1$ | 1.7 | $0^1$ | 0 | 1.7 |
| Imp04 | $0^1$ | $1.7^1$ | $0^1$ | $9.5^1$ | 11.2 |
| San02 | $0^1$ | 0 | $0^1$ | $3.2^1$ | 3.2 |
| Tol03 | $0^1$ | 0 | $0^1$ | $7.4^1$ | 7.4 |
| Total | 0 | 3.4 | 0 | 21.2 | 24.5 |

[1] = Stable associations previously formed
[2] = Unstable associations

Endophytes NEA3, NEA2 and E34 have not been successfully inoculated E1 is broadly compatible

TABLE 26

Perennial Ryegrass Isogenic Inoculations

|  | NEA3 | NEA2 | E1 | E34 | Total |
|---|---|---|---|---|---|
| A. Number of inoculations performed ||||||
| Bea02 | 30 | 30 | 55 | 26 | 141 |
| Bro08 | 80 | 80 | 30 | NI | 190 |
| Imp04 | 80 | 80 | 30 | 15 | 205 |
| San02 | 80 | 80 | 55 | 30 | 245 |
| Tol03 | 80 | 80 | 80 | 40 | 280 |
| Total | 350 | 350 | 250 | 111 | 1061 |
| B. Number of inoculations tested ||||||
| Bea02 | 17 | 18 | 19 | 26 | 80 |
| Bro08 | 39 | 43 | 18 | NI | 100 |
| Imp04 | 71 | 58 | 12 | 12 | 153 |
| San02 | 51 | 55 | 8 | 19 | 133 |
| Tol03 | 37 | 41 | 17 | 26 | 121 |
| Total | 215 | 215 | 74 | 83 | 587 |
| C. Number of successful inoculations ||||||
| Bea02 | 0 | 0 | 9 | 0 | 9 |
| Bro08 | 0 | 0 | 13 | NI | 13 |
| Imp04 | 0 | 0 | 10 | 0 | 10 |

TABLE 26-continued

Perennial Ryegrass Isogenic Inoculations

|  | NEA3 | NEA2 | E1 | E34 | Total |
|---|---|---|---|---|---|
| San02 | 0 | 0 | 6 | 0 | 6 |
| Tol03 | 0 | 0 | 10 | 0 | 10 |
| Total | 0 | 0 | 48 | 0 | 48 |
| D. Percent of successful inoculations | | | | | |
| Bea02 | 0 | 0 | 47.4 | 0 | 11.8 |
| Bro08 | 0 | 0 | 72.2 | NI | 24.1 |
| Imp04 | 0 | 0 | 83.3 | 0 | 20.8 |
| San02 | 0 | 0 | 75.0 | 0 | 18.8 |
| Tol03 | 0 | 0 | 58.8 | 0 | 14.7 |
| Total | 0 | 0 | 64.9 | 0 | 16.2 |

NI not inoculated

Vegetative Stability of E1 Endophyte in Priority Ryegrass Host Panel Genotypes

TABLE 27

Vegetative stability of E1 endophyte in priority ryegrass host panel genotypes. Plants were re-sampled 6-12 months after initial inoculation (bottom line).

| Plant Genotype | Endophyte E1 | No. of dead plants after resampling |
|---|---|---|
| Impact (Imp04) | 10/12<br>1/5 | 0 |
| Barsandra (San02) | 6/8<br>5/5 | 0 |
| Tolosa (Tol03) | 10/17<br>7/8 | 5 |
| Bealey (Bea02) | 9/19<br>8/8 | 2 |
| Bronsyn (Bro08) | 13/18<br>0/8 | 0 |

Summary of Endophyte Stability in Isogenic Host Associations
  Host and endophyte specific effects were observed
    Identified stable host-endophyte associations for novel endophytes, establishing designer associations
      e.g. Impact—NEA10; Tolosa—NEA12; Barsandra—E1
  Significant genotype×genotype (G×G) effects highlight the importance of breeding for symbiota
    Bronsyn and Impact exhibited higher inoculation success rates—better range of compatibility
    E1 exhibits high rates of successful inoculation and has intermediate compatibility NEA11, NEA10 and ST endophytes are highly stable over time
Vegetative stability issues with NEA12
Emphasis on maintaining and characterising highly valuable associations

Example 12—Metabolic Profiling of Isogenic Host—Endophyte Associations

TABLE 28

Metabolic profiling of isogenic host-endophyte associations
In-depth metabolic profiling of novel isogenic host-endophyte associations

| Endophyte | Endogenous Toxin Profile | Confirmed Toxin Profile | Origin | Species |
|---|---|---|---|---|
| ST | L/E/P | Y (L/E/P) |  | N. lolii |
| AR1 | −/−/P | N.A |  | N. lolii |
| 15285 | $L^a$/−/P | Y (L/−/P) | Portugal | N. lolii |
| 15441 | −/−/− | $N^c$ | Italy | N. lolii |
| 15931 | −/E/P | N.A | Former Soviet Union | N. lolii |
| 01030 44 F2 | −/E/n.d$^b$ | N.A | Spain | N. lolii |
| NEA10 | −/E/n.d | Y (-/E/P) | Spain | N. lolii |
| NEA11 | −/E/n.d | Y (-/E/P) | France | LpTG-2 |
| NEA12 | −/−/− | Y (−/−/−) | France | Non-N. lolii |

$^a$Negligible levels of lolitrem B
$^b$Peramine not measured in Agriseeds samples
$^c$Differential response: Bealey, Meridian and Source plant −/−/−; Barsandra and Barfest L/E/P. Not selected for further analysis
N.A No stable isogenic host-endophyte associations formed FIG. 47 shows a detailed characterisation of the known knowns and their precursors.

Procedure:
1. Establish methodologies for semi-quantitative analysis of known alkaloids (LEPJ)
2. Compare semi-quantitative alkaloid (LEPJ) profiles of E$^+$ versus E$^-$ host plants
3. Compare semi-quantitative alkaloid profiles for diverse endophytes in an isogenic host
4. Assess stability of alkaloid (LEPJ) profile of selected endophytes across different isogenic hosts Host genotypes were confirmed using the host-panel identification test (FIG. 48). Ten replicates of each host-endophyte association were tested.

Two confirmed endophyte positive plants split into 4 replicates
Plants regularly trimmed to promote tillering
2 years later (first column of table 29)—Plants re-potted to 10 replicates
2 months later (second column of table 29)—Endophyte positive plants re-potted to 15 replicates
Endophyte status was tested using SSR markers

TABLE 29

Endophyte status

| Host genotype | ST | | NEA10 | | NEA11 | | NEA12 | | E1 | |
|---|---|---|---|---|---|---|---|---|---|---|
| Impact (Imp04) | 6/10 | 7/15 | 10/10 | 15/15 | 8/8 | 7/7 | 9/10 | 11/15 | 10/10 | 10/15 |
| Basandra (San02) | 7/10 | 10/15 |  |  | 5/10 | 13/15 | 5/10 | 14/22 |  |  |
| Tolosa (Tol03) | 6/10 | 11/15 |  |  | 9/10 | 11/15 | 8/10 | 11/15 |  |  |
| Bealey (Bea02) | 6/10 | 11/15 |  |  | 6/10 | 15/15 |  |  |  |  |
| Bronsyn (Bro08) | 9/10 | 11/15 |  |  | 8/10 | 11/15 |  |  |  |  |

FIGS. 49 and 50 show in-depth metabolic profiling of novel isogenic host-endophyte associations.

Ten replicates per host-endophyte association (20*10=200 samples).
Complete randomised block design
Two organs (pseudostem and leaves) were harvested following 6 weeks growth under controlled conditions
After 6 weeks regrowth there was a second harvest
Water supply: 50 ml/day
14 hours light (620 mmolm$^{-2}$s$^{-1}$ light intensity)/21° C.
10 hours dark/16° C.

Outcome:
To determine the pattern of metabolic variation between endophytes, host plants and organ types.

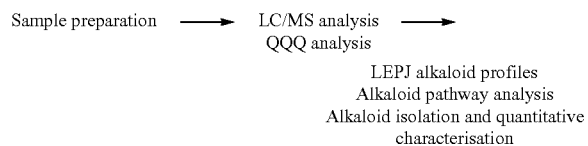

Current Study:
Freeze dried pseudostem material
50 mg of freeze dried powder
Extracted twice in 1 ml of methanol:water (80:20, v:v)
FIG. 51 shows LEPJ: the known knowns.
FIG. 52 shows accurate mass of LEPJ.

TABLE 30 accurate mass of LEPJ

| RT(min) | m/z | Accurate mass | MS2 | Identity |
|---|---|---|---|---|
| 3 | 248(H+) | 248.15022 | 206, 231, 175 | Peramine |
| 4.7 | 534(H+) | 534.27002 | 223, 268 | Ergovaline |
| 10.3 | 686(H+) | 686.40369 | 628, 238 | Lolitrem B |
| 10.3 | 646(H+) | 646.37238 | 280, 222, 588.33 | Janthitrem |

FIGS. 53 and 54 show identification of LEPJ.
FIG. 55 shows quantification of LEPJ.
FIG. 56 shows a comparison of semi-quantitative alkaloid (LEPJ) profiles of E$^+$ versus E$^-$ host plants.
FIG. 57 shows a comparison of semi-quantitative alkaloid profiles for diverse endophytes in an isogenic host (Imp04).

FIG. 58 shows an assessment of stability of alkaloid (LEPJ) profile of selected endophytes across different isogenic hosts.
Significant genotype×genotype (G×G) effects highlight the importance of breeding for symbiota
Specific LEPJ alkaloid production varies between different endophytes inoculated into the same isogenic host
  e.g. NEA11 inoculated into Impact (Imp04) produces more peramine and less ergovaline than NEA10 inoculated into the same host genotype
LEPJ alkaloid production varies between different host plants harbouring the same endophyte indicating host genotype effects
  e.g. ergovaline was not detected in Bealey (Bea02) and Barsandra (San02) inoculated with ST and NEA11 and was detected in relatively high quantities in Bronsyn (Bro08) inoculated with the same endophytes
Assessment of an endophyte that matches the specifications and is stable across germplasm pools.
Genic content can be used to predict presence/absence of lolitrem B
Semi-quantitative LC-MS can be used to assess relative amounts of LEPJ across germplasm pools
NEA12 forms stable associations with some germplasm backgrounds, produces J across the hosts assessed, does not produce LEP and exhibits broad spectrum antifungal activity
NEA11 is a highly compatible endophyte that produces relatively less P, and more E than ST across a range of host backgrounds, but no LJ
E1 is a highly compatible endophyte that does not produce LEPJ in Imp04, but does produce J in Bro08
NEA10 forms stable associations within a limited host background and produces more E and less P than NEA11 (and by inference ST)
FIG. 187 shows a semi-quantitative LC-MS used to assess relative amounts of LEPJ across germplasm pools.
Pathway Analysis
Lolitrem B and ergovaline biosynthetic pathways are known in *N. lolii*
Perform pathway analysis to determine if gene deletions result in changes in production of precursors of known knowns (LPEJ) and direct flux to synthesis of other known toxins
FIG. 59 shows lolitrem B biosynthesis.
FIG. 188 shows production of lolitrems in planta.
FIG. 189 shows production of ergot alkaloids in planta.

TABLE 34 pathway analysis Lolitrem B

| | Compound | Tested results | | | Reference | | | |
| | | Accurate Mass ([M + H]) | Retention time | LC/MS/MS Fragment | Chemical formula [M + H] | Accurate Mass ([M + H]) | LC/MS/MS Fragment | Reference |
|---|---|---|---|---|---|---|---|---|
| Lolitrems | paspaline | 422.3074 | 11.2 | 407; 130; 376; 184 | C28H40NO2 | 422.305904 | 406, 130, 388 | Saikia et al., 2006 |
| | 13-desoxy paxilline | 420.25406 | 9.85 | 130, 405, 388 | C27H34NO3 | 420.253869 | 130 or 198 | Nicholson et al., 2009 |
| | paxilline | 436.24936 | 10.2 | 418; 130 | C27H34NO4 | 436.248784 | 420, 418 | Babu et al., 2008 |
| | terpendole I | 454.25836 | 10.27 | N.D.$^a$ | C27H36NO5 | 454.259349 | | Young et al., 2009 |
| | prenylate terpendole I | 522.3205 | 10.27 | N.D. | C32H44NO5 | 522.321949 | | Young et al., 2009 |
| | terpendole C | 520.30481 | 8.9; 10.2 | 502, 484, 184; | C32H42NO5 | 520.306299 | 504(446); 502(444) | Babu et al., 2008 |
| | lolitriol | 620.35992 | 8 | 562; 238; 602 | C37H50NO7 | 620.358729 | 238 | Young et al., 2009 |
| | lolitrem E | 688.42065 | 10.75 | 628, 238, 588 | C42H58NO7 | 688.421329 | 630; 238 | Grancher et al., 2004 |
| | lolitrem B | 686.40552 | 10.29 | 630; 238; 588 | C42H56NO7 | 686.405679 | 628, 586, 238; 196 | Young et al., 2009 |

TABLE 34-continued pathway analysis Lolitrem B

| | | Tested results | | | | Reference | | |
|---|---|---|---|---|---|---|---|---|
| | Compound | Accurate Mass ([M + H]) | Retention time | LC/MS/MS Fragment | Chemical formula [M + H] | Accurate Mass ([M + H]) | LC/MS/MS Fragment | Reference |
| Aflatrem | lolitrem J | 662.37744 | 10.3 | 643, 564, 208 | C39H52NO8 | 662.369294 | 238 | Young et al., 2009 |
| | lolitrem K | 602.34802 | 10.3 | 544, 238 | C37H48NO6 | 602.348164 | 238 | Young et al., 2009 |
| | paspalicine | 418.23749 | 10.2 | 400, 362, 130 | C27H32NO3 | 418.238219 | 403; 130 | Nicholson et al., 2009 |
| | paspalicinol | 420.25314 | 9.75 | 405,130, 370, 388 | C27H34NO3 | 420.253869 | 405 | Nicholson et al., 2009 |
| | paspalininol | 436.24796 | 10.2 | 130; 376; 418; | C27H34NO4 | 436.248784 | 411 | Nicholson et al., 2009 |
| | paspalinine | 434.23242 | 10.11 | 416, 402, 370, 288 | C27H32NO4 | 434.233134 | 419(MS3: 360); 130 | Nicholson et al., 2009 |
| | aflatrem | 502.29199 | 10.2 | 484, 460, 443, 198 | C32H40NO4 | 502.295734 | 198 | Nicholson et al., 2009 |

TABLE 35 pathway analysis ergot alkaloids

| | | Tested results | | | | Reference | | |
|---|---|---|---|---|---|---|---|---|
| | Compound | Accurate Mass ([M + H]) | Retention time | LC/MS/MS Fragment | Chemical formula [M + H] | Accurate Mass ([M + H]) | LC/MS/MS Fragment | Reference |
| Ergot alkaloids | tryptophan | 205.09717 | 2.87 | 187 | C11H13N2O2 | 205.097703 | | Panaccione et al., 2003 |
| | chanoclavine | 257.16461 | 3.6 | 168; 208; 226 | C16H21N2O | 257.165388 | 212; 198; 184; 189; 202 | Lorenz; 2010 |
| | secolysergine | 241.17004 | 4.43 | 210; 198; 185 | C16H21N2 | 241.170473 | 210; 185 | Panaccione et al., 2003 Fleetwood et al., 2007 |
| | agroclavine | 239.15443 | 4.4 | 221; 208; 183 | C16H19N2 | 239.154823 | | Lehner et al., 2004 |
| | setoclavine | 255.14899 | 3.51 | 223, 208 | C16H19N2O | 255.149738 | 223 | Liras et al., 2001 |
| | elymoclavine | 255.14899; | 3.57 | 237; 223; 208 | C16H18N2O | 255.149738 | 268; 223; | Lehner et al., 2004 |
| | lysergic acid | 269.1358 | 4.71 | 223; 208; 180 | C16H17N2O2 | 269.129003 | 223; | Fleetwood et al., 2007 |
| | lysergyl peptide lactam | 518.27539 | 4.75 | 223 | C29H36N5O4 | 518.27673 | 223; | Lehner et al., 2004 |
| | lysergyl alanine | 340.16537 | 3.31 | 223; 208 | C19H22N3O3 | 340.166117 | 223 | Panaccione et al., 2003; Fleetwood et al., 2007 |
| | ergovaline | 534.27094 | 4.78 | 516; 342; 263; 223 | C29H36N5O5 | 534.271645 | 268; 223; 208 | Panaccione et al., 2003 Fleetwood et al., 2007 |
| Other ergot alkaloids | lysergamide | 268.1441 | 3 | 223; 198; | C16H18N3O | 268.144987 | 223 | Fleetwood et al., 2007 |
| | lysergol | 255.14899 | 3.51 | 237; 223; 186 | C16H19N2O | 255.149738 | | Lehner et al., 2004 |
| | ergotamine | N.P.[b] | | | C33H36N5O5 | 582.271645 | 268; 223; 208 | Lehner et al., 2004 |
| | ergocornine | N.P. | | | C31H40N5O5 | 562.302945 | | Lehner et al., 2004 |
| | ergocryptine | N.P. | | | C32H42N5O5 | 576.318595 | | Lehner et al., 2004 |
| | ergocrystine | N.P. | | | C35H40N5O6 | 610.302945 | | Lehner et al., 2004 |
| | ergonovine | N.P. | | | C19H24N3O2 | 326.186852 | | Lehner et al., 2004 |
| | ergosine | N.P. | | | C30H38N5O5 | 548.287295 | | Lehner et al., 2004 |
| | dihydro-ergocristine | N.P. | | | C35H42N5O5 | 612.318595 | | Lehner et al., 2004 |
| | ergostine | N.P. | | | C34H38N5O5 | 596.287295 | | Lehner et al., 2004 |
| | dihydro-ergocryptine | N.P. | | | C32H44N5O5 | 578.334245 | | Lehner et al., 2004 |
| | dihydro-ergocornine | N.P. | | | C31H42N5O5 | 564.318595 | | Lehner et al., 2004 |
| | ergotamine dehydrate | N.P. | | | C33H34N5O4 | 564.26108 | | Lehner et al., 2004 |
| | ergoptine | N.P. | | | C31H40N5O5 | 562.302945 | | Lehner et al., 2004 |
| | ergonine | N.P. | | | C30H38N5O5 | 548.287295 | | Lehner et al., 2004 |
| | nicergoline | N.P. | | | C24H27BrN3O3 | 484.123578 | | Lehner et al., 2004 |
| | ergometrine | N.P. | | | C19H24N3O2 | 326.186852 | | Lehner et al., 2004 |

TABLE 36 pathway analysis peramine and janthitrems

| | | Tested results | | | | Reference | | |
|---|---|---|---|---|---|---|---|---|
| | Compound | Accurate Mass ([M + H]) | Retention time | LC/MS/MS Fragment | Chemical formula [M + H] | Accurate Mass ([M + H]) | LC/MS/MS Fragment | Reference |
| Peramine | Peramine | 248.15062 | 3 | 206; 231; 175 | C12H18N5O5 | 248.151135 | 231(16.4), 206(100), 175.2(6.4), | Koulman et al., 2007 |
| | Imidacloprid | 256.05881 | 3.51 | 238; 228; 226; 214; 19 | C9H11ClN5O2 | 256.060127 | 210, 212, 209, 175 | Koulman et al., 2007 |
| | 4-Hydroxy-imidacloprid | 272.05338 | 3.9 | N.D. | C9H11ClN5O3 | 272.055043 | 228, 226.1, 242 | Koulman et al., 2007 |
| Janthitrems | Janthitrem I | 646.3736 | 10.24 | 628; 588; 222; 280 | C39H52NO7 | 646.3744 | 280, 222, 588 | Babu et al., 2008 |
| | Janthitrem I | 602.34802 | 10.29 | 564; 544 | C37H48NO6 | 602.348164 | 544, 526 | Babu et al., 2008 |
| | Janthitrem I | 586.35278 | 11.5 | 568; 542; 488 | C37H48NO5 | 586.353249 | 568, 510(MS3:440) | Babu et al., 2008 |
| | Janthitrem I | 570.35547 | 11.83 | 552; 538; 496 | C37H48NO4 | 570.358334 | 554(496) | Babu et al., 2008 |

FIG. 61 shows an analysis of the lolitrem B biosynthetic pathway.

FIG. 62 shows the paspalinine—A tremorgen pathway.

FIG. 63 shows a pathway analysis: paspalinine—A tremorgen.

FIG. 64 shows the presence of lolitrem and paspalinine in symbiota.

TABLE 37 presence of lolitrem in symbiota

| Lolitrem | Endophyte Genotypes | | | | | |
|---|---|---|---|---|---|---|
| 686(10.30) | ST | NEA10 | NEA11 | NEA12 | E− | E1 |
| Barsandra | + | NA | − | − | − | NA |
| Bealey | + | NA | − | NA | − | NA |
| Bronsyn | + | NA | − | NA | − | − |
| Impact | NA | − | − | − | − | − |
| Tolosa | + | NA | − | − | − | − |

TABLE 38 presence of paspalinine in symbiota

| Paspalinine | Endophyte Genotypes | | | | | |
|---|---|---|---|---|---|---|
| 434(10.17) | ST | NEA10 | NEA11 | NEA12 | E− | E1 |
| Barsandra | + | NA | − | − | − | NA |
| Bealey | + | NA | + | NA | − | NA |
| Bronsyn | + | NA | − | NA | − | − |
| Impact | NA | + | − | − | − | − |
| Tolosa | + | NA | + | − | − | − |

TABLE 39 in-depth metabolic profiling of novel isogenic host-endophyte associations

| | | Host-Endophyte Symbiota | | | | | | | | | |
|---|---|---|---|---|---|---|---|---|---|---|---|
| | Compound | Bea02 E− | Bro08 E− | Imp04 E− | San02 E− | Tol03 E− | Imp04 NEA10 | Bea02 NEA11 | Bro08 NEA11 | Imp04 NEA11 | San02 NEA11 |
| Lolitrems | paspaline | − | − | − | − | − | + | + | + | + | + |
| | 13-desoxy paxilline | − | − | − | − | − | + | + | + | + | + |
| | paxilline | − | − | − | − | − | + | + | + | + | + |
| | terpendole I | − | − | − | − | − | + | + | + | + | + |
| | prenylated terpendole I | − | − | − | − | − | + | + | + | + | + |
| | terpendole C | − | − | − | − | − | + | + | + | + | + |
| | lolitriol | − | − | − | − | − | − | − | − | − | − |
| | lolitrem E | − | − | − | − | − | − | − | − | − | − |
| | lolitrem B | − | − | − | − | − | − | − | − | − | − |
| | lolitrem J | − | − | − | − | − | − | − | − | − | − |
| | lolitrem K | − | − | − | − | − | − | − | − | − | − |
| Aflatrem | paspalicine | − | − | − | − | − | + | + | + | + | + |
| | paspalicinol | − | − | − | − | − | + | + | + | + | + |
| | paspalininol | − | − | − | − | − | + | + | + | + | + |
| | paspalinine | − | − | − | − | − | + | + | + | + | + |
| | aflatrem | − | − | − | − | − | + | + | + | + | − |
| Ergot Alkaloids | tryptophan | + | + | + | + | + | + | + | + | + | + |
| | chanoclavine | − | − | − | − | − | + | + | + | + | + |
| | secolysergine | − | − | − | − | − | − | − | − | + | + |
| | agroclavine | − | − | + | + | + | + | + | + | + | + |

TABLE 39-continued in-depth metabolic profiling of novel isogenic host-endophyte associations

| | | | | | | | | | | | |
|---|---|---|---|---|---|---|---|---|---|---|---|
| | setoclavine | − | − | − | + | + | + | + | + | + | + |
| | elymoclavine | − | − | − | − | − | + | + | + | + | + |
| | lysergic acid | + | + | + | + | + | + | + | + | + | + |
| | lysergyl peptide lactam | − | − | − | − | − | + | + | − | + | − |
| | lysergyl alanine | − | − | − | − | − | + | + | + | + | + |
| | lysergamide | − | − | − | − | − | + | + | + | + | + |
| | ergovaline | − | − | − | − | − | + | +(Trace) | + | + | +(Trace) |
| | lysergol | − | − | − | − | − | + | + | + | + | + |
| Peramine | Peramine | +(Trace) | +(Trace) | +(Trace) | +(Trace) | +(Trace) | + | + | + | + | + |
| | Imidacloprid | − | − | − | − | + | − | − | − | − | + |
| | 4-Hydroxy-Imidacloprid | + | − | + | + | + | + | + | + | + | + |
| Janthitrem | Janthitrem I | − | − | − | − | − | − | − | − | − | − |
| | Janthitrem A | − | − | − | − | − | − | − | − | − | − |
| | Janthitrem B | − | − | − | − | − | − | − | − | − | − |
| | Janthitrem C | + | + | + | + | + | + | + | + | + | + |

| | | Host-Endophyte Symbiota | | | | | | | | | |
|---|---|---|---|---|---|---|---|---|---|---|---|
| | Compound | Tol03 NEA11 | Imp04 NEA12 | San02 NEA12 | Tol03 NEA12 | Bro03 E1 | Imp04 E1 | Bea02 ST | Bro08 ST | San02 ST | Tol03 ST |
| Lolitrems | paspaline | + | + | + | + | + | + | + | + | + | + |
| | 13-desoxy paxilline | + | + | + | + | − | − | + | + | + | + |
| | paxilline | + | + | +(Trace) | +(Trace) | − | − | + | + | + | + |
| | terpendole I | + | + | − | + | − | − | + | + | + | + |
| | prenylated terpendole I | + | + | − | + | − | − | + | + | − | + |
| | terpendole C | + | + | − | + | − | − | + | + | + | + |
| | lolitriol | − | − | − | − | − | − | + | + | + | + |
| | lolitrem E | − | − | − | − | − | − | + | + | + | + |
| | lolitrem B | − | − | − | − | − | − | + | + | − | + |
| | lolitrem J | − | − | − | − | − | − | − | − | − | − |
| | lolitrem K | − | − | − | − | − | − | + | + | + | + |
| Aflatrem | paspalicine | + | + | − | + | − | − | + | + | + | + |
| | paspalicinol | + | + | + | + | − | − | + | + | + | + |
| | paspalininol | + | + | − | + | − | − | + | + | + | + |
| | paspalinine | + | + | − | + | − | − | + | + | + | + |
| | aflatrem | + | + | − | + | − | − | + | + | − | + |
| Ergot Alkaloids | tryptophan | + | + | + | + | + | + | + | + | + | + |
| | chanoclavine | + | − | − | − | − | − | + | + | + | + |
| | secolysergine | − | − | − | − | − | − | + | + | + | + |
| | agroclavine | + | + | − | − | − | + | + | + | + | + |
| | setoclavine | + | − | + | + | − | + | + | + | + | + |
| | elymoclavine | + | − | − | − | − | − | + | + | + | + |
| | lysergic acid | + | + | + | + | + | + | + | + | + | + |
| | lysergyl peptide lactam | + | − | − | − | − | − | + | + | + | + |
| | lysergyl alanine | + | − | − | − | − | − | + | + | + | + |
| | lysergamide | + | − | − | − | − | − | + | + | + | + |
| | ergovaline | + | − | − | − | − | − | +(Trace) | + | + | + |
| | lysergol | + | − | − | − | − | − | + | + | + | + |
| Peramine | Peramine | + | +(Trace) | +(Trace) | +(Trace) | +(Trace) | +(Trace) | + | + | + | + |
| | Imidacloprid | + | − | + | + | − | − | − | − | + | − |
| | 4-Hydroxy-Imidacloprid | + | + | + | + | + | + | + | + | + | + |
| Janthitrem | Janthitrem I | − | + | + | + | + | +(Trace) | − | − | − | − |
| | Janthitrem A | − | − | − | + | + | − | + | + | + | + |
| | Janthitrem B | − | + | + | + | + | + | − | − | − | − |
| | Janthitrem C | + | + | + | + | + | + | + | + | + | + |

FIG. 65 shows that Peramine is present in planta in trace amounts in absence of a peramine-producing endophyte.

Example 13—Endophyte Effect on Symbiotum Performance

Assessment of endophyte effect on symbiotum performance in isogenic host background is done through measurements of:
- tiller number
- shoot weight
- root weight
- root length
- root:shoot ratio FIG. 66 shows the procedure used to assess changes to host phenotype mediated by the endophyte.

FIG. 67 shows endophyte effect on symbiotum performance.

ANOVA

Significant endophyte effects on all measured traits
No significant combined endophyte/nitrate effects
No effect of nitrate on endophyte vegetative stability

TABLE 40

Assessment of endophyte effect on symbiotum performance in isogenic host background through measurements of:
Column 3: tiller number; Column 4 Shoot Fresh Weight (g);
Column 5: Root Length (cm); Column 6: Root Fresh Weight (g).

| | | | | | |
|---|---|---|---|---|---|
| F probability | Endophyte | <0.001 | <0.001 | <0.001 | <0.001 |
| | Nitrate | <0.001 | 0.005 | 0.492 | 0.846 |
| | Endophyte/Nitrate | 0.065 | 0.208 | 0.905 | 0.847 |
| $LSD_{0.05}$ | Endophyte | 4.115 | 1.001 | 3.945 | 0.599 |
| | Nitrate | 3.360 | 1.036 | 5.107 | 0.560 |
| | Endophyte/Nitrate | 7.099 | 1.829 | 7.786 | 1.065 |

Eight replicates per isogenic association were assessed for phenotypic performance
Plants were grown in sand pots for 4 weeks to establish
Treatments were applied at week 4: Drought and waterlogging
Harvest 1 at 8 weeks
Harvest 2 at 12 weeks
FIG. 68 shows plants before the T1 harvest.
FIG. 69 shows performance as measured by tiller number.
There were Significant genotype×genotype (G×G) effects
Significant variation between host plants
Significant effects of endophyte on performance
This highlights the importance of ab initio breeding and selection of symbiota.

Example 14—Genome Survey Sequencing of Endophytes

Progress in Performance of Different Sequencing Platforms
Roche 454
 400-500 bp reads
 1 million reads per run
 12× coverage
Illumina GAIIx
 150 bp paired end reads
 8 lanes per flow cell
 20 million paired end reads per lane
 12 samples per lane
 10× coverage per sample
Illumina HiSeq 2000
 100 bp paired end reads
 8 lanes per flow cell
 2 flow cells per run
 250 million paired end reads per lane
 24 samples per lane
 20-30× coverage per sample
Pangenome Analysis of *Neotyphodium* Endophytes
Sequence Analysis Using the 454 Sequencing Platform
 Ten *N. lolii* and non-*N. lolii* genomes sequenced
 A reference genome for *N. lolii* generated
 Nuclear architecture, including gene content, characterised
 Intraspecific polymorphisms identified, highlighting the importance of sequencing different *N. lolii* genomes
 Relationships between metabolic diversity and gene loss-gain for some toxins identified
 Comparison with the related sexual form revealed gene loss from both lineages as a source of phenotypic diversity
 Comparison of the mitochondrial genome sequence with another member of the Clavicipitaceae revealed it is highly conserved, with differences in genome size due to indels in intergenic and intronic regions
 FIG. 70 shows sequence analysis using the 454 sequencing platform.
Sequence Analysis Using the Illumina Sequencing Platform
 23 perennial ryegrass endophyte strains sequenced:
  16 *N. lolii*
  3 LpTG-2
  4 non-*N. lolii*
 Reference genome construction—ST
 Representatives of diversity of perennial ryegrass endophytes for pan-genome analysis
 Current commercial endophytes
  NEA2, NEA3, NEA4, AR1
 Future (potentially) commercial endophytes
  NEA10, NEA11, NEA12, E1
 Within cluster analysis of genetic diversity
 Endophytes from distinct geographical origins
  ST (Grasslands Samson)—$NA_6$ (Morocco) and C9 (Spain)
 Endophytes from the same geographical origin
  NEA12 (France)—15310 and 15311
 FIG. 71 shows sequence analysis using the Illumina sequencing platform.
 FIG. 72 shows a summary of sequenced perennial ryegrass endophyte genomes.
 FIG. 73 shows a summary of sequenced perennial ryegrass endophyte genomes.
Key Research Activities
 Incorporation of GAII and HiSeq data to assemble and map a diverse range of endophyte strains and genes
 Completion of the reference genome sequence assembly for ST endophyte
 High resolution genome sequence analysis of 'identical' strains
 Pan-genome sequence analysis of endophyte strains representing the diversity of perennial ryegrass endophytes
*N. Lolii* Standard Toxic Reference Genome Refinement and Pangenome Analysis
 Until recently all endophyte genome sequencing was performed using the Roche 454 platform
 There is now additional sequence data available from an independent platform (Illumina GAII & HiSeq2000) for a large number of endophyte strains and species This is useful as the two methods use fundamentally different sequencing chemistry hence one can be used to complement the other

*N. lolii* Standard Toxic (ST) is the reference strain for which we have the most 454 sequence data What gains are there from using both sets of data for this endophyte?

Figure 74:
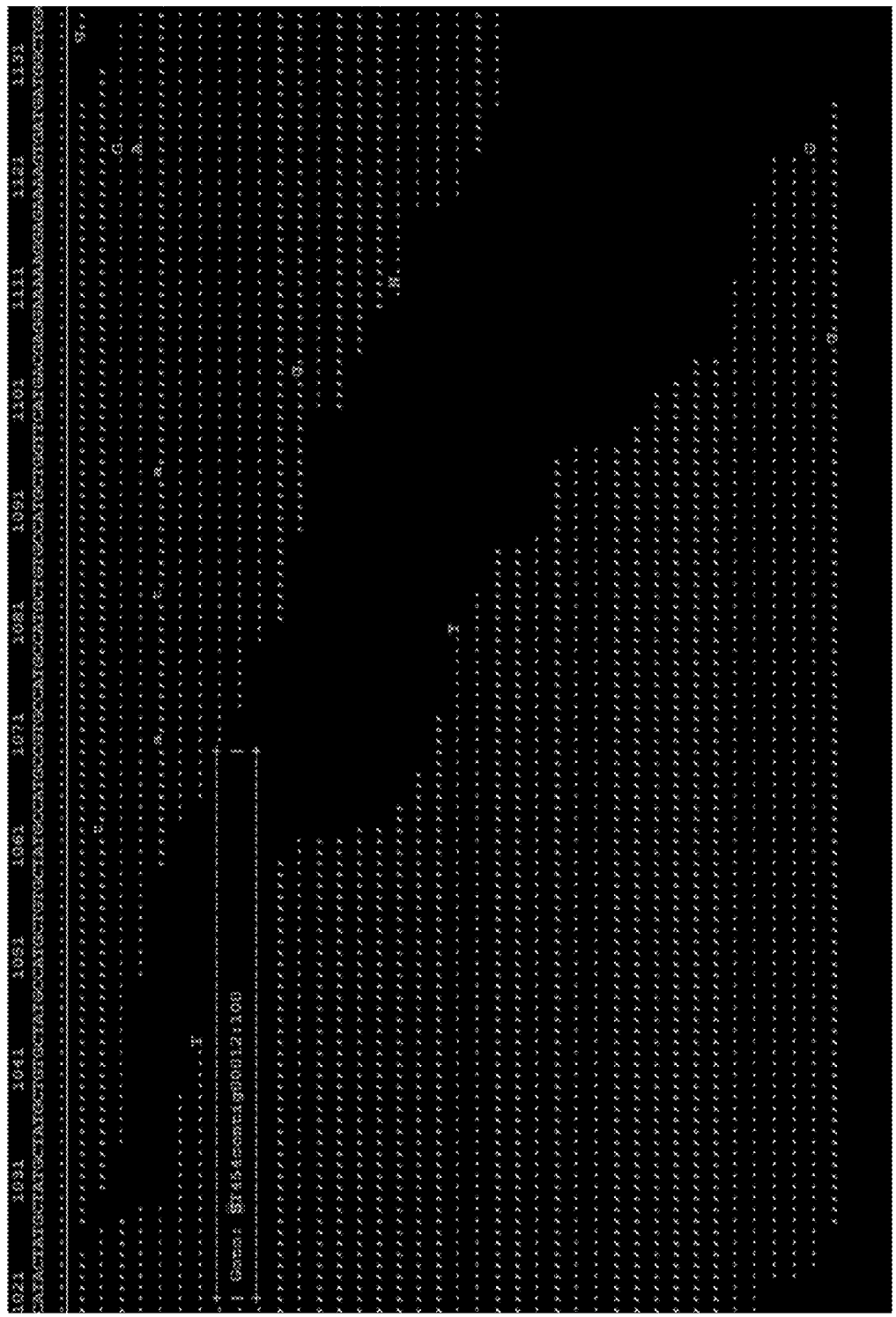
Figure 75:
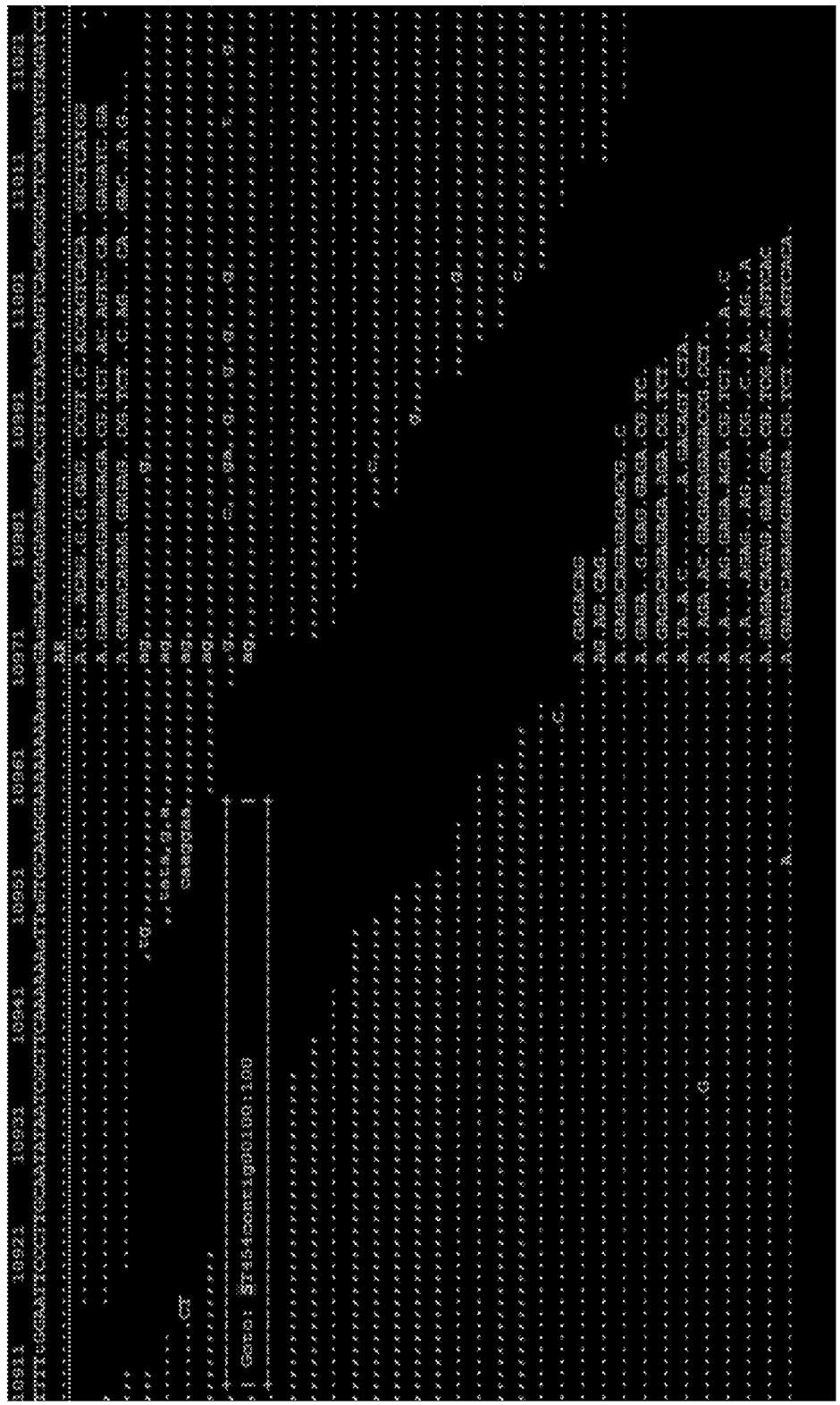
Figure 76:
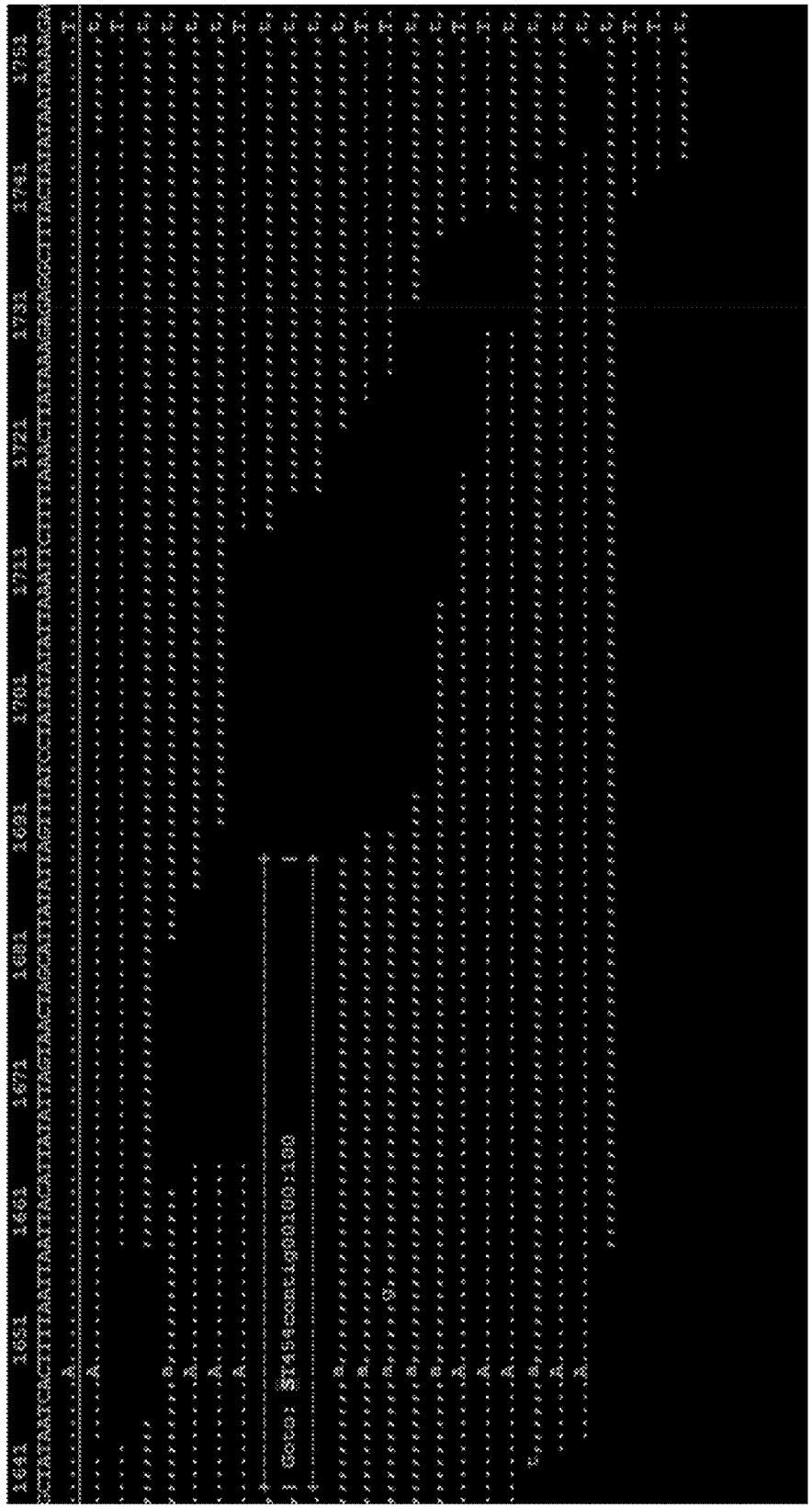
Figure 77:
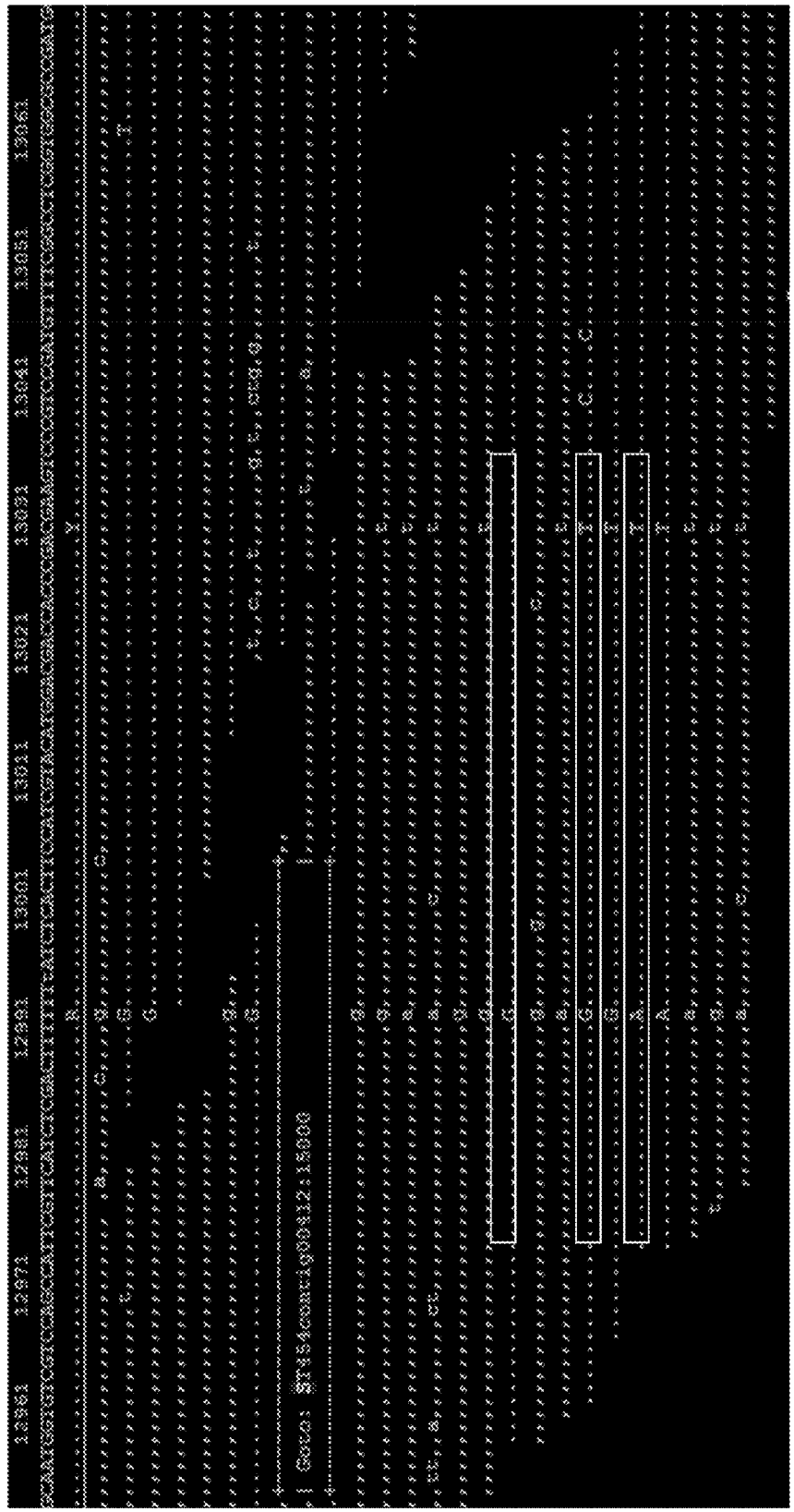
Figure 78:
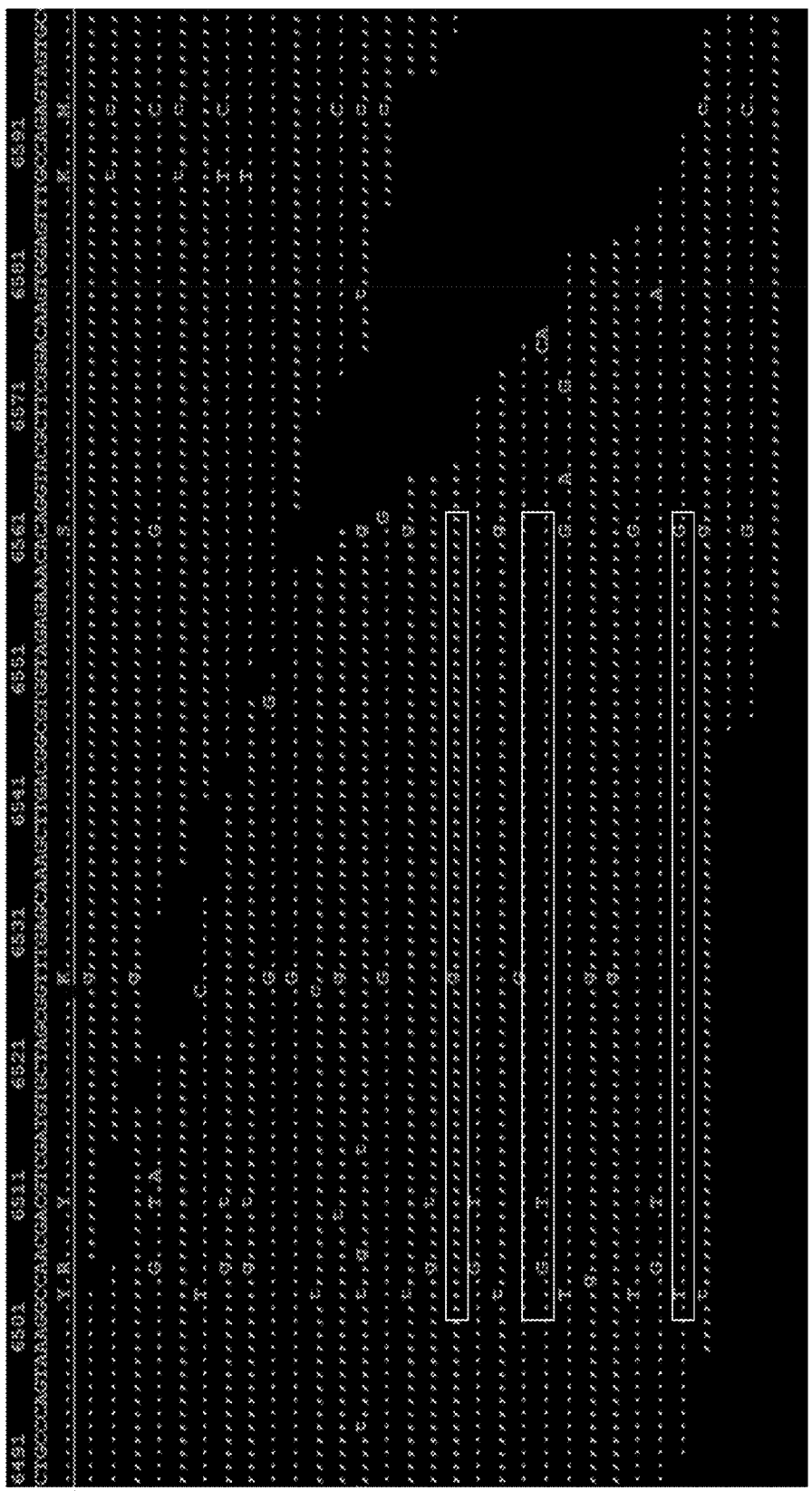

FIGS. 74-78 show Illumina reads v 454 contigs. FIG. 74 shows that in general the Illumina data confirms 454 data. FIG. 75 shows that the Illumina data can correct for 454 homo-polymer error. FIG. 76 shows that Illumina data from other strains identifies strain specific SNPs. FIG. 77 shows that Illumina data from other species identifies haplotypes of duplicated/triplicated genes e.g FEtc7-58. FIG. 78 shows 'triplicate' genes e.g. FEtc7-58.

Graphical Interactive Viewing and Analysis: Read Level

FIG. 79 shows 454 FLX v 454 Titanium v Illumina GAII coverage display.

FIG. 80 shows 454 FLX v 454 Titanium v Illumina GAII v Hi Seq coverage display.

FIG. 81 shows Homo polymer correction: graphical view

FIG. 82 shows Homo polymer correction: base view

FIG. 83 shows Pan-genome SNP calling: graphical view, read level

FIG. 84 shows 77 independent sequencing runs, ordered by similarity. These can display common SNPs.

FIG. 85 shows that independent sequencing runs can also display strain specific deletions.

FIG. 86 shows that independent sequencing runs can predict amino acid changes from SNP data.

Use of Illumina Data to Refine the 454 Sequence Assembly Method

Generate an assembly using Newbler (Roche assembly software) and refine using information from Illumina sequence data (mate pair, read depth etc) and Newbler assembly data (links between contigs, highly similar contigs)

Some Definitions:
⇒ Contig Continuous unambiguous assembled sequence
⇒ Scaffold Sequence containing more than one Contig whose connections and orientations relative to each other are known, but which are connected by ambiguous sequence
⇒ N50 Length of contig in which 50% of the total assembled length is contained in contigs longer that that length FIG. 87 shows that contig number decreases with rounds of assembly refinement.

FIG. 88 shows that N50 increases with rounds of assembly refinement.

FIG. 89 shows that assembly refinement decreases the number of scaffolds, and single 'unscaffolded' contigs.

FIG. 90 shows that average number of bases per contig increases with assembly refinement.

Current Status of Reference Genome Sequence Assembly of ST Endophyte
⇒ 2,494 contigs, totaling 33,804,495 bp
⇒ 1,496 of these contigs in 449 scaffolds, largest 395,697 bp, total 25,953,091 bp
⇒ 998 single unscaffolded contigs, containing 7,851,404 bp
⇒ Augustus gene prediction program predicts 10,821 protein encoding genes
⇒ The ST reference genome provides a basis for generating the pangenome of other *N. lolii* and related fungi.

Review of Candidate Endophyte Status

Previous candidate evaluation process:
Identified E+ accessions (77)
Identified novel, genetically diverse endophyte genotypes
Identified 42 primary endophyte candidates subjected to metabolic profiling in endogenous host background
Eliminated lolitrem B-producing endophyte candidates (29)
Eliminated duplicate endophyte genotypes (5)
Identified 8 primary endophyte candidates for advancement

TABLE 41

Review of Candidate Endophyte Status

| Endophyte Identifier | Species | Origin | Endogenous Toxin Profile | Isolated | Confirmed Toxin Profile |
|---|---|---|---|---|---|
| 15285[3] | *N. lolii* | Portugal | L[a]/—/P | ✓ | L/—/P |
| 15441[3] | *N. lolii* | Italy | —/—/— | ✓ | L/E/P |
| 15656 | *N. lolii* | Turkey | —/—/— | x[b] | |
| 15931[2] | *N. lolii* | Former Soviet Union | —/E/P | ✓ | ND[c] |
| F2[2] | *N. lolii* | Spain | —/E/ND | ✓ | ND[d] |
| NEA10[1] | *N. lolii* | Spain | —/E/ND | ✓ | —/E/P |
| NEA11[1] | LpTG-2 | France | —/E/ND | ✓ | —/E/P |
| NEA12[1] | Non-*N. lolii* | France | —/—/— | ✓ | —/—/— |

[a] = negligible levels in endogenous background
[b] = unable to isolate from original source plant
[c] = inoculated into isogenic panel but unstable
[d] = recalcitrant to inoculation into isogenic panel
[1] = Candidates with suitable profile advanced in program
[2] = Candidates with suitable profile not advanced due to stability issues
[3] = Candidates with apparent unsuitable profiles Potential to consider 15931 and F2 endophytes in new paradigm of large-scale establishment of grass-endophyte symbiota for ab initio selection.

Example 15—Overview of Generation of Novel Designer *Neotyphodium* Endophyte Variant Strains Through Mutagenesis The objective of this work was to create novel variants of the perennial ryegrass endophyte, *Neotyphodium lolii*, through induced polyploidisation and mutagenesis, with desirable properties such as enhanced bioactivities (e.g. antifungal acitivity), and/or altered plant colonization ability and stability of grass host—endophyte variant associations (e.g. altered in vitro growth), and/or altered growth performance (e.g. enhanced plant vigour, enhanced drought tolerance, enhanced water use efficiency) of corresponding grass host—endophyte variant associations. These grass host—endophyte variant associations are referred to as novel 'designer' grass-endophyte associations.

Experimental Strategies for the Generation and Characterisation of Novel Designer *Neotyphodium* Endophyte Variant Strains Through Mutagenesis The experimental activities thus included:
1. Establishment of phenotypic screens for novel 'designer' grass-endophyte associations such as:
Enhanced biotic stress tolerance
Enhanced drought tolerance and enhanced water use efficiency
Enhanced plant vigour 2. Targeted generation (i.e. polyploidisation and X-ray mutagenesis) and characterisation (i.e. antifungal bioassays, in vitro growth rate, genome survey sequencing [GSS]) of novel 'designer' endophytes 3. Breeding of 'designer' grass endophyte associations Delivery of designer endophytes into grass (e.g. perennial tyegrass) germplasm development process.

Establishment of Phenotypic Screens for Novel 'Designer' Grass-Endophyte Associations Assessment of enhanced biotic stress tolerance using NEA12 is shown in FIGS. 92 and 93. FIG. 92 shows in vitro bioassays to assess antifungal activity of *Neotyphodium* endophytes. FIG. 93 shows a detached leaf assay to assess resistance to crown rust (*Puccinia coronata* f. sp. *lolii*).

Assessment of enhanced drought tolerance and enhanced water use efficiency is shown in FIG. 94. This involved glasshouse and field trial screens for drought tolerance, survival and recovery, regrowth after drought, metabolic profiling and multiple trait dissection (based on assessments and measurements associated with plant morphology, plant physiology, plant biochemistry).

Generation of Designer *N Lolii* Genotypes by Polyploidisation

This involved creation of novel variation in *Neotyphodium* endophytes without the use of transgenic technology. Colchicine has been widely and successfully used for chromosome doubling in plants, e.g. perennial ryegrass. It inhibits chromosome segregation during mitosis inducing autopolyploidisation (chromosome doubling; see FIG. 95). This enables the generation of novel endophytes through induced chromosome doubling and may be applicable to the production of artificial polyploid endophytes.

The experimental work flow for chromosome doubling is shown in FIG. 96.

Flow cytometry calibrations to assess DNA content in *Neotyphodium* endophytes are shown in FIG. 97. Peaks indicate relative nuclear DNA content.

Flow cytometry analysis of NEA12$^{dh}$ strains is shown in FIG. 98 and Table 42.

1. ST is highly stable, broadly compatible. 2. NEA12 produces JANTHITREM only. 3. AR1 produces PERAMINE only.

TABLE 42

Colchicine treated endophyte strains (ST, NEA12 and AR1 endophyte strains) subjected to colchicine treatments (at different colchicine concentrations in %) leading to the recovery of endophyte colonies (# of colonies) used for flow cytometry analysis

| Endophyte | Colchicine treatment (%) | # of colonies | # colonies analysed |
|---|---|---|---|
| N. lolii ST | 0.2 | 12 | 12 |
| N. lolii NEA12 | 0.1 | 60 | 2 |
| N. lolii NEA12 | 0.2 | 60 | 18 |
| N. lolii AR1 | 0.1 | 60 | 0 |
| N. lolii AR1 | 0.2 | 60 | 0 |

Analysis of In Vitro Growth of NEA12$^{dh}$ *Neotyphodium* Variant Endophyte Strains Analysis of growth rate of NEA12$^{dh}$ *Neotyphodium* variant endophyte strains in in vitro culture after 8 weeks is shown in FIG. 99. In an initial screen, analysis of variance identified two NEA12$^{dh}$ *Neotyphodium* variant endophyte strains (NEA12$^{dh17}$ and NEA12$^{dh4}$) showing significantly different in vitro growth rate to the control NEA12 endophyte:

NEA12$^{dh17}$ grows significantly faster (p<0.01**)
NEA12$^{dh4}$ grows significantly slower (p<0.05*)

Analysis of growth rate of NEA12$^{dh}$ *Neotyphodium* variant endophyte strains in in vitro culture over 5 weeks is shown in FIG. 100. In a validation screen, Student's t-tests identified two NEA12$^{dh}$ *Neotyphodium* variant endophyte strains (NEA12$^{dh17}$ and NEA12$^{dh15}$) showing significantly different in vitro growth rate to the control NEA12 endophyte:

NEA$^{dh17}$ grows significantly faster (p<0.01**)
NEA12$^{dh15}$ grows significantly slower (p<0.01**)

Antifungal Bioassays of NEA12$^{dh}$ *Neotyphodium* Variant Endophyte Strains

A list of fungal pathogens (causing a range of fungal diseases and infecting a range of different plant hosts) that were included in antifungal bioassays used to analyse NEA12$^{dh}$ *Neotyphodium* variant endophyte strains to assess their spectrum of antifungal activities is shown in Table 43.

TABLE 43

Fungal pathogens (causing a range of fungal diseases and infecting a range of different plant hosts) included in antifungal bioassays to analyse NEA12$^{dh}$ *Neotyphodium* variant endophyte strains to assess their spectrum of antifungal activities

| Fungus | Disease | Hosts |
|---|---|---|
| *Alternaria alternate* | leaf spot, rot, blight | Numerous (dead plant materials) |
| *Bipolaris portulacae* | Damping-off | *Asteraceae* (daisies), *Portulacaceae* (purslane) |
| *Botrytis cinerea* | Stem rot, mould, seedling wilt | Many dicots, few monocots |
| *Colletotrichum graminicola* | Leaf spot, stalk rot | Poaceae (especially *Zea mays*) |
| *Drechslera brizae* | Leaf blight | Poaceae (*Briza* spp.) |
| *Phoma sorghina* | Spot (leaf, glume, seed), Root rot, Dying-off | Poaceae (grasses) |
| *Rhizoctonia cerealis* | Spot (wheat) Yellow patch (turfgrass) | Poaceae (grasses) |
| *Trichoderma harzianum* | Green mould, Parasite of other fungi | Many dicots, few monocots, Fungi |

Antifungal bioassays of NEA12$^{dh}$ *Neotyphodium* variant endophyte strains are shown in FIGS. 101 and 102. Twenty NEA12$^{dh}$ strains were screened for changes in antifungal activity. Four NEA12$^{dh}$ strains (i.e. dh5, dh6, dh13 and dh14) were identified as having greater antifungal activity compared to NEA12.

Genome Survey Sequencing and Sequence Analysis of NEA12$^{dh}$ *Neotyphodium* Variant Endophyte Strains NEA12$^{dh}$ *Neotyphodium* variant endophyte strains with enhanced antifungal activity, showing faster in vitro growth rate and higher DNA content were subjected to genome survey sequencing (GSS). Sequence data was generated for 10 NEA12$^{dh}$ strains and control NEA12 strain (highlighted in blue on Table 44).

TABLE 44

List of NEA12$^{dh}$ *Neotyphodium* variant endophyte strains showing different antifungal activity [higher than control or equal to control (standard, Std)] and different in vitro growth [slower than control, faster than conrol or equal to control (standard, Std)] compared to control NEA12 strain

| Endophyte | Antifungal | Growth |
|---|---|---|
| NEA12 | Std | Std |
| NEA12dh1 | Std | Std |
| NEA12dh2 | Std | Std |
| NEA12dh3 | Std | Std |
| NEA12dh4 | Std | Slower |

TABLE 44-continued

List of NEA12$^{dh}$ Neotyphodium variant endophyte strains showing different antifungal activity [higher than control or equal to control (standard, Std)] and different in vitro growth [slower than control, faster than conrol or equal to control (standard, Std)] compared to control NEA12 strain

| Endophyte | Antifungal | Growth |
|---|---|---|
| NEA12dh5 | Higher | Std |
| NEA12dh6 | Higher | Std |
| NEA12dh7 | Std | Std |
| NEA12dh8 | Std | Std |
| NEA12dh9 | Std | Std |
| NEA12dh10 | Std | Std |
| NEA12dh11 | Std | Std |
| NEA12dh12 | Std | Std |
| NEA12dh13 | Higher | Std |
| NEA12dh14 | Higher | Std |
| NEA12dh15 | Std | Slower |
| NEA12dh16 | Std | Std |
| NEA12dh17 | Std | Faster |
| NEA12dh18 | Std | Std |
| NEA12dh19 | Std | Std |
| NEA12dh20 | Std | Std |

Genome survey sequencing (GSS) data obtained for NEA12$^{dh}$ Neotyphodium variant endophyte strains derived from colchicine treated NEA12 control strain (highlighted in blue on Table 44) were analysed as follows:

De-novo assembly of the GSS data from NEA12 control strain—to act as a reference genome sequence for the analysis of the NEA12$^{dh}$ Neotyphodium variant endophyte strains Map the GSS data sequence reads from the NEA12$^{dh}$ Neotyphodium variant endophyte strains to the NEA12 reference genome sequence Identify potentially duplicated regions, i.e. regions with higher than expected sequence coverage Identify gene sequences that may have been duplicated Analysis of GSS read depth of NEA12$^{dh}$ Neotyphodium variant endophyte strains is shown in FIG. 103. Analysis of sequence contigs that appeared to have higher than expected read depth indicates that no major duplication event has occurred (excepting whole genome events). The patterns of read depth across these contigs are not identical between strains. This suggests there are differences between the NEA12$^{dh}$ Neotyphodium variant endophyte strains and the control NEA12 strain.

Analysis of GSS sequence assemblies for the NEA12$^{dh}$ Neotyphodium variant endophyte strains and the control NEA12 strain is shown in Table 45.

TABLE 45

Analysis of GSS sequence assemblies for the NEA12$^{dh}$ Neotyphodium variant endophyte strains and the control NEA12 strain

| Strain | # contigs | N50 | Max contig | # bases |
|---|---|---|---|---|
| NEA12 | 143202 | 28621 | 181461 | 32734984 |
| NEA12dh5 | 305031 | 29444 | 191191 | 30994592 |
| NEA12dh17 | 274394 | 37802 | 209957 | 30777017 |
| NEA12dh18 | 282692 | 30717 | 177813 | 30889903 |

Independent de novo sequence assemblies were performed using parameters identical to those used in assembling the genome sequence for the control NEA12 endophyte strain. Differences in sequence assembly statistics may indicate genomic differences between strains. GSS data obtained for the NEA12$^{dh}$ Neotyphodium variant endophyte strains and used in the sequence assemblies reveal fewer bases incorporated into the sequence assembly and produce more sequence contigs.

Increased numbers of smaller sequence contigs may be caused by transposon movement/replication.

Analysis of sequence reads mapping to the NEA12 genome sequence assembly is shown in FIG. 104. While we do not wish to be restricted by theory, if the genomes were the same no difference in the number of sequence reads mapping to the reference genome sequence would be expected. NEA12$^{dh}$ Neotyphodium variant endophyte strains range from 35-70% sequence reads mapping to NEA12 sequence contigs >5 kb in size. There are differences between the genome sequences of the NEA12$^{dh}$ Neotyphodium variant endophyte strains and the control NEA12 strain.

Summary of Results on Generation and Characterisation of Novel Designer Neotyphodium Variant Endophyte Strains Through Colchicine Treatment Based Mutagenesis Sequence read depth changes were analysed in NEA12$^{dh}$ Neotyphodium variant endophyte strains compared with the control NEA12 strain. Whilst no large partial genome sequence duplication events were detected, the occurrence of full genome duplication events in the NEA12$^{dh}$ Neotyphodium variant endophyte strains cannot be excluded based on the GSS sequence analysis.

De novo sequence assemblies were independently performed on GSS data obtained from the NEA12$^{dh}$ Neotyphodium variant endophyte strains. Differences in sequence assembly statistics indicate that genomic changes were caused by the colchicine-treatment in the NEA12$^{dh}$ Neotyphodium variant endophyte strains. The number of sequence reads from NEA12$^{dh}$ Neotyphodium variant endophyte strains mapping to the NEA12 reference genome sequence varies between strains. All GSS data analyses performed on the NEA12$^{dh}$ Neotyphodium variant endophyte strains indicate genomic differences.

In summary, the following novel designer endophytes were generated by colchicine treatment of NEA12 endophytes:

Four NEA12$^{dh}$ Neotyphodium variant endophyte strains (dh5, dh6, dh13 and dh14) with enhanced bioprotective properties (i.e. antifungal bioactivities);

One NEA12$^{dh}$ Neotyphodium variant endophyte strain (dh17) with higher in vitro growth rate than control NEA12 strain (i.e. potentially with enhanced stability/host colonization ability);

Ten NEA12$^{dh}$ Neotyphodium variant endophyte strains (including dh5, dh6, dh13, dh14 and dh17) and control NEA12 strain subjected to genome survey sequencing; and Five NEA12$^{dh}$ Neotyphodium variant endophyte strains (including dh5, dh13 and dh17) selected and subjected to isogenic inoculation in planta.

In Planta Isogenic Inoculation in Perennial Ryegrass with NEA12$^{dh}$ Neotyphodium Variant Endophyte Strains The following NEA12$^{dh}$ Neotyphodium variant endophyte strains and control NEA12 strain were used for in planta isogenic inoculation in perennial ryegrass:NEA12
NEA12dh5 High antifungal activity
NEA12dh13 High antifungal activity
NEA12dh4 Slow-growing
NEA12dh15 Slow-growing
NEA12dh17 Fast-growing

TABLE 46

Isogenic inoculation of perennial ryegrass genotypes (IMP04 and TOL03) with NEA12dh *Neotyphodium* variant endophyte strains. Numbers indicate number of perennial ryegrass plants of the two genotypes subjected to isogenic inoculation with the different NEA12dh *Neotyphodium* variant endophyte strains.

| Plant Genotype | NEA12 dh4 | NEA12 dh5 | NEA12 dh13 | NEA12 dh15 | NEA12 dh17 | NEA12 |
|---|---|---|---|---|---|---|
| IMP04 | 30 (1/19) | 30 (0/14) | 30 (0/21) | 30 | 32 (2/19) | 30 (0/6) |
| TOL03 | 25 | 30 | 30 | 20 | 30 | 20 |

Generation of Designer *N lolii* Genotypes by X-Ray Mutagenesis

The generation of designer *Neotyphodium* endophytes genotypes by X-ray mutagenesis offers the opportunity to create novel endophyte variant strains with enhanced properties, such as enhanced stability in grass hosts, broader host compatibility as well as improved toxin profiles e.g. following elimination of, the production of the detrimental alkaloid lolitrem B in the highly stable and broadly compatible ST endophyte.

Such an novel designer endophyte would be advantageous over existing commercial endophytes, such as AR1 and AR37, as it would be highly stable and broadly compatible and with optimal toxin profile.

FIG. 105 shows an experimental work flow for X-ray mutagenesis of endophyte strains.

FIG. 106 shows the indole-diterpene biosynthetic pathway. Lolitrem B is the major toxin that causes ryegrass staggers, a disease of grazing animals. Ten genes in 3 gene clusters are required for lolitrem biosynthesis. We focused initial analysis on 3 Ltm genes, one from each gene cluster. Optimised multiplex PCR analysis was designed and implemented.

Screening of X-Ray Irradiated *N. lolii* Strains

In a preliminary primary screen >5,000 colonies of X-ray irradiated *N. lolii*—established as an initial resource of novel variation of *N. lolii* endoophytes induced through X-ray mutagenesis and representing a mutagenised *N. lolii* endophyte strain collection—of were screened by multiplex PCR analysis for the presence of targeted Ltm genes leading to a preliminary identification of ~140 putative lolitrem B gene cluster PCR-negative colonies (~2.5% of 5,000 colonies screened). In a secondary screen high quality DNA was extracted (140 liquid cultures) and PCR analysis conducted. This identified 2 putative deletion mutants for one of the lolitrem B genes (ltm J).

TABLE 47

Putative X-ray irradiation-induced ltm gene deletion mutants of *N. lolii* derived from irradiation with 30 Gy dose. The colony number represents the unique identifier of the putative X-ray irradiation-induced ltm gene deletion mutant (i.e. 139-6 and 145-15).

| Dose (Gy) | Colony | LtmJ | LtmC | LtmM |
|---|---|---|---|---|
| 30 Gy (1 irraditation) | 139-6 | (−) | (−) | (−)? |
| 30 Gy (1 irraditation) | 145-15 | (−) | (+) | (+) |

(−) represents PCR-negative result for respective ltm gene analysis, (+) represents PCR-positive result for respective ltm gene analysis.

Antifungal Bioassays of Designer X-Ray Irradiated *N. lolii* Variant Strains

There were eight X-ray irradiated *N. lolii* variant strains (i.e. X-ray mutagenesis derived variant strains 1-35, 4-7, 7-22, 7-47, 123-20, 124-6, 139-6, 144-16 and 145-15) and one control *N. lolii* strain (i.e. ST endophyte strain).

Five fungal pathogens (causing a range of fungal diseases and infecting a range of different plant hosts) were included in antifungal bioassays used to analyse the X-ray irradiated *N. lolii* variant strains, as follows:

Bipolaris portulacae
Colletotrichum graminicola
Drechslera brizae
Phoma sorghina
Rhizoctonia cerealis No significant difference in antifungal activities of X-ray irradiated *N. lolii* variant strains tested was observed compared to the spectrum of antifungal activities observed for the control ST endophyte strain.

In Vitro Growth of Designer X-Ray Irradiated *N. lolii* Variant Strains

Results from the analysis of in vitro growth rate of designer X-ray irradiated *N. lolii* variant strains are shown in FIG. 107, with a statistical analysis of in vitro growth undertaken at week 5 for the X-irradiated *N. lolii* variant strains compared to the control ST strain, revealing significant differences in in vitro growth rates as follows:

$p<0.05$* (for X-irradiated *N. lolii* variant strain 139-6)
$p<0.01$** (for all other mutants)

Genome Survey Sequencing of Designer X-Ray Irradiated *N. lolii* Variant Strains Eight X-ray irradiated *N. lolii* ST variant strains and corresponding control ST strain were subjected to genome survey sequencing (GSS), leading to 46-fold to 79-fold genome sequence coverage for the different strains as shown in Table 48.

TABLE 48

Genome sequence coverage obtained in genome survey sequencing for for 8 X-ray irradiated *N. lolii* ST variant strains and corresponding control ST strain

| Strain | Description | Coverage |
|---|---|---|
| ST | ST | 23x |
| 139-6 | ST irradiated | 61x |
| 145-15 | ST irradiated | 52x |
| 144-16 | ST irradiated | 46x |
| 1_35 | ST irradiated | 79x |
| 4_7 | ST irradiated | 46x |
| 7_22 | ST irradiated | 53x |
| 7_47 | ST irradiated | 38x |
| 123-20 | ST irradiated | 54x |
| 124-6 | ST irradiated | 75x |

Detecting Genome Sequence Variation in Designer X-Ray Irradiated *N. lolii* Variant Strains Results from the analysis to detect genome sequence variation in X-ray irradiated *N. lolli* variant strains are shown in FIG. 109. Corresponding results on the detection of single nucleotide polymorphisms (SNPs) are shown in FIG. 110 and results on the detection of small insertions/deletions (INDELs) are shown in FIG. 111. Differences in sequence read depth and pair insert size in X-ray irradiated *N. lolii* variant deletion mutant strains are shown in FIG. 112.

Results on sequence analysis for Ltm gene clusters are shown in FIG. 108. No deletions, large or small, were found in the coding or regulatory sequences of ltm gene clusters. No SNPs, insertions or translocations were found in the coding or regulatory sequences of ltm gene clusters.

Spectrum of Genome Sequence Changes Detected in the X-Ray Irradiated *N. lolii* Variant Strains FIG. 113 shows numbers of SNPs detected in genic regions of X-ray irradiated *N. lolii* variant deletion mutant strains. There are large differences in the number of SNPs detected in the X-ray irradiated *N. lolii* variant deletion mutant strains and compared to the control ST strain. All X-ray irradiated *N. lolii* variant deletion mutant strains have over double the number of SNPs per Mb across genic regions compared to the control ST strain. X-ray irradiated *N. lolii* variant deletion mutant strains have on average 6 SNPs per Mb, where the control ST strain has 2 SNPs per Mb.

FIG. 114 shows numbers of INDELs in genic regions of X-ray irradiated *N. lolii* variant deletion mutant strains. All X-ray irradiated *N. lolii* variant deletion mutant strains contain more indels in genic regions than the control ST strain. The difference in indel numbers between the X-ray irradiated *N. lolii* variant deletion mutant strains and the control ST strain is on average 134 indels per Mb. When grouped by irradiation treatment (i.e. irradiation dose applied and number of repeat irradiations) there appears to be a peak in number of indels at 10Gy*2 treatment, consistent with the results obtained in the SNP detection analysis.

FIG. 115 shows the spectrum of genome sequence changes in the form of deletions detected in X-ray irradiated *N. lolii* variant deletion mutant strains.

Table 49 shows examples of some of these genome sequence deletions detected in X-ray irradiated *N. lolii* variant deletion mutant strains.

TABLE 49

Deletions detected in genome sequences of X-ray irradiated *N. lolii* variant deletion mutant strains. Bold indicates deletions confirmed by changes in sequence read coverage. The remainder are potential transposon deletions.

| Strain | Radiation Treatment | Deletion |
|---|---|---|
| 123_20 | 30 Gy*2 | Contig00915 (268 bp) |
| 124_6 | 30 Gy*2 | Partial duplication |
| 139_6 | 30 Gy | Partial duplication |
| 144_16 | 30 Gy | |
| 145_15 | 30 Gy | Partial duplication |
| 1_35 | 10 Gy | Contig00831 (3.6 kb) |
| 4_7 | 10 Gy | |
| 7_22 | 10 Gy*2 | |
| 7_47 | 10 Gy*2 | Contig01131 (0.6 kb), contig01082 (4.2 kb), contig02985 (1 kb), contig02725 (83 bp), contig01095 (130 bp) |

The X-ray irradiated *N. lolii* variant deletion mutant strain #7_47, which was generated following two X-irradiation treatments at 10 Gy dose (10Gy*2) of *N. lolii* ST endophyte, had the greatest number of large deletions.

Annotation of Deleted Sequences in the Genomes of X-Ray Irradiated *N. lolii* Variant Deletion Mutant Strains X-Ray Irradiated *N. lolii* Variant Mutant Strain 1_35:

For the X-ray irradiated *N. lolii* variant mutant strain 1_35 the following deleted sequences in ST454Contig00831 contig with a ~4,400-8,000 bp length was detected, with this genome sequence region containing the following two predicted genes:

ST454contig00831_AUGUSTUS_gene_3318:6018 (847 letters)

1) ref |XP_386347.1| hypothetical protein FG06171.1 [*Gibberella* 660×0.0 gb|EAW12630.1|DUF500 domain protein [*Aspergillus* NRRL 1]; 253×9e-66, and ST454contig00831_AUGUSTUS_gene_3958:4728 (183 letters); and 2) gb|EAW13545.1| 2,3-cyclic-nucleotide 2-phosphodiesterase [*Aspergillus* 32×2.4

X-Ray Irradiated *N. lolii* Variant Mutant Strain 7_47:

For the X-ray irradiated *N. lolii* variant mutant strain 7_47 the following deleted sequences in ST454Contig01082, ST454Contig01131 and ST454Contig02985, with these genome sequence regions containing no predicted genes:

Query=ST454contig01082 length=9120 numreads=287 gb|AAA21442.1| putative poi polyprotein [*Magnaporthe grisea*] 145 1e-32

Query=ST454contig02985 length=2414 numreads=99 gb|AAA21442.1| putative pol polyprotein [*Magnaporthe grisea*] 92 2e-17

Mutagenesis Index of X-Ray Irradiated *N. Lolii* Variant Deletion Mutant Strains FIG. 116 shows SNPs and Indels per Mb in genic regions of X-ray irradiated *N. lolii* variant deletion mutant strains derived from X-ray irradiation of *N. lolii* at different levels of irradiation. Strain 1_35 has a 3.6 kb deletion; Strain 7_47 has 3 deletions (4.2 kb, 1 kb, 0.6 kb in length). Strain 124_6 has a partial duplication. Strains 139_6 and 145_15 have partial duplications.

Given that ST endophyte has approximately 443.5 genes per Mb, using 10Gy*2 treatment, the expected rate of SNP/INDEL occurrence is 0.33 per gene in the genome.

Summary

X-ray irradiated *N. lolii* variant deletion mutant strains were analysed for many types of genome sequence variation i.e. deletions, SNPs, INDELs, inversions and translocations. SNPs, INDELs, deletions and duplications were identified in the genome survey sequences of X-ray irradiated *N. lolii* variant deletion mutant strains. There was an apparent peak in number of SNPs and INDELs in X-ray irradiated *N. lolii* variant deletion mutant strains recovered from administering 10Gy*2 X-ray irradiation treatment to *N. lolii* ST endophyte. The X-ray irradiated *N. lolii* variant deletion mutant strain 7_47 had 3 large deletions. It was demonstrated that this mutagenesis method based on X-ray irradiation can be used to create novel designer *Neotyphodium* endophyte strains, and enabled:

5,000 X-ray irradiated *N. lolii* variant endophyte strains derived from X-ray irradiation of ST *N. lolii* endophyte were screened;

140 putative X-ray irradiated *N. lolii* variant endophyte mutant strains were identified;

9 X-ray irradiated *N. lolii* variant endophyte mutant strains were subjected to antifungal bioassays;

9 X-ray irradiated *N. lolii* variant endophyte mutant strains were subjected to in vitro growth assays;

9 X-ray irradiated *N. lolii* variant endophyte mutant strains were subjected to genome survey sequencing;

2 X-ray irradiated *N. lolii* variant endophyte mutant strains with gene deletions (1_35 and 7_47) were identified; and 3 X-ray irradiated *N. lolii* variant endophyte mutant strains with gene duplications (124_6, 139_6 and 145_15) were identified.

In Planta Isogenic Inoculation in Perennial Ryegrass with X-Ray Irradiated *N. lolii* Variant Endophyte Mutant Strains

TABLE 50

Isogenic inoculation of perennial ryegrass genotypes (IMP04 and TOL03) with X-ray irradiated *N. lolii* variant endophyte mutant strains. Numbers indicate number of perennial ryegrass plants of the two genotypes subjected to isogenic inoculation with the different X-ray irradiated *N. lolii* variant endophyte mutant strains (i.e. ST-IRM 139-6, ST-IRM 145-15, ST-IRM 144-16, ST-IRM 1-35 and ST-IRM 7-47) and control ST endophyte strain.

| Plant Genotype | ST-IRM 139-6 | ST-IRM 145-15 | ST-IRM 144-16 | ST-IRM 1-35 | ST-IRM 7-47 | ST |
|---|---|---|---|---|---|---|
| IMP04 | 30 | 25 | 30 | 30 | 30 | 25 |
| TOL03 | 25 | 0 | 25 | 30 | 30 | 20 |

Metabolic Profiling of Colchicine Treatment-Derived NEA12dh and X-Ray Irradiation-Derived *Neotyphodium* Variant Endophyte Strains Results from metabolic profiling of colchicine treatment derived NEA12dh endophyte variant strains is shown in FIG. 117.

Results from metabolic profiling of X-ray irradiation treatment derived *N. lolii* ST endophyte variant strains is shown in FIG. 118.

The following endophytes were grown on PDB for 3 weeks:
Control *N. lolii* ST endophyte strain
X-ray irradiation treatment derived *N. lolii* ST endophyte variant strain 4-7
X-ray irradiation treatment derived *N. lolii* ST endophyte variant strain 139-6
X-ray irradiation treatment derived *N. lolii* ST endophyte variant strain 144-16
X-ray irradiation treatment derived *N. lolii* ST endophyte variant strain 145-15 and subjected to metabolic profiling using LCMS on corresponding
1. Liquid filtrate
2. Mycelial extract The X-ray irradiation treatment derived *N. lolii* ST endophyte variant strains could be readily distinguished from control *N. lolii* ST strain using mycelia extracts or filtrates alone.

Example 16—Method for Large-Scale Generation of Grass-Endophyte Symbiota (Artificial Seeds)

The objective of the work was to develop an efficient, robust and low-cost method for large-scale production of grass endophyte symbiota. The method should be:
a) applicable to inoculation of 10s-100s of endophyte in 100s-1000s of grass genotypes;
b) applicable to perennial ryegrass, tall fescue and *Brachiaria*; and
c) applicable to inoculation of novel and designer endophytes with de novo generated genetic variation [i.e. induced mutagenesis (ionizing radiation, colchicine), targeted mutagenesis, transgenesis, cisgenesis, intragenesis, etc.].

The method should further enable next-generation ab initio molecular breeding, selection and evaluation of grass-endophyte symbiota [rather than breeding and selection of grass host followed by endophyte inoculation and symbiota evaluation only].

The experimental strategies—and corresponding experimental steps—implemented include:

1. Large-scale perennial ryegrass seed-derived embryo isolation and artificial seed production
    A. Develop an efficient, low-cost, large-scale seed surface-sterilization method;
    B. Develop an efficient, low-cost, large-scale seed-derived embryo isolation method;
    C. Develop an efficient, low-cost, large-scale artificial seed production method;
    D. Test germination frequency and germination stages of artificial seeds;
    E. Assess endophyte presence in seedlings derived from artificial seeds generated with embryos isolated from endophyte-plus seeds;
2. Large-scale endophyte inoculation into perennial ryegrass artificial seeds
    F. Develop an efficient, low-cost, large-scale endophyte inoculation method for artificial seeds [based on seed-derived embryo inoculation with endophyte mycelium followed by artificial seed production including double/multiple coating (inner layer plus endophyte, outer layer as 'pseudo-aleurone/endosperm') of artificial seeds]; and
    E. Assess endophyte presence in seedlings derived from artificial seeds generated with embryos isolated from endophyte-minus seeds inoculated with novel endophytes.

Large-Scale Perennial Ryegrass Seed-Derived Embryo Isolation and Artificial Seed Production Seed Surface Sterilization Method The seed surface sterilization method implemented includes the following steps:
Day 1: seeds were soaked in 10% sulphuric acid O/N
Day 2: treated with 10% Domestos for 20 min and stored at 24 C after wash with distilled sterile water
Day 3: treated with 10% Domestos for 20 min and stored at 24 C after wash with distilled sterile water, followed by embryo isolation [see B) below].

Four independent experiments were conducted with 200 seeds each.

No bacterial or fungal contamination was observed.

Embryo Isolation Method

Based on the successful seed sterilization method [see A) above], 1,000 ryegrass seed-derived embryos can be isolated by one person within 4 hours.

Artificial Seed Production Method

Ca-Alginate Coating of Perennial Ryegrass Embryos into Artificial Seeds i) Coating with Ca-Alginate Matrix without Added Nutrients
   For the Ca-alginate coating of perennial ryegrass embryos into artificial seeds using a coating with Ca-alginate matrix without added nutrients, the following steps were undertaken:
   Embryos were freshly isolated and mixed with 3% sodium alginate solution
   Alginate drops were placed into 50 mM calcium chloride solution while stirring at 60 rpm. Each drop contains one embryo.
   Artificial seeds were collected after 15 min stirring and washed with sufficient distilled sterile water
   Artificial seeds were placed on germination medium MS or MS+1 mg/L BAP.

FIG. 119 shows artificial seeds generated through Ca-alginate coating of perennial ryegrass embryos using a coating with Ca-alginate matrix without added nutrients.

ii) Coating with Ca-Alginate Matrix with Added Nutrients
   For the Ca-alginate coating of perennial ryegrass embryos into artificial seeds using a coating with Ca-alginate matrix with added nutrients, the following steps were undertaken:

Embryos were freshly isolated and mixed with 3% sodium alginate in modified MS medium consisting of MS (without CaCl2)+750 mg/L glutamine+5 µM CuSO$_4$+1.95 g/L MES Alginate drops (containing individual embryos) were placed in 50 mM calcium chloride solution while stirring at 60 rpm.

Each drop contains a single seed-derived isolated embryo.

Artificial seeds were collected after 15 min stirring and thoroughly washed with distilled sterile water medium.

Artificial seeds were placed on MS medium plates for germination.

iii) Coating with Coloured Ca-Alginate Matrix

For the Ca-alginate coating of perennial ryegrass embryos into artificial seeds using a coating with coloured Ca-alginate matrix with added nutrients, the following steps were undertaken:

Embryos were freshly isolated and mixed with 3% sodium alginate in modified MS medium consisting of MS (without CaCl2)+750 mg/L glutamine+5 µM CuSO$_4$+1.95 g/L MES Different food dyes [i.e. 10 µL/ml Queen Green (90610) or Queen Pink (92330)] were added to the sodium alginate coating solution to colour coating matrix thus establishing basis to demonstrate potential for multi-layer coating.

Alginate drops (containing individual embryos) were placed in 50 mM calcium chloride solution while stirring at 60 rpm.

Each drop contains a single seed-derived isolated embryo.

Artificial seeds were collected after 15 min stirring and thoroughly washed with distilled sterile water medium.

Artificial seeds were placed on MS medium plates for germination.

FIG. 120 shows Ca-alginate coating of perennial ryegrass embryos into artificial seeds using coating with coloured Ca-alginate matrix.

iv) Coating with Multiple Ca-Alginate Matrix Layers

For the Ca-alginate coating of perennial ryegrass embryos into artificial seeds using a coating with multiple Ca-alginate matrix layers, the following steps were undertaken:

Embryos were freshly isolated and mixed with 3% sodium alginate in modified MS medium [consisting of MS (without CaCl$_2$)+750 mg/L glutamine+5 µM CuSO$_4$+1.95 g/L MES] as the first coating layer (layer A) to make artificial seeds.

Alginate drops (containing individual embryos) were placed in 50 mM calcium chloride solution while stirring at 60 rpm. Each drop contains a single seed-derived isolated embryo.

Artificial seeds coated with layer A were collected after 15 min—stirring and thoroughly washed with distilled sterile water medium. The average diameter of the artificial seed freshly coated with layer A is 4 mm. Artificial seeds coated with layer A were placed in Petri dish and allowed to air-dry for 1-2 hours in a laminar flow cabinet. The diameter of the air-dried artificial seed coated with layer A is 2 mm.

Air-dried artificial seeds coated with layer A were mixed with 3% sodium alginate in modified MS medium [consisting of MS (without CaCl2)+750 mg/L glutamine+5 µM CuSO$_4$+1.95 g/L MES] coloured with food dye [i.e. 10 µL/ml Queen Green (90610)] as the second coating layer (layer B) to make double-coated artificial seeds; following the same procedure.

FIG. 121 shows Ca-alginate coating of perennial ryegrass embryos into artificial seeds using coating with multiple Ca-alginate matrix layers.

FIG. 122 show Ca-alginate coating of perennial ryegrass embryos into artificial seeds using coating with multiple Ca-alginate matrix layers. Freshly isolated seed-derived embryos of perennial ryegrass are individually placed in wells of a) 96-well or b) 384-well plates. With the aid of a disposable syringe sodium alginate solution is added to the individual wells and single embryos in alginate solutions are loaded in the syringe. With the aid of the syringe individual embryos coated with alginate solution are dropped into polymerising CaCl$_2$ solution under agitation for production of artificial seeds. The use of 96-well plate is preferred over the 384 well plate for production of artificial seeds of perennial ryegrass.

Assessing Germination Frequency of Artificial Seeds

In order to assess germination frequency of artificial seeds, the following steps were undertaken:

Germination of Seeds, Embryos and Artificial Seeds of Perennial Ryegrass Cv. Bronsyn E$^-$ (Endophyte Free, 2668 Seed Batch)

Seed germination frequency was comparatively assessed for (FIG. 123):

a) Original seeds: 1% germination frequency on filter paper b) Surface-sterilized seeds: 10% germination frequency on filter paper c) Isolated embryos: 48% germination frequency on germination medium d) Artificial seeds (with germination medium): 40% germination frequency on MS medium Germination of Seeds, Embryos and Artificial Seeds of Perennial Ryegrass Cv. Bronsyn E+ (Endophyte Plus, 2667 Seed Batch)

Seed germination frequency was comparatively assessed for (FIG. 124):

a) Original seeds: 10% germination frequency on filter paper b) Surface-sterilized seeds: 30% germination frequency on filter paper c) Isolated embryos: 90% germination frequency on germination medium d) Artificial seeds (with germination medium): 81% germination frequency on MS medium FIG. 125 shows germination of artificial seeds and development of artificial-seed derived seedlings in perennial ryegrass.

Assessing Endophyte Presence in Seedlings Derived from Artificial Seeds

In order to assess endophyte presence in seedlings derived from artificial seeds, the following experiments were undertaken:

Endophyte Presence in Seedlings Derived from Seeds and Artificial Seeds of Perennial Ryegrass Seed Cv. Bronsyn E+(Endophyte Plus, 2667 Seed Batch)

Twenty seedlings of Bronsyn E$^+$ (2667) seeds germinated on filter paper were transferred to soil.

Twenty five seedlings from germinated artificial seeds generated with Bronsyn E plus (2667) seed-derived embryos were transferred to soil. The embryos in artificial seeds were sterilized using 10% H$_2$SO$_4$ overnight treatment.

Following 6 week grow-out of seedlings derived from seeds and artificial seeds, endophyte presence was assessed based on endophyte-specific SSR test.

Twenty seedlings of Bronsyn E plus (2667; containing ST endophyte) seeds germinated on filter paper were transferred to soil, leading to 13 of 19 seedlings (68%) testing positive for ST endophyte presence in the endophyte-specific SSR test.

Twenty five seedlings from germinated artificial seeds generated with Bronsyn E plus (2667) seed-derived embryos were transferred to soil. The embryos in artificial seeds were sterilized using 10% $H_2SO_4$ overnight treatment, leading to 19 of 23 seedlings (83%) testing positive for ST endophyte in the endophyte-specific SSR test, clearly indicating that the methods for seed surface sterilization, large-scale embryo isolation, and artificial seed production with Ca-alginate coating do not negatively affect viability of a resident endophyte.

Large-Scale Inoculation of Endophytes in Perennial Ryegrass Artificial Seeds

Different methods for the large-scale inoculation of endophtyes in perennial ryegrass artificial seeds were developed, with examples of methods 1 to 3 described below:

Inoculation of Isolated Seed-Derived Embryos with Endophyte Mycelium and Production of Endophyte-Infected Artificial Seeds in Perennial Ryegrass Freshly isolated seed-derived embryos of perennial ryegrass are individually placed in wells of a) 96-well and b) endophyte mycelium suspension added to individual wells and allowed to partly air-dry under laminar flow prior to c) production of artificial seeds coated with Ca-alginate layer (FIG. 126).

Method 1: Direct Inoculation of Isolated Embryos with Endophyte Suspension Prior to Ca-Alginate Coating Method 1, inoculation of isolated seed-derived embryos with endophyte mycelium and production of endophyte-infected artificial seeds in perennial ryegrass, is based, on direct inoculation of isolated embryos with endophyte suspension prior to Ca-alginate coating as follows:

Freshly isolated embryos of perennial ryegrass are incubated with endophyte suspension (1/16 dilution) for 30 mins at RT in individual wells of 96-well plates.

Inoculation suspension is removed from well and inoculated embryos are allowed to partly air-dry on filter paper disks.

Artificial seeds are produced (FIG. 127) with endophyte-inoculated embryos with 3% sodium alginate-containing modified MS growth medium [MS (without $CaCl_2$) 750 mg/L glutamine+5 µM $CuSO_4$+1.95 g MES+1 mg/l BAP].

Artificial seeds are allowed to germinate on MS medium for germination.

Freshly isolated embryos of perennial ryegrass are directly inoculated with endophyte suspension (1/8 dilution), partly air-dried and then coated with Ca-alginate in individual wells of 96-well plates.

Artificial seeds from perennial ryegrass directly inoculated with endophyte and then coated with Ca-alginate layer are able to germinate on MS germination medium (FIG. 128).

Method 2: Direct Coating of Isolated Embryos with Endophyte-Containing Ca-Alginate Layer Method 2, inoculation of isolated seed-derived embryos with endophyte mycelium and production of endophyte-infected artificial seeds in perennial ryegrass, is based on direct coating of isolated embryos with endophyte-containing Ca-alginate layer as follows:

Embryos of perennial ryegrass are freshly isolated in endophyte suspension (1/16 dilution) in individual wells of 96-well plates.

Two-fold concentration sodium alginate (6%) modified MS medium [MS (without $CaCl_2$)+750 mg/L glutamine+5 µM $CuSO_4$+1.95 g MES+1 mg/l BAP] is added to the individual wells to coat embryos with an endophyte-containing alginate layer Artificial seeds are produced with endophyte-layer coated embryos (FIG. 129).

Artificial seeds are allowed to germinate on MS medium for germination

Embryos of perennial ryegrass are freshly isolated and coated with endophyte suspension (1/8 or 1/16 dilutions) with Ca-alginate then added to generate an endophyte-containing alginate layer coating the embryos in individual wells of 96-well plates.

Following culture, endophyte out-growth is observed from the endophyte-containing alginate layer used to coat the isolated embryos of perennial ryegrass (irrespectively of endophyte suspension dilution rate used; FIG. 130) demonstrating viability of the endophyte included in the Ca-alginate coating layer.

Method 3: Double-Coating of Artificial Seeds Generated from Endophyte Inoculated Isolated Embryos Method 3, inoculation of isolated seed-derived embryos with endophyte mycelium and production of endophyte-infected artificial seeds in perennial ryegrass, is based on double-coating of artificial seeds generated from endophyte-inoculated isolated embryos as follows:

Freshly isolated embryos of perennial ryegrass are coated with an endophyte suspension (1/16 dilution), mixed with alginate[6% Ca-alginate in modified MS medium (without $CaCl_2$)+750 mg/L glutamine+5 µM $CuSO_4$+1.95 g MES+1 mg/l BAP] to generate a first coating layer containing endophytes in individual wells of 96-well plates.

Artificial seeds with a first endophyte-containing alginate layer coating freshly isolated embryos of perennial ryegrass are blot-dried on filter paper in laminar air flow for 30 mins and then coated with a second alginate layer of 3% Ca-alginate without any nutrients.

Double-coated artificial seeds with endophyte-containing layer coated embryos of perennial ryegrass are then germinated on MS medium Second coating with nutrient deprived medium of endophyte-inoculated artificial seeds aims to reduce endophyte out-growth during germination and restrict endophyte growth in close proximity to isolated perennial ryegrass embryo (FIG. 131).

Artificial seeds with a first endophyte-containing alginate layer coating freshly isolated embryos of perennial ryegrass are blot-dried on, filter paper in laminar air flow for 30 mins and then coated with a second alginate layer of 3% Ca-alginate without any nutrients.

Endophyte growth is mainly restricted to inner alginate coating layer for a period of up to 3 weeks (FIG. 132).

Embryos of perennial ryegrass are freshly isolated directly in endophyte suspension (1/8 dilution), then partly air-died and coated with a first alginate layer [3% Ca-alginate in modified MS medium (without $CaCl_2$)+750 mg/L glutamine+5 µM $CuSO_4$+1.95 g MES+1 mg/l BAP] in individual wells of 96-well plates.

Artificial seeds with directly endophyte-inoculated embryos of perennial ryegrass are stored at 4 C overnight and then coated with a second alginate layer of 3% Ca-alginate without any nutrients.

Double-coated artificial seeds with directly endophyte-inoculated embryos of perennial ryegrass are then germinated on MS medium.

Double-coated artificial seeds with directly endophyte-inoculated embryos of perennial ryegrass germinated on MS medium show germination rates comparable to the original seed batch used for embryo isolation (FIG. 133).

Assessing Endophyte Presence in Seedlings Derived from Artificial Seeds with Seed-Derived Embryos Inoculated with Novel Endophytes In order to assess endophyte presence in seedlings derived from artificial seeds with seed-derived embryos inoculated with novel endophytes (e.g. NEA11) using Method 1, the following experiment was undertaken:

Endophyte Presence in Seedlings Derived from Artificial Seeds Produced with Embryos from Perennial Ryegrass Seed Cv. Bronsyn E– (Endophyte Minus, 2668 Seed Batch) Inoculated with Novel Endophyte NEM11

Following 6 week grow-out of seedlings derived from artificial seeds, endophyte presence was assessed based on endophyte-specific SSR test.

Twenty-three seedlings from germinated artificial seeds generated with Bronsyn E minus (2668) seed-derived embryos inoculated with NEA11 using Method 1 were transferred to soil. 6 of 23 seedlings (i.e. 26%) tested positive for NEA11 endophyte presence in the endophyte-specific SSR test demonstrating the establishment of symbiota (Table 51). Endophyte presence in symbiota established from germinated artificial seeds generated with perennial ryegrass seed-derived embryos inoculated with novel endophyte NEA11 using Method 1 was confirmed following 3 months after transfer to soil.

TABLE 51

Assessing Endophyte Presence in Seedlings Derived from Artificial Seeds with Seed-Derived Embryos Inoculated with Novel Endophytes Large-Scale Inoculation of Designer Endophytes in Perennial Ryegrass Artificial Seeds

| | SSR Marker | | | | | | |
|---|---|---|---|---|---|---|---|
| | NLESTA1QA09 | | NLESTA1NG03 | | NLESTA1CC05 | | |
| Seedling | Allele 1 | Allele 2 | Allele 1 | Allele 2 | Allele 1 | Allele 2 | Endophyte detected |
| 2668_14 | 153 | 184 | 226 | | 167 | | NEA11 |
| 2668_15 | 153 | 184 | 226 | | 167 | | NEA11 |
| 2668_1 | 153 | 184 | 226 | | 167 | | NEA11 |
| 2_2 | 153 | 184 | 226 | | 167 | | NEA11 |
| 2668 Bbl | 153 | 184 | 226 | | 167 | | NEA11 |
| 2668_13 | 153 | 184 | 226 | | 167 | | NEA11 |

Large-scale inoculation of designer endophtyes derived from induced mutagenesis through colchicine-treatment (e.g. NEA12dh17) or derived from X-ray mutagenesis (e.g. IRM1-35) in perennial ryegrass artificial seeds is carried out using methods 1 to 3 described above.

Freshly isolated embryos of perennial ryegrass are incubated with designer endophyte (e.g. NEA12dh17, IRM1-35) suspension (1/16 dilution) for 30 mins at RT in individual wells of 96-well plates.

Inoculation suspension is removed from well and inoculated embryos are allowed to partly air-dry on filter paper disks.

Artificial seeds are produced with designer endophyte-inoculated embryos with 3% sodium alginate-containing modified MS growth medium [MS (without $CaCl_2$)+750 mg/L glutamine+5 µM $CuSO_4$+1.95 g MES+ 1 mg/l BAP].

Artificial seeds are allowed to germinate on MS medium for germination.

Freshly isolated embryos of perennial ryegrass are directly inoculated with designer endophyte (e.g. NEA12dh17, IRM1-35) suspension (1/8 dilution), partly air-dried and then coated with Ca-alginate in individual wells of 96-well plates.

Artificial seeds from perennial ryegrass directly inoculated with designer endophytes (e.g. NEA12dh17, IRM1-35) and then coated with Ca-alginate layer are able to germinate on MS germination medium leading to the establishment of symbiota. Designer endophyte presence and identity in the symbiota generated following large-scale inoculation of designer endophtyes derived from induced mutagenesis through colchicine-treatment (e.g. NEA12dh17) or derived from X-ray mutagenesis (e.g. IRM1-35) in perennial ryegrass artificial seeds is demonstrated using an endophyte-specific SSR test.

Large-Scale Inoculation of Transgenic Endophytes in Perennial Ryegrass Artificial Seeds Large-scale inoculation of transgenic endophtyes derived from genetic transformation of NEA12 endophyte with plasmid containing a chimeric gene for expression of the DsRed fluorescent marker gene (e.g. NEA12-DsRed) in perennial ryegrass artificial seeds is carried out using method 1 described above.

Freshly isolated embryos of perennial ryegrass are incubated with transgenic endophyte (e.g. NEA12-DsRed) suspension (1/16 dilution) for 30 mins at RT in individual wells of 96-well plates.

Inoculation suspension is removed from well and inoculated embryos are allowed to partly air-dry on filter paper disks.

Artificial seeds are produced with transgenic endophyte-inoculated embryos with 3% sodium alginate-containing modified MS growth medium [MS (without $CaCl_2$)+750 mg/L glutamine+5 µM $CuSO_4$+1.95 g MES+1 mg/l BAP].

Artificial seeds are allowed to germinate on MS medium for germination.

Freshly isolated embryos of perennial ryegrass are directly inoculated with transgenic endophyte (e.g. NEA12-DsRed) suspension (1/8 dilution), partly air-dried and then coated with Ca-alginate in individual wells of 96-well plates.

Artificial seeds from perennial ryegrass directly inoculated with transgenic endophyte (e.g. NEA12-DsRed) and then coated with Ca-alginate layer are able to germinate on MS germination medium leading to the establishment of symbiota with transgenic endophytes. Transgenic endophyte presence and identity in the symbiota generated following large-scale inoculation of transgenic endophtye (e.g. NEA12-DsRed) in perennial ryegrass artificial seeds is demonstrated using an endophyte-specific SSR and transgene-specific PCR test.

Large-Scale Inoculation of Novel Endophytes in Tall Fescue Artificial Seeds

Large-scale inoculation of novel endophtyes from tall fescue (e.g. NEA17, NEA19, NEA20) in tall fescue artificial seeds is carried out using method 1 described above. Freshly isolated embryos of tall fescue are incubated with novel fescue endophytes (e.g. NEA17, NEA19, NEA20) suspension (1/16 dilution) for 30 mins at RT in individual wells of 96-well plates.

Inoculation suspension is removed from well and inoculated embryos are allowed to partly air-dry on filter paper disks.

Artificial seeds are produced with novel endophyte-inoculated embryos with 3% sodium alginate-containing modified MS growth medium [MS (without $CaCl_2$)+750 mg/L glutamine+5 µM $CuSO_4$+1.95 g MES+1 mg/l BAP].

Artificial seeds are allowed to germinate on MS medium for germination.

Freshly isolated embryos of tall fescue are directly inoculated with novel fescue endophytes (e.g. NEA17, NEA19, NEA20) suspension (1/8 dilution), partly air-dried and then coated with Ca-alginate in individual wells of 96-well plates.

Artificial seeds from tall fescue directly inoculated with novel fescue endophytes (e.g. NEA17, NEA19, NEA20) and then coated with Ca-alginate layer are able to germinate on MS germination medium leading to the establishment of symbiota. Novel endophyte presence and identity in the symbiota generated following large-scale inoculation of novel fescue endophtyes (e.g. NEA17, NEA19, NEA20) in tall fescue artificial seeds are demonstrated using an endophyte-specific SSR test.

Example 17—Method for Selection of Stable Symbiota

Generational Stability and Viability of Perennial Ryegrass Endophytes

Experience within the forage genetic supply industry (technically orientated pasture plant seed breeding commercial companies) has created a series of requirements for stability of endophyte presence in grass crops grown from certified seed batches. In terms of inter-generational stability (that is, the presence of endophyte in a seed batch from one generation of varietal multiplication as compared to its offspring generation), the maximum level of loss that can be generated is 5%, but ideally not more than 2-3% loss per generation. Furthermore, due to requirements for warehouse storage of large-scale seed batches, the endophyte must be stable and viable (allowing recolonisation of the germinated seeding) in seed for at least 3 years after harvest.

Experimental strategies that can be applied to identify and predict intergenerational stability and viability include:

The use of molecular genetic marker technology, such as endophyte-specific simple sequence repeat (SSR) assays, to identify the presence or absence of endophyte on the basis of a diagnostic PCR test (presence versus absence, and characteristic size of generated PCR product). This test is appropriate to track changes in stability in plant populations from successive populations. However, it does not confirm viability in the seed.

Quantitative PCR (qPCR) is a method for detection of endophyte-specific gene expression, and is hence appropriate for retrospective confirmation of endophyte viability in seed, given germination of seedlings.

Accelerated ageing (AA) is an artificial method, based on application of specific temperature and relative humidity (RH) conditions (Gundel et al., 2009), that can mimic the effects of longer-term storage on endophyte viability over a short-period of time (Happ et al., 1993). AA tests are hence suitable to differentiate seed quality among commercially acceptable perennial ryegrass seed lots (Wang et at, 2004) in order to provide a predictive assay within a time-frame suitable for commercial decisions.

The objective of the study in question was therefore to develop an AA method for seed of grass-endophyte symbiota, which can be applied to merit ranking of endophytes based on their predicted viability in stored seed. The method is also applicable for selection of stable symbiota with long-term viable endophytes for deployment as a tool in next-generation ab initio molecular breeding, selection and evaluation of grass-endophyte symbiota [rather than breeding and selection of grass host followed by endophyte inoculation and symbiotum evaluation only]. The method is applicable to symbiota of both perennial ryegrass and tall fescue [different host genetic backgrounds; different endophytes].

The AA method was developed using a range of humidity levels and treatment times of accelerated ageing followed by different storage times and conditions (summarised in Table 52), as applied to a number of novel endophyte-grass associations (different endophytes i.e. ST, AR1, NEA3, NEA2, NEA6 and AR37; Table 52) in a single genetic background (i.e. cv. Bronsyn).

TABLE 52

Conditions for accelerated ageing

| Experimental stage | Condition | Variation in condition | | | |
|---|---|---|---|---|---|
| Accelerated Ageing | Temperature (° C.) | 42° C. | | | |
| | Humidity level (%) | 100% | 80% | Control | |
| | Time (days) | 4 days | 7 days | 0 days | |
| Storage | Temperature (° C.) | 15-25° C. | 40° C. | 3-5° C. | −20° C. |
| | Time (months) | 0 days (control) | 8 | 14 | ongoing |

FIG. 134 shows an outline of the AA process. In summary:
Following treatment:
  400 seed (100 per replication) per treatment were germinated without storage
  400 seed (100 per replication) per treatment were placed in storage
Following 14 days of germination, seedlings were counted and the germination rate was recorded
Seedlings were grown for 8 weeks prior to assessing endophyte presence

TABLE 53

Endophyte strains inoculated into sub-populations (non-isogenic) of perennial ryegrass cv. Bronsyn E = Ergovaline; L = Lolitrem B; P = Peramine

| Endophyte strain | Type | Origin | Alkaloids |
|---|---|---|---|
| ST | Wild type | | L + E + P |
| NEA3 | Novel | Agriseeds | E + P |
| NEA2 | Novel | Agriseeds | E + P |

TABLE 53-continued

Endophyte strains inoculated into sub-populations
(non-isogenic) of perennial ryegrass cv.
Bronsyn E = Ergovaline; L = Lolitrem B; P = Peramine

| Endophyte strain | Type | Origin | Alkaloids |
| --- | --- | --- | --- |
| NEA6 | Novel | Agriseeds | E + P |
| AR1 | Novel | AgResearch | P |
| AR37 | Novel | AgResearch | Janthitrems |
| E− | | | |

FIG. 135 shows the results of seed germination rate of perennial ryegrass cv. Bronsyn containing different endophytes after AA treatment of seed followed by seed storage.
These results indicated that:
There was no effect of endophyte presence on symbiotum seed viability [see control treatment, no AA]
Accelerated ageing at high humidity [i.e. 80% HR] and storage at high temperature [i.e. 40 C] has the highest impact on germination [i.e. loss of germination at 24 months in storage].

FIG. 136 shows the corresponding data on endophyte viability in seed from perennial ryegrass cv. Bronsyn with different endophytes after AA treatment of seed followed by seed storage.
These results indicated that:
AA [i.e. 80% RH for 7 days] is highly informative for prediction of endophyte viability in stored seed
Endophyte viability declines slightly during medium term storage [i.e. 14 months] at room temperature
Seed storage at high temperature [i.e. 40 C] leads to a rapid decline in endophyte viability
Viability of the novel endophytes NEA3, NEA2 and NEA6 is lower than for ST, AR1 and AR37

The study was then extended to assess applicability of the AA method for prediction of endophyte viability in stored seed for different endophytes (i.e. ST, NEA10, NEA 11, NEA12, E1 and AR1) in different host genetic backgrounds (i.e. cvs. Bronsyn, Alto, Trojan and Bealey) (FIG. 190, Table 55).

TABLE 55

Variations in condition for accelerated ageing

| Experimental stage | Condition | Variation in condition | | |
| --- | --- | --- | --- | --- |
| Accelerated Ageing | Temperature (° C.) | 42° C. | | |
| | Humidity level (%) | 100% | 80% | Control |
| | Time (days) | 4 days | 7 days | 0 days |

FIG. 137 shows the seed germination rates of symbiota representing different endophytes in different host genetic backgrounds after accelerated ageing treatment of seed.

FIG. 138 shows endophyte viability values for different endophytes in different host genetic backgrounds after accelerated ageing treatment of seed.
These results indicated that:
AA treatment has a high impact on endophyte viability.
AA treatment at 100% RH for 4-7 days is highly informative for prediction of endophyte viability in seed.
AA allows to ranking of endophytes based on viability across a range of host distinct genetic backgrounds.
The rank order of viability ranking among novel endophytes is E1<NEA10<NEA11 and NEA12.

FIG. 139 shows the endophyte viability values of different endophytes in different host genetic backgrounds after accelerated ageing treatment of seed.
AA treatment [i.e. 100% RH for 4 d or 7 d] was hence demonstrated to reduce endophyte viability thus allowing for its potential use as a selection tool for stable associations.
These results demonstrate that AA treatment can be used for selection of stable symbiota generated by artificial inoculation.
AA treatment offers the opportunity to be applied as a selection tool for stability of symbiota
AA treatment [i.e. 100% RH for 4-7 days] reduces endophyte viability, and so can be used for highly effective counter-selection against unstable associations that would prove to be problematic in commercial practice.
AA treatment permits symbiota to be ranked based on their stability
Identification or selection of stable symbiota was demonstrated for the following combinations: NEA10 in Alto, NEA11 in Bealey, NEA12 in Trojan and in Alto.

The AA protocol is extended to seed of tall fescue-endophyte associations, by extension of the protocol for prediction of host-endophyte association viability that was developed for perennial ryegrass seed; including testing of multiple fescue endophytes (AR542 [MaxP™/MaxQ™/ArkPlus™]; E34; KY31) in one or more tall fescue genetic backgrounds. Conditions for AA are described in Table 56 and tall fescue-endophyte symbiota evaluated are described in Table 57.

TABLE 56

Comparison of accelerated ageing and storage

| Experimental stage | Condition | Variation in condition | | | |
| --- | --- | --- | --- | --- | --- |
| Accelerated Ageing | Temperature (° C.) | 42° C. | | | |
| | Humidity level (%) | 100% | 80% | Control | |
| | Time (days) | 4 days | 7 days | 0 days | |
| Storage | Temperature (° C.) | 15-25° C. | 40° C. | 3-5° C. | −20° C. |
| | Time (months) | 0 (control) | 6 | 12 | ongoing |

TABLE 57

Tall fescue-endophyte symbiota subjected to
treatments for accelerated ageing and storage

| Grass Host | Endophyte |
| --- | --- |
| Quantum II | Max-P |
| Bar Optima | E34 |
| Jesup | Max-Q |
| Kentucky 31 | KY31 |

In conclusion:
A method for AA treatment [i.e. 80%-100% RH for 4-7 days] was established.
The method allowed prediction of endophyte viability in stored seed (based on a range of endophytes assessed in single and different host genetic backgrounds).
The method permitted merit ranking of novel endophytes according to predicted viability in stored seed (based on a range of endophytes assessed in single host genetic background).

The method permitted selection and ranking of symbiota according to stability.

Example 18—Method for Rapid Endophyte Viability Assessment

Objective:

The objective of the work was to develop a fast, reliable and low-cost method for determining endophyte viability in perennial ryegrass seed. The corresponding assay requirements were defined as follows.

Assay Requirements:
1. Rapid determination—3 to 5 day-old seedlings
2. Robust and reliable
3. Sensitive enough to use from single seed to seed batches
4. Specific to *Neotyphodium* endophytes (i.e. does not detect other fungi)
5. Detects live endophyte only A design for an early endophyte gene expression-based TaqMan assay is illustrated in FIG. 186.

The steps in the assay design were as follows:
a) Transcriptome sequence data available for Bronsyn +/−ST (6 week old tillers) plants were used to identify candidate endophyte-specific genes expressed in planta, through BLAST sequence analysis of data against database containing endophyte, other fungi, *Brachypodium* gene sequences;
b) Five endophyte-specific genes expressed in planta (6 week old tillers of perennial ryegrass plants from Bronsyn) were identified—LtmJ and 4 uncharacterised proteins (7490, 8263, 0005, 2232);
c) Primers were designed for the TaqMan assay as follows:
   DNA primers and probe—both dead and live endophyte samples will amplify
   RNA primers and probe—only live, viable endophyte samples will amplify
   Primers for Bronsyn GAPDH plant gene for seed viability assessment
   DNA primers and probe—both viable and unviable seed will amplify
   RNA primers and probe—only viable seeds will amplify FIG. 140 shows primers designed for TaqMan assay.

TaqMan Primer Functionality

TaqMan primer functionality was tested on samples from:
6 week-old tillers of Bronsyn+ST
6 week-old tillers of Bronsyn endophyte free as negative control
ST mycelium from in vitro endophyte culture as positive control to enable addressing the following experimental hypotheses:
a) Can the endophyte-specific transcripts [i.e. LtmJ and 4 uncharacterised proteins (7490, 8263, 0005 and 2232)] be detected in separately extracted DNA and RNA samples of ST endophyte mycelium?
b) Can the plant-specific gene [i.e. GAPDH] transcript be detected in samples of separately extracted RNA and DNA of perennial ryegrass leaf material?
c) Can endophyte-specific transcripts [i.e. LtmJ and 4 uncharacterised proteins (7490, 8263, 0005, 2232)] be detected in samples of separately extracted RNA and DNA from endophyte-infected perennial ryegrass [Bronsyn+ST] leaf material?

FIG. 141 shows TaqMan primer functionality test for the endophyte-specific gene LtmJ
There was No RNA in ST culture as expected
Only expressed in planta.
FIG. 142 shows TaqMan primer functionality test for the endophyte-specific gene 7490
FIG. 143 shows TaqMan primer functionality test for the endophyte-specific gene 8263
FIG. 144 shows TaqMan primer functionality test for the endophyte-specific gene 0005
FIG. 145 shows TaqMan primer functionality test for the endophyte-specific gene 2232
FIG. 146 shows TaqMan assay control—no template.
FIG. 147 shows TaqMan assay control—Plant GAPDH.
The results obtained can be summarised as follows:
LtmJ primers work well and LtmJ is not transcribed in endophyte (ST) in vitro culture as expected since Ltm gene is only expressed in planta
Primers designed for the other 4 endophyte-specific genes encoding uncharacterised proteins and expressed in tillers of established grass-endophyte symbiota all function (endophyte viability assessment)

RNA/DNA Co-Extraction from Pooled Samples of Endophyte-Infected Perennial Ryegrass Plants In addition, experiments were undertaken using samples generated by co-extraction of both DNA and RNA in a single step from:
Co-extraction of both DNA and RNA in single step
   6 week-old tillers of perennial ryegrass cv. Bronsyn+ ST endophyte
   6 week-old tillers of perennial ryegrass cv. Bronsyn endophyte free
   7. day-old isolated germinating seed-derived epicotyls (pooled samples) from perennial ryegrass cv. Bronsyn+ST endophyte.
Test TaqMan primers on co-extracted DNA/RNA
   Test primers for in planta-expressed endophyte-specific genes 7490 and 0005.
Is the co-extracted DNA/RNA sample of sufficient quality for primers/probes to work?
Do the endophyte-specific test genes expressed in 7 day-old epicotyls from grass-endophyte symbiota enable early in planta endophyte viability assessment?

FIG. 148 shows Detection in Co-Extracted DNA/RNA Pooled Samples for the Endophyte-Specific Gene 7490.
FIG. 149 shows Detection in Co-Extracted DNA/RNA Pooled Samples for the Endophyte-Specific Gene 0005.
FIG. 150 shows a control (no template) for Detection in Co-Extracted DNA/RNA Pooled Samples.

RNA/DNA Co-Extraction from Individual 10 Day-Old Germinating Seed-Derived Epicotyls In addition, experiments were undertaken using samples generated by co-extraction of both DNA and RNA in a single step from:
   10 day-old isolated germinating seed-derived epicotyls (individual seeds)
   7 day-old isolated germinating seed-derived epicotyls (pooled seeds)
These samples were used to test the designed TaqMan primers on co-extracted DNA/RNA, specifically to test primers designed for in planta-expressed endophyte-specific genes 7490, 0005 and 2232 to answer the following question:
   Can endophyte-specific test gene expression be detected in RNA/DNA co-extracted samples from individual 10 day-old isolated germinating seed-derived epicotyls?
FIG. 151 shows detection in co-extracted DNA/RNA samples from individual 10 day old epicotyls of the endophyte-specific gene 2232.

FIG. 152 shows detection in co-extracted DNA/RNA samples from individual 10 day old epicotyls of the endophyte-specific gene 7490.

FIG. 153 shows detection in co-extracted DNA/RNA samples from individual 10 day old epicotyls of the endophyte-specific gene 0005.

FIG. 154 shows a control (no template) for detection in co-extracted DNA/RNA samples from individual 10 day old epicotyls.

Is Endophyte-Specific Gene Expression Detectable at Earlier Developmental Stages?

In addition, to assess if endophyte-specific gene expression is detectable at earlier developmental stages, experiments were undertaken using samples generated by co-extraction of both DNA and RNA in single step from:

7-day old isolated germinating seed-derived epicotyls (pooled)

5 day-old isolated germinating seed-derived epicotyls (pooled)

3 day-old isolated germinating seed-derived epicotyls (pooled)

These samples were used to test the designed TaqMan primers on co-extracted DNA/RNA, specifically to test primers designed for in planta-expressed endophyte-specific genes 7490, 0005 and 2232 to answer the following question:

Are the endophyte-specific genes expressed earlier than 7 days?

FIG. 155 shows detection in co-extracted DNA/RNA from 3, 5 and 7 day-old pooled epicotyls of the endophyte specific gene 2232.

FIG. 156 shows detection in co-extracted DNA/RNA from 3, 5 and 7 day-old pooled epicotyls of the endophyte specific gene 7490.

FIG. 157 shows detection in co-extracted DNA/RNA from 3, 5 and 7 day-old pooled epicotyls of the endophyte specific gene 0005.

Is Endophyte-Specific Gene Expression Detectable at Earlier Developmental Stages in a Single Whole Germinating Seed?

In addition, to assess if endophyte-specific gene expression is detectable at earlier (<3 days) developmental stages in a sample from a single whole germinating seed, experiments were undertaken using samples generated by co-extraction of DNA and RNA from single-seed samples from:

3 day-old isolated germinating seed-derived epicotyls (control)

3 day-old single whole germinating seeds (i.e. individual whole seed including epicotyl)

2 day-old single whole germinating seeds (i.e. individual whole seed including epicotyl)

1 day-old single whole germinating seeds (i.e. individual whole seed including epicotyl).

and to confirm that there sufficient signal from a single whole germinating seed and that the assay can be undertaken on 100 single whole germinating seeds individually to enable a quantitative assessment of endophyte viability at % level.

Assay Validation

Assay validation is undertaken by assessing:

a) endophyte-specific gene expression to be detected in symbiota with novel endophytes i.e. endophytes other than ST e.g. AR1, AR37, NEA2, NEA6, NEA10, NEA11, NEA12 and E1;

b) endophyte-specific gene expression to be detected in symbiota with different host genetic backgrounds i.e. perennial ryegrass from e.g. genotypes Bronsyn and Alto;

Furthermore, for assay validation, results from the quantitative rapid assay (i.e. endophyte-specific gene expression-based assay at single whole germinating seed level; 3-10 days) are compared with assays detecting endophyte colonisation of host and symbiota establishment (i.e. current endophyte DNA detection-based assay at 6 week-old plant level).

In addition, the assay developed for perennial ryegrass-endophyte symbiota is assessed for its applicability with primers designed for detecting endophyte-specific gene expression in tall fescue-endophyte symbiota i.e. seeds from different endophytes (e.g. E34, E77, E79 and E80) in different tall fescue genetic backgrounds (e.g. BarOptima, BarSelect and BarElite), as well as in grass-endophyte associations of *Acremonium* endophytes in *Brachiaria* and *Urochloa* grasses.

Example 19—Molecular Phenotyping as Tool in Ab Initio Breeding I

Significant genotype×genotype (G×G) effects have been observed in the process of identifying stable host-endophyte associations for novel endophytes.

Designer associations are compatible, stable and may be selected for at a population level for additional phenotypes (performance, alkaloid production, etc.). For instance, particularly stable associations have been observed in the following combinations (ryegrass variety—novel endophyte):

Impact—NEA10

Tolosa—NEA12

Bealey—E1

The objectives of the study were therefore to develop molecular phenotyping as a tool in ab initio breeding and selection of symbiota, based on the following steps:

Deployment of multiple endophytes across members of multiple host grass populations Metabolic profiling of relevant alkaloid content.

Selection on the basis of individual symbiota performance.

In order to identify individual plants within a population with optimal alkaloid production, 80 plants from a single population of perennial ryegrass variety Bealey, which contains, a mixture of two distinct endophyte strains (NEA2 and NEA6) were subjected to semi-quantitative metabolic profiling. Variation of alkaloid profile and content was observed across the population of plants (FIG. 158). The two endophyte strains have been observed to exhibit different characteristic alkaloid profiles: NEA2 has previously been described (van Zijll de Jong et al. 2008) as producing lolitrem B, no ergovaline and moderate levels of peramine, while NEA6 produces low levels of lolitrem B, moderate ergovaline and moderate peramine. Identification of lolitrem B-producing plants within the population confirmed the presence of NEA2 (in a majority of the plants) rather than NEA6.

FIG. 158 shows metabolic profiling of a population of perennial ryegrass-endophyte symbiota The study was then extended to identify individual plants within a population with favourable (high peramine, low ergovaline, no/low lolitrem B) toxin profiles. A genetic identity test based on SSR analysis was critical for identification of endophyte presence and identity and to enable accurate selection. Genetic variation within the plant host appeared to influence the favourable toxin profile within a sub-group characterised by a single endophyte genotype (e.g. NEA6), as shown by quantitative variation across a group of peramine-producing plants (FIG. 159, Table 58). The data can be used for breeding selection processes.

TABLE 58

SSR marker analysis of selected samples

| Sample name | QA09 | NG03 | CC05 | Endophyte detected | Quantitative score | peramine | ergovaline | lolitrem B |
|---|---|---|---|---|---|---|---|---|
| 2B | 171 | 328 | 165 | NEA2 | 3 | 20024646 | 229761 | 2093005 |
| 4A | 194 | 226 | 187 | NEA6 | 3 | 4322114 | 1593878 | 0 |
| 11A | 194 | 226 | 187 | NEA6 | 3 | 3980110 | 1062058 | 0 |
| 15B |  | 226 | 187 | NEA6 | 2 | 0 | 0 | 0 |
| 27B | 171 | 328 | 165 | NEA2 | 3 | 20788755 | 206953 | 904985 |
| 30A | 171 | 328 | 165 | NEA2 | 3 | 11367920 | 161304 | 675423 |
| 44A | 171 | 328 | 165 | NEA2 | 3 | 9964578 | 233454 | 436925 |
| 46A | 194 | 226 | 187 | NEA6 | 3 | 9706442 | 1505812 | 0 |

In summary, this study demonstrated:
1. Development of a molecular phenotyping method for alkaloid (P/E/L) production as a tool for ab initio molecular breeding of perennial ryegrass-endophyte symbiota.
2. Deployment of molecular phenotyping method in proof-of-concept ab initio selection of perennial ryegrass-endophyte symbiota consisting of two endophytes in one grass host population.
3. Effective selection of sub-population of perennial ryegrass-endophyte symbiota consisting of two endophyte and multiple grass host genotypes for optimal alkaloid (P/E/L) production.

Example 20—Molecular Phenotyping as Tool in Ab Initio Breeding II

Current, forage grass breeding does not examine a wide range of compounds or molecules, largely due to cost restrictions. Breeding improved forages through the application of molecular phenotyping of the symbiota for improved herbage quality can deliver forage cultivars with elite ruminant nutrient profile.

The objective of this work was to develop high throughput cost effective molecular phenotyping protocols that can be used as a tool in breeding symbiota. This was achieved through the following steps:
Quantification of herbage quality, measured by water soluble carbohydrate (WSC):protein ratio
Improved WSC:Protein ratio is expected to improve productivity as well as reducing the environmental impact of the farming system
Selection on the basis of individual symbiota performance
Identification of Individual Plants within a Population with Optimal WSC:Protein Ratio FIG. 160 shows the results of molecular phenotyping of a population of symbiota to enable ab initio breeding and selection.
Water Soluble Carbohydrate Quantification
Several methods exist for the quantification of WSC in plants samples, however none have been widely adopted in forage breeding due to various limitations in throughput and cost.
The protocol developed is based upon an enzymatic assay, with the key improvement being the application of robotic automation to sample processing that delivers the following system:

Fast and semi-automated
Provides individual concentrations for glucose, sucrose, fructose and fructans
Accurate, with demonstrated application in perennial ryegrass
Demonstrated correlation of the enzymatic method to HPLC results
FIG. 161 shows the production of glucose-6-phosphate from glucose.
FIG. 162 shows the presence of water soluble carbohydrates in a population of symbiota.
The protocol developed and has been exemplified by the following experiment:
A collection of c. 1000 perennial ryegrass genotypes×4 clonal replicates with 3 technical replicates were sampled at the three leaf stage from an established field trial.
Samples were heat-treated and then freeze dried before being processed through the semi-automated pipeline of carbohydrate extraction and enzymatic determination of the glucose, fructose, sucrose and fructan content.
c. 400 plants a day processed using this protocol.
Plants with high and low carbohydrate levels were identified and subsequently were taken forward for an experimental proof-of-concept breeding step
FIG. 163 shows quantification of proteins.
Measurement of protein can be achieved using several methods currently, however none have been widely adopted in forage breeding due to various limitations in throughput and cost.
The protocol developed is based upon an established colorimetric assay, with the key improvement being the application of robotic automation to sample processing, that delivers the following system:
Measuring true plant protein
Colorimetric quantification method
Extensive testing of different extraction buffers and colorimetric methods has identified the current method as most optimal—extraction with weak NaOH and quantification using Bradford assay, detection using plate reader.
Achievements
In summary, the following was achieved:
1. An automated molecular phenotyping method for water soluble carbohydrate and total protein was developed as a tool for ab initio molecular breeding of perennial ryegrass-endophyte symbiota;
2. These molecular phenotyping methods were deployed in proof-of-concept screens across large perennial ryegrass populations;

3. A sub-population of perennial ryegrass plants with higher water soluble carbohydrate levels was selected in a 'proof-of-concept' breeding step Example 21—Method for Endophyte Identification in Symbiota Seed Bulk vs. Individual Plant Testing for Endophyte Presence, Identity and Incidence Eight perennial ryegrass lines were tested for NEA2/NEA6 endophyte presence, identity and proportion using SSR markers.

85 plants per line
23×10 seed bulks per line

TABLE 59

Cultivars and sources

| Cultivar/Line | Source |
|---|---|
| Bealey NEA2 | Nucleus'11 |
| Bealey NEA2 | 11235AT2 |
| Bealey NEA2 | 12138A |
| Trojan NEA2/NEA6 | 951T1 |
| Trojan NEA2/NEA6 | 13181A |
| Trojan NEA2/NEA6 | 13206 |
| Bealey NEA2 | Nucleus'02 |
| Bealey NEA2 | RG0339 |

TABLE 60

Expected SSR profile

| | Expected SSR profile (allele size in base pairs) | | | | | | |
|---|---|---|---|---|---|---|---|
| SSR Marker | Standard Toxic (ST) | NEA2 | NEA3 | NEA6 | NEA10 | NEA11 | NEA12 | RBG-E1 |
| NLESTA1QA09 | 149 | 171 | 198 | 194 | 194 | 153, 184 | 188 | 160 |
| NLESTA1NG03 | 226 | 328 | 226 | 226 | 226 | 226 | 217 | 217 |
| NLESTA1CC05 | 164 | 167 | 203 | 187 | 187 | 167 | 138 | 135 |
| B11 | 176 | 176 | 208 | 199 | 183 | 356, 360 | 131 | 164 |

TABLE 61

Individual plants

| | | Endophyte Identification | | | | Proportion of NEA2 & NEA6 in endophyte positive samples | |
|---|---|---|---|---|---|---|---|
| Line/Cultivar | Source | NEA2 | NEA6 | E | Major endophyte detected | Proportion of NEA2 (%) | Proportion of NEA6 (%) |
| Bealey NEA2 | Nucleus'11 | 65 | 11 | 9 | NEA2 | 85.5 | 14.5 |
| Bealey NEA2 | 11235AT2 | 57 | 12 | 16 | NEA2 | 82.6 | 17.4 |
| Bealey NEA2 | 12138A | 39 | 3 | 42 | NEA2 | 92.9 | 7.1 |
| Trojan NEA2/NEA6 | 951T1 | 28 | 19 | 39 | NEA2 | 59.6 | 40.4 |
| Trojan NEA2/NEA6 | 13181A | 26 | 34 | 25 | NEA6 | 43.3 | 56.7 |
| Trojan NEA2/NEA6 | 13206 | 18 | 46 | 21 | NEA6 | 28.1 | 71.9 |
| Bealey NEA2 | Nucleus'02 | 63 | 11 | 11 | NEA2 | 85.1 | 14.9 |
| Bealey NEA2 | RG0339 | 63 | 8 | 14 | NEA2 | 88.7 | 11.3 |
| Total | | 359 | 144 | 176 | | | |

TABLE 62

Seed bulks

| | | Endophyte Identification (in no. of seed bulks) | | | | Major endophyte detected in seed lot |
|---|---|---|---|---|---|---|
| Line/Cultivar | Source | NEA2 | NEA2/NEA6 | NEA6 | E⁻ | |
| Bealey NEA2 | Nucleus'11 | 6 | 17 | 0 | 0 | NEA2 |
| Bealey NEA2 | 11235AT2 | 7 | 16 | 0 | 0 | NEA2 |
| Bealey NEA2 | 12138A | 13 | 10 | 0 | 0 | NEA2 |
| Trojan NEA2/NEA6 | 951T1 | 4 | 19 | 0 | 0 | NEA2 |
| Trojan NEA2/NEA6 | 13181A | 0 | 23 | 0 | 0 | Both NEA2 & NEA6 |
| Trojan NEA2/NEA6 | 13206 | 0 | 23 | 0 | 0 | Both NEA2 & NEA6 |
| Bealey NEA2 | Nucleus'02 | 10 | 13 | 0 | 0 | NEA2 |
| Bealey NEA2 | RG0339 | 12 | 11 | 0 | 0 | NEA2 |

Summary
  NEA2 was identified as the predominant endophyte in Bealey NEA2/NEA6
  Proportions of NEA2/NEA6 in Bealey have not altered over the 2002-2011 period.
  Roughly equal proportions of NEA2/NEA6 were observed in Trojan.

Tillers testing is a robust method for unequivocally assessing endophyte presence, identity and incidence.
  Determines the exact percentage of specific endophyte strain incidence in each line.
  Identifies endophyte free plants.
Bulked seed testing is an indicative method for assessing endophyte incidence.
  Determines the relative proportion of each endophyte in a particular line.
  Does not allow to identify endophyte free individuals.
Genetic Purity of Endophyte-Inoculated Perennial Ryegrass Lines
  Seed samples from five lines
    Coded as Lp513, Lp539, Lp613, Lp660, Lp667
  Multiple seed bulks (23 per line) analysed with 3 markers
    Diagnostic capacity to discriminate ST, NEA2, NEA6
  Lp513, Lp613—contain NEA6>NEA2
  Lp660—contains NEA2, ST, trace NEA6
  Lp667—contains ST, NEA6
  Lp539—contains ST only
  Relationship to previous assessments of NEA2, NEA6 incidence?
  Origin of ST endophyte incursions?
Achievements
  1. Established methods for determining endophyte presence, identity and incidence in individual tiller samples
  2. Established methods for determining endophyte presence, identity and incidence in bulked seed samples.

Example 22—Method for Allelic Content Characterisation in Symbiota Genotypes

Method for Allelic Content Characterisation in Host Genotypes
SNP based marker tools have been developed in perennial ryegrass, transferred to Italian ryegrass and developed in tall fescue.
Comprehensive cultivar catalogues have been developed of genetic diversity and relatedness between available germplasm.
Clonal breeding nurseries have been established and genotyped to assist with breeding decisions.
SNP based marker tools have been developed to co-genotype host plant and endophyte.
SNP tools have been developed to assess seed, batch purity and endophyte content on c. 1,000 seed in a sequence based assay system.
Co-genotyping of the symbiota has been developed and exemplified.
  Protocol:
    Grind 2.5 g seed
    Extract DNA
    Perform 384 PCRs on DNA
    Pool PCR products
    Ligate on illumina adaptors
    Amplify sample
    Sequence on the illumina HiSeq2000—1-2% spike on a single lane
    Process data using a two step pipeline created in LINUX
    Analyse data using a pair of custom R scripts
  FIGS. 164 and 165 show genetic diversity and relatedness between germplasm.
Genotyping By Sequencing
  Protocols under development—application of reduced costs of sequencing to:
    Saturate genome with molecular markers
    Low cost per sample
    High throughput possible
    Genome sequence data will assist development
    Initial study in maize and barley
    24,186 markers mapped onto the barley genetic map
    c. 200,000 markers developed in maize
    Published protocol—Elshire et al May 2011 PlosOne
    96 initial custom barcodes developed inhouse.
  FIG. 166 shows genotyping by sequencing.
  FIG. 167 shows procedure for genotyping by sequencing.
Breeding Selection Program
  With expanding data sets available to breeding programs selection of plants will require sophisticated computational tools for maximal gain.
Program Method:
  Selection of a sub-set of phenotypically elite individuals that conserve all allelic variants.
Program Design:
  User defines the size of a sub-set to select.
  Program selects a sub-set of individuals that preserve all allelic variation seen in the population.
  Program selects to the size of the user defined sub-set elite individuals.
  Outputs plant identities, mean phenotype value and number of missing alleles.
  Phenotype value, is a single figure, but composite values can be generated.
  Example: Selection of 150 plants from 1,000 plants—processing time c. 1 hour.
Potential Schema For Cultivar Sub-Selection
  From cultivars represented in the clonal nursery PG one50 and LP443 were chosen for sub-selection.
  Select for within cultivar based on phenomic performance and or associated markers, while maintaining overall population allelic frequencies.
  Expected that c. 6% elite plants would be identified, while c. 20-30 individuals would be needed to retain population diversity.
  Target trait in the initial attempt was quality—digestibility and WSC.
  Identified cohorts of plants from the nursery that would be polycrossed.
  Crossing performed—seeds harvested and counted—germination to follow.
  Trial of PG one50 vs PG one50 subselect as well as LP443 vs LP443 subselect to follow.
  Application amenable to many traits greater success likely with higher heritabilities.
Achievements
  1. Established methods for genotyping symbiota from leaf tissue samples.
  2. Established methods for genotyping symbiota from seed bulk samples.
  3. Established computational breeding tools for selection of elite individuals whilst preserving genetic diversity in a population.

Example 23—Genomic Selection in Forage Plant Species

Abstract
Genomic selection (GS) is a powerful new method for exploitation of DNA sequence polymorphisms in domestic animal and crop plant improvement, through prediction of breeding values based on all markers distributed genome-wide. Forage grasses and legumes, which support a broad range of global pastoral industries, provide important targets for GS implementation, as many key target traits for improvement are difficult or expensive to measure, and are measured late in the life-cycle of selection candidates. A number of biological factors that vary across the range of candidate species, such as reproductive mode and polyploid genome architecture, present both challenges and opportunities for GS. The generic attributes of forage breeding programs are described, along with the status of genomic resources for a representative species group (ryegrasses). A breeding scheme for ryegrass incorporating GS is described, allowing two rounds of selection for key agronomic traits within a time-period previously required for a single round, potentially leading to doubling of genetic gain rate for such characters. An extremely limited extent of linkage disequilibrium, which is the major challenge for GS implementation in ryegrass breeding, is addressed. The strategy also incorporates recent advances in DNA sequencing technology to minimise costs.

An alternative approach is to simultaneously use all genome-wide distributed markers to predict breeding values, in an approach known as genomic selection (GS) (Meuwissen et al. 2001). GS uses a panel of markers which are sufficiently dense such that all QTLs are expected to be in LD with at least one marker locus. There are two advantages of GS over MAS. Firstly, all of the genetic variance may potentially be captured by the markers, as marker effects do not need to exceed the significance threshold in order to be used to predict breeding value. Secondly, marker effects are not biased upwards by multiple testing. This is in contrast to marker effects obtained from GWAS: due to the large number tested, it is likely to be those markers with favourable error terms that exceed the significance threshold (Beavis 1994).

In order to implement GS, a reference population of individuals with both known genotypes and phenotypes is used to derive a prediction equation which predicts genomic estimated breeding values (GEBVs) from marker genotypes. This prediction equation can then be used to estimate breeding values for selection candidates for which genotypes, but potentially no phenotypes, have been obtained. In simulation studies the accuracy of GEBV (the correlation of the GEBV with the true breeding value, which determines the rate of genetic gain) for selection candidates may be as high as 0.85 (Meuwissen et al. 2001). In practice, accuracy values as large as this have not yet been reported, although accuracies of GEBV up to 0.71 have been reported in Holstein-Friesian dairy cattle (Van Raden et al. 2009).

The implication of the availability of GEBVs for improvement programs can be profound. GS enables accurate selection decisions to be made early in the life-cycle of the target organism, at the price only of genotyping with the marker panel. It follows that the impact of GS on rate of genetic gain will be highest for traits which are either:

Expensive or difficult to measure, such as herbage quality in forages or grain quality in cereals.

Measurable only by significant damage to or destruction of the individual, such as nematode infection resistance in cereals, hence preventing subsequent breeding from that individual.

Expressed late in life, such as crop grain yield, or after the individual has been selected for breeding, such as survival or vegetative persistence.

The potential value of GS for crop plant breeding has been recognised (Heffner et al. 2009; Janninck et al. 2010). In forages, yield and quality of herbage are the key traits for forage improvement, and support feed conversion into unit quantities of meat or milk. These characters provide good candidates for GS, as they require expensive and/or destructive late-life measurement. Traits such as in-field persistence are also of obvious interest. This article provides a review of current knowledge relevant to the prospects for GS in forages, and describes possible strategies for implementation.

Biology of Target Species

In considering the prospects for applying principles of GS to forage species, relevant aspects of biology such as reproductive mode, polyploid status and symbiotic interactions must be considered. These factors may differ markedly from the properties of those outcrossing, diploid animal species for which the approach was pioneered. The major pasture species for current and future use in Australian pastoral agriculture are classified with respect to these multiple biological factors in Table 63, and commentary is made on implications of each factor for GS application in subsequent sections.

TABLE 63

Summary information for biological factors influencing feasibility of GS implementation in forage species

| | Species | | | | | |
|---|---|---|---|---|---|---|
| Attribute | Perennial ryegrass | Italian ryegrass | Warm-season grasses | Tall fescue | White clover | Alfalfa |
| Taxonomic group | Grass | Grass | Grass | Grass | Legume | Legume |
| Reproductive mode | SI | SI | Apomictic | SI | SI | SI |
| Annuality-perenniality | Perennial | Biennial | Perennial | Perennial | Perennial | Perennial |
| Ploidy level | Diploid | Diploid | Diploid Autotetraploid | Allohexaploid | Allotetraploid | Autotetraploid |
| Symbiotic plant-microbe association | Fungal (*Neotyphodium lolii*, LpTG2) | Fungal (*Neotyphodium occultans*) | Fungal (*Acremonium implicatum-Brachiaria* spp.) | Fungal (*Neotyphodium coenophialum*, FaTG2, FaTG3) | Bacterial (*Rhizobium leguminosarum*) | Bacterial (*Rhizobium meliloti*) |

TABLE 63-continued

Summary information for biological factors influencing feasibility of
GS implementation in forage species

| Attribute | Species | | | | | |
|---|---|---|---|---|---|---|
| | Perennial ryegrass | Italian ryegrass | Warm-season grasses | Tall fescue | White clover | Alfalfa |
| Key Issues for implementation of GS | Non-extensive LD, likely high Ne, development of efficient GBS methods | | Capacity to select at sexual level and transition elite genotypes to apomictic level | Limited knowledge of LD and Ne, technical constraints on SNP discovery and validation, development of efficient GBS methods | | Limited knowledge of LD and Ne, development of efficient GBS methods capable of determining allele dosage |

1.1 Taxonomic Classification

A number of plant species are important for global pastoral agriculture, the majority belonging to either the grass (Poaceae) or legume (Fabaceae) families. Grasses and legumes are either cultivated separately, or in combination as companion species in a mixed sward. The most important temperate pasture grass species are members of the *Lolium-Festuca* species complex (ryegrasses and fescues), two closely related genera residing within the Poeae tribe of the cool-season grass sub-family Pooideae, In contrast, various species of warm-season pasture grass (members of the genera *Brachiaria, Paspalum, Eragrostis* and *Pennisetum*) belong to several tribes within the sub-family Panicoideae.

The key cool-season species predominantly belong to the genera *Medicago* (medics, including alfalfa [*Medicago sativa* L.]) and *Trifolium* (clovers, including white clover [*Trifolium repens* L.] and red clover [*Trifolium pratense* L.]) within the Trifolieae tribe of the Fabaceae clade Hologalegina. There are also a number of agronomically important warm-season pasture legumes, including members of the genera *Chamaecrista, Macroptilium, Stylosanthes, Centrosema* and *Desmodium*.

1.2 Reproductive Mode

The majority of temperate forage species (with the exception of subterranean clover, *T. subterraneum* L.) exhibit obligate outbreeding (allogamy), dependent on cross-pollination. Examples include perennial ryegrass, Italian ryegrass, tall fescue, meadow fescue (*Festuca pratensis* Huds. syn. *L. pratense*), white clover and alfalfa. Inhibition of inbreeding is due to genetically-controlled self-incompatibility (SI) systems, in which incompatible pollen-stigma interactions arise from specific matching of SI locus alleles in male and female reproductive tissues.

Gametophytic SI (GSI) systems, in which the male gamete phenotype is determined solely by its own haploid genotype, are characteristic of forage grasses and legumes. For a pasture grass species such as perennial ryegrass, SI contributes to a high level of heterozygosity and heterogeneity, such that intra-population diversity typically exceeds inter-population variability (Guthridge et al. 2001: Wang et al. 2009). This is important for prospects of successful GS application in these species, as discussed below. Limited knowledge of SI allele content for specific genotypes is a potential obstacle to targeted varietal development, especially for restricted-base cultivars (Guthridge et al. 2001), which are based on small numbers of foundation clones. Effects on fertility and seed yield and constraints on permutation of beneficial genetic variants are most acute under self-fertilisation, or crosses between close-bred genotypes such as full-sibs. In the context of GS implementation, obligate outbreeding leads to high levels of genotypic heterozygosity and rates of polymorphism that are likely to be higher than in livestock species (e.g. The Bovine HapMap Consortium 2009) to which GS has been successfully applied.

Apomixis represents a different reproductive mode, in which embryonic development proceeds in the absence of a paternal contribution from an unreduced egg cell. The products of apomixis are therefore clones of the maternal genotype. A parthenogenic propagation system is highly attractive to plant breeders, due to the ability to preserve and multiply elite genotypes (Spielman et al. 2003). Apomixis is usually associated with hybridity and/or polyploidy, and expression of the trait is generally incomplete, such that a mixture of sexual and asexual fertilisation products is obtained from a single plant. Variation is also observed within species, with fully sexual diploid genotypes and facultative apomictic polyploid genotypes within a single population. Apomictic warm-season grasses which are targets for breeding improvement include several species of *Brachiaria* (signal grass), *Paspalum* (dallis grass) and *Pennisetum* (relatives of cultivated pearl millet), as well as *Eragrostis curvula* (Schrad.) Nees (weeping lovegrass) (Pessino et al. 1999). For GS, selection at the allogamous sexual diploid level for optimal genotypes could be very effectively linked with large-scale propagation based on transition to a polyploid, parthenogenic level.

Target species also vary in terms of annual or perennial growth habit, the majority being short- or long-lived perennials. This property is potentially advantageous for GS, as clonal replicates from a single fully genotyped individual may be evaluated for multiple traits across a number of distinct environments, providing increased confidence in phenotypic evaluation for derivation of GEBVs. Parthenogenic, propagation of single genotypes through apomixis may permit a similar quality of information to be obtained.

1.3 Polyploidy

For allopolyploids, which derive from hybridisation events between distinct taxa, the most important effects on feasibility of GS are two-fold; the significant challenge presented to the process of SNP discovery and validation; and the requirement to reliably assay SNPs associated with causal polymorphisms if such mutations only segregate from a single sub-genome (Kaur et al. 2012). The former arises due to a requirement to distinguish between genuine SNPs (homologous variants between alleles within a sub-genome), homoeologous sequence variants (HSVs) (arising among corresponding loci in each sub-genome) and paralogous sequence variants (PSVs) (arising among duplicated genes both within and between sub-genomes) (Hand et al. 2008; Lawless et al. 2009). Partial solutions for this problem have been established for allotetraploid (2n=4x=32) white clover (Hand et al. 2008) and allohexaploid tall fescue (2n=6x=42) (Hand et al. 2010), based on depth of sequencing (Margulies et al. 2005), and comparisons to diploid (2×) progenitor taxa for prediction of sub-genome structure.

Autopolyploid forage species, typically arising from chromosome doubling events within single taxa, include alfalfa and artificially generated varieties of ryegrasses, as well as species such as cocksfoot (*Dactylis glomerate* L.), bird's foot trefoil (*Lotus comiculatus* L.) and smooth brome grass (*Bromus inermis* L.). Although SNP discovery in autopolyploids is likely to be less complex than for allopolyploids, additional challenges for GS studies may be expected to arise due to requirements for quantitative genotyping (determination of allelic dosage), accurate haplotype reconstruction and verification of marker-trait gene linkage.

1.4 Symbiotic Plant-Microbe Associations

Both pasture grasses and legumes form mutually beneficial symbiotic associations with asexual microbial species. Schemes for GS implementation could hence be designed to target co-selection of adapted symbiota, in order to optimise the compatibility and stability of associations. The best-characterised of grass endophytes are fungal species of the order Ascomycota and family Claviceptaceae. In the temperate grasses, anamorph-teleomorph relationships, due to presence and absence of a sexual state, are observed between members of the genera *Neotyphodium* and *Epichloe*. *Neotyphodium* endophytes confer beneficial effects on the host grass through deterrence of invertebrate herbivory and amelioration of abiotic stress tolerance, in return for physical protection and nutrition.

Legume species form symbiotic interactions with a range of proteobacterial species, most belonging to the order Rhizobiales. The rhizobia are sequestered within specialised nodules on the roots of legume plants, and perform biological fixation of atmospheric nitrogen ($N_2$) to ammonium ($NH_4^+$) in an oxygen-limited environment (Sessitsch et al. 2001).

1.5 Target Traits

Herbage yield and quality are the primary production traits for forage species. The latter is primarily controlled by variation for digestibility (associated with cellulose and lignin polymer content in cell walls) and availability of oligosaccharide carbohydrates for energy provision to the grazing animal (Cogan et al. 2005). Other aspects of quality include reduction of bloating in ruminants, associated with protein-rich leguminous diets and ameliorated by the presence of condensed tannins. Biotic stress resistance characters include responses to viral, bacterial and fungal pathogens, and to invertebrate pests. Examples include alfalfa mosaic virus (AMV) of both lucerne and white clover and the crown pathogen of ryegrasses (*Puccinia coronata* f. sp. *lolii*) (Dracatos et al. 2010). Abiotic stress-related traits include tolerance to waterlogging (Pearson et al. 2010) and drought in forage grasses, and to aluminium toxicity, phosphorus deficiency and saline stress in clovers. Capacity to produce sufficient quantities of viable seed is important for both grass and pasture legume varieties. All of these traits are good targets for GS, due to requirements for laborious, expensive, destructive or late life-cycle measurement.

Structure and Objectives of Pasture Plant Breeding Programs

Many different forms of breeding program have been implemented for pasture plant species. A generic scheme, which describes most of the relevant features of such breeding programs, is depicted in FIG. 168. The majority of commercial activities have been based on a strategy that begins with establishment of a base population of up to 10,000 individuals, followed by seed multiplication within families, generating up 100,000 individuals for mass selection. Evaluation for persistence under grazing pressure or visual assessment (as spaced plants in the field) is used for sub-selection with a reduction by a factor of 10 in the number of genotypes evaluated. A surviving group of up to 1,000 potential parental clones undergo further assessment for key performance characteristics such as yield and persistence. Determination of parental breeding value may be obtained through the use of a number of experimental methods (Vogel and Pedersen 1993). In half-sib progeny testing (HSPT), maternally-derived progeny from a selected genotype are evaluated in replicated phenotypic trials to minimise confounding environmental variation, obtaining information on the general combining ability (GCA) of the parent. Full-sib progeny testing (FPST) measures the specific combining ability (SCA) of a parental genotype through identification of superior pair-cross derived families. Within- and between-family selection (WBFS) involves establishment of multiple polycrosses (random intermatings between selected individuals), harvest and bulking of equal seed numbers from each mother plant, and establishment and evaluation of replicated spaced-plant half-sib progeny nurseries for key production characters.

Following selection of foundation (Syn0) genotypes, a synthetic 1 (Syn1) population is generated, usually by polycrossing, less commonly by combination of $F_1$ seed from crosses between each parent in a diallel structure. The number of foundation individuals may vary from as low as 4 for perennial ryegrass (although higher for Italian ryegrass), to 50-100 for polyploid species such as tall wheat grass and alfalfa (Bray and Irwin 1999). Synthetic 2 (Syn2) populations are then obtained by Syn1 multiplication, through seed harvest from maternal parents fertilised within a single common pollen cloud. The Syn2 populations are then assessed in multiple environments for key traits, leading to the selection of one population for commercial release as a variety.

Commercial breeding programs that implement specific versions of this generic scheme will typically involve two cycles of selective genetic recombination and subsequent selection/evaluation within a 6-9 year period (FIG. 168). Given the extended time-frame for these stages, there are major opportunities for acceleration of genetic gain based on GS strategies. However, implementation of GS in commercial forage breeding programs is likely to require major structural alterations to fully exploit the technology, at least at the existing stage of development of genomic technologies. In current systems, foundation clones have rarely been retained, and details of lineage structure have not generally been recorded, precluding pedigree-based calculation of estimated breeding values. The value of individual genotypes in this paradigm has been relatively low, limiting the opportunity to apply strategies that depend on expensive genotyping analysis and/or phenotypic characterisation. A transition to pedigree-based breeding (or at least the use of marker information to capture pedigree structure) through clonal nursery evaluation of specific genotypes is hence an important step towards implementation of GS in pasture plant breeding.

Requirements for GS Application to Breeding of Ryegrasses

Of the major forage species, the ryegrasses and alfalfa currently possess the best-developed suites of genetic and genomic resources. However, as the genetic systems of ryegrasses are arguably more similar (as outbreeding, diploid taxa) to those of domestic animals, these species provide a potential test-case for development of GS strategies in forages. In order for this objective to be achieved, a number of key limitations must be overcome.

1.6 Availability of Sequence Polymorphisms

GS requires a panel of sequence polymorphism distributed genome-wide capable of genotypic assay across a large number of individuals at reasonable cost. SNPs have become established as the marker of choice for the GS application in most species, given high abundance in the genome, and the availability of accurate and inexpensive detection technologies. However, other types of molecular markers could theoretically also be used for GS subject to meeting the criteria described above.

Development of genomic resources for perennial ryegrass has until recently been relatively slow compared to major cereal species such as rice, maize, wheat and barley. Initial large-scale SNP discovery for perennial ryegrass was performed through functional selection of gene sequences, amplicon generation from parents of full-sib mapping families, followed by cloning, sequencing, alignment and validation through the use of a Mendelian transmission test (Cogan et al. 2006). This method was applied to genes from multiple functional classes, detecting high levels of nucleotide diversity from limited numbers of sampled haplotypes. The consensus from multiple SNP discovery studies (Cogan et al. 2006; Xing et al. 2007; Dracatos et al. 2008; Dracatos et al. 2009; Brazauskas et al. 2010; Fiil et al. 2011) is that SNP frequency typically varies between 1 per 20-150 bp, depending on gene identity and number of genotypes. DNA sequencing of pooled gene-specific amplicons from multiple (c. 500 genotypes) further suggests a high 'global' average value of between 1 per 20-25 bp (Cogan et al. 2010a).

A number of approaches have been implemented to generate larger numbers of SNPs with genome-wide distribution. In one early approach, groups of candidate genes were selected and pooled amplicons from these regions were sequenced using the second-generation Roche GS FLX platform. Derived SNPs were formatted for genotyping using the Illumine GoldenGate™ oligonucleotide ligation-amplification 384-plex assay (Cogan et al. 2010c). An approach that allows discovery of a larger number of SNPs, with broader genome coverage, is based on comparative genomics to select exon regions that are regularly distributed across the ryegrass genome for pooled sequencing. 'Proof-of-concept' for this activity has come from fine-scale genetic and physical mapping of the Si loci (Shinozuka et al. 2010). A more general strategy entailed the exploitation of physical mapping data from bread wheat, for which conserved synteny with perennial ryegrass has been previously defined (Jones et al. 2002a), to align with the draft genome of *B. distachyon*, and hence use regularly spaced *Brachypodium* gene templates to selected orthologous ryegrass ESTs for amplicon design and pooled sequencing (Cogan et al. 2010d).

Complexity reduction methods are also useful to survey the whole gene space, using methods such as $C_0t$ filtration and hypomethylation (Forster et al. 2010). Collectively, the discovery activities described above have delivered c. 20,000 predicted SNP loci, sufficient to support an initial design for an integrated high-density oligonucleotide-based genotyping chip, analogous to those used in livestock GWAS and GS studies. However, the dramatic increase in power of current sequence technologies suggest that whole genome sequencing per se, coupled with comparison between contrasted genotypes, is now a more cost effective route to genome-wide SNP discovery. Complete assembly of a complex Poaceae genome is still highly challenging for second-generation platforms (Gupta 2008). However, assembly of the gene-space as unigene contigs is now feasible based on sequencing with Illumina Hi-Seq, which has delivered c. 60× coverage of the perennial ryegrass genome (Cogan et al. 2011).

In the near future, SNP discovery and subsequent genotyping in species such as ryegrasses, are likely to converge through a transition from genotyping per se to 'genotyping-by-sequencing' (GBS) methods (Huang et al. 2009, Elshire et al. 2011). For instance, the restriction site-associated DNA (RAD) method (Baird at al., 2008) provides access to an essentially unlimited set of sequence polymorphisms through second-generation sequencing of reduced complexity representations from specific genotypes (Wang et al. 2011). This approach is likely to be essential for ryegrass and other forage species, in order to obtain the large numbers of markers and low-cost of genotyping that are necessary given the population structures and current breeding practices for these crops.

1.7 The Challenge of Limited LD in Ryegrasses

Two key questions for design of any GS experiment are the number of required SNPs, and the number of individuals that must be genotyped and phenotyped in the reference population in order to predict GEBVs for selection candidates with useful accuracy. The answer in both instances depends critically on extent of LD in the target species. LD is commonly measured by the $r^2$ statistic, which may also be interpreted as the proportion of variance explained by a SNP which has an association with a QTL. The extent of genome wide LD is largely determined by past effective population size, particularly in outbreeding species with a large $N_e$. The expectation of $r^2$ is $$\frac{1}{4N_e c + 1}$$

where $N_e$ is effective population size and c is the map distance between loci in Morgans (Sved 1971). Meuwissen (2009) demonstrated by simulation that to achieve very accurate genomic estimated breeding values (GEBV), $10*N_e*L$ markers are required, where L is the genome length in Morgans. If estimates of $N_e$ are not available, and $r^2$ between markers has been estimated, Calus et al. (2008) demonstrated that GEBV with an accuracy greater than 0.7 could be predicted provided $r^2$ between adjacent markers was on average above 0.27. Given this threshold as a guideline, what are the prospects for GS in perennial ryegrass?

Results from multiple linkage disequilibrium (LD) studies (Ponting et al. 2007; Auzanneau et al. 2007; Xing et al. 2007, Fiil et al. 2011) have revealed a typically rapid decay pattern, over less than 1 kb. For example, Ponting et al. (2007) demonstrated that LD, as measured by $r^2$, decayed to less than 0.27 within 1000 bp in most population types (including ecotypes and cultivars). Fiil et al. (2011) also found that LD decayed rapidly within the representative genes, although some genes exhibited much slower rates of decay.

Both the extremely high frequency of polymorphism, and rapid decay of LD, suggest a very large past $N_e$ value for perennial ryegrass. For comparison, in humans, LD decays to 0.27 at approximately 25 kb, so $N_e$ for ryegrass is likely to be larger than the tens of thousands estimated for the human population (e.g Tenesa et al. 2007). In cattle, LD decays to 0.27 at approximately 50 kb, and ancestral population sizes are in the order of 2000-3000 (Bovine Hap Map Consortium 2009). These comparisons suggest that very dense markers will be necessary to implement GS in ryegrasses. Strategies to deal with this problem are discussed below.

It should be noted that the pattern of LD in ryegrass is very different to that observed in crops like maize, for which LD within heterotic groups, and even across highly diverse germplasm, is extensive (Van Inghelandt et al. 2011; Yan et al. 2009). This property allows accurate estimation of GEBVs; for instance, Riedelshiemer et al. (2012) reported accuracies of GEBV of 0.72 for biomass in maize using a set of 56,110 SNPs, while Albrecht et al. (2012) reported accuracies of GEBV of 0.72-0.74 for grain yield in test cross progeny, using only 1,152 SNPs.

The second element for design of a GS experiment is to determine the number of fully phenotyped and genotyped individuals that are required in the reference population. The accuracy of GEBVs in individuals with no phenotype of their own can be derived deterministically and depends on number of individuals genotyped and phenotyped in the reference population, heritability of the trait, and number of loci affecting the trait (Goddard 2008; Daetwyler et al. 2008). Given that little knowledge is available regarding the number of loci affecting most agronomically important traits, equivalence between number of loci and number of independent chromosome segments in the population is a conservative assumption, and this can be calculated from $N_e$ and L. This deterministic prediction suggests that large reference populations are required to predict accurate GEBVs, particularly for low heritability traits (FIG. 169), and agrees well with accuracies that have been achieved in dairy cattle breeding experiments (Hayes et al. 2009). Once again, given that $N_e$ is likely to be very large in ryegrass populations, the deterministic prediction would indicate that extremely (and impractically) large reference populations would be required to implement GS for ryegrass, in the absence of any strategy to reduce LD. Such strategies hence become a key component of GS implementation for ryegrasses. Furthermore, it is important to recognise that GS may deliver gains even if marker density is not as high as suggested values, and the size of the reference population is lower than desired, provided some structure is present within the population (such as, for example, if full-sib or half-sib matings are common). SNP markers may also be used to trace the pedigree of the population and the inheritance of large chromosomal blocks from parents and other recent ancestors. Habier et al (2008) demonstrated that a considerable proportion of GEBV accuracy was actually derived from these sources, particularly when $N_e$ has recently contracted, as must have occurred in most forage breeding programs. In the strategy outlined below, an artificial reduction in $N_e$ and therefore increased extent of LD is specifically exploited.

Strategies for Application of GS to Forage Breeding Programs

As described above, experimental evidence suggests that LD in perennial ryegrass is limited, and strategies are required to mitigate this effect in order to effectively implement GS. One strategy is to consider the LD which exists within families (within which $N_e$ is very small), which is equivalent to the use of linkage information to predict GEBV. Algorithms which use LD and linkage simultaneously to predict GEBV are already available (Meuwissen and Goddard 2004). Furthermore, although requiring definitive demonstration, recent decline in $N_e$ values is anticipated for forage species, due to a focus on use of specific germplasm pools within breeding programs. This is an advantage for GS, as evaluation of fewer chromosome segments is required in the reference population (although inbreeding effects must be carefully managed). Whether the decline in $N_e$ has been sufficiently large to permit use of reference populations of practical size may only be answered through interpretation of experimental data, and this is one of the first questions that will be addressed when genome-wide SNP data becomes available. Irrespective of the outcome, the scheme presented here begins with a further reduction of $N_e$.

A potential GS scheme for ryegrass which largely exploits within family information for genomic predictions is now described (FIG. 170). A key feature of our scheme is a reduction in generation interval, which in existing breeding programs is usually very long, because only completed varieties or newly-accessed germplasm pools are generally used for the generation of first-phase crosses (see FIG. 168). An opportunity to accelerate genetic gain with GS through shortening of the generation interval could be achieved through introduction of elite genotypes from the first round of selection directly into the second and subsequent rounds of selection. The identity of elite genotypes to include at this stage would be based on GEBVs for traits such as herbage yield, quality and persistence.

Another feature of the scheme is the use of GBS. Although chip-based formatting of currently known SNP loci for highly multiplexed genotyping is logistically feasible, set-up costs of design (due to the relatively small-size of the international research and development community) and current processing costs (corresponding to several hundreds of US$ per sample) are unlikely to be acceptable for forage species. In contrast, bar-coded multiplexed samples on the Illumina Hi-Seq platform could potentially deliver high-density SNP data at price points in the vicinity of an order of magnitude lower (e.g. c. US$20 per sample), with costs likely to decline further in the near future (Elshire et al. 2011). Given provision of data from such an 'open' genotyping system, the large number of polymorphisms necessary to enable GS would become readily accessible.

Establishment of the Base Population

1. The scheme begins with evaluation of available elite germplasm. This is achieved by establishment of a spaced plant in-field nursery incorporating individual genotypes (c. 1,000) from multiple elite germplasm sources, with a moderate level of clonal replication (e.g. four-fold), to obtain c. 4,000 ramets. Direct phenotypic evaluation of genotypes in the nursery is performed for yield, herbage quality and other traits which can be measured at this stage (FIG. 170, box A). As many current elite varieties of perennial ryegrass have a restricted-base, being derived from a small number of parents (4-6), the inclusion of commercial germplasm will pre-dispose towards a reduction of $N_e$ from the outset.

2. Selection of the 150 best-performing plants is performed based on nursery data, augmented by historical data on elite genotype performance and maximised diversity indices for paircrossing, in order to reduce $N_e$. A series of paired paired lop-crosses' between these selected superior individuals is made. In order to allow more accurate prediction of breeding values between progeny sets, and to further reduce $N_e$, 50 genotypes are designated as 'bigamous' parents, as each is mated to two separately selected 'monogamous' parents. This procedure obtains 50 pairs of $F_1$ families, each pair being half-sibs based on the common bigamous parent (FIG. 170, box B)

3. GBS of the 150 parents is performed based on a complexity reduction sequencing method (e.g. Baird et al. 2008; Elshire et al. 2011) to identify genome-wide SNP variation within the parental group. (FIG. 3, box B)

Mini-Sward Evaluation and Selection

4. Seed from each full-sib family is harvested for establishment of mini-swards for evaluation[1] of persistence, disease resistance and performance in a sward environment (in order to allow estimation of competition effects). Spaced-plant mini-swards are established containing 100 $F_1$ genotypes from each family, with 10 cm spacing in a 1 $m^2$ area, corresponding to 10,000 plant genotypes in total[2]. Depending on logistical constraints, each $F_1$ family-specific mini-sward may be replicated for additional evaluation. For instance, three-fold replication would require establishment of 30,000 distinct plant genotypes in mini-swards. Phenotypic evaluation is performed for the $F_1$ families in the mini-sward setting for target traits (e.g. yield, quality, disease resistance and persistence) (FIG. 3, box C). The large number of plants in the mini-sward may only require genotypic analysis using low-density SNP assays (e.g. 384-plex Illumine GoldenGate™ assays), as imputation can be used to infer their genotypes at the SNPs identified in step 3. Habier et al. (2009) demonstrated that this process can be achieved very accurately if parents are genotyped for the

[1]The capacity to obtain sufficient seed for establishment of mini-swards is based on the following estimate: number of seed produced by a single reproductive tiller=50; number of reproductive tillers per plant may be as high as 50 (large pot grown plants) or as low as 4, but c. 10 is taken as a reasonable minimum expectation when clones are prepared for crossing; so number of seed produced per plant=c. 500; so number of seed produced by typical pair-cross=1,000; minimum germination rate=75%; so 500-750 potential germinants available.

[2]Due to the likelihood of pronounced edge-effects; a guard of plants from a generic variety would be established around each 10×10 array. densely spaced markers, as is the case in this example (for which parents have been genotyped for a very large number of loci by GBS).

5. Using the imputed data and individual plant performance data from the mini-swards, SNP prediction equations for persistency, competition effects and other traits are updated (FIG. 170, box C).

6. A new parental population with 150 genotypes is selected (using GEBVs for all traits) from the first-round (from 30,000, at a selection frequency of 0.5%), which are maintained with minimal replication in order to mitigate plant loss (FIG. 170, box D). These individuals are subjected to GBS as described in step 3.

Nursery Evaluation Step

7. Crossing of these selected individuals is performed in the next round of the selection cycle, in order to generate a full replacement nursery population of 4,000 ramets (FIG. 170, box B). These individuals are genotyped using the low-density marker panel, genotypes are imputed and GEBVs are calculated for persistence and disease resistance. These data are combined with GEBVs for yield and herbage quality (which include information from the individual's own record), and 150 individuals are selected to generate progeny for the mini-sward step.

Figure 1:
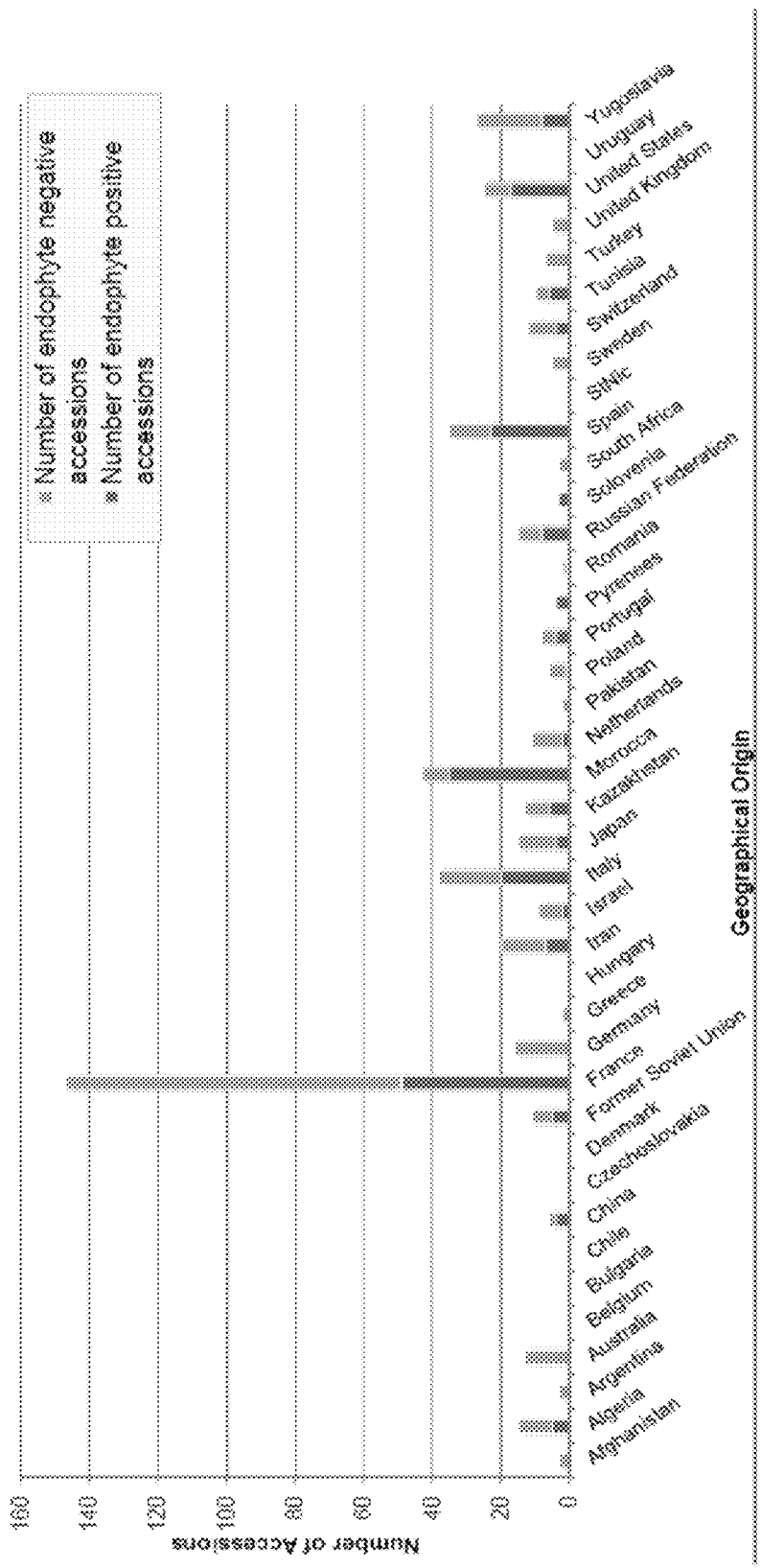
FIG. 1 shows genotypic analysis of endophyte content in accessions from a targeted fescue germplasm collection.

Steps 4-7 as described above may be repeated with periodic evaluation of genetic gain. When sufficient genetic gain has been made to clearly distinguish a new 'pre-variety' then diversion of a sub-set of the 150 selected genotypes into synthetic population development can occur. A total of 16 genotypes (c. 10% selection intensity) may be chosen to derive 4 polycross groups of four parental genotypes each, on the basis of predicted performance and genetic distance, to produce restricted-base pre-varieties. Multi-site evaluation will be used to measure phenotypic attributes such as yield, quality and persistence of these synthetics (FIG. 3, box E). This scheme is intended to deliver maximum genetic gain through rapid cycling of crossing activity based on GS predictions, particularly for persistence and disease resistance. In contrast to the scheme presented, in FIG. 1, recombination and selection takes place as part of each cycle, rather than intermittently within a more protracted period. The major logistical requirements, which are for mini-sward establishment and evaluation, may be reduced by a more radical strategy, in which seed from all initial pair-crosses is pooled and sowed in a single large-scale closed-spaced trial. Elite individuals would then be identified by phenotypic evaluation and assigned to cross-of-origin through low-density SNP-based genotypic analysis.

Although derivation of GEBVs would reduce the requirements for full-scale phenotyping, apart from during the first round of selection, it is anticipated that retention of the parental genotypes and maintenance of the spaced plant nursery would allow refinement of predictions through evaluation of additional traits, or long-term monitoring of previously measured traits. The value of a spaced plant nursery system would also be enhanced through evaluation of genotype×environment (G×E) effects. This, objective would ideally be achieved through establishment of clonal replicates in different target environments, and GEBVs could then be generated for each environment.

One of the key objectives of this proposed scheme is to enhance the significance of individual genotypes during breeding practice, which have traditionally been negligible compared to the population as a whole. Retention, intensive phenotypic characterisation and use in a fully recorded (based on SNP genotype) pedigree structure will deliver at least part of this worth.

CONCLUSIONS

Although forage species have been relatively undeveloped in terms of molecular breeding compared to other major crop plants, GS implementation has the potential to deliver major advances, mainly through the capacity to complete multiple selection rounds within the time conventionally used for single rounds. This outcome is possible if accurate GEBVs can be predicted for traits such as persistence and disease resistance. Information on these traits is currently obtained only after potential selection candidates are up to five years of age. However, if GS is to be implemented in forage species, a number of challenges must be overcome. The relative deficiencies of DNA marker resources, and influence of polyploid genome structures for some species, constitute the first challenge. Barriers to marker availability will rapidly disappear as GBS becomes less expensive, while enhanced methods for genotypic analysis of polyploid genomes have also been developed (Gidskehaug et al. 2011).

The two major remaining challenges are the very limited extent of LD in forage species such as ryegrasses, and restricted opportunities to implement GS in current breeding programs. In this review, the first factor is addressed through use both of linkage information within families to increase the accuracy of GEBV prediction, and, in the longer-term, reduction of $N_e$ in populations by breeding from elite varieties. Undesirable correlated effects of inbreeding depression under such schemes could be managed through incorporation of measures of genomic diversity into the selection criteria (e.g. Pryce et al. 2012). To address the second factor, a breeding scheme has been proposed which permits GS to accelerate genetic gain through compression of selection round duration. However, implementation of this scheme would require significant restructuring of current breeding schemes.

Although field- and glasshouse-based evaluation systems using largely visual assessment criteria have been sufficient to enable varietal improvement to date, effective use of molecular breeding systems is also dependent on access to more accurate and detailed phenotypic values (Furbank et al. 2009; Houle et al. 2010), for instance, those delivered by 'whole-of-lifetime' measurements of plant growth and performance from automated glasshouse and image analysis phenomics platforms. The accurate quantification of phenotypic variation using next-generation technologies is a major challenge and opportunity for forage breeding (Walter et al. 2012).

Example 24—Genomic Selection of Plant-Symbiome Associations

Artificial selection methods are dependent on a two-step process: firstly, recombination to generate new arrangements of genetic elements, and secondly, differential sampling of newly generated genotypes on the basis of superior phenotypic selection. Asexual symbionts (e.g. endphytes, bacteria) do not participate in the recombination events during sexual reproduction of the host plant. Generation of variability in host-symbiont pairs is hence combinatorial in nature, and the full power of genomic selection for favourable expression of the symbiotic association will depend on capability to generate as broad a range of pair-wise combinations between host genotype and symbiont genotype as possible. The potential diversity space for co-selection with the symbiont may be estimated as: [Number Target germplasm pools]×[Number Distinct symbiont genotypes]. As this number is very large, selective sampling for maximum symbiont diversity using a genetic algorithm is desirable.

Symbionts which reproduce sexually (e.g. some fungi) provide an additional opportunity to select symbionts within populations for most beneficial effect on the host plant. Here, genomic characterisation and subsequent genomic selection of symbionts would be needed. The combinatorial nature would remain at least as complex, but it could potentially increase to: [Number target germplasm pools]×[Number distinct symbiont genotypes]×[Number variants within symbiont genotype group].

Such methods are also applicable in the case of hosts which differ in potential to attract symbiont populations (both quantity and diversity). Hence, genomic selection may be used to determine host affinity to symbiont spectra, diversity and quantity.

Such methods are also applicable to co-select of legume-rhizobia symbioses, symbioses with mycorrhizae, favourable host-symbiont genome interactions and host-symbiont-environmental interactions.

Example 25—Leaf and Root Microbiomes in Temperate Grass: Perennial Ryegrass (Lolium perenne)

Clonal Lolium perenne plants, both with and without the fungal endophyte Standard Toxic Neotyphodium lolii were grown in 6 different hydroponic solutions representing different nutritional conditions. No carbon source was present, so that the endophyte must grow on carbon from the plant.

After 3 weeks of treatment with biweekly replenishment of media to maintain ion concentrations, plants were washed to remove residual media and roots and leaves were snap frozen in liquid $N_2$. RNA was extracted from leaves and roots of 5 replicate plants per treatment (120 samples).

This RNA was used to construct cDNA RNA seq libraries which were analysed by RNAseq analysis (Ilummina HiSeq sequencing). The libraries were analysed using blastn and a single database hit recorded per sequence read. The database queried contained plant nuclear genes, a representative plant chloroplast, and mitochondrial genome, the fungal endophyte nuclear and mitochondria genome, and sequences representing other fungi, bacteria, algae, insects and rhizaria. A second database contained approx. 120,000 named 16S sequences. Hits were recorded as being above a cut off of 80% identity and 40 bp overlap and grouped as to their origin.

The vast majority of reads mapped to plant database sequences. However significant reads mapped to the other classes of organisms. FIG. 171 shows the percent of total reads mapped mapping to algae, bacteria, fungi (other than endophyte), insects and rhizaria in the leaves and roots of endophyte free and endophyte containing plants in the full hydroponics media. This reveals a higher level of microbes associated with roots compared to leaves.

Example 26—16S Analysis of Microbiome in Perennial Ryegrass (Lolium perenne)

Clonal Lolium perenne plants, both with and without Standard Toxic Neotyphodium lolii were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was, created. Database sequences were extracted if there were hits recorded in at least 10 different libraries.

These database sequences were classified taxonomically using the Ribiosomal Database Project classifier (available at rdp.cme.msu.edu) and grouped to show the taxonimic distribution of the microbes represented in the Lolium perenne microbiome. As the plant chloroplast is of microbial origin, plant chloroplast sequences are present in the 16S sequence database. Reads mapping to these sequences were not included in the taxonomic summary.

FIG. 172 shows matches counted (16S blastn hit >98% identity over an overlap of >40 bp; mapping >10 samples). 11,000-164,000 reads were assigned to 16S per sample. Distribution of 2774 bacterial phyla (non-plant chloroplast).

Example 27—Leaf and Root Microbiomes in Perennial Ryegrass (Lolium perenne)

Clonal Lolium perenne plants, both with and without Standard Toxic. Neotyphodium lolii were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was created. The matrix of 16S counts for 16S sequences that had hits in 10 or more libraries was analysed as to the sum of the counts for each database sequence by plant organ. These sums were themselves summed by taxonomic class of bacteria.

FIG. 173 plots the sum by bacterial class of read counts from leaves and roots respectively. This reveals that some classes of bacteria are predominantly found in leaves (eg *Cyanobacteria*) or roots (eg *Sphingobacteria*) whereas other classes are found in both leaves and roots (eg *Gammaproteobacteria*). 470 16S sequences had hits in at least 10 leaf and 10 root libraries.

Example 28—Leaf and Root Microbiomes in Perennial Ryegrass (*Lolium Perenne*). Metagenomics Reveals Differences in Bacterial Species Predominance in Shoot and Root Microbiomes Clonal *Lolium perenne* plants, both with and without Standard Toxic *Neotyphodium lolii* were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was created. The counts values in this matrix (present in at least 10 samples) were log transformed to base 2 and this matrix was loaded into the the MultiExperimentViewer software (part of the TM4 software suite www.tm4.org). This log transformed matrix was used for hierarchical clustering of the sample sets using average linkage with Pearson correlation, and the order of the samples optimised.

This produced the sample tree shown in FIG. 174. The clustering demonstrates that the bacterial counts matrix from the roots contains a signature that can classify the nutritional status of the plant-microbiome associations (i.e. symbiota). In addition the leaf bacterial microbiome clearly differentiates roots from leaves (ie. different bacteria are predominant in different organs eg. leaves versus roots). However the leaf bacterial microbiome does not classify the nutritional status (hierarchical clustering of bacterial counts classifies root treatments but not leaf treatments).

Example 29—Leaf and Root Microbiomes in Perennial Ryegrass (*Lolium Perenne*). Differences in Bacterial Species Predominance Depending on Symbiotum Nutritional Status Clonal *Lolium perenne* plants, both with and without Standard Toxic *Neotyphodium lolii* were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was created. The counts values in this matrix were log transformed to base 2 and this matrix was loaded into the MultiExperimentViewer software (part of the TM4 software suite www.tm4.org). The 16S sequences were then used for Cluster Affinity Search Technique analysis using Pearson correlation and a threshold of 0.75. The resulting clusters were then individually hierarchically clustered using average linkage with Pearson correlation and the 16S sequence order optimised.

This produced 1036 clusters. Of these clusters 11 contained more than 10 genes and contained 47% of the genes in the matrix. Examples of 2 of these 11 clusters are shown in FIGS. 175 and 176. These display (cluster5) bacterial sequences whose abundance is increased in response to a low ammonia hydroponic treatments, and (cluster2) bacterial sequences whose abundance is repressed in response to low ammonia and low nitrate treatment.

Example 30—Leaf and Root Microbiomes in Perennial Ryegrass (*Lolium Perenne*). Metagenome Analysis of Bacterial Microbiome in Symbiota Reveals Range of Bacterial Species Known to be N Fixers and Phytostimulators of Grasses Clonal *Lolium perenne* plants, both with and without Standard Toxic *Neotyphodium lolii* were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was used to construct cDNA RNA seq libraries which were analysed by Ilummina HiSeq sequencing. The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was created.

This matrix was filtered to show reads mapping to sequences annotated as *Azospirillum* species. The counts mapping to these 12 sequences per library are shown in FIG. 177. *Azospirillum* species are known to associate with monocotyledenous plants, and also to fix atmospheric nitrogen and produce phytohormones (phytostimulators of grasses). At least one of the 12 species can be seen to have counts that increase in low all low ammonia samples, where fixation of atmospheric nitrogen would be of utility to plants associated with the bacteria fixing the nitrogen. Thus, *Azospirillum* species were induced in number under low N.

Example 31—Leaf and Root Microbiomes in Antarctic Hairgrass (*Deschamsia Antarctica*). Metagenomics Reveals Diverse Plant Bacterial Microbiome

*Deschampsia antartica* plants, from two different accessions (Da2 and Da17) were grown in 6 different hydroponic solutions representing different nutritional conditions. These were used to examine abundant bacteria in leaf and root microbiomes through metagenomics.

After 3 weeks of treatment with biweekly replenishment of media to maintain ion concentrations, RNA was extracted from leaves and roots of 5 replicate plants per treatment. This RNA was pooled and used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria in plants grown under different nutritional regimes. A hit was counted above a threshold of 98% identity and 40 bp. The hits were counted per database sequence per library and a counts matrix of hits per database sequence per library analysed was created. Database sequences were extracted if hit count per library analysed was greater than or equal to 100 counts.

These database sequences were classified taxonomically using the Ribiosomal Database Project classifier (available at rdp.cme.msu.edu) and grouped to show the taxonimic distribution of the microbes represented in the *Deschampsia antartica* leaf and root microbiome across bacterial phyla (FIG. 178). There were 203 16S sequences out of 7109 sequences identified.

Example 32—Leaf and Root Microbiomes in Antarctic Hairgrass (*Deschamsia antarctica*). Metagenomics Reveals Defferences in Bacterial Species Predominance in Shoot and Root Microbiomes

*Deschampsia antartica* plants, from two different accessions (Da2 and Da17) were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was pooled and used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of, hits per database sequence per library analysed was created. Database sequences were extracted if hit count per library analysed was greater than or equal to 100 counts.

This counts matrix was modified, by each database sequence by library count value being divided by the average counts value for that sequence across all the libraries. This modified matrix was loaded into the MultiExperimentViewer software (part of the TM4 software suite www.tm4.org) and used for hierarchical clustering of the 16S sequences using average linkage with Pearson correlation.

The heat map shown in FIG. 179 displays differences in bacterial species predominance in shoots and roots.

Example 33—Leaf and Root Microbiomes in Antarctic Hairgrass (*Deschamsia antarctica*). Differences in Bacterial Species Predominace in Shoot and Root Microbiomes Depending on Symbiotum Nutritional Status

*Deschampsia antartica* plants, from two different accessions (Da2 and Da17) were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was pooled and used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was created. Database sequences were extracted if hit count per library analysed was greater than or equal to 100 counts.

This counts matrix was modified, by each database sequence by library count value being divided by the average counts value for that sequence across all the libraries. This modified matrix was loaded into the MultiExperimentViewer software (part of the TM4 software suite www.tm4.org) and used for hierarchical clustering of the 16S sequences using average linkage with Pearson correlation.

FIG. 180 shows a zoomed region of the heat map, displaying differences in bacterial species predominance in response to differing nutritional status in root samples.

Example 34—Leaf and Root Microbiomes in Antarctic Hairgrass (*Deschamsia antarctica*). Differences in Bacterial Species Predominace in Shoot and Root Microbiomes Depending on Symbiotum Nutritional Status

*Deschampsia antartica* plants, from two different accessions (Da2 and Da17) were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was pooled and used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was created. Database sequences were extracted if hit count per library analysed was greater than or equal to 100 counts.

This counts matrix was modified, by each database sequence by library count value being divided by the average counts value for that sequence across all the libraries. This modified matrix was loaded into the MultiExperiment-Viewer software (part of the TM4 software suite www.tm4.org) and used for hierarchical clustering of the 16S sequences using average linkage with Pearson correlation.

FIG. 181 shows a zoomed region of the heat map, displaying differences in bacterial species predominance in response to differing nutritional status in leaf samples. The predominant bacterial species in leaf microbiome are predominantly *Cyanobacteria*. The bacterial species differ in response to N in leaves (ie. low N).

Example 35—Leaf and Root Microbiomes in Antarctic Hairgrass (*Deschamsia antarctica*). Metagenome Analysis of Bacterial Microbiome in Symbiote Reveals Range of Bacterial Species Known to be N Fixers and Phytostimulators of Grasses

*Deschampsia antartica* plants, from two different accessions (Da2 and Da17) were grown in 6 different hydroponic solutions representing different nutritional conditions.

After 3 weeks of treatment with biweekly replenishment of media to maintain ion concentrations, RNA was extracted from leaves and roots of 5 replicate plants per treatment. This RNA was pooled and used to construct cDNA RNA seq libraries which were analysed by Ilummina HiSeq sequencing.

The reads from these libraries were analysed using blastn and a single database hit recorded per sequence read. In this case the database consisted of 117101 16S rRNA sequences. The rRNA sequences are used to taxonomically identify bacteria. A hit was counted above a threshold of 98% identity and 40 bp. The hits were counted per database sequence per library and a counts matrix of hits per database sequence per library analysed was created. Database sequences were extracted if hit count per library analysed was greater than or equal to 100 counts.

This counts matrix was modified, by each database sequence by library count value being divided by the average counts value for that sequence across all the libraries. This modified matrix was loaded into the MultiExperiment-Viewer software (part of the TM4 software suite www.tm4.org) and used for hierarchical clustering of the 16S sequences using average linkage with Pearson correlation.

FIG. 182 shows a zoomed region of the heat map displaying *Azospirillum* species clustered together. These bacteria are known to associate with monocotyledenous plants, and also to fix atmospheric nitrogen and produce phytohormones (phytostimulator of grasses). These bacteria are shown to be more predominant in low nitrogen nutrient solutions in root samples. Thus, *Azospirillum* species were induced in number under low N.

Example 36—Summary

These examples demonstrate that metagenomics of grass symbiomes reveals compex endo/epiphytic microbiomes and species diversity in grass microbiomes. There is also variation in microbiome between grass species, between roots and shoots, and across environmental conditions. The microbiome profile reveals species diversity for symbiome performance enhancement, microbiome profiling across genotypes and environments, microbiome monitoring and microbiome inoculation.

Example 37—Maximising Performance of Ruminants Through Genomic Selection for Optimum Interaction of Individual Ruminant Genomes and Rumen Microflora Profiles Ruminants are unique in their ability to turn low quality forage into meat, milk and fibre. This unique ability is as a result of the rumen, an organ of the digestive tract which is host to vast multitudes of bacteria and other micro-organisms. The profile of rumen micro-organisms can be obtained by taking a sample of rumen fluid, or alternatively profiling the faeces, and counting the abundance of species, for example through meta-genome sequencing. This profile differs between ruminant species and between individuals. Differences in rumen profile may be associated with differences in feed conversion efficiency, milk composition and health outcomes. Thus, selecting to maximise phenotypic performance of ruminants may be achieved through genomic selection for optimum individual ruminant genome by rumen profile. Given the number of micro-organisms in the rumen is very large, and the number of genes in the genomes of ruminants is approximately 20,000, a genetic algorithm is required to prioritise sample combination based on diversity.

Example 38—Endophyte Inoculation Method in Perennial Ryegrass

This example describes enhancement of endophyte inoculation frequency following puncturing isolated embryos of perennial ryegrass with an hypodermic needle prior to inoculation using method 1 (direct inoculation) or method 2 (coating with endophyte containing Ca-alginate layer).

Embryos isolated from perennial ryegrass seeds were inoculated with endophyte NEA11 using either methods 1 or 2, with endophyte suspensions at different dilution rates (¼, ⅛, 1/16; see FIG. 183) subjected, with and without wounding of embryos with an hypodermic needle. Puncturing of embryos prior to inoculation greatly enhanced inoculation efficiency, demonstrated by SSR-based endophyte detection in 6 week old symbiota recovered from artificial seeds derived from inoculated embryos (see Table 64).

TABLE 64

Number and frequency of endophyte-inoculated perennial ryegrass plants recovered following different endophyte inoculation treatment methods

| Treatment | Method | PDB conc. | Wounding | Endophyte Detected NEA11 | E− | Inoculation % |
|---|---|---|---|---|---|---|
| A | 1 | 1/16 | No | 0 | 42 | 0 |
| B | 1 | ⅛ | No | 0 | 42 | 0 |
| C | 1 | ⅛ | Puncture | 11 | 29 | 27.5 |
| D | 2 | 1/16 | No | 0 | 42 | 0 |
| E | 2 | ⅛ | No | 0 | 42 | 0 |
| F | 2 | ⅛ | Puncture | 9 | 9 | 50 |

Method 1: Direct Inoculation of Isolated Embryos with Endophyte Suspension Prior to Ca-Alginate Coating
Method 2: Direct Coating of Isolated Embryos with Endophyte-Containing Ca-Alginate Layer

Example 39—Endophyte Inoculation Method in Perennial Ryegrass and Tall Fescue This example describes enhancement of endophyte inoculation frequency following puncturing isolated embryos of perennial ryegrass (*L. perenne*) and tall fescue (*F. arundinacea*) with an hypodermic needle prior to inoculation using method 1 (direct inoculation) or method 2 (coating with endophyte containing Ca-alginate layer).

Method 1: Direct Inoculation of Isolated Embryos with Endophyte Suspension Prior to Ca-Alginate Coating Method 2: Direct Coating of Isolated Embryos with Endophyte-Containing Ca-Alginate Layer Embryos isolated from seeds from different varieties were inoculated with different endophytes (NEA11 and NEA17) using either methods 1 or 2, with and without wounding of embryos with hypodermic needle. Puncturing of embryos prior to inoculation greatly enhanced inoculation efficiency, demonstrated by SSR-based endophyte detection in 6 week-old symbiota recovered from artificial seeds derived from inoculated embryos (see Table 65).

TABLE 65

SSR-based endophyte detection in 6 week-old symbiota recovered from artificial seeds derived from inoculated embryos

| Species | Variety | Experiment | Endophyte | No. of artificial seeds Method 1 | | | No. of artificial seeds Method 1 plus wounding | | |
|---|---|---|---|---|---|---|---|---|---|
| | | | | Total | Negative | Positive | Total | Negative | Positive |
| *L. perenne* | Alto | 1 | NEA11 (LpTG-2) | 42 | 42 | 0 | 20 | 16 | 4 |
| | | 2 | NEA11 (LpTG-2) | 21 | 21 | 0 | 21 | 20 | 1 |
| | | 3 | NEA11 (LpTG-2) | 84 | 84 | 0 | 40 | 29 | 11 |
| *F. arundinacea* | Dovey | 1 | NEA11 (LpTG-2) | 42 | 42 | 0 | 40 | 39 | 1 |
| *L. perenne* | Alto | 1 | NEA17 (FaTG-2) | 42 | 42 | 0 | 42 | 42 | 0 |
| *F. arundinacea* | Dovey | 1 | NEA17 (FaTG-2) | 70 | 70 | 0 | 35 | 35 | 0 |
| | Finesse | 2 | NEA17 (FaTG-2) | 42 | 42 | 0 | 70 | 70 | 0 |

| Species | Variety | Experiment | Endophyte | No. of artificial seeds Method 2 | | | No. of artificial seeds Method 2 plus wounding | | |
|---|---|---|---|---|---|---|---|---|---|
| | | | | Total | Negative | Positive | Total | Negative | Positive |
| *L. perenne* | Alto | 1 | NEA11 (LpTG-2) | 84 | 84 | 0 | 18 | 9 | 9 |

Example 40—A Method to Discover Host Genotype by Microbiome Profile Interaction in Dairy Cattle Here, we describe a method to map regions of the host genome that affect the rumen microbial profile, and illustrate this with an example.

Methods

The method consists of efficiently testing large numbers of DNA polymorphisms of the host for their effect on rumen microbiome profiles.

A rumen microbiome profile consists of, for each cow, the counts of sequence reads derived from a rumen sample that map to either the species, or contigs of a rumen metagenome assembly, or 16S sequences (for example see Brulc et al. 2009, Hess et al. 2011).

The matrix of counts per cow mapping to each of n contigs or species, or partial assemblies of species, can then be treated as phenotypes in a genome wide association with DNA polymorphisms of the hosts own genome, so a model can be fitted to the data:

$$y = mu + Xb + e$$

Where for each contig/species/partial species assembly, y is the vector of counts for m cows, mu is the mean, X is m×1 design vector assigning the genotype of the host to the record, and e is a vector of random residual effects.

As n, the number of contigs/species or partial species assemblies is likely to be large, the power to identify DNA polymorphisms in the host genome may be increased by considering associations across the contigs/species/partial assemblies. This may be done efficiently by conducting the genome wide association study for each contig, then accumulating the information across contigs, by taking the most significant region for each contig, and then assessing the proportion of times across all contigs that the region is most significant. This may identify master host regulators of rumen microbiome profiles. This may be done in sliding windows of 100 kb, to take into account the effect of highly variable linkage disequilibrium in cattle populations.

EXAMPLE

The data were from 15 Holstein-Fresian dairy cows, grazing at DPI Ellinbank research station. Each cow had genotypes for 624,930 SNP, from the Illumina Bovine HD array.

Rumen samples were taken from each of the cows during a methane measurement experiment. DNA was extracted for each sample, and libraries were prepared of 300 bp random fragments. Then paired end sequencing was performed on Illumina HiSeq. The sequence reads were mapped to the rumen metagenome assembly (8092 contigs) described by Hess et al. 2011.

Five example genome wide association studies (for five different contigs) are shown in FIG. 184.

A region on chromosome 21 was identified that may be a master regulator of rumen microbiome profiles, as it associated with sequence read counts in 3 out of the five contigs.

REFERENCES

Albrecht, T, V. Wimmer, H. J. Auinger, M. Erbe, C. Knaak, M. Ouzunova, H. Simianer, and C. C. Schön, 2011:

Genome-based prediction of testcross values in maize. Theor. Appl. Genet. 123, 339-350.

Auzanneau, J., C. Huyghe, B. Julier, and P. Barre, 2007: Linkage disequilibrium in synthetic varieties of perennial ryegrass. Theor. Appl. Genet. 92, 837-847.

Baird, N. A., P. D. Etter, T. S. Atwood, M. C. Currey, A. L. Shiver, Z. A. Lewis, E. U. Selker, W. A. Cresko, and E. A. Johnson, 2008: Rapid SNP discovery and genetic mapping using sequenced RAD markers. PLoS One 3, e3376.

Beavis W. D., 1994: QTL analyses: power, precision and accuracy. In: A. Paterson (ed.) Molecular Dissection of Complex Traits, 145-162. CRC, Boca Raton, La., USA.

Brazauskas, G., I. Pagăkinskienè, T. Asp, and T. Lübberstedt, 2010: Nucleotide diversity and linkage disequilibrium in five Lolium perenne genes with putative role in shoot morphology. Plant Sci. 179, 194-201.

Bray, R. A., and J. A. G Irwin, 1999: *Medicago sativa* L. (lucerne) cv. Hallmark. Aus. J. Exp. Agric. 39, 643-644.

Brulc, J. M., et al, (2009) Gene-centric metagenomics of the fiber-adherent bovine rumen microbiome reveals forage specific glycoside hydrolases. PNAS. 106, 1948-1953.

Cogan, N. O. I., K. F. Smith, T. Yamada, M. G. Francki, A. C. Vecchies, E. S. Jones, G. C. Spangenberg, and J. W. Forster, 2005: QTL analysis and comparative genomics of herbage quality traits in perennial ryegrass (*Lolium perenne* L.). Theor. Appl. Genet. 110, 364-380.

Cogan, N. O. I., R. C. Ponting, A. C. Vecchies M. C. Drayton, J. George, M. P. Dobrowolski, T. I. Sawbridge, G. C. Spangenberg, K. F. Smith, and J. W. Forster, 2006: Gene-associated single nucleotide polymorphism (SNP) discovery in perennial ryegrass (*Lolium perenne* L.). Mol. Genet. Genom. 276, 101-112.

Cogan, N. O. I., R. C. Baillie, M. C. Drayton, K. Savin, C. Anderson, G. C. Spangenberg, and J. W. Forster, J. W., 2010a: Massively-parallel sequencing technology permits direct detection of novel SNP haplotypes in perennial ryegrass (*Lolium perenne* L.). Molecular Breeding of Forage and Turf 2010, Abstract P-6, 51-52. Buenos Aires, Argentina.

Cogan, N. O. I., J. Wang, G. Ye, C. Bandaranayake, M. L. Hand, R. C. Baillie, M, C. Drayton K. Lawless, M. P. Dobrowolski S. Erb, K. F. Smith, and J. W. Forster, J. W., 2010b: Association mapping of forage quality traits in perennial ryegrass (*Lolium perenne* L.). Molecular Breeding of Forage and Turf 2010, Abstract P-148, 211. Buenos Aires, Argentina.

Cogan, N. O. I., R. C. Baillie, M. L. Hand, M. C. Drayton P. Tian, T. Webster R. Chapman. G. C. Spangenberg, and J. W. Forster, 2010c:Accelerated SNP discovery in perennial ryegrass based on pooled amplicon resequencing. Molecular Breeding of Forage and Turf 2010, Abstract P-4, 47-48. Buenos Aires, Argentina.

Cogan, N. O. I, M. L. Hand, T. I. Sawbridge, R. C. Baillie, and J. W. Forster, 2010d: Comparative genomics in the grass family Poaceae for structured genome-wide SNP discovery in perennial ryegrass (*Lolium perenne* L.). Molecular Breeding of Forage and Turf 2010, Abstract P-5, 49-50. Buenos Aires, Argentina.

Cogan, N. O. I., J. Wang, C. Inch, D. Pickett, R. Elton, R. C. Baillie, M. C. Drayton, H. Shinozuka, and J. W. Forster, 2011: Genomic tools for pasture plant breeding. Plant and Animal Genome XIX, Abstract W335. San Diego, Calif., USA.

Daetwyler, H. D., B. Villanueva, B., and J. A. Woolliams, 2008: Accuracy of predicting the genetic risk of disease using a genome-wide approach. PLoS One 3, e3395.

Dekkers, J. C. M., 2004: Commercial application of marker- and gene assisted selection in livestock: strategies and lessons. J Anim. Sci. 82, E-Suppl: E313-E328.

Dracatos, P. M., N. O. I. Cogan, M. P. Dobrowolski, T. I. Sawbridge, G. C. Spangenberg, K. F. Smith, and J. W. Forster, 2008: Discovery and genetic mapping of single nucleotide polymorphisms in candidate genes for pathogen defense response in perennial ryegrass (*Lolium perenne* L.). Theor. Appl. Genet. 117, 203-219.

Dracatos, P. M., N. O. I. Cogan, T. I. Sawbridge, A. R. Gendall, K. F. Smith, G. C. Spangenberg, and J. W. Forster, 2009: Molecular characterisation and genetic mapping of candidate genes for qualitative disease resistance in perennial ryegrass (*Lolium perenne* L.). BMC Plant Biol. 9, 62.

Dracatos, P. M., N. O. I. Cogan, P. J. Keane, K. F. Smith, and J. W. Forster, 2010: Biology and genetics of crown rust disease in ryegrasses. Crop Sci. 50, 1605-1624.

Dumsday, J. L., K. F. Smith, J. W. Forster, E. S. Jones, 2003: SSR-based genetic linkage analysis of resistance to crown rust (*Puccinia coronata* Corda f. sp. *lolii*) in perennial ryegrass (*Lolium perenne* L.). Plant Pathol. 52, 628-637.

Elshire, R. J., J. C. Glaubitz, Q. Sun, J. A. Poland, K. Kawamoto, E. S. Buckler, and S. E. Mitchell, 2011: A robust, simple genotyping-by-sequencing (GBS) approach for high diversity species. PLoS One 6, e19379.

Faville, M., A. C. Vecchies, M. Schreiber, M. C. Drayton, L. J. Hughes, E. S. Jones, K. M. Guthridge, K. F. Smith, T. Sawbridge G. C. Spangenberg, G. T. Bryan, and J. W. Forster, 2004: Functionally-associated molecular genetic marker map construction in to perennial ryegrass (*Lolium perenne* L.). Theor. Appl. Genet. 110, 12-32.

Fiil, A., I. Lenk, K. Petersen, C. S. Jensen, K. K. Nielsen, B. Schejbel, J. R. Andersen, and T. Lübberstedt, 2011: Nucleotide diversity and linkage disequilibrium of nine genes with putative effects on flowering time in perennial ryegrass (*Lolium perenne* L.). Plant Sci. 180, 228-37.

Forster, J. W., N. O. I. Cogan, M. P. Dobrowolski, E. van Zijll de Jong, G. C. Spangenberg, and K. F. Smith, 2008a: Molecular breeding technologies for forage and turf plants. In: C. Kole and A. Abbott (eds.) Principles and Practices of Plant Genomics Volume 2: Molecular Breeding, 395-430. Science Publishers, Inc., New Hampshire, USA.

Forster, J. W., N. O. I Cogan, M. P. Dobrowolski, M. G. Francki, G. C Spangenberg, and K. F. Smith, 2008b): Functionally-associated molecular genetic markers for temperate pasture plant improvement. In: R. J. Henry (ed.) Plant Genotyping II: SNP Technology, 154-187. CABI Press, Wallingford, Oxford, UK.

Forster, J. W., N. O. I. Cogan, J. Wang, G. Ye, C. Bandaranayake, M. L. Hand, R. C. Baillie, M. C., Drayton, K. Lawless, M. P. Dobrowolski, S. Erb, and K. F. Smith, 2010: Development and implementation of molecular genetic tools for enhancement of herbage quality and other agronomic traits in perennial ryegrass (*Lolium perenne* L.). Molecular Breeding of Forage and Turf 2010, Abstract, 18-19. Buenos Aires, Argentina.

Furbank, R. T., 2009: Plant phenomics: from gene to form and function. Funct. Plant Biol. 36, v-vi.

Ganal, M. W., G. Durstewitz, A. Polley, A. Bérard, E. S. Buckler, A. Charcosset, J. D. Clarke, E. M. Graner, M. Hansen, J. Joets, M. C. Le Paslier, M. D. McMullen, P. Montalent, M. Rose, C. C. Schön, Q. Sun, H. Walter, O. C. Martin, and M. Falque, 2011: A large maize (*Zea mays* L.) SNP genotyping array: development and germplasm genotyping, and genetic mapping to compare with the B73 reference genome. PLoS One. 6, e28334.

Gidskehaug, L, M. Kent, B. J. Hayes, and S. Lien, 2011: Genotype calling and mapping of multisite variants using an Atlantic salmon iSelect SNP array. Bioinformatics 27, 303-310.

Goddard, M. E., 2009: Genomic selection: Prediction of accuracy and maximisation of long term response. Genetica 136, 245-257.

Gout, M., and S. Jones, 2006: Estimates of the annual sales of proprietary cultivars in Australia, and the value of pastures to the livestock and cropping industries. Presentation made to Pastures Australia. Adelaide, Australia, February 2006.

Gupta, P. K., 2008: Single-molecule DNA sequencing technologies for future genomics research. Trends Biotechnol. 26, 602-611.

Guthridge, K. M., M. P. Dupal, R. Kölliker, E. S. Jones, K. F. Smith, and J. W. Forster, 2001: AFLP analysis of genetic diversity within and between populations of perennial ryegrass (Lolium perenne L.). Euphytica 122, 191-201.

Hand, M. L., R. C. Ponting, M. C. Drayton, K. A. Lawless, N. O. I. Cogan, E. C. Brummer, T. I. Sawbridge, G. C. Spangenberg, K. F. Smith, and J. W. Forster, 2008: Identification of homologous, homoeologous and paralogous sequence variants in an outbreeding allopolyploid species based on comparison with progenitor taxa. Mol. Genet. Genom. 280, 293-304.

Hand, M. L., N. O. I. Cogan, A. V. Stewart, and J. W. Forster, 2010: Evolutionary history of tall fescue morphotypes inferred from molecular phylogenetics of the Lolium-Festuca species complex. BMC Evol. Biol. 10, 303.

Hayes, B. J., H. D. Daetwyler, P. Bowman, G. Moser, B. Tier, R. Crump, M. Khatkar, H. Raadsma, and M. E. Goddard, 2009: Accuracy of genomic selection: comparing theory and results Proc. 14th Conf. Assoc. Advanc. Anim. Br. Genet. 14, 34.

Hayward, M. D., J. W. Forster, J. G. Jones O. Dolstra, C. Evans, N. J. McAdam, K. G.

Hossain, M. Stammers, J. A. K., Will M. O. Humphreys, and G. M. Evans, (1998) Genetic analysis of Lolium. I. Identification of linkage groups and the establishment of a genetic map. Plant Breed. 117, 451-455.

Heffner, E. L., M. E. Sorrells, and J.-L. Jannink, (2009) Genomic selection for crop improvement. Crop Sci. 49, 1-12.

Henderson, C. R., 1984: Applications of linear models in animal breeding. University of Guelph, Ontario, Canada.

Hess, M. et al, (2011) Metagenomic Discovery of Biomass-Degrading Genes and Genomes from Cow Rumen. Science 331, 463-467.

Houle, D., D. R. Govindaraju, and S. Omholt, 2010: Phenomics; the next challenge. Nature Rev. Genet. 11, 855-866.

Huang, X., Q. Feng, Q. Qian, Q. Zhao, L. Wang, A. Wang, J. Guan, D. Fan, Q. Weng, T. Huang, G. Dong, T. Sang, and B. Han, 2009: High-throughput genotyping by whole-genome sequencing. Genome Res. 19, 1068-1076.

Huang, X., X. Wei. T. Sang, Q. Zhao, Q. Feng, Y. Zhao, C. Li, C. Zhu, T. Lu, Z. Zhang, M. Li, D. Fan, Y. Guo, A. Wang, L. Wang, L. Deng, W. Li, Y. Lu, Q. Weng, K. Liu, T. Huang, T. Zhou, Y. Jing, W. Li, Z. Lin, E. S. Buckler, Q. Qian, Q. F. Zhang, J. Li, and B. Han, 2010: Genome-wide association studies of 14 agronomic traits in rice landraces. Nat. Genet. 42, 961-967.

Janninck, J.-L., A. J. Lorenz, and H. Iwata, 2010: Genomic selection in plant breeding: from theory to practice. Briefings Funct. Genom. 9, 166-177.

Jones, E. S., M. P. Dupal, R. Kölliker, M. C. Drayton, and J. W. Forster 2001: Development and characterisation of simple sequence repeat (SSR) markers for perennial ryegrass (Lolium perenne L.). Theor. Appl. Genet. 102, 405-415.

Jones, E. S., N. L. Mahoney, M. D. Hayward, I. P. Armstead, J. G. Jones, M. O. Humphreys, I. P. King, T. Kishida, T. Yamada, F. Balfourier, G. Charmet, and J. W. Forster, 2002a: An enhanced molecular marker-based map of perennial ryegrass (Lolium perenne) reveals comparative relationships with other Poaceae genomes. Genome 45, 282-295.

Jones, E. S., M. P. Dupal, J. L. Dumsday, L. J. Hughes, and J. W. Forster, 2002: An SSR-based genetic linkage map for perennial ryegrass (Lolium perenne L.). Theor. Appl. Genet. 105, 577-584.

Kaur, S., M. G. Francki, and J. W. Forster, 2012: Identification, characterisation and interpretation of single nucleotide sequence variation in allopolyploid crop species. Plant Biotech. J. 10, 125-138.

Lawless, K. A., M. C. Drayton, M. L. Hand, R. C. Ponting, N. O. I Cogan, T. I. Sawbridge, K. F. Smith, G. C. Spangenberg, and J. W. Forster, J. W., 2009): Interpretation of SNP haplotype complexity in white clover (Trifolium repens L.), an outbreeding allotetraploid species. In: T. Yamada, and G. Spangenberg (eds.) Molecular Breeding of Forage and Turf: The Proceedings of the $5^{th}$ International Symposium on the Molecular Breeding of Forage and Turf, 211-221. Springer, New York, USA.

Lango Allen, H, K. Estrada, G. Lettre, S. I. Berndt, M. Weedon, et al., 2010: Hundreds of variants clustered in genomic loci and biological pathways affect hUman height. Nature 467, 832-838.

Mackay, T. F. C., 2001: The genetic architecture of quantitative traits. Annu. Rev. Genet. 35, 303-339.

Margulies, M., M. Egholm, W. E. Altman, S. Attiya, J. S. Bader, L. A. Bemben, J. Berka, M. S. Braverman, Y.-J. Chen, Z. Chen, S. B. Dewell, L. Du, J. M. Fierro, X. V. Gomes, B. C. Godwin, W. He, S. Helgesen, C. H. Ho, G. P. Irzyk, S. C. Jando, M. L. I. Alenquer, T. P. Jarvie, K. B. Jirage, J.-B. Kim, J. R. Knight, J. R. Lanza, J. H. Leamon, S. M. Lefkowitz, M. Lei, J. Li, K. L. Lohman, H. Lu, V. B. Makhijani, K. E. McDade; M. P. McKenna, E. W. Myers, E. Nickerson, J. R. Nobile, R. Plant, B. P. Puc, M. T. Ronan, G. T. Roth, G. J. Sarkis, J. F. Simons, J. W. Simpson, M. Srinivasan, K. R. Tartaro, A. Tomasz, K. A. Vogt, G. A. Volkmer, S. H. Wang, Y. Wang, M. P. Weiner, P. Yu, R. F. Begley, and J. M. Rothberg, 2005: Genome sequencing in microfabricated high-density picolitre reactors. Nature 437, 376-380.

Meuwissen, T. H. E., B. J. Hayes, and M. E. Goddard, 2001: Prediction of total genetic value using genome-wide dense marker maps. Genetics 157, 1819-1829.

Meuwissen, T. H. E., and M. E. Goddard, 1996: The use of marker haplotypes in animal breeding schemes. Genet. Sel. Evol. 28, 161-176.

Meuwissen, T. H., and M. E. Goddard, 2004: Mapping multiple QTL using linkage disequilibrium and linkage analysis information and multitrait data. Genet. Sel. Evol. 36, 261-279.

Meuwissen, T. H. E., 2009: Accuracy of breeding values of 'unrelated' individuals predicted by dense SNP genotyping. Genet Sel Eva 41, 35.

Odegård, J., M. H. Yazdi, A. K. Sonesson, and T. H. E. Meuwissen, 2009: Incorporating desirable genetic characteristics from an inferior into a superior population using genomic selection. Genetics 181, 737-745.

Pearson, A. N. O. I. Cogan, R. C. Baillie, M. L. Hand, H. Shinozuka S. Erb, T. Wilkinson, G. A. Keamey, A. R. Gendall, K. F. Smith, and J. W. Forster, 2011: Identification of QTLs for morphological traits influencing waterlogging tolerance in perennial ryegrass (*Lolium perenne* L.). Theor. Appl. Genet. 122, 609-622.

Pessino, S. C., J. P. A. Ortiz, M. D. Hayward, and C. L. Quarin, 1999: The molecular genetics of gametophytic apomixis. Hereditas 130, 1-11.

Ponting, R. C., M. C., Drayton, N. O. I. Cogan, M. P. Dobrowolski, K. F. Smith, G. C. Spangenberg, and J. W. Forster, 2007: SNP discovery, validation, haplotype structure and linkage disequilibrium in full-length herbage nutritive quality genes of perennial ryegrass (*Lolium perenne* L.). Mol. Genet. Genomics, 278, 589-597.

Pryce, J. E., B. J. Hayes, and M. E. Goddard, 2012: Novel strategies to minimize progeny inbreeding while maximizing genetic gain using genomic information. J. Dairy Sci. 95, 377-388. Riedelsheimer, C, A. Czedik-Eysenberg, C. Grieder, J. Lisec, F. Technow, R. Sulpice, T. Altmann, M. Stitt, L. Willmitzer, and A. E. Melchinger, 2012: Genomic and metabolic prediction of complex heterotic traits in hybrid maize. Nat Genet. 15, 217-220.

Sanna, S., A. U. Jackson, R. Nagaraja, C. J Willer, et al., 2008: Common variants in the GDF5-UQCC region are associated with variation in human height. Nat. Genet. 40, 198-203.

Sessitsch, A., J. G. Howieson, X. Perret, H. Antoun, and E. Martinez-Romero, 2002: Advances in *Rhizobium* research. Crit. Rev. Plant Sci. 21, 323-378.

Shinozuka, H., N. O. I. Cogan, K. F. Smith, G. C. Spangenberg, and J. W. Forster, 2010: Fine-scale comparative genetic and physical mapping supports map-based cloning strategies for the self-incompatibility loci of perennial ryegrass (*Lolium perenne* L.). Plant Mol. Biol. 72, 343-355.

Skøt, L., J. Humphreys, M. O. Humphreys, D. Thorogood, J. Gallagher, R. Sanderson, I. P. Armstead, and I. D. Thomas, 2007: Association of candidate genes with flowering time and water-soluble carbohydrate content in *Lolium perenne* (L.). Genetics 177, 535-547.

Skøt, L., R. Sanderson, A. Thomas, K. Skøt, D. Thorogood, G. Latypovëa, T. Asp, and I. Armstead, 2011: Allelic variation in the perennial ryegrass FLOWERING LOCUS T gene is associated with changes in flowering time across a range of populations. Plant Physiol. 155, 1013-1022.

Spelman, R. J., D. J. Garrick, and J. A. M. van Arendonk, 1999: Utilisation of genetic variation by marker assisted selection in commercial dairy cattle populations. Livest. Prod. Sci. 59: 51-60.

Spielman, M., R. Vinkenoog, and R. J. Scott, 2003: Genetic mechanisms of apomixis. Philos. Trans. R. Soc. Lond. B. Biol. Sci., 358, 1095-1103.

Sved, J. A., 1971: Linkage disequilibrium and homozygosity of chromosome segments in finite populations. Theor. Popul. Biol. 2, 125-141.

Tian, F., P. J. Bradbury, P. J. Brown, H. Hung, Q. Sun, S. Flint-Garcia, T. R. Rocheford, M. D. McMullen, J. B. Holland, and E. S. Buckler, 2011: Genome-wide association study of leaf architecture in the maize nested association mapping population. Nature Genet. 43, 159-162.

Gibbs, R. A., Taylor, J. F. and Van Tassell, C. P. et al., The Bovine Hapmap Consortium, 2009: Genome-wide survey of SNP variation uncovers the genetic structure of cattle breeds. Science 324, 528-532.

VanRaden, P. M., C. P. Van Tassell, G. R. Wiggans, T. S. Sonstegard, R. D. Schnabel, J. F. Taylor, and F. Schenkel, 2009: Invited review: Reliability of genomic predictions for North American Holstein bulls. J. Dairy Sci. 92, 16-24.

Turner L. B., M. Farrell, M. O. Humphreys, and O. Dolstra, 2010: Testing water-soluble carbohydrate QTL effects in perennial ryegrass (*Lolium perenne* L.) by marker selection. Theor. Appl. Genet. 121, 1405-1417.

Vogel, K. P., and J. F. Pedersen, 1993: Breeding systems for cross-pollinated perennial grasses. Plant Breed. Revs. 11, 251-274.

Walter, A., B. Studer, and R. Kölliker, 2012: Advanced phenotyping offer opportunities for improved breeding of forage and turf species. Ann. Bot., 110, 1271-1279.

Wang, J., M. P. Dobrowolski, N. O. I. Cogan, J. W. Forster, and K. F. Smith, 2009: Assignment of individual genotypes to specific forage cultivars of perennial ryegrass (*Lolium perenne* L.) based on SSR markers. Crop Sci. 49, 49-58.

Wang, L., A. Wang, X. Huang, Q. Zhao, G. Dong, Q. Qian, T. Aang, B. Han, 2011: Mapping 49 quantitative trait loci at high resolution through sequencing-based genotyping of rice recombinant inbred lines. Theor. Appl. Genet. 122, 327-340.

Wilkins, P. W., and M. O. Humphreys, 2003: Progress in breeding perennial forage grasses for temperate agriculture. J. Agric. Sci. 140, 129-150.

Van Inghelandt, D., J. C. Reif, B. S. Dhillon, P. Flament, and A. E. Melchinger, 2011: Extent and genome-wide distribution of linkage disequilibrium in commercial maize germplasm. Theor Appl Genet. 123, 11-20.

Visscher, P. M., 2008: Sizing up human height variation. Nat. Genet. 40, 489 490.

Xing, Y., U. Frie, B. Schejbel, T. Asp, and T. Lübberstedt, 2007: Nucleotide diversity and linkage disequilibrium in 11 expressed resistance candidate genes in *Lolium perenne*. BMC Plant Biol. 7: 43.

Yan, J., T. Shah, M. L. Warburton, E. S. Buckler, M. D. McMullen, and J. Crouch, 2009: Genetic characterization and linkage disequilibrium estimation of a global maize collection using SNP markers. PLoS One 4, e8451.

The claims defining the invention are as follows:

1. A method for producing an improved organism including:
   (i) providing a library of plant germplasm; and a library of symbionts;
   (ii) inoculating the germplasm library with one or more symbionts selected from the symbiont library to generate symbiota [and optionally breeding the symbiota to produce offspring symbiota];
   (iii) screening and/or evaluating the symbiota for desired symbiota characteristic(s) and then selecting symbiota exhibiting desired characteristic (s) and then selecting symbiota exhibiting desired characteristic(s); and
   (iv) subsequently identifying, culturing or otherwise using the symbiota exhibiting desired characteristic(s) to produce the improved plant;
   wherein:
   said library of plant germplasm includes 100s to 1000s of genotypes;
   said library of symbionts includes 10s to 100s of genotypes; and said step of [breeding, selecting,] screening and/or evaluating the symbiota includes a step of genetic analysis and/or metabolic analysis; and said step of screening and/or evaluating the symbiota includes subjecting symbiota to a rapid endophyte viability assay, said assay including:

growing the inoculated germplasm or symbiota to 1 to 10 days old;

extracting DNA and/or RNA from the symbiota: and subjecting the extracted DNA and/or RNA to an assay for in planta expressed endophyte-specific genes to enable early in planta endophyte viability assessment.

2. The method according to claim 1, wherein the symbiont(s) is capable of forming symbiotic associations with the plant.

3. The method according to claim 2, wherein the symbiont is selected from one or more of fungi, viruses, bacteria and other microbes.

4. The method according to claim 3, wherein the symbiont(s) includes a genetic variation selected to enhance symbiont trait introgression.

5. The method according to claim 4, wherein the genetic variation is introduced via one or more of random mutagenesis, di-poly-ploidisation, targeted mutagenesis, cisgenesis; transgenesis; intragenesis.

6. The method according to claim 1, wherein the organism is a plant having symbiotic compatibility with an endophyte.

7. The method according to claim 6, wherein the plant germplasm is present as an embryo.

8. The method according to claim 7, wherein the embryo is coated with a symbiont-containing coating layer, to form an artificial seed.

9. The method according to claim 8, wherein the embryo is treated to create one or more points of entry for the symbiont.

10. The method according to claim 1, wherein a population of plant germplasm is inoculated with a population of symbionts, so that favourable host-symbiont associations may be identified.

11. The method according to claim 1, wherein the screening step (iii) includes screening artificial seeds and/or their offspring for compatibility and/or stability by accelerated ageing and selecting symbiota exhibiting desired characteristics, wherein ageing is accelerated by subjecting the seeds and/or their offspring to high temperature and/or high moisture content.

12. The method according to claim 1, wherein the plant is a grass or a legume.

13. The method according to claim 1, wherein the [inoculated germplasm or] symbiota are grown to 3 to 5 days.

14. The method according to claim 1, wherein the DNA/RNA is co-extracted in a single step.

* * * * *